(12) United States Patent
Amann et al.

(10) Patent No.: US 11,780,919 B2
(45) Date of Patent: Oct. 10, 2023

(54) BISPECIFIC ANTIGEN BINDING MOLECULES TARGETING OX40 AND FAP

(71) Applicant: Hoffmann-La Roche Inc., Little Falls, NJ (US)

(72) Inventors: Maria Amann, Schlieren (CH); Juergen Peter Bachl, Basel (CH); Alexander Bujotzek, Penzberg (DE); Carina Cantrill, Basel (CH); Harald Duerr, Penzberg (DE); Janine Faigle, Penzberg (DE); Sabine Imhof-Jung, Penzberg (DE); Christian Klein, Schlieren (CH); Thomas Kraft, Penzberg (DE); Estelle Marrer-Berger, Basel (CH); Ekkehard Moessner, Schlieren (CH); Laurene Pousse, Schlieren (CH); Petra Rueger, Penzberg (DE); Johannes Sam, Schlieren (CH); Roland Staack, Penzberg (DE); Dietrich Tuerck, Basel (CH); Pablo Umana, Schlieren (CH); Joerg Zielonka, Schlieren (CH)

(73) Assignee: Hoffmann-La Roche Inc., Little Falls, NJ (US)

(*) Notice: Subject to any disclaimer, the term of this patent is extended or adjusted under 35 U.S.C. 154(b) by 80 days.

(21) Appl. No.: 17/218,948

(22) Filed: Mar. 31, 2021

(65) Prior Publication Data
US 2022/0025046 A1    Jan. 27, 2022

(30) Foreign Application Priority Data
Apr. 1, 2020 (EP) ..................... 20167624

(51) Int. Cl.
| A61K 39/00 | (2006.01) |
| C07K 16/28 | (2006.01) |
| A61P 35/00 | (2006.01) |
| A61K 45/06 | (2006.01) |
| C07K 16/30 | (2006.01) |
| C07K 16/46 | (2006.01) |

(52) U.S. Cl.
CPC .......... *C07K 16/2809* (2013.01); *A61K 45/06* (2013.01); *A61P 35/00* (2018.01); *C07K 16/2878* (2013.01); *C07K 16/30* (2013.01); *C07K 16/468* (2013.01); *A61K 2039/505* (2013.01); *C07K 2317/565* (2013.01); *C07K 2317/622* (2013.01)

(58) Field of Classification Search
CPC .................. C07K 16/2878; C07K 2317/31
See application file for complete search history.

(56) References Cited

U.S. PATENT DOCUMENTS

| 9,011,847 | B2 | 4/2015 | Bacac et al. |
| 10,253,110 | B2 | 4/2019 | Bacac et al. |
| 10,392,445 | B2 | 8/2019 | Amann et al. |
| 10,464,981 | B2 | 11/2019 | Amann et al. |
| 10,526,413 | B2 | 1/2020 | Amann et al. |
| 10,577,429 | B2 | 3/2020 | Bacac et al. |
| 11,242,396 | B2 * | 2/2022 | Bruenker ............. C07K 16/468 |
| 2017/0174786 | A1 | 6/2017 | Bacac et al. |
| 2017/0247467 | A1 | 8/2017 | Amann et al. |
| 2018/0230215 | A1 | 8/2018 | Hofer et al. |
| 2018/0282409 | A1 | 10/2018 | Koller et al. |
| 2018/0340030 | A1 | 11/2018 | Bruenker et al. |
| 2019/0016771 | A1 | 1/2019 | Amann et al. |
| 2019/0185566 | A1 | 6/2019 | Koller et al. |
| 2019/0194291 | A1 | 6/2019 | Bruenker et al. |
| 2019/0211113 | A1 | 7/2019 | Amann et al. |
| 2019/0248877 | A1 | 8/2019 | Amann et al. |
| 2019/0382507 | A1 | 12/2019 | Amann et al. |
| 2020/0071411 | A1 | 3/2020 | Amann et al. |
| 2020/0079873 | A1 | 3/2020 | Bacac et al. |
| 2020/0190206 | A1 | 6/2020 | Koller et al. |
| 2020/0190207 | A1 | 6/2020 | Bruenker et al. |
| 2020/0231691 | A1 | 7/2020 | Grau-Richards et al. |
| 2020/0247904 | A1 | 8/2020 | Amann et al. |
| 2020/0270321 | A1 | 8/2020 | Amann et al. |
| 2020/0277392 | A1 | 9/2020 | Amann et al. |
| 2020/0317774 | A1 | 10/2020 | Hofer et al. |
| 2020/0325225 | A1 | 10/2020 | Bacac et al. |
| 2020/0325238 | A1 | 10/2020 | Bacac et al. |
| 2020/0347115 | A1 | 11/2020 | Duerr et al. |
| 2020/0392237 | A1 | 12/2020 | Bacac et al. |
| 2021/0009656 | A1 | 1/2021 | Bruenker et al. |
| 2021/0024610 | A1 | 1/2021 | Koller et al. |
| 2021/0070882 | A1 | 3/2021 | Bacac et al. |
| 2021/0095002 | A1 | 4/2021 | Claus et al. |
| 2021/0163617 | A1 | 6/2021 | Ferrara Koller et al. |
| 2021/0188992 | A1 | 6/2021 | Bruenker et al. |
| 2021/0253724 | A1 | 8/2021 | Claus et al. |
| 2021/0292426 | A1 * | 9/2021 | Duerr ................... C07K 16/468 |

FOREIGN PATENT DOCUMENTS

| WO | 02/020565 A2 | 3/2002 |
| WO | 2010/145792 A1 | 12/2010 |
| WO | 2012/130831 A1 | 10/2012 |
| WO | 2015/153513 A1 | 10/2015 |
| WO | 2016/062734 A1 | 4/2016 |

(Continued)

OTHER PUBLICATIONS

U.S. Appl. No. 15/941,519, filed Mar. 30, 2018, Published, US 2018/0230215.

(Continued)

*Primary Examiner* — Sheela J. Huff
(74) *Attorney, Agent, or Firm* — Lawrence S. Graham

(57) ABSTRACT

The invention relates to novel bispecific antigen binding molecules, comprising at least two antigen binding domains capable of specific binding to OX40 and a particular antigen binding domain capable of specific binding to Fibroblast Activation Protein (FAP), and to methods of producing these molecules and to methods of using the same.

24 Claims, 67 Drawing Sheets

Specification includes a Sequence Listing.

(56) References Cited

FOREIGN PATENT DOCUMENTS

| WO | 2016/075278 A1 | 5/2016 |
|---|---|---|
| WO | 2016/079076 A1 | 5/2016 |
| WO | 2017/055398 A2 | 4/2017 |
| WO | 2017/060144 A1 | 4/2017 |
| WO | 2018/197533 A1 | 11/2018 |
| WO | 2019/086497 A2 | 5/2019 |
| WO | 2019/086500 A2 | 5/2019 |
| WO | WO 2019/086500 | 5/2019 |
| WO | 2020/070035 A1 | 4/2020 |
| WO | 2020/070041 A1 | 4/2020 |
| WO | WO 2020/070035 | 4/2020 |
| WO | 2020/007817 A1 | 9/2020 |
| WO | 2020/208049 A1 | 10/2020 |
| WO | WO 2020/208049 | 10/2020 |
| WO | 2020/260329 A1 | 12/2020 |
| WO | WO 2020/260329 | 12/2020 |

OTHER PUBLICATIONS

U.S. Appl. No. 16/689,880, filed Nov. 20, 2019, Published, US 2020/0317774.
U.S. Appl. No. 15/281,493, filed Sep. 30, 2016, Published, US 2017/0174786.
U.S. Appl. No. 16/877,150, filed May 18, 2020, Published, US 2021/0070882.
U.S. Appl. No. 15/087,405, filed Mar. 31, 2016, Granted, U.S. Pat. No. 10,464,981.
U.S. Appl. No. 16/653,652, filed Oct. 15, 2019, Published, US 2020/0270321.
U.S. Appl. No. 16/184,147, filed Nov. 8, 2018, Published, US 2019/0194291.
U.S. Appl. No. 17/030,251, filed Sep. 23, 2020, Published, US 2021/0009656.
U.S. Appl. No. 15/763,868, filed Mar. 28, 2018, Published, US 2018/0282409.
U.S. Appl. No. 16/446,4861, filed Jun. 19, 2019, Published, US 2020/0190206.
U.S. Appl. No. 17/125,533, filed Dec. 17, 2020, Published, US 2021/0253724, WO 2020/007817.
U.S. Appl. No. 16/820,504, filed Mar. 16, 2020, Published, US 2020/0325238.
U.S. Appl. No. 17/017,576, filed Sep. 23, 2020, Published, US 2021/016361.
U.S. Appl. No. 15/067,024, filed Mar. 10, 2016, Granted, U.S. Pat. No. 10,392,445.
U.S. Appl. No. 16/522,391, filed Jul. 25, 2019, Published, US 2020/0247904.
U.S. Appl. No. 16/522,412, filed Jul. 25, 2019, Published, US 2019/0382507.
U.S. Appl. No. 15/280,379, filed Sep. 29, 2016, Granted, U.S. Pat. No. 10,526,413.
U.S. Appl. No. 16/684,258, filed Nov. 14, 2019, Published, US 2020/0071411.
U.S. Appl. No. 15/280,386, filed Sep. 29, 2016, Published, US 2017/0247467.
U.S. Appl. No. 16/218,266, filed Dec. 12, 2018, Published, US 2019/0211113.
U.S. Appl. No. 16/144,687, filed Sep. 27, 2018, Published, US 2019/0016771 A1.
U.S. Appl. No. 16/861,801, filed Apr. 29, 2020, Published, US 2020/0347115 A1.
U.S. Appl. No. 16/825,773, filed Mar. 20, 2020, Published, US 2020/0325225.
U.S. Appl. No. 17/017,942, filed Sep. 19, 2020, Published, US 2021/0095002.
U.S. Appl. No. 17/066,711, filed Oct. 9, 2020, Published, US 2021/0024610.
U.S. Appl. No. 16/186,443, filed Nov. 9, 2018, Published, US 2019/0248877.
U.S. Appl. No. 16/584,931, filed Sep. 26, 2019, Published, US 2020/0277392.
U.S. Appl. No. 16/581,756, filed Sep. 25, 2019, Published, US 2020/0231691.
U.S. Appl. No. 16/189,041, filed Nov. 13, 2018, Published, US 2019/0185566.
U.S. Appl. No. 13/205,743, filed Aug. 9, 2011, Granted, U.S. Pat. No. 9,011,847.
U.S. Appl. No. 14/661,839, filed Mar. 18, 2015, Granted, U.S. Pat. No. 10,253,110.
U.S. Appl. No. 14/661,833, filed Mar. 18, 2015, Granted, U.S. Pat. No. 10,577,429.
U.S. Appl. No. 16/378,320, filed Apr. 8, 2019, Published, US 2020/0079873.
U.S. Appl. No. 16/860,552, filed Apr. 28, 2020, Published, US 2020/0392237.
U.S. Appl. No. 15/943,821, filed Apr. 3, 2018, Published, US 2018/0340030.
Chen et al., "Conversion of Peripheral CD4+CD25 Naive T Cells to CD4+CD25+ Regulatory T Cells by TGF-beta Induction of Transcription Factor Foxp3" J. Exp. Med. (2003) 198(12):1875-1886.
Croft, M. et al., "The significance of OX40 and OX40L to T-cell biology and immune disease," Immunol. Rev. (2009) 229(1):173-191.
Curotto de Lafaille et al., "Natural and Adaptive Foxp3+ Regulatory T Cells: More of the Same or a Division of Labor?" Immunity (2009) 30:626-635.
Gramaglia, I., et al., "Ox-40 Ligand: A Potent Costimulatory Molecule for Sustaining Primary CD4 T Cell Responses" J. Immunol. (1998) 161(12):6510-6517.
Holland et al., "Autoantibodies to Variable Heavy (VH) Chain Ig Sequences in Humans Impact the Safety and Clinical Pharmacology of a VH Domain Antibody Antagonist of TNF-α Receptor 1" J. Clin. Immunol. (2013) 33:1192-1203.
Hori et al., "Control of Regulatory T Cell Development by the Transcription Factor Foxp3" Science (2003) 299(5609):1057-1061.
Igawa et al., "Reduced elimination of IgG antibodies by engineering the variable region" Protein Engineering, Design & Selection (2010) 23(5):385-392.
International Search Report and Written Opinion for PCT/EP2021/058435, dated Jun. 21, 2021, pp. 1-15.
Jensen et al., "Signaling Through OX40 Enhances Antitumor Immunity" Semin. Oncol. (2010) 37(5):524-532.
Kim et al., "Evading pre-existing anti-hinge antibody binding by hinge engineering" mABS (2016) 8(8):1536-1547.
Pyzik et al., "The Neonatal Fc Receptor (FcRn): A Misnomer?" Front. Immunol. (2019) 1540:1-24.
Sakaguchi et al., "Regulatory T Cells and Immune Tolerance" Cell (2008) 133:775-787.
Zhang et al., "OX40 Costimulation Inhibits Foxp3 Expression and Treg Induction via BATF3-Dependent and Independent Mechanisms" Cell Rep. (2018) 24:607-618.
Zhang et al., "Revealing a Positive Charge Patch on a Recombinant Monoclonal Antibody by Chemical Labeling and Mass Spectrometry" Anal. Chem. (2011) 83:8501-8508.

\* cited by examiner

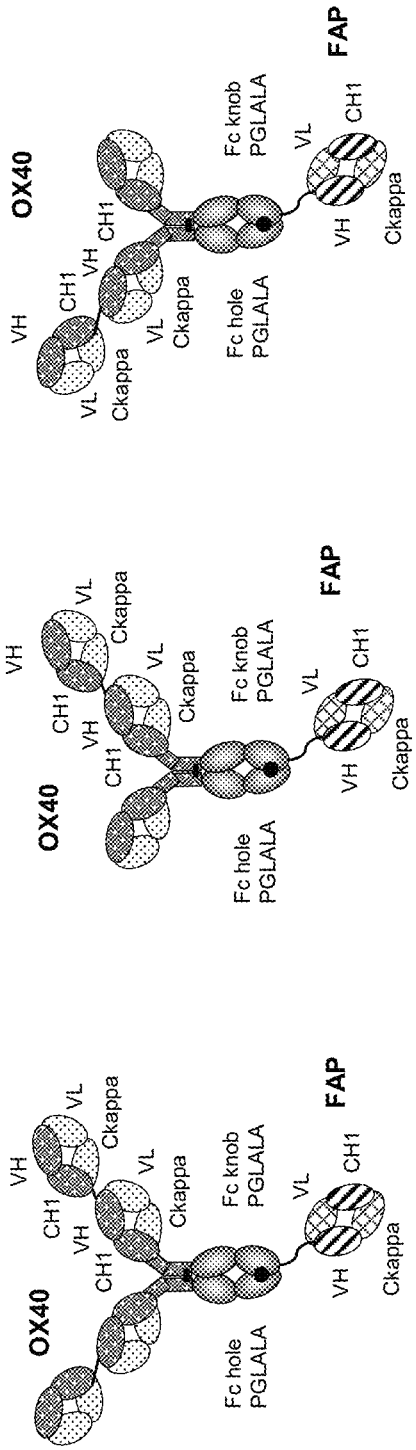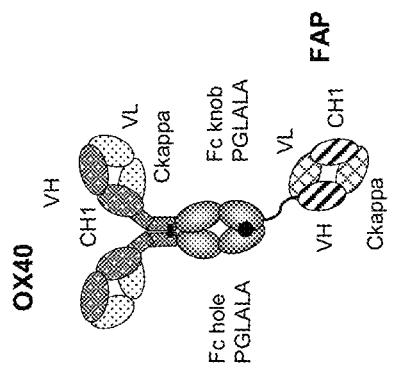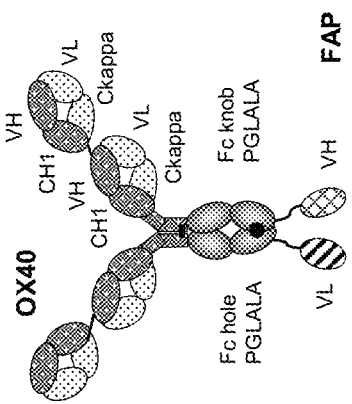
FIG.1A FIG.1B FIG.1C FIG.1D FIG.1E

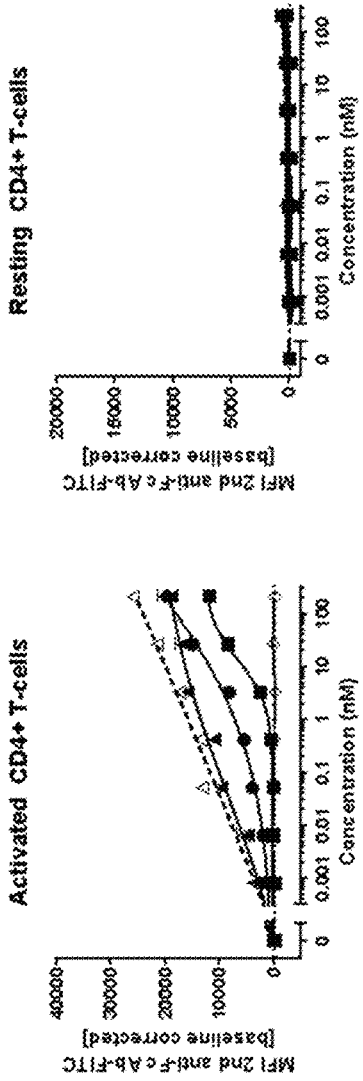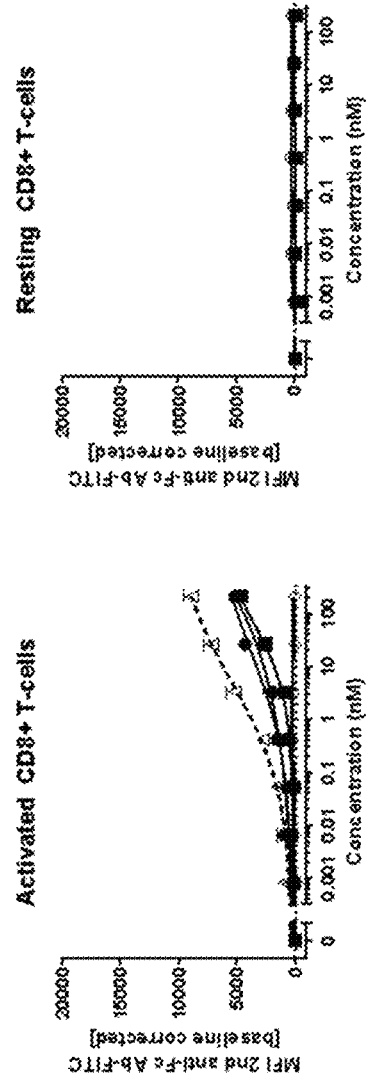

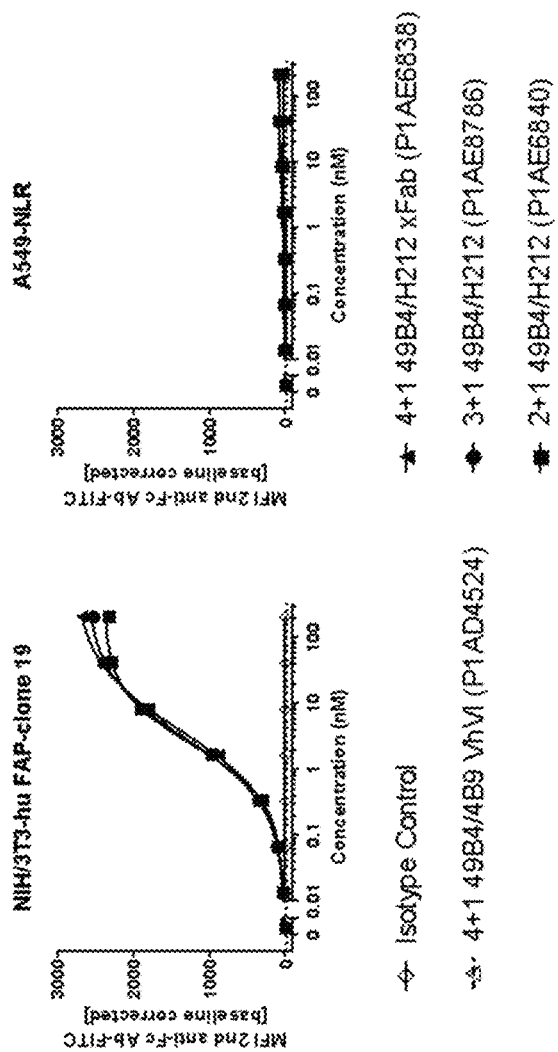

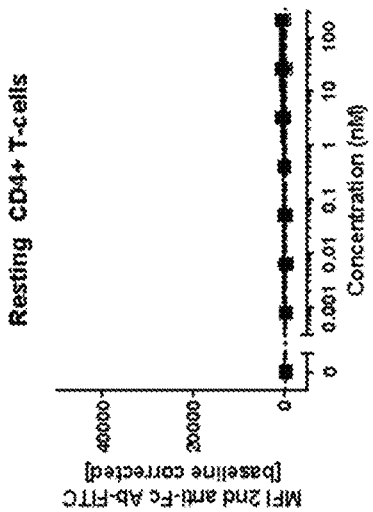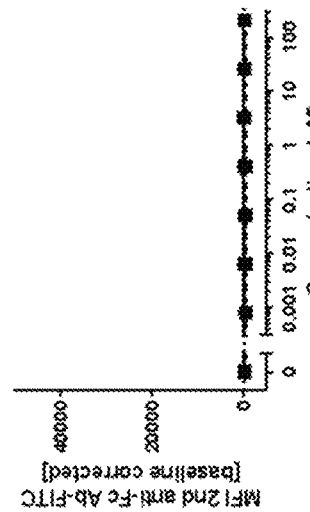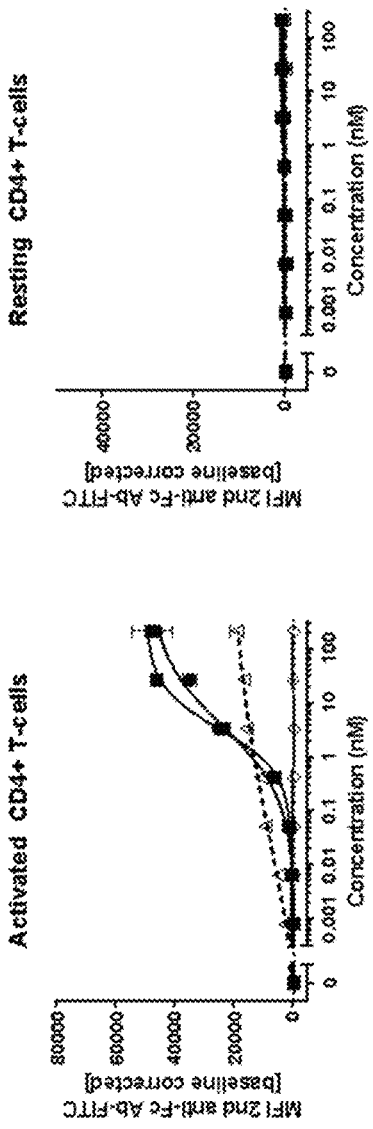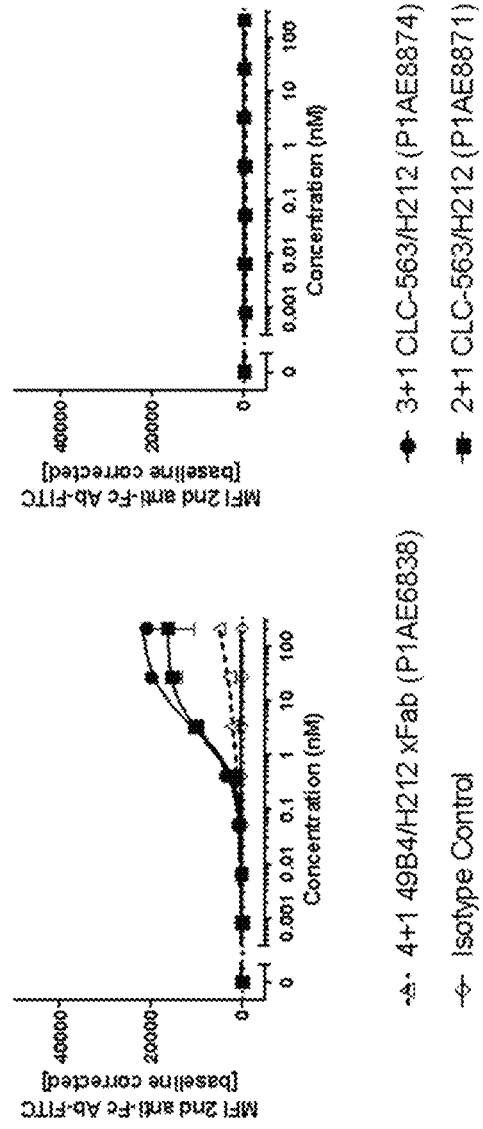

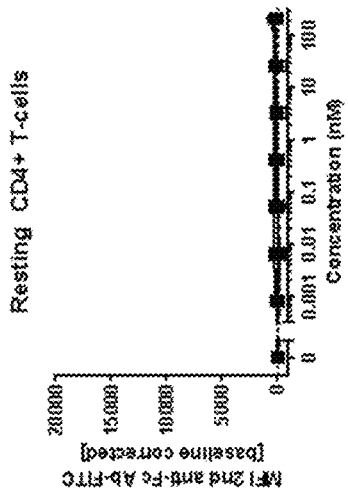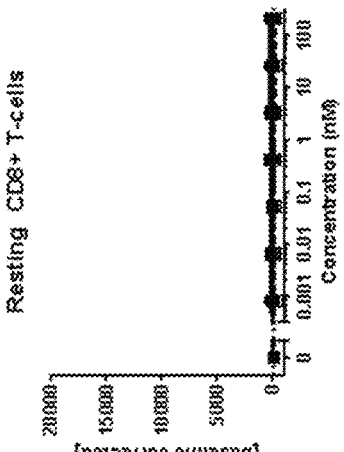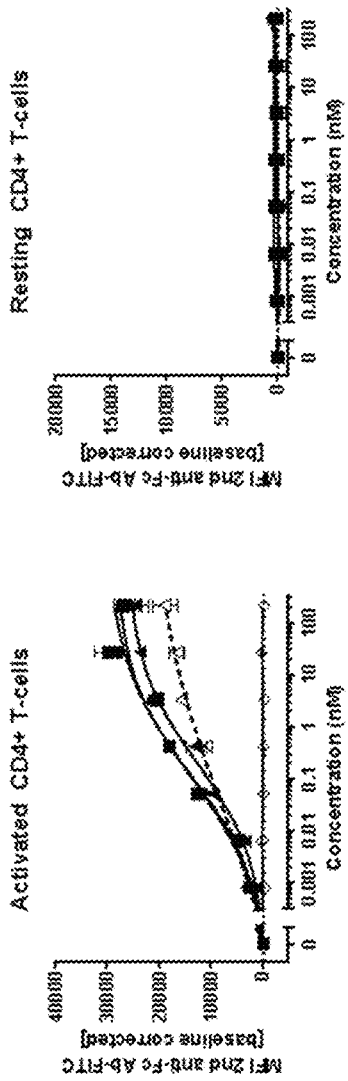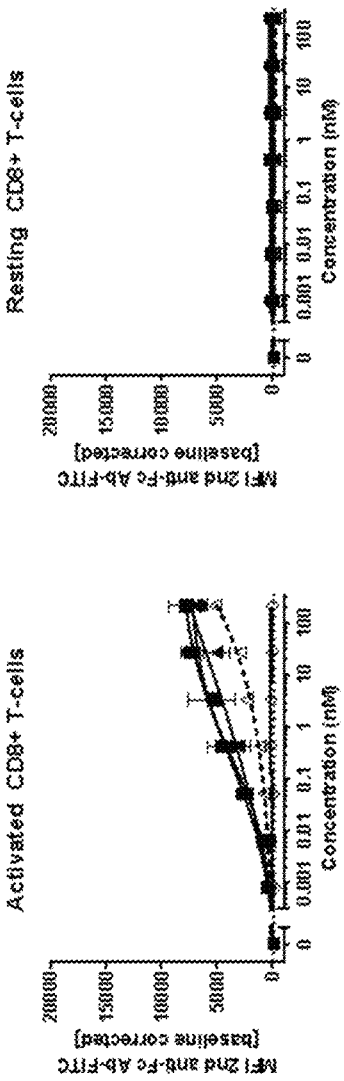

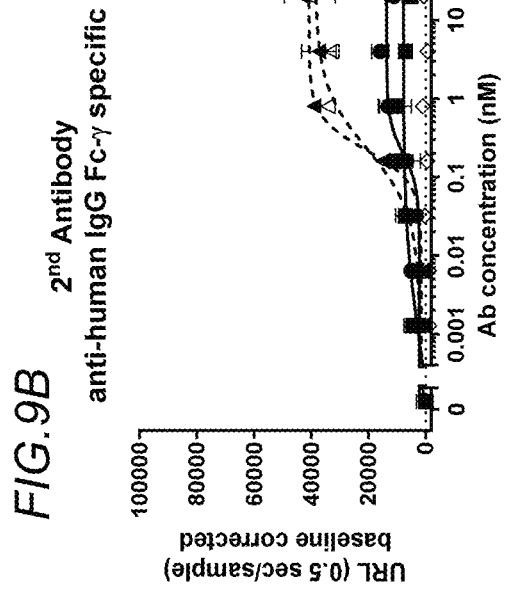
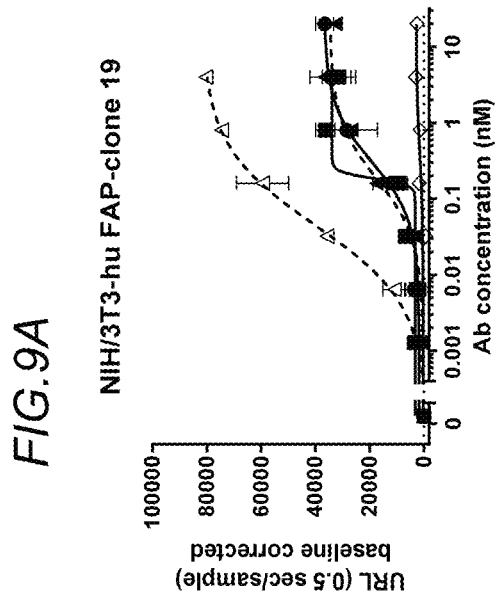
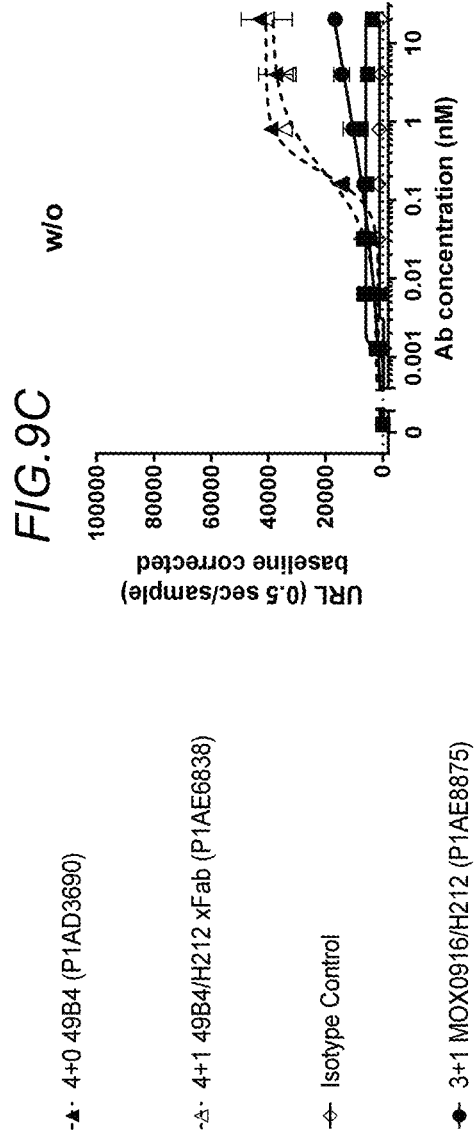

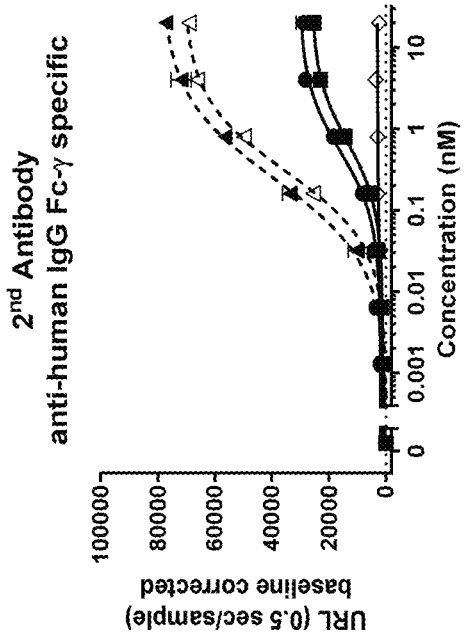
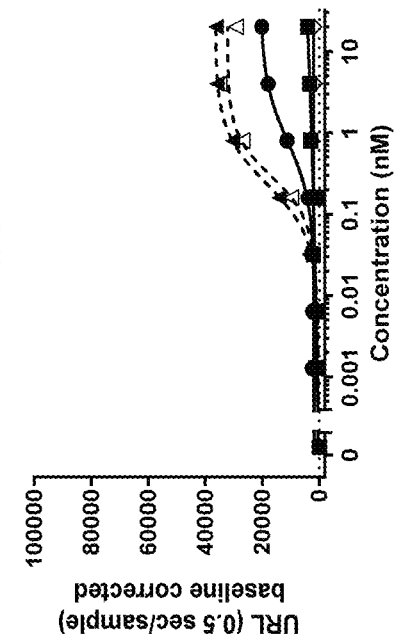
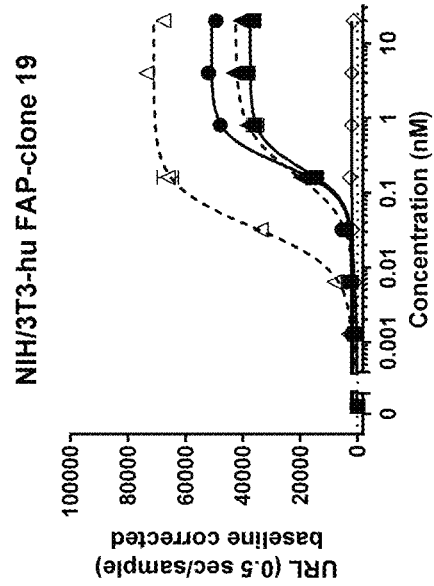

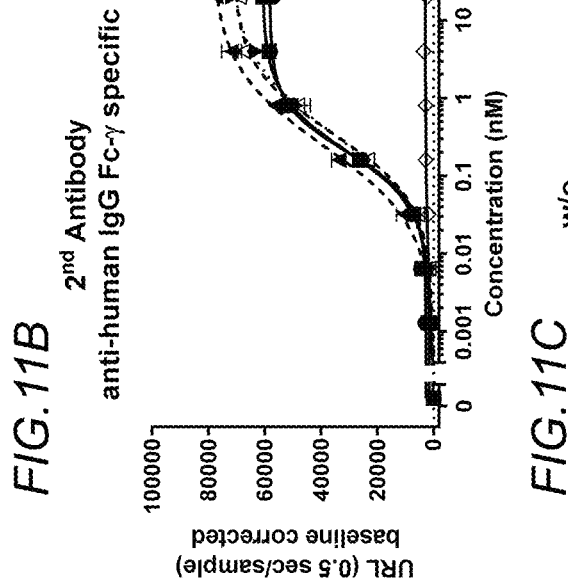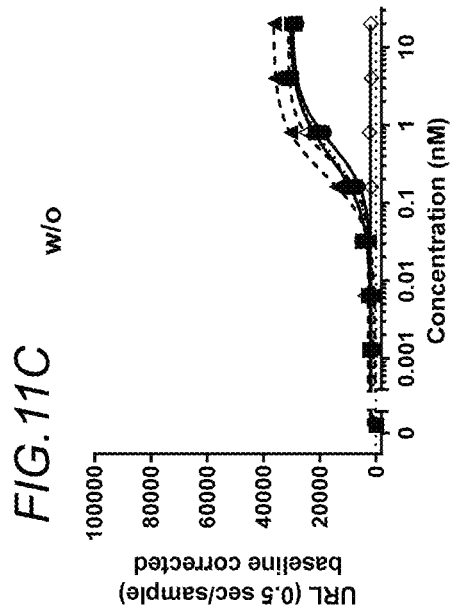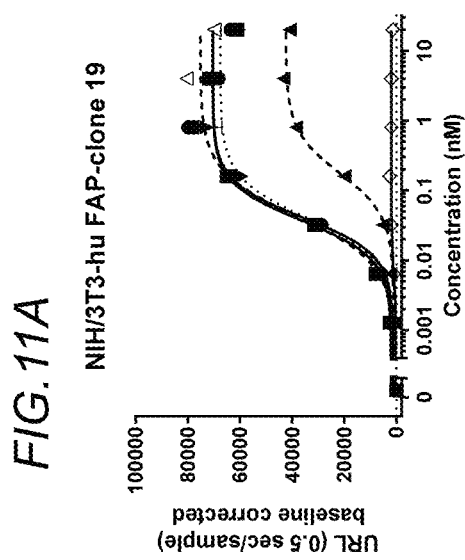

4B9 FAP clone

1G1a (h212) FAP clone

49B4 OX40 clone

8H9 OX40 clone

CLC563 OX40 clone

MOXR0916 OX40 clone

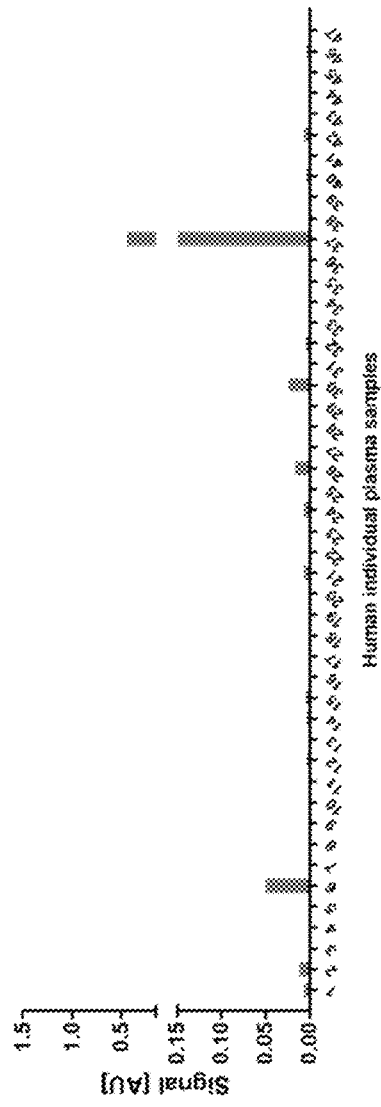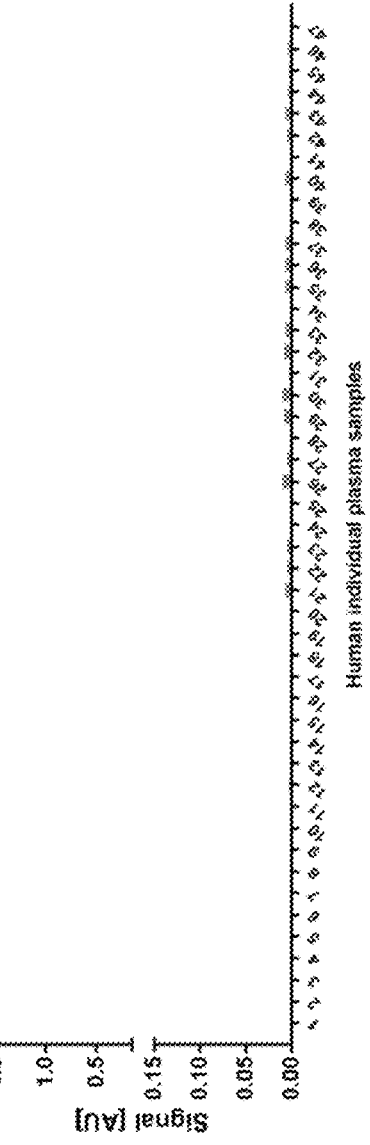
FIG.33A
FIG.33B

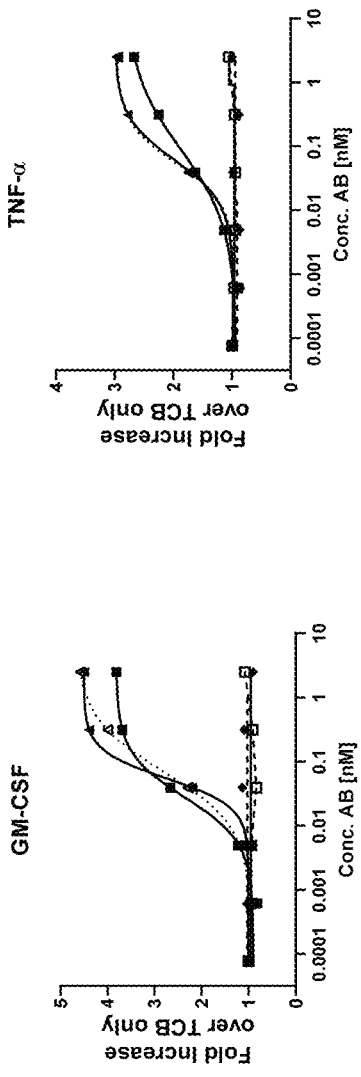
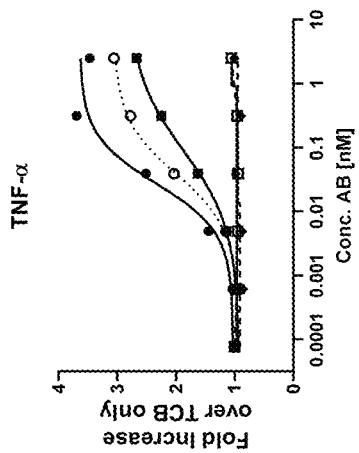
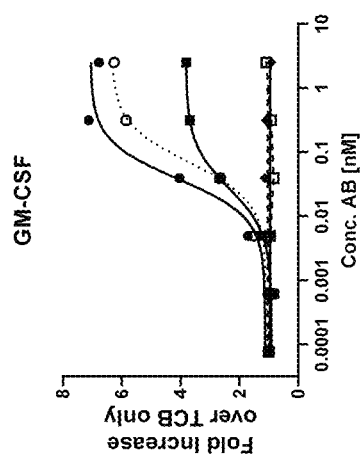
FIG. 37A  FIG. 37B  FIG. 37C  FIG. 37D

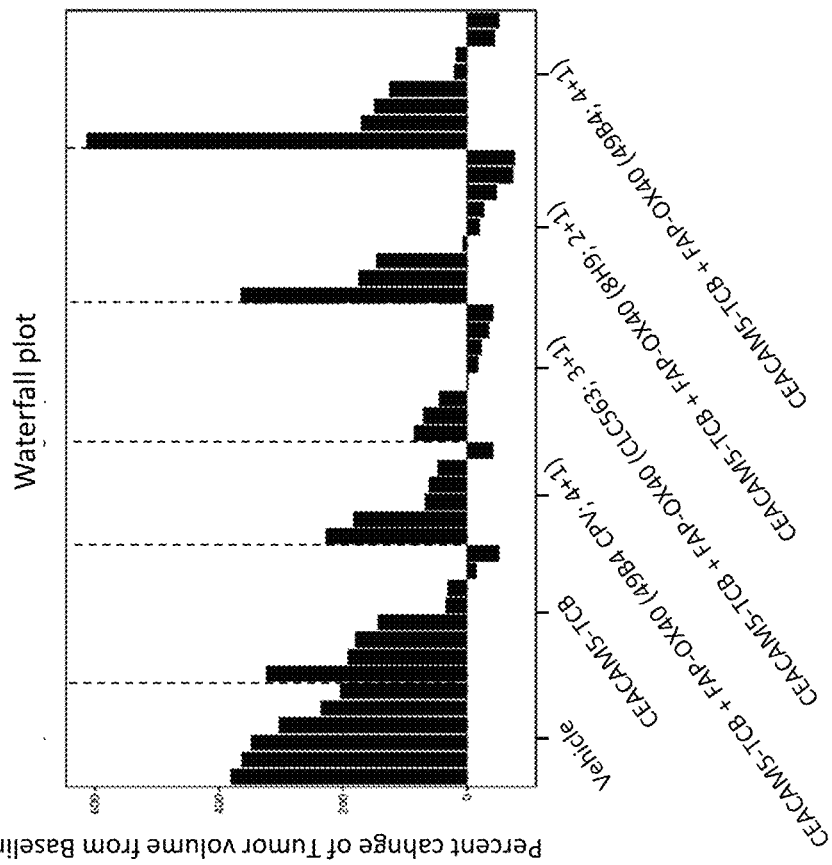
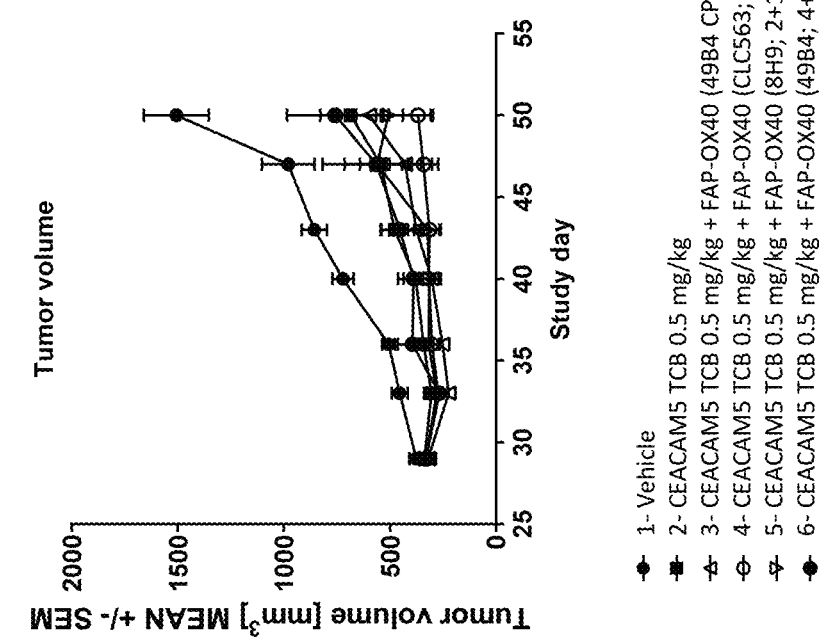
FIG.50A
FIG.50B

SEQUENCE LISTING

<160> NUMBER OF SEQ ID NOS: 166

<210> SEQ ID NO 1
<211> LENGTH: 249
<212> TYPE: PRT
<213> ORGANISM: Homo sapiens

<400> SEQUENCE: 1

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

```
Ser Ser Lys Pro Cys Lys Pro Cys Thr Trp Cys Asn Leu Arg Ser Gly
    50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala Val Ala Ala Ile Leu Gly
            180                 185                 190

Leu Gly Leu Val Leu Gly Leu Leu Gly Pro Leu Ala Ile Leu Leu Ala
        195                 200                 205

Leu Tyr Leu Leu Arg Arg Asp Gln Arg Leu Pro Pro Asp Ala His Lys
210                 215                 220

Pro Pro Gly Gly Gly Ser Phe Arg Thr Pro Ile Gln Glu Glu Gln Ala
225                 230                 235                 240

Asp Ala His Ser Thr Leu Ala Lys Ile
                245

<210> SEQ ID NO 2
<211> LENGTH: 760
<212> TYPE: PRT
<213> ORGANISM: Homo sapiens

<400> SEQUENCE: 2

Met Lys Thr Trp Val Lys Ile Val Phe Gly Val Ala Thr Ser Ala Val
1               5                   10                  15

Leu Ala Leu Leu Val Met Cys Ile Val Leu Arg Pro Ser Arg Val His
                20                  25                  30

Asn Ser Glu Glu Asn Thr Met Arg Ala Leu Thr Leu Lys Asp Ile Leu
            35                  40                  45

Asn Gly Thr Phe Ser Tyr Lys Thr Phe Phe Pro Asn Trp Ile Ser Gly
        50                  55                  60

Gln Glu Tyr Leu His Gln Ser Ala Asp Asn Asn Ile Val Leu Tyr Asn
65                  70                  75                  80

Ile Glu Thr Gly Gln Ser Tyr Thr Ile Leu Ser Asn Arg Thr Met Lys
                85                  90                  95

Ser Val Asn Ala Ser Asn Tyr Gly Leu Ser Pro Asp Arg Gln Phe Val
            100                 105                 110

Tyr Leu Glu Ser Asp Tyr Ser Lys Leu Trp Arg Tyr Ser Tyr Thr Ala
        115                 120                 125

Thr Tyr Tyr Ile Tyr Asp Leu Ser Asn Gly Glu Phe Val Arg Gly Asn
130                 135                 140

Glu Leu Pro Arg Pro Ile Gln Tyr Leu Cys Trp Ser Pro Val Gly Ser
145                 150                 155                 160

Lys Leu Ala Tyr Val Tyr Gln Asn Asn Ile Tyr Leu Lys Gln Arg Pro
                165                 170                 175
```

```
Gly Asp Pro Pro Phe Gln Ile Thr Phe Asn Gly Arg Glu Asn Lys Ile
                180                 185                 190

Phe Asn Gly Ile Pro Asp Trp Val Tyr Glu Glu Met Leu Ala Thr
            195                 200                 205

Lys Tyr Ala Leu Trp Trp Ser Pro Asn Gly Lys Phe Leu Ala Tyr Ala
        210                 215                 220

Glu Phe Asn Asp Thr Asp Ile Pro Val Ile Ala Tyr Ser Tyr Tyr Gly
225                 230                 235                 240

Asp Glu Gln Tyr Pro Arg Thr Ile Asn Ile Pro Tyr Pro Lys Ala Gly
                245                 250                 255

Ala Lys Asn Pro Val Val Arg Ile Phe Ile Ile Asp Thr Thr Tyr Pro
            260                 265                 270

Ala Tyr Val Gly Pro Gln Glu Val Pro Val Pro Ala Met Ile Ala Ser
        275                 280                 285

Ser Asp Tyr Tyr Phe Ser Trp Leu Thr Trp Val Thr Asp Glu Arg Val
290                 295                 300

Cys Leu Gln Trp Leu Lys Arg Val Gln Asn Val Ser Val Leu Ser Ile
305                 310                 315                 320

Cys Asp Phe Arg Glu Asp Trp Gln Thr Trp Asp Cys Pro Lys Thr Gln
                325                 330                 335

Glu His Ile Glu Glu Ser Arg Thr Gly Trp Ala Gly Gly Phe Phe Val
            340                 345                 350

Ser Thr Pro Val Phe Ser Tyr Asp Ala Ile Ser Tyr Tyr Lys Ile Phe
        355                 360                 365

Ser Asp Lys Asp Gly Tyr Lys His Ile His Tyr Ile Lys Asp Thr Val
370                 375                 380

Glu Asn Ala Ile Gln Ile Thr Ser Gly Lys Trp Glu Ala Ile Asn Ile
385                 390                 395                 400

Phe Arg Val Thr Gln Asp Ser Leu Phe Tyr Ser Ser Asn Glu Phe Glu
                405                 410                 415

Glu Tyr Pro Gly Arg Arg Asn Ile Tyr Arg Ile Ser Ile Gly Ser Tyr
            420                 425                 430

Pro Pro Ser Lys Lys Cys Val Thr Cys His Leu Arg Lys Glu Arg Cys
        435                 440                 445

Gln Tyr Tyr Thr Ala Ser Phe Ser Asp Tyr Ala Lys Tyr Tyr Ala Leu
        450                 455                 460

Val Cys Tyr Gly Pro Gly Ile Pro Ile Ser Thr Leu His Asp Gly Arg
465                 470                 475                 480

Thr Asp Gln Glu Ile Lys Ile Leu Glu Glu Asn Lys Glu Leu Glu Asn
                485                 490                 495

Ala Leu Lys Asn Ile Gln Leu Pro Lys Glu Ile Lys Lys Leu Glu
            500                 505                 510

Val Asp Glu Ile Thr Leu Trp Tyr Lys Met Ile Leu Pro Pro Gln Phe
        515                 520                 525

Asp Arg Ser Lys Lys Tyr Pro Leu Leu Ile Gln Val Tyr Gly Gly Pro
        530                 535                 540

Cys Ser Gln Ser Val Arg Ser Val Phe Ala Val Asn Trp Ile Ser Tyr
545                 550                 555                 560

Leu Ala Ser Lys Glu Gly Met Val Ile Ala Leu Val Asp Gly Arg Gly
                565                 570                 575

Thr Ala Phe Gln Gly Asp Lys Leu Leu Tyr Ala Val Tyr Arg Lys Leu
            580                 585                 590
```

-continued

```
Gly Val Tyr Glu Val Glu Asp Gln Ile Thr Ala Val Arg Lys Phe Ile
            595                 600                 605

Glu Met Gly Phe Ile Asp Glu Lys Arg Ile Ala Ile Trp Gly Trp Ser
        610                 615                 620

Tyr Gly Gly Tyr Val Ser Ser Leu Ala Leu Ala Ser Gly Thr Gly Leu
625                 630                 635                 640

Phe Lys Cys Gly Ile Ala Val Ala Pro Val Ser Ser Trp Glu Tyr Tyr
                645                 650                 655

Ala Ser Val Tyr Thr Glu Arg Phe Met Gly Leu Pro Thr Lys Asp Asp
            660                 665                 670

Asn Leu Glu His Tyr Lys Asn Ser Thr Val Met Ala Arg Ala Glu Tyr
        675                 680                 685

Phe Arg Asn Val Asp Tyr Leu Leu Ile His Gly Thr Ala Asp Asp Asn
    690                 695                 700

Val His Phe Gln Asn Ser Ala Gln Ile Ala Lys Ala Leu Val Asn Ala
705                 710                 715                 720

Gln Val Asp Phe Gln Ala Met Trp Tyr Ser Asp Gln Asn His Gly Leu
                725                 730                 735

Ser Gly Leu Ser Thr Asn His Leu Tyr Thr His Met Thr His Phe Leu
            740                 745                 750

Lys Gln Cys Phe Ser Leu Ser Asp
        755                 760

<210> SEQ ID NO 3
<211> LENGTH: 5
<212> TYPE: PRT
<213> ORGANISM: Artificial Sequence
<220> FEATURE:
<223> OTHER INFORMATION: FAP (212) CDR-H1

<400> SEQUENCE: 3

Asp Tyr Asn Met Asp
1               5

<210> SEQ ID NO 4
<211> LENGTH: 17
<212> TYPE: PRT
<213> ORGANISM: Artificial Sequence
<220> FEATURE:
<223> OTHER INFORMATION: FAP (212) CDR-H2

<400> SEQUENCE: 4

Asp Ile Tyr Pro Asn Thr Gly Gly Thr Ile Tyr Asn Gln Lys Phe Lys
1               5                   10                  15

Gly

<210> SEQ ID NO 5
<211> LENGTH: 10
<212> TYPE: PRT
<213> ORGANISM: Artificial Sequence
<220> FEATURE:
<223> OTHER INFORMATION: FAP (212) CDR-H3

<400> SEQUENCE: 5

Phe Arg Gly Ile His Tyr Ala Met Asp Tyr
1               5                   10

<210> SEQ ID NO 6
<211> LENGTH: 15
<212> TYPE: PRT
<213> ORGANISM: Artificial Sequence
```

```
<220> FEATURE:
<223> OTHER INFORMATION: FAP (212) CDR-L1

<400> SEQUENCE: 6

Arg Ala Ser Glu Ser Val Asp Asn Tyr Gly Leu Ser Phe Ile Asn
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: FAP (212) CDR-L2

<400> SEQUENCE: 7

Gly Thr Ser Asn Arg Gly Ser
1               5

<210> SEQ ID NO 8
<211> LENGTH: 9
<212> TYPE: PRT
<213> ORGANISM: Artificial Sequence
<220> FEATURE:
<223> OTHER INFORMATION: FAP (212) CDR-L3

<400> SEQUENCE: 8

Gln Gln Ser Asn Glu Val Pro Tyr Thr
1               5

<210> SEQ ID NO 9
<211> LENGTH: 119
<212> TYPE: PRT
<213> ORGANISM: Artificial Sequence
<220> FEATURE:
<223> OTHER INFORMATION: FAP (212) VH

<400> SEQUENCE: 9

Glu Val Leu Leu Gln Gln Ser Gly Pro Glu Leu Val Lys Pro Gly Ala
1               5                   10                  15

Ser Val Lys Ile Ala Cys Lys Ala Ser Gly Tyr Thr Leu Thr Asp Tyr
            20                  25                  30

Asn Met Asp Trp Val Arg Gln Ser His Gly Lys Ser Leu Glu Trp Ile
        35                  40                  45

Gly Asp Ile Tyr Pro Asn Thr Gly Gly Thr Ile Tyr Asn Gln Lys Phe
    50                  55                  60

Lys Gly Lys Ala Thr Leu Thr Ile Asp Lys Ser Ser Ser Thr Ala Tyr
65                  70                  75                  80

Met Asp Leu Arg Ser Leu Thr Ser Glu Asp Thr Ala Val Tyr Tyr Cys
                85                  90                  95

Thr Arg Phe Arg Gly Ile His Tyr Ala Met Asp Tyr Trp Gly Gln Gly
            100                 105                 110

Thr Ser Val Thr Val Ser Ser
        115

<210> SEQ ID NO 10
<211> LENGTH: 111
<212> TYPE: PRT
<213> ORGANISM: Artificial Sequence
<220> FEATURE:
<223> OTHER INFORMATION: FAP (212) VL
```

```
<400> SEQUENCE: 10

Asp Ile Val Leu Thr Gln Ser Pro Val Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Leu Ser Phe Ile Asn Trp Phe Gln Gln Lys Pro Gly Gln Pro Pro
        35                  40                  45

Lys Leu Leu Ile Tyr Gly Thr Ser Asn Arg Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Asn
                85                  90                  95

Glu Val Pro Tyr Thr Phe Gly Gly Gly Thr Asn Leu Glu Ile Lys
            100                 105                 110

<210> SEQ ID NO 11
<211> LENGTH: 17
<212> TYPE: PRT
<213> ORGANISM: Artificial Sequence
<220> FEATURE:
<223> OTHER INFORMATION: FAP (VH1G3a) CDR-H2

<400> SEQUENCE: 11

Asp Ile Tyr Pro Asn Thr Gly Gly Thr Ile Tyr Ala Gln Lys Phe Gln
1               5                   10                  15

Gly

<210> SEQ ID NO 12
<211> LENGTH: 17
<212> TYPE: PRT
<213> ORGANISM: Artificial Sequence
<220> FEATURE:
<223> OTHER INFORMATION: FAP (VH2G3a) CDR-H2

<400> SEQUENCE: 12

Asp Ile Tyr Pro Asn Thr Gly Gly Thr Ile Tyr Ala Asp Ser Val Lys
1               5                   10                  15

Gly

<210> SEQ ID NO 13
<211> LENGTH: 15
<212> TYPE: PRT
<213> ORGANISM: Artificial Sequence
<220> FEATURE:
<223> OTHER INFORMATION: FAP (VL1G3a) CDR-L1

<400> SEQUENCE: 13

Arg Ala Ser Glu Ser Val Asp Asn Tyr Gly Leu Ser Phe Leu Ala
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: FAP (VL2G3a) CDR-L1

<400> SEQUENCE: 14

Arg Ala Ser Glu Ser Ile Asp Asn Tyr Gly Leu Ser Phe Leu Asn
1               5                   10                  15
```

<210> SEQ ID NO 15
<211> LENGTH: 119
<212> TYPE: PRT
<213> ORGANISM: Artificial Sequence
<220> FEATURE:
<223> OTHER INFORMATION: FAP (VH1G1a)

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Asp Tyr
            20                  25                  30

Asn Met Asp Trp Val Arg Gln Ala Pro Gly Gln Gly Leu Glu Trp Ile
        35                  40                  45

Gly Asp Ile Tyr Pro Asn Thr Gly Gly Thr Ile Tyr Asn Gln Lys Phe
    50                  55                  60

Lys Gly Arg Val Thr Met Thr Ile Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Thr Arg Phe Arg Gly Ile His Tyr Ala Met Asp Tyr Trp Gly Gln Gly
            100                 105                 110

Thr Thr Val Thr Val Ser Ser
        115

<210> SEQ ID NO 16
<211> LENGTH: 119
<212> TYPE: PRT
<213> ORGANISM: Artificial Sequence
<220> FEATURE:
<223> OTHER INFORMATION: FAP (VH1G2a)

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Asp Tyr
            20                  25                  30

Asn Met Asp Trp Val Arg Gln Ala Pro Gly Lys Ser Leu Glu Trp Ile
        35                  40                  45

Gly Asp Ile Tyr Pro Asn Thr Gly Gly Thr Ile Tyr Asn Gln Lys Phe
    50                  55                  60

Lys Gly Arg Val Thr Met Thr Ile Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Phe Arg Gly Ile His Tyr Ala Met Asp Tyr Trp Gly Gln Gly
            100                 105                 110

Thr Thr Val Thr Val Ser Ser
        115

<210> SEQ ID NO 17
<211> LENGTH: 119
<212> TYPE: PRT
<213> ORGANISM: Artificial Sequence
<220> FEATURE:
<223> OTHER INFORMATION: FAP (VH1G3a)

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Asp Tyr
            20                  25                  30

Asn Met Asp Trp Val Arg Gln Ala Pro Gly Gln Gly Leu Glu Trp Ile
        35                  40                  45

Gly Asp Ile Tyr Pro Asn Thr Gly Gly Thr Ile Tyr Ala Gln Lys Phe
    50                  55                  60

Gln Gly Arg Val Thr Met Thr Ile Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Phe Arg Gly Ile His Tyr Ala Met Asp Tyr Trp Gly Gln Gly
            100                 105                 110

Thr Thr Val Thr Val Ser Ser
            115

<210> SEQ ID NO 18
<211> LENGTH: 119
<212> TYPE: PRT
<213> ORGANISM: Artificial Sequence
<220> FEATURE:
<223> OTHER INFORMATION: FAP (VH2G1a)

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Thr Leu Thr Asp Tyr
            20                  25                  30

Asn Met Asp Trp Val Arg Gln Ala Pro Gly Lys Gly Leu Glu Trp Val
        35                  40                  45

Gly Asp Ile Tyr Pro Asn Thr Gly Gly Thr Ile Tyr Asn Gln Lys Phe
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Phe Arg Gly Ile His Tyr Ala Met Asp Tyr Trp Gly Gln Gly
            100                 105                 110

Thr Thr Val Thr Val Ser Ser
            115

<210> SEQ ID NO 19
<211> LENGTH: 119
<212> TYPE: PRT
<213> ORGANISM: Artificial Sequence
<220> FEATURE:
<223> OTHER INFORMATION: FAP (VH2G2a)

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Thr Leu Thr Asp Tyr
            20                  25                  30

Asn Met Asp Trp Val Arg Gln Ala Pro Gly Lys Gly Leu Glu Trp Val
        35                  40                  45

Gly Asp Ile Tyr Pro Asn Thr Gly Gly Thr Ile Tyr Asn Gln Lys Phe
      50                  55                  60

Lys Gly Arg Phe Thr Ile Ser Ile Asp Lys Ser Lys Asn Thr Ala Tyr
 65                  70                  75                  80

Leu Gln Met Asn Ser Leu Arg Ala Glu Asp Thr Ala Val Tyr Tyr Cys
                  85                  90                  95

Thr Arg Phe Arg Gly Ile His Tyr Ala Met Asp Tyr Trp Gly Gln Gly
                100                 105                 110

Thr Thr Val Thr Val Ser Ser
            115

<210> SEQ ID NO 20
<211> LENGTH: 119
<212> TYPE: PRT
<213> ORGANISM: Artificial Sequence
<220> FEATURE:
<223> OTHER INFORMATION: FAP (VH2G3a)

<400> SEQUENCE: 20

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Tyr Thr Leu Thr Asp Tyr
                 20                  25                  30

Asn Met Asp Trp Val Arg Gln Ala Pro Gly Lys Gly Leu Glu Trp Val
             35                  40                  45

Gly Asp Ile Tyr Pro Asn Thr Gly Gly Thr Ile Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                  85                  90                  95

Thr Arg Phe Arg Gly Ile His Tyr Ala Met Asp Tyr Trp Gly Gln Gly
                100                 105                 110

Thr Thr Val Thr Val Ser Ser
            115

<210> SEQ ID NO 21
<211> LENGTH: 111
<212> TYPE: PRT
<213> ORGANISM: Artificial Sequence
<220> FEATURE:
<223> OTHER INFORMATION: FAP (VL1G1a)

<400> SEQUENCE: 21

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Glu Ser Val Asp Asn Tyr
                 20                  25                  30

Gly Leu Ser Phe Ile Asn Trp Phe Gln Gln Lys Pro Gly Gln Ala Pro
             35                  40                  45

Arg Leu Leu Ile Tyr Gly Thr Ser Asn Arg Gly Ser Gly Ile Pro Ala
     50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Phe Cys Gln Gln Ser Asn
                  85                  90                  95

Glu Val Pro Tyr Thr Phe Gly Gly Gly Thr Lys Val Glu Ile Lys
                100                 105                 110

<210> SEQ ID NO 22
<211> LENGTH: 111
<212> TYPE: PRT
<213> ORGANISM: Artificial Sequence
<220> FEATURE:
<223> OTHER INFORMATION: FAP (VL1G2a)

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Leu Ser Phe Ile Asn Trp Phe Gln Gln Lys Pro Gly Gln Pro Pro
        35                  40                  45

Arg Leu Leu Ile Tyr Gly Thr Ser Asn Arg Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Asn
                85                  90                  95

Glu Val Pro Tyr Thr Phe Gly Gly Gly Thr Lys Val Glu Ile Lys
            100                 105                 110

<210> SEQ ID NO 23
<211> LENGTH: 111
<212> TYPE: PRT
<213> ORGANISM: Artificial Sequence
<220> FEATURE:
<223> OTHER INFORMATION: FAP (VL1G3a)

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Leu Ser Phe Leu Ala Trp Phe Gln Gln Lys Pro Gly Gln Ala Pro
        35                  40                  45

Arg Leu Leu Ile Tyr Gly Thr Ser Asn Arg Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Asn
                85                  90                  95

Glu Val Pro Tyr Thr Phe Gly Gly Gly Thr Lys Val Glu Ile Lys
            100                 105                 110

<210> SEQ ID NO 24
<211> LENGTH: 111
<212> TYPE: PRT
<213> ORGANISM: Artificial Sequence
<220> FEATURE:
<223> OTHER INFORMATION: FAP (VL2G1a)

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

```
Gly Leu Ser Phe Ile Asn Trp Phe Gln Gln Lys Pro Gly Lys Ala Pro
            35                  40                  45

Lys Leu Leu Ile Tyr Gly Thr Ser Asn Arg Gly Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Phe Cys Gln Gln Ser Asn
                 85                  90                  95

Glu Val Pro Tyr Thr Phe Gly Gly Gly Thr Lys Val Glu Ile Lys
                100                 105                 110

<210> SEQ ID NO 25
<211> LENGTH: 111
<212> TYPE: PRT
<213> ORGANISM: Artificial Sequence
<220> FEATURE:
<223> OTHER INFORMATION: FAP (VL2G2a)

<400> SEQUENCE: 25

Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Ser Val Asp Asn Tyr
                20                  25                  30

Gly Leu Ser Phe Ile Asn Trp Phe Gln Gln Lys Pro Gly Gln Pro Pro
            35                  40                  45

Lys Leu Leu Ile Tyr Gly Thr Ser Asn Arg Gly Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Met Tyr Phe Cys Gln Gln Ser Asn
                 85                  90                  95

Glu Val Pro Tyr Thr Phe Gly Gly Gly Thr Lys Val Glu Ile Lys
                100                 105                 110

<210> SEQ ID NO 26
<211> LENGTH: 111
<212> TYPE: PRT
<213> ORGANISM: Artificial Sequence
<220> FEATURE:
<223> OTHER INFORMATION: FAP (VL2G3a)

<400> SEQUENCE: 26

Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Ser Ile Asp Asn Tyr
                20                  25                  30

Gly Leu Ser Phe Leu Asn Trp Phe Gln Gln Lys Pro Gly Lys Ala Pro
            35                  40                  45

Lys Leu Leu Ile Tyr Gly Thr Ser Asn Arg Gly Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Phe Cys Gln Gln Ser Asn
                 85                  90                  95

Glu Val Pro Tyr Thr Phe Gly Gly Gly Thr Lys Val Glu Ile Lys
                100                 105                 110

<210> SEQ ID NO 27
```

```
<211> LENGTH: 5
<212> TYPE: PRT
<213> ORGANISM: Artificial sequence
<220> FEATURE:
<223> OTHER INFORMATION: anti-OX40 (49B4) CDR-H1

<400> SEQUENCE: 27

Ser Tyr Ala Ile Ser
1               5

<210> SEQ ID NO 28
<211> LENGTH: 17
<212> TYPE: PRT
<213> ORGANISM: Artificial sequence
<220> FEATURE:
<223> OTHER INFORMATION: anti-OX40 (49B4) CDR-H2

<400> SEQUENCE: 28

Gly Ile Ile Pro Ile Phe Gly Thr Ala Asn Tyr Ala Gln Lys Phe Gln
1               5                   10                  15

Gly

<210> SEQ ID NO 29
<211> LENGTH: 9
<212> TYPE: PRT
<213> ORGANISM: Artificial sequence
<220> FEATURE:
<223> OTHER INFORMATION: anti-OX40 (49B4) CDR-H3

<400> SEQUENCE: 29

Glu Tyr Tyr Arg Gly Pro Tyr Asp Tyr
1               5

<210> SEQ ID NO 30
<211> LENGTH: 11
<212> TYPE: PRT
<213> ORGANISM: Artificial sequence
<220> FEATURE:
<223> OTHER INFORMATION: anti-OX40 (49B4) CDR-L1

<400> SEQUENCE: 30

Arg Ala Ser Gln Ser Ile Ser Ser Trp Leu Ala
1               5                   10

<210> SEQ ID NO 31
<211> LENGTH: 7
<212> TYPE: PRT
<213> ORGANISM: Artificial sequence
<220> FEATURE:
<223> OTHER INFORMATION: anti-OX40 (49B4) CDR-L2

<400> SEQUENCE: 31

Asp Ala Ser Ser Leu Glu Ser
1               5

<210> SEQ ID NO 32
<211> LENGTH: 9
<212> TYPE: PRT
<213> ORGANISM: Artificial sequence
<220> FEATURE:
<223> OTHER INFORMATION: anti-OX40 (49B4) CDR-L3

<400> SEQUENCE: 32

Gln Gln Tyr Ser Ser Gln Pro Tyr Thr
1               5
```

```
<210> SEQ ID NO 33
<211> LENGTH: 118
<212> TYPE: PRT
<213> ORGANISM: Artificial sequence
<220> FEATURE:
<223> OTHER INFORMATION: OX40 (49B4) VH

<400> SEQUENCE: 33

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser
        115

<210> SEQ ID NO 34
<211> LENGTH: 107
<212> TYPE: PRT
<213> ORGANISM: Artificial sequence
<220> FEATURE:
<223> OTHER INFORMATION: OX40 (49B4) VL

<400> SEQUENCE: 34

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Gln Pro Tyr
                85                  90                  95

Thr Phe Gly Gln Gly Thr Lys Val Glu Ile Lys
            100                 105

<210> SEQ ID NO 35
<211> LENGTH: 5
<212> TYPE: PRT
<213> ORGANISM: Artificial sequence
<220> FEATURE:
<223> OTHER INFORMATION: anti-OX40 (CLC563) CDR-H1

<400> SEQUENCE: 35

Ser Tyr Ala Met Ser
1               5

<210> SEQ ID NO 36
```

```
<211> LENGTH: 17
<212> TYPE: PRT
<213> ORGANISM: Artificial sequence
<220> FEATURE:
<223> OTHER INFORMATION: anti-OX40 (CLC563) CDR-H2

<400> SEQUENCE: 36

Ala Ile Ser Gly Ser Gly Gly Ser Thr Tyr Tyr Ala Asp Ser Val Lys
1               5                   10                  15
Gly

<210> SEQ ID NO 37
<211> LENGTH: 7
<212> TYPE: PRT
<213> ORGANISM: Artificial sequence
<220> FEATURE:
<223> OTHER INFORMATION: anti-OX40 (CLC563) CDR-H3

<400> SEQUENCE: 37

Asp Val Gly Ala Phe Asp Tyr
1               5

<210> SEQ ID NO 38
<211> LENGTH: 12
<212> TYPE: PRT
<213> ORGANISM: Artificial sequence
<220> FEATURE:
<223> OTHER INFORMATION: anti-OX40 (CLC563) CDR-L1

<400> SEQUENCE: 38

Arg Ala Ser Gln Ser Val Ser Ser Ser Tyr Leu Ala
1               5                   10

<210> SEQ ID NO 39
<211> LENGTH: 7
<212> TYPE: PRT
<213> ORGANISM: Artificial sequence
<220> FEATURE:
<223> OTHER INFORMATION: anti-OX40 (CLC563) CDR-L2

<400> SEQUENCE: 39

Gly Ala Ser Ser Arg Ala Thr
1               5

<210> SEQ ID NO 40
<211> LENGTH: 9
<212> TYPE: PRT
<213> ORGANISM: Artificial sequence
<220> FEATURE:
<223> OTHER INFORMATION: anti-OX40 (CLC563) CDR-L3

<400> SEQUENCE: 40

Gln Gln Tyr Gly Ser Ser Pro Leu Thr
1               5

<210> SEQ ID NO 41
<211> LENGTH: 116
<212> TYPE: PRT
<213> ORGANISM: Artificial sequence
<220> FEATURE:
<223> OTHER INFORMATION: OX40 (CLC-563) VH

<400> SEQUENCE: 41

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
            20                  25                  30
Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Asp Val Gly Ala Phe Asp Tyr Trp Gly Gln Gly Ala Leu Val
            100                 105                 110

Thr Val Ser Ser
        115

<210> SEQ ID NO 42
<211> LENGTH: 108
<212> TYPE: PRT
<213> ORGANISM: Artificial sequence
<220> FEATURE:
<223> OTHER INFORMATION: OX40 (CLC-563) VL

<400> SEQUENCE: 42

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys
            100                 105

<210> SEQ ID NO 43
<211> LENGTH: 5
<212> TYPE: PRT
<213> ORGANISM: Artificial Sequence
<220> FEATURE:
<223> OTHER INFORMATION: OX40 (MOXR0916)  CDR-H1

<400> SEQUENCE: 43

Asp Ser Tyr Met Ser
1               5

<210> SEQ ID NO 44
<211> LENGTH: 17
<212> TYPE: PRT
<213> ORGANISM: Artificial Sequence
<220> FEATURE:
<223> OTHER INFORMATION: OX40 (MOXR0916)  CDR-H2

<400> SEQUENCE: 44

Asp Met Tyr Pro Asp Asn Gly Asp Ser Ser Tyr Asn Gln Lys Phe Arg
1               5                   10                  15

Glu
```

<210> SEQ ID NO 45
<211> LENGTH: 8
<212> TYPE: PRT
<213> ORGANISM: Artificial Sequence
<220> FEATURE:
<223> OTHER INFORMATION: OX40 (MOXR0916) CDR-H3

<400> SEQUENCE: 45

Ala Pro Arg Trp Tyr Phe Ser Val
1               5

<210> SEQ ID NO 46
<211> LENGTH: 11
<212> TYPE: PRT
<213> ORGANISM: Artificial Sequence
<220> FEATURE:
<223> OTHER INFORMATION: OX40 (MOXR0916) CDR-L1

<400> SEQUENCE: 46

Arg Ala Ser Gln Asp Ile Ser Asn Tyr Leu Asn
1               5                   10

<210> SEQ ID NO 47
<211> LENGTH: 7
<212> TYPE: PRT
<213> ORGANISM: Artificial Sequence
<220> FEATURE:
<223> OTHER INFORMATION: OX40 (MOXR0916) CDR-L2

<400> SEQUENCE: 47

Tyr Thr Ser Arg Leu Arg Ser
1               5

<210> SEQ ID NO 48
<211> LENGTH: 9
<212> TYPE: PRT
<213> ORGANISM: Artificial Sequence
<220> FEATURE:
<223> OTHER INFORMATION: OX40 (MOXR0916) CDR-L3

<400> SEQUENCE: 48

Gln Gln Gly His Thr Leu Pro Pro Thr
1               5

<210> SEQ ID NO 49
<211> LENGTH: 117
<212> TYPE: PRT
<213> ORGANISM: Artificial Sequence
<220> FEATURE:
<223> OTHER INFORMATION: OX40 (MOXR0916) VH

<400> SEQUENCE: 49

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 50
<211> LENGTH: 107
<212> TYPE: PRT
<213> ORGANISM: Artificial Sequence
<220> FEATURE:
<223> OTHER INFORMATION: OX40 (MOXR0916) VL

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 51
<211> LENGTH: 5
<212> TYPE: PRT
<213> ORGANISM: Artificial Sequence
<220> FEATURE:
<223> OTHER INFORMATION: OX40 (8H9)  CDR-H1

<400> SEQUENCE: 51

Ser Tyr Ala Ile Ser
1               5

<210> SEQ ID NO 52
<211> LENGTH: 17
<212> TYPE: PRT
<213> ORGANISM: Artificial Sequence
<220> FEATURE:
<223> OTHER INFORMATION: OX40 (8H9)  CDR-H2

<400> SEQUENCE: 52

Gly Ile Ile Pro Ile Phe Gly Thr Ala Asn Tyr Ala Gln Lys Phe Gln
1               5                   10                  15

Gly

<210> SEQ ID NO 53
<211> LENGTH: 7
<212> TYPE: PRT
<213> ORGANISM: Artificial sequence
<220> FEATURE:
<223> OTHER INFORMATION: anti-OX40 CDR-H3

<400> SEQUENCE: 53

Glu Tyr Gly Trp Met Asp Tyr
1               5

-continued

<210> SEQ ID NO 54
<211> LENGTH: 11
<212> TYPE: PRT
<213> ORGANISM: Artificial Sequence
<220> FEATURE:
<223> OTHER INFORMATION: OX40 (8H9) CDR-L1

<400> SEQUENCE: 54

Arg Ala Ser Gln Ser Ile Ser Ser Trp Leu Ala
1               5                   10

<210> SEQ ID NO 55
<211> LENGTH: 7
<212> TYPE: PRT
<213> ORGANISM: Artificial Sequence
<220> FEATURE:
<223> OTHER INFORMATION: OX40 (8H9) CDR-L2

<400> SEQUENCE: 55

Asp Ala Ser Ser Leu Glu Ser
1               5

<210> SEQ ID NO 56
<211> LENGTH: 10
<212> TYPE: PRT
<213> ORGANISM: Artificial sequence
<220> FEATURE:
<223> OTHER INFORMATION: anti-OX40 CDR-L3

<400> SEQUENCE: 56

Gln Gln Tyr Leu Thr Tyr Ser Arg Phe Thr
1               5                   10

<210> SEQ ID NO 57
<211> LENGTH: 116
<212> TYPE: PRT
<213> ORGANISM: Artificial sequence
<220> FEATURE:
<223> OTHER INFORMATION: 8H9 VH

<400> SEQUENCE: 57

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Gly Trp Met Asp Tyr Trp Gly Gln Gly Thr Thr Val
            100                 105                 110

Thr Val Ser Ser
        115

<210> SEQ ID NO 58
<211> LENGTH: 108
<212> TYPE: PRT
<213> ORGANISM: Artificial sequence
<220> FEATURE:

-continued

<223> OTHER INFORMATION: 8H9 VL

<400> SEQUENCE: 58

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Leu Thr Tyr Ser Arg
                85                  90                  95

Phe Thr Phe Gly Gln Gly Thr Lys Val Glu Ile Lys
            100                 105

<210> SEQ ID NO 59
<211> LENGTH: 118
<212> TYPE: PRT
<213> ORGANISM: Artificial Sequence
<220> FEATURE:
<223> OTHER INFORMATION: OX40 (49B4_K73E) VH

<400> SEQUENCE: 59

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser
        115

<210> SEQ ID NO 60
<211> LENGTH: 118
<212> TYPE: PRT
<213> ORGANISM: Artificial Sequence
<220> FEATURE:
<223> OTHER INFORMATION: OX40 (49B4_K23T_K73E) VH

<400> SEQUENCE: 60

Gln Val Gln Leu Val Gln Ser Gly Ala Glu Val Lys Lys Pro Gly Ser
1               5                   10                  15

Ser Val Lys Val Ser Cys Thr Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe

```
            50                  55                  60
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Tyr Tyr Arg Gly Pro Tyr Asp Tyr Trp Gly Gln Gly Thr
                100                 105                 110

Thr Val Thr Val Ser Ser
            115

<210> SEQ ID NO 61
<211> LENGTH: 118
<212> TYPE: PRT
<213> ORGANISM: Artificial Sequence
<220> FEATURE:
<223> OTHER INFORMATION: OX40 (49B4_K23E_K73E) VH

<400> SEQUENCE: 61

Gln Val Gln Leu Val Gln Ser Gly Ala Glu Val Lys Lys Pro Gly Ser
 1               5                  10                  15

Ser Val Lys Val Ser Cys Glu Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Tyr Tyr Arg Gly Pro Tyr Asp Tyr Trp Gly Gln Gly Thr
                100                 105                 110

Thr Val Thr Val Ser Ser
            115

<210> SEQ ID NO 62
<211> LENGTH: 748
<212> TYPE: PRT
<213> ORGANISM: Artificial Sequence
<220> FEATURE:
<223> OTHER INFORMATION: hu FAP ectodomain+poly-lys-tag+his6-tag

<400> SEQUENCE: 62

Arg Pro Ser Arg Val His Asn Ser Glu Glu Asn Thr Met Arg Ala Leu
 1               5                  10                  15

Thr Leu Lys Asp Ile Leu Asn Gly Thr Phe Ser Tyr Lys Thr Phe Phe
                20                  25                  30

Pro Asn Trp Ile Ser Gly Gln Glu Tyr Leu His Gln Ser Ala Asp Asn
            35                  40                  45

Asn Ile Val Leu Tyr Asn Ile Glu Thr Gly Gln Ser Tyr Thr Ile Leu
        50                  55                  60

Ser Asn Arg Thr Met Lys Ser Val Asn Ala Ser Asn Tyr Gly Leu Ser
 65                  70                  75                  80

Pro Asp Arg Gln Phe Val Tyr Leu Glu Ser Asp Tyr Ser Lys Leu Trp
                 85                  90                  95

Arg Tyr Ser Tyr Thr Ala Thr Tyr Tyr Ile Tyr Asp Leu Ser Asn Gly
                100                 105                 110
```

```
Glu Phe Val Arg Gly Asn Glu Leu Pro Arg Pro Ile Gln Tyr Leu Cys
            115                 120                 125
Trp Ser Pro Val Gly Ser Lys Leu Ala Tyr Val Tyr Gln Asn Asn Ile
        130                 135                 140
Tyr Leu Lys Gln Arg Pro Gly Asp Pro Phe Gln Ile Thr Phe Asn
145                 150                 155                 160
Gly Arg Glu Asn Lys Ile Phe Asn Gly Ile Pro Asp Trp Val Tyr Glu
                165                 170                 175
Glu Glu Met Leu Ala Thr Lys Tyr Ala Leu Trp Trp Ser Pro Asn Gly
            180                 185                 190
Lys Phe Leu Ala Tyr Ala Glu Phe Asn Asp Thr Asp Ile Pro Val Ile
        195                 200                 205
Ala Tyr Ser Tyr Tyr Gly Asp Glu Gln Tyr Pro Arg Thr Ile Asn Ile
    210                 215                 220
Pro Tyr Pro Lys Ala Gly Ala Lys Asn Pro Val Val Arg Ile Phe Ile
225                 230                 235                 240
Ile Asp Thr Thr Tyr Pro Ala Tyr Val Gly Pro Gln Glu Val Pro Val
                245                 250                 255
Pro Ala Met Ile Ala Ser Ser Asp Tyr Tyr Phe Ser Trp Leu Thr Trp
            260                 265                 270
Val Thr Asp Glu Arg Val Cys Leu Gln Trp Leu Lys Arg Val Gln Asn
        275                 280                 285
Val Ser Val Leu Ser Ile Cys Asp Phe Arg Glu Asp Trp Gln Thr Trp
    290                 295                 300
Asp Cys Pro Lys Thr Gln Glu His Ile Glu Glu Ser Arg Thr Gly Trp
305                 310                 315                 320
Ala Gly Gly Phe Phe Val Ser Thr Pro Val Phe Ser Tyr Asp Ala Ile
                325                 330                 335
Ser Tyr Tyr Lys Ile Phe Ser Asp Lys Asp Gly Tyr Lys His Ile His
            340                 345                 350
Tyr Ile Lys Asp Thr Val Glu Asn Ala Ile Gln Ile Thr Ser Gly Lys
        355                 360                 365
Trp Glu Ala Ile Asn Ile Phe Arg Val Thr Gln Asp Ser Leu Phe Tyr
    370                 375                 380
Ser Ser Asn Glu Phe Glu Glu Tyr Pro Gly Arg Arg Asn Ile Tyr Arg
385                 390                 395                 400
Ile Ser Ile Gly Ser Tyr Pro Pro Ser Lys Lys Cys Val Thr Cys His
                405                 410                 415
Leu Arg Lys Glu Arg Cys Gln Tyr Tyr Thr Ala Ser Phe Ser Asp Tyr
            420                 425                 430
Ala Lys Tyr Tyr Ala Leu Val Cys Tyr Gly Pro Gly Ile Pro Ile Ser
        435                 440                 445
Thr Leu His Asp Gly Arg Thr Asp Gln Glu Ile Lys Ile Leu Glu Glu
    450                 455                 460
Asn Lys Glu Leu Glu Asn Ala Leu Lys Asn Ile Gln Leu Pro Lys Glu
465                 470                 475                 480
Glu Ile Lys Lys Leu Glu Val Asp Glu Ile Thr Leu Trp Tyr Lys Met
                485                 490                 495
Ile Leu Pro Pro Gln Phe Asp Arg Ser Lys Lys Tyr Pro Leu Leu Ile
            500                 505                 510
Gln Val Tyr Gly Gly Pro Cys Ser Gln Ser Val Arg Ser Val Phe Ala
        515                 520                 525
Val Asn Trp Ile Ser Tyr Leu Ala Ser Lys Glu Gly Met Val Ile Ala
```

```
                530             535             540
Leu Val Asp Gly Arg Gly Thr Ala Phe Gln Gly Asp Lys Leu Leu Tyr
545                 550                 555                 560

Ala Val Tyr Arg Lys Leu Gly Val Tyr Glu Val Glu Asp Gln Ile Thr
                565                 570                 575

Ala Val Arg Lys Phe Ile Glu Met Gly Phe Ile Asp Glu Lys Arg Ile
                580                 585                 590

Ala Ile Trp Gly Trp Ser Tyr Gly Gly Tyr Val Ser Ser Leu Ala Leu
                595                 600                 605

Ala Ser Gly Thr Gly Leu Phe Lys Cys Gly Ile Ala Val Ala Pro Val
                610                 615                 620

Ser Ser Trp Glu Tyr Tyr Ala Ser Val Tyr Thr Glu Arg Phe Met Gly
625                 630                 635                 640

Leu Pro Thr Lys Asp Asp Asn Leu Glu His Tyr Lys Asn Ser Thr Val
                645                 650                 655

Met Ala Arg Ala Glu Tyr Phe Arg Asn Val Asp Tyr Leu Leu Ile His
                660                 665                 670

Gly Thr Ala Asp Asp Asn Val His Phe Gln Asn Ser Ala Gln Ile Ala
                675                 680                 685

Lys Ala Leu Val Asn Ala Gln Val Asp Phe Gln Ala Met Trp Tyr Ser
                690                 695                 700

Asp Gln Asn His Gly Leu Ser Gly Leu Ser Thr Asn His Leu Tyr Thr
705                 710                 715                 720

His Met Thr His Phe Leu Lys Gln Cys Phe Ser Leu Ser Asp Gly Lys
                725                 730                 735

Lys Lys Lys Lys Lys Gly His His His His His
                740                 745
```

<210> SEQ ID NO 63
<211> LENGTH: 761
<212> TYPE: PRT
<213> ORGANISM: Mus musculus

<400> SEQUENCE: 63

```
Met Lys Thr Trp Leu Lys Thr Val Phe Gly Val Thr Thr Leu Ala Ala
1               5                   10                  15

Leu Ala Leu Val Val Ile Cys Ile Val Leu Arg Pro Ser Arg Val Tyr
                20                  25                  30

Lys Pro Glu Gly Asn Thr Lys Arg Ala Leu Thr Leu Lys Asp Ile Leu
                35                  40                  45

Asn Gly Thr Phe Ser Tyr Lys Thr Tyr Phe Pro Asn Trp Ile Ser Glu
                50                  55                  60

Gln Glu Tyr Leu His Gln Ser Glu Asp Asn Ile Val Phe Tyr Asn
65                  70                  75                  80

Ile Glu Thr Arg Glu Ser Tyr Ile Ile Leu Ser Asn Ser Thr Met Lys
                85                  90                  95

Ser Val Asn Ala Thr Asp Tyr Gly Leu Ser Pro Asp Arg Gln Phe Val
                100                 105                 110

Tyr Leu Glu Ser Asp Tyr Ser Lys Leu Trp Arg Tyr Ser Tyr Thr Ala
                115                 120                 125

Thr Tyr Tyr Ile Tyr Asp Leu Gln Asn Gly Glu Phe Val Arg Gly Tyr
                130                 135                 140

Glu Leu Pro Arg Pro Ile Gln Tyr Leu Cys Trp Ser Pro Val Gly Ser
145                 150                 155                 160
```

```
Lys Leu Ala Tyr Val Tyr Gln Asn Asn Ile Tyr Leu Lys Gln Arg Pro
            165                 170                 175
Gly Asp Pro Pro Phe Gln Ile Thr Tyr Thr Gly Arg Glu Asn Arg Ile
        180                 185                 190
Phe Asn Gly Ile Pro Asp Trp Val Tyr Glu Glu Met Leu Ala Thr
        195                 200                 205
Lys Tyr Ala Leu Trp Trp Ser Pro Asp Gly Lys Phe Leu Ala Tyr Val
        210                 215                 220
Glu Phe Asn Asp Ser Asp Ile Pro Ile Ile Ala Tyr Ser Tyr Tyr Gly
225                 230                 235                 240
Asp Gly Gln Tyr Pro Arg Thr Ile Asn Ile Pro Tyr Pro Lys Ala Gly
            245                 250                 255
Ala Lys Asn Pro Val Val Arg Val Phe Ile Val Asp Thr Thr Tyr Pro
        260                 265                 270
His His Val Gly Pro Met Glu Val Pro Val Pro Glu Met Ile Ala Ser
        275                 280                 285
Ser Asp Tyr Tyr Phe Ser Trp Leu Thr Trp Val Ser Ser Glu Arg Val
        290                 295                 300
Cys Leu Gln Trp Leu Lys Arg Val Gln Asn Val Ser Val Leu Ser Ile
305                 310                 315                 320
Cys Asp Phe Arg Glu Asp Trp His Ala Trp Glu Cys Pro Lys Asn Gln
            325                 330                 335
Glu His Val Glu Glu Ser Arg Thr Gly Trp Ala Gly Phe Val
        340                 345                 350
Ser Thr Pro Ala Phe Ser Gln Asp Ala Thr Ser Tyr Tyr Lys Ile Phe
        355                 360                 365
Ser Asp Lys Asp Gly Tyr Lys His Ile His Tyr Ile Lys Asp Thr Val
        370                 375                 380
Glu Asn Ala Ile Gln Ile Thr Ser Gly Lys Trp Glu Ala Ile Tyr Ile
385                 390                 395                 400
Phe Arg Val Thr Gln Asp Ser Leu Phe Tyr Ser Ser Asn Glu Phe Glu
            405                 410                 415
Gly Tyr Pro Gly Arg Arg Asn Ile Tyr Arg Ile Ser Ile Gly Asn Ser
        420                 425                 430
Pro Pro Ser Lys Lys Cys Val Thr Cys His Leu Arg Lys Glu Arg Cys
        435                 440                 445
Gln Tyr Tyr Thr Ala Ser Phe Ser Tyr Lys Ala Lys Tyr Tyr Ala Leu
        450                 455                 460
Val Cys Tyr Gly Pro Gly Leu Pro Ile Ser Thr Leu His Asp Gly Arg
465                 470                 475                 480
Thr Asp Gln Glu Ile Gln Val Leu Glu Glu Asn Lys Glu Leu Glu Asn
            485                 490                 495
Ser Leu Arg Asn Ile Gln Leu Pro Lys Val Glu Ile Lys Lys Leu Lys
        500                 505                 510
Asp Gly Gly Leu Thr Phe Trp Tyr Lys Met Ile Leu Pro Pro Gln Phe
        515                 520                 525
Asp Arg Ser Lys Lys Tyr Pro Leu Leu Ile Gln Val Tyr Gly Gly Pro
        530                 535                 540
Cys Ser Gln Ser Val Lys Ser Val Phe Ala Val Asn Trp Ile Thr Tyr
545                 550                 555                 560
Leu Ala Ser Lys Glu Gly Ile Val Ile Ala Leu Val Asp Gly Arg Gly
            565                 570                 575
Thr Ala Phe Gln Gly Asp Lys Phe Leu His Ala Val Tyr Arg Lys Leu
```

```
                    580                 585                 590
Gly Val Tyr Glu Val Glu Asp Gln Leu Thr Ala Val Arg Lys Phe Ile
            595                 600                 605

Glu Met Gly Phe Ile Asp Glu Arg Ile Ala Ile Trp Gly Trp Ser
        610                 615                 620

Tyr Gly Gly Tyr Val Ser Ser Leu Ala Leu Ala Ser Gly Thr Gly Leu
625                 630                 635                 640

Phe Lys Cys Gly Ile Ala Val Ala Pro Val Ser Ser Trp Glu Tyr Tyr
                    645                 650                 655

Ala Ser Ile Tyr Ser Glu Arg Phe Met Gly Leu Pro Thr Lys Asp Asp
            660                 665                 670

Asn Leu Glu His Tyr Lys Asn Ser Thr Val Met Ala Arg Ala Glu Tyr
        675                 680                 685

Phe Arg Asn Val Asp Tyr Leu Leu Ile His Gly Thr Ala Asp Asp Asn
    690                 695                 700

Val His Phe Gln Asn Ser Ala Gln Ile Ala Lys Ala Leu Val Asn Ala
705                 710                 715                 720

Gln Val Asp Phe Gln Ala Met Trp Tyr Ser Asp Gln Asn His Gly Ile
                    725                 730                 735

Ser Ser Gly Arg Ser Gln Asn His Leu Tyr Thr His Met Thr His Phe
            740                 745                 750

Leu Lys Gln Cys Phe Ser Leu Ser Asp
        755                 760

<210> SEQ ID NO 64
<211> LENGTH: 749
<212> TYPE: PRT
<213> ORGANISM: Artificial Sequence
<220> FEATURE:
<223> OTHER INFORMATION: Murine FAP ectodomain+poly-lys-tag+his6-tag

<400> SEQUENCE: 64

Arg Pro Ser Arg Val Tyr Lys Pro Glu Gly Asn Thr Lys Arg Ala Leu
1               5                   10                  15

Thr Leu Lys Asp Ile Leu Asn Gly Thr Phe Ser Tyr Lys Thr Tyr Phe
            20                  25                  30

Pro Asn Trp Ile Ser Glu Gln Glu Tyr Leu His Gln Ser Glu Asp Asp
        35                  40                  45

Asn Ile Val Phe Tyr Asn Ile Glu Thr Arg Glu Ser Tyr Ile Ile Leu
    50                  55                  60

Ser Asn Ser Thr Met Lys Ser Val Asn Ala Thr Asp Tyr Gly Leu Ser
65                  70                  75                  80

Pro Asp Arg Gln Phe Val Tyr Leu Glu Ser Asp Tyr Ser Lys Leu Trp
                85                  90                  95

Arg Tyr Ser Tyr Thr Ala Thr Tyr Tyr Ile Tyr Asp Leu Gln Asn Gly
            100                 105                 110

Glu Phe Val Arg Gly Tyr Glu Leu Pro Arg Pro Ile Gln Tyr Leu Cys
        115                 120                 125

Trp Ser Pro Val Gly Ser Lys Leu Ala Tyr Val Tyr Gln Asn Asn Ile
    130                 135                 140

Tyr Leu Lys Gln Arg Pro Gly Asp Pro Pro Phe Gln Ile Thr Tyr Thr
145                 150                 155                 160

Gly Arg Glu Asn Arg Ile Phe Asn Gly Ile Pro Asp Trp Val Tyr Glu
                165                 170                 175

Glu Glu Met Leu Ala Thr Lys Tyr Ala Leu Trp Trp Ser Pro Asp Gly
```

```
            180                 185                 190
Lys Phe Leu Ala Tyr Val Glu Phe Asn Asp Ser Asp Ile Pro Ile Ile
            195                 200                 205
Ala Tyr Ser Tyr Tyr Gly Asp Gly Gln Tyr Pro Arg Thr Ile Asn Ile
            210                 215                 220
Pro Tyr Pro Lys Ala Gly Ala Lys Asn Pro Val Val Arg Val Phe Ile
225                 230                 235                 240
Val Asp Thr Thr Tyr Pro His His Val Gly Pro Met Glu Val Pro Val
                245                 250                 255
Pro Glu Met Ile Ala Ser Ser Asp Tyr Tyr Phe Ser Trp Leu Thr Trp
                260                 265                 270
Val Ser Ser Glu Arg Val Cys Leu Gln Trp Leu Lys Arg Val Gln Asn
                275                 280                 285
Val Ser Val Leu Ser Ile Cys Asp Phe Arg Glu Asp Trp His Ala Trp
                290                 295                 300
Glu Cys Pro Lys Asn Gln Glu His Val Glu Glu Ser Arg Thr Gly Trp
305                 310                 315                 320
Ala Gly Gly Phe Phe Val Ser Thr Pro Ala Phe Ser Gln Asp Ala Thr
                325                 330                 335
Ser Tyr Tyr Lys Ile Phe Ser Asp Lys Asp Gly Tyr Lys His Ile His
                340                 345                 350
Tyr Ile Lys Asp Thr Val Glu Asn Ala Ile Gln Ile Thr Ser Gly Lys
                355                 360                 365
Trp Glu Ala Ile Tyr Ile Phe Arg Val Thr Gln Asp Ser Leu Phe Tyr
                370                 375                 380
Ser Ser Asn Glu Phe Glu Gly Tyr Pro Gly Arg Arg Asn Ile Tyr Arg
385                 390                 395                 400
Ile Ser Ile Gly Asn Ser Pro Pro Ser Lys Lys Cys Val Thr Cys His
                405                 410                 415
Leu Arg Lys Glu Arg Cys Gln Tyr Tyr Thr Ala Ser Phe Ser Tyr Lys
                420                 425                 430
Ala Lys Tyr Tyr Ala Leu Val Cys Tyr Gly Pro Gly Leu Pro Ile Ser
                435                 440                 445
Thr Leu His Asp Gly Arg Thr Asp Gln Glu Ile Gln Val Leu Glu Glu
                450                 455                 460
Asn Lys Glu Leu Glu Asn Ser Leu Arg Asn Ile Gln Leu Pro Lys Val
465                 470                 475                 480
Glu Ile Lys Lys Leu Lys Asp Gly Gly Leu Thr Phe Trp Tyr Lys Met
                485                 490                 495
Ile Leu Pro Pro Gln Phe Asp Arg Ser Lys Lys Tyr Pro Leu Leu Ile
                500                 505                 510
Gln Val Tyr Gly Gly Pro Cys Ser Gln Ser Val Lys Ser Val Phe Ala
                515                 520                 525
Val Asn Trp Ile Thr Tyr Leu Ala Ser Lys Glu Gly Ile Val Ile Ala
                530                 535                 540
Leu Val Asp Gly Arg Gly Thr Ala Phe Gln Gly Asp Lys Phe Leu His
545                 550                 555                 560
Ala Val Tyr Arg Lys Leu Gly Val Tyr Glu Val Glu Asp Gln Leu Thr
                565                 570                 575
Ala Val Arg Lys Phe Ile Glu Met Gly Phe Ile Asp Glu Glu Arg Ile
                580                 585                 590
Ala Ile Trp Gly Trp Ser Tyr Gly Gly Tyr Val Ser Ser Leu Ala Leu
                595                 600                 605
```

```
Ala Ser Gly Thr Gly Leu Phe Lys Cys Gly Ile Ala Val Ala Pro Val
        610                 615                 620

Ser Ser Trp Glu Tyr Tyr Ala Ser Ile Tyr Ser Glu Arg Phe Met Gly
625                 630                 635                 640

Leu Pro Thr Lys Asp Asp Asn Leu Glu His Tyr Lys Asn Ser Thr Val
                645                 650                 655

Met Ala Arg Ala Glu Tyr Phe Arg Asn Val Asp Tyr Leu Leu Ile His
                660                 665                 670

Gly Thr Ala Asp Asp Asn Val His Phe Gln Asn Ser Ala Gln Ile Ala
                675                 680                 685

Lys Ala Leu Val Asn Ala Gln Val Asp Phe Gln Ala Met Trp Tyr Ser
        690                 695                 700

Asp Gln Asn His Gly Ile Leu Ser Gly Arg Ser Gln Asn His Leu Tyr
705                 710                 715                 720

Thr His Met Thr His Phe Leu Lys Gln Cys Phe Ser Leu Ser Asp Gly
                725                 730                 735

Lys Lys Lys Lys Lys Lys Gly His His His His
                740                 745

<210> SEQ ID NO 65
<211> LENGTH: 748
<212> TYPE: PRT
<213> ORGANISM: Artificial Sequence
<220> FEATURE:
<223> OTHER INFORMATION: Cynomolgus FAP ectodomain+poly-lys-tag+his6-tag

<400> SEQUENCE: 65

Arg Pro Pro Arg Val His Asn Ser Glu Glu Asn Thr Met Arg Ala Leu
1               5                   10                  15

Thr Leu Lys Asp Ile Leu Asn Gly Thr Phe Ser Tyr Lys Thr Phe Phe
                20                  25                  30

Pro Asn Trp Ile Ser Gly Gln Glu Tyr Leu His Gln Ser Ala Asp Asn
            35                  40                  45

Asn Ile Val Leu Tyr Asn Ile Glu Thr Gly Gln Ser Tyr Thr Ile Leu
        50                  55                  60

Ser Asn Arg Thr Met Lys Ser Val Asn Ala Ser Asn Tyr Gly Leu Ser
65                  70                  75                  80

Pro Asp Arg Gln Phe Val Tyr Leu Glu Ser Asp Tyr Ser Lys Leu Trp
                85                  90                  95

Arg Tyr Ser Tyr Thr Ala Thr Tyr Tyr Ile Tyr Asp Leu Ser Asn Gly
            100                 105                 110

Glu Phe Val Arg Gly Asn Glu Leu Pro Arg Pro Ile Gln Tyr Leu Cys
        115                 120                 125

Trp Ser Pro Val Gly Ser Lys Leu Ala Tyr Val Tyr Gln Asn Asn Ile
130                 135                 140

Tyr Leu Lys Gln Arg Pro Gly Asp Pro Pro Phe Gln Ile Thr Phe Asn
145                 150                 155                 160

Gly Arg Glu Asn Lys Ile Phe Asn Gly Ile Pro Asp Trp Val Tyr Glu
                165                 170                 175

Glu Glu Met Leu Ala Thr Lys Tyr Ala Leu Trp Trp Ser Pro Asn Gly
            180                 185                 190

Lys Phe Leu Ala Tyr Ala Glu Phe Asn Asp Thr Asp Ile Pro Val Ile
        195                 200                 205

Ala Tyr Ser Tyr Tyr Gly Asp Glu Gln Tyr Pro Arg Thr Ile Asn Ile
210                 215                 220
```

```
Pro Tyr Pro Lys Ala Gly Ala Lys Asn Pro Phe Val Arg Ile Phe Ile
225                 230                 235                 240

Ile Asp Thr Thr Tyr Pro Ala Tyr Val Gly Pro Gln Glu Val Pro Val
            245                 250                 255

Pro Ala Met Ile Ala Ser Ser Asp Tyr Tyr Phe Ser Trp Leu Thr Trp
            260                 265                 270

Val Thr Asp Glu Arg Val Cys Leu Gln Trp Leu Lys Arg Val Gln Asn
            275                 280                 285

Val Ser Val Leu Ser Ile Cys Asp Phe Arg Glu Asp Trp Gln Thr Trp
            290                 295                 300

Asp Cys Pro Lys Thr Gln Glu His Ile Glu Glu Ser Arg Thr Gly Trp
305                 310                 315                 320

Ala Gly Gly Phe Phe Val Ser Thr Pro Val Phe Ser Tyr Asp Ala Ile
            325                 330                 335

Ser Tyr Tyr Lys Ile Phe Ser Asp Lys Asp Gly Tyr Lys His Ile His
            340                 345                 350

Tyr Ile Lys Asp Thr Val Glu Asn Ala Ile Gln Ile Thr Ser Gly Lys
            355                 360                 365

Trp Glu Ala Ile Asn Ile Phe Arg Val Thr Gln Asp Ser Leu Phe Tyr
370                 375                 380

Ser Ser Asn Glu Phe Glu Asp Tyr Pro Gly Arg Arg Asn Ile Tyr Arg
385                 390                 395                 400

Ile Ser Ile Gly Ser Tyr Pro Pro Ser Lys Lys Cys Val Thr Cys His
            405                 410                 415

Leu Arg Lys Glu Arg Cys Gln Tyr Tyr Thr Ala Ser Phe Ser Asp Tyr
            420                 425                 430

Ala Lys Tyr Tyr Ala Leu Val Cys Tyr Gly Pro Gly Ile Pro Ile Ser
            435                 440                 445

Thr Leu His Asp Gly Arg Thr Asp Gln Glu Ile Lys Ile Leu Glu Glu
            450                 455                 460

Asn Lys Glu Leu Glu Asn Ala Leu Lys Asn Ile Gln Leu Pro Lys Glu
465                 470                 475                 480

Glu Ile Lys Lys Leu Glu Val Asp Glu Ile Thr Leu Trp Tyr Lys Met
            485                 490                 495

Ile Leu Pro Pro Gln Phe Asp Arg Ser Lys Lys Tyr Pro Leu Leu Ile
            500                 505                 510

Gln Val Tyr Gly Gly Pro Cys Ser Gln Ser Val Arg Ser Val Phe Ala
            515                 520                 525

Val Asn Trp Ile Ser Tyr Leu Ala Ser Lys Glu Gly Met Val Ile Ala
            530                 535                 540

Leu Val Asp Gly Arg Gly Thr Ala Phe Gln Gly Asp Lys Leu Leu Tyr
545                 550                 555                 560

Ala Val Tyr Arg Lys Leu Gly Val Tyr Glu Val Glu Asp Gln Ile Thr
            565                 570                 575

Ala Val Arg Lys Phe Ile Glu Met Gly Phe Ile Asp Glu Lys Arg Ile
            580                 585                 590

Ala Ile Trp Gly Trp Ser Tyr Gly Gly Tyr Val Ser Ser Leu Ala Leu
            595                 600                 605

Ala Ser Gly Thr Gly Leu Phe Lys Cys Gly Ile Ala Val Ala Pro Val
            610                 615                 620

Ser Ser Trp Glu Tyr Tyr Ala Ser Val Tyr Thr Glu Arg Phe Met Gly
625                 630                 635                 640
```

-continued

```
Leu Pro Thr Lys Asp Asp Asn Leu Glu His Tyr Lys Asn Ser Thr Val
                645                 650                 655
Met Ala Arg Ala Glu Tyr Phe Arg Asn Val Asp Tyr Leu Leu Ile His
            660                 665                 670
Gly Thr Ala Asp Asp Asn Val His Phe Gln Asn Ser Ala Gln Ile Ala
        675                 680                 685
Lys Ala Leu Val Asn Ala Gln Val Asp Phe Gln Ala Met Trp Tyr Ser
    690                 695                 700
Asp Gln Asn His Gly Leu Ser Gly Leu Ser Thr Asn His Leu Tyr Thr
705                 710                 715                 720
His Met Thr His Phe Leu Lys Gln Cys Phe Ser Leu Ser Asp Gly Lys
                725                 730                 735
Lys Lys Lys Lys Lys Gly His His His His His
                740                 745

<210> SEQ ID NO 66
<211> LENGTH: 272
<212> TYPE: PRT
<213> ORGANISM: Mus musculus

<400> SEQUENCE: 66

Met Tyr Val Trp Val Gln Gln Pro Thr Ala Leu Leu Leu Ala Leu
1               5                   10                  15
Thr Leu Gly Val Thr Ala Arg Arg Leu Asn Cys Val Lys His Thr Tyr
                20                  25                  30
Pro Ser Gly His Lys Cys Cys Arg Glu Cys Gln Pro Gly His Gly Met
            35                  40                  45
Val Ser Arg Cys Asp His Thr Arg Asp Thr Leu Cys His Pro Cys Glu
    50                  55                  60
Thr Gly Phe Tyr Asn Glu Ala Val Asn Tyr Asp Thr Cys Lys Gln Cys
65                  70                  75                  80
Thr Gln Cys Asn His Arg Ser Gly Ser Glu Leu Lys Gln Asn Cys Thr
                85                  90                  95
Pro Thr Gln Asp Thr Val Cys Arg Cys Arg Pro Gly Thr Gln Pro Arg
            100                 105                 110
Gln Asp Ser Gly Tyr Lys Leu Gly Val Asp Cys Val Pro Cys Pro Pro
        115                 120                 125
Gly His Phe Ser Pro Gly Asn Asn Gln Ala Cys Lys Pro Trp Thr Asn
    130                 135                 140
Cys Thr Leu Ser Gly Lys Gln Thr Arg His Pro Ala Ser Asp Ser Leu
145                 150                 155                 160
Asp Ala Val Cys Glu Asp Arg Ser Leu Leu Ala Thr Leu Leu Trp Glu
                165                 170                 175
Thr Gln Arg Pro Thr Phe Arg Pro Thr Thr Val Gln Ser Thr Thr Val
            180                 185                 190
Trp Pro Arg Thr Ser Glu Leu Pro Ser Pro Thr Leu Val Thr Pro
        195                 200                 205
Glu Gly Pro Ala Phe Ala Val Leu Leu Gly Leu Gly Leu Gly Leu Leu
    210                 215                 220
Ala Pro Leu Thr Val Leu Leu Ala Leu Tyr Leu Leu Arg Lys Ala Trp
225                 230                 235                 240
Arg Leu Pro Asn Thr Pro Lys Pro Cys Trp Gly Asn Ser Phe Arg Thr
                245                 250                 255
Pro Ile Gln Glu Glu His Thr Asp Ala His Phe Thr Leu Ala Lys Ile
            260                 265                 270
```

```
<210> SEQ ID NO 67
<211> LENGTH: 5
<212> TYPE: PRT
<213> ORGANISM: Artificial Sequence
<220> FEATURE:
<223> OTHER INFORMATION: G4S peptide linker

<400> SEQUENCE: 67

Gly Gly Gly Gly Ser
1               5

<210> SEQ ID NO 68
<211> LENGTH: 10
<212> TYPE: PRT
<213> ORGANISM: Artificial Sequence
<220> FEATURE:
<223> OTHER INFORMATION: (G4S)2

<400> SEQUENCE: 68

Gly Gly Gly Gly Ser Gly Gly Gly Gly Ser
1               5                   10

<210> SEQ ID NO 69
<211> LENGTH: 10
<212> TYPE: PRT
<213> ORGANISM: Artificial Sequence
<220> FEATURE:
<223> OTHER INFORMATION: (SG4)2

<400> SEQUENCE: 69

Ser Gly Gly Gly Gly Ser Gly Gly Gly Gly
1               5                   10

<210> SEQ ID NO 70
<211> LENGTH: 14
<212> TYPE: PRT
<213> ORGANISM: Artificial Sequence
<220> FEATURE:
<223> OTHER INFORMATION: peptide linker

<400> SEQUENCE: 70

Gly Gly Gly Gly Ser Gly Gly Gly Gly Ser Gly Gly Gly Gly
1               5                   10

<210> SEQ ID NO 71
<211> LENGTH: 10
<212> TYPE: PRT
<213> ORGANISM: Artificial Sequence
<220> FEATURE:
<223> OTHER INFORMATION: peptide linker

<400> SEQUENCE: 71

Gly Ser Pro Gly Ser Ser Ser Ser Gly Ser
1               5                   10

<210> SEQ ID NO 72
<211> LENGTH: 15
<212> TYPE: PRT
<213> ORGANISM: Artificial Sequence
<220> FEATURE:
<223> OTHER INFORMATION: peptide linker 2

<400> SEQUENCE: 72

Gly Gly Gly Gly Ser Gly Gly Gly Gly Ser Gly Gly Gly Gly Ser
1               5                   10                  15
```

```
<210> SEQ ID NO 73
<211> LENGTH: 20
<212> TYPE: PRT
<213> ORGANISM: Artificial Sequence
<220> FEATURE:
<223> OTHER INFORMATION: peptide linker 3

<400> SEQUENCE: 73

Gly Gly Gly Gly Ser Gly Gly Gly Ser Gly Gly Gly Gly Ser Gly
1               5                   10                  15

Gly Gly Gly Ser
            20

<210> SEQ ID NO 74
<211> LENGTH: 8
<212> TYPE: PRT
<213> ORGANISM: Artificial Sequence
<220> FEATURE:
<223> OTHER INFORMATION: peptide linker 4

<400> SEQUENCE: 74

Gly Ser Gly Ser Gly Ser Gly Ser
1               5

<210> SEQ ID NO 75
<211> LENGTH: 8
<212> TYPE: PRT
<213> ORGANISM: Artificial Sequence
<220> FEATURE:
<223> OTHER INFORMATION: peptide linker 5

<400> SEQUENCE: 75

Gly Ser Gly Ser Gly Asn Gly Ser
1               5

<210> SEQ ID NO 76
<211> LENGTH: 8
<212> TYPE: PRT
<213> ORGANISM: Artificial Sequence
<220> FEATURE:
<223> OTHER INFORMATION: peptide linker 6

<400> SEQUENCE: 76

Gly Gly Ser Gly Ser Gly Ser Gly
1               5

<210> SEQ ID NO 77
<211> LENGTH: 6
<212> TYPE: PRT
<213> ORGANISM: Artificial Sequence
<220> FEATURE:
<223> OTHER INFORMATION: peptide linker 7

<400> SEQUENCE: 77

Gly Gly Ser Gly Ser Gly
1               5

<210> SEQ ID NO 78
<211> LENGTH: 4
<212> TYPE: PRT
<213> ORGANISM: Artificial Sequence
<220> FEATURE:
<223> OTHER INFORMATION: peptide linker 8

<400> SEQUENCE: 78

Gly Gly Ser Gly
```

-continued

```
<210> SEQ ID NO 79
<211> LENGTH: 8
<212> TYPE: PRT
<213> ORGANISM: Artificial Sequence
<220> FEATURE:
<223> OTHER INFORMATION: peptide linker 9

<400> SEQUENCE: 79

Gly Gly Ser Gly Asn Gly Ser Gly
1               5

<210> SEQ ID NO 80
<211> LENGTH: 8
<212> TYPE: PRT
<213> ORGANISM: Artificial Sequence
<220> FEATURE:
<223> OTHER INFORMATION: peptide linker 10

<400> SEQUENCE: 80

Gly Gly Asn Gly Ser Gly Ser Gly
1               5

<210> SEQ ID NO 81
<211> LENGTH: 6
<212> TYPE: PRT
<213> ORGANISM: Artificial Sequence
<220> FEATURE:
<223> OTHER INFORMATION: peptide linker 11

<400> SEQUENCE: 81

Gly Gly Asn Gly Ser Gly
1               5

<210> SEQ ID NO 82
<211> LENGTH: 227
<212> TYPE: PRT
<213> ORGANISM: Artificial Sequence
<220> FEATURE:
<223> OTHER INFORMATION: Fc knob chain

<400> SEQUENCE: 82

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
        130                 135                 140

Leu Trp Cys Leu Val Lys Gly Phe Tyr Pro Ser Asp Ile Ala Val Glu
```

```
                145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
                210                 215                 220

Pro Gly Lys
225

<210> SEQ ID NO 83
<211> LENGTH: 227
<212> TYPE: PRT
<213> ORGANISM: Artificial Sequence
<220> FEATURE:
<223> OTHER INFORMATION: Fc hole chain

<400> SEQUENCE: 83

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
                35                  40                  45

Glu Asp Pro Glu Val Lys Phe Asn Trp Tyr Val Asp Gly Val Glu Val
            50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
                210                 215                 220

Pro Gly Lys
225

<210> SEQ ID NO 84
<211> LENGTH: 20
<212> TYPE: PRT
<213> ORGANISM: Artificial Sequence
<220> FEATURE:
<223> OTHER INFORMATION: Acceptor framework IGHJ6*01/02
```

<400> SEQUENCE: 84

Tyr Tyr Tyr Tyr Tyr Gly Met Asp Val Trp Gly Gln Gly Thr Thr Val
1               5                   10                  15

Thr Val Ser Ser
            20

<210> SEQ ID NO 85
<211> LENGTH: 12
<212> TYPE: PRT
<213> ORGANISM: Artificial Sequence
<220> FEATURE:
<223> OTHER INFORMATION: Acceptor framework IGKJ4*01/02

<400> SEQUENCE: 85

Leu Thr Phe Gly Gly Gly Thr Lys Val Glu Ile Lys
1               5                   10

<210> SEQ ID NO 86
<211> LENGTH: 924
<212> TYPE: PRT
<213> ORGANISM: Artificial Sequence
<220> FEATURE:
<223> OTHER INFORMATION: OX40(49B4) VHCH1- OX40(49B4) VHCH1- Fc
      knob_PGLALA- FAP(1G1a) VHCL

<400> SEQUENCE: 86

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Glu Lys Val Glu Pro Lys Ser Cys Gly Gly Gly
    210                 215                 220

Gly Ser Gly Gly Gly Gly Gln Val Gln Leu Val Gln Ser Gly Ala
225                 230                 235                 240

Glu Val Lys Lys Pro Gly Ser Ser Val Lys Val Ser Cys Lys Ala Ser

```
            245                 250                 255
Gly Gly Thr Phe Ser Ser Tyr Ala Ile Ser Trp Val Arg Gln Ala Pro
            260                 265                 270
Gly Gln Gly Leu Glu Trp Met Gly Gly Ile Ile Pro Ile Phe Gly Thr
            275                 280                 285
Ala Asn Tyr Ala Gln Lys Phe Gln Gly Arg Val Thr Ile Thr Ala Asp
            290                 295                 300
Lys Ser Thr Ser Thr Ala Tyr Met Glu Leu Ser Ser Leu Arg Ser Glu
305                 310                 315                 320
Asp Thr Ala Val Tyr Tyr Cys Ala Arg Glu Tyr Tyr Arg Gly Pro Tyr
                325                 330                 335
Asp Tyr Trp Gly Gln Gly Thr Thr Val Thr Val Ser Ser Ala Ser Thr
                340                 345                 350
Lys Gly Pro Ser Val Phe Pro Leu Ala Pro Ser Ser Lys Ser Thr Ser
                355                 360                 365
Gly Gly Thr Ala Ala Leu Gly Cys Leu Val Glu Asp Tyr Phe Pro Glu
                370                 375                 380
Pro Val Thr Val Ser Trp Asn Ser Gly Ala Leu Thr Ser Gly Val His
385                 390                 395                 400
Thr Phe Pro Ala Val Leu Gln Ser Ser Gly Leu Tyr Ser Leu Ser Ser
                405                 410                 415
Val Val Thr Val Pro Ser Ser Ser Leu Gly Thr Gln Thr Tyr Ile Cys
                420                 425                 430
Asn Val Asn His Lys Pro Ser Asn Thr Lys Val Asp Glu Lys Val Glu
                435                 440                 445
Pro Lys Ser Cys Asp Lys Thr His Thr Cys Pro Pro Cys Pro Ala Pro
450                 455                 460
Glu Ala Ala Gly Gly Pro Ser Val Phe Leu Phe Pro Pro Lys Pro Lys
465                 470                 475                 480
Asp Thr Leu Met Ile Ser Arg Thr Pro Glu Val Thr Cys Val Val Val
                485                 490                 495
Asp Val Ser His Glu Asp Pro Glu Val Lys Phe Asn Trp Tyr Val Asp
                500                 505                 510
Gly Val Glu Val His Asn Ala Lys Thr Lys Pro Arg Glu Glu Gln Tyr
            515                 520                 525
Asn Ser Thr Tyr Arg Val Val Ser Val Leu Thr Val Leu His Gln Asp
            530                 535                 540
Trp Leu Asn Gly Lys Glu Tyr Lys Cys Lys Val Ser Asn Lys Ala Leu
545                 550                 555                 560
Gly Ala Pro Ile Glu Lys Thr Ile Ser Lys Ala Lys Gly Gln Pro Arg
                565                 570                 575
Glu Pro Gln Val Tyr Thr Leu Pro Pro Cys Arg Asp Glu Leu Thr Lys
                580                 585                 590
Asn Gln Val Ser Leu Trp Cys Leu Val Lys Gly Phe Tyr Pro Ser Asp
                595                 600                 605
Ile Ala Val Glu Trp Glu Ser Asn Gly Gln Pro Glu Asn Asn Tyr Lys
                610                 615                 620
Thr Thr Pro Pro Val Leu Asp Ser Asp Gly Ser Phe Phe Leu Tyr Ser
625                 630                 635                 640
Lys Leu Thr Val Asp Lys Ser Arg Trp Gln Gln Gly Asn Val Phe Ser
                645                 650                 655
Cys Ser Val Met His Glu Ala Leu His Asn His Tyr Thr Gln Lys Ser
                660                 665                 670
```

```
Leu Ser Leu Ser Pro Gly Gly Gly Gly Ser Gly Gly Gly Ser
        675                 680                 685

Gly Gly Gly Ser Gly Gly Ser Gly Gly Gln Val Gln Leu Val Gln
    690                 695                 700

Ser Gly Ala Glu Val Lys Lys Pro Gly Ala Ser Val Lys Val Ser Cys
705                 710                 715                 720

Lys Ala Ser Gly Tyr Thr Leu Thr Asp Tyr Asn Met Asp Trp Val Arg
                725                 730                 735

Gln Ala Pro Gly Gln Gly Leu Glu Trp Ile Gly Asp Ile Tyr Pro Asn
            740                 745                 750

Thr Gly Gly Thr Ile Tyr Asn Gln Lys Phe Lys Gly Arg Val Thr Met
        755                 760                 765

Thr Ile Asp Thr Ser Thr Ser Thr Val Tyr Met Glu Leu Ser Ser Leu
    770                 775                 780

Arg Ser Glu Asp Thr Ala Val Tyr Tyr Cys Thr Arg Phe Arg Gly Ile
785                 790                 795                 800

His Tyr Ala Met Asp Tyr Trp Gly Gln Gly Thr Thr Val Thr Val Ser
                805                 810                 815

Ser Ala Ser Val Ala Ala Pro Ser Val Phe Ile Phe Pro Pro Ser Asp
            820                 825                 830

Glu Gln Leu Lys Ser Gly Thr Ala Ser Val Val Cys Leu Leu Asn Asn
        835                 840                 845

Phe Tyr Pro Arg Glu Ala Lys Val Gln Trp Lys Val Asp Asn Ala Leu
    850                 855                 860

Gln Ser Gly Asn Ser Gln Glu Ser Val Thr Glu Gln Asp Ser Lys Asp
865                 870                 875                 880

Ser Thr Tyr Ser Leu Ser Ser Thr Leu Thr Leu Ser Lys Ala Asp Tyr
                885                 890                 895

Glu Lys His Lys Val Tyr Ala Cys Glu Val Thr His Gln Gly Leu Ser
            900                 905                 910

Ser Pro Val Thr Lys Ser Phe Asn Arg Gly Glu Cys
        915                 920

<210> SEQ ID NO 87
<211> LENGTH: 214
<212> TYPE: PRT
<213> ORGANISM: Artificial Sequence
<220> FEATURE:
<223> OTHER INFORMATION: OX40(49B4) light chain

<400> SEQUENCE: 87

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Gln Pro Tyr
                85                  90                  95

Thr Phe Gly Gln Gly Thr Lys Val Glu Ile Lys Arg Thr Val Ala Ala
            100                 105                 110
```

```
Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 88
<211> LENGTH: 216
<212> TYPE: PRT
<213> ORGANISM: Artificial Sequence
<220> FEATURE:
<223> OTHER INFORMATION: FAP(1G1a) VLCH1-light chain

<400> SEQUENCE: 88

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Leu Ser Phe Ile Asn Trp Phe Gln Gln Lys Pro Gly Gln Ala Pro
        35                  40                  45

Arg Leu Leu Ile Tyr Gly Thr Ser Asn Arg Gly Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Asn
                85                  90                  95

Glu Val Pro Tyr Thr Phe Gly Gly Gly Thr Lys Val Glu Ile Lys Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys
    210                 215

<210> SEQ ID NO 89
<211> LENGTH: 678
<212> TYPE: PRT
<213> ORGANISM: Artificial Sequence
```

<220> FEATURE:
<223> OTHER INFORMATION: OX40(49B4) VHCH1-OX40(49B4) VHCH1-Fc
hole_PGLALA

<400> SEQUENCE: 89

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Lys Phe
    50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Tyr Tyr Arg Gly Pro Tyr Asp Tyr Trp Gly Gln Gly Thr
            100                 105                 110
Thr Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
130                 135                 140
Cys Leu Val Glu Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Glu Lys Val Glu Pro Lys Ser Cys Gly Gly Gly
    210                 215                 220
Gly Ser Gly Gly Ser Gly Gln Val Gln Leu Val Gln Ser Gly Ala
225                 230                 235                 240
Glu Val Lys Lys Pro Gly Ser Ser Val Lys Val Ser Cys Lys Ala Ser
                245                 250                 255
Gly Gly Thr Phe Ser Ser Tyr Ala Ile Ser Trp Val Arg Gln Ala Pro
            260                 265                 270
Gly Gln Gly Leu Glu Trp Met Gly Gly Ile Ile Pro Ile Phe Gly Thr
        275                 280                 285
Ala Asn Tyr Ala Gln Lys Phe Gln Gly Arg Val Thr Ile Thr Ala Asp
    290                 295                 300
Lys Ser Thr Ser Thr Ala Tyr Met Glu Leu Ser Ser Leu Arg Ser Glu
305                 310                 315                 320
Asp Thr Ala Val Tyr Tyr Cys Ala Arg Glu Tyr Tyr Arg Gly Pro Tyr
                325                 330                 335
Asp Tyr Trp Gly Gln Gly Thr Thr Val Thr Val Ser Ser Ala Ser Thr
            340                 345                 350
Lys Gly Pro Ser Val Phe Pro Leu Ala Pro Ser Ser Lys Ser Thr Ser
        355                 360                 365
Gly Gly Thr Ala Ala Leu Gly Cys Leu Val Glu Asp Tyr Phe Pro Glu
    370                 375                 380
Pro Val Thr Val Ser Trp Asn Ser Gly Ala Leu Thr Ser Gly Val His
```

```
                385                 390                 395                 400
        Thr Phe Pro Ala Val Leu Gln Ser Ser Gly Leu Tyr Ser Leu Ser Ser
                        405                 410                 415

Val Val Thr Val Pro Ser Ser Ser Leu Gly Thr Gln Thr Tyr Ile Cys
                        420                 425                 430

Asn Val Asn His Lys Pro Ser Asn Thr Lys Val Asp Glu Lys Val Glu
                        435                 440                 445

Pro Lys Ser Cys Asp Lys Thr His Thr Cys Pro Pro Cys Pro Ala Pro
        450                 455                 460

Glu Ala Ala Gly Gly Pro Ser Val Phe Leu Phe Pro Pro Lys Pro Lys
        465                 470                 475                 480

Asp Thr Leu Met Ile Ser Arg Thr Pro Glu Val Thr Cys Val Val Val
                        485                 490                 495

Asp Val Ser His Glu Asp Pro Glu Val Lys Phe Asn Trp Tyr Val Asp
                        500                 505                 510

Gly Val Glu Val His Asn Ala Lys Thr Lys Pro Arg Glu Glu Gln Tyr
                        515                 520                 525

Asn Ser Thr Tyr Arg Val Val Ser Val Leu Thr Val Leu His Gln Asp
                        530                 535                 540

Trp Leu Asn Gly Lys Glu Tyr Lys Cys Lys Val Ser Asn Lys Ala Leu
        545                 550                 555                 560

Gly Ala Pro Ile Glu Lys Thr Ile Ser Lys Ala Lys Gly Gln Pro Arg
                        565                 570                 575

Glu Pro Gln Val Cys Thr Leu Pro Pro Ser Arg Asp Glu Leu Thr Lys
                        580                 585                 590

Asn Gln Val Ser Leu Ser Cys Ala Val Lys Gly Phe Tyr Pro Ser Asp
                        595                 600                 605

Ile Ala Val Glu Trp Glu Ser Asn Gly Gln Pro Glu Asn Asn Tyr Lys
                        610                 615                 620

Thr Thr Pro Pro Val Leu Asp Ser Asp Gly Ser Phe Phe Leu Val Ser
        625                 630                 635                 640

Lys Leu Thr Val Asp Lys Ser Arg Trp Gln Gln Gly Asn Val Phe Ser
                        645                 650                 655

Cys Ser Val Met His Glu Ala Leu His Asn His Tyr Thr Gln Lys Ser
                        660                 665                 670

Leu Ser Leu Ser Pro Gly
                        675

<210> SEQ ID NO 90
<211> LENGTH: 447
<212> TYPE: PRT
<213> ORGANISM: Artificial Sequence
<220> FEATURE:
<223> OTHER INFORMATION: OX40(49B4) VHCH1- Fc hole_PGLALA

<400> SEQUENCE: 90

Gln Val Gln Leu Val Gln Ser Gly Ala Glu Val Lys Lys Pro Gly Ser
        1               5                   10                  15

Ser Val Lys Val Ser Cys Lys Ala Ser Gly Gly Thr Phe Ser Ser Tyr
                        20                  25                  30

Ala Ile Ser Trp Val Arg Gln Ala Pro Gly Gln Gly Leu Glu Trp Met
                        35                  40                  45

Gly Gly Ile Ile Pro Ile Phe Gly Thr Ala Asn Tyr Ala Gln Lys Phe
                        50                  55                  60

Gln Gly Arg Val Thr Ile Thr Ala Asp Lys Ser Thr Ser Thr Ala Tyr
```

```
            65                  70                  75                  80
Met Glu Leu Ser Ser Leu Arg Ser Glu Asp Thr Ala Val Tyr Tyr Cys
                    85                  90                  95

Ala Arg Glu Tyr Tyr Arg Gly Pro Tyr Asp Tyr Trp Gly Gln Gly Thr
                100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Glu Lys Val Glu Pro Lys Ser Cys Asp Lys Thr
            210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Cys Thr Leu
                340                 345                 350

Pro Pro Ser Arg Asp Glu Leu Thr Lys Asn Gln Val Ser Leu Ser Cys
            355                 360                 365

Ala Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
                435                 440                 445

<210> SEQ ID NO 91
<211> LENGTH: 693
<212> TYPE: PRT
<213> ORGANISM: Artificial Sequence
<220> FEATURE:
<223> OTHER INFORMATION: OX40(49B4) VHCH1- Fc knob_PGLALA- FAP(1G1a)
      VHCL
```

<400> SEQUENCE: 91

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Glu Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Asp Glu Leu Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
```

```
                    405                 410                 415
Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Gly
            435                 440                 445

Gly Gly Gly Ser Gly Gly Gly Ser Gly Gly Gly Ser Gly Gly
        450                 455                 460

Ser Gly Gly Gln Val Gln Leu Val Gln Ser Gly Ala Glu Val Lys Lys
465                 470                 475                 480

Pro Gly Ala Ser Val Lys Val Ser Cys Lys Ala Ser Gly Tyr Thr Leu
                485                 490                 495

Thr Asp Tyr Asn Met Asp Trp Val Arg Gln Ala Pro Gly Gln Gly Leu
            500                 505                 510

Glu Trp Ile Gly Asp Ile Tyr Pro Asn Thr Gly Thr Ile Tyr Asn
        515                 520                 525

Gln Lys Phe Lys Gly Arg Val Thr Met Thr Ile Asp Thr Ser Thr Ser
530                 535                 540

Thr Val Tyr Met Glu Leu Ser Ser Leu Arg Ser Glu Asp Thr Ala Val
545                 550                 555                 560

Tyr Tyr Cys Thr Arg Phe Arg Gly Ile His Tyr Ala Met Asp Tyr Trp
                565                 570                 575

Gly Gln Gly Thr Thr Val Thr Val Ser Ser Ala Ser Val Ala Ala Pro
            580                 585                 590

Ser Val Phe Ile Phe Pro Pro Ser Asp Glu Gln Leu Lys Ser Gly Thr
        595                 600                 605

Ala Ser Val Val Cys Leu Leu Asn Asn Phe Tyr Pro Arg Glu Ala Lys
610                 615                 620

Val Gln Trp Lys Val Asp Asn Ala Leu Gln Ser Gly Asn Ser Gln Glu
625                 630                 635                 640

Ser Val Thr Glu Gln Asp Ser Lys Asp Ser Thr Tyr Ser Leu Ser Ser
                645                 650                 655

Thr Leu Thr Leu Ser Lys Ala Asp Tyr Glu Lys His Lys Val Tyr Ala
            660                 665                 670

Cys Glu Val Thr His Gln Gly Leu Ser Ser Pro Val Thr Lys Ser Phe
        675                 680                 685

Asn Arg Gly Glu Cys
        690

<210> SEQ ID NO 92
<211> LENGTH: 920
<212> TYPE: PRT
<213> ORGANISM: Artificial Sequence
<220> FEATURE:
<223> OTHER INFORMATION: OX40(CLC563) VHCH1- OX40(CLC563) VHCH1- Fc
      knob_PGLALA- FAP(1G1a) VHCL

<400> SEQUENCE: 92

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Asp Val Gly Ala Phe Asp Tyr Trp Gly Gln Gly Ala Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Gly Gly Gly Gly Ser
210                 215                 220

Gly Gly Ser Gly Gly Glu Val Gln Leu Leu Glu Ser Gly Gly Gly Leu
225                 230                 235                 240

Val Gln Pro Gly Gly Ser Leu Arg Leu Ser Cys Ala Ala Ser Gly Phe
                245                 250                 255

Thr Phe Ser Ser Tyr Ala Met Ser Trp Val Arg Gln Ala Pro Gly Lys
            260                 265                 270

Gly Leu Glu Trp Val Ser Ala Ile Ser Gly Ser Gly Gly Ser Thr Tyr
        275                 280                 285

Tyr Ala Asp Ser Val Lys Gly Arg Phe Thr Ile Ser Arg Asp Asn Ser
290                 295                 300

Lys Asn Thr Leu Tyr Leu Gln Met Asn Ser Leu Arg Ala Glu Asp Thr
305                 310                 315                 320

Ala Val Tyr Tyr Cys Ala Leu Asp Val Gly Ala Phe Asp Tyr Trp Gly
                325                 330                 335

Gln Gly Ala Leu Val Thr Val Ser Ser Ala Ser Thr Lys Gly Pro Ser
            340                 345                 350

Val Phe Pro Leu Ala Pro Ser Ser Lys Ser Thr Ser Gly Gly Thr Ala
        355                 360                 365

Ala Leu Gly Cys Leu Val Glu Asp Tyr Phe Pro Glu Pro Val Thr Val
370                 375                 380

Ser Trp Asn Ser Gly Ala Leu Thr Ser Gly Val His Thr Phe Pro Ala
385                 390                 395                 400

Val Leu Gln Ser Ser Gly Leu Tyr Ser Leu Ser Ser Val Val Thr Val
                405                 410                 415

Pro Ser Ser Ser Leu Gly Thr Gln Thr Tyr Ile Cys Asn Val Asn His
            420                 425                 430

Lys Pro Ser Asn Thr Lys Val Asp Glu Lys Val Glu Pro Lys Ser Cys
        435                 440                 445

Asp Lys Thr His Thr Cys Pro Pro Cys Pro Ala Pro Glu Ala Ala Gly
450                 455                 460

Gly Pro Ser Val Phe Leu Phe Pro Pro Lys Pro Lys Asp Thr Leu Met
465                 470                 475                 480

Ile Ser Arg Thr Pro Glu Val Thr Cys Val Val Val Asp Val Ser His
```

```
                485                 490                 495
Glu Asp Pro Glu Val Lys Phe Asn Trp Tyr Val Asp Gly Val Glu Val
            500                 505                 510

His Asn Ala Lys Thr Lys Pro Arg Glu Glu Gln Tyr Asn Ser Thr Tyr
            515                 520                 525

Arg Val Val Ser Val Leu Thr Val Leu His Gln Asp Trp Leu Asn Gly
            530                 535                 540

Lys Glu Tyr Lys Cys Lys Val Ser Asn Lys Ala Leu Gly Ala Pro Ile
545                 550                 555                 560

Glu Lys Thr Ile Ser Lys Ala Lys Gly Gln Pro Arg Glu Pro Gln Val
            565                 570                 575

Tyr Thr Leu Pro Pro Cys Arg Asp Glu Leu Thr Lys Asn Gln Val Ser
            580                 585                 590

Leu Trp Cys Leu Val Lys Gly Phe Tyr Pro Ser Asp Ile Ala Val Glu
            595                 600                 605

Trp Glu Ser Asn Gly Gln Pro Glu Asn Asn Tyr Lys Thr Thr Pro Pro
            610                 615                 620

Val Leu Asp Ser Asp Gly Ser Phe Phe Leu Tyr Ser Lys Leu Thr Val
625                 630                 635                 640

Asp Lys Ser Arg Trp Gln Gln Gly Asn Val Phe Ser Cys Ser Val Met
            645                 650                 655

His Glu Ala Leu His Asn His Tyr Thr Gln Lys Ser Leu Ser Leu Ser
            660                 665                 670

Pro Gly Gly Gly Gly Ser Gly Gly Gly Ser Gly Gly Gly Gly
            675                 680                 685

Ser Gly Gly Ser Gly Gly Gln Val Gln Leu Val Gln Ser Gly Ala Glu
            690                 695                 700

Val Lys Lys Pro Gly Ala Ser Val Lys Val Ser Cys Lys Ala Ser Gly
705                 710                 715                 720

Tyr Thr Leu Thr Asp Tyr Asn Met Asp Trp Val Arg Gln Ala Pro Gly
            725                 730                 735

Gln Gly Leu Glu Trp Ile Gly Asp Ile Tyr Pro Asn Thr Gly Gly Thr
            740                 745                 750

Ile Tyr Asn Gln Lys Phe Lys Gly Arg Val Thr Met Thr Ile Asp Thr
            755                 760                 765

Ser Thr Ser Thr Val Tyr Met Glu Leu Ser Ser Leu Arg Ser Glu Asp
            770                 775                 780

Thr Ala Val Tyr Tyr Cys Thr Arg Phe Arg Gly Ile His Tyr Ala Met
785                 790                 795                 800

Asp Tyr Trp Gly Gln Gly Thr Thr Val Thr Val Ser Ser Ala Ser Val
            805                 810                 815

Ala Ala Pro Ser Val Phe Ile Phe Pro Pro Ser Asp Glu Gln Leu Lys
            820                 825                 830

Ser Gly Thr Ala Ser Val Val Cys Leu Leu Asn Asn Phe Tyr Pro Arg
            835                 840                 845

Glu Ala Lys Val Gln Trp Lys Val Asp Asn Ala Leu Gln Ser Gly Asn
            850                 855                 860

Ser Gln Glu Ser Val Thr Glu Gln Asp Ser Lys Asp Ser Thr Tyr Ser
865                 870                 875                 880

Leu Ser Ser Thr Leu Thr Leu Ser Lys Ala Asp Tyr Glu Lys His Lys
            885                 890                 895

Val Tyr Ala Cys Glu Val Thr His Gln Gly Leu Ser Ser Pro Val Thr
            900                 905                 910
```

```
Lys Ser Phe Asn Arg Gly Glu Cys
        915                 920

<210> SEQ ID NO 93
<211> LENGTH: 215
<212> TYPE: PRT
<213> ORGANISM: Artificial Sequence
<220> FEATURE:
<223> OTHER INFORMATION: OX40(CLC563) light chain

<400> SEQUENCE: 93

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Arg Lys Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 94
<211> LENGTH: 217
<212> TYPE: PRT
<213> ORGANISM: Artificial Sequence
<220> FEATURE:
<223> OTHER INFORMATION: FAP(1G1a) VLCH1-light chain (EPKSCD)

<400> SEQUENCE: 94

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Leu Ser Phe Ile Asn Trp Phe Gln Gln Lys Pro Gly Gln Ala Pro
        35                  40                  45

Arg Leu Leu Ile Tyr Gly Thr Ser Asn Arg Gly Ser Gly Ile Pro Ala
    50                  55                  60

Arg Phe Ser Gly Ser Gly Ser Gly Thr Asp Phe Thr Leu Thr Ile Ser
```

```
            65                  70                  75                  80
Ser Leu Glu Pro Glu Asp Phe Ala Val Tyr Phe Cys Gln Gln Ser Asn
                85                  90                  95

Glu Val Pro Tyr Thr Phe Gly Gly Gly Thr Lys Val Glu Ile Lys Ser
            100                 105                 110

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp
210                 215

<210> SEQ ID NO 95
<211> LENGTH: 674
<212> TYPE: PRT
<213> ORGANISM: Artificial Sequence
<220> FEATURE:
<223> OTHER INFORMATION: OX40(CLC563) VHCH1-OX40(CLC563) VHCH1-Fc
      hole_PGLALA

<400> SEQUENCE: 95

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Asp Val Gly Ala Phe Asp Tyr Trp Gly Gln Gly Ala Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205
```

```
Lys Val Asp Glu Lys Val Glu Pro Lys Ser Cys Gly Gly Gly Ser
    210             215                 220

Gly Gly Ser Gly Gly Glu Val Gln Leu Leu Glu Ser Gly Gly Leu
225             230                 235                 240

Val Gln Pro Gly Gly Ser Leu Arg Leu Ser Cys Ala Ala Ser Gly Phe
            245                 250                 255

Thr Phe Ser Ser Tyr Ala Met Ser Trp Val Arg Gln Ala Pro Gly Lys
            260                 265                 270

Gly Leu Glu Trp Val Ser Ala Ile Ser Gly Ser Gly Gly Ser Thr Tyr
            275                 280                 285

Tyr Ala Asp Ser Val Lys Gly Arg Phe Thr Ile Ser Arg Asp Asn Ser
290                 295                 300

Lys Asn Thr Leu Tyr Leu Gln Met Asn Ser Leu Arg Ala Glu Asp Thr
305                 310                 315                 320

Ala Val Tyr Tyr Cys Ala Leu Asp Val Gly Ala Phe Asp Tyr Trp Gly
                325                 330                 335

Gln Gly Ala Leu Val Thr Val Ser Ser Ala Ser Thr Lys Gly Pro Ser
            340                 345                 350

Val Phe Pro Leu Ala Pro Ser Ser Lys Ser Thr Ser Gly Gly Thr Ala
            355                 360                 365

Ala Leu Gly Cys Leu Val Glu Asp Tyr Phe Pro Glu Pro Val Thr Val
370                 375                 380

Ser Trp Asn Ser Gly Ala Leu Thr Ser Gly Val His Thr Phe Pro Ala
385                 390                 395                 400

Val Leu Gln Ser Ser Gly Leu Tyr Ser Leu Ser Ser Val Val Thr Val
                405                 410                 415

Pro Ser Ser Ser Leu Gly Thr Gln Thr Tyr Ile Cys Asn Val Asn His
            420                 425                 430

Lys Pro Ser Asn Thr Lys Val Asp Glu Lys Val Glu Pro Lys Ser Cys
            435                 440                 445

Asp Lys Thr His Thr Cys Pro Pro Cys Pro Ala Pro Glu Ala Ala Gly
            450                 455                 460

Gly Pro Ser Val Phe Leu Phe Pro Pro Lys Pro Lys Asp Thr Leu Met
465                 470                 475                 480

Ile Ser Arg Thr Pro Glu Val Thr Cys Val Val Val Asp Val Ser His
                485                 490                 495

Glu Asp Pro Glu Val Lys Phe Asn Trp Tyr Val Asp Gly Val Glu Val
            500                 505                 510

His Asn Ala Lys Thr Lys Pro Arg Glu Glu Gln Tyr Asn Ser Thr Tyr
            515                 520                 525

Arg Val Val Ser Val Leu Thr Val Leu His Gln Asp Trp Leu Asn Gly
530                 535                 540

Lys Glu Tyr Lys Cys Lys Val Ser Asn Lys Ala Leu Gly Ala Pro Ile
545                 550                 555                 560

Glu Lys Thr Ile Ser Lys Ala Lys Gly Gln Pro Arg Glu Pro Gln Val
                565                 570                 575

Cys Thr Leu Pro Pro Ser Arg Asp Glu Leu Thr Lys Asn Gln Val Ser
            580                 585                 590

Leu Ser Cys Ala Val Lys Gly Phe Tyr Pro Ser Asp Ile Ala Val Glu
            595                 600                 605

Trp Glu Ser Asn Gly Gln Pro Glu Asn Asn Tyr Lys Thr Thr Pro Pro
610                 615                 620

Val Leu Asp Ser Asp Gly Ser Phe Phe Leu Val Ser Lys Leu Thr Val
```

```
                    625                 630                 635                 640
Asp Lys Ser Arg Trp Gln Gln Gly Asn Val Phe Ser Cys Ser Val Met
                        645                 650                 655

His Glu Ala Leu His Asn His Tyr Thr Gln Lys Ser Leu Ser Leu Ser
                        660                 665                 670

Pro Gly

<210> SEQ ID NO 96
<211> LENGTH: 217
<212> TYPE: PRT
<213> ORGANISM: Artificial Sequence
<220> FEATURE:
<223> OTHER INFORMATION: FAP(1G1a) VLCH1-light chain (EPKSCS)

<400> SEQUENCE: 96

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
                20                  25                  30

Gly Leu Ser Phe Ile Asn Trp Phe Gln Gln Lys Pro Gly Gln Ala Pro
            35                  40                  45

Arg Leu Leu Ile Tyr Gly Thr Ser Asn Arg Gly Ser Gly Ile Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Asn
                85                  90                  95

Glu Val Pro Tyr Thr Phe Gly Gly Gly Thr Lys Val Glu Ile Lys Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Ser
    210                 215

<210> SEQ ID NO 97
<211> LENGTH: 691
<212> TYPE: PRT
<213> ORGANISM: Artificial Sequence
<220> FEATURE:
<223> OTHER INFORMATION: OX40(CLC563) VHCH1- Fc knob_PGLALA- FAP(1G1a)
      VHCL

<400> SEQUENCE: 97

Glu Val Gln Leu Leu Glu Ser Gly Gly Gly Leu Val Gln Pro Gly Gly
1               5                   10                  15

Ser Leu Arg Leu Ser Cys Ala Ser Gly Phe Thr Phe Ser Ser Tyr
                20                  25                  30
```

```
Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Asp Val Gly Ala Phe Asp Tyr Trp Gly Gln Gly Ala Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Asp Lys Thr His Thr
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Cys Arg Asp Glu Leu Thr Lys Asn Gln Val Ser Leu Trp Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Gly Gly Gly
        435                 440                 445

Gly Ser Gly Gly Gly Gly Ser Gly Gly Gly Gly Ser Gly Gly Ser Gly
```

-continued

```
              450                 455                 460
Gly Gln Val Gln Leu Val Gln Ser Gly Ala Glu Val Lys Lys Pro Gly
465                 470                 475                 480

Ala Ser Val Lys Val Ser Cys Lys Ala Ser Gly Tyr Thr Leu Thr Asp
                485                 490                 495

Tyr Asn Met Asp Trp Val Arg Gln Ala Pro Gly Gln Gly Leu Glu Trp
            500                 505                 510

Ile Gly Asp Ile Tyr Pro Asn Thr Gly Gly Thr Ile Tyr Asn Gln Lys
        515                 520                 525

Phe Lys Gly Arg Val Thr Met Thr Ile Asp Thr Ser Thr Ser Thr Val
    530                 535                 540

Tyr Met Glu Leu Ser Ser Leu Arg Ser Glu Asp Thr Ala Val Tyr Tyr
545                 550                 555                 560

Cys Thr Arg Phe Arg Gly Ile His Tyr Ala Met Asp Tyr Trp Gly Gln
                565                 570                 575

Gly Thr Thr Val Thr Val Ser Ser Ala Ser Val Ala Ala Pro Ser Val
            580                 585                 590

Phe Ile Phe Pro Pro Ser Asp Glu Gln Leu Lys Ser Gly Thr Ala Ser
        595                 600                 605

Val Val Cys Leu Leu Asn Asn Phe Tyr Pro Arg Glu Ala Lys Val Gln
    610                 615                 620

Trp Lys Val Asp Asn Ala Leu Gln Ser Gly Asn Ser Gln Glu Ser Val
625                 630                 635                 640

Thr Glu Gln Asp Ser Lys Asp Ser Thr Tyr Ser Leu Ser Ser Thr Leu
                645                 650                 655

Thr Leu Ser Lys Ala Asp Tyr Glu Lys His Lys Val Tyr Ala Cys Glu
            660                 665                 670

Val Thr His Gln Gly Leu Ser Ser Pro Val Thr Lys Ser Phe Asn Arg
        675                 680                 685

Gly Glu Cys
    690

<210> SEQ ID NO 98
<211> LENGTH: 445
<212> TYPE: PRT
<213> ORGANISM: Artificial Sequence
<220> FEATURE:
<223> OTHER INFORMATION: OX40(CLC563) VHCH1 Fc hole_PGLALA

<400> SEQUENCE: 98

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Asp Val Gly Ala Phe Asp Tyr Trp Gly Gln Gly Ala Leu Val
            100                 105                 110

Thr Val Ser Ser Ala Ser Thr Lys Gly Pro Ser Val Phe Pro Leu Ala
```

-continued

```
            115                 120                 125
Pro Ser Ser Lys Ser Thr Ser Gly Gly Thr Ala Ala Leu Gly Cys Leu
130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Glu Lys Val Glu Pro Lys Ser Cys Asp Lys Thr His Thr
210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
            325                 330                 335

Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Ser Cys Ala Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445
```

<210> SEQ ID NO 99
<211> LENGTH: 692
<212> TYPE: PRT
<213> ORGANISM: Artificial Sequence
<220> FEATURE:
<223> OTHER INFORMATION: OX40(MOXR0916) VHCH1- Fc knob_PGLALA- FAP (1G1a) VHCL

<400> SEQUENCE: 99

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30
```

```
Tyr Met Ser Trp Val Arg Gln Ala Pro Gly Gln Gly Leu Glu Trp Ile
        35                  40                  45
Gly Asp Met Tyr Pro Asp Asn Gly Asp Ser Ser Tyr Asn Gln Lys Phe
 50                  55                  60
Arg Glu Arg Val Thr Ile Thr Arg Asp Thr Ser Thr Ser Thr Ala Tyr
 65                  70                  75                  80
Leu Glu Leu Ser Ser Leu Arg Ser Glu Asp Thr Ala Val Tyr Tyr Cys
                 85                  90                  95
Val Leu Ala Pro Arg Trp Tyr Phe Ser Val Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Glu Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Glu Lys Val Glu Pro Lys Ser Cys Asp Lys Thr His
    210                 215                 220
Thr Cys Pro Pro Cys Pro Ala Pro Glu Ala Ala Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Gly Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Cys Arg Asp Glu Leu Thr Lys Asn Gln Val Ser Leu Trp Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Gly Gly
        435                 440                 445
Gly Gly Ser Gly Gly Gly Gly Ser Gly Gly Gly Gly Ser Gly Gly Ser
```

```
            450                 455                 460
Gly Gly Gln Val Gln Leu Val Gln Ser Gly Ala Glu Val Lys Lys Pro
465                 470                 475                 480

Gly Ala Ser Val Lys Val Ser Cys Lys Ala Ser Gly Tyr Thr Leu Thr
                485                 490                 495

Asp Tyr Asn Met Asp Trp Val Arg Gln Ala Pro Gly Gln Gly Leu Glu
            500                 505                 510

Trp Ile Gly Asp Ile Tyr Pro Asn Thr Gly Gly Thr Ile Tyr Asn Gln
        515                 520                 525

Lys Phe Lys Gly Arg Val Thr Met Thr Ile Asp Thr Ser Thr Ser Thr
530                 535                 540

Val Tyr Met Glu Leu Ser Ser Leu Arg Ser Glu Asp Thr Ala Val Tyr
545                 550                 555                 560

Tyr Cys Thr Arg Phe Arg Gly Ile His Tyr Ala Met Asp Tyr Trp Gly
                565                 570                 575

Gln Gly Thr Thr Val Thr Val Ser Ser Ala Ser Val Ala Ala Pro Ser
            580                 585                 590

Val Phe Ile Phe Pro Pro Ser Asp Glu Gln Leu Lys Ser Gly Thr Ala
        595                 600                 605

Ser Val Val Cys Leu Leu Asn Asn Phe Tyr Pro Arg Glu Ala Lys Val
610                 615                 620

Gln Trp Lys Val Asp Asn Ala Leu Gln Ser Gly Asn Ser Gln Glu Ser
625                 630                 635                 640

Val Thr Glu Gln Asp Ser Lys Asp Ser Thr Tyr Ser Leu Ser Ser Thr
                645                 650                 655

Leu Thr Leu Ser Lys Ala Asp Tyr Glu Lys His Lys Val Tyr Ala Cys
            660                 665                 670

Glu Val Thr His Gln Gly Leu Ser Ser Pro Val Thr Lys Ser Phe Asn
        675                 680                 685

Arg Gly Glu Cys
    690

<210> SEQ ID NO 100
<211> LENGTH: 214
<212> TYPE: PRT
<213> ORGANISM: Artificial Sequence
<220> FEATURE:
<223> OTHER INFORMATION: OX40(MOXR0916) light chain

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Arg Lys Leu Lys Ser Gly
```

-continued

```
                115                 120                 125
Thr Ala Ser Val Val Cys Leu Leu Asn Asn Phe Tyr Pro Arg Glu Ala
            130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
                195                 200                 205
Phe Asn Arg Gly Glu Cys
            210
```

<210> SEQ ID NO 101
<211> LENGTH: 676
<212> TYPE: PRT
<213> ORGANISM: Artificial Sequence
<220> FEATURE:
<223> OTHER INFORMATION: OX40(MOXR0916) VHCH1- OX40(MOXR0916) VHCH1- Fc hole_PGLALA

<400> SEQUENCE: 101

```
Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Ser
                20                  25                  30
Tyr Met Ser Trp Val Arg Gln Ala Pro Gly Gln Gly Leu Glu Trp Ile
            35                  40                  45
Gly Asp Met Tyr Pro Asp Asn Gly Asp Ser Ser Tyr Asn Gln Lys Phe
        50                  55                  60
Arg Glu Arg Val Thr Ile Thr Arg Asp Thr Ser Thr Ser Thr Ala Tyr
65                  70                  75                  80
Leu Glu Leu Ser Ser Leu Arg Ser Glu Asp Thr Ala Val Tyr Tyr Cys
                85                  90                  95
Val Leu Ala Pro Arg Trp Tyr Phe Ser Val Trp Gly Gln Gly Thr Leu
                100                 105                 110
Val Thr Val Ser Ser Ala Ser Thr Lys Gly Pro Ser Val Phe Pro Leu
            115                 120                 125
Ala Pro Ser Ser Lys Ser Thr Ser Gly Gly Thr Ala Ala Leu Gly Cys
        130                 135                 140
Leu Val Glu Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Glu Lys Val Glu Pro Lys Ser Cys Gly Gly Gly Gly
    210                 215                 220
Ser Gly Gly Ser Gly Gly Glu Val Gln Leu Val Gln Ser Gly Ala Glu
225                 230                 235                 240
Val Lys Lys Pro Gly Ala Ser Val Lys Val Ser Cys Lys Ala Ser Gly
                245                 250                 255
```

-continued

```
Tyr Thr Phe Thr Asp Ser Tyr Met Ser Trp Val Arg Gln Ala Pro Gly
            260                 265                 270

Gln Gly Leu Glu Trp Ile Gly Asp Met Tyr Pro Asp Asn Gly Asp Ser
            275                 280                 285

Ser Tyr Asn Gln Lys Phe Arg Glu Arg Val Thr Ile Thr Arg Asp Thr
    290                 295                 300

Ser Thr Ser Thr Ala Tyr Leu Glu Leu Ser Ser Leu Arg Ser Glu Asp
305                 310                 315                 320

Thr Ala Val Tyr Tyr Cys Val Leu Ala Pro Arg Trp Tyr Phe Ser Val
                325                 330                 335

Trp Gly Gln Gly Thr Leu Val Thr Val Ser Ser Ala Ser Thr Lys Gly
            340                 345                 350

Pro Ser Val Phe Pro Leu Ala Pro Ser Ser Lys Ser Thr Ser Gly Gly
            355                 360                 365

Thr Ala Ala Leu Gly Cys Leu Val Glu Asp Tyr Phe Pro Glu Pro Val
    370                 375                 380

Thr Val Ser Trp Asn Ser Gly Ala Leu Thr Ser Gly Val His Thr Phe
385                 390                 395                 400

Pro Ala Val Leu Gln Ser Ser Gly Leu Tyr Ser Leu Ser Ser Val Val
                405                 410                 415

Thr Val Pro Ser Ser Ser Leu Gly Thr Gln Thr Tyr Ile Cys Asn Val
            420                 425                 430

Asn His Lys Pro Ser Asn Thr Lys Val Asp Glu Lys Val Glu Pro Lys
            435                 440                 445

Ser Cys Asp Lys Thr His Thr Cys Pro Pro Cys Pro Ala Pro Glu Ala
    450                 455                 460

Ala Gly Gly Pro Ser Val Phe Leu Phe Pro Pro Lys Pro Lys Asp Thr
465                 470                 475                 480

Leu Met Ile Ser Arg Thr Pro Glu Val Thr Cys Val Val Val Asp Val
                485                 490                 495

Ser His Glu Asp Pro Glu Val Lys Phe Asn Trp Tyr Val Asp Gly Val
            500                 505                 510

Glu Val His Asn Ala Lys Thr Lys Pro Arg Glu Glu Gln Tyr Asn Ser
            515                 520                 525

Thr Tyr Arg Val Val Ser Val Leu Thr Val Leu His Gln Asp Trp Leu
    530                 535                 540

Asn Gly Lys Glu Tyr Lys Cys Lys Val Ser Asn Lys Ala Leu Gly Ala
545                 550                 555                 560

Pro Ile Glu Lys Thr Ile Ser Lys Ala Lys Gly Gln Pro Arg Glu Pro
                565                 570                 575

Gln Val Cys Thr Leu Pro Pro Ser Arg Asp Glu Leu Thr Lys Asn Gln
            580                 585                 590

Val Ser Leu Ser Cys Ala Val Lys Gly Phe Tyr Pro Ser Asp Ile Ala
            595                 600                 605

Val Glu Trp Glu Ser Asn Gly Gln Pro Glu Asn Tyr Lys Thr Thr
    610                 615                 620

Pro Pro Val Leu Asp Ser Asp Gly Ser Phe Phe Leu Val Ser Lys Leu
625                 630                 635                 640

Thr Val Asp Lys Ser Arg Trp Gln Gln Gly Asn Val Phe Ser Cys Ser
                645                 650                 655

Val Met His Glu Ala Leu His Asn His Tyr Thr Gln Lys Ser Leu Ser
            660                 665                 670

Leu Ser Pro Gly
```

-continued

```
            675

<210> SEQ ID NO 102
<211> LENGTH: 446
<212> TYPE: PRT
<213> ORGANISM: Artificial Sequence
<220> FEATURE:
<223> OTHER INFORMATION: OX40(MOXR0916) VHCH1- Fc hole_PGLALA

<400> SEQUENCE: 102
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Glu Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Glu Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Cys Thr Leu Pro
            340                 345                 350

Pro Ser Arg Asp Glu Leu Thr Lys Asn Gln Val Ser Leu Ser Cys Ala

```
            355                 360                 365
Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 103
<211> LENGTH: 691
<212> TYPE: PRT
<213> ORGANISM: Artificial Sequence
<220> FEATURE:
<223> OTHER INFORMATION: OX40(8H9) VHCH1- Fc knob_PGLALA-FAP(1G1a) VHCL

<400> SEQUENCE: 103

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Gly Trp Met Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
```

-continued

```
                275                 280                 285
Lys Pro Arg Glu Glu Gln Tyr Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Ala Leu Gly Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Cys Arg Asp Glu Leu Thr Lys Asn Gln Val Ser Leu Trp Cys Leu Val
            355                 360                 365
Lys Gly Phe Tyr Pro Ser Asp Ile Ala Val Glu Trp Glu Ser Asn Gly
            370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Gly Gly Gly
            435                 440                 445
Gly Ser Gly Gly Gly Gly Ser Gly Gly Gly Gly Ser Gly Gly Ser Gly
450                 455                 460
Gly Gln Val Gln Leu Val Gln Ser Gly Ala Glu Val Lys Lys Pro Gly
465                 470                 475                 480
Ala Ser Val Lys Val Ser Cys Lys Ala Ser Gly Tyr Thr Leu Thr Asp
                485                 490                 495
Tyr Asn Met Asp Trp Val Arg Gln Ala Pro Gly Gln Gly Leu Glu Trp
            500                 505                 510
Ile Gly Asp Ile Tyr Pro Asn Thr Gly Gly Thr Ile Tyr Asn Gln Lys
            515                 520                 525
Phe Lys Gly Arg Val Thr Met Thr Ile Asp Thr Ser Thr Ser Thr Val
530                 535                 540
Tyr Met Glu Leu Ser Ser Leu Arg Ser Glu Asp Thr Ala Val Tyr Tyr
545                 550                 555                 560
Cys Thr Arg Phe Arg Gly Ile His Tyr Ala Met Asp Tyr Trp Gly Gln
                565                 570                 575
Gly Thr Thr Val Thr Val Ser Ser Ala Ser Val Ala Ala Pro Ser Val
            580                 585                 590
Phe Ile Phe Pro Pro Ser Asp Glu Gln Leu Lys Ser Gly Thr Ala Ser
            595                 600                 605
Val Val Cys Leu Leu Asn Asn Phe Tyr Pro Arg Glu Ala Lys Val Gln
            610                 615                 620
Trp Lys Val Asp Asn Ala Leu Gln Ser Gly Asn Ser Gln Glu Ser Val
625                 630                 635                 640
Thr Glu Gln Asp Ser Lys Asp Ser Thr Tyr Ser Leu Ser Ser Thr Leu
                645                 650                 655
Thr Leu Ser Lys Ala Asp Tyr Glu Lys His Lys Val Tyr Ala Cys Glu
            660                 665                 670
Val Thr His Gln Gly Leu Ser Ser Pro Val Thr Lys Ser Phe Asn Arg
            675                 680                 685
Gly Glu Cys
690
```

<210> SEQ ID NO 104
<211> LENGTH: 215
<212> TYPE: PRT
<213> ORGANISM: Artificial Sequence
<220> FEATURE:
<223> OTHER INFORMATION: OX40(8H9) light chain

<400> SEQUENCE: 104

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Leu Thr Tyr Ser Arg
                85                  90                  95

Phe Thr Phe Gly Gln Gly Thr Lys Val Glu Ile Lys Arg Thr Val Ala
            100                 105                 110

Ala Pro Ser Val Phe Ile Phe Pro Pro Ser Asp Arg Lys Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 105
<211> LENGTH: 674
<212> TYPE: PRT
<213> ORGANISM: Artificial Sequence
<220> FEATURE:
<223> OTHER INFORMATION: OX40(8H9) VHCH1- OX40(8H9) VHCH1- Fc
      hole_PGLALA

<400> SEQUENCE: 105

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ala Arg Glu Tyr Gly Trp Met Asp Tyr Trp Gly Gln Gly Thr Thr Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Glu Lys Val Glu Pro Lys Ser Cys Gly Gly Gly Gly Ser
        210                 215                 220

Gly Gly Ser Gly Gly Gln Val Gln Leu Val Gln Ser Gly Ala Glu Val
225                 230                 235                 240

Lys Lys Pro Gly Ser Ser Val Lys Val Ser Cys Lys Ala Ser Gly Gly
                245                 250                 255

Thr Phe Ser Ser Tyr Ala Ile Ser Trp Val Arg Gln Ala Pro Gly Gln
            260                 265                 270

Gly Leu Glu Trp Met Gly Gly Ile Ile Pro Ile Phe Gly Thr Ala Asn
            275                 280                 285

Tyr Ala Gln Lys Phe Gln Gly Arg Val Thr Ile Thr Ala Asp Lys Ser
        290                 295                 300

Thr Ser Thr Ala Tyr Met Glu Leu Ser Ser Leu Arg Ser Glu Asp Thr
305                 310                 315                 320

Ala Val Tyr Tyr Cys Ala Arg Glu Tyr Gly Trp Met Asp Tyr Trp Gly
                325                 330                 335

Gln Gly Thr Thr Val Thr Val Ser Ser Ala Ser Thr Lys Gly Pro Ser
            340                 345                 350

Val Phe Pro Leu Ala Pro Ser Ser Lys Ser Thr Ser Gly Gly Thr Ala
            355                 360                 365

Ala Leu Gly Cys Leu Val Glu Asp Tyr Phe Pro Glu Pro Val Thr Val
        370                 375                 380

Ser Trp Asn Ser Gly Ala Leu Thr Ser Gly Val His Thr Phe Pro Ala
385                 390                 395                 400

Val Leu Gln Ser Ser Gly Leu Tyr Ser Leu Ser Ser Val Val Thr Val
                405                 410                 415

Pro Ser Ser Ser Leu Gly Thr Gln Thr Tyr Ile Cys Asn Val Asn His
            420                 425                 430

Lys Pro Ser Asn Thr Lys Val Asp Glu Lys Val Glu Pro Lys Ser Cys
        435                 440                 445

Asp Lys Thr His Thr Cys Pro Pro Cys Pro Ala Pro Glu Ala Ala Gly
        450                 455                 460

Gly Pro Ser Val Phe Leu Phe Pro Pro Lys Pro Lys Asp Thr Leu Met
465                 470                 475                 480

Ile Ser Arg Thr Pro Glu Val Thr Cys Val Val Val Asp Val Ser His
                485                 490                 495

Glu Asp Pro Glu Val Lys Phe Asn Trp Tyr Val Asp Gly Val Glu Val
```

-continued

```
                500                 505                 510
His Asn Ala Lys Thr Lys Pro Arg Glu Glu Gln Tyr Asn Ser Thr Tyr
            515                 520                 525

Arg Val Val Ser Val Leu Thr Val Leu His Gln Asp Trp Leu Asn Gly
        530                 535                 540

Lys Glu Tyr Lys Cys Lys Val Ser Asn Lys Ala Leu Gly Ala Pro Ile
545                 550                 555                 560

Glu Lys Thr Ile Ser Lys Ala Lys Gly Gln Pro Arg Glu Pro Gln Val
                565                 570                 575

Cys Thr Leu Pro Pro Ser Arg Asp Glu Leu Thr Lys Asn Gln Val Ser
            580                 585                 590

Leu Ser Cys Ala Val Lys Gly Phe Tyr Pro Ser Asp Ile Ala Val Glu
        595                 600                 605

Trp Glu Ser Asn Gly Gln Pro Glu Asn Asn Tyr Lys Thr Thr Pro Pro
610                 615                 620

Val Leu Asp Ser Asp Gly Ser Phe Phe Leu Val Ser Lys Leu Thr Val
625                 630                 635                 640

Asp Lys Ser Arg Trp Gln Gln Gly Asn Val Phe Ser Cys Ser Val Met
                645                 650                 655

His Glu Ala Leu His Asn His Tyr Thr Gln Lys Ser Leu Ser Leu Ser
            660                 665                 670

Pro Gly

<210> SEQ ID NO 106
<211> LENGTH: 445
<212> TYPE: PRT
<213> ORGANISM: Artificial Sequence
<220> FEATURE:
<223> OTHER INFORMATION: OX40(8H9) VHCH1- Fc hole_PGLALA

<400> SEQUENCE: 106

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Gly Trp Met Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190
```

Gly Thr Gln Thr Tyr Ile Cys Asn Val Asn His Lys Pro Ser Asn Thr
            195                 200                 205

Lys Val Asp Glu Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Cys Thr Leu Pro Pro
            340                 345                 350

Ser Arg Asp Glu Leu Thr Lys Asn Gln Val Ser Leu Ser Cys Ala Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
    435                 440                 445

<210> SEQ ID NO 107
<211> LENGTH: 924
<212> TYPE: PRT
<213> ORGANISM: Artificial Sequence
<220> FEATURE:
<223> OTHER INFORMATION: OX40(49B4_K73E) VHCH1- OX40(49B4_K73E) VHCH1-
      Fc knob_PGLALA- FAP(1G1a) VHCL

<400> SEQUENCE: 107

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr

```
            100                 105                 110
Thr Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
            130                 135                 140
Cys Leu Val Glu Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                    165                 170                 175
Ser Ser Gly Leu Tyr Ser Leu Ser Ser Val Val Thr Val Pro Ser Ser
                    180                 185                 190
Ser Leu Gly Thr Gln Thr Tyr Ile Cys Asn Val Asn His Lys Pro Ser
                    195                 200                 205
Asn Thr Lys Val Asp Glu Lys Val Glu Pro Lys Ser Cys Gly Gly Gly
            210                 215                 220
Gly Ser Gly Gly Ser Gly Gly Gln Val Gln Leu Val Gln Ser Gly Ala
225                 230                 235                 240
Glu Val Lys Lys Pro Gly Ser Ser Val Lys Val Ser Cys Lys Ala Ser
                    245                 250                 255
Gly Gly Thr Phe Ser Ser Tyr Ala Ile Ser Trp Val Arg Gln Ala Pro
                    260                 265                 270
Gly Gln Gly Leu Glu Trp Met Gly Gly Ile Ile Pro Ile Phe Gly Thr
                    275                 280                 285
Ala Asn Tyr Ala Gln Lys Phe Gln Gly Arg Val Thr Ile Thr Ala Asp
            290                 295                 300
Glu Ser Thr Ser Thr Ala Tyr Met Glu Leu Ser Ser Leu Arg Ser Glu
305                 310                 315                 320
Asp Thr Ala Val Tyr Tyr Cys Ala Arg Glu Tyr Arg Gly Pro Tyr
                    325                 330                 335
Asp Tyr Trp Gly Gln Gly Thr Thr Val Thr Val Ser Ser Ala Ser Thr
                    340                 345                 350
Lys Gly Pro Ser Val Phe Pro Leu Ala Pro Ser Ser Lys Ser Thr Ser
                    355                 360                 365
Gly Gly Thr Ala Ala Leu Gly Cys Leu Val Glu Asp Tyr Phe Pro Glu
            370                 375                 380
Pro Val Thr Val Ser Trp Asn Ser Gly Ala Leu Thr Ser Gly Val His
385                 390                 395                 400
Thr Phe Pro Ala Val Leu Gln Ser Ser Gly Leu Tyr Ser Leu Ser Ser
                    405                 410                 415
Val Val Thr Val Pro Ser Ser Ser Leu Gly Thr Gln Thr Tyr Ile Cys
                    420                 425                 430
Asn Val Asn His Lys Pro Ser Asn Thr Lys Val Asp Glu Lys Val Glu
                    435                 440                 445
Pro Lys Ser Cys Asp Lys Thr His Thr Cys Pro Pro Cys Pro Ala Pro
            450                 455                 460
Glu Ala Ala Gly Gly Pro Ser Val Phe Leu Phe Pro Pro Lys Pro Lys
465                 470                 475                 480
Asp Thr Leu Met Ile Ser Arg Thr Pro Glu Val Thr Cys Val Val Val
                    485                 490                 495
Asp Val Ser His Glu Asp Pro Glu Val Lys Phe Asn Trp Tyr Val Asp
                    500                 505                 510
Gly Val Glu Val His Asn Ala Lys Thr Lys Pro Arg Glu Glu Gln Tyr
                    515                 520                 525
```

Asn Ser Thr Tyr Arg Val Val Ser Val Leu Thr Val His Gln Asp
    530                 535                 540

Trp Leu Asn Gly Lys Glu Tyr Lys Cys Lys Val Ser Asn Lys Ala Leu
545                 550                 555                 560

Gly Ala Pro Ile Glu Lys Thr Ile Ser Lys Ala Lys Gly Gln Pro Arg
                565                 570                 575

Glu Pro Gln Val Tyr Thr Leu Pro Pro Cys Arg Asp Glu Leu Thr Lys
            580                 585                 590

Asn Gln Val Ser Leu Trp Cys Leu Val Lys Gly Phe Tyr Pro Ser Asp
        595                 600                 605

Ile Ala Val Glu Trp Glu Ser Asn Gly Gln Pro Glu Asn Asn Tyr Lys
610                 615                 620

Thr Thr Pro Pro Val Leu Asp Ser Asp Gly Ser Phe Phe Leu Tyr Ser
625                 630                 635                 640

Lys Leu Thr Val Asp Lys Ser Arg Trp Gln Gln Gly Asn Val Phe Ser
                645                 650                 655

Cys Ser Val Met His Glu Ala Leu His Asn His Tyr Thr Gln Lys Ser
                660                 665                 670

Leu Ser Leu Ser Pro Gly Gly Gly Gly Ser Gly Gly Gly Ser
            675                 680                 685

Gly Gly Gly Gly Ser Gly Ser Gly Gly Gln Val Gln Leu Val Gln
690                 695                 700

Ser Gly Ala Glu Val Lys Lys Pro Gly Ala Ser Val Lys Val Ser Cys
705                 710                 715                 720

Lys Ala Ser Gly Tyr Thr Leu Thr Asp Tyr Asn Met Asp Trp Val Arg
                725                 730                 735

Gln Ala Pro Gly Gln Gly Leu Glu Trp Ile Gly Asp Ile Tyr Pro Asn
            740                 745                 750

Thr Gly Gly Thr Ile Tyr Asn Gln Lys Phe Lys Gly Arg Val Thr Met
        755                 760                 765

Thr Ile Asp Thr Ser Thr Ser Thr Val Tyr Met Glu Leu Ser Ser Leu
770                 775                 780

Arg Ser Glu Asp Thr Ala Val Tyr Tyr Cys Thr Arg Phe Arg Gly Ile
785                 790                 795                 800

His Tyr Ala Met Asp Tyr Trp Gly Gln Gly Thr Thr Val Thr Val Ser
                805                 810                 815

Ser Ala Ser Val Ala Ala Pro Ser Val Phe Ile Phe Pro Pro Ser Asp
            820                 825                 830

Glu Gln Leu Lys Ser Gly Thr Ala Ser Val Val Cys Leu Leu Asn Asn
        835                 840                 845

Phe Tyr Pro Arg Glu Ala Lys Val Gln Trp Lys Val Asp Asn Ala Leu
850                 855                 860

Gln Ser Gly Asn Ser Gln Glu Ser Val Thr Glu Gln Asp Ser Lys Asp
865                 870                 875                 880

Ser Thr Tyr Ser Leu Ser Ser Thr Leu Thr Leu Ser Lys Ala Asp Tyr
                885                 890                 895

Glu Lys His Lys Val Tyr Ala Cys Glu Val Thr His Gln Gly Leu Ser
            900                 905                 910

Ser Pro Val Thr Lys Ser Phe Asn Arg Gly Glu Cys
        915                 920

<210> SEQ ID NO 108
<211> LENGTH: 678

```
<212> TYPE: PRT
<213> ORGANISM: Artificial Sequence
<220> FEATURE:
<223> OTHER INFORMATION: OX40(49B4_K73E) VHCH1-OX40(49B4_K73E) VHCH1-Fc
      hole_PGLALA

<400> SEQUENCE: 108
```

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ser |
| 1 | | | | 5 | | | | | 10 | | | | | 15 | |
| Ser | Val | Lys | Val | Ser | Cys | Lys | Ala | Ser | Gly | Gly | Thr | Phe | Ser | Ser | Tyr |
| | | | 20 | | | | | 25 | | | | | 30 | | |
| Ala | Ile | Ser | Trp | Val | Arg | Gln | Ala | Pro | Gly | Gln | Gly | Leu | Glu | Trp | Met |
| | | | 35 | | | | | 40 | | | | | 45 | | |
| Gly | Gly | Ile | Ile | Pro | Ile | Phe | Gly | Thr | Ala | Asn | Tyr | Ala | Gln | Lys | Phe |
| 50 | | | | | 55 | | | | | 60 | | | | | |
| Gln | Gly | Arg | Val | Thr | Ile | Thr | Ala | Asp | Glu | Ser | Thr | Ser | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Arg | Glu | Tyr | Tyr | Arg | Gly | Pro | Tyr | Asp | Tyr | Trp | Gly | Gln | Gly | Thr |
| | | | 100 | | | | | 105 | | | | | 110 | | |
| Thr | Val | Thr | Val | Ser | Ser | Ala | Ser | Thr | Lys | Gly | Pro | Ser | Val | Phe | Pro |
| | | | 115 | | | | | 120 | | | | | 125 | | |
| Leu | Ala | Pro | Ser | Ser | Lys | Ser | Thr | Ser | Gly | Gly | Thr | Ala | Ala | Leu | Gly |
| 130 | | | | | 135 | | | | | 140 | | | | | |
| Cys | Leu | Val | Glu | Asp | Tyr | Phe | Pro | Glu | Pro | Val | Thr | Val | Ser | Trp | Asn |
| 145 | | | | | 150 | | | | | 155 | | | | | 160 |
| Ser | Gly | Ala | Leu | Thr | Ser | Gly | Val | His | Thr | Phe | Pro | Ala | Val | Leu | Gln |
| | | | | 165 | | | | | 170 | | | | | 175 | |
| Ser | Ser | Gly | Leu | Tyr | Ser | Leu | Ser | Val | Val | Thr | Val | Pro | Ser | Ser | |
| | | | 180 | | | | | 185 | | | | | 190 | | |
| Ser | Leu | Gly | Thr | Gln | Thr | Tyr | Ile | Cys | Asn | Val | Asn | His | Lys | Pro | Ser |
| | | | 195 | | | | | 200 | | | | | 205 | | |
| Asn | Thr | Lys | Val | Asp | Glu | Lys | Val | Glu | Pro | Lys | Ser | Cys | Gly | Gly | Gly |
| 210 | | | | | 215 | | | | | 220 | | | | | |
| Gly | Ser | Gly | Gly | Ser | Gly | Gly | Gln | Val | Gln | Leu | Val | Gln | Ser | Gly | Ala |
| 225 | | | | | 230 | | | | | 235 | | | | | 240 |
| Glu | Val | Lys | Lys | Pro | Gly | Ser | Ser | Val | Lys | Val | Ser | Cys | Lys | Ala | Ser |
| | | | | 245 | | | | | 250 | | | | | 255 | |
| Gly | Gly | Thr | Phe | Ser | Ser | Tyr | Ala | Ile | Ser | Trp | Val | Arg | Gln | Ala | Pro |
| | | | 260 | | | | | 265 | | | | | 270 | | |
| Gly | Gln | Gly | Leu | Glu | Trp | Met | Gly | Gly | Ile | Ile | Pro | Ile | Phe | Gly | Thr |
| | | | 275 | | | | | 280 | | | | | 285 | | |
| Ala | Asn | Tyr | Ala | Gln | Lys | Phe | Gln | Gly | Arg | Val | Thr | Ile | Thr | Ala | Asp |
| | | | 290 | | | | | 295 | | | | | 300 | | |
| Glu | Ser | Thr | Ser | Thr | Ala | Tyr | Met | Glu | Leu | Ser | Ser | Leu | Arg | Ser | Glu |
| 305 | | | | | 310 | | | | | 315 | | | | | 320 |
| Asp | Thr | Ala | Val | Tyr | Tyr | Cys | Ala | Arg | Glu | Tyr | Tyr | Arg | Gly | Pro | Tyr |
| | | | | 325 | | | | | 330 | | | | | 335 | |
| Asp | Tyr | Trp | Gly | Gln | Gly | Thr | Thr | Val | Thr | Val | Ser | Ser | Ala | Ser | Thr |
| | | | 340 | | | | | 345 | | | | | 350 | | |
| Lys | Gly | Pro | Ser | Val | Phe | Pro | Leu | Ala | Pro | Ser | Ser | Lys | Ser | Thr | Ser |
| | | | 355 | | | | | 360 | | | | | 365 | | |
| Gly | Gly | Thr | Ala | Ala | Leu | Gly | Cys | Leu | Val | Glu | Asp | Tyr | Phe | Pro | Glu |
| 370 | | | | | 375 | | | | | 380 | | | | | |

Pro Val Thr Val Ser Trp Asn Ser Gly Ala Leu Thr Ser Gly Val His
385                 390                 395                 400

Thr Phe Pro Ala Val Leu Gln Ser Ser Gly Leu Tyr Ser Leu Ser Ser
            405                 410                 415

Val Val Thr Val Pro Ser Ser Ser Leu Gly Thr Gln Thr Tyr Ile Cys
            420                 425                 430

Asn Val Asn His Lys Pro Ser Asn Thr Lys Val Asp Glu Lys Val Glu
            435                 440                 445

Pro Lys Ser Cys Asp Lys Thr His Thr Cys Pro Pro Cys Pro Ala Pro
450                 455                 460

Glu Ala Ala Gly Gly Pro Ser Val Phe Leu Phe Pro Pro Lys Pro Lys
465                 470                 475                 480

Asp Thr Leu Met Ile Ser Arg Thr Pro Glu Val Thr Cys Val Val Val
            485                 490                 495

Asp Val Ser His Glu Asp Pro Glu Val Lys Phe Asn Trp Tyr Val Asp
            500                 505                 510

Gly Val Glu Val His Asn Ala Lys Thr Lys Pro Arg Glu Glu Gln Tyr
            515                 520                 525

Asn Ser Thr Tyr Arg Val Val Ser Val Leu Thr Val Leu His Gln Asp
530                 535                 540

Trp Leu Asn Gly Lys Glu Tyr Lys Cys Lys Val Ser Asn Lys Ala Leu
545                 550                 555                 560

Gly Ala Pro Ile Glu Lys Thr Ile Ser Lys Ala Lys Gly Gln Pro Arg
            565                 570                 575

Glu Pro Gln Val Cys Thr Leu Pro Pro Ser Arg Asp Glu Leu Thr Lys
            580                 585                 590

Asn Gln Val Ser Leu Ser Cys Ala Val Lys Gly Phe Tyr Pro Ser Asp
            595                 600                 605

Ile Ala Val Glu Trp Glu Ser Asn Gly Gln Pro Glu Asn Asn Tyr Lys
610                 615                 620

Thr Thr Pro Pro Val Leu Asp Ser Asp Gly Ser Phe Phe Leu Val Ser
625                 630                 635                 640

Lys Leu Thr Val Asp Lys Ser Arg Trp Gln Gln Gly Asn Val Phe Ser
            645                 650                 655

Cys Ser Val Met His Glu Ala Leu His Asn His Tyr Thr Gln Lys Ser
            660                 665                 670

Leu Ser Leu Ser Pro Gly
            675

<210> SEQ ID NO 109
<211> LENGTH: 924
<212> TYPE: PRT
<213> ORGANISM: Artificial Sequence
<220> FEATURE:
<223> OTHER INFORMATION: OX40(49B4_K23T_K73E) VHCH1-
      OX40(49B4_K23T_K73E) VHCH1- Fc knob_PGLALA- FAP(1G1a) VHCL

<400> SEQUENCE: 109

Gln Val Gln Leu Val Gln Ser Gly Ala Glu Val Lys Lys Pro Gly Ser
1               5                   10                  15

Ser Val Lys Val Ser Cys Thr Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe

```
                50                  55                  60
        Gln Gly Arg Val Thr Ile Thr Ala Asp Glu Ser Thr Ser Thr Ala Tyr
         65                  70                  75                  80

Met Glu Leu Ser Ser Leu Arg Ser Glu Asp Thr Ala Val Tyr Tyr Cys
                             85                  90                  95

Ala Arg Glu Tyr Tyr Arg Gly Pro Tyr Asp Tyr Trp Gly Gln Gly Thr
                        100                 105                 110

Thr Val Thr Val Ser Ser Ala Ser Thr Lys Gly Pro Ser Val Phe Pro
                    115                 120                 125

Leu Ala Pro Ser Ser Lys Ser Thr Ser Gly Gly Thr Ala Ala Leu Gly
                130                 135                 140

Cys Leu Val Glu Asp Tyr Phe Pro Glu Pro Val Thr Val Ser Trp Asn
        145                 150                 155                 160

Ser Gly Ala Leu Thr Ser Gly Val His Thr Phe Pro Ala Val Leu Gln
                        165                 170                 175

Ser Ser Gly Leu Tyr Ser Leu Ser Ser Val Val Thr Val Pro Ser Ser
                        180                 185                 190

Ser Leu Gly Thr Gln Thr Tyr Ile Cys Asn Val Asn His Lys Pro Ser
                        195                 200                 205

Asn Thr Lys Val Asp Glu Lys Val Glu Pro Lys Ser Cys Gly Gly Gly
        210                 215                 220

Gly Ser Gly Gly Ser Gly Gly Gln Val Gln Leu Val Gln Ser Gly Ala
        225                 230                 235                 240

Glu Val Lys Lys Pro Gly Ser Ser Val Lys Val Ser Cys Thr Ala Ser
                        245                 250                 255

Gly Gly Thr Phe Ser Ser Tyr Ala Ile Ser Trp Val Arg Gln Ala Pro
                        260                 265                 270

Gly Gln Gly Leu Glu Trp Met Gly Gly Ile Ile Pro Ile Phe Gly Thr
                        275                 280                 285

Ala Asn Tyr Ala Gln Lys Phe Gln Gly Arg Val Thr Ile Thr Ala Asp
                        290                 295                 300

Glu Ser Thr Ser Thr Ala Tyr Met Glu Leu Ser Ser Leu Arg Ser Glu
        305                 310                 315                 320

Asp Thr Ala Val Tyr Tyr Cys Ala Arg Glu Tyr Tyr Arg Gly Pro Tyr
                        325                 330                 335

Asp Tyr Trp Gly Gln Gly Thr Thr Val Thr Val Ser Ser Ala Ser Thr
                        340                 345                 350

Lys Gly Pro Ser Val Phe Pro Leu Ala Pro Ser Ser Lys Ser Thr Ser
                        355                 360                 365

Gly Gly Thr Ala Ala Leu Gly Cys Leu Val Glu Asp Tyr Phe Pro Glu
                        370                 375                 380

Pro Val Thr Val Ser Trp Asn Ser Gly Ala Leu Thr Ser Gly Val His
        385                 390                 395                 400

Thr Phe Pro Ala Val Leu Gln Ser Ser Gly Leu Tyr Ser Leu Ser Ser
                        405                 410                 415

Val Val Thr Val Pro Ser Ser Ser Leu Gly Thr Gln Thr Tyr Ile Cys
                        420                 425                 430

Asn Val Asn His Lys Pro Ser Asn Thr Lys Val Asp Glu Lys Val Glu
                        435                 440                 445

Pro Lys Ser Cys Asp Lys Thr His Thr Cys Pro Pro Cys Pro Ala Pro
                        450                 455                 460

Glu Ala Ala Gly Gly Pro Ser Val Phe Leu Phe Pro Pro Lys Pro Lys
        465                 470                 475                 480
```

```
Asp Thr Leu Met Ile Ser Arg Thr Pro Glu Val Thr Cys Val Val Val
                485                 490                 495
Asp Val Ser His Glu Asp Pro Glu Val Lys Phe Asn Trp Tyr Val Asp
                500                 505                 510
Gly Val Glu Val His Asn Ala Lys Thr Lys Pro Arg Glu Glu Gln Tyr
                515                 520                 525
Asn Ser Thr Tyr Arg Val Val Ser Val Leu Thr Val Leu His Gln Asp
                530                 535                 540
Trp Leu Asn Gly Lys Glu Tyr Lys Cys Lys Val Ser Asn Lys Ala Leu
545                 550                 555                 560
Gly Ala Pro Ile Glu Lys Thr Ile Ser Lys Ala Lys Gly Gln Pro Arg
                565                 570                 575
Glu Pro Gln Val Tyr Thr Leu Pro Pro Cys Arg Asp Glu Leu Thr Lys
                580                 585                 590
Asn Gln Val Ser Leu Trp Cys Leu Val Lys Gly Phe Tyr Pro Ser Asp
                595                 600                 605
Ile Ala Val Glu Trp Glu Ser Asn Gly Gln Pro Glu Asn Asn Tyr Lys
                610                 615                 620
Thr Thr Pro Pro Val Leu Asp Ser Asp Gly Ser Phe Phe Leu Tyr Ser
625                 630                 635                 640
Lys Leu Thr Val Asp Lys Ser Arg Trp Gln Gln Gly Asn Val Phe Ser
                645                 650                 655
Cys Ser Val Met His Glu Ala Leu His Asn His Tyr Thr Gln Lys Ser
                660                 665                 670
Leu Ser Leu Ser Pro Gly Gly Gly Gly Ser Gly Gly Gly Gly Ser
                675                 680                 685
Gly Gly Gly Gly Ser Gly Gly Ser Gly Gly Gln Val Gln Leu Val Gln
                690                 695                 700
Ser Gly Ala Glu Val Lys Lys Pro Gly Ala Ser Val Lys Val Ser Cys
705                 710                 715                 720
Lys Ala Ser Gly Tyr Thr Leu Thr Asp Tyr Asn Met Asp Trp Val Arg
                725                 730                 735
Gln Ala Pro Gly Gln Gly Leu Glu Trp Ile Gly Asp Ile Tyr Pro Asn
                740                 745                 750
Thr Gly Gly Thr Ile Tyr Asn Gln Lys Phe Lys Gly Arg Val Thr Met
                755                 760                 765
Thr Ile Asp Thr Ser Thr Ser Thr Val Tyr Met Glu Leu Ser Ser Leu
                770                 775                 780
Arg Ser Glu Asp Thr Ala Val Tyr Tyr Cys Thr Arg Phe Arg Gly Ile
785                 790                 795                 800
His Tyr Ala Met Asp Tyr Trp Gly Gln Gly Thr Thr Val Thr Val Ser
                805                 810                 815
Ser Ala Ser Val Ala Ala Pro Ser Val Phe Ile Phe Pro Pro Ser Asp
                820                 825                 830
Glu Gln Leu Lys Ser Gly Thr Ala Ser Val Val Cys Leu Leu Asn Asn
                835                 840                 845
Phe Tyr Pro Arg Glu Ala Lys Val Gln Trp Lys Val Asp Asn Ala Leu
                850                 855                 860
Gln Ser Gly Asn Ser Gln Glu Ser Val Thr Glu Gln Asp Ser Lys Asp
865                 870                 875                 880
Ser Thr Tyr Ser Leu Ser Ser Thr Leu Thr Leu Ser Lys Ala Asp Tyr
                885                 890                 895
```

Glu Lys His Lys Val Tyr Ala Cys Glu Val Thr His Gln Gly Leu Ser
            900                 905                 910

Ser Pro Val Thr Lys Ser Phe Asn Arg Gly Glu Cys
            915                 920

<210> SEQ ID NO 110
<211> LENGTH: 678
<212> TYPE: PRT
<213> ORGANISM: Artificial Sequence
<220> FEATURE:
<223> OTHER INFORMATION: OX40(49B4_K23T_K73E)
      VHCH1-OX40(49B4_K23T_K73E) VHCH1-Fc hole_PGLALA

<400> SEQUENCE: 110

Gln Val Gln Leu Val Gln Ser Gly Ala Glu Val Lys Lys Pro Gly Ser
1               5                   10                  15

Ser Val Lys Val Ser Cys Thr Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Glu Lys Val Glu Pro Lys Ser Cys Gly Gly Gly
    210                 215                 220

Gly Ser Gly Gly Ser Gly Gly Gln Val Gln Leu Val Gln Ser Gly Ala
225                 230                 235                 240

Glu Val Lys Lys Pro Gly Ser Ser Val Lys Val Ser Cys Thr Ala Ser
                245                 250                 255

Gly Gly Thr Phe Ser Ser Tyr Ala Ile Ser Trp Val Arg Gln Ala Pro
            260                 265                 270

Gly Gln Gly Leu Glu Trp Met Gly Gly Ile Ile Pro Ile Phe Gly Thr
            275                 280                 285

Ala Asn Tyr Ala Gln Lys Phe Gln Gly Arg Val Thr Ile Thr Ala Asp
    290                 295                 300

Glu Ser Thr Ser Thr Ala Tyr Met Glu Leu Ser Ser Leu Arg Ser Glu
305                 310                 315                 320

Asp Thr Ala Val Tyr Tyr Cys Ala Arg Glu Tyr Tyr Arg Gly Pro Tyr
                325                 330                 335

-continued

Asp Tyr Trp Gly Gln Gly Thr Thr Val Thr Val Ser Ser Ala Ser Thr
            340                 345                 350

Lys Gly Pro Ser Val Phe Pro Leu Ala Pro Ser Ser Lys Ser Thr Ser
        355                 360                 365

Gly Gly Thr Ala Ala Leu Gly Cys Leu Val Glu Asp Tyr Phe Pro Glu
    370                 375                 380

Pro Val Thr Val Ser Trp Asn Ser Gly Ala Leu Thr Ser Gly Val His
385                 390                 395                 400

Thr Phe Pro Ala Val Leu Gln Ser Ser Gly Leu Tyr Ser Leu Ser Ser
                405                 410                 415

Val Val Thr Val Pro Ser Ser Ser Leu Gly Thr Gln Thr Tyr Ile Cys
            420                 425                 430

Asn Val Asn His Lys Pro Ser Asn Thr Lys Val Asp Glu Lys Val Glu
        435                 440                 445

Pro Lys Ser Cys Asp Lys Thr His Thr Cys Pro Pro Cys Pro Ala Pro
    450                 455                 460

Glu Ala Ala Gly Gly Pro Ser Val Phe Leu Phe Pro Pro Lys Pro Lys
465                 470                 475                 480

Asp Thr Leu Met Ile Ser Arg Thr Pro Glu Val Thr Cys Val Val Val
                485                 490                 495

Asp Val Ser His Glu Asp Pro Glu Val Lys Phe Asn Trp Tyr Val Asp
            500                 505                 510

Gly Val Glu Val His Asn Ala Lys Thr Lys Pro Arg Glu Glu Gln Tyr
        515                 520                 525

Asn Ser Thr Tyr Arg Val Val Ser Val Leu Thr Val Leu His Gln Asp
    530                 535                 540

Trp Leu Asn Gly Lys Glu Tyr Lys Cys Lys Val Ser Asn Lys Ala Leu
545                 550                 555                 560

Gly Ala Pro Ile Glu Lys Thr Ile Ser Lys Ala Lys Gly Gln Pro Arg
                565                 570                 575

Glu Pro Gln Val Cys Thr Leu Pro Pro Ser Arg Asp Glu Leu Thr Lys
            580                 585                 590

Asn Gln Val Ser Leu Ser Cys Ala Val Lys Gly Phe Tyr Pro Ser Asp
        595                 600                 605

Ile Ala Val Glu Trp Glu Ser Asn Gly Gln Pro Glu Asn Asn Tyr Lys
    610                 615                 620

Thr Thr Pro Pro Val Leu Asp Ser Asp Gly Ser Phe Phe Leu Val Ser
625                 630                 635                 640

Lys Leu Thr Val Asp Lys Ser Arg Trp Gln Gln Gly Asn Val Phe Ser
                645                 650                 655

Cys Ser Val Met His Glu Ala Leu His Asn His Tyr Thr Gln Lys Ser
            660                 665                 670

Leu Ser Leu Ser Pro Gly
            675

<210> SEQ ID NO 111
<211> LENGTH: 924
<212> TYPE: PRT
<213> ORGANISM: Artificial Sequence
<220> FEATURE:
<223> OTHER INFORMATION: OX40(49B4_K23E_K73E) VHCH1-
      OX40(49B4_K23E_K73E) VHCH1- Fc knob_PGLALA- FAP(1G1a) VHCL

<400> SEQUENCE: 111

Gln Val Gln Leu Val Gln Ser Gly Ala Glu Val Lys Lys Pro Gly Ser

```
1               5                   10                  15
Ser Val Lys Val Ser Cys Glu Ala Ser Gly Gly Thr Phe Ser Ser Tyr
                20                  25                  30

Ala Ile Ser Trp Val Arg Gln Ala Pro Gly Gln Gly Leu Glu Trp Met
                35                  40                  45

Gly Gly Ile Ile Pro Ile Phe Gly Thr Ala Asn Tyr Ala Gln Lys Phe
            50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
                100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Glu Lys Val Glu Pro Lys Ser Cys Gly Gly Gly
            210                 215                 220

Gly Ser Gly Gly Ser Gly Gly Gln Val Gln Leu Val Gln Ser Gly Ala
225                 230                 235                 240

Glu Val Lys Lys Pro Gly Ser Ser Val Lys Val Ser Cys Glu Ala Ser
                245                 250                 255

Gly Gly Thr Phe Ser Ser Tyr Ala Ile Ser Trp Val Arg Gln Ala Pro
                260                 265                 270

Gly Gln Gly Leu Glu Trp Met Gly Gly Ile Ile Pro Ile Phe Gly Thr
            275                 280                 285

Ala Asn Tyr Ala Gln Lys Phe Gln Gly Arg Val Thr Ile Thr Ala Asp
            290                 295                 300

Glu Ser Thr Ser Thr Ala Tyr Met Glu Leu Ser Ser Leu Arg Ser Glu
305                 310                 315                 320

Asp Thr Ala Val Tyr Tyr Cys Ala Arg Glu Tyr Tyr Arg Gly Pro Tyr
                325                 330                 335

Asp Tyr Trp Gly Gln Gly Thr Thr Val Thr Val Ser Ser Ala Ser Thr
                340                 345                 350

Lys Gly Pro Ser Val Phe Pro Leu Ala Pro Ser Ser Lys Ser Thr Ser
                355                 360                 365

Gly Gly Thr Ala Ala Leu Gly Cys Leu Val Glu Asp Tyr Phe Pro Glu
            370                 375                 380

Pro Val Thr Val Ser Trp Asn Ser Gly Ala Leu Thr Ser Gly Val His
385                 390                 395                 400

Thr Phe Pro Ala Val Leu Gln Ser Ser Gly Leu Tyr Ser Leu Ser Ser
                405                 410                 415

Val Val Thr Val Pro Ser Ser Ser Leu Gly Thr Gln Thr Tyr Ile Cys
            420                 425                 430
```

```
Asn Val Asn His Lys Pro Ser Asn Thr Lys Val Asp Glu Lys Val Glu
        435                 440                 445

Pro Lys Ser Cys Asp Lys Thr His Thr Cys Pro Pro Cys Pro Ala Pro
450                 455                 460

Glu Ala Ala Gly Gly Pro Ser Val Phe Leu Phe Pro Pro Lys Pro Lys
465                 470                 475                 480

Asp Thr Leu Met Ile Ser Arg Thr Pro Glu Val Thr Cys Val Val Val
                485                 490                 495

Asp Val Ser His Glu Asp Pro Glu Val Lys Phe Asn Trp Tyr Val Asp
            500                 505                 510

Gly Val Glu Val His Asn Ala Lys Thr Lys Pro Arg Glu Glu Gln Tyr
        515                 520                 525

Asn Ser Thr Tyr Arg Val Val Ser Val Leu Thr Val Leu His Gln Asp
    530                 535                 540

Trp Leu Asn Gly Lys Glu Tyr Lys Cys Lys Val Ser Asn Lys Ala Leu
545                 550                 555                 560

Gly Ala Pro Ile Glu Lys Thr Ile Ser Lys Ala Lys Gly Gln Pro Arg
                565                 570                 575

Glu Pro Gln Val Tyr Thr Leu Pro Pro Cys Arg Asp Glu Leu Thr Lys
            580                 585                 590

Asn Gln Val Ser Leu Trp Cys Leu Val Lys Gly Phe Tyr Pro Ser Asp
        595                 600                 605

Ile Ala Val Glu Trp Glu Ser Asn Gly Gln Pro Glu Asn Asn Tyr Lys
    610                 615                 620

Thr Thr Pro Pro Val Leu Asp Ser Asp Gly Ser Phe Phe Leu Tyr Ser
625                 630                 635                 640

Lys Leu Thr Val Asp Lys Ser Arg Trp Gln Gln Gly Asn Val Phe Ser
                645                 650                 655

Cys Ser Val Met His Glu Ala Leu His Asn His Tyr Thr Gln Lys Ser
            660                 665                 670

Leu Ser Leu Ser Pro Gly Gly Gly Gly Ser Gly Gly Gly Gly Ser
        675                 680                 685

Gly Gly Gly Gly Ser Gly Gly Ser Gly Gly Gln Val Gln Leu Val Gln
    690                 695                 700

Ser Gly Ala Glu Val Lys Lys Pro Gly Ala Ser Val Lys Val Ser Cys
705                 710                 715                 720

Lys Ala Ser Gly Tyr Thr Leu Thr Asp Tyr Asn Met Asp Trp Val Arg
                725                 730                 735

Gln Ala Pro Gly Gln Gly Leu Glu Trp Ile Gly Asp Ile Tyr Pro Asn
            740                 745                 750

Thr Gly Gly Thr Ile Tyr Asn Gln Lys Phe Lys Gly Arg Val Thr Met
        755                 760                 765

Thr Ile Asp Thr Ser Thr Ser Thr Val Tyr Met Glu Leu Ser Ser Leu
    770                 775                 780

Arg Ser Glu Asp Thr Ala Val Tyr Tyr Cys Thr Arg Phe Arg Gly Ile
785                 790                 795                 800

His Tyr Ala Met Asp Tyr Trp Gly Gln Gly Thr Thr Val Thr Val Ser
                805                 810                 815

Ser Ala Ser Val Ala Ala Pro Ser Val Phe Ile Phe Pro Pro Ser Asp
            820                 825                 830

Glu Gln Leu Lys Ser Gly Thr Ala Ser Val Val Cys Leu Leu Asn Asn
        835                 840                 845
```

```
Phe Tyr Pro Arg Glu Ala Lys Val Gln Trp Lys Val Asp Asn Ala Leu
            850                 855                 860
Gln Ser Gly Asn Ser Gln Glu Ser Val Thr Glu Gln Asp Ser Lys Asp
865                 870                 875                 880
Ser Thr Tyr Ser Leu Ser Ser Thr Leu Thr Leu Ser Lys Ala Asp Tyr
                885                 890                 895
Glu Lys His Lys Val Tyr Ala Cys Glu Val Thr His Gln Gly Leu Ser
            900                 905                 910
Ser Pro Val Thr Lys Ser Phe Asn Arg Gly Glu Cys
            915                 920

<210> SEQ ID NO 112
<211> LENGTH: 678
<212> TYPE: PRT
<213> ORGANISM: Artificial Sequence
<220> FEATURE:
<223> OTHER INFORMATION: OX40(49B4_K23E_K73E)
      VHCH1-OX40(49B4_K23E_K73E) VHCH1-Fc hole_PGLALA

<400> SEQUENCE: 112

Gln Val Gln Leu Val Gln Ser Gly Ala Glu Val Lys Lys Pro Gly Ser
1               5                   10                  15
Ser Val Lys Val Ser Cys Glu Ala Ser Gly Gly Thr Phe Ser Ser Tyr
                20                  25                  30
Ala Ile Ser Trp Val Arg Gln Ala Pro Gly Gln Gly Leu Glu Trp Met
            35                  40                  45
Gly Gly Ile Ile Pro Ile Phe Gly Thr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Tyr Tyr Arg Gly Pro Tyr Asp Tyr Trp Gly Gln Gly Thr
            100                 105                 110
Thr Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Glu Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Glu Lys Val Glu Pro Lys Ser Cys Gly Gly Gly
    210                 215                 220
Gly Ser Gly Gly Ser Gly Gly Gln Val Gln Leu Val Gln Ser Gly Ala
225                 230                 235                 240
Glu Val Lys Lys Pro Gly Ser Ser Val Lys Val Ser Cys Glu Ala Ser
                245                 250                 255
Gly Gly Thr Phe Ser Ser Tyr Ala Ile Ser Trp Val Arg Gln Ala Pro
            260                 265                 270
Gly Gln Gly Leu Glu Trp Met Gly Gly Ile Ile Pro Ile Phe Gly Thr
        275                 280                 285
```

Ala Asn Tyr Ala Gln Lys Phe Gln Gly Arg Val Thr Ile Thr Ala Asp
290                 295                 300

Glu Ser Thr Ser Thr Ala Tyr Met Glu Leu Ser Ser Leu Arg Ser Glu
305                 310                 315                 320

Asp Thr Ala Val Tyr Tyr Cys Ala Arg Glu Tyr Tyr Arg Gly Pro Tyr
            325                 330                 335

Asp Tyr Trp Gly Gln Gly Thr Thr Val Thr Val Ser Ser Ala Ser Thr
            340                 345                 350

Lys Gly Pro Ser Val Phe Pro Leu Ala Pro Ser Ser Lys Ser Thr Ser
            355                 360                 365

Gly Gly Thr Ala Ala Leu Gly Cys Leu Val Glu Asp Tyr Phe Pro Glu
            370                 375                 380

Pro Val Thr Val Ser Trp Asn Ser Gly Ala Leu Thr Ser Gly Val His
385                 390                 395                 400

Thr Phe Pro Ala Val Leu Gln Ser Ser Gly Leu Tyr Ser Leu Ser Ser
            405                 410                 415

Val Val Thr Val Pro Ser Ser Leu Gly Thr Gln Thr Tyr Ile Cys
            420                 425                 430

Asn Val Asn His Lys Pro Ser Asn Thr Lys Val Asp Glu Lys Val Glu
            435                 440                 445

Pro Lys Ser Cys Asp Lys Thr His Thr Cys Pro Pro Cys Pro Ala Pro
450                 455                 460

Glu Ala Ala Gly Gly Pro Ser Val Phe Leu Phe Pro Pro Lys Pro Lys
465                 470                 475                 480

Asp Thr Leu Met Ile Ser Arg Thr Pro Glu Val Thr Cys Val Val Val
            485                 490                 495

Asp Val Ser His Glu Asp Pro Glu Val Lys Phe Asn Trp Tyr Val Asp
            500                 505                 510

Gly Val Glu Val His Asn Ala Lys Thr Lys Pro Arg Glu Glu Gln Tyr
            515                 520                 525

Asn Ser Thr Tyr Arg Val Val Ser Val Leu Thr Val Leu His Gln Asp
            530                 535                 540

Trp Leu Asn Gly Lys Glu Tyr Lys Cys Lys Val Ser Asn Lys Ala Leu
545                 550                 555                 560

Gly Ala Pro Ile Glu Lys Thr Ile Ser Lys Ala Lys Gly Gln Pro Arg
            565                 570                 575

Glu Pro Gln Val Cys Thr Leu Pro Pro Ser Arg Asp Glu Leu Thr Lys
            580                 585                 590

Asn Gln Val Ser Leu Ser Cys Ala Val Lys Gly Phe Tyr Pro Ser Asp
            595                 600                 605

Ile Ala Val Glu Trp Glu Ser Asn Gly Gln Pro Glu Asn Asn Tyr Lys
            610                 615                 620

Thr Thr Pro Pro Val Leu Asp Ser Asp Gly Ser Phe Phe Leu Val Ser
625                 630                 635                 640

Lys Leu Thr Val Asp Lys Ser Arg Trp Gln Gln Gly Asn Val Phe Ser
            645                 650                 655

Cys Ser Val Met His Glu Ala Leu His Asn His Tyr Thr Gln Lys Ser
            660                 665                 670

Leu Ser Leu Ser Pro Gly
            675

<210> SEQ ID NO 113
<211> LENGTH: 807

<212> TYPE: PRT
<213> ORGANISM: Artificial Sequence
<220> FEATURE:
<223> OTHER INFORMATION: OX40(49B4) VHCH1- OX40(49B4) VHCH1- Fc hole_PGLALA - FAP(4B9) VL

<400> SEQUENCE: 113

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Gly Gly
    210                 215                 220

Gly Gly Ser Gly Gly Gly Gly Ser Gln Val Gln Leu Val Gln Ser Gly
225                 230                 235                 240

Ala Glu Val Lys Lys Pro Gly Ser Ser Val Lys Val Ser Cys Lys Ala
                245                 250                 255

Ser Gly Gly Thr Phe Ser Ser Tyr Ala Ile Ser Trp Val Arg Gln Ala
            260                 265                 270

Pro Gly Gln Gly Leu Glu Trp Met Gly Gly Ile Ile Pro Ile Phe Gly
        275                 280                 285

Thr Ala Asn Tyr Ala Gln Lys Phe Gln Gly Arg Val Thr Ile Thr Ala
    290                 295                 300

Asp Lys Ser Thr Ser Thr Ala Tyr Met Glu Leu Ser Ser Leu Arg Ser
305                 310                 315                 320

Glu Asp Thr Ala Val Tyr Tyr Cys Ala Arg Glu Tyr Tyr Arg Gly Pro
                325                 330                 335

Tyr Asp Tyr Trp Gly Gln Gly Thr Thr Val Thr Val Ser Ser Ala Ser
            340                 345                 350

Thr Lys Gly Pro Ser Val Phe Pro Leu Ala Pro Ser Ser Lys Ser Thr
        355                 360                 365

Ser Gly Gly Thr Ala Ala Leu Gly Cys Leu Val Lys Asp Tyr Phe Pro
    370                 375                 380

-continued

Glu Pro Val Thr Val Ser Trp Asn Ser Gly Ala Leu Thr Ser Gly Val
385                 390                 395                 400

His Thr Phe Pro Ala Val Leu Gln Ser Ser Gly Leu Tyr Ser Leu Ser
            405                 410                 415

Ser Val Val Thr Val Pro Ser Ser Leu Gly Thr Gln Thr Tyr Ile
        420                 425                 430

Cys Asn Val Asn His Lys Pro Ser Asn Thr Lys Val Asp Lys Lys Val
        435                 440                 445

Glu Pro Lys Ser Cys Asp Lys Thr His Thr Cys Pro Pro Cys Pro Ala
450                 455                 460

Pro Glu Ala Ala Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
            485                 490                 495

Val Asp Val Ser His Glu Asp Pro Glu Val Lys Phe Asn Trp Tyr Val
        500                 505                 510

Asp Gly Val Glu Val His Asn Ala Lys Thr Lys Pro Arg Glu Glu Gln
        515                 520                 525

Tyr Asn Ser Thr Tyr Arg Val Val Ser Val Leu Thr Val Leu His Gln
530                 535                 540

Asp Trp Leu Asn Gly Lys Glu Tyr Lys Cys Lys Val Ser Asn Lys Ala
545                 550                 555                 560

Leu Gly Ala Pro Ile Glu Lys Thr Ile Ser Lys Ala Lys Gly Gln Pro
            565                 570                 575

Arg Glu Pro Gln Val Cys Thr Leu Pro Pro Ser Arg Asp Glu Leu Thr
        580                 585                 590

Lys Asn Gln Val Ser Leu Ser Cys Ala Val Lys Gly Phe Tyr Pro Ser
        595                 600                 605

Asp Ile Ala Val Glu Trp Glu Ser Asn Gly Gln Pro Glu Asn Asn Tyr
        610                 615                 620

Lys Thr Thr Pro Pro Val Leu Asp Ser Asp Gly Ser Phe Phe Leu Val
625                 630                 635                 640

Ser Lys Leu Thr Val Asp Lys Ser Arg Trp Gln Gln Gly Asn Val Phe
            645                 650                 655

Ser Cys Ser Val Met His Glu Ala Leu His Asn His Tyr Thr Gln Lys
        660                 665                 670

Ser Leu Ser Leu Ser Pro Gly Gly Gly Gly Ser Gly Gly Gly Gly
        675                 680                 685

Ser Gly Gly Gly Gly Ser Gly Gly Gly Ser Glu Ile Val Leu Thr
    690                 695                 700

Gln Ser Pro Gly Thr Leu Ser Leu Ser Pro Gly Glu Arg Ala Thr Leu
705                 710                 715                 720

Ser Cys Arg Ala Ser Gln Ser Val Thr Ser Ser Tyr Leu Ala Trp Tyr
            725                 730                 735

Gln Gln Lys Pro Gly Gln Ala Pro Arg Leu Leu Ile Asn Val Gly Ser
        740                 745                 750

Arg Arg Ala Thr Gly Ile Pro Asp Arg Phe Ser Gly Ser Gly Ser Gly
        755                 760                 765

Thr Asp Phe Thr Leu Thr Ile Ser Arg Leu Glu Pro Glu Asp Phe Ala
        770                 775                 780

Val Tyr Tyr Cys Gln Gln Gly Ile Met Leu Pro Pro Thr Phe Gly Gln
785                 790                 795                 800

<210> SEQ ID NO 114
<211> LENGTH: 816
<212> TYPE: PRT
<213> ORGANISM: Artificial Sequence
<220> FEATURE:
<223> OTHER INFORMATION: OX40(49B4) VHCH1- OX40(49B4) VHCH1- Fc knob_PGLALA - FAP(4B9) VH

<400> SEQUENCE: 114

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Lys Phe
    50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Tyr Tyr Arg Gly Pro Tyr Asp Tyr Trp Gly Gln Gly Thr
            100                 105                 110
Thr Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Gly Gly
    210                 215                 220
Gly Gly Ser Gly Gly Gly Ser Gln Val Gln Leu Val Gln Ser Gly
225                 230                 235                 240
Ala Glu Val Lys Lys Pro Gly Ser Ser Val Lys Val Ser Cys Lys Ala
                245                 250                 255
Ser Gly Gly Thr Phe Ser Ser Tyr Ala Ile Ser Trp Val Arg Gln Ala
            260                 265                 270
Pro Gly Gln Gly Leu Glu Trp Met Gly Gly Ile Ile Pro Ile Phe Gly
        275                 280                 285
Thr Ala Asn Tyr Ala Gln Lys Phe Gln Gly Arg Val Thr Ile Thr Ala
    290                 295                 300
Asp Lys Ser Thr Ser Thr Ala Tyr Met Glu Leu Ser Ser Leu Arg Ser
305                 310                 315                 320
Glu Asp Thr Ala Val Tyr Tyr Cys Ala Arg Glu Tyr Tyr Arg Gly Pro
                325                 330                 335
Tyr Asp Tyr Trp Gly Gln Gly Thr Thr Val Thr Val Ser Ser Ala Ser
            340                 345                 350
```

```
Thr Lys Gly Pro Ser Val Phe Pro Leu Ala Pro Ser Ser Lys Ser Thr
        355                 360                 365

Ser Gly Gly Thr Ala Ala Leu Gly Cys Leu Val Lys Asp Tyr Phe Pro
    370                 375                 380

Glu Pro Val Thr Val Ser Trp Asn Ser Gly Ala Leu Thr Ser Gly Val
385                 390                 395                 400

His Thr Phe Pro Ala Val Leu Gln Ser Ser Gly Leu Tyr Ser Leu Ser
                405                 410                 415

Ser Val Val Thr Val Pro Ser Ser Ser Leu Gly Thr Gln Thr Tyr Ile
            420                 425                 430

Cys Asn Val Asn His Lys Pro Ser Asn Thr Lys Val Asp Lys Lys Val
            435                 440                 445

Glu Pro Lys Ser Cys Asp Lys Thr His Thr Cys Pro Pro Cys Pro Ala
450                 455                 460

Pro Glu Ala Ala Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
                485                 490                 495

Val Asp Val Ser His Glu Asp Pro Glu Val Lys Phe Asn Trp Tyr Val
            500                 505                 510

Asp Gly Val Glu Val His Asn Ala Lys Thr Lys Pro Arg Glu Glu Gln
            515                 520                 525

Tyr Asn Ser Thr Tyr Arg Val Val Ser Val Leu Thr Val Leu His Gln
    530                 535                 540

Asp Trp Leu Asn Gly Lys Glu Tyr Lys Cys Lys Val Ser Asn Lys Ala
545                 550                 555                 560

Leu Gly Ala Pro Ile Glu Lys Thr Ile Ser Lys Ala Lys Gly Gln Pro
                565                 570                 575

Arg Glu Pro Gln Val Tyr Thr Leu Pro Pro Cys Arg Asp Glu Leu Thr
            580                 585                 590

Lys Asn Gln Val Ser Leu Trp Cys Leu Val Lys Gly Phe Tyr Pro Ser
            595                 600                 605

Asp Ile Ala Val Glu Trp Glu Ser Asn Gly Gln Pro Glu Asn Asn Tyr
    610                 615                 620

Lys Thr Thr Pro Pro Val Leu Asp Ser Asp Gly Ser Phe Phe Leu Tyr
625                 630                 635                 640

Ser Lys Leu Thr Val Asp Lys Ser Arg Trp Gln Gln Gly Asn Val Phe
                645                 650                 655

Ser Cys Ser Val Met His Glu Ala Leu His Asn His Tyr Thr Gln Lys
            660                 665                 670

Ser Leu Ser Leu Ser Pro Gly Gly Gly Gly Ser Gly Gly Gly Gly
    675                 680                 685

Ser Gly Gly Gly Ser Gly Gly Gly Ser Glu Val Gln Leu Leu
    690                 695                 700

Glu Ser Gly Gly Gly Leu Val Gln Pro Gly Gly Ser Leu Arg Leu Ser
705                 710                 715                 720

Cys Ala Ala Ser Gly Phe Thr Phe Ser Ser Tyr Ala Met Ser Trp Val
                725                 730                 735

Arg Gln Ala Pro Gly Lys Gly Leu Glu Trp Val Ser Ala Ile Ile Gly
            740                 745                 750

Ser Gly Ala Ser Thr Tyr Tyr Ala Asp Ser Val Lys Gly Arg Phe Thr
    755                 760                 765
```

```
Ile Ser Arg Asp Asn Ser Lys Asn Thr Leu Tyr Leu Gln Met Asn Ser
            770                 775                 780
Leu Arg Ala Glu Asp Thr Ala Val Tyr Tyr Cys Ala Lys Gly Trp Phe
785                 790                 795                 800
Gly Gly Phe Asn Tyr Trp Gly Gln Gly Thr Leu Val Thr Val Ser Ser
                805                 810                 815

<210> SEQ ID NO 115
<211> LENGTH: 214
<212> TYPE: PRT
<213> ORGANISM: Artificial Sequence
<220> FEATURE:
<223> OTHER INFORMATION: OX40 (49B4) VLCkappa

<400> SEQUENCE: 115

Asp Ile Gln Met Thr Gln Ser Pro Ser Thr Leu Ser Ala Ser Val Gly
1               5                   10                  15
Asp Arg Val Thr Ile Thr Cys Arg Ala Ser Gln Ser Ile Ser Ser Trp
            20                  25                  30
Leu Ala Trp Tyr Gln Gln Lys Pro Gly Lys Ala Pro Lys Leu Leu Ile
        35                  40                  45
Tyr Asp Ala Ser Ser Leu Glu Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Asp Asp Phe Ala Thr Tyr Tyr Cys Gln Gln Tyr Ser Ser Gln Pro Tyr
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 116
<211> LENGTH: 678
<212> TYPE: PRT
<213> ORGANISM: Artificial Sequence
<220> FEATURE:
<223> OTHER INFORMATION: OX40(49B4) VHCH1- OX40(49B4) VHCH1- IgG1
      Fc _PGLALA

<400> SEQUENCE: 116

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
```

```
                35                  40                  45
Gly Gly Ile Ile Pro Ile Phe Gly Thr Ala Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Tyr Tyr Arg Gly Pro Tyr Asp Tyr Trp Gly Gln Gly Thr
                100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Gly Gly
210                 215                 220

Gly Gly Ser Gly Gly Gly Gly Ser Gln Val Gln Leu Val Gln Ser Gly
225                 230                 235                 240

Ala Glu Val Lys Lys Pro Gly Ser Ser Val Lys Val Ser Cys Lys Ala
                245                 250                 255

Ser Gly Gly Thr Phe Ser Ser Tyr Ala Ile Ser Trp Val Arg Gln Ala
            260                 265                 270

Pro Gly Gln Gly Leu Glu Trp Met Gly Gly Ile Ile Pro Ile Phe Gly
        275                 280                 285

Thr Ala Asn Tyr Ala Gln Lys Phe Gln Gly Arg Val Thr Ile Thr Ala
290                 295                 300

Asp Lys Ser Thr Ser Thr Ala Tyr Met Glu Leu Ser Ser Leu Arg Ser
305                 310                 315                 320

Glu Asp Thr Ala Val Tyr Tyr Cys Ala Arg Glu Tyr Tyr Arg Gly Pro
                325                 330                 335

Tyr Asp Tyr Trp Gly Gln Gly Thr Thr Val Thr Val Ser Ser Ala Ser
            340                 345                 350

Thr Lys Gly Pro Ser Val Phe Pro Leu Ala Pro Ser Ser Lys Ser Thr
        355                 360                 365

Ser Gly Gly Thr Ala Ala Leu Gly Cys Leu Val Lys Asp Tyr Phe Pro
    370                 375                 380

Glu Pro Val Thr Val Ser Trp Asn Ser Gly Ala Leu Thr Ser Gly Val
385                 390                 395                 400

His Thr Phe Pro Ala Val Leu Gln Ser Ser Gly Leu Tyr Ser Leu Ser
                405                 410                 415

Ser Val Val Thr Val Pro Ser Ser Ser Leu Gly Thr Gln Thr Tyr Ile
            420                 425                 430

Cys Asn Val Asn His Lys Pro Ser Asn Thr Lys Val Asp Lys Lys Val
        435                 440                 445

Glu Pro Lys Ser Cys Asp Lys Thr His Thr Cys Pro Pro Cys Pro Ala
    450                 455                 460
```

-continued

```
Pro Glu Ala Ala Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
            485                 490                 495

Val Asp Val Ser His Glu Asp Pro Glu Val Lys Phe Asn Trp Tyr Val
        500                 505                 510

Asp Gly Val Glu Val His Asn Ala Lys Thr Lys Pro Arg Glu Glu Gln
    515                 520                 525

Tyr Asn Ser Thr Tyr Arg Val Val Ser Val Leu Thr Val Leu His Gln
530                 535                 540

Asp Trp Leu Asn Gly Lys Glu Tyr Lys Cys Lys Val Ser Asn Lys Ala
545                 550                 555                 560

Leu Gly Ala Pro Ile Glu Lys Thr Ile Ser Lys Ala Lys Gly Gln Pro
                565                 570                 575

Arg Glu Pro Gln Val Tyr Thr Leu Pro Pro Ser Arg Asp Glu Leu Thr
            580                 585                 590

Lys Asn Gln Val Ser Leu Thr Cys Leu Val Lys Gly Phe Tyr Pro Ser
        595                 600                 605

Asp Ile Ala Val Glu Trp Glu Ser Asn Gly Gln Pro Glu Asn Asn Tyr
    610                 615                 620

Lys Thr Thr Pro Pro Val Leu Asp Ser Asp Gly Ser Phe Phe Leu Tyr
625                 630                 635                 640

Ser Lys Leu Thr Val Asp Lys Ser Arg Trp Gln Gln Gly Asn Val Phe
                645                 650                 655

Ser Cys Ser Val Met His Glu Ala Leu His Asn His Tyr Thr Gln Lys
            660                 665                 670

Ser Leu Ser Leu Ser Pro
            675
```

<210> SEQ ID NO 117
<211> LENGTH: 5
<212> TYPE: PRT
<213> ORGANISM: Artificial Sequence
<220> FEATURE:
<223> OTHER INFORMATION: CD3-HCDR1

<400> SEQUENCE: 117

```
Thr Tyr Ala Met Asn
1               5
```

<210> SEQ ID NO 118
<211> LENGTH: 19
<212> TYPE: PRT
<213> ORGANISM: Artificial Sequence
<220> FEATURE:
<223> OTHER INFORMATION: CD3-HCDR2

<400> SEQUENCE: 118

```
Arg Ile Arg Ser Lys Tyr Asn Asn Tyr Ala Thr Tyr Tyr Ala Asp Ser
1               5                   10                  15

Val Lys Gly
```

<210> SEQ ID NO 119
<211> LENGTH: 14
<212> TYPE: PRT
<213> ORGANISM: Artificial Sequence
<220> FEATURE:
<223> OTHER INFORMATION: CD3-HCDR3

-continued

<400> SEQUENCE: 119

His Gly Asn Phe Gly Asn Ser Tyr Val Ser Trp Phe Ala Tyr
1               5                   10

<210> SEQ ID NO 120
<211> LENGTH: 14
<212> TYPE: PRT
<213> ORGANISM: Artificial Sequence
<220> FEATURE:
<223> OTHER INFORMATION: CD3-LCDR1

<400> SEQUENCE: 120

Gly Ser Ser Thr Gly Ala Val Thr Thr Ser Asn Tyr Ala Asn
1               5                   10

<210> SEQ ID NO 121
<211> LENGTH: 7
<212> TYPE: PRT
<213> ORGANISM: Artificial Sequence
<220> FEATURE:
<223> OTHER INFORMATION: CD3-LCDR2

<400> SEQUENCE: 121

Gly Thr Asn Lys Arg Ala Pro
1               5

<210> SEQ ID NO 122
<211> LENGTH: 9
<212> TYPE: PRT
<213> ORGANISM: Artificial Sequence
<220> FEATURE:
<223> OTHER INFORMATION: CD3-LCDR3

<400> SEQUENCE: 122

Ala Leu Trp Tyr Ser Asn Leu Trp Val
1               5

<210> SEQ ID NO 123
<211> LENGTH: 125
<212> TYPE: PRT
<213> ORGANISM: Artificial Sequence
<220> FEATURE:
<223> OTHER INFORMATION: CD3 VH

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

```
<210> SEQ ID NO 124
<211> LENGTH: 109
<212> TYPE: PRT
<213> ORGANISM: Artificial Sequence
<220> FEATURE:
<223> OTHER INFORMATION: CD3 VL

<400> SEQUENCE: 124
```

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

```
<210> SEQ ID NO 125
<211> LENGTH: 5
<212> TYPE: PRT
<213> ORGANISM: Artificial Sequence
<220> FEATURE:
<223> OTHER INFORMATION: CD3 (Cl22) CDR-H1

<400> SEQUENCE: 125
```

Ser Tyr Ala Met Asn
1               5

```
<210> SEQ ID NO 126
<211> LENGTH: 19
<212> TYPE: PRT
<213> ORGANISM: Artificial Sequence
<220> FEATURE:
<223> OTHER INFORMATION: CD3 (Cl22) CDR-H2

<400> SEQUENCE: 126
```

Arg Ile Arg Ser Lys Tyr Asn Asn Tyr Ala Thr Tyr Tyr Ala Asp Ser
1               5                   10                  15

Val Lys Gly

```
<210> SEQ ID NO 127
<211> LENGTH: 14
<212> TYPE: PRT
<213> ORGANISM: Artificial Sequence
<220> FEATURE:
<223> OTHER INFORMATION: CD3 (Cl22) CDR-H3

<400> SEQUENCE: 127
```

His Thr Thr Phe Pro Ser Ser Tyr Val Ser Tyr Tyr Gly Tyr
1               5                   10

```
<210> SEQ ID NO 128
<211> LENGTH: 14
<212> TYPE: PRT
<213> ORGANISM: Artificial Sequence
<220> FEATURE:
<223> OTHER INFORMATION: CD3 (Cl22) CDR-L1
```

```
<400> SEQUENCE: 128

Gly Ser Ser Thr Gly Ala Val Thr Thr Ser Asn Tyr Ala Asn
1               5                   10

<210> SEQ ID NO 129
<211> LENGTH: 7
<212> TYPE: PRT
<213> ORGANISM: Artificial Sequence
<220> FEATURE:
<223> OTHER INFORMATION: CD3 (Cl22) CDR-L2

<400> SEQUENCE: 129

Gly Thr Asn Lys Arg Ala Pro
1               5

<210> SEQ ID NO 130
<211> LENGTH: 9
<212> TYPE: PRT
<213> ORGANISM: Artificial Sequence
<220> FEATURE:
<223> OTHER INFORMATION: CD3 (Cl22) CDR-L3

<400> SEQUENCE: 130

Ala Leu Trp Tyr Ser Asn Leu Trp Val
1               5

<210> SEQ ID NO 131
<211> LENGTH: 125
<212> TYPE: PRT
<213> ORGANISM: Artificial Sequence
<220> FEATURE:
<223> OTHER INFORMATION: CD3 (Cl22) VH

<400> SEQUENCE: 131

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Gln Phe Ser Ser Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Thr Thr Phe Pro Ser Tyr Val Ser Tyr Tyr
            100                 105                 110

Gly Tyr Trp Gly Gln Gly Thr Leu Val Thr Val Ser Ser
        115                 120                 125

<210> SEQ ID NO 132
<211> LENGTH: 109
<212> TYPE: PRT
<213> ORGANISM: Artificial Sequence
<220> FEATURE:
<223> OTHER INFORMATION: CD3 (Cl22) VL

<400> SEQUENCE: 132

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
```

```
                20                  25                  30

Asn Tyr Ala Asn Trp Val Gln Glu Lys Pro Gly Gln Ala Phe Arg Gly
            35                  40                  45

Leu Ile Gly Gly Thr Asn Lys Arg Ala Pro Gly Thr Pro Ala Arg Phe
        50                  55                  60

Ser Gly Ser Leu Leu Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 133
<211> LENGTH: 10
<212> TYPE: PRT
<213> ORGANISM: Artificial Sequence
<220> FEATURE:
<223> OTHER INFORMATION: CD3 (V9) CDR-H1

<400> SEQUENCE: 133

Gly Tyr Ser Phe Thr Gly Tyr Thr Met Asn
1               5                   10

<210> SEQ ID NO 134
<211> LENGTH: 17
<212> TYPE: PRT
<213> ORGANISM: Artificial Sequence
<220> FEATURE:
<223> OTHER INFORMATION: CD3 (V9) CDR-H2

<400> SEQUENCE: 134

Leu Ile Asn Pro Tyr Lys Gly Val Ser Thr Tyr Asn Gln Lys Phe Lys
1               5                   10                  15

Asp

<210> SEQ ID NO 135
<211> LENGTH: 13
<212> TYPE: PRT
<213> ORGANISM: Artificial Sequence
<220> FEATURE:
<223> OTHER INFORMATION: CD3 (V9) CDR-H3

<400> SEQUENCE: 135

Ser Gly Tyr Tyr Gly Asp Ser Asp Trp Tyr Phe Asp Val
1               5                   10

<210> SEQ ID NO 136
<211> LENGTH: 11
<212> TYPE: PRT
<213> ORGANISM: Artificial Sequence
<220> FEATURE:
<223> OTHER INFORMATION: CD3 (V9) CDR-L1

<400> SEQUENCE: 136

Arg Ala Ser Gln Asp Ile Arg Asn Tyr Leu Asn
1               5                   10

<210> SEQ ID NO 137
<211> LENGTH: 7
<212> TYPE: PRT
<213> ORGANISM: Artificial Sequence
<220> FEATURE:
<223> OTHER INFORMATION: CD3 (V9) CDR-L2
```

```
<400> SEQUENCE: 137

Tyr Thr Ser Arg Leu Glu Ser
1               5

<210> SEQ ID NO 138
<211> LENGTH: 9
<212> TYPE: PRT
<213> ORGANISM: Artificial Sequence
<220> FEATURE:
<223> OTHER INFORMATION: CD3 (V9) CDR-L3

<400> SEQUENCE: 138

Gln Gln Gly Asn Thr Leu Pro Trp Thr
1               5

<210> SEQ ID NO 139
<211> LENGTH: 122
<212> TYPE: PRT
<213> ORGANISM: Artificial Sequence
<220> FEATURE:
<223> OTHER INFORMATION: CD3 (V9) VH

<400> SEQUENCE: 139

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
    50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser
        115                 120

<210> SEQ ID NO 140
<211> LENGTH: 107
<212> TYPE: PRT
<213> ORGANISM: Artificial Sequence
<220> FEATURE:
<223> OTHER INFORMATION: CD3 (V9) VL

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95
```

-continued

```
Thr Phe Gly Gln Gly Thr Lys Val Glu Ile Lys
            100                 105

<210> SEQ ID NO 141
<211> LENGTH: 215
<212> TYPE: PRT
<213> ORGANISM: Artificial Sequence
<220> FEATURE:
<223> OTHER INFORMATION: Light chain "CEA 2F1" (CEA TCB)

<400> SEQUENCE: 141

Asp Ile Gln Met Thr Gln Ser Pro Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 142
<211> LENGTH: 214
<212> TYPE: PRT
<213> ORGANISM: Artificial Sequence
<220> FEATURE:
<223> OTHER INFORMATION: Light Chain humanized CD3 CH2527 (Crossfab,
      VL-CH1)(CEA TCB)

<400> SEQUENCE: 142

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60
```

-continued

```
Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys
    210

<210> SEQ ID NO 143
<211> LENGTH: 692
<212> TYPE: PRT
<213> ORGANISM: Artificial Sequence
<220> FEATURE:
<223> OTHER INFORMATION: CEA CH1A1A 98/99 - humanized CD3 CH2527
      (Crossfab VH-Ck)-Fc(knob) P329GLALA (CEA TCB)

<400> SEQUENCE: 143

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Glu Phe
             20                  25                  30

Gly Met Asn Trp Val Arg Gln Ala Pro Gly Gln Gly Leu Glu Trp Met
         35                  40                  45

Gly Trp Ile Asn Thr Lys Thr Gly Glu Ala Thr Tyr Val Glu Glu Phe
 50                  55                  60

Lys Gly Arg Val Thr Phe Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

```
Lys Pro Ser Asn Thr Lys Val Asp Lys Val Glu Pro Lys Ser Cys
210                 215                 220

Asp Gly Gly Gly Gly Ser Gly Gly Gly Ser Glu Val Gln Leu Leu
225                 230                 235                 240

Glu Ser Gly Gly Gly Leu Val Gln Pro Gly Gly Ser Leu Arg Leu Ser
                    245                 250                 255

Cys Ala Ala Ser Gly Phe Thr Phe Ser Thr Tyr Ala Met Asn Trp Val
                260                 265                 270

Arg Gln Ala Pro Gly Lys Gly Leu Glu Trp Val Ser Arg Ile Arg Ser
            275                 280                 285

Lys Tyr Asn Asn Tyr Ala Thr Tyr Tyr Ala Asp Ser Val Lys Gly Arg
        290                 295                 300

Phe Thr Ile Ser Arg Asp Asp Ser Lys Asn Thr Leu Tyr Leu Gln Met
305                 310                 315                 320

Asn Ser Leu Arg Ala Glu Asp Thr Ala Val Tyr Tyr Cys Val Arg His
                325                 330                 335

Gly Asn Phe Gly Asn Ser Tyr Val Ser Trp Phe Ala Tyr Trp Gly Gln
            340                 345                 350

Gly Thr Leu Val Thr Val Ser Ser Ala Ser Val Ala Ala Pro Ser Val
        355                 360                 365

Phe Ile Phe Pro Pro Ser Asp Glu Gln Leu Lys Ser Gly Thr Ala Ser
370                 375                 380

Val Val Cys Leu Leu Asn Asn Phe Tyr Pro Arg Glu Ala Lys Val Gln
385                 390                 395                 400

Trp Lys Val Asp Asn Ala Leu Gln Ser Gly Asn Ser Gln Glu Ser Val
                405                 410                 415

Thr Glu Gln Asp Ser Lys Asp Ser Thr Tyr Ser Leu Ser Ser Thr Leu
            420                 425                 430

Thr Leu Ser Lys Ala Asp Tyr Glu Lys His Lys Val Tyr Ala Cys Glu
        435                 440                 445

Val Thr His Gln Gly Leu Ser Ser Pro Val Thr Lys Ser Phe Asn Arg
    450                 455                 460

Gly Glu Cys Asp Lys Thr His Thr Cys Pro Pro Cys Pro Ala Pro Glu
465                 470                 475                 480

Ala Ala Gly Gly Pro Ser Val Phe Leu Phe Pro Pro Lys Pro Lys Asp
                485                 490                 495

Thr Leu Met Ile Ser Arg Thr Pro Glu Val Thr Cys Val Val Val Asp
            500                 505                 510

Val Ser His Glu Asp Pro Glu Val Lys Phe Asn Trp Tyr Val Asp Gly
        515                 520                 525

Val Glu Val His Asn Ala Lys Thr Lys Pro Arg Glu Glu Gln Tyr Asn
    530                 535                 540

Ser Thr Tyr Arg Val Val Ser Val Leu Thr Val Leu His Gln Asp Trp
545                 550                 555                 560

Leu Asn Gly Lys Glu Tyr Lys Cys Lys Val Ser Asn Lys Ala Leu Gly
                565                 570                 575

Ala Pro Ile Glu Lys Thr Ile Ser Lys Ala Lys Gly Gln Pro Arg Glu
            580                 585                 590

Pro Gln Val Tyr Thr Leu Pro Pro Cys Arg Asp Glu Leu Thr Lys Asn
        595                 600                 605

Gln Val Ser Leu Trp Cys Leu Val Lys Gly Phe Tyr Pro Ser Asp Ile
    610                 615                 620
```

```
Ala Val Glu Trp Glu Ser Asn Gly Gln Pro Glu Asn Asn Tyr Lys Thr
625                 630                 635                 640

Thr Pro Pro Val Leu Asp Ser Asp Gly Ser Phe Phe Leu Tyr Ser Lys
            645                 650                 655

Leu Thr Val Asp Lys Ser Arg Trp Gln Gln Gly Asn Val Phe Ser Cys
            660                 665                 670

Ser Val Met His Glu Ala Leu His Asn His Tyr Thr Gln Lys Ser Leu
        675                 680                 685

Ser Leu Ser Pro
    690

<210> SEQ ID NO 144
<211> LENGTH: 449
<212> TYPE: PRT
<213> ORGANISM: Artificial Sequence
<220> FEATURE:
<223> OTHER INFORMATION: CEA CH1A1A 98/99 (VH-CH1)-Fc(hole) P329GLALA
      (CEA TCB)

<400> SEQUENCE: 144

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285
```

-continued

```
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Gly Ala Pro Ile
                325                 330                 335
Glu Lys Thr Ile Ser Lys Ala Lys Gly Gln Pro Arg Glu Pro Gln Val
            340                 345                 350
Cys Thr Leu Pro Pro Ser Arg Asp Glu Leu Thr Lys Asn Gln Val Ser
        355                 360                 365
Leu Ser Cys Ala Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Val Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445

Pro

<210> SEQ ID NO 145
<211> LENGTH: 232
<212> TYPE: PRT
<213> ORGANISM: Artificial Sequence
<220> FEATURE:
<223> OTHER INFORMATION: CD3 VH-CL (CEACAM5 TCB)

<400> SEQUENCE: 145

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Thr Tyr
            20                  25                  30
Ala Met Asn Trp Val Arg Gln Ala Pro Gly Lys Gly Leu Glu Trp Val
        35                  40                  45
Ser Arg Ile Arg Ser Lys Tyr Asn Asn Tyr Ala Thr Tyr Tyr Ala Asp
    50                  55                  60
Ser Val Lys Gly Arg Phe Thr Ile Ser Arg Asp Asp Ser Lys Asn Thr
65                  70                  75                  80
Leu Tyr Leu Gln Met Asn Ser Leu Arg Ala Glu Asp Thr Ala Val Tyr
                85                  90                  95
Tyr Cys Val Arg His Gly Asn Phe Gly Asn Ser Tyr Val Ser Trp Phe
            100                 105                 110
Ala Tyr Trp Gly Gln Gly Thr Leu Val Thr Val Ser Ser Ala Ser Val
        115                 120                 125
Ala Ala Pro Ser Val Phe Ile Phe Pro Pro Ser Asp Glu Gln Leu Lys
    130                 135                 140
Ser Gly Thr Ala Ser Val Val Cys Leu Leu Asn Asn Phe Tyr Pro Arg
145                 150                 155                 160
Glu Ala Lys Val Gln Trp Lys Val Asp Asn Ala Leu Gln Ser Gly Asn
                165                 170                 175
Ser Gln Glu Ser Val Thr Glu Gln Asp Ser Lys Asp Ser Thr Tyr Ser
            180                 185                 190
```

```
Leu Ser Ser Thr Leu Thr Leu Ser Lys Ala Asp Tyr Glu Lys His Lys
            195                 200                 205

Val Tyr Ala Cys Glu Val Thr His Gln Gly Leu Ser Ser Pro Val Thr
210                 215                 220

Lys Ser Phe Asn Arg Gly Glu Cys
225                 230

<210> SEQ ID NO 146
<211> LENGTH: 449
<212> TYPE: PRT
<213> ORGANISM: Artificial Sequence
<220> FEATURE:
<223> OTHER INFORMATION: humanized CEA VH-CH1(EE)-Fc (hole, P329G LALA)
      (CEACAM5 TCB)

<400> SEQUENCE: 146

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Met His Trp Val Arg Gln Ala Pro Gly Gln Gly Leu Glu Trp Met
        35                  40                  45

Gly Arg Ile Asp Pro Ala Asn Gly Asn Ser Lys Tyr Val Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Glu Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320
```

```
Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro

<210> SEQ ID NO 147
<211> LENGTH: 674
<212> TYPE: PRT
<213> ORGANISM: Artificial Sequence
<220> FEATURE:
<223> OTHER INFORMATION: humanized CEA VH-CH1(EE)-CD3 VL-CH1-Fc (knob,
      P329G LALA)(CEACAM5 TCB)

<400> SEQUENCE: 147

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Met His Trp Val Arg Gln Ala Pro Gly Gln Gly Leu Glu Trp Met
        35                  40                  45

Gly Arg Ile Asp Pro Ala Asn Gly Asn Ser Lys Tyr Val Pro Lys Phe
    50                  55                  60

Gln Gly Arg Val Thr Ile Thr Ala Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Glu Lys Val Glu Pro Lys Ser Cys
    210                 215                 220
```

-continued

```
Asp Gly Gly Gly Gly Ser Gly Gly Gly Ser Gln Ala Val Val Thr
225                 230                 235                 240

Gln Glu Pro Ser Leu Thr Val Ser Pro Gly Thr Val Thr Leu Thr
            245                 250                 255

Cys Gly Ser Ser Thr Gly Ala Val Thr Thr Ser Asn Tyr Ala Asn Trp
                260                 265                 270

Val Gln Glu Lys Pro Gly Gln Ala Phe Arg Gly Leu Ile Gly Gly Thr
        275                 280                 285

Asn Lys Arg Ala Pro Gly Thr Pro Ala Arg Phe Ser Gly Ser Leu Leu
        290                 295                 300

Gly Gly Lys Ala Ala Leu Thr Leu Ser Gly Ala Gln Pro Glu Asp Glu
305                 310                 315                 320

Ala Glu Tyr Tyr Cys Ala Leu Trp Tyr Ser Asn Leu Trp Val Phe Gly
                325                 330                 335

Gly Gly Thr Lys Leu Thr Val Leu Ser Ser Ala Ser Thr Lys Gly Pro
            340                 345                 350

Ser Val Phe Pro Leu Ala Pro Ser Ser Lys Ser Thr Ser Gly Gly Thr
    355                 360                 365

Ala Ala Leu Gly Cys Leu Val Lys Asp Tyr Phe Pro Glu Pro Val Thr
370                 375                 380

Val Ser Trp Asn Ser Gly Ala Leu Thr Ser Gly Val His Thr Phe Pro
385                 390                 395                 400

Ala Val Leu Gln Ser Ser Gly Leu Tyr Ser Leu Ser Ser Val Val Thr
                405                 410                 415

Val Pro Ser Ser Ser Leu Gly Thr Gln Thr Tyr Ile Cys Asn Val Asn
                420                 425                 430

His Lys Pro Ser Asn Thr Lys Val Asp Lys Lys Val Glu Pro Lys Ser
            435                 440                 445

Cys Asp Lys Thr His Thr Cys Pro Pro Cys Pro Ala Pro Glu Ala Ala
    450                 455                 460

Gly Gly Pro Ser Val Phe Leu Phe Pro Pro Lys Pro Lys Asp Thr Leu
465                 470                 475                 480

Met Ile Ser Arg Thr Pro Glu Val Thr Cys Val Val Val Asp Val Ser
                485                 490                 495

His Glu Asp Pro Glu Val Lys Phe Asn Trp Tyr Val Asp Gly Val Glu
            500                 505                 510

Val His Asn Ala Lys Thr Lys Pro Arg Glu Glu Gln Tyr Asn Ser Thr
        515                 520                 525

Tyr Arg Val Val Ser Val Leu Thr Val Leu His Gln Asp Trp Leu Asn
        530                 535                 540

Gly Lys Glu Tyr Lys Cys Lys Val Ser Asn Lys Ala Leu Gly Ala Pro
545                 550                 555                 560

Ile Glu Lys Thr Ile Ser Lys Ala Lys Gly Gln Pro Arg Glu Pro Gln
                565                 570                 575

Val Tyr Thr Leu Pro Pro Cys Arg Asp Glu Leu Thr Lys Asn Gln Val
            580                 585                 590

Ser Leu Trp Cys Leu Val Lys Gly Phe Tyr Pro Ser Asp Ile Ala Val
        595                 600                 605

Glu Trp Glu Ser Asn Gly Gln Pro Glu Asn Asn Tyr Lys Thr Thr Pro
    610                 615                 620

Pro Val Leu Asp Ser Asp Gly Ser Phe Phe Leu Tyr Ser Lys Leu Thr
625                 630                 635                 640
```

```
Val Asp Lys Ser Arg Trp Gln Gln Gly Asn Val Phe Ser Cys Ser Val
            645                 650                 655

Met His Glu Ala Leu His Asn His Tyr Thr Gln Lys Ser Leu Ser Leu
        660                 665                 670

Ser Pro

<210> SEQ ID NO 148
<211> LENGTH: 218
<212> TYPE: PRT
<213> ORGANISM: Artificial Sequence
<220> FEATURE:
<223> OTHER INFORMATION: humanized CEA VL-CL(RK) (CEACAM5 TCB)

<400> SEQUENCE: 148

Glu Ile Val Leu Thr Gln Ser Pro Ala Thr Leu Ser Leu Ser Pro Gly
1               5                   10                  15

Glu Arg Ala Thr Leu Ser Cys Arg Ala Gly Glu Ser Val Asp Ile Phe
            20                  25                  30

Gly Val Gly Phe Leu His Trp Tyr Gln Gln Lys Pro Gly Gln Ala Pro
        35                  40                  45

Arg Leu Leu Ile Tyr Arg Ala Ser Asn Arg Ala Thr Gly Ile Pro Ala
50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Thr Asn
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Arg Lys
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 149
<211> LENGTH: 118
<212> TYPE: PRT
<213> ORGANISM: Artificial Sequence
<220> FEATURE:
<223> OTHER INFORMATION: VH (PD-L1)

<400> SEQUENCE: 149

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45
```

```
Ala Trp Ile Ser Pro Tyr Gly Gly Ser Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg His Trp Pro Gly Gly Phe Asp Tyr Trp Gly Gln Gly Thr
                100                 105                 110

Leu Val Thr Val Ser Ser
                115

<210> SEQ ID NO 150
<211> LENGTH: 107
<212> TYPE: PRT
<213> ORGANISM: Artificial Sequence
<220> FEATURE:
<223> OTHER INFORMATION: VL (PD-L1)

<400> SEQUENCE: 150

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Thr Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Leu Tyr His Pro Ala
                 85                  90                  95

Thr Phe Gly Gln Gly Thr Lys Val Glu Ile Lys
                100                 105

<210> SEQ ID NO 151
<211> LENGTH: 121
<212> TYPE: PRT
<213> ORGANISM: Artificial Sequence
<220> FEATURE:
<223> OTHER INFORMATION: VH (PD-L1)

<400> SEQUENCE: 151

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
                 20                  25                  30

Trp Met Ser Trp Val Arg Gln Ala Pro Gly Lys Gly Leu Glu Trp Val
             35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Gly Trp Phe Gly Glu Leu Ala Phe Asp Tyr Trp Gly
                100                 105                 110

Gln Gly Thr Leu Val Thr Val Ser Ser
            115                 120
```

<210> SEQ ID NO 152
<211> LENGTH: 108
<212> TYPE: PRT
<213> ORGANISM: Artificial Sequence
<220> FEATURE:
<223> OTHER INFORMATION: VL (PD-L1)

<400> SEQUENCE: 152

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105

<210> SEQ ID NO 153
<211> LENGTH: 107
<212> TYPE: PRT
<213> ORGANISM: Homo Sapiens

<400> SEQUENCE: 153

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Trp Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Glu Ser Thr Tyr Arg Trp Ser Val Leu Thr Val Leu His Gln Asp Trp
65                  70                  75                  80

Leu Asn Gly Lys Glu Tyr Lys Cys Lys Val Ser Asn Lys Ala Leu Pro
                85                  90                  95

Ala Pro Ile Glu Lys Thr Ile Ser Lys Ala Lys
            100                 105

<210> SEQ ID NO 154
<211> LENGTH: 105
<212> TYPE: PRT
<213> ORGANISM: Homo Sapiens

<400> SEQUENCE: 154

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe

```
            50                  55                  60
Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                     85                  90                  95

Thr Gln Lys Ser Leu Ser Leu Ser Pro
                100                 105

<210> SEQ ID NO 155
<211> LENGTH: 330
<212> TYPE: PRT
<213> ORGANISM: Homo Sapiens

<400> SEQUENCE: 155

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

Gln Lys Ser Leu Ser Leu Ser Pro Gly Lys
            325                 330

<210> SEQ ID NO 156
<211> LENGTH: 330
<212> TYPE: PRT
<213> ORGANISM: Homo Sapiens

<400> SEQUENCE: 156

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 157
<211> LENGTH: 326
<212> TYPE: PRT
<213> ORGANISM: Homo Sapiens

<400> SEQUENCE: 157

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65              70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 158
<211> LENGTH: 377
<212> TYPE: PRT
<213> ORGANISM: Homo Sapiens

<400> SEQUENCE: 158

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Thr Cys Asn Val Asn His Lys Pro Ser Asn Thr Lys Val Asp Lys
                 85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
            115                 120                 125

Cys Pro Glu Pro Lys Ser Cys Asp Thr Pro Pro Pro Cys Pro Arg Cys
130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 159
<211> LENGTH: 327
<212> TYPE: PRT
<213> ORGANISM: Homo Sapiens

<400> SEQUENCE: 159

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
```

```
                20                  25                  30
    Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
                130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
                210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 160
<211> LENGTH: 10
<212> TYPE: PRT
<213> ORGANISM: Homo Sapiens
<220> FEATURE:
<221> NAME/KEY: MISC_FEATURE
<222> LOCATION: (8)..(8)
<223> OTHER INFORMATION: X is S or P

<400> SEQUENCE: 160

Asp Lys Thr His Thr Cys Pro Xaa Cys Pro
1               5                   10

<210> SEQ ID NO 161
<211> LENGTH: 7
<212> TYPE: PRT
<213> ORGANISM: Homo Sapiens
```

```
<220> FEATURE:
<221> NAME/KEY: MISC_FEATURE
<222> LOCATION: (5)..(5)
<223> OTHER INFORMATION: X is S or P

<400> SEQUENCE: 161

His Thr Cys Pro Xaa Cys Pro
1               5

<210> SEQ ID NO 162
<211> LENGTH: 5
<212> TYPE: PRT
<213> ORGANISM: Homo Sapiens
<220> FEATURE:
<221> NAME/KEY: MISC_FEATURE
<222> LOCATION: (3)..(3)
<223> OTHER INFORMATION: X is S or P

<400> SEQUENCE: 162

Cys Pro Xaa Cys Pro
1               5

<210> SEQ ID NO 163
<211> LENGTH: 5
<212> TYPE: PRT
<213> ORGANISM: Homo Sapiens

<400> SEQUENCE: 163

Glu Pro Lys Ser Cys
1               5

<210> SEQ ID NO 164
<211> LENGTH: 6
<212> TYPE: PRT
<213> ORGANISM: Artificial Sequence
<220> FEATURE:
<223> OTHER INFORMATION: CH1 connector C-terminal end D-variant

<400> SEQUENCE: 164

Glu Pro Lys Ser Cys Asp
1               5

<210> SEQ ID NO 165
<211> LENGTH: 6
<212> TYPE: PRT
<213> ORGANISM: Artificial Sequence
<220> FEATURE:
<223> OTHER INFORMATION: CH1 connector C-terminal end S-variant

<400> SEQUENCE: 165

Glu Pro Lys Ser Cys Ser
1               5

<210> SEQ ID NO 166
<211> LENGTH: 98
<212> TYPE: PRT
<213> ORGANISM: Homo Sapiens

<400> SEQUENCE: 166

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

-continued

```
Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                 85                  90                  95

Lys Val
```

BISPECIFIC ANTIGEN BINDING MOLECULES TARGETING OX40 AND FAP

CROSS REFERENCE TO RELATED APPLICATIONS

This application claims priority to EP Application No. 20167624.4, filed Apr. 1, 2020, which is incorporated herein by reference in its entirety.

SEQUENCE LISTING

This application contains a Sequence Listing which has been submitted electronically in ASCII format and is hereby incorporated by reference in its entirety. Said ASCII copy, created on Mar. 24, 2021, is named "P36026-US_Sequence_Listing_ST25.txt" and is 297,611 bytes in size.

FIELD OF THE INVENTION

The invention relates to new bispecific antigen binding molecules, comprising at least two antigen binding domains capable of specific binding to OX40 and an antigen binding domain capable of specific binding to Fibroblast Activation Protein (FAP), and a Fc domain, in particular a Fc domain comprising one or more amino acid substitution that reduces binding to an Fc receptor and/or effector function. Further aspects of the invention are methods of producing these molecules and methods of using the same.

BACKGROUND

Cancer is one of the leading causes of death worldwide despite several new agents providing survival benefits to patients. Despite advances in treatment options, prognosis of patients with advanced cancer remains poor. Many cancer indications have a poor prognosis, and the management of most advanced solid tumors remains challenging because of the high rate of tumor recurrence or the development of distant metastases. Patients with advanced solid tumors have clearly benefitted from checkpoint inhibitor (CPI) therapy. Even after treatment discontinuation it can extend the overall survival in a subset of patients, likely via the generation of a memory immune response. Although this has changed the treatment landscape in many cancer types, unfortunately 60-80% of patients with metastatic disease do not derive long-term benefit from this type of cancer immunotherapy. Consequently, there is a persisting and urgent medical need to develop new and optimal therapies that can be added to existing treatments to increase survival of cancer patients without causing unacceptable toxicity.

The immune suppressive microenvironment in certain tumors is high in co-inhibitory signals, e.g. PD-L1, but lacks sufficient expression of OX40 ligand. OX40 (CD134; TNFRSF4) is a member of the tumor-necrosis factor (TNF) receptor superfamily that is transiently expressed by T cells upon engagement of the T-cell receptor (TCR). OX40 engagement modulates bi-directionally the interaction of T cells with OX40L$^+$ antigen presenting cells (e.g. B cells, dendritic cells (DCs), monocytes). In the context of TCR engagement, OX40 provides costimulatory signals predominantly to CD4$^+$, but also to CD8$^+$ effector T cells, resulting in enhanced proliferation, survival, and effector function (e.g. cytokine secretion). Conversely, OX40 signaling leads to functional inhibition and loss of regulatory T cells. OX40 agonism counterbalances TGF-β effects, (e.g. impedes FoxP3 induction) and lowers IL-10 secretion. In murine tumor models, OX40 engagement by an agonist anti-OX40 antibody can promote anti-tumor T-cell responses, tumor shrinkage and reproducible abscopal effects. Monotherapy efficacy of OX40 agonists was in general low, but strong anti-tumor efficacy was achieved in combination with immunogenic treatments (chemotherapy, radiation and vaccination), check point inhibitors (PD-1, CTLA-4) and other costimulatory agonists such as 4-1BB, ICOS or GITR.

Fibroblast activation protein-α (FAP) is a serine protease highly expressed on the cell surface of cancer-associated stroma cells of >90% of human epithelial malignancies, on reticular fibroblasts, which are in the T cell priming zones of the lymph nodes, and can be found on activated fibroblasts in normal tissues. High prevalence in various cancer indications allows its usage as targeting moiety for drugs that should accumulate within the tumor environment.

One means to restore OX40 co-stimulation specifically in the tumor microenvironment are bispecific antibodies comprised of at least one antigen binding domain for fibroblast activating protein (FAP) in the tumor stroma, and at least one antigen binding domain for OX40. For example, such bispecific antibodies have been described in WO 2017/055398 A2 and WO 2017/060144 A1. Crosslinking and surface immobilization of such bispecific molecules by cell surface FAP creates a highly agonistic matrix for OX40 positive T cells, where it supports NFκB mediated effector functions and can replace ligation by OX40 Ligand. High FAP expression is reported for a plethora of human tumor indications, either on tumor cells themselves or on immune suppressive cancer associated fibroblasts (CAFs). There is thus a need for improved FAP-targeted OX40 bispecific antibodies with excellent pharmacological properties such as better shelf-life, less immunogenicity and with less unspecific interactions such as hypersensitivity reactions or uncontrolled cytokine release.

SUMMARY OF THE INVENTION

This invention relates to new bispecific antigen binding molecules capable of specific binding to OX40 and Fibroblast Activation Protein (FAP) with improved properties, wherein the OX40 co-stimulation is provided by cross-linking through FAP expressed on tumor stroma cells and potentially also through FAP intermediately expressed in secondary lymphoid tissues. The antigen binding molecules of this invention are thus able to trigger OX40 not only effectively, but also very selectively at the desired site while overcoming the need for FcγR cross-linking thereby reducing side effects. The new bispecific antigen binding molecules are characterized by comprising a new FAP antigen binding domain fused to the C-terminus of the Fc domain and improved pharmacokinetic properties.

The bispecific antigen binding molecules of the present invention combine at least two antigen binding domains capable of specific binding to the costimulatory TNF receptor family member OX40, with an antigen binding domain targeting Fibroblast Activation Protein (FAP) comprising a new murine anti-human FAP clone 212 and humanized variants thereof. These bispecific antigen binding molecules are OX40 agonists and advantageous as they will preferably activate costimulatory OX40 receptors close to the tumor site where FAP is expressed because they are able to bind to FAP with high affinity. The molecules are further designed to have an advantageous pharmacokinetic profile to optimize the treatment regimen resulting in an enhanced safety to efficacy balance.

In one aspect, the invention provides a bispecific antigen binding molecule, comprising
(a) at least two antigen binding domains capable of specific binding to OX40,
(b) an antigen binding domain capable of specific binding to Fibroblast Activation Protein (FAP) comprising a heavy chain variable region ($V_H$FAP) comprising
(i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8, and
(c) a Fc region composed of a first and a second subunit capable of stable association.

In one aspect, the Fc region comprises one or more amino acid substitution that reduces the binding affinity of the antibody to an Fc receptor and/or effector function.

In one further aspect, provided is a bispecific antigen binding molecule, wherein the antigen binding domain capable of specific binding to FAP comprises a heavy chain variable region ($V_H$FAP) comprising an amino acid sequence that is at least about 90% identical to the amino acid sequence of SEQ ID NO:9, and a light chain variable region ($V_L$FAP) comprising an amino acid sequence that is at least about 90% identical to the amino acid sequence of SEQ ID NO:10. In one aspect, the antigen binding domain capable of specific binding to FAP comprises a heavy chain variable region ($V_H$FAP) comprising the amino acid sequence of SEQ ID NO:9, and a light chain variable region ($V_L$FAP) comprising the amino acid sequence of SEQ ID NO:10.

In another aspect, the antigen binding domain capable of specific binding to FAP comprises a heavy chain variable region ($V_H$FAP) comprising an amino acid sequence selected from the group consisting of SEQ ID NO:15, SEQ ID NO:16, SEQ ID NO:17, SEQ ID NO:18, SEQ ID NO:19 and SEQ ID NO:20, and a light chain variable region ($V_L$FAP) comprising an amino acid sequence selected from the group consisting of SEQ ID NO:21, SEQ ID NO:22, SEQ ID NO:23, SEQ ID NO:24, SEQ ID NO:25 and SEQ ID NO:26. In one aspect, the antigen binding domain capable of specific binding to FAP comprises (a) a heavy chain variable region ($V_H$FAP) comprising the amino acid sequence of SEQ ID NO:15 and a light chain variable region ($V_L$FAP) comprising the amino acid sequence of SEQ ID NO:21, (b) a heavy chain variable region ($V_H$FAP) comprising the amino acid sequence of SEQ ID NO:16 and a light chain variable region ($V_L$FAP) comprising the amino acid sequence of SEQ ID NO:21, (c) a heavy chain variable region ($V_H$FAP) comprising the amino acid sequence of SEQ ID NO:16 and a light chain variable region ($V_L$FAP) comprising the amino acid sequence of SEQ ID NO:22, or (d) a heavy chain variable region ($V_H$FAP) comprising the amino acid sequence of SEQ ID NO:19 and a light chain variable region ($V_L$FAP) comprising the amino acid sequence of SEQ ID NO:25. Particularly, the antigen binding domain capable of specific binding to FAP comprises (a) a heavy chain variable region ($V_H$FAP) comprising the amino acid sequence of SEQ ID NO:15 and a light chain variable region ($V_L$FAP) comprising the amino acid sequence of SEQ ID NO:21.

In one aspect, the antigen binding domains capable of specific binding to OX40 bind to a polypeptide comprising, or consisting of, the amino acid sequence of SEQ ID NO:1.

In a further aspect, provided is a bispecific antigen binding molecule, wherein the antigen binding domains capable of specific binding to OX40 (each) comprise
(a) a heavy chain variable region ($V_H$OX40) comprising (i) CDR-H1 comprising the amino acid sequence of SEQ ID NO:27, (ii) CDR-H2 comprising the amino acid sequence of SEQ ID NO:28, and (iii) CDR-H3 comprising the amino acid sequence of SEQ ID NO:29, and a light chain variable region ($V_L$OX40) comprising (iv) CDR-L1 comprising the amino acid sequence of SEQ ID NO:30, (v) CDR-L2 comprising the amino acid sequence of SEQ ID NO:31, and (vi) CDR-L3 comprising the amino acid sequence of SEQ ID NO:32, or
(b) a heavy chain variable region ($V_H$OX40) comprising (i) CDR-H1 comprising the amino acid sequence of SEQ ID NO:35, (ii) CDR-H2 comprising the amino acid sequence of SEQ ID NO:36, and (iii) CDR-H3 comprising the amino acid sequence of SEQ ID NO:37, and a light chain variable region ($V_L$OX40) comprising (iv) CDR-L1 comprising the amino acid sequence of SEQ ID NO:38, (v) CDR-L2 comprising the amino acid sequence of SEQ ID NO:39, and (vi) CDR-L3 comprising the amino acid sequence of SEQ ID NO:40, or
(c) a heavy chain variable region ($V_H$OX40) comprising (i) CDR-H1 comprising the amino acid sequence of SEQ ID NO:43, (ii) CDR-H2 comprising the amino acid sequence of SEQ ID NO:44, and (iii) CDR-H3 comprising the amino acid sequence of SEQ ID NO:45, and a light chain variable region ($V_L$OX40) comprising (iv) CDR-L1 comprising the amino acid sequence of SEQ ID NO:46, (v) CDR-L2 comprising the amino acid sequence of SEQ ID NO:47, and (vi) CDR-L3 comprising the amino acid sequence of SEQ ID NO:48, or
(d) a heavy chain variable region ($V_H$OX40) comprising (i) CDR-H1 comprising the amino acid sequence of SEQ ID NO:51, (ii) CDR-H2 comprising the amino acid sequence of SEQ ID NO:52, and (iii) CDR-H3 comprising the amino acid sequence of SEQ ID NO:53, and a light chain variable region ($V_L$OX40) comprising (iv) CDR-L1 comprising the amino acid sequence of SEQ ID NO:54, (v) CDR-L2 comprising the amino acid sequence of SEQ ID NO:55, and (vi) CDR-L3 comprising the amino acid sequence of SEQ ID NO:56.

In one aspect, the antigen binding domains capable of specific binding to OX40 (each) comprise a heavy chain variable region ($V_H$OX40) comprising (i) CDR-H1 comprising the amino acid sequence of SEQ ID NO:27, (ii) CDR-H2 comprising the amino acid sequence of SEQ ID NO:28, and (iii) CDR-H3 comprising the amino acid sequence of SEQ ID NO:29, and a light chain variable region ($V_L$OX40) comprising (iv) CDR-L1 comprising the amino acid sequence of SEQ ID NO:30, (v) CDR-L2 comprising the amino acid sequence of SEQ ID NO:31, and (vi) CDR-L3 comprising the amino acid sequence of SEQ ID NO:32. In a further aspect, the antigen binding domains capable of specific binding to OX40 comprise a heavy chain variable region ($V_H$OX40) comprising (i) CDR-H1 comprising the amino acid sequence of SEQ ID NO:35, (ii) CDR-H2 comprising the amino acid sequence of SEQ ID NO:36, and (iii) CDR-H3 comprising the amino acid sequence of SEQ ID NO:37, and a light chain variable region ($V_L$OX40) comprising (iv) CDR-L1 comprising the amino acid sequence of SEQ ID NO:38, (v) CDR-L2 comprising the amino acid sequence of SEQ ID NO:39, and (vi) CDR-L3 comprising the amino acid sequence of SEQ ID NO:40. In another aspect, the antigen binding domains capable of specific binding to OX40 comprise a heavy chain variable region (V$_H$OX40) comprising (i) CDR-H1 comprising the amino acid sequence of SEQ ID NO:43, (ii) CDR-H2 comprising the amino acid sequence of SEQ ID NO:44, and (iii) CDR-H3 comprising the amino acid sequence of SEQ ID NO:45, and a light chain variable region (V$_L$OX40) comprising (iv) CDR-L1 comprising the amino acid sequence of SEQ ID NO:46, (v) CDR-L2 comprising the amino acid sequence of SEQ ID NO:47, and (vi) CDR-L3 comprising the amino acid sequence of SEQ ID NO:48. In yet another aspect, the antigen binding domains capable of specific binding to OX40 comprise a heavy chain variable region (V$_H$OX40) comprising (i) CDR-H1 comprising the amino acid sequence of SEQ ID NO:51, (ii) CDR-H2 comprising the amino acid sequence of SEQ ID NO:52, and (iii) CDR-H3 comprising the amino acid sequence of SEQ ID NO:53, and a light chain variable region (V$_L$OX40) comprising (iv) CDR-L1 comprising the amino acid sequence of SEQ ID NO:54, (v) CDR-L2 comprising the amino acid sequence of SEQ ID NO:55, and (vi) CDR-L3 comprising the amino acid sequence of SEQ ID NO:56.

In one aspect, provided is a bispecific antigen binding molecule as defined herein before, wherein the antigen binding domains capable of specific binding to OX40 (each) comprise (i) a heavy chain variable region (V$_H$OX40) comprising the amino acid sequence of SEQ ID NO:33 and a light chain variable region (V$_L$OX40) comprising the amino acid sequence of SEQ ID NO:34, or (ii) a heavy chain variable region (V$_H$OX40) comprising the amino acid sequence of SEQ ID NO:41 and a light chain variable region (V$_L$OX40) comprising the amino acid sequence of SEQ ID NO:42, or (iii) a heavy chain variable region (V$_H$OX40) comprising the amino acid sequence of SEQ ID NO:49 and a light chain variable region (V$_L$OX40) comprising the amino acid sequence of SEQ ID NO:50, or (iv) a heavy chain variable region (V$_H$OX40) comprising the amino acid sequence of SEQ ID NO:57 and a light chain variable region (V$_L$OX40) comprising the amino acid sequence of SEQ ID NO:58.

In one aspect, provided is a bispecific antigen binding molecule as defined herein before, wherein the antigen binding domains capable of specific binding to OX40 (each) comprise a heavy chain variable region (V$_H$OX40) comprising the amino acid sequence of SEQ ID NO:33 and a light chain variable region (V$_L$OX40) comprising the amino acid sequence of SEQ ID NO:34. In another aspect, provided is a bispecific antigen binding molecule as defined herein before, wherein the antigen binding domain capable of specific binding to OX40 comprises a heavy chain variable region (V$_H$OX40) comprising the amino acid sequence of SEQ ID NO:41 and a light chain variable region (V$_L$OX40) comprising the amino acid sequence of SEQ ID NO:42. In a further aspect, provided is a bispecific antigen binding molecule as defined herein before, wherein the antigen binding domain capable of specific binding to OX40 comprises a heavy chain variable region (V$_H$OX40) comprising the amino acid sequence of SEQ ID NO:49 and a light chain variable region (V$_L$OX40) comprising the amino acid sequence of SEQ ID NO:50. In yet as further aspect, provided is a bispecific antigen binding molecule as defined herein before, wherein the antigen binding domain capable of specific binding to OX40 comprises a heavy chain variable region (V$_H$OX40) comprising the amino acid sequence of SEQ ID NO:57 and a light chain variable region (V$_L$OX40) comprising the amino acid sequence of SEQ ID NO:58.

In a particular aspect, provided is a bispecific antigen binding molecule as defined herein before, wherein the antigen binding domains capable of specific binding to OX40 (each) comprise a heavy chain variable region (V$_H$OX40) comprising the amino acid sequence of SEQ ID NO:41 and a light chain variable region (V$_L$OX40) comprising the amino acid sequence of SEQ ID NO:42.

In another aspect, provided is a bispecific antigen binding molecule as defined herein before, the antigen binding domains capable of specific binding to OX40 comprise (i) a heavy chain variable region (V$_H$OX40) comprising the amino acid sequence of SEQ ID NO:59 and a light chain variable region (V$_L$OX40) comprising the amino acid sequence of SEQ ID NO:34, or (ii) a heavy chain variable region (V$_H$OX40) comprising the amino acid sequence of SEQ ID NO:60 and a light chain variable region (V$_L$OX40) comprising the amino acid sequence of SEQ ID NO:34, or (iii) a heavy chain variable region (V$_H$OX40) comprising the amino acid sequence of SEQ ID NO:61 and a light chain variable region (V$_L$OX40) comprising the amino acid sequence of SEQ ID NO:34.

In one aspect, provided is a bispecific antigen binding molecule as defined herein before, wherein the antigen binding domain capable of specific binding to OX40 comprises a heavy chain variable region (V$_H$OX40) comprising the amino acid sequence of SEQ ID NO:59 and a light chain variable region (V$_L$OX40) comprising the amino acid sequence of SEQ ID NO:34. In one aspect, the antigen binding domain capable of specific binding to OX40 comprises a heavy chain variable region (V$_H$OX40) comprising the amino acid sequence of SEQ ID NO:60 and a light chain variable region (V$_L$OX40) comprising the amino acid sequence of SEQ ID NO:34. In a further aspect, the antigen binding domain capable of specific binding to OX40 comprises a heavy chain variable region (V$_H$OX40) comprising the amino acid sequence of SEQ ID NO:61 and a light chain variable region (V$_L$OX40) comprising the amino acid sequence of SEQ ID NO:34.

In another aspect, the bispecific antigen binding molecule is a humanized or a chimeric antibody, in particular a humanized antibody. In a further aspect, the bispecific antigen binding molecule comprises an IgG Fc region, particularly an IgG1 Fc region or an IgG4 Fc region. In particular, the Fc region comprises one or more amino acid substitution that reduces the binding affinity of the antibody to an Fc receptor and/or effector function. In one particular aspect, provided is a bispecific antigen binding molecule, wherein the Fc region is of human IgG1 subclass with the amino acid mutations L234A, L235A and P329G (numbering according to Kabat EU index).

In another aspect, provided is a bispecific antigen binding molecule as defined herein before, wherein the first subunit of the Fc region comprises knobs and the second subunit of the Fc region comprises holes according to the knobs into holes method. In particular, provided is a bispecific antigen binding molecule, wherein the first subunit of the Fc region comprises the amino acid substitutions S354C and T366W (numbering according to Kabat EU index) and the second subunit of the Fc region comprises the amino acid substitutions Y349C, T366S and Y407V (numbering according to Kabat EU index). In yet another aspect, the Fc region is of murine origin and the first subunit of the Fc region comprises the amino acid substitutions K392D and K409D (numbering according to Kabat EU index) and the second subunit of the Fc region comprises the amino acid substitutions E356K and D399K (numbering according to Kabat EU index). More particularly, provided is a bispecific antigen binding molecule, wherein the first subunit of the Fc region comprises the amino acid substitutions S354C and T366W (numbering according to Kabat EU index) and the second subunit of the Fc region comprises the amino acid substitutions Y349C, T366S and Y407V (numbering according to Kabat EU index).

In a further aspect, provided is a bispecific antigen binding molecule, wherein the bispecific antigen binding molecule comprises
(a) at least two Fab fragments capable of specific binding to OX40 each connected to the N-terminus of one of subunits of the Fc region, and
(b) one cross-Fab fragment capable of specific binding to FAP fused to the C-terminus of one of subunits of the Fc region, and
(c) the Fc region composed of a first and a second subunit capable of stable association.

Thus, provided is a bispecific antigen binding molecule that provides bivalent binding towards OX40 and monovalent binding towards FAP (2+1 format). In particular, the bispecific antigen binding molecule comprises one cross-Fab fragment capable of specific binding to FAP, wherein the VH-Ckappa chain of the cross-fab fragment capable of specific binding to FAP is fused to the C-terminus of one of subunits of the Fc region. In one particular aspect, the VH-Ckappa chain of the cross-fab fragment capable of specific binding to FAP is fused to the C-terminus of one of first subunit of the Fc region comprising the amino acid substitutions S354C and T366W (numbering according to Kabat EU index), i.e. to the knob chain.

In one aspect, provided is a bispecific antigen binding molecule, wherein the bispecific antigen binding molecule consists of
(aa) a first Fab fragment capable of specific binding to OX40,
(ab) a second Fab fragment capable of specific binding to OX40,
(b) a cross-Fab fragment capable of specific binding to FAP fused to the C-terminus of one of subunits of the Fc region, and
(c) the Fc region composed of a first and a second subunit capable of stable association, wherein the first Fab fragment (aa) is fused at the C-terminus of the VH-CH1 chain to the N-terminus of the first subunit and the second Fab fragment (ab) is fused at the C-terminus of the VH-CH1 chain to the N-terminus of the second subunit.

Thus, provided is a bispecific antigen binding molecule that provides bivalent binding towards OX40 and monovalent binding towards FAP (2+1 format).

In another aspect, provided is a bispecific antigen binding molecule, wherein the bispecific antigen binding molecule consists of
(aa) a first Fab fragment capable of specific binding to OX40,
(ab) a second Fab fragment capable of specific binding to OX40,
(ac) a third Fab fragment capable of specific binding to OX40,
(b) a cross-Fab fragment capable of specific binding to FAP fused to the C-terminus of one of subunits of the Fc region, and
(c) the Fc region composed of a first and a second subunit capable of stable association, wherein the second Fab fragment (ab) is fused at the C-terminus of the VH-CH1 chain to the N-terminus of the VH-CH1 chain of the first Fab fragment (aa), which is in turn fused at its C-terminus to the N-terminus of the first subunit, and the third Fab fragment (ac) is fused at the C-terminus of the Fab heavy chain to the N-terminus of the second subunit.

Thus, provided is a bispecific antigen binding molecule that provides trivalent binding towards OX40 and monovalent binding towards FAP (3+1 format).

In one aspect, provided is a bispecific antigen binding molecule, wherein the bispecific antigen binding molecule consists of
(aa) a first Fab fragment capable of specific binding to OX40,
(ab) a second Fab fragment capable of specific binding to OX40,
(ac) a third Fab fragment capable of specific binding to OX40,
(b) a cross-Fab fragment capable of specific binding to FAP fused to the C-terminus of one of subunits of the Fc region, and
(c) the Fc region composed of a first and a second subunit capable of stable association, wherein the second Fab fragment (ab) is fused at the C-terminus of the VH-CH1 chain to the N-terminus of the VH-CH1 chain of the first Fab fragment (aa), which is in turn fused at its C-terminus to the N-terminus of the second subunit of the Fc region comprising the amino acid substitutions Y349C, T366S and Y407V (numbering according to Kabat EU index), and the third Fab fragment (ac) is fused at the C-terminus of the Fab heavy chain to the N-terminus of the first subunit comprising the amino acid substitutions S354C and T366W (numbering according to Kabat EU index). In particular, the VH-Ckappa chain of the cross-fab fragment capable of specific binding to FAP is fused to the C-terminus of the first subunit of the Fc region comprising the amino acid substitutions S354C and T366W (numbering according to Kabat EU index).

In one aspect, provided is a bispecific antigen binding molecule comprising (a) two heavy chains, one heavy chain comprising two VH-CH1 chains of a Fab fragment capable of specific binding to OX40 that are connected to each other, optionally by a peptide linker, and a Fc region subunit and one heavy chain comprising a VH-CH1 chain of a Fab fragment capable of specific binding to OX40 and a Fc region subunit, (b) three light chains, each light chain comprising a VL and Ckappa domain of a Fab fragment capable of specific binding to OX40, and (c) a cross-Fab fragment capable of specific binding to FAP comprising a VL-CH1 light chain and a VH-Ckappa chain, wherein the VH-Ckappa chain is connected to the C-terminus of one of the two heavy chains of (a), optionally by a peptide linker.

In one aspect, provided is a bispecific antigen binding molecule, wherein the bispecific antigen binding molecule consists of
(aa) a first Fab fragment capable of specific binding to OX40,
(ab) a second Fab fragment capable of specific binding to OX40,
(ac) a third Fab fragment capable of specific binding to OX40,
(ad) a fourth Fab fragment capable of specific binding to OX40,
(b) a cross-Fab fragment capable of specific binding to FAP fused to the C-terminus of one of subunits of the Fc region, and (c) the Fc region composed of a first and a second subunit capable of stable association, wherein the second Fab fragment (ab) is fused at the C-terminus of the VH-CH1 chain to the N-terminus of the VH-CH1 chain of the first Fab fragment (aa), which is in turn fused at its C-terminus to the N-terminus of the first subunit, and the fourth Fab fragment (ad) is fused at the C-terminus of the VH-CH1 chain to the N-terminus of the VH-CH1 chain of the third Fab fragment (ac), which is in turn fused at its C-terminus to the N-terminus of the second subunit.

Thus, provided is a bispecific antigen binding molecule that provides tetravalent binding towards OX40 and monovalent binding towards FAP (4+1 format). In one particular aspect, the VH-Ckappa chain of the cross-fab fragment capable of specific binding to FAP is fused to the C-terminus of the first subunit of the Fc region comprising the amino acid substitutions S354C and T366W (numbering according to Kabat EU index).

In one aspect, provided is a bispecific antigen binding molecule, wherein each of the two heavy chains comprises two VH-CH1 chains of a Fab fragment capable of specific binding to OX40 that are fused to each other, optionally by a peptide linker. Thus, in one aspect, the invention provides a bispecific antigen binding molecule comprising (a) two heavy chains, each heavy chain comprising two VH-CH1 chains of a Fab fragment capable of specific binding to OX40 that are connected to each other, optionally by a peptide linker, and a Fc region subunit, (b) four light chains, each light chain comprising a VL and Ckappa domain of a Fab fragment capable of specific binding to OX40, and (c) a cross-Fab fragment capable of specific binding to FAP comprising a VL-CH1 light chain and a VH-Ckappa chain, wherein the VH-Ckappa chain is connected to the C-terminus of one of the two heavy chains of (a), optionally by a peptide linker.

According to another aspect of the invention, there is provided isolated nucleic acid encoding a bispecific antigen binding molecule as described herein before. The invention further provides a vector, particularly an expression vector, comprising the isolated nucleic acid of the invention, and a host cell comprising the isolated nucleic acid or the expression vector of the invention. In some aspects, the host cell is a eukaryotic cell, particularly a mammalian cell. In another aspect, provided is a method of producing a bispecific antigen binding molecule as described herein before, comprising culturing the host cell as described above under conditions suitable for the expression of the bispecific antigen binding molecule, and isolating the bispecific antigen binding molecule. The invention also encompasses the bispecific antigen binding molecule that specifically binds to OX40 and to FAP produced by the method of the invention.

The invention further provides a pharmaceutical composition comprising a bispecific antigen binding molecule as described herein before and a pharmaceutically acceptable carrier. In one aspect, the pharmaceutical composition comprises an additional therapeutic agent.

Also encompassed by the invention is the bispecific antigen binding molecule or the antibody as described herein before, or the pharmaceutical composition comprising the bispecific antigen binding molecule, for use as a medicament.

In one aspect, provided is a bispecific antigen binding molecule as described herein before or the pharmaceutical composition of the invention, for use
(i) in inducing immune stimulation,
(ii) in stimulating tumor-specific T cell response,
(iii) in causing apoptosis of tumor cells,
(iv) in the treatment of cancer,
(v) in delaying progression of cancer,
(vi) in prolonging the survival of a patient suffering from cancer,
(vii) in the treatment of infections.

In a specific aspect, provided is the bispecific antigen binding molecule as described herein before or the pharmaceutical composition of the invention, for use in the treatment of cancer. In another specific aspect, the invention provides the bispecific antigen binding molecule as described herein before for use in the treatment of cancer, wherein the bispecific antigen binding molecule is for administration in combination with a chemotherapeutic agent, radiation and/or other agents for use in cancer immunotherapy. In one aspect, provided is a bispecific agonistic OX40 antigen binding molecule or a pharmaceutical composition for use in the treatment of cancer, wherein the bispecific agonistic OX40 antigen binding molecule is for administration in combination with a T-cell activating anti-CD3 bispecific antibody, for example an anti-CEA/anti-CD3 bispecific antibody. In one further aspect, the bispecific antigen binding molecule as described herein is for use in the treatment of cancer, wherein the bispecific antigen binding molecule is for administration in combination with an agent blocking PD-L1/PD-1 interaction such as PD-L1 antibody, for example atezolizumab, or a PD-1 antibody, for example nivolumab or pembrolizumab. In another aspect, provided is the bispecific antigen binding molecule as described herein before or the pharmaceutical composition of the invention, for use in up-regulating or prolonging cytotoxic T cell activity.

In a further aspect, the invention provides a method of inhibiting the growth of tumor cells in an individual comprising administering to the individual an effective amount of the bispecific antigen binding molecule as described herein before, or the pharmaceutical composition of the invention, to inhibit the growth of the tumor cells. In another aspect, the invention provides a method of treating or delaying cancer in an individual comprising administering to the individual an effective amount of the bispecific antigen binding molecule as described herein before, or the pharmaceutical composition of the invention.

Also provided is the use of the bispecific antigen binding molecule as described herein before for the manufacture of a medicament for the treatment of a disease in an individual in need thereof, in particular for the manufacture of a medicament for the treatment of cancer, as well as a method of treating a disease in an individual, comprising administering to said individual a therapeutically effective amount of a composition comprising the bispecific antigen binding molecule of the invention in a pharmaceutically acceptable form. In a specific aspect, the disease is cancer. In any of the above aspects the individual is a mammal, particularly a human.

BRIEF DESCRIPTION OF THE DRAWINGS

FIG. 1A to FIG. E show schematic representations of bispecific antigen binding molecules which specifically bind to human OX40 and to FAP. FIG. 1A shows a schematic representation of a bispecific FAP-OX40 antibody in a 4+1 format consisting of four OX40 binding Fab fragments combined with one FAP (1G1a) binding moiety as crossFab fragment, wherein the VH-Ckappa chain is fused at the C-terminus of the Fc knob chain (tetravalent for OX40 and monovalent for FAP). FIG. 1B shows a schematic representation of a bispecific FAP-OX40 antibody in a 3+1 format consisting of three OX40 binding Fab fragments combined with one FAP (1G1a) binding moiety as crossFab fragment, wherein the VH-Ckappa chain is fused at the C-terminus of the Fc knob chain (trivalent for OX40 and monovalent for FAP). The arm comprising two OX40 binding Fab fragments fused to each other is on Fc knob chain. FIG. 1C shows a schematic representation of a bispecific FAP-OX40 antibody in a 3+1 format consisting of three OX40 binding Fab fragments combined with one FAP (1G1a) binding moiety as crossFab fragment, wherein the VH-Ckappa chain is fused at the C-terminus of the Fc knob chain (trivalent for OX40 and monovalent for FAP). The arm comprising two OX40 binding Fab fragments fused to each other is on Fc hole chain. FIG. 1D shows a schematic representation of a bispecific FAP-OX40 antibody in a 2+1 format consisting of two OX40 binding Fab fragments combined with one FAP (1G1a) binding moiety as crossFab fragment, wherein the VH-Ckappa chain is fused at the C-terminus of the Fc knob chain (bivalent for OX40 and monovalent for FAP). FIG. 1E shows a schematic representation of a bispecific FAP-OX40 antibody P1AD4524 in a 4+1 format consisting of four OX40 binding Fab fragments combined with one FAP (4B9) binding moiety as VH and VL domain, wherein the VL domain is fused at the C-terminus of the Fc knob chain and the VH domain is fused at the C-terminus of the Fc hole chain (tetravalent for OX40 and monovalent for FAP). The black point symbolizes knob-into-hole mutations.

FIG. 2A to FIG. 2F show the cellular binding of bispecific antigen binding molecules comprising OX40 clone 49B4 in different formats. The FAP antigen binding domain H212 is the humanized version of FAP clone 212 that is called FAP (1G1a) herein. Human FAP negative tumor cells (A549-NLR)(FIG. 2F), FAP positive fibroblasts (NIH/3T3-huFAP-clone 19) (FIG. 2E), OX40 positive activated PBMC (activated CD4 and CD8 T cells, FIG. 2A and FIG. 2C, respectively) as well as OX40 negative resting PBMC (resting CD4 and CD8 T cells, FIG. 2B and FIG. 2D, respectively) were incubated with indicated serial dilutions of test antibody detected then by fluorescently labeled 2nd antibody against human Fcγ. Living cells were gated and the mean fluorescence intensity of the secondary antibody, baseline corrected by the media-only sample, was plotted from duplicates. Error bars indicate the SEM.

FIG. 5A to FIG. 5F show the cellular binding of bispecific antigen binding molecules comprising OX40 clone CLC563 in different formats and in comparison with a bispecific antigen binding molecule comprising OX40 clone 49B4 in 4+1 format (P1AE6838). Human FAP negative tumor cells (A549-NLR)(FIG. 5F), FAP positive fibroblasts (NIH/3T3-huFAP-clone 19) (FIG. 5E), OX40 positive activated PBMC (activated CD4 and CD8 T cells, FIG. 5A and FIG. 5C, respectively) as well as OX40 negative resting PBMC (resting CD4 and CD8 T cells, FIG. 5B and FIG. 5D, respectively) were incubated with indicated serial dilutions of test antibody detected then by fluorescently labeled 2nd antibody against human Fcγ. Living cells were gated and the mean fluorescence intensity of the secondary antibody, baseline corrected by the media-only sample, was plotted from duplicates. Error bars indicate the SEM. The clone CLC-563 bound with nanomolar affinity to OX40 positive cells, with comparable strength as tri- and bivalent antibody.

FIG. 6A to FIG. 6F show the cellular binding of bispecific antigen binding molecules comprising different variants of OX40 clone 49B4 with amino acid mutations in the VH domain in different formats and in comparison with a bispecific antigen binding molecule comprising OX40 clone 49B4 in 4+1 format (P1AE6838). Human FAP negative tumor cells (A549-NLR)(FIG. 6F), FAP positive fibroblasts (NIH/3T3-huFAP-clone 19) (FIG. 6E), OX40 positive activated PBMC (activated CD4 and CD8 T cells, FIG. 6A and FIG. 6C, respectively) as well as OX40 negative resting PBMC (resting CD4 and CD8 T cells, FIG. 6B and FIG. 6D, respectively) were incubated with indicated serial dilutions of test antibody detected then by fluorescently labeled 2nd antibody against human Fcγ. Living cells were gated and the mean fluorescence intensity of the secondary antibody, baseline corrected by the media-only sample, was plotted from duplicates. Error bars indicate the SEM. All antigen binding molecules comprising OX40 (49B4) variants with amino acid mutations showed slightly improved binding to OX40 positive cells compared to antigen binding molecule including clone 49B4.

FIG. 9A to FIG. 9C show the NFκB-mediated luciferase expression activity in OX40 expressing reporter cell line HeLa_hOx40_NFκB_Luc1 of different bispecific antigen binding molecules comprising OX40 clone MOXR0916. The concentration of the bispecific antigen binding molecules in different formats or its controls are blotted against the units of released light (URL) measured after incubation and addition of Luciferase detection solution. Shown is the NFκB induction of the 3+1 or 2+1 formats, either crosslinked with human FAP expressing NIH/3T3 fibroblasts (FIG. 9A), a secondary antibody at a 2 to 1 ratio (FIG. 9B) or w/o further crosslinking (FIG. 9C). The isotype control antibody did not induce any NFκB activation. All OX40 containing constructs induced dose dependent NFκB activation. The tetravalent format comprising four OX40 Fab fragments induced a certain NFκB activation due to the assembly of the trimeric core OX40 receptor-signaling unit already in the absence of crosslinking and was most potent. The bispecific antigen binding molecules comprising OX40 clone MOXR0916 in a trivalent or bivalent format showed accordingly less bioactivity. Additional crosslinking by human FAP expressing fibroblasts via the FAP binding moiety, or by a secondary crosslinking antibody vie the Fc region of the OX40 antigen binding molecule further increased the NFκB activation. The clone OX40 (MOXR0916) achieved the highest induction of NFκB activation already in the 2+1 format, no further benefit was obtained with the 3+1 format. Shown is the mean of duplicates. Error bars represent the SEM.

FIG. 10A to FIG. 10C show the NFκB-mediated luciferase expression activity in OX40 expressing reporter cell line HeLa_hOx40_NFκB_Luc1 of different bispecific antigen binding molecules comprising OX40 clone CLC563. The concentration of the bispecific antigen binding molecules in different formats or its controls are blotted against the units of released light (URL) measured after incubation and addition of Luciferase detection solution. Shown is the NFκB induction of the 3+1 or 2+1 formats, either crosslinked with human FAP expressing NIH/3T3 fibroblasts (FIG. 10A), a secondary antibody at a 2 to 1 ratio (FIG. 10B) or w/o further crosslinking (FIG. 10C). The isotype control antibody did not induce any NFκB activation. All OX40 containing constructs induced dose dependent NFκB activation. The tetravalent format comprising four OX40 Fab fragments induced a certain NFκB activation due to the assembly of the trimeric core OX40 receptor-signaling unit already in the absence of crosslinking and was most potent. The bispecific antigen binding molecules comprising OX40 clone CLC563 in a trivalent or bivalent format showed less bioactivity. Additional crosslinking by human FAP expressing fibroblasts via the FAP binding moiety, or by a secondary crosslinking antibody vie the Fc region of the OX40 antigen binding molecule further increased the NFκB activation. The clone OX40 (CLC563) achieved the highest induction of NFκB activation in the 3+1 format, which was slightly more potent than the 2+1 format. Shown is the mean of duplicates. Error bars represent the SEM.

FIG. 11A to FIG. 11C show the NFκB-mediated luciferase expression activity in OX40 expressing reporter cell line HeLa_hOx40_NFκB_Luc1 of different variants of OX40 clone 49B4 with amino acid mutations in the VH domain in different formats and in comparison with a bispecific antigen binding molecule comprising OX40 clone 49B4 in 4+1 format (P1AE6838). The concentration of the bispecific antigen binding molecules in different formats or its controls are blotted against the units of released light (URL) measured after incubation and addition of Luciferase detection solution. Shown is the NFκB induction, either cross-linked with human FAP expressing NIH/3T3 fibroblasts (FIG. 11A), a secondary antibody at a 2 to 1 ratio (FIG. 11B) or w/o further crosslinking (FIG. 11C). The isotype control antibody did not induce any NFκB activation. All amino acid variants induced dose dependent NKκB activation to a similar extent than the OX40 (49B4) antibody in the 4+1 format. The tetravalent use of OX40 antigen binding domains induced a certain NFκB activation due to the assembly of the trimeric core OX40 receptor-signaling unit. Additional crosslinking by human FAP expressing fibroblasts via the FAP binding moiety, or by a secondary crosslinking antibody vie the Fc region of the OX40 antigen binding molecule further increases the NFκB activation, which was already evident at lower concentrations. Shown is the mean of duplicates. Error bars represent the SEM.

FIG. 12A shows the number of CD4$^+$ T cells and FIG. 12B shows the CD25 activation marker expression on CD4$^+$ T cells at endpoint. Increased proliferation and CD25 activation marker expression were observed with FAP-targeted tetravalent OX40 antigen binding molecules in a dose-dependent manner. Bivalent molecules led to reduced bioactivity as compared to tetravalent in line with the fact that 49B4 is an avidity-driven OX40 antibody. The untargeted OX40 molecule showed minimal activity at the highest tested concentration whereas isotype control showed no activation after baseline-correction. Shown is the mean of triplicates. Error bars represent the SEM.

FIG. 13A shows the number of CD4$^+$ T cells and FIG. 13B shows the CD25 activation marker expression on CD4$^+$ T cells at endpoint. Increased proliferation and CD25 activation marker expression were observed with FAP-targeted tetravalent OX40 antigen binding molecules in a dose-dependent manner. Trivalent and to a bigger extent bivalent OX40 antigen binding molecules led to reduced bioactivity as compared to tetravalent, in line with the fact that 49B4 is an avidity driven antibody. Isotype control showed no activation after baseline-correction. Shown is the mean of triplicates. Error bars represent the SEM.

FIG. 14A shows the number of CD4$^+$ T cells and FIG. 14B shows the CD25 activation marker expression on CD4$^+$ T cells at endpoint. Increased proliferation and CD25 activation marker expression were observed with FAP-targeted tetravalent OX40 antigen binding molecules in a dose-dependent manner. Trivalent and bivalent antigen binding molecules comprising clone 8H9 led to slightly reduced maximal response as compared to tetravalent clone 49B4, with comparable sub-nanomolar $EC_{50}$. Isotype control showed no activation after baseline-correction. Shown is the mean of triplicates. Error bars represent the SEM.

FIG. 15A shows the number of CD4$^+$ T cells and FIG. 15B shows the CD25 activation marker expression on CD4$^+$ T cells at endpoint. Increased proliferation and CD25 activation marker expression were observed with FAP-targeted tetravalent OX40 antigen binding molecules in a dose-dependent manner. Trivalent and bivalent antigen binding molecules comprising clone MOXR0916 led to similar numbers of CD4$^+$ T cells and reduced maximal CD25 expression as compared to the tetravalent molecule comprising clone 49B4. The drop in CD4$^+$ T cells at the highest tested concentration of the MOXR0916 containing molecules is an indicator of activation induced cell death. Isotype control showed no activation after baseline-correction. Shown is the mean of triplicates. Error bars represent the SEM.

FIG. 16A shows the number of CD4$^+$ T cells and FIG. 16B shows the CD25 activation marker expression on CD4$^+$ T cells at endpoint. Increased proliferation and CD25 activation marker expression were observed with FAP-targeted tetravalent OX40 antigen binding molecules in a dose-dependent manner. Trivalent and bivalent antigen binding molecules comprising clone CLC563 led to similar numbers of CD4$^+$ T cells and reduced maximal CD25 expression as compared to the tetravalent molecule comprising clone 49B4. Isotype control showed no activation after baseline-correction. Shown is the mean of triplicates. Error bars represent the SEM.

FIG. 17A shows the number of CD8$^+$ T cells and FIG. 17B shows the CD25 activation marker expression on CD4$^+$ T cells at endpoint. Increased proliferation and CD25 activation marker expression were observed with FAP-targeted tetravalent OX40 antigen binding molecules in a dose-dependent manner. The three tetravalent amino acid variants displayed comparable activity than that of the parental antibody in terms of CD8$^+$ T cells proliferation and CD25 upregulation on CD4$^+$ T cells. Isotype control showed no activation after baseline-correction. Shown is the mean of triplicates. Error bars represent the SEM.

Figure 18:
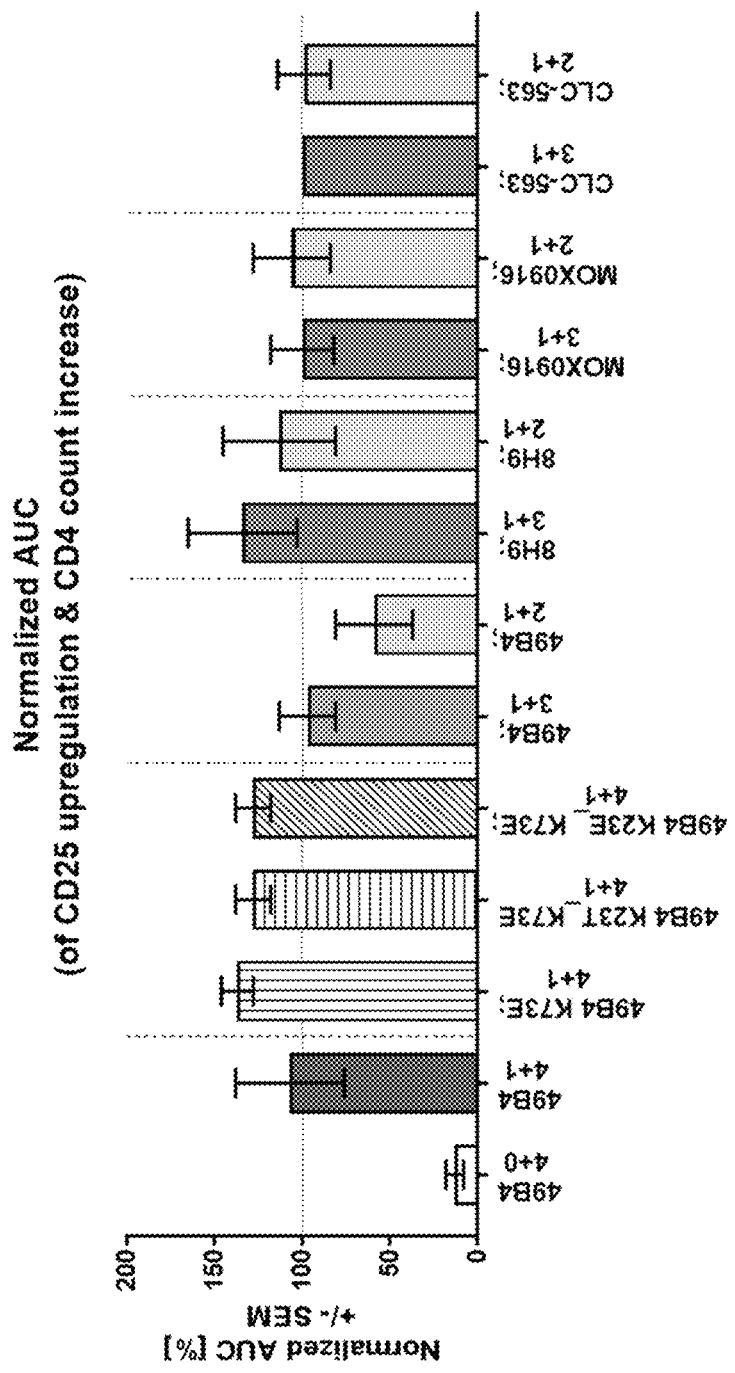

A normalized overview of the areas under the curve (AUC) of the CD25 activation marker expression on CD4$^+$ T cells as measured at endpoint for all antigen binding molecules is provided in FIG. 18.

Figure 19:
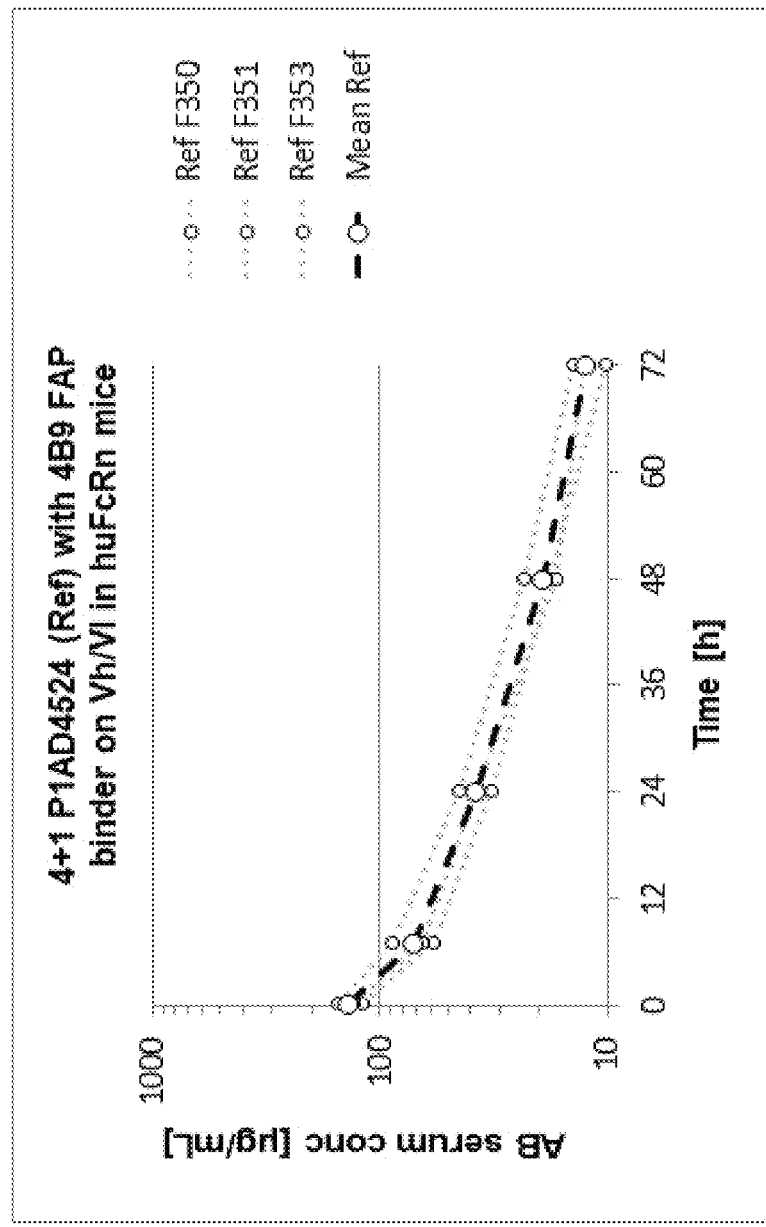

FIG. 19 shows the serum concentration-time profiles of the reference molecule P1AD4524 as measured in three different female HuFcRn mice (F350, F351 and F353) and the mean curve.

Figure 20C:
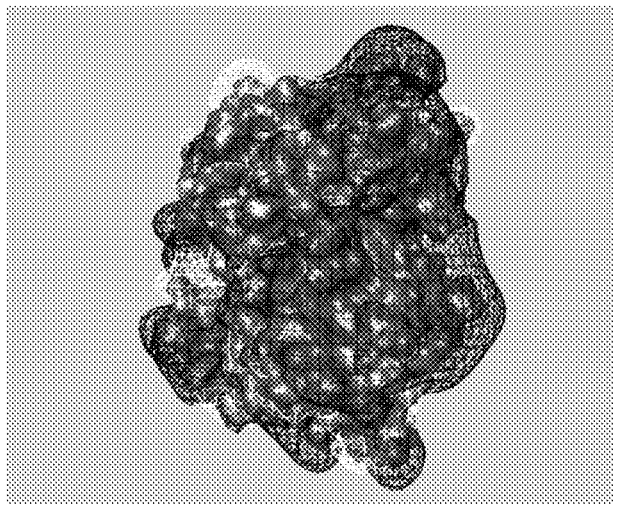
Figure 20B:
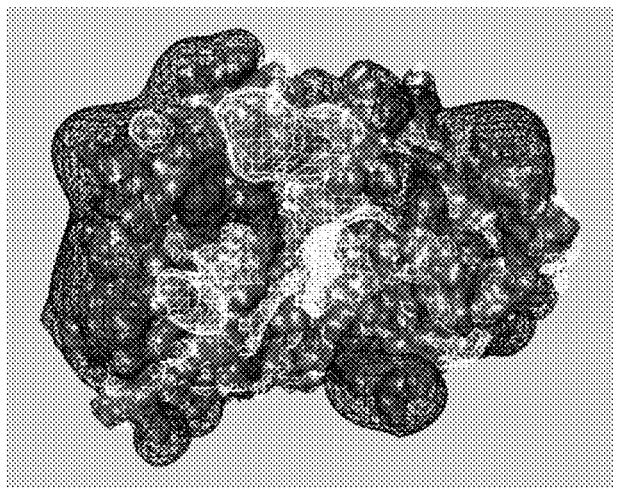
Figure 20A:
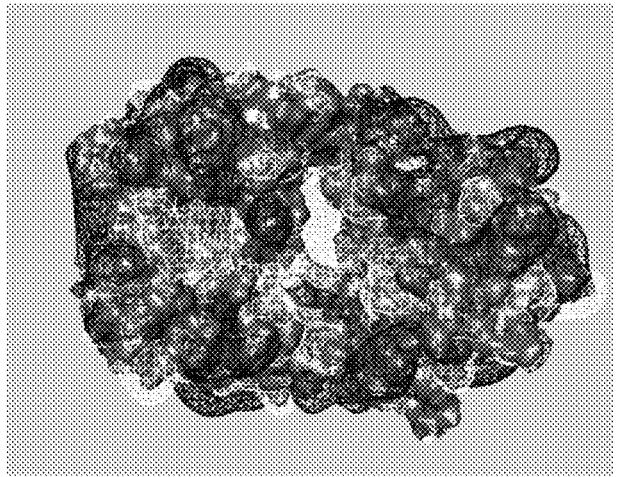
Figure 20F:
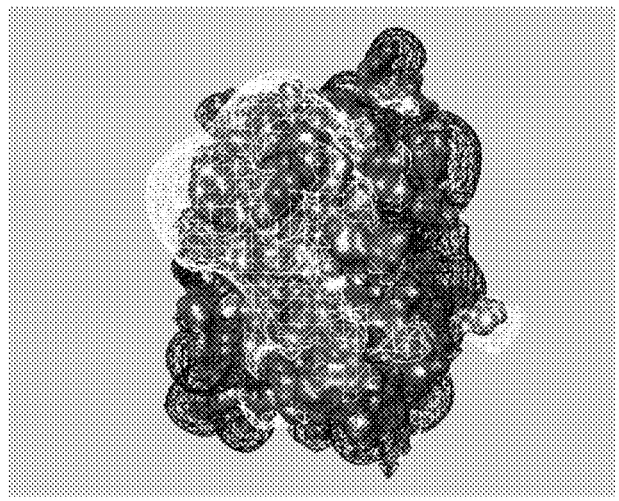
Figure 20E:
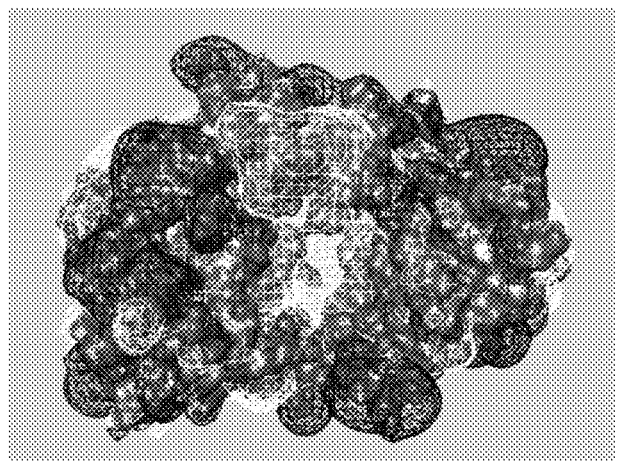
Figure 20D:
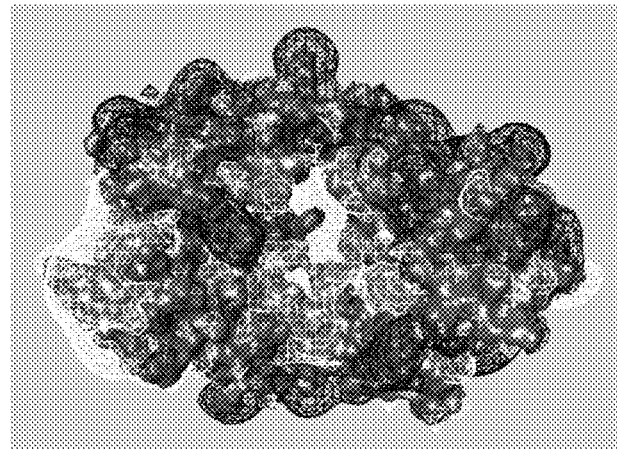

FIG. 20A to FIG. 20C show an isopotential surface area of the Fab region of FAP clone 4B9 as included in the reference compound P1AD4524. Black mesh depicts positively charged patches while white mesh depicts negatively charged patches. FIG. 20A allows a view from the back, FIG. 20B shows the view from the front and FIG. 20C illustrates the top of the antibody. FIG. 20D to FIG. 20F show the isopotential surface area of the Fab region of FAP clone 1G1a as included in molecules of the present invention. Black mesh depicts positively charged patches while white mesh depicts negatively charged patches. FIG. 20D allows a view from the back, FIG. 20E shows the view from the front and FIG. 20F illustrates the top of the Fab.

Figure 21:
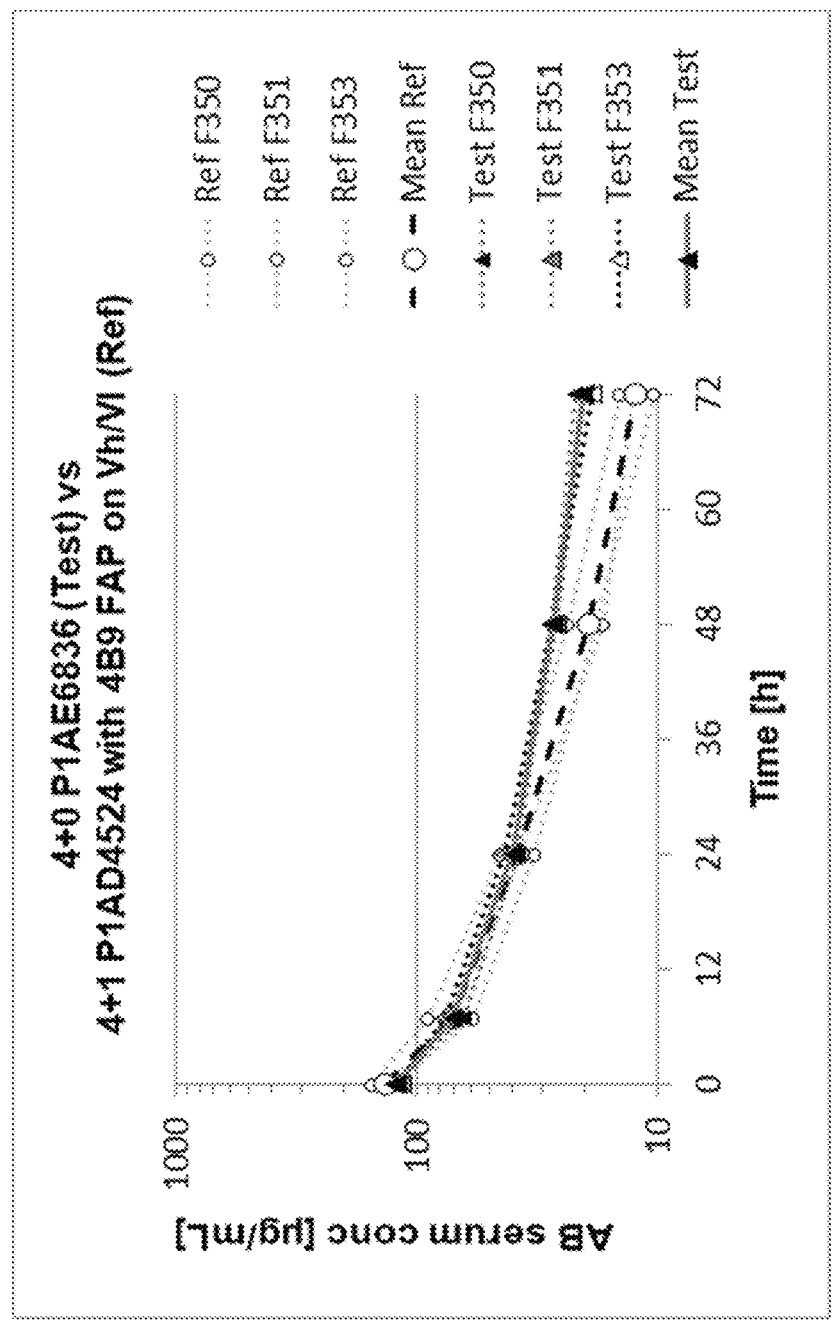

FIG. 21 shows the serum concentration-time profiles of bispecific antigen binding molecule P1AE6836 comprising the FAP antibody 1G1a in comparison to the reference molecule P1AD4524 as measured in three different female HuFcRn mice (F350, F351 and F353) and the mean curve.

Figure 22C:
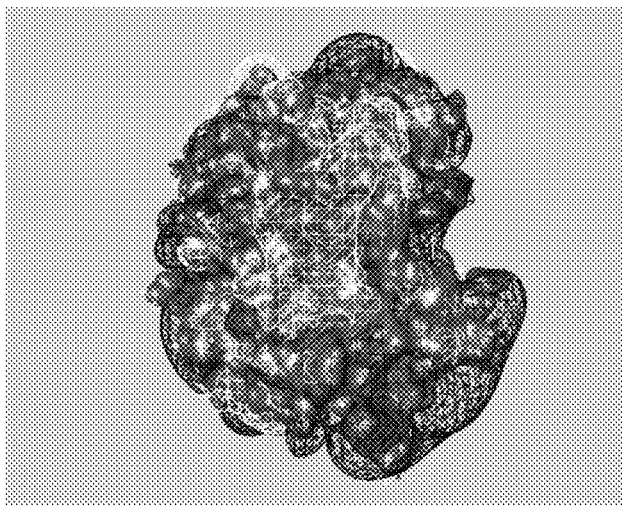
Figure 22B:
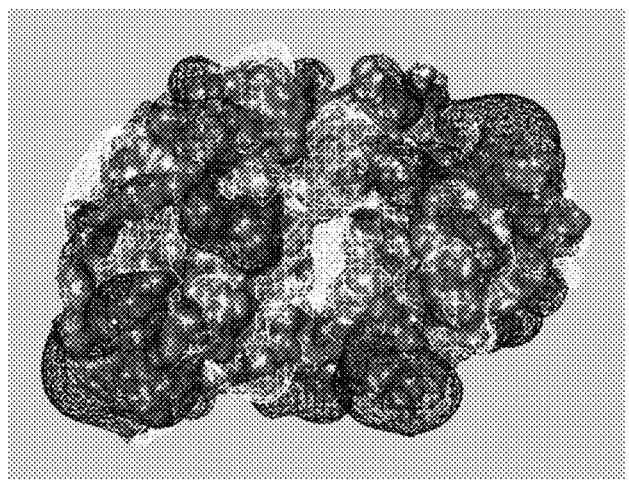
Figure 22A:
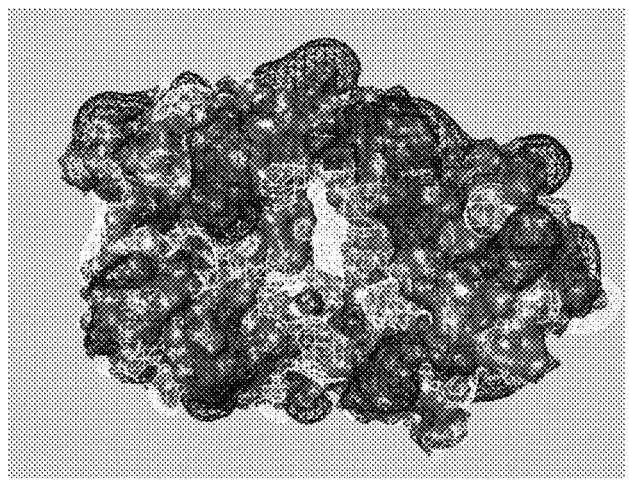

FIG. 22A to FIG. 22C show an isopotential surface area of the Fab region of OX40 clone 49B9 as included in the reference compound P1AD4524. Black mesh depicts positively charged patches while white mesh depicts negatively charged patches. FIG. 22A allows a view from the back, FIG. 22B shows the view from the front and FIG. 22C illustrates the top of the antibody.

Figure 23C:
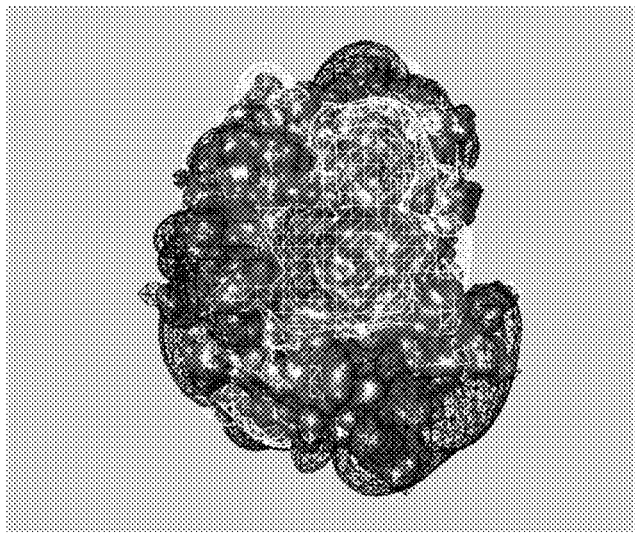
Figure 23B:
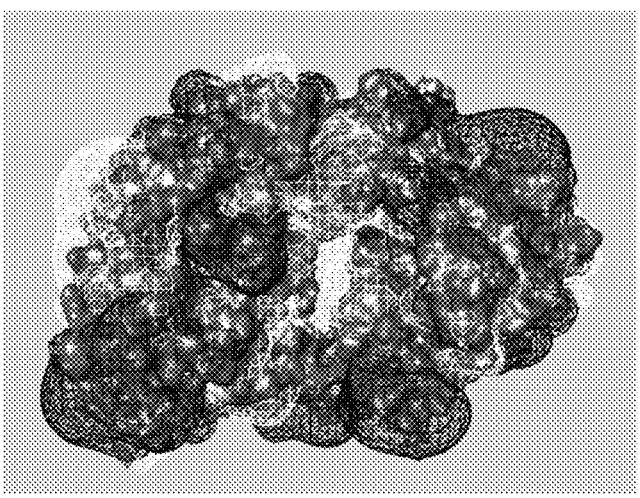
Figure 23A:
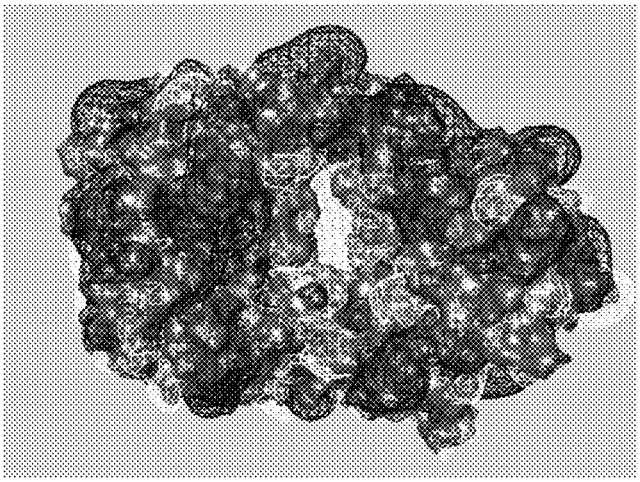

FIG. 23A to FIG. 23C show an isopotential surface area of the Fab region of OX40 clone 8H9. Black mesh depicts positively charged patches while white mesh depicts negatively charged patches. FIG. 23A allows a view from the back, FIG. 23B shows the view from the front and FIG. 23C illustrates the top of the antibody.

Figure 24A:
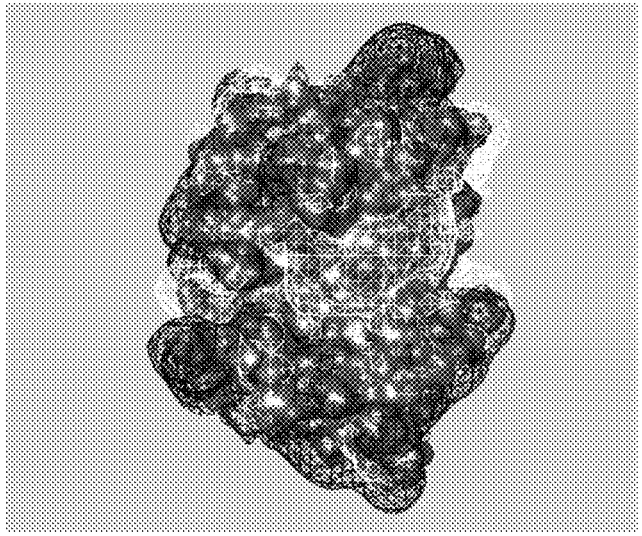
Figure 24B:
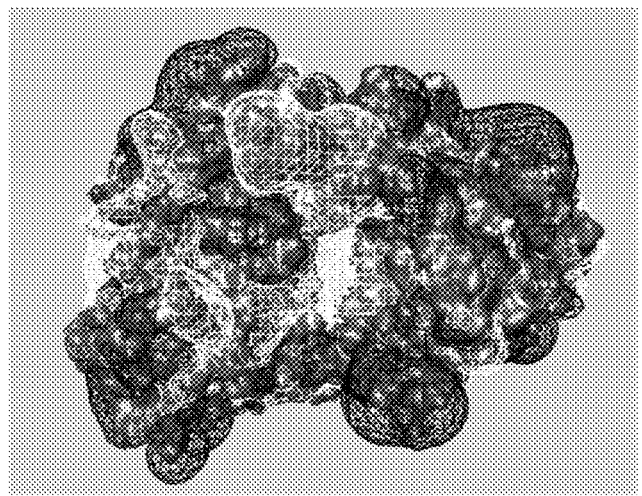
Figure 24C:
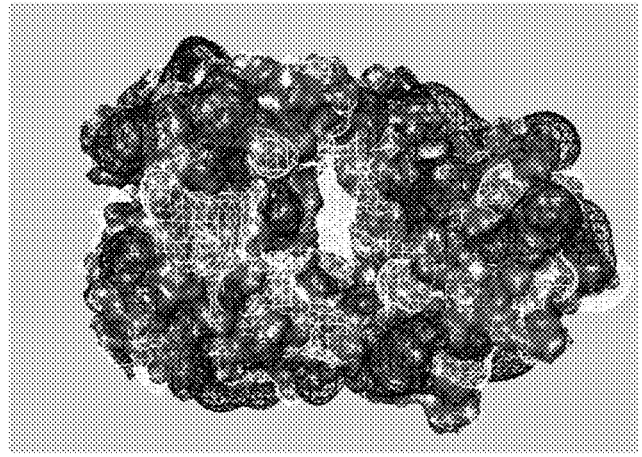

FIG. 24A to FIG. 24C show an isopotential surface area of the Fab region of OX40 clone CLC563. Black mesh depicts positively charged patches while white mesh depicts negatively charged patches. FIG. 24A allows a view from the back, FIG. 24B shows the view from the front and FIG. 24C illustrates the top of the antibody.

Figure 25A:
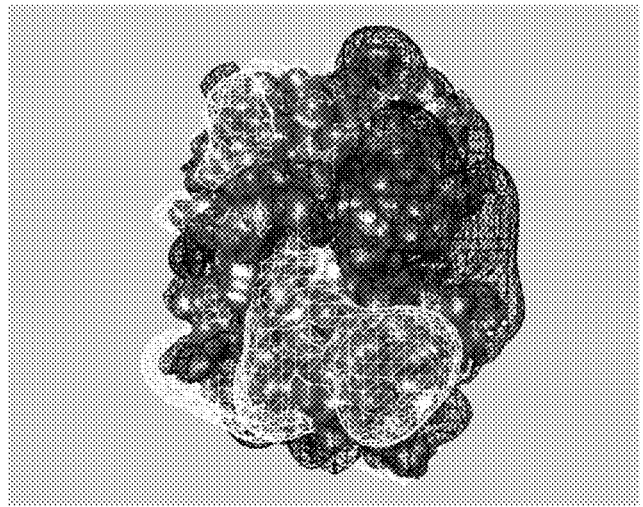
Figure 25B:
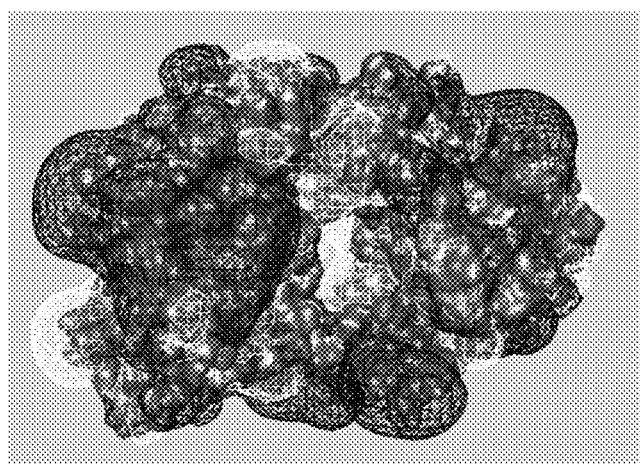
Figure 25C:
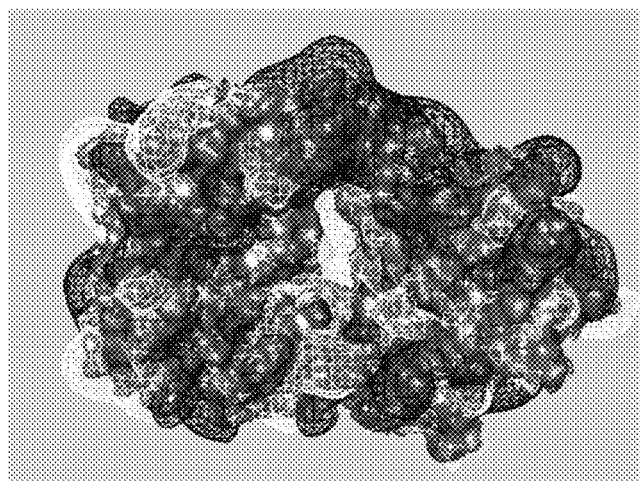

FIG. 25A to FIG. 25C show an isopotential surface area of the Fab region of OX40 clone MOXR0916. Black mesh depicts positively charged patches while white mesh depicts negatively charged patches. FIG. 25A allows a view from the back, FIG. 25B shows the view from the front and FIG. 25C illustrates the top of the antibody.

Figure 26:
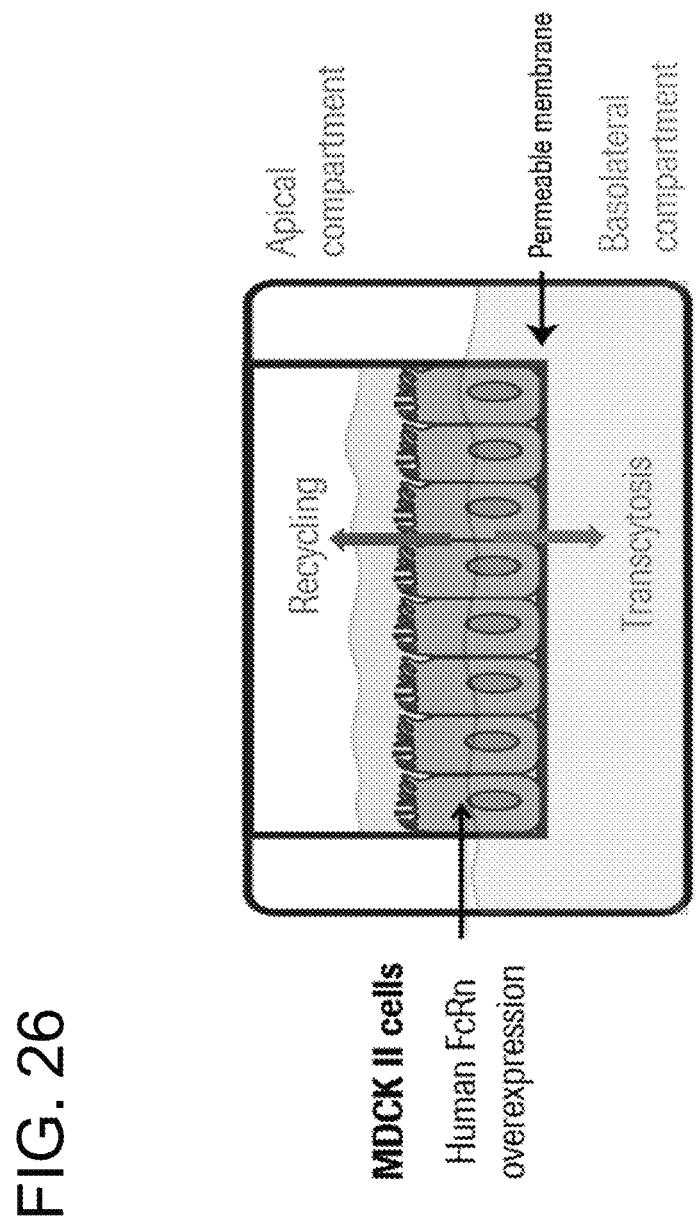

FIG. 26 is a schematic drawing of the transwell system used in the ARC assay. Madin-Darby Canine Kidney cells (MDCK) are seeded in the apical compartment of a transwell system. The MDCK cells have been transfected with the human FcRn.

Figure 27A:
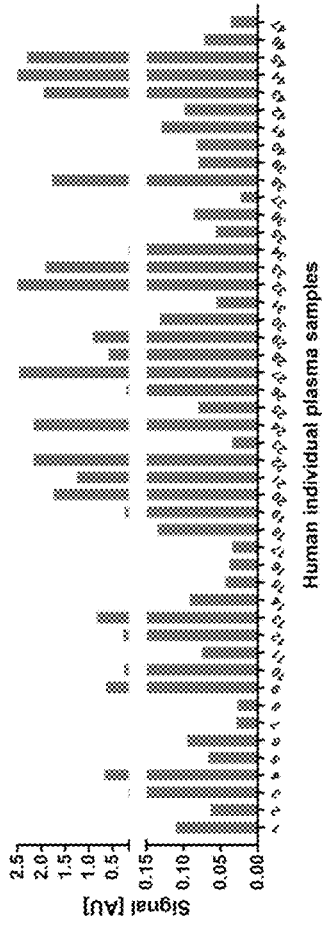
Figure 27B:
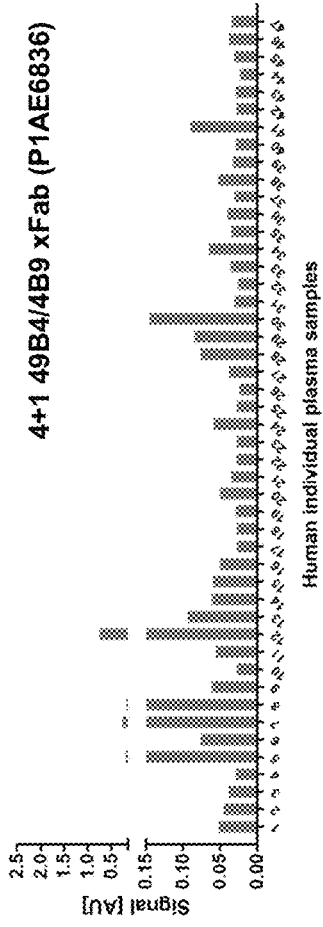
Figure 27C:
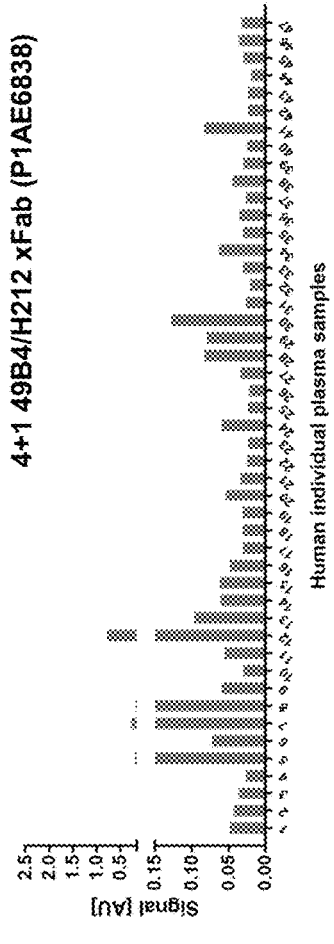

FIG. 27A to FIG. 27C show the preexisting Anti-Drug Antibody (ADA) reactivity in a panel of human individual plasma samples as measured with the assay described in Example 7.1. High incidence with high signals was observed for the bispecific antigen binding molecule OX40 (49B4)×FAP (4B9) (4+1) as described in WO 2017/060144 A1 wherein a VH and VL domain are c-terminally linked to each of the heavy chains (FIG. 27A). Less incidence was detected for bispecific antigen binding molecules wherein the VH and VL domain fused to the C-termini of the Fc domain were replaced by a Fab fragment. However, there still seem to be preexisting anti-drug antibodies against the Fab fragment as can be seen for OX40 (49B4)×FAP (4B9) (4+1) in FIG. 27B and for OX40 (49B4)×FAP (1G1a) (4+1) in FIG. 27C. 1G1a is a humanized variant of FAP clone 212 (H212).

Figure 28:
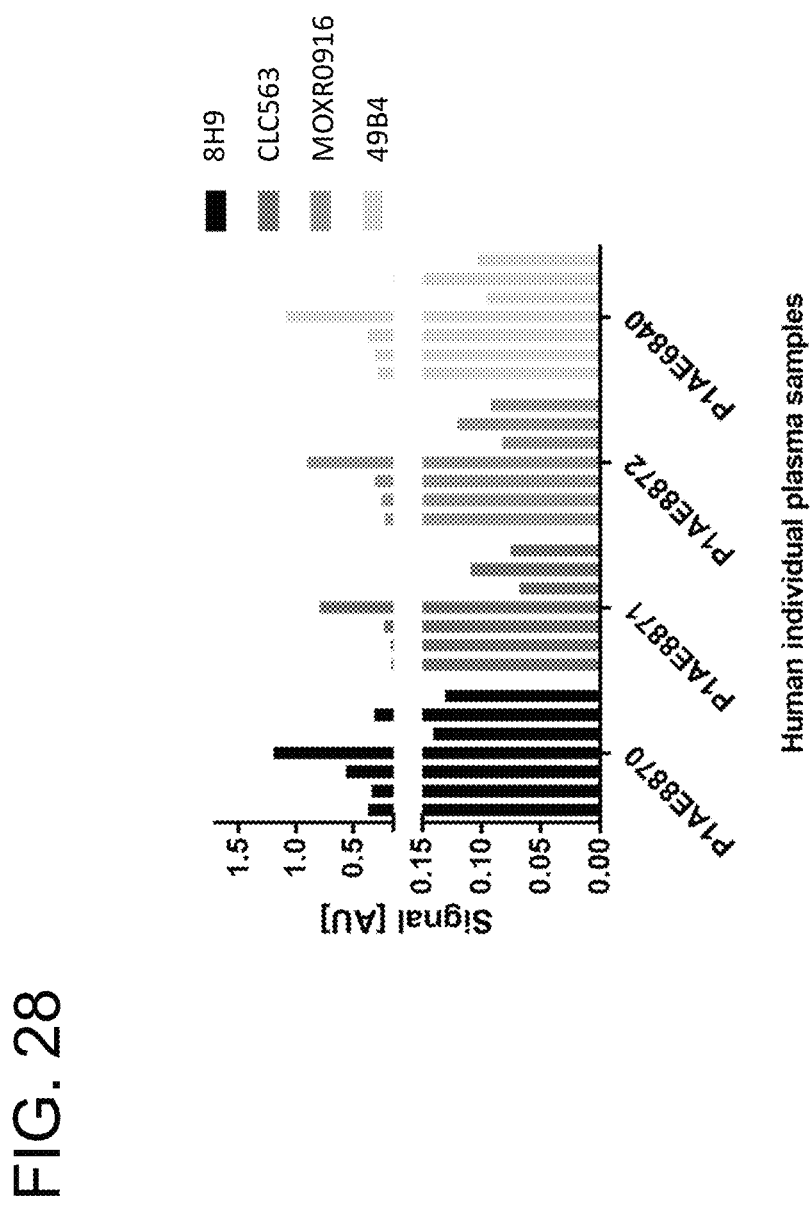

FIG. 28 compares the preexisting Anti-Drug Antibody (ADA) reactivity of bispecific antigen binding molecules in 2+1 format comprising different anti-OX40 clones (49B4, 8H9, MOXR0916 and CLC-563) in a panel of human individual plasma samples.

Figure 29A:
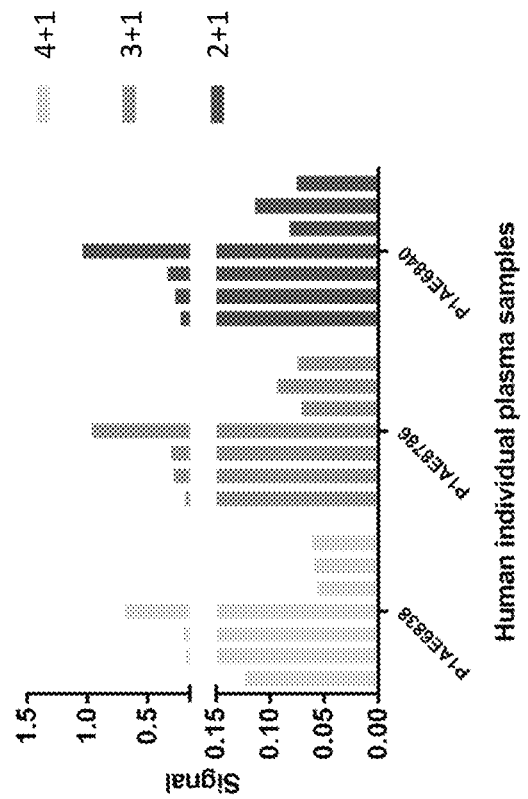
Figure 29B:
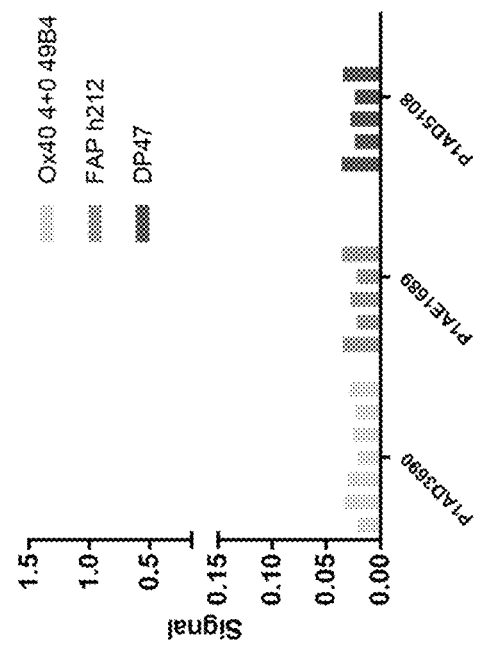

FIG. 29A shows that the control molecules, i.e. an untargeted tetravalent OX40 (49B4) antigen binding molecule (P1AD3690), the FAP (1G1a) antibody (P1AE1689) or a Germline control antibody (DP47) did not cause preexisting Anti-Drug Antibody (ADA) reactivity, whereas the bispecific antigen molecules comprising a Fab fragment fused at the C-terminus of the Fc domain all caused preexisting IgG interference as shown in FIG. 29B. Surprisingly, the smaller 2+1 molecule induced a slightly higher incidence than the molecules in 3+1 and 4+1 format.

Figure 30A:
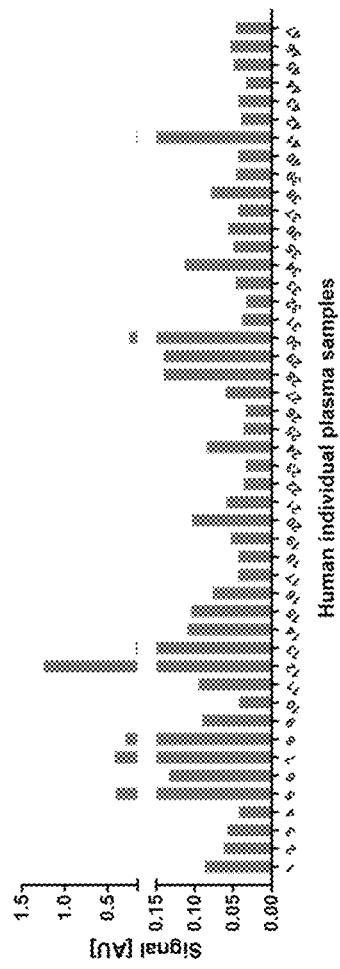
Figure 30B:
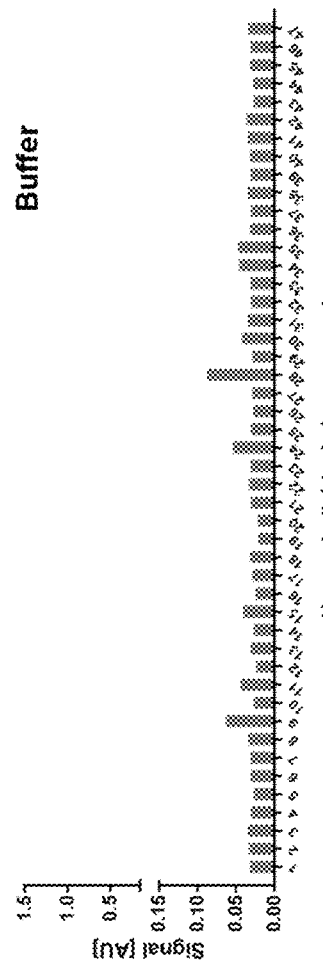
Figure 30C:
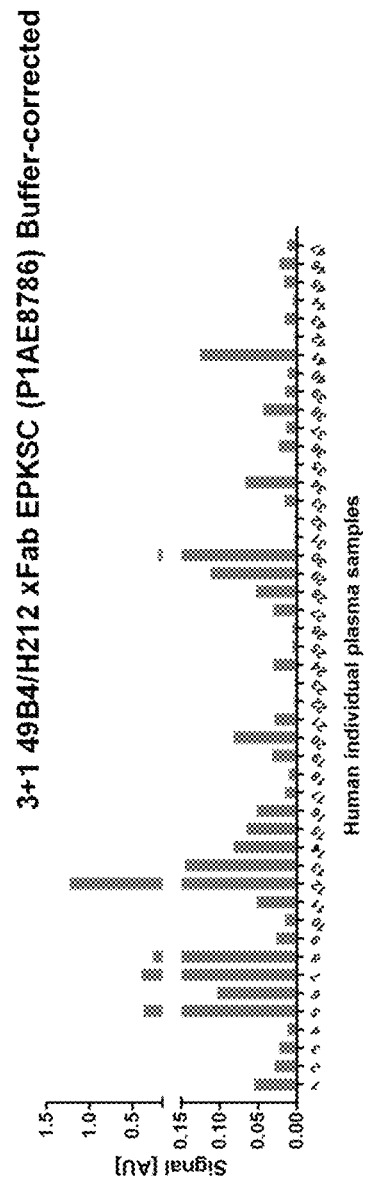

FIG. 30A to FIG. 30C relate to the testing of the preexisting Anti-Drug Antibody (ADA) reactivity of the bispecific antigen binding molecule OX40 (49B4)×FAP (1G1a) (3+1). The molecule comprising a CH1 domain with a "free" C-terminus EPKSC induces preexisting ADA reactivity as can be seen in FIG. 30A. The individual background signal of the buffer as measured by performing the assay without the drug molecule is shown in FIG. 30B and FIG. 30C shows the preexisting ADA reactivity of the molecule with the background signal substracted.

Figure 31A:
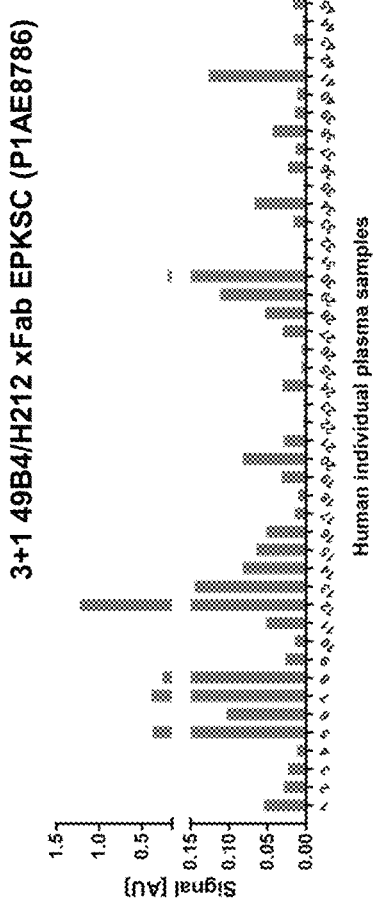
Figure 31B:
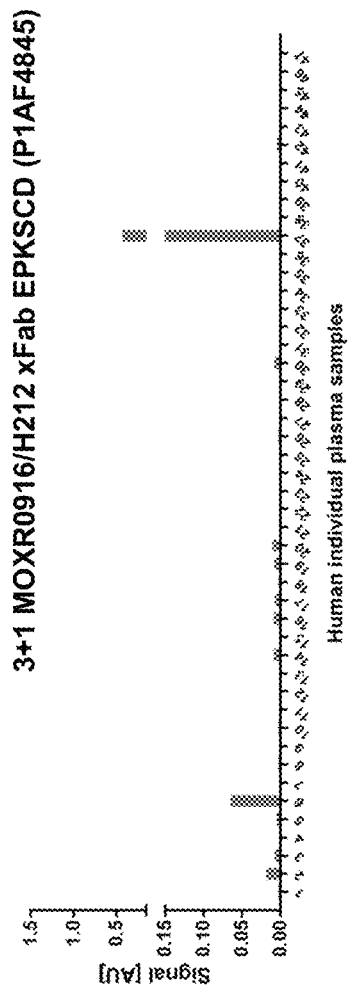
Figure 31C:
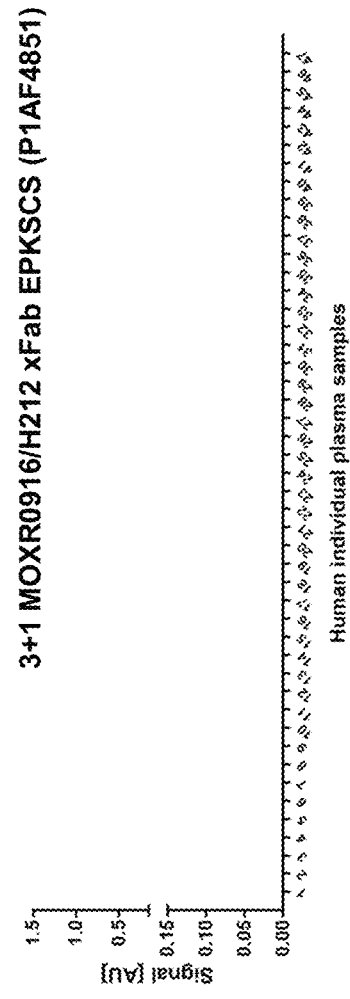

FIG. 31A to FIG. 31C: The preexisting Anti-Drug Antibody (ADA) reactivity in a panel of human individual plasma samples of the bispecific antigen binding molecule OX40 (49B4)×FAP (1G1a) (3+1) as determined in FIG. 30C is also shown in FIG. 31A and compared with the preexisting IgG reactivity induced by the bispecific molecule OX40 (MOXR0916)×FAP (1G1a) (3+1) comprising a EPKSCD terminus (FIG. 31B) or by the bispecific molecule OX40 (MOXR0916)×FAP (1G1a) (3+1) comprising a EPKSCS terminus (FIG. 31C). A massive reduction was observed with the EPKSD variant whereas the EPKSCS variant led to complete elimination of preexisting ADA reactivity.

Figure 32A:
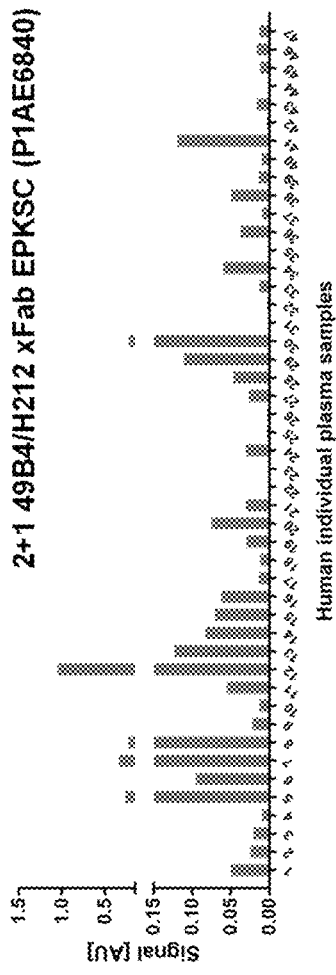
Figure 32B:
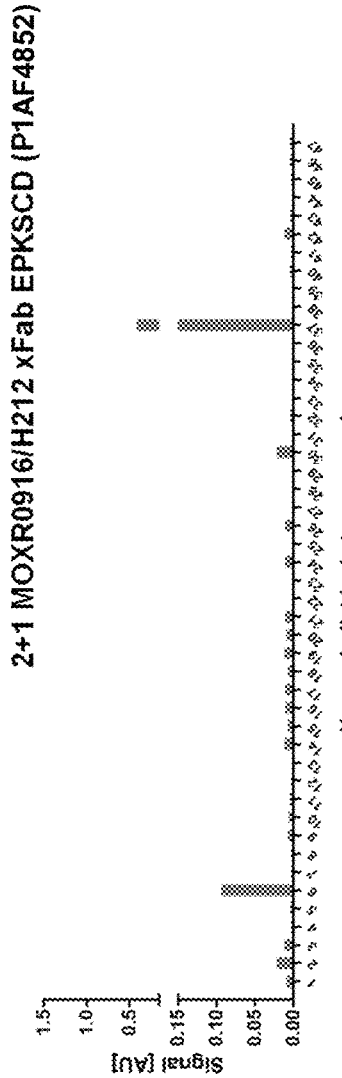
Figure 32C:
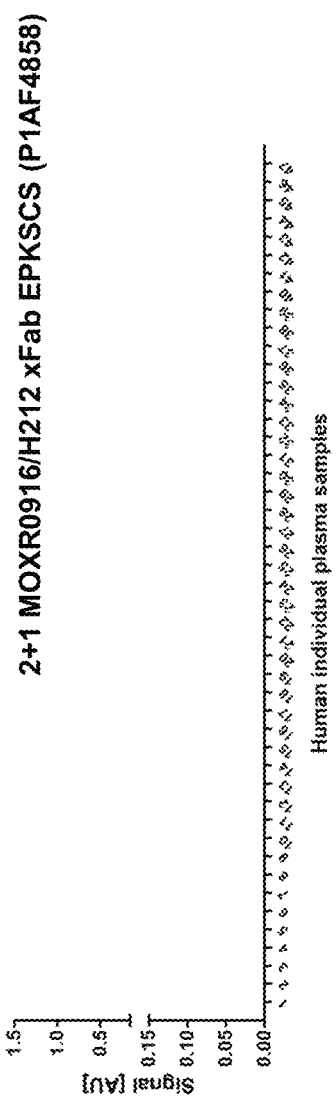

FIG. 32A to FIG. 32C show a respective molecule set in 2+1 format, and confirm the previous results that a bispecific antigen binding molecule OX40 (MOXR0916)×FAP (1G1a) (2+1) with EPKSCD terminus, P1AF4852 (FIG. 32B) reduces, while a bispecific antigen binding molecule OX40 (MOXR0916)×FAP (1G1a) (2+1) with EPKSCS terminus, P1AF4858 (FIG. 32C) eliminates the reactivity with preexisting antibodies in plasma compared to a molecule OX40 (49B4)×FAP (1G1a) (2+1) with a free C-terminus EPKSC (P1AE6840, FIG. 32A).

FIG. 33A to FIG. 33F confirm that the same effect was observed with three other examples. The preexisting ADA reactivity in a panel of human individual plasma samples is shown for OX40 (CLC563)×FAP (1G1a) (3+1) with EPKSCD terminus (P1AF6454) in FIG. 33A, for OX40 (CLC563)×FAP (1G1a) (3+1) with EPKSCS terminus (P1AF6455) in FIG. 33B, for OX40 (CLC563)×FAP (1G1a) (4+1) with EPKSCD terminus (P1AF7205) in FIG. 33C, for OX40 (CLC563)×FAP (1G1a) (4+1) with EPKSCS terminus (P1AF7217) in FIG. 33D, for OX40 (49B4_K23E_K73E)×FAP (1G1a) (3+1) with EPKSCD terminus (P1AF6456) in FIG. 33E and for OX40 (49B4_K23E_K73E)×FAP (1G1a) (3+1) with EPKSCS terminus (P1AF6457) in FIG. 33F.

Figure 34A:
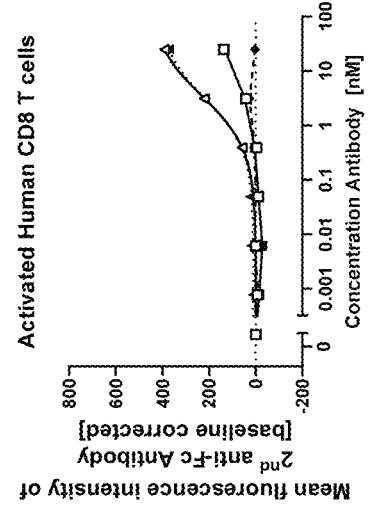
Figure 34C:
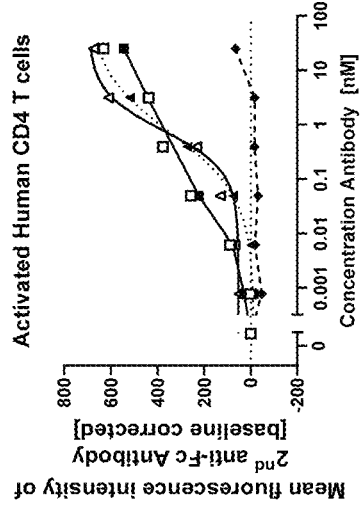
Figure 34B:
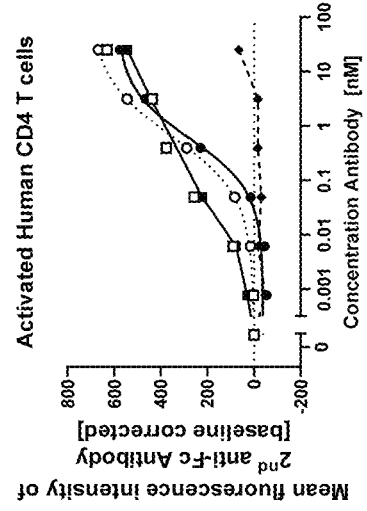
Figure 34D:
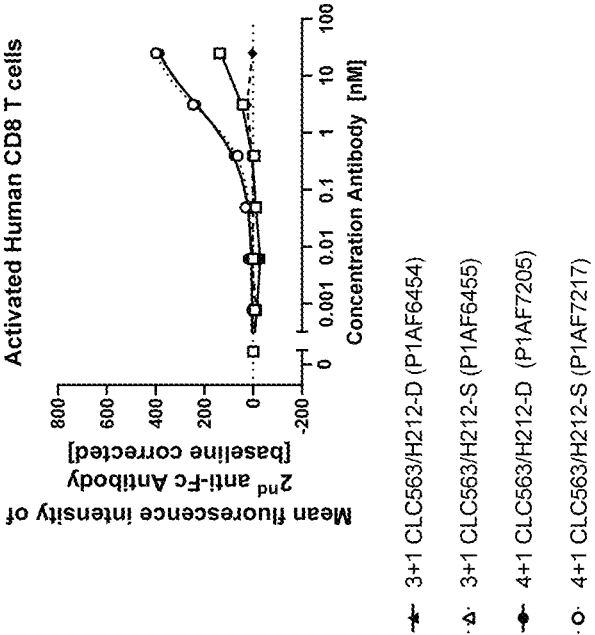
Figure 34E:
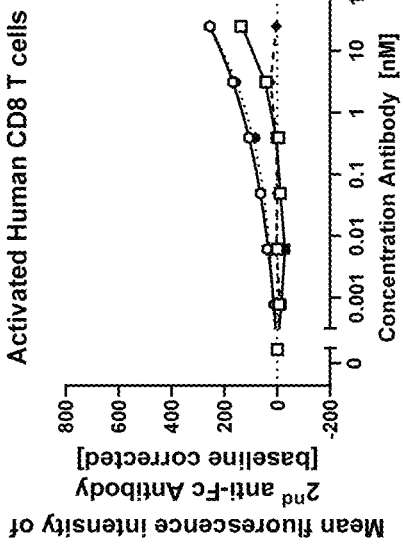
Figure 34F:
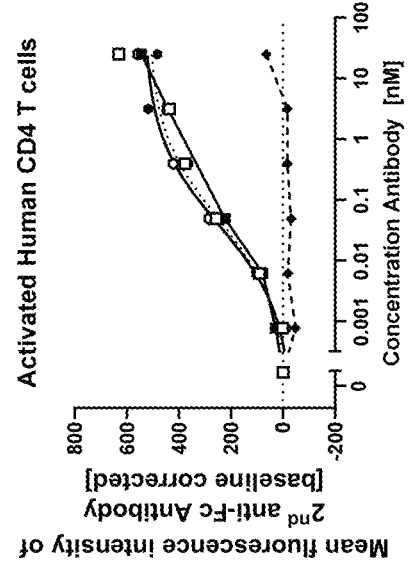

FIG. 34A to FIG. 34F show the cellular binding of bispecific antigen-binding molecules comprising OX40 clones OX40(49B4_K23E_K73E) or OX40(CLC563) in 3+1 and 4+1 formats as D- and S-variant as indicated. OX40 positive activated PBMC gated on activated CD4 cells (FIG. 34A, FIG. 34C, FIG. 34E) and activated CD8 T cells (FIG. 34C, FIG. 34D, FIG. 34F), respectively, were incubated with indicated serial dilutions of test antibody detected then by fluorescently labeled 2nd antibody against human Fcγ. Living cells were gated and the mean fluorescence intensity of the secondary antibody, baseline corrected by the media-only sample, was plotted from duplicates. FIG. 34A shows the binding of the OX40(CLC563) 3+1 constructs as D- and S-variants to activated CD4 cells and the binding to activated CD8 T cells is shown in FIG. 34B. In FIG. 34C and FIG. 34D is shown the binding of the OX40(CLC563) 4+1 constructs as D- and S-variants on activated CD4 cells and on activated CD8 cells, respectively. The binding of OX40 (49B4_K23E_K73E) 4+1 constructs as D- and S-variant to activated CD4 cells and to activated CD8 T cells is shown in FIG. 34E and FIG. 34F, respectively. As control molecules, the untargeted tetravalent OX40(49B4) 4+0 construct (P1AD3690), the tetravalent OX40(49B4)-FAP(4B9) 4+1 construct (P1AD4524) and isotype control were used.

FIG. 35A to FIG. 35F show the NFκB-mediated luciferase expression activity in OX40 expressing reporter cell line HeLa_hOx40_NFκB_Luc1. The concentration of bispecific antigen binding molecules comprising OX40 clones OX40 (49B4_K23E_K73E) or OX40(CLC563) in 3+1 and 4+1 formats as D and S variant are blotted against the units of released light (URL) measured after incubation and addition of Luciferase detection solution. Shown is the NFκB induction, either crosslinked with human FAP expressing NIH/ 3T3 fibroblasts (FIG. 35A for the OX40(CLC563) 3+1 constructs as D- and S-variants, FIG. 35C for the OX40 (CLC563) 4+1 constructs as D- and S-variants and FIG. 35E for the OX40(49B4_K23E_K73E) 4+1 constructs as D- and S-variant), or without further crosslinking (FIG. 35B for the OX40(CLC563) 3+1 constructs as D- and S-variants, FIG. 35D for the OX40(CLC563) 4+1 constructs as D- and S-variants and FIG. 35F for the OX40(49B4_K23E_K73E) 4+1 constructs as D- and S-variant). The isotype control antibody did not induce any NFκB activation. All OX40 containing constructs induced dose dependent NFκB activation. The tetravalent format comprising four OX40 Fab fragments induced a certain NFκB activation due to the assembly of the trimeric core OX40 receptor-signaling unit already in the absence of crosslinking. The S and D variant performed similar. Shown is the mean of duplicates. Error bars represent the SEM.

FIG. 36A to FIG. 36F show the primary T cell bioactivity of bispecific antigen-binding molecules comprising OX40 clones OX40(49B4_K23E_K73E) or OX40(CLC563) in 3+1 and 4+1 formats as D and S variant as indicated. The evaluated bioactivity marker was here the CD25 activation marker expression on CD4$^+$ T cells (FIG. 36A for OX40 (CLC563) 3+1 constructs, FIG. 36C for OX40(CLC563) 4+1 constructs and FIG. 36E for OX40(49B4_K23E_K73E) 4+1 constructs) and CD8$^+$ T cells (FIG. 36B for OX40 (CLC563) 3+1 constructs, FIG. 36D for OX40(CLC563) 4+1 constructs and FIG. 36F for OX40(49B4_K23E_K73E) 4+1 constructs) cells at endpoint. Increased proliferation and CD25 activation marker expression were observed with FAP-targeted OX40 antigen binding molecules in a dose-dependent manner. The untargeted OX40 molecule showed activity only at the highest tested concentrations whereas isotype control showed no activation after baseline-correction. No statistically significant difference could be detected between the S- and D-variants. Shown is the mean of duplicates. Error bars represent the SEM.

FIG. 37A to FIG. 37F show that co-stimulation with FAP targeted OX40 agonists enhances the cytokine secretion of PBMC induced by CEACAM5 TCB mediated lysis of tumor cells. PBMC were cocultured with MKN45 NLR target cells, FAP NIH/3T3-huFAP clone 19, CECAM5 TCB [2 nM] and bispecific antigen binding molecules comprising OX40 clones OX40(49B4_K23E_K73E) or OX40 (CLC563) in 3+1 and 4+1 formats as D and S variant as indicated for 48 hrs. The evaluated bioactivity marker was here the fold increase of GM-CSF (FIG. 37A for OX40 (CLC563) 3+1 constructs, FIG. 37C for OX40(CLC563) 4+1 constructs and FIG. 37E for OX40(49B4_K23E_K73E) 4+1 constructs) and TNF-α (FIG. 37B for OX40(CLC563) 3+1 constructs, FIG. 37D for OX40(CLC563) 4+1 constructs and FIG. 37F for OX40(49B4_K23E_K73E) 4+1 constructs), over TCB only treated samples in the assay supernatant. Cytokine induction was only seen for FAP-crosslinked OX40 agonists in a dose-dependent manner. The untargeted OX40 control molecule (P1AD3690) and isotype control showed no activity here. The S-variants show a trend to reduced bioactivity compared to the D-variants. Shown is the mean of triplicates.

FIG. 38A to FIG. 38F also show that co-stimulation with FAP-targeted OX40 agonists enhances the cytokine secretion of PBMC induced by CEACAM5 TCB mediated lysis of tumor cells. PBMC were cocultured with MKN45 NLR target cells, FAP$^+$ NIH/3T3-huFAP clone 19, CECAM5 TCB [2 nM] and bispecific antigen binding molecules comprising OX40 clones OX40(49B4_K23E_K73E) or OX40(CLC563) in 3+1 and 4+1 formats as D and S variant as indicated for 48 hrs. The evaluated bioactivity marker was here the fold increase of IFNγ (FIG. 38A for OX40 (CLC563) 3+1 constructs, FIG. 38C for OX40(CLC563) 4+1 constructs and FIG. 38E for OX40(49B4_K23E_K73E) 4+1 constructs) and IL-2 (FIG. 38B for OX40(CLC563) 3+1 constructs, FIG. 38D for OX40(CLC563) 4+1 constructs and FIG. 38F for OX40(49B4_K23E_K73E) 4+1 constructs), over TCB only treated samples in the assay supernatant. Cytokine induction was only observed for FAP-crosslinked OX40 agonists in a dose-dependent manner. The untargeted OX40 control molecule (P1AD3690) and isotype control showed no activity here. The S-variants show a trend to reduced bioactivity compared to the D-variant. Shown is the mean of triplicates.

Figure 38A:
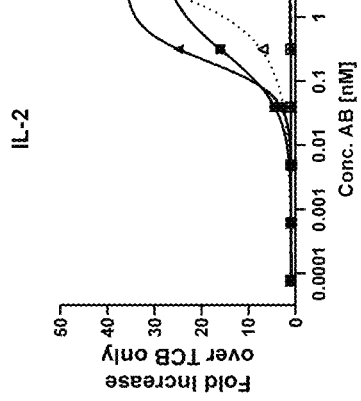
Figure 38B:
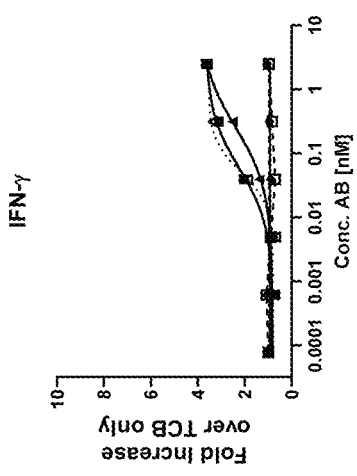
Figure 38C:
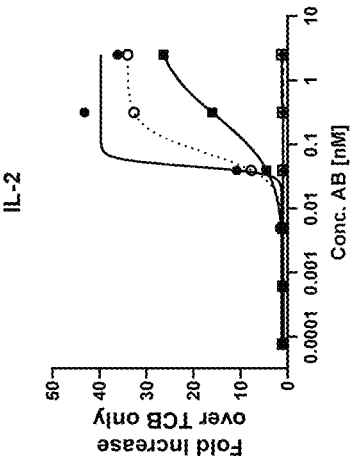
Figure 38D:
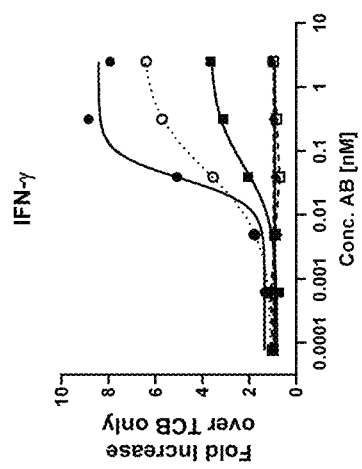
Figure 38F:
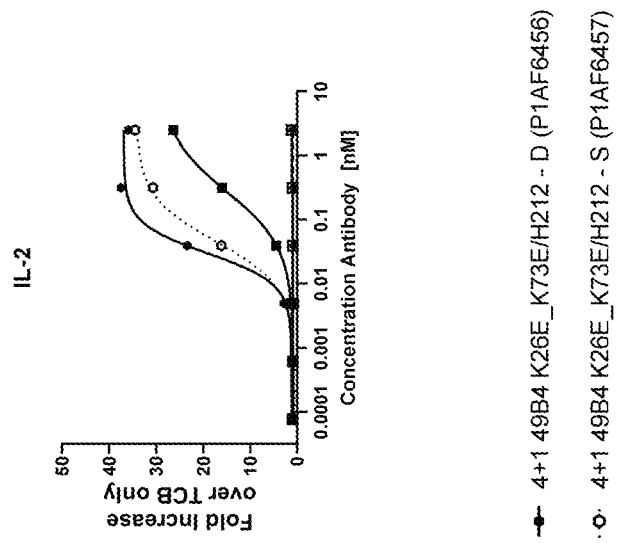
Figure 38E:
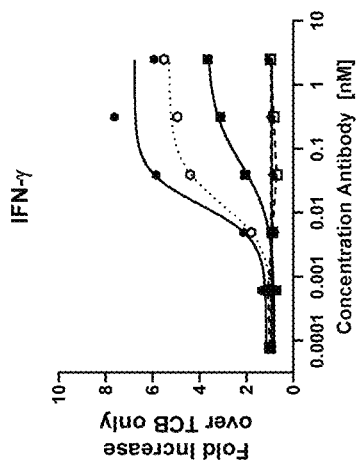
Figure 39:
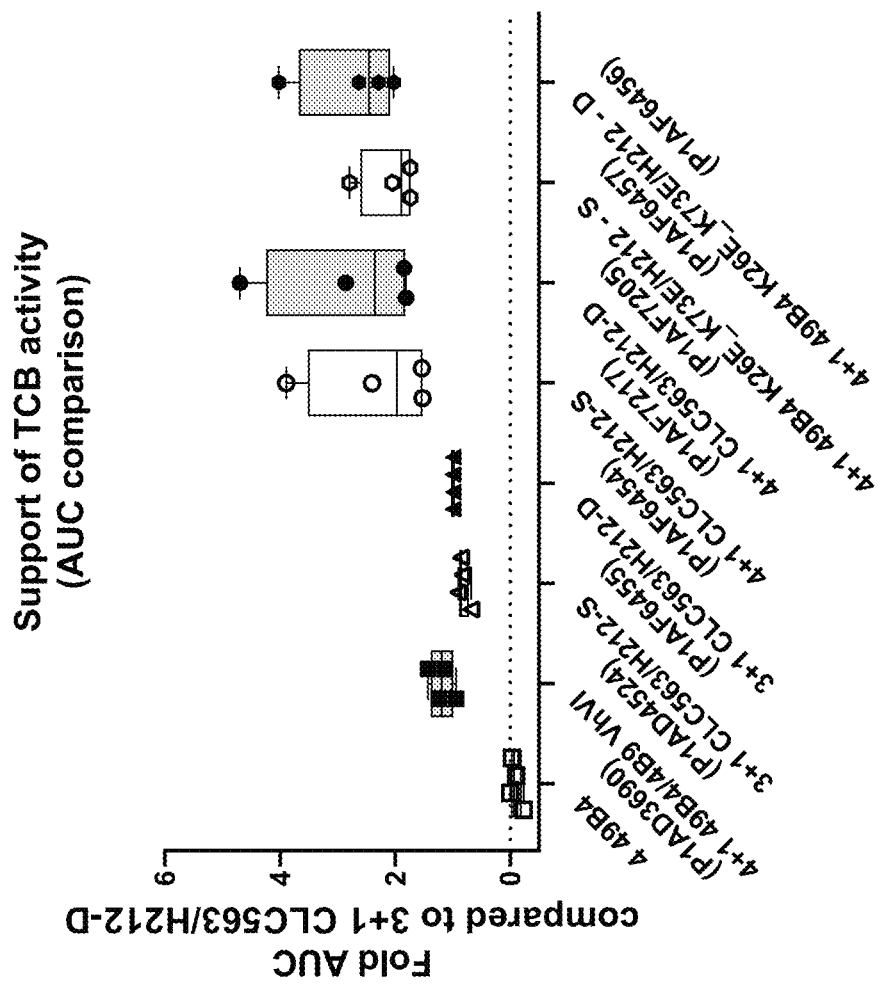

FIG. 39 summarizes the data and shows that co-stimulation with all FAP targeted OX40 agonists enhances the cytokine secretion of PBMC induced by CEACAM5 TCB mediated lysis of tumor cells. The AUC of the dose response curves in FIG. 37A to FIG. 37F and FIG. 38A to FIG. 38F were calculated and normalized against that of the OX40 (CLC563)×FAP(1G1a_EPKSCD) 3+1 antigen binding molecule (P1AF6454, also called 3+1 CLC563/H212-D). Each symbol represents one cytokine in the Box-Whisker Blot.

Figure 40A:
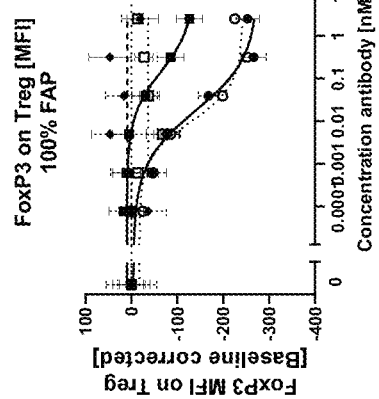
Figure 40B:
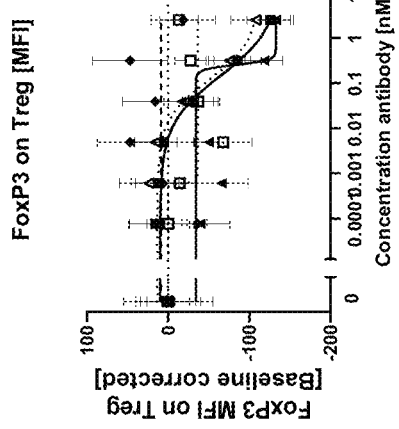
Figure 40C:
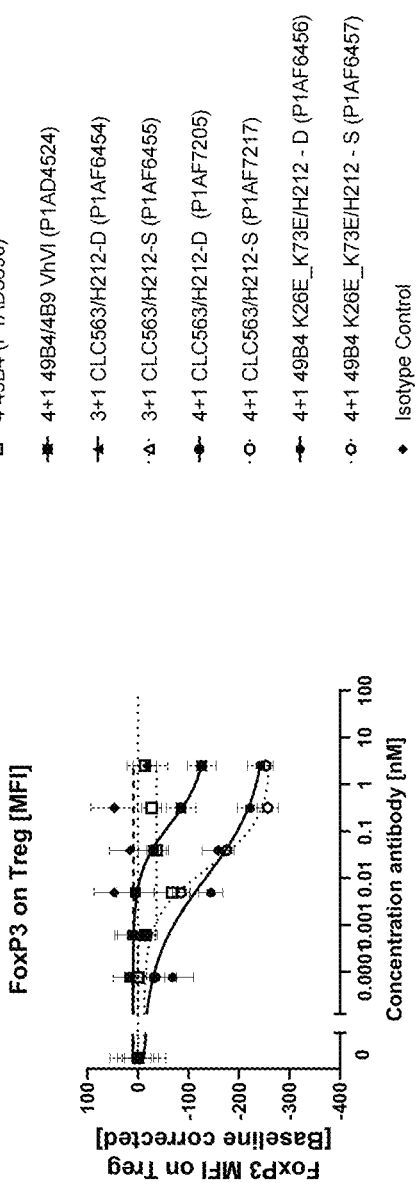

FIG. 40A to FIG. 40C show that co-stimulation with FAP targeted OX40 agonists suppresses the induction of FoxP3 on Treg cells by TGFβ. Human PBMC preparations containing naive CD4 T cells were cultured in the presence of TGFβ during T cell activation with antibodies against CD28 and CD3. OX40 agonism was provided through serial dilution rows of bispecific antigen binding molecules comprising OX40 clones OX40(CLC563) or OX40 (49B4_K23E_K73E) in 3+1 and 4+1 formats as D and S variant. Crosslinking was provided by FAP antigen coated to beads. OX40 agonism interfered with Treg induction visible by reduced FoxP3 expression. Alive CD4$^+$CD25$^+$Treg singlet cells were gated and the MFI of the αFoxP3 antibody reported. The FoxP3 MFI of each concentration was corrected by the MFI of the sample without OX40 antibody, thus only TGBβ, present. FIG. 40A shows the effect of OX40(CLC563) 3+1 constructs, FIG. 40B for OX40 (CLC563) 4+1 constructs and FIG. 40C for OX40 (49B4_K23E_K73E) 4+1 constructs. The D and S variant of each FAP targeted OX40 bispecific antigen binding molecule suppressed FoxP3 to a similar range. Shown is the mean of triplicates, error bars represent the SEM.

Figure 41:
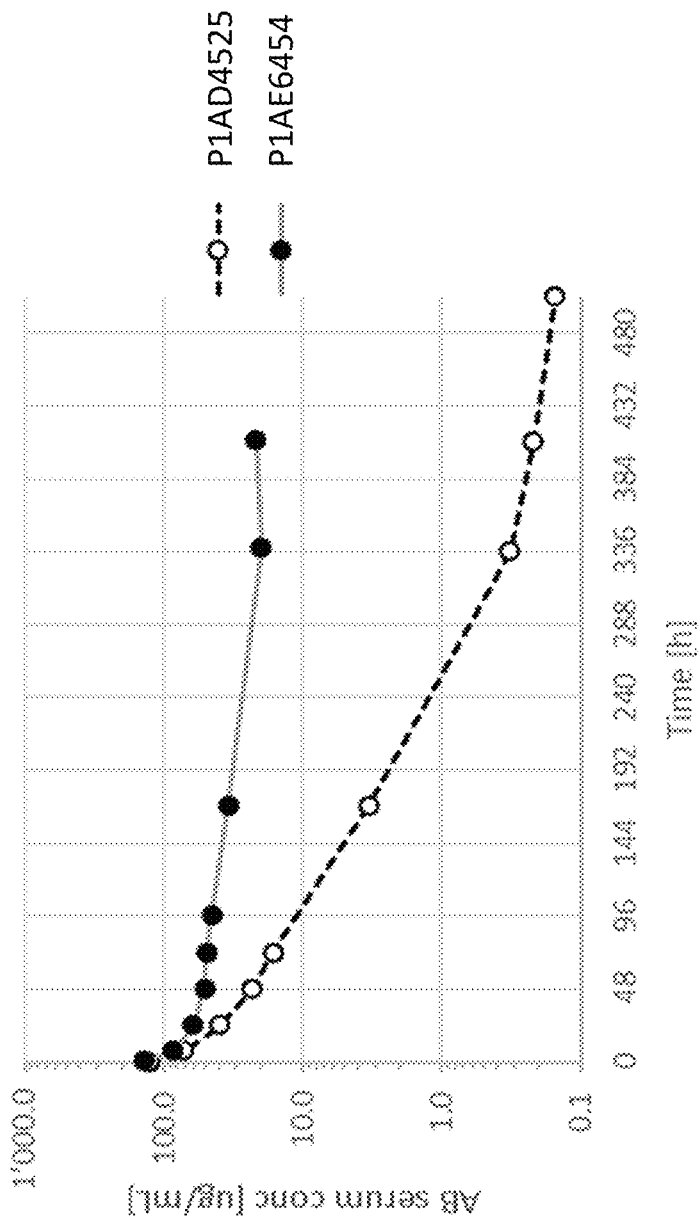

FIG. 41 shows the single dose plasma concentration-time profiles in Hu FcRn mice for the OX40(CLC563)×FAP (1G1a_EPKSCD) 3+1 antigen binding molecule (P1AE6454) and for the OX40(49B4)×FAP(4B9) 4+1 antigen binding molecule (P1AD4524).

Figure 42A:
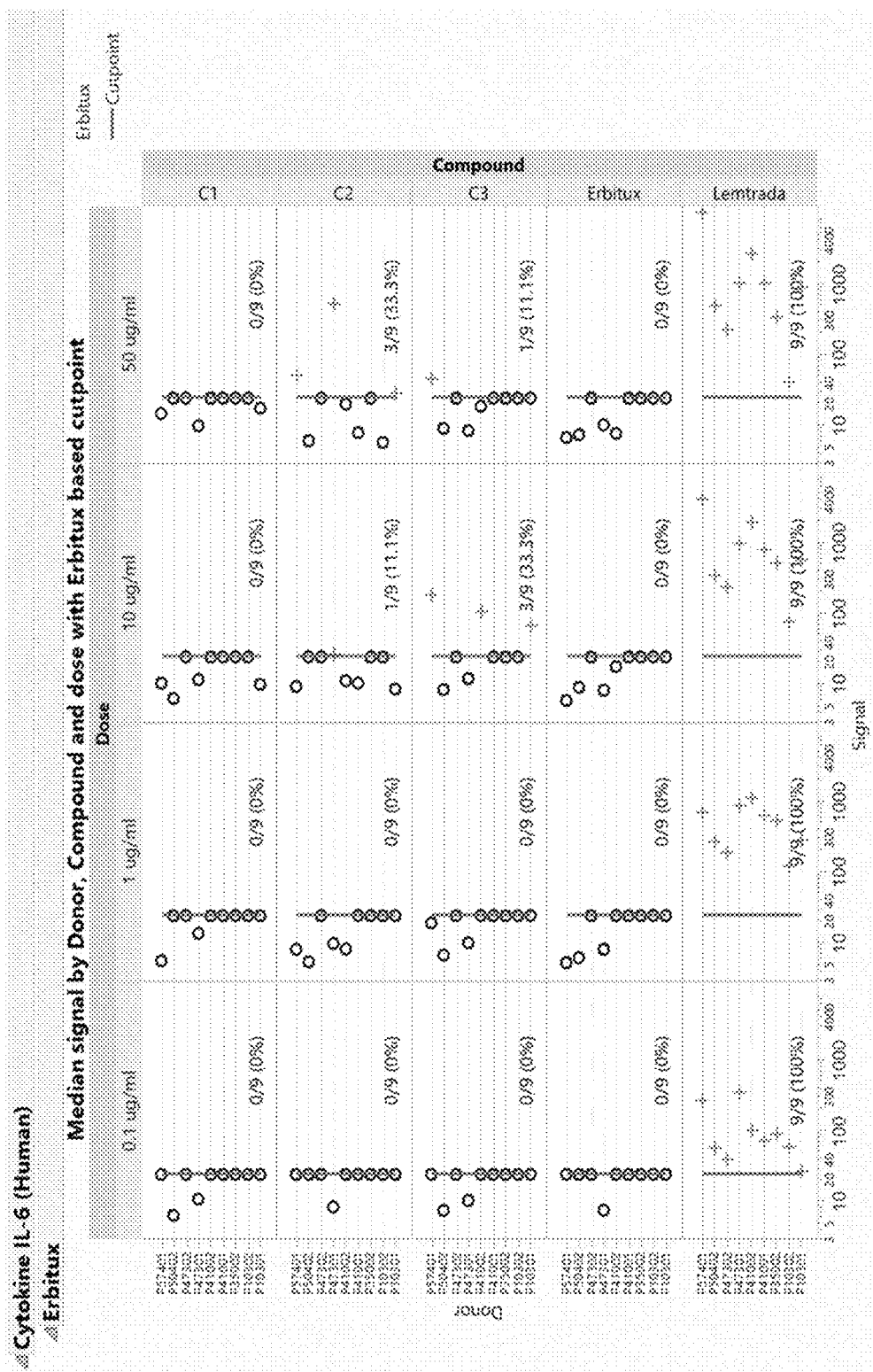
Figure 42B:
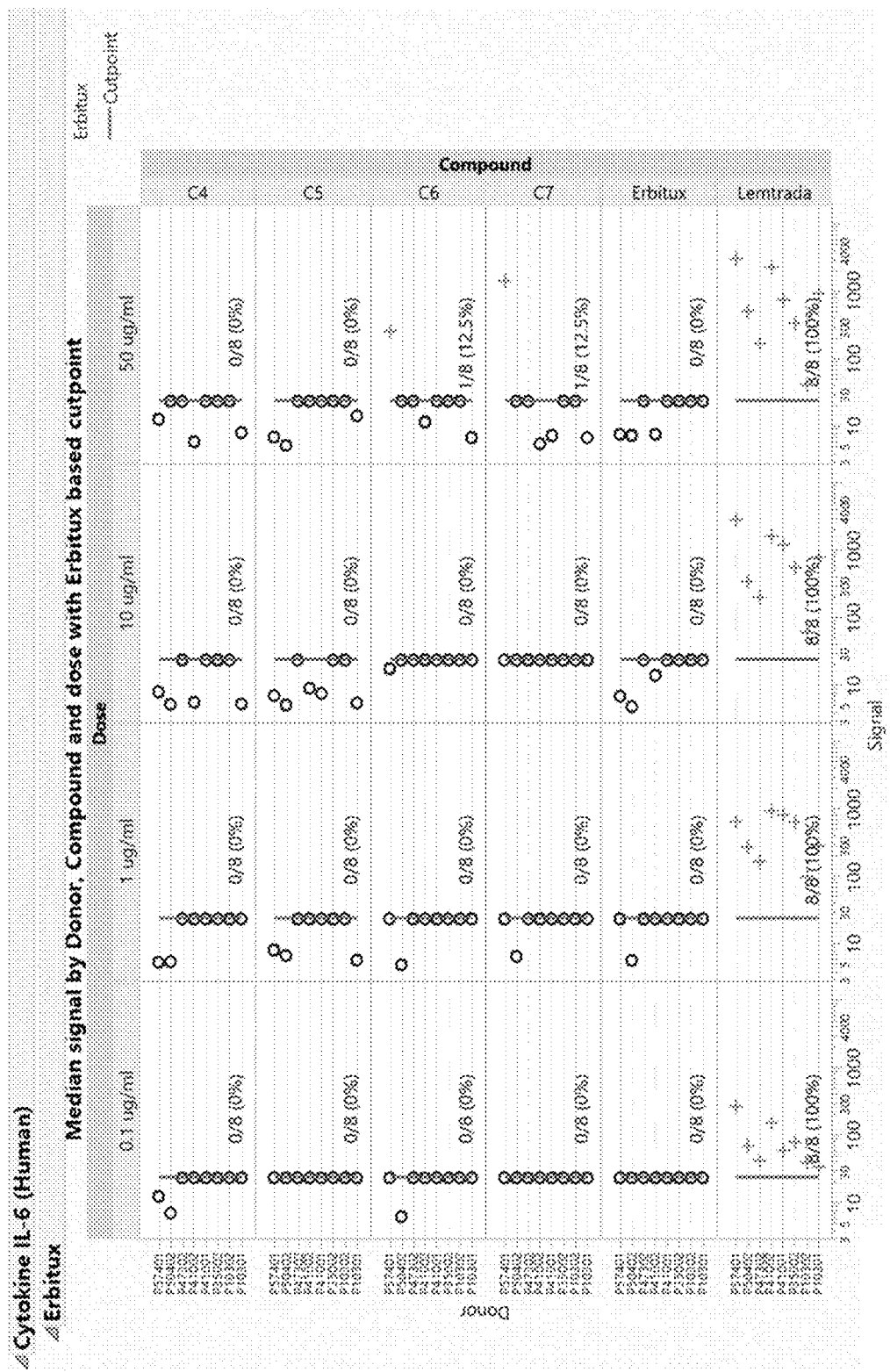

FIG. 42A and FIG. 42B show the release of the cytokine IL-6 in human whole blood samples when incubated with FAP×OX40 bispecific antigen binding molecules. Shown is the median signal for each donor and different concentrations in relation to the signal of Erbitux® as negative comparator. In FIG. 42A the median signals for the bispecific antibodies C1, C2 und C3 (see Example 8.1.1) are shown, whereas the median signals for the bispecific antibodies C4, C5, C6 and C7 are shown in FIG. 42B.

Figure 43A:
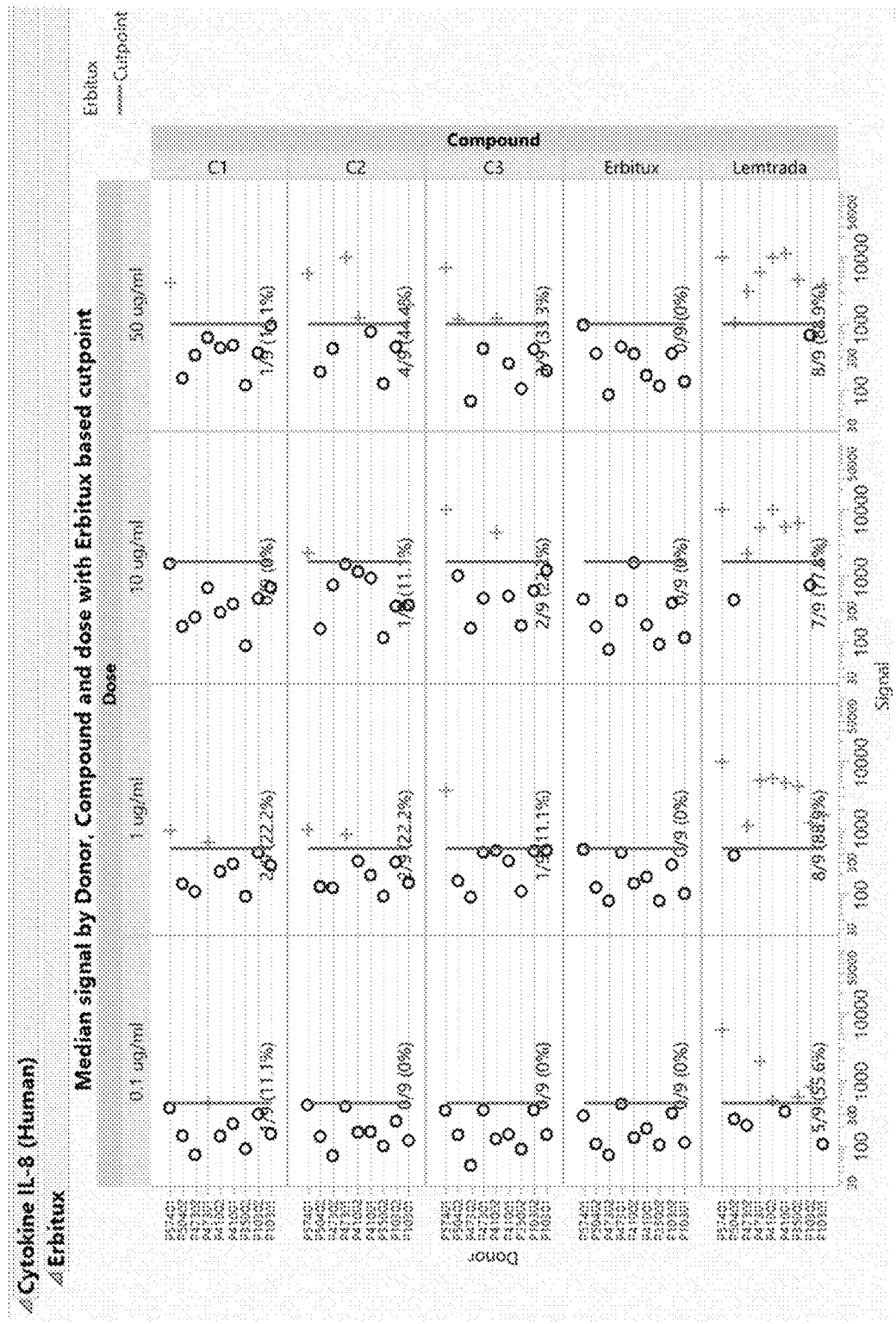
Figure 43B:
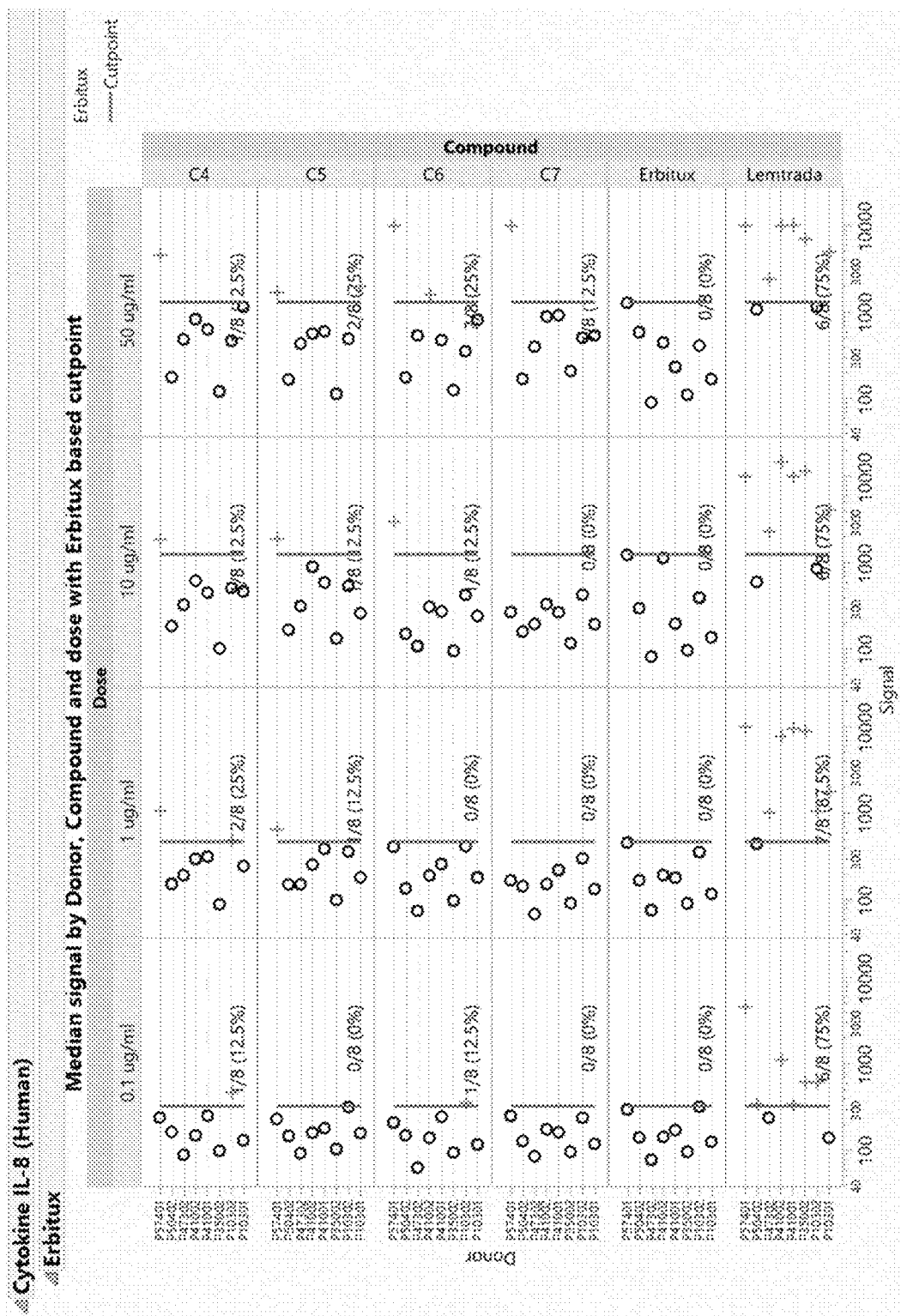

FIG. 43A and FIG. 43B show the release of the cytokine IL-8 in human whole blood samples when incubated with FAP×OX40 bispecific antigen binding molecules. Shown is the median signal for each donor and different concentrations in relation to the signal of Erbitux® as negative comparator. In FIG. 43A the median signals for the bispecific antibodies C1, C2 und C3 (see Example 8.1.1 and in FIG. 43B the median signals for the bispecific antibodies C4, C5, C6 and C7 are shown.

Figure 44A:
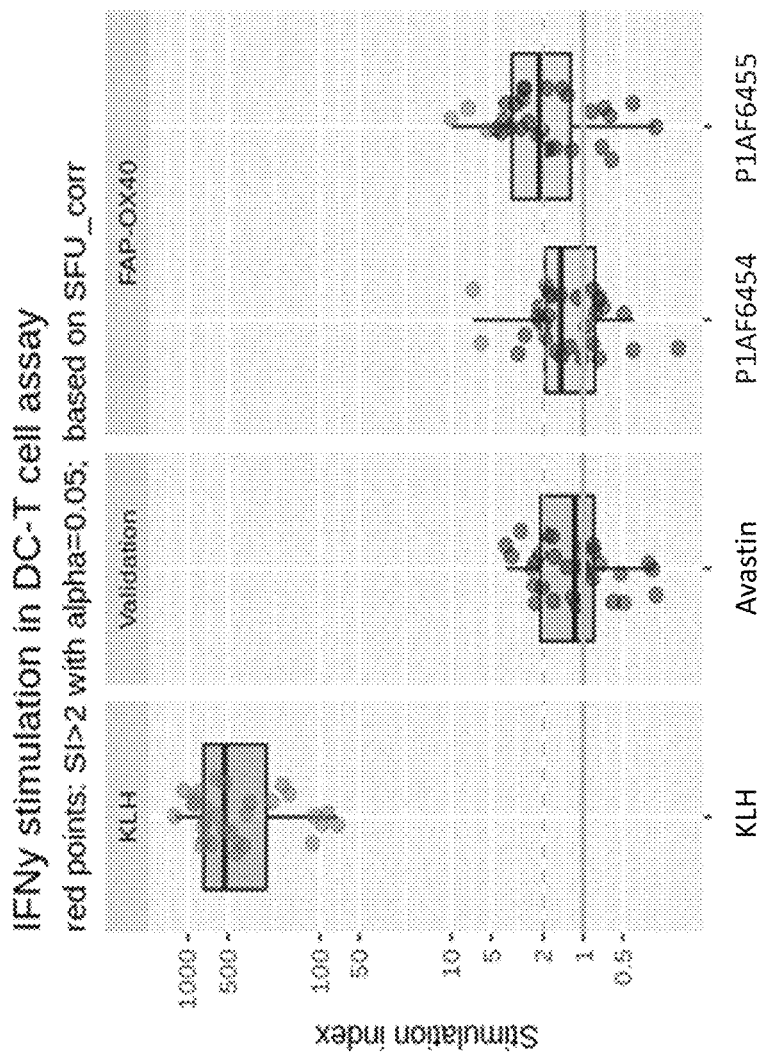
Figure 44B:
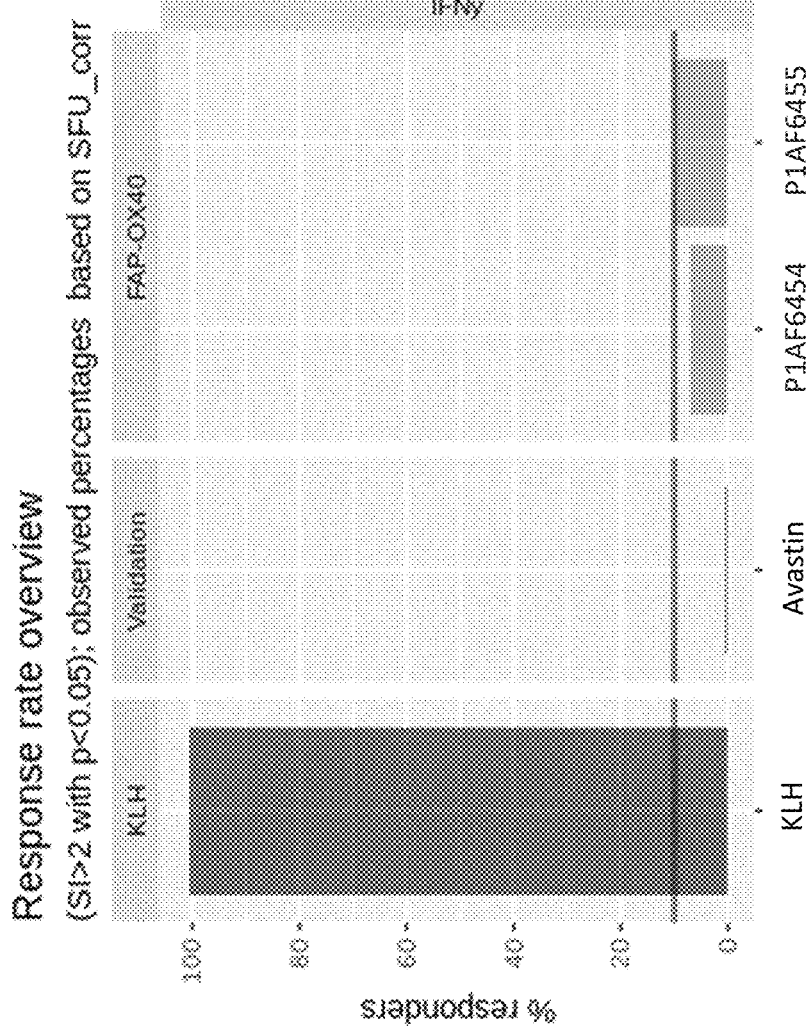

FIG. 44A and FIG. 44B show the results of the DC:CD4$^+$ T cell assay evaluating the sequence-related risk of immunogenicity of the bispecific FAP×OX40 antibodies P1AF6454 and P1AF6455 in comparison to Keyhole limpet haemocyanin (KLH) as positive control and Bevacizumab (Avastin®). The IFNγ stimulation plotted against a stimulation index is shown in FIG. 44A and FIG. 44B gives the response rate overview in % responders.

Figure 45A:
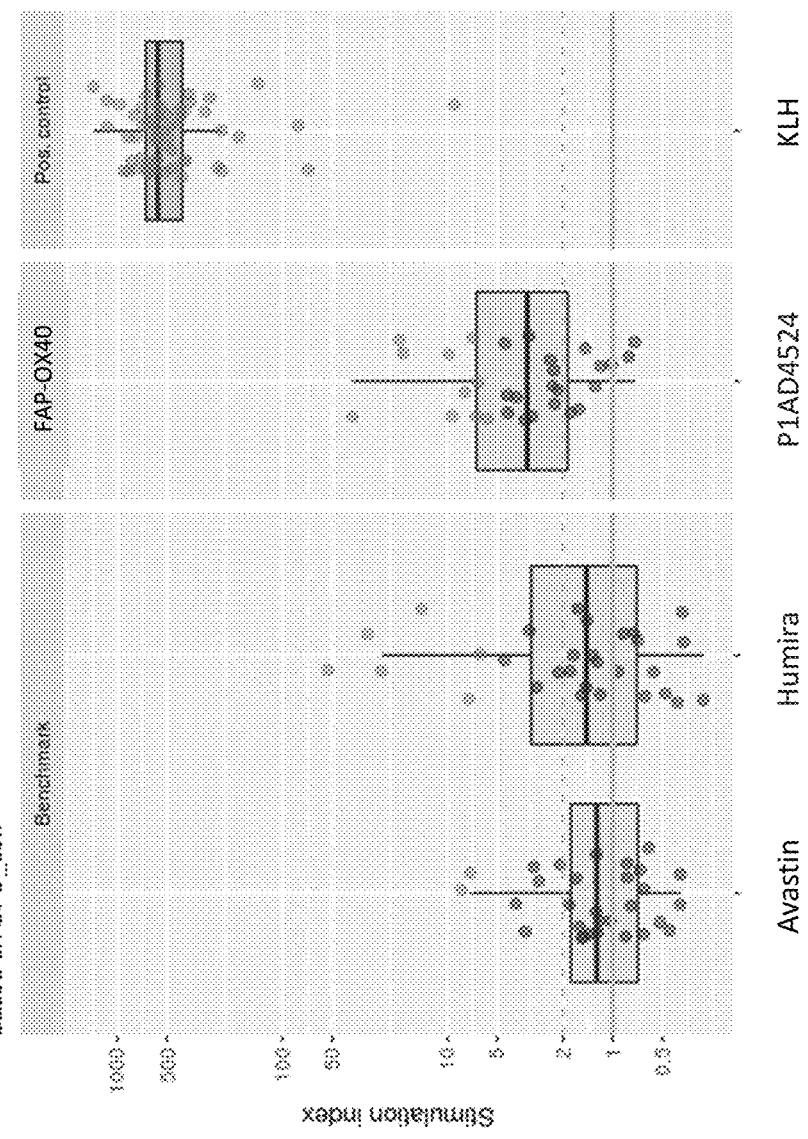
Figure 45B:
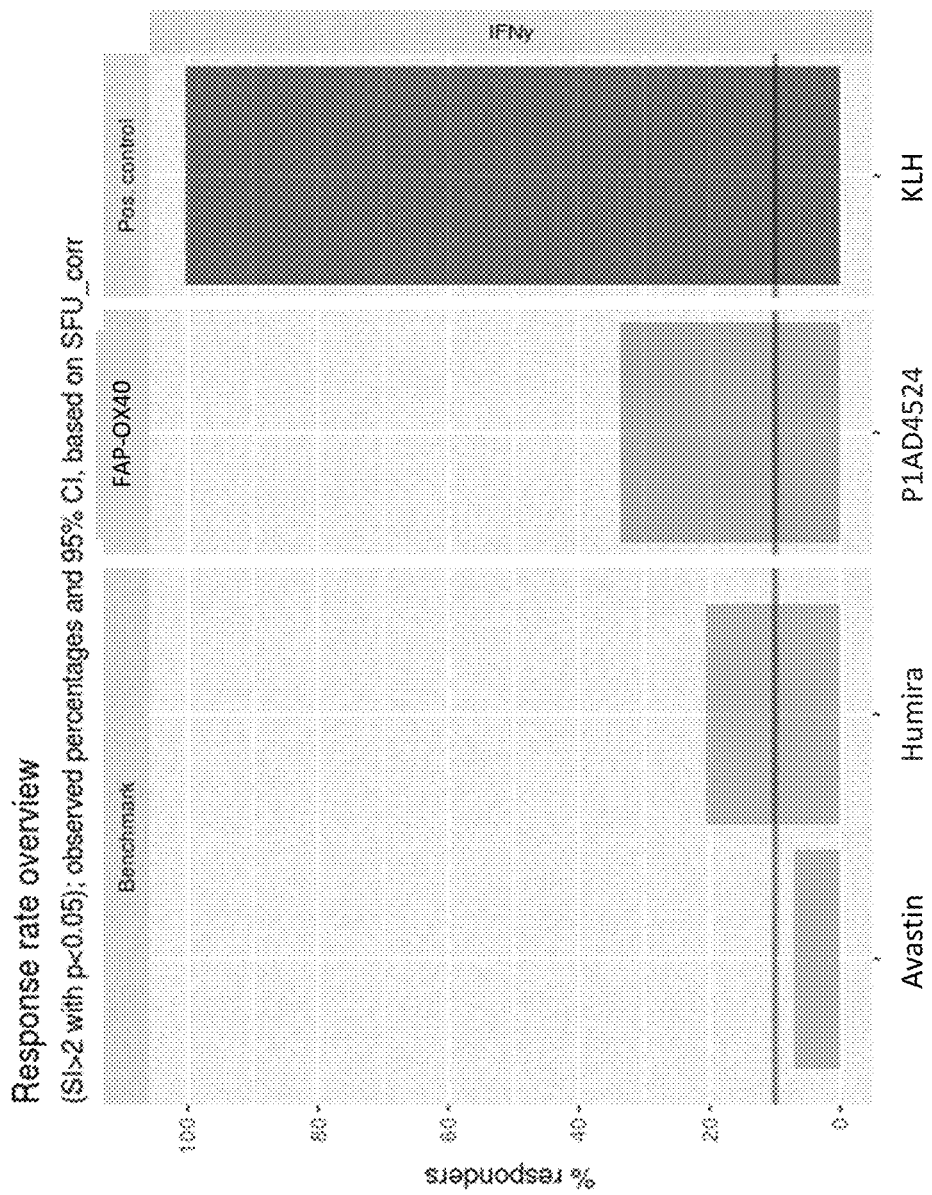

FIG. 45A and FIG. 45B relate to the results of the DC:CD4$^+$ T cell assay evaluating P1AD4525 against Keyhole limpet haemocyanin (KLH) as positive control and Bevacizumab (Avastin®) and adalimumab (Humira®). The IFNγ stimulation plotted against a stimulation index is shown in FIG. 45A and FIG. 45B gives the response rate overview in % responders.

Figure 46:
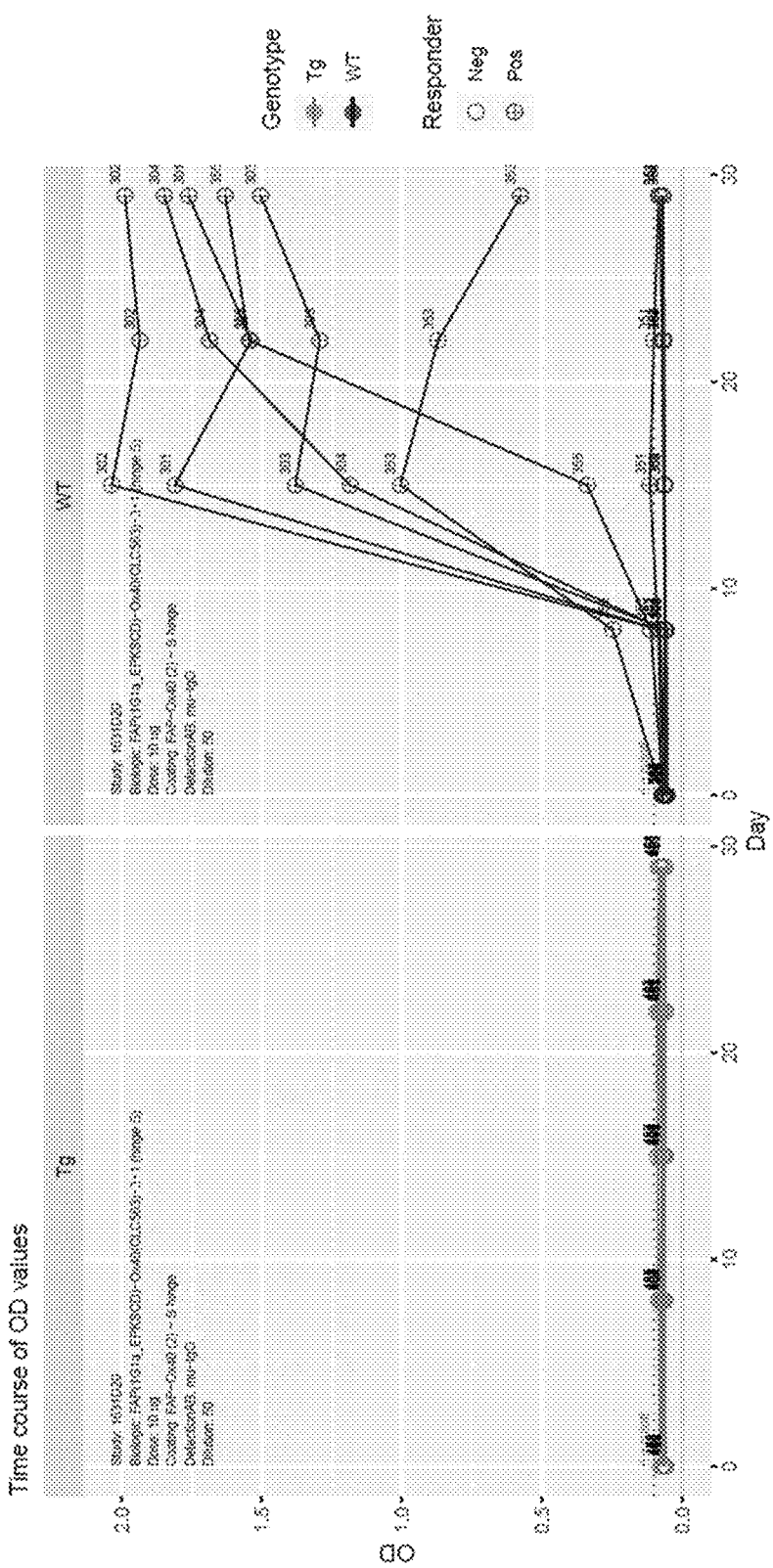
Figure 47:
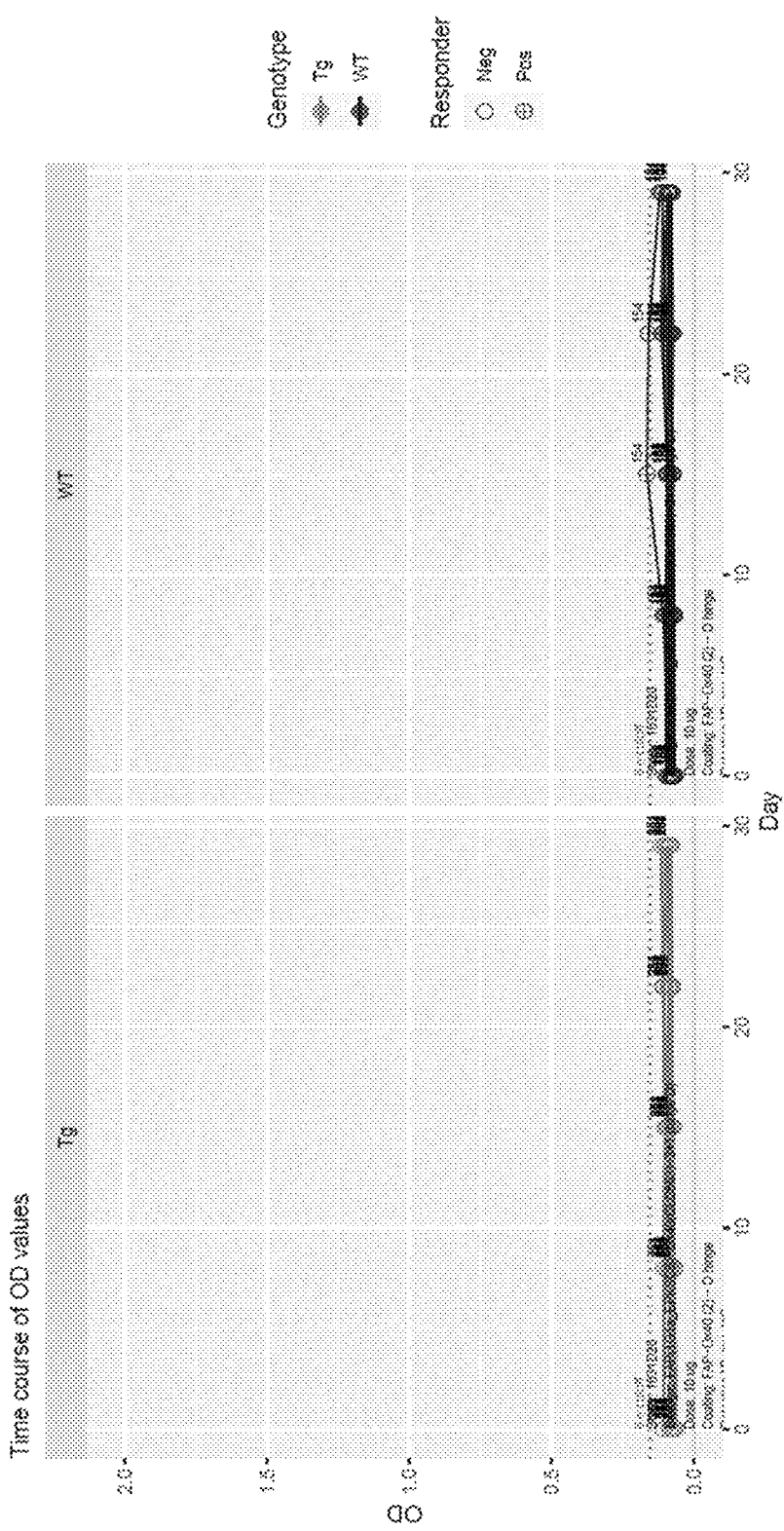
Figure 48:
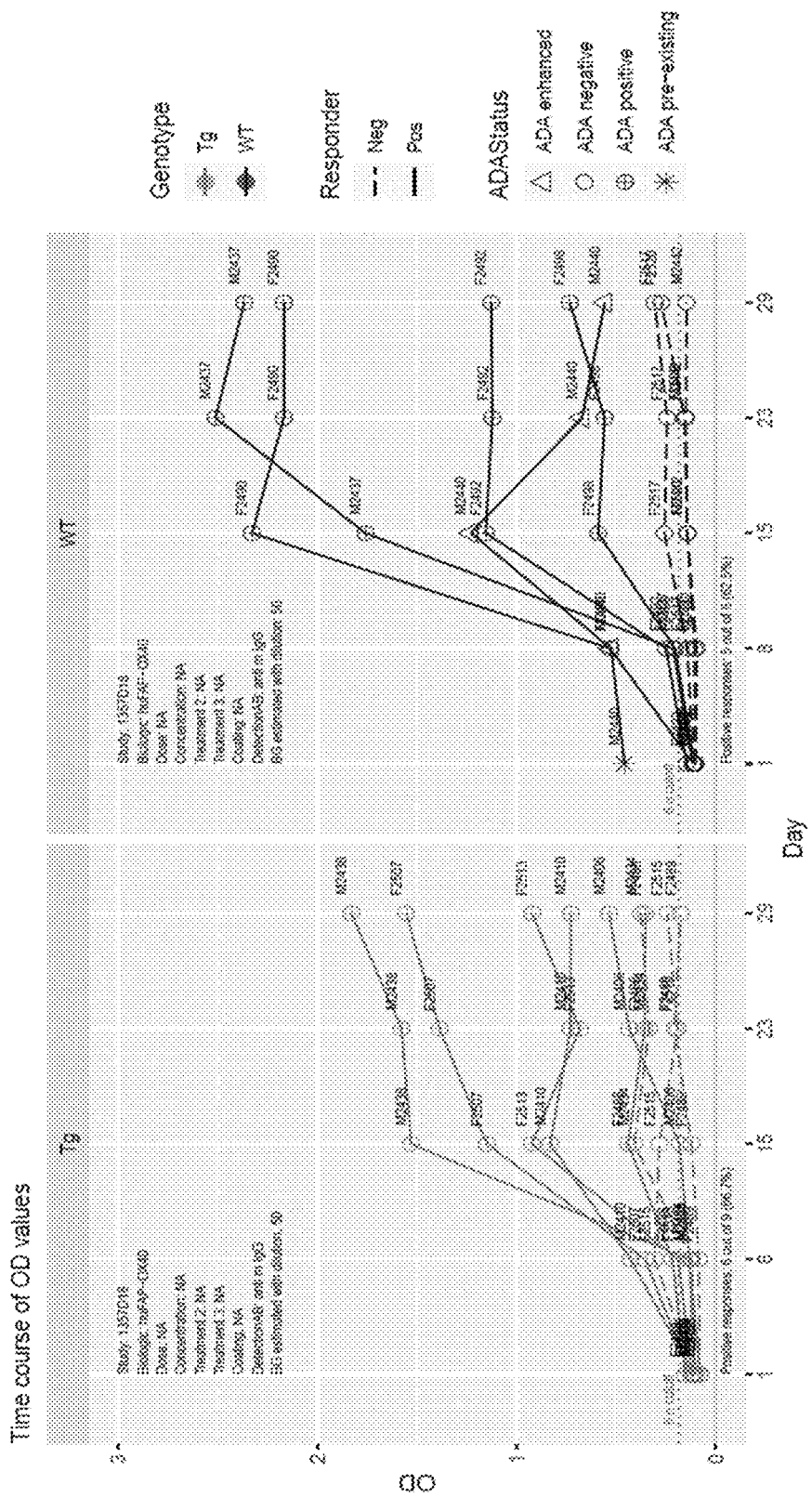

FIG. 46, FIG. 47 and FIG. 48 show the results of a 4-week immunogenicity study in C57BL/6 wild type mice and in transgenic C57BL/6-Tg (hIgG1,k,l) mice that are immunologically tolerant to human IgG1 antibodies. The immune responses for the two individual mouse groups treated with P1AF6455 are shown in FIG. 46, those for the two individual mouse groups treated with P1AF6454 are shown in FIG. 47, and the immune responses obtained for the two individual mouse groups treated with P1AD4524 are illustrated in FIG. 48.

Figure 49:
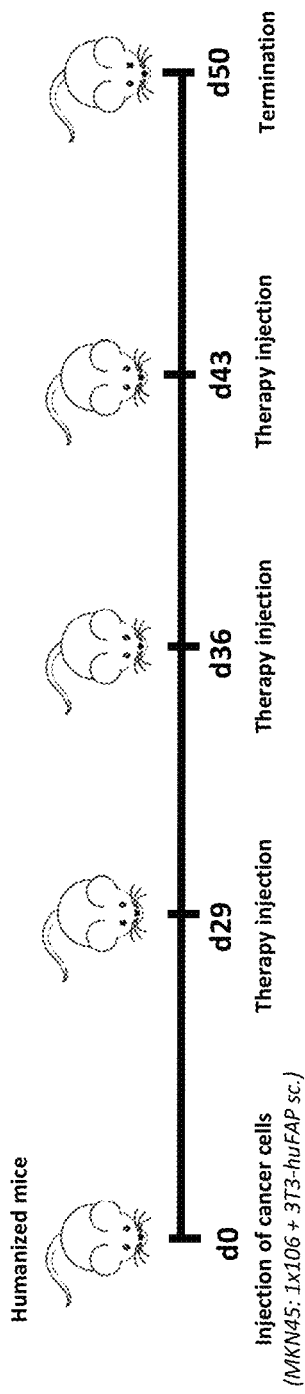

FIG. 49 shows the study design of an efficacy study with bispecific FAP×OX40 antibodies (comparison of different OX40 clones) in combination with CEACAM5 TCB in MKN45 Xenograft in humanized mice. Shown is the design and the different treatment groups. Compared were bispecific FAP×OX40 antibodies comprising the antibodies OX40 (49B4_K23E_K73E, here called 49B4 CPV), OX40 (CLC563), OX40 (8H9) and OX40 (49B4).

FIG. 50A and FIG. 50B show the results of the efficacy study with the FAP×OX40 bispecific antibodies in combination with CEACAM5 TCB in MKN45 Xenograft in humanized mice. Shown is the average tumor volume (FIG. 50A) or the percent change of tumor volume in individual mice for the different treatment groups as plotted on the y-axis (FIG. 50B).

DETAILED DESCRIPTION OF THE INVENTION

Definitions

Unless defined otherwise, technical and scientific terms used herein have the same meaning as generally used in the art to which this invention belongs. For purposes of interpreting this specification, the following definitions will apply and whenever appropriate, terms used in the singular will also include the plural and vice versa.

As used herein, the term "antigen binding molecule" refers in its broadest sense to a molecule that specifically binds an antigenic determinant. Examples of antigen binding molecules are antibodies, antibody fragments and scaffold antigen binding proteins.

As used herein, the term "antigen binding domain capable of specific binding to a target cell antigen" or "moiety capable of specific binding to a target cell antigen" refers to a polypeptide molecule that specifically binds to an antigenic determinant. In one aspect, the antigen binding domain is able to activate signaling through its target cell antigen. In a particular aspect, the antigen binding domain is able to direct the entity to which it is attached (e.g. the OX40 agonistic antibody) to a target site, for example to a specific type of tumor cell or tumor stroma bearing the antigenic determinant. Antigen binding domains capable of specific binding to a target cell antigen include antibodies and fragments thereof as further defined herein. In addition, antigen binding domains capable of specific binding to a target cell antigen include scaffold antigen binding proteins as further defined herein, e.g. binding domains which are based on designed repeat proteins or designed repeat domains (see e.g. WO 2002/020565). In particular, the antigen binding domain capable of specific binding to a target cell antigen is an antigen binding domain capable of specific binding to Fibroblast Activation Protein (FAP).

In relation to an antibody or fragment thereof, the term "antigen binding domain capable of specific binding to a target cell antigen" refers to the part of the molecule that comprises the area which specifically binds to and is complementary to part or all of an antigen. An antigen binding domain capable of specific antigen binding may be provided, for example, by one or more antibody variable domains (also called antibody variable regions). Particularly, an antigen binding domain capable of specific antigen binding comprises an antibody light chain variable region (VL) and an antibody heavy chain variable region (VH). In one particular aspect, the "antigen binding domain capable of specific binding to a target cell antigen" is a Fab fragment or a cross-Fab fragment.

The term "antibody" herein is used in the broadest sense and encompasses various antibody structures, including but not limited to monoclonal antibodies, polyclonal antibodies, monospecific and multispecific antibodies (e.g., bispecific antibodies), and antibody fragments so long as they exhibit the desired antigen-binding activity.

The term "monoclonal antibody" as used herein refers to an antibody obtained from a population of substantially homogeneous antibodies, i.e., the individual antibodies comprising the population are identical and/or bind the same epitope, except for possible variant antibodies, e.g. containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen.

The term "monospecific" antibody as used herein denotes an antibody that has one or more binding sites each of which bind to the same epitope of the same antigen. The term "bispecific" means that the antigen binding molecule is able to specifically bind to at least two distinct antigenic determinants. Typically, a bispecific antigen binding molecule comprises two antigen binding sites, each of which is specific for a different antigenic determinant. In certain embodiments the bispecific antigen binding molecule is capable of simultaneously binding two antigenic determinants, particularly two antigenic determinants expressed on two distinct cells. A bispecific antigen binding molecule as described herein can also form part of a multispecific antibody.

The term "valent" as used within the current application denotes the presence of a specified number of binding sites specific for one distinct antigenic determinant in an antigen binding molecule that are specific for one distinct antigenic determinant. As such, the terms "bivalent", "trivalent", "tetravalent", and "hexavalent" denote the presence of two binding sites, three binding sites, four binding sites, and six binding sites specific for a certain antigenic determinant, respectively, in an antigen binding molecule. In particular aspects of the invention, the bispecific antigen binding molecules according to the invention can be monovalent for a certain antigenic determinant, meaning that they have only one binding site for said antigenic determinant or they can be bivalent or tetravalent for a certain antigenic determinant, meaning that they have two binding sites or four binding sites, respectively, for said antigenic determinant.

The terms "full length antibody", "intact antibody", and "whole antibody" are used herein interchangeably to refer to an antibody having a structure substantially similar to a native antibody structure. "Native antibodies" refer to naturally occurring immunoglobulin molecules with varying structures. For example, native IgG-class antibodies are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a light chain constant domain (CL), also called a light chain constant region. The heavy chain of an antibody may be assigned to one of five types, called α (IgA), δ (IgD), ε (IgE), γ (IgG), or μ (IgM), some of which may be further divided into subtypes, e.g. γ1 (IgG1), γ2 (IgG2), γ3 (IgG3), γ4 (IgG4), α1 (IgA1) and α2 (IgA2). The light chain of an antibody may be assigned to one of two types, called kappa (κ) and lambda (λ), based on the amino acid sequence of its constant domain.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies, triabodies, tetrabodies, cross-Fab fragments; linear antibodies; single-chain antibody molecules (e.g. scFv); and single domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046. Diabodies are antibody fragments with two antigen-binding sites that may be bivalent or bispecific, see, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g. U.S. Pat. No. 6,248,516 B1). Antibody fragments can be made by various techniques, including but not limited to proteolytic digestion of an intact antibody as well as production by recombinant host cells (e.g. E. coli or phage), as described herein.

Papain digestion of intact antibodies produces two identical antigen-binding fragments, called "Fab" fragments containing each the heavy- and light-chain variable domains and also the constant domain of the light chain and the first constant domain (CH1) of the heavy chain. As used herein, Thus, the term "Fab fragment" refers to an antibody fragment comprising a light chain fragment comprising a VL domain and a constant domain of a light chain (CL), and a VH domain and a first constant domain (CH1) of a heavy chain. Fab' fragments differ from Fab fragments by the addition of a few residues at the carboxy terminus of the heavy chain CH1 domain including one or more cysteins from the antibody hinge region. Fab'-SH are Fab' fragments wherein the cysteine residue(s) of the constant domains bear a free thiol group. Pepsin treatment yields an F(ab')$_2$ fragment that has two antigen-combining sites (two Fab fragments) and a part of the Fc region. According to the present invention, the term "Fab fragment" also includes "cross-Fab fragments" or "crossover Fab fragments" as defined below.

The term "cross-Fab fragment" or "xFab fragment" or "crossover Fab fragment" refers to a Fab fragment, wherein either the variable regions or the constant regions of the heavy and light chain are exchanged. Two different chain compositions of a crossover Fab molecule are possible and comprised in the bispecific antibodies of the invention: On the one hand, the variable regions of the Fab heavy and light chain are exchanged, i.e. the crossover Fab molecule comprises a peptide chain composed of the light chain variable region (VL) and the heavy chain constant region (CH1), and a peptide chain composed of the heavy chain variable region (VH) and the light chain constant region (CL). This crossover Fab molecule is also referred to as CrossFab$_{(VLVH)}$. On the other hand, when the constant regions of the Fab heavy and light chain are exchanged, the crossover Fab molecule comprises a peptide chain composed of the heavy chain variable region (VH) and the light chain constant region (CL), and a peptide chain composed of the light chain variable region (VL) and the heavy chain constant region (CH1). This crossover Fab molecule is also referred to as CrossFab$_{(CLCH1)}$.

A "single chain Fab fragment" or "scFab" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments are stabilized via the natural disulfide bond between the CL domain and the CH1 domain. In addition, these single chain Fab molecules might be further stabilized by generation of interchain disulfide bonds via insertion of cysteine residues (e.g. position 44 in the variable heavy chain and position 100 in the variable light chain according to Kabat numbering).

A "crossover single chain Fab fragment" or "x-scFab" is a is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CL-linker-VL-CH1 and b) VL-CH1-linker-VH-CL; wherein VH and VL form together an antigen-binding site which binds specifically to an antigen and wherein said linker is a polypeptide of at least 30 amino acids. In addition, these x-scFab molecules might be further stabilized by generation of interchain disulfide bonds via insertion of cysteine residues (e.g. position 44 in the variable heavy chain and position 100 in the variable light chain according to Kabat numbering).

A "single-chain variable fragment (scFv)" is a fusion protein of the variable regions of the heavy ($V_H$) and light chains ($V_L$) of an antibody, connected with a short linker peptide of ten to about 25 amino acids. The linker is usually rich in glycine for flexibility, as well as serine or threonine for solubility, and can either connect the N-terminus of the $V_H$ with the C-terminus of the $V_L$, or vice versa. This protein retains the specificity of the original antibody, despite removal of the constant regions and the introduction of the linker. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

"Scaffold antigen binding proteins" are known in the art, for example, fibronectin and designed ankyrin repeat proteins (DARPins) have been used as alternative scaffolds for antigen-binding domains, see, e.g., Gebauer and Skerra, Engineered protein scaffolds as next-generation antibody therapeutics. Curr Opin Chem Biol 13:245-255 (2009) and Stumpp et al., Darpins: A new generation of protein therapeutics. Drug Discovery Today 13: 695-701 (2008). In one aspect of the invention, a scaffold antigen binding protein is selected from the group consisting of CTLA-4 (Evibody), Lipocalins (Anticalin), a Protein A-derived molecule such as Z-domain of Protein A (Affibody), an A-domain (Avimer/Maxibody), a serum transferrin (trans-body); a designed ankyrin repeat protein (DARPin), a variable domain of antibody light chain or heavy chain (single-domain antibody, sdAb), a variable domain of antibody heavy chain (nanobody, aVH), VNAR fragments, a fibronectin (AdNectin), a C-type lectin domain (Tetranectin); a variable domain of a new antigen receptor beta-lactamase ($V_{NAR}$ fragments), a human gamma-crystallin or ubiquitin (Affilin molecules); a kunitz type domain of human protease inhibitors, microbodies such as the proteins from the knottin family, peptide aptamers and fibronectin (adnectin). CTLA-4 (Cytotoxic T Lymphocyte-associated Antigen 4) is a CD28-family receptor expressed on mainly CD4$^+$ T-cells. Its extracellular domain has a variable domain-like Ig fold. Loops corresponding to CDRs of antibodies can be substituted with heterologous sequence to confer different binding properties. CTLA-4 molecules engineered to have different binding specificities are also known as Evibodies (e.g. U.S. Pat. No. 7,166,697B1). Evibodies are around the same size as the isolated variable region of an antibody (e.g. a domain antibody). For further details see Journal of Immunological Methods 248 (1-2), 31-45 (2001). Lipocalins are a family of extracellular proteins which transport small hydrophobic molecules such as steroids, bilins, retinoids and lipids. They have a rigid beta-sheet secondary structure with a number of loops at the open end of the conical structure which can be engineered to bind to different target antigens. Anticalins are between 160-180 amino acids in size, and are derived from lipocalins. For further details see Biochim Biophys Acta 1482: 337-350 (2000), U.S. Pat. No. 7,250,297B1 and US20070224633. An affibody is a scaffold derived from Protein A of Staphylococcus aureus which can be engineered to bind to antigen. The domain consists of a three-helical bundle of approximately 58 amino acids. Libraries have been generated by randomization of surface residues. For further details see Protein Eng. Des. Sel. 2004, 17, 455-462 and EP 1641818A1. Avimers are multidomain proteins derived from the A-domain scaffold family. The native domains of approximately 35 amino acids adopt a defined disulfide bonded structure. Diversity is generated by shuffling of the natural variation exhibited by the family of A-domains. For further details see Nature Biotechnology 23(12), 1556-1561 (2005) and Expert Opinion on Investigational Drugs 16(6), 909-917 (June 2007). A transferrin is a monomeric serum transport glycoprotein. Transferrins can be engineered to bind different target antigens by insertion of peptide sequences in a permissive surface loop. Examples of engineered transferrin scaffolds include the Trans-body. For further details see J. Biol. Chem 274, 24066-24073 (1999). Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two alpha-helices and a beta-turn. They can be engineered to bind different target antigens by randomizing residues in the first alpha-helix and a beta-turn of each repeat. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1. A single-domain antibody is an antibody fragment consisting of a single monomeric variable antibody domain. The first single domains were derived from the variable domain of the antibody heavy chain from camelids (nanobodies or VHH fragments). Furthermore, the term single-domain antibody includes an autonomous human heavy chain variable domain (aVH) or $V_{NAR}$ fragments derived from sharks. Fibronectin is a scaffold which can be engineered to bind to antigen. Adnectins consists of a backbone of the natural amino acid sequence of the 10th domain of the 15 repeating units of human fibronectin type III (FN3). Three loops at one end of the .beta.-sandwich can be engineered to enable an Adnectin to specifically recognize a therapeutic target of interest. For further details see Protein Eng. Des. Sel. 18, 435-444 (2005), US20080139791, WO2005056764 and U.S. Pat. No. 6,818,418B1. Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5, 783-797 (2005). Microbodies are derived from naturally occurring microproteins of 25-50 amino acids in length which contain 3-4 cysteine bridges—examples of microproteins include KalataBI and conotoxin and knottins. The microproteins have a loop which can beengineered to include upto amino acids without affecting the overall fold of the microprotein. For further details of engineered knottin domains, see WO2008098796.

An "antigen binding molecule that binds to the same epitope" as a reference molecule refers to an antigen binding molecule that blocks binding of the reference molecule to its antigen in a competition assay by 50% or more, and conversely, the reference molecule blocks binding of the antigen binding molecule to its antigen in a competition assay by 50% or more. An "antigen binding molecule that does not bind to the same epitope" as a reference molecule refers to an antigen binding molecule that does not block binding of the reference molecule to its antigen in a competition assay by 50% or more, and conversely, the reference molecule does not block binding of the antigen binding molecule to its antigen in a competition assay by 50% or more.

The term "antigen binding domain" or "antigen-binding site" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more variable domains (also called variable regions). Preferably, an antigen binding domain comprises an antibody light chain variable region (VL) and an antibody heavy chain variable region (VH).

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins useful as antigens herein can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants.

By "specific binding" is meant that the binding is selective for the antigen and can be discriminated from unwanted or non-specific interactions. The ability of an antigen binding molecule to bind to a specific antigen can be measured either through an enzyme-linked immunosorbent assay (ELISA) or other techniques familiar to one of skill in the art, e.g. Surface Plasmon Resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding molecule to an unrelated protein is less than about 10% of the binding of the antigen binding molecule to the antigen as measured, e.g. by SPR. In certain embodiments, an molecule that binds to the antigen has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g. from $10^{-9}$ M to $10^{-13}$ M).

"Affinity" or "binding affinity" refers to the strength of the sum total of non-covalent interactions between a single binding site of a molecule (e.g. an antibody) and its binding partner (e.g. an antigen). Unless indicated otherwise, as used herein, "binding affinity" refers to intrinsic binding affinity which reflects a 1:1 interaction between members of a binding pair (e.g. antibody and antigen). The affinity of a molecule X for its partner Y can generally be represented by the dissociation constant (Kd), which is the ratio of dissociation and association rate constants (koff and kon, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

A "target cell antigen" as used herein refers to an antigenic determinant presented on the surface of a target cell, in particular a target cell in a tumor such as a cancer cell or a cell of the tumor stroma. Thus, the target cell antigen is a tumor-associated antigen. In particular, the tumor target cell antigen is Fibroblast Activation Protein (FAP).

The term "Fibroblast activation protein (FAP)", also known as Prolyl endopeptidase FAP or Seprase (EC 3.4.21), refers to any native FAP from any vertebrate source, including mammals such as primates (e.g. humans) non-human primates (e.g. cynomolgus monkeys) and rodents (e.g. mice and rats), unless otherwise indicated. The term encompasses "full-length," unprocessed FAP as well as any form of FAP that results from processing in the cell. The term also encompasses naturally occurring variants of FAP, e.g., splice variants or allelic variants. In one embodiment, the antigen binding molecule of the invention is capable of specific binding to human, mouse and/or cynomolgus FAP. The amino acid sequence of human FAP is shown in UniProt www.uniprot.org accession no. Q12884 (version 149, SEQ ID NO:2), or NCBI (www.ncbi.nlm.nih.gov/) RefSeq NP_004451.2. The extracellular domain (ECD) of human FAP extends from amino acid position 26 to 760. The amino acid sequence of a His-tagged human FAP ECD is shown in SEQ ID NO:62. The amino acid sequence of mouse FAP is shown in UniProt accession no. P97321 (version 126, SEQ ID NO:63), or NCBI Refseq NP_032012.1. The extracellular domain (ECD) of mouse FAP extends from amino acid position 26 to 761. SEQ ID NO:64 shows the amino acid of a His-tagged mouse FAP ECD. SEQ ID NO:65 shows the amino acid of a His-tagged cynomolgus FAP ECD. Preferably, an anti-FAP binding molecule of the invention binds to the extracellular domain of FAP.

The term "variable region" or "variable domain" refers to the domain of an antibody heavy or light chain that is involved in binding the antigen binding molecule to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co., page 91 (2007). A single VH or VL domain may be sufficient to confer antigen-binding specificity.

The term "hypervariable region" or "HVR" as used herein refers to each of the regions of an antibody variable domain which are hypervariable in sequence and which determine antigen binding specificity, for example "complementarity determining regions" ("CDRs"). Generally, antibodies comprise six CDRs: three in the VH (CDR-H1, CDR-H2, CDR-H3), and three in the VL (CDR-L1, CDR-L2, CDR-L3). Exemplary CDRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, Md. (1991)); and (c) antigen contacts occurring at amino acid residues 27c-36 (L1), 46-55 (L2), 89-96 (L3), 30-35b (H1), 47-58 (H2), and 93-101 (H3) (MacCallum et al. *J Mol. Biol.* 262: 732-745 (1996)).

Unless otherwise indicated, the CDRs are determined according to Kabat et al., supra. One of skill in the art will understand that the CDR designations can also be determined according to Chothia, supra, McCallum, supra, or any other scientifically accepted nomenclature system.

"Framework" or "FR" refers to variable domain residues other than complementary determining regions (CDRs). The FR of a variable domain generally consists of four FR domains: FR1, FR2, FR3, and FR4. Accordingly, the CDR and FR sequences generally appear in the following sequence in VH (or VL): FR1-CDR-H1(CDR-L1)-FR2-CDR-H2(CDR-L2)-FR3-CDR-H3(CDR-L3)-FR4.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g. $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ respectively.

A "humanized" antibody refers to a chimeric antibody comprising amino acid residues from non-human CDRs and amino acid residues from human FRs. In certain embodiments, a humanized antibody will comprise substantially all of at least one, and typically two, variable domains, in which all or substantially all of the CDRs correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to Cq binding and/or Fc receptor (FcR) binding.

The term "CH1 domain" denotes the part of an antibody heavy chain polypeptide that extends approximately from EU position 118 to EU position 215 (EU numbering system according to Kabat). In one aspect, a CH1 domain has the amino acid sequence of ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKV (SEQ ID NO:166). Usually, a segment having the amino acid sequence of EPKSC (SEQ ID NO:163) is following to link the CH1 domain to the hinge region. The inventors found that a CH1 domain that is not fused to a hinge region may lead to reactivity with pre-existing antibodies (ADAs) in the human body which are not present if a variant EPKSCD (SEQ ID NO:164) or EPKSCS (SEQ ID NO:165) is present. A CH1 domain with a free C-terminal end can be found for instance in a crossfab fragment.

The term "hinge region" denotes the part of an antibody heavy chain polypeptide that joins in a wild-type antibody heavy chain the CH1 domain and the CH2 domain, e. g. from about position 216 to about position 230 according to the EU number system of Kabat, or from about position 226 to about position 230 according to the EU number system of Kabat. The hinge regions of other IgG subclasses can be determined by aligning with the hinge-region cysteine residues of the IgG1 subclass sequence. The hinge region is normally a dimeric molecule consisting of two polypeptides with identical amino acid sequence. The hinge region generally comprises up to 25 amino acid residues and is flexible allowing the associated target binding sites to move independently. The hinge region can be subdivided into three domains: the upper, the middle, and the lower hinge domain (see e.g. Roux, et al., J. Immunol. 161 (1998) 4083). In one aspect, the hinge region has the amino acid sequence DKTHTCPXCP (SEQ ID NO:160), wherein X is either S or P. In one aspect, the hinge region has the amino acid sequence HTCPXCP (SEQ ID NO:161), wherein X is either S or P. In one aspect, the hinge region has the amino acid sequence CPXCP (SEQ ID NO:162), wherein X is either S or P.

The term "Fc domain" or "Fc region" herein is used to define a C-terminal region of an antibody heavy chain that contains at least a portion of the constant region. The term includes native sequence Fc regions and variant Fc regions. An IgG Fc region comprises an IgG CH2 and an IgG CH3 domain. The "CH2 domain" of a human IgG Fc region usually extends from an amino acid residue at about position 231 to an amino acid residue at about position 340. (EU numbering system according to Kabat). In one aspect, a CH2 domain has the amino acid sequence of APELLGGPSV FLFPPKPKDT LMISRTPEVT CVWDVSHEDP EVKFNWYVDG VEVHNAKTKP REEQESTYRW SVLTVLHQDW LNGKEYKCKV SNKALPAPIE KTISKAK (SEQ ID NO:153). The CH2 domain is unique in that it is not closely paired with another domain. Rather, two N-linked branched carbohydrate chains are interposed between the two CH2 domains of an intact native Fc-region. It has been speculated that the carbohydrate may provide a substitute for the domain-domain pairing and help stabilize the CH2 domain. Burton, Mol. Immunol. 22 (1985) 161-206. In one embodiment, a carbohydrate chain is attached to the CH2 domain. The CH2 domain herein may be a native sequence CH2 domain or variant CH2 domain. The "CH3 domain" comprises the stretch of residues C-terminal to a CH2 domain in an Fc region (i.e. from an amino acid residue at about position 341 to an amino acid residue at about position 447 according to EU numbering system according to Kabat of an IgG). In one aspect, the CH3 domain has the amino acid sequence of GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLS PG (SEQ ID NO:154). The CH3 region herein may be a native sequence CH3 domain or a variant CH3 domain (e.g. a CH3 domain with an introduced "protuberance" ("knob") in one chain thereof and a corresponding introduced "cavity" ("hole") in the other chain thereof; see U.S. Pat. No. 5,821,333, expressly incorporated herein by reference). Such variant CH3 domains may be used to promote heterodimerization of two non-identical antibody heavy chains as herein described. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

The term "wild-type Fc domain" denotes an amino acid sequence identical to the amino acid sequence of an Fc domain found in nature. Wild-type human Fc domains include a native human IgG1 Fc-region (non-A and A allotypes), native human IgG2 Fc-region, native human IgG3 Fc-region, and native human IgG4 Fc-region as well as naturally occurring variants thereof. Wild-type Fc-regions are denoted in SEQ ID NO:155 (IgG1, caucasian allotype), SEQ ID NO: 156 (IgG1, afroamerican allotype), SEQ ID NO:157 (IgG2), SEQ ID NO:158 (IgG3) and SEQ ID NO:159 (IgG4). The term "variant (human) Fc domain" denotes an amino acid sequence which differs from that of a "wild-type" (human) Fc domain amino acid sequence by virtue of at least one "amino acid mutation". In one aspect, the variant Fc-region has at least one amino acid mutation compared to a native Fc-region, e.g. from about one to about ten amino acid mutations, and in one aspect from about one to about five amino acid mutations in a native Fc-region. In one aspect, the (variant) Fc-region has at least about 95% homology with a wild-type Fc-region.

The "knob-into-hole" technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). The protuberance and cavity can be made by altering the nucleic acid encoding the polypeptides, e.g. by site-specific mutagenesis, or by peptide synthesis. In a specific embodiment a knob modification comprises the amino acid substitution T366W in one of the two subunits of the Fc domain, and the hole modification comprises the amino acid substitutions T366S, L368A and Y407V in the other one of the two subunits of the Fc domain. In a further specific embodiment, the subunit of the Fc domain comprising the knob modification additionally comprises the amino acid substitution S354C, and the subunit of the Fc domain comprising the hole modification additionally comprises the amino acid substitution Y349C. Introduction of these two cysteine residues results in the formation of a disulfide bridge between the two subunits of the Fc region, thus further stabilizing the dimer (Carter, J Immunol Methods 248, 7-15 (2001)).

A "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U. et al., Science 247:1306-10 (1990)).

The term "effector function" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

Fc receptor binding dependent effector functions can be mediated by the interaction of the Fc-region of an antibody with Fc receptors (FcRs), which are specialized cell surface receptors on hematopoietic cells. Fc receptors belong to the immunoglobulin superfamily, and have been shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC) (see e.g. Van de Winkel, J. G. and Anderson, C. L., J. Leukoc. Biol. 49 (1991) 511-524). FcRs are defined by their specificity for immunoglobulin isotypes: Fc receptors for IgG antibodies are referred to as FcγR. Fc receptor binding is described e.g. in Ravetch, J. V. and Kinet, J. P., Annu. Rev. Immunol. 9 (1991) 457-492, Capel, P. J., et al., Immunomethods 4 (1994) 25-34; de Haas, M., et al., J. Lab. Clin. Med. 126 (1995) 330-341; and Gessner, J. E., et al., Ann. Hematol. 76 (1998) 231-248.

Cross-linking of receptors for the Fc-region of IgG antibodies (FcγR) triggers a wide variety of effector functions including phagocytosis, antibody-dependent cellular cytotoxicity, and release of inflammatory mediators, as well as immune complex clearance and regulation of antibody production. In humans, three classes of FcγR have been characterized, which are:

FcγRI (CD64) binds monomeric IgG with high affinity and is expressed on macrophages, monocytes, neutrophils and eosinophils. Modification in the Fc-region IgG at least at one of the amino acid residues E233-G236, P238, D265, N297, A327 and P329 (numbering according to EU index of Kabat) reduce binding to FcγRI. IgG2 residues at positions 233-236, substituted into IgG1 and IgG4, reduced binding to FcγRI by $10^3$-fold and eliminated the human monocyte response to antibody-sensitized red blood cells (Armour, K. L., et al., Eur. J. Immunol. 29 (1999) 2613-2624).

FcγRII (CD32) binds complexed IgG with medium to low affinity and is widely expressed. This receptor can be divided into two sub-types, FcγRIIA and FcγRIIB. FcγRIIA is found on many cells involved in killing (e.g. macrophages, monocytes, neutrophils) and seems able to activate the killing process. FcγRIIB seems to play a role in inhibitory processes and is found on B cells, macrophages and on mast cells and eosinophils. On B-cells it seems to function to suppress further immunoglobulin production and isotype switching to, for example, the IgE class. On macrophages, FcγRIIB acts to inhibit phagocytosis as mediated through FcγRIIA. On eosinophils and mast cells the B-form may help to suppress activation of these cells through IgE binding to its separate receptor. Reduced binding for FcγRIIA is found e.g. for antibodies comprising an IgG Fc-region with mutations at least at one of the amino acid residues E233-G236, P238, D265, N297, A327, P329, D270, Q295, A327, R292, and K414 (numbering according to EU index of Kabat).

FcγRIII (CD16) binds IgG with medium to low affinity and exists as two types. FcγRIIIA is found on NK cells, macrophages, eosinophils and some monocytes and T cells and mediates ADCC. FcγRIIIB is highly expressed on neutrophils. Reduced binding to FcγRIIIA is found e.g. for antibodies comprising an IgG Fc-region with mutation at least at one of the amino acid residues E233-G236, P238, D265, N297, A327, P329, D270, Q295, A327, S239, E269, E293, Y296, V303, A327, K338 and D376 (numbering according to EU index of Kabat).

Mapping of the binding sites on human IgG1 for Fc receptors, the above mentioned mutation sites and methods for measuring binding to FcγRI and FcγRIIA are described in Shields, R. L., et al. J. Biol. Chem. 276 (2001) 6591-6604.

The term "ADCC" or "antibody-dependent cellular cytotoxicity" is a function mediated by Fc receptor binding and refers to lysis of target cells by an antibody as reported herein in the presence of effector cells. The capacity of the antibody to induce the initial steps mediating ADCC is investigated by measuring their binding to Fcγ receptors expressing cells, such as cells, recombinantly expressing FcγRI and/or FcγRIIA or NK cells (expressing essentially FcγRIIIA). In particular, binding to FcγR on NK cells is measured.

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89). A particular activating Fc receptor is human FcγRIIIa (see UniProt accession no. P08637, version 141).

The term "OX40", as used herein, refers to any native OX40 from any vertebrate source, including mammals such as primates (e.g. humans) and rodents (e.g., mice and rats), unless otherwise indicated. The term encompasses "full-length," unprocessed OX40 as well as any form of OX40 that results from processing in the cell. The term also encompasses naturally occurring variants of OX40, e.g., splice variants or allelic variants. The amino acid sequence of an exemplary human OX40 is shown in SEQ ID NO:1 (Uniprot P43489, version 112) and the amino acid sequence of an exemplary murine OX40 is shown in SEQ ID NO:66 (Uniprot P47741, version 101).

The term "OX40 agonist" as used herein includes any moiety that agonizes the OX40/OX40L interaction. OX40 as used in this context refers preferably to human OX40, thus the OX40 agonist is preferably an agonist of human OX40. Typically, the moiety will be an agonistic OX40 antibody or antibody fragment, in particular a Fab fragment.

The terms "anti-OX40 antibody", "anti-OX40", "OX40 antibody" and "an antibody that specifically binds to OX40" refer to an antibody that is capable of binding OX40 with sufficient affinity such that the antibody is useful as a diagnostic and/or therapeutic agent in targeting OX40. In one aspect, the extent of binding of an anti-OX40 antibody to an unrelated, non-OX40 protein is less than about 10% of the binding of the antibody to OX40 as measured, e.g., by flow cytometry (FACS). In certain embodiments, an antibody that binds to OX40 has a dissociation constant ($K_D$) of ≤1 μM, ≤100 nM, ≤10 nM, ≤1 nM, ≤0.1 nM, ≤0.01 nM, or ≤0.001 nM (e.g. $10^{-6}$ M or less, e.g. from $10^{-6}$[68] M to $10^{-13}$ M, e.g., from $10^{-8}$ M to $10^{-10}$ M).

The term "peptide linker" refers to a peptide comprising one or more amino acids, typically about 2 to 20 amino acids. Peptide linkers are known in the art or are described herein. Suitable, non-immunogenic linker peptides are, for example, $(G_4S)_n$, $(SG_4)_n$ or $G_4(SG_4)_n$ peptide linkers, wherein "n" is generally a number between 1 and 10, typically between 2 and 4, in particular 2, i.e. the peptides selected from the group consisting of GGGGS (SEQ ID NO:67), GGGGSGGGGS (SEQ ID NO:68), SGGGGSGGGG (SEQ ID NO:69) and GGGGSGGGGSGGGG (SEQ ID NO:70), but also include the sequences GSPGSSSSGS (SEQ ID NO:71), $(G_4S)_3$ (SEQ ID NO:72), $(G_4S)_4$ (SEQ ID NO:73), GSGSGSGS (SEQ ID NO:74), GSGSGNGS (SEQ ID NO:75), GGSGSGSG (SEQ ID NO:76), GGSGSG (SEQ ID NO:77), GGSG (SEQ ID NO:78), GGSGNGSG (SEQ ID NO:79), GGNGSGSG (SEQ ID NO:80) and GGNGSG (SEQ ID NO:81). Peptide linkers of particular interest are (G4S) (SEQ ID NO:67), $(G_4S)_2$ or GGGGSGGGGS (SEQ ID NO:68), $(G_4S)_3$ (SEQ ID NO:72) and $(G_4S)_4$ (SEQ ID NO:73).

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

By "fused" or "connected" is meant that the components (e.g. a heavy chain of an antibody and a Fab fragment) are linked by peptide bonds, either directly or via one or more peptide linkers.

"Percent (%) amino acid sequence identity" with respect to a reference polypeptide (protein) sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN. SAWI or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In certain embodiments, amino acid sequence variants of the bispecific antigen binding molecules provided herein are contemplated. For example, it may be desirable to improve the binding affinity and/or other biological properties of the TNF ligand trimer-containing antigen binding molecules. Amino acid sequence variants of the TNF ligand trimer-containing antigen binding molecules may be prepared by introducing appropriate modifications into the nucleotide sequence encoding the molecules, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding. Sites of interest for substitutional mutagenesis include the HVRs and Framework (FRs). Conservative substitutions are provided in Table B under the heading "Preferred Substitutions" and further described below in reference to amino acid side chain classes (1) to (6). Amino acid substitutions may be introduced into the molecule of interest and the products screened for a desired activity, e.g., retained/improved antigen binding, decreased immunogenicity, or improved ADCC or CDC.

TABLE A

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ilie;
(2) neutral hydrophilic: Cys, Ser, Thr, Asn, Gin;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "amino acid sequence variants" includes substantial variants wherein there are amino acid substitutions in one or more hypervariable region residues of a parent antigen binding molecule (e.g. a humanized or human antibody). Generally, the resulting variant(s) selected for further study will have modifications (e.g., improvements) in certain biological properties (e.g., increased affinity, reduced immunogenicity) relative to the parent antigen binding molecule and/or will have substantially retained certain biological properties of the parent antigen binding molecule. An exemplary substitutional variant is an affinity matured antibody, which may be conveniently generated, e.g., using phage display-based affinity maturation techniques such as those described herein. Briefly, one or more HVR residues are mutated and the variant antigen binding molecules displayed on phage and screened for a particular biological activity (e.g. binding affinity). In certain embodiments, substitutions, insertions, or deletions may occur within one or more HVRs so long as such alterations do not substantially reduce the ability of the antigen binding molecule to bind antigen. For example, conservative alterations (e.g., conservative substitutions as provided herein) that do not substantially reduce binding affinity may be made in HVRs. A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antigen binding molecule complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include bispecific antigen binding molecules of the invention with an N-terminal methionyl residue. Other insertional variants of the molecule include the fusion to the N- or C-terminus to a polypeptide which increases the serum half-life of the bispecific antigen binding molecules.

In certain embodiments, the bispecific antigen binding molecules provided herein are altered to increase or decrease the extent to which the antibody is glycosylated. Glycosylation variants of the molecules may be conveniently obtained by altering the amino acid sequence such that one or more glycosylation sites is created or removed. Where the antigen binding molecule comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in TNF family ligand trimer-containing antigen binding molecule may be made in order to create variants with certain improved properties. In one aspect, variants of bispecific antigen binding molecules or antibodies of the invention are provided having a carbohydrate structure that lacks fucose attached (directly or indirectly) to an Fc region. Such fucosylation variants may have improved ADCC function, see e.g. US Patent Publication Nos. US 2003/0157108 (Presta, L.) or US 2004/0093621 (Kyowa Hakko Kogyo Co., Ltd). In another aspect, variants of the bispecific antigen binding molecules or antibodies of the invention are provided with bisected oligosaccharides, e.g., in which a biantennary oligosaccharide attached to the Fc region is bisected by GlcNAc. Such variants may have reduced fucosylation and/or improved ADCC function, see for example WO 2003/011878 (Jean-Mairet et al.); U.S. Pat. No. 6,602,684 (Umana et al.); and US 2005/0123546 (Umana et al.). Variants with at least one galactose residue in the oligosaccharide attached to the Fc region are also provided. Such antibody variants may have improved CDC function and are described, e.g., in WO 1997/30087 (Patel et al.); WO 1998/58964 (Raju, S.); and WO 1999/22764 (Raju, S.).

In certain aspects, it may be desirable to create cysteine engineered variants of the bispecific antigen binding molecules of the invention, e.g., "thioMAbs," in which one or more residues of the molecule are substituted with cysteine residues. In particular aspects, the substituted residues occur at accessible sites of the molecule. By substituting those residues with cysteine, reactive thiol groups are thereby positioned at accessible sites of the antibody and may be used to conjugate the antibody to other moieties, such as drug moieties or linker-drug moieties, to create an immunoconjugate. In certain aspects, any one or more of the following residues may be substituted with cysteine: V205 (Kabat numbering) of the light chain; A118 (EU numbering) of the heavy chain; and S400 (EU numbering) of the heavy chain Fc region. Cysteine engineered antigen binding molecules may be generated as described, e.g., in U.S. Pat. No. 7,521,541.

The term "nucleic acid" or "polynucleotide" includes any compound and/or substance that comprises a polymer of nucleotides. Each nucleotide is composed of a base, specifically a purine- or pyrimidine base (i.e. cytosine (C), guanine (G), adenine (A), thymine (T) or uracil (U)), a sugar (i.e. deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Herein, the term nucleic acid molecule encompasses deoxyribonucleic acid (DNA) including e.g., complementary DNA (cDNA) and genomic DNA, ribonucleic acid (RNA), in particular messenger RNA (mRNA), synthetic forms of DNA or RNA, and mixed polymers comprising two or more of these molecules. The nucleic acid molecule may be linear or circular. In addition, the term nucleic acid molecule includes both, sense and antisense strands, as well as single stranded and double stranded forms. Moreover, the herein described nucleic acid molecule can contain naturally occurring or non-naturally occurring nucleotides. Examples of non-naturally occurring nucleotides include modified nucleotide bases with derivatized sugars or phosphate backbone linkages or chemically modified residues. Nucleic acid molecules also encompass DNA and RNA molecules which are suitable as a vector for direct expression of an antibody of the invention in vitro and/or in vivo, e.g., in a host or patient. Such DNA (e.g., cDNA) or RNA (e.g., mRNA) vectors, can be unmodified or modified. For example, mRNA can be chemically modified to enhance the stability of the RNA vector and/or expression of the encoded molecule so that mRNA can be injected into a subject to generate the antibody in vivo (see e.g., Stadler et al, Nature Medicine 2017, published online 12 Jun. 2017, doi:10.1038/nm.4356 or EP 2 101 823 B1).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding a bispecific antigen binding molecule or antibody" refers to one or more nucleic acid molecules encoding the heavy and light chains (or fragments thereof) of the bispecific antigen binding molecule or antibody, including such nucleic acid molecule(s) in a single vector or separate vectors, and such nucleic acid molecule(s) present at one or more locations in a host cell.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the bispecific antigen binding molecules of the present invention. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" or "pharmaceutical formulation" refers to a preparation which is in such form as to permit the biological activity of an active ingredient contained therein to be effective, and which contains no additional components which are unacceptably toxic to a subject to which the pharmaceutical composition would be administered.

A "pharmaceutically acceptable carrier" refers to an ingredient in a pharmaceutical composition or formulation, other than an active ingredient, which is nontoxic to a subject. A pharmaceutically acceptable carrier includes, but is not limited to, a buffer, excipient, stabilizer, or preservative.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the molecules of the invention are used to delay development of a disease or to slow the progression of a disease.

The term "cancer" as used herein refers to proliferative diseases, such as lymphomas, lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

The term "chemotherapeutic agent" as used herein refers to a chemical compound useful in the treatment of cancer. In one aspect, the chemotherapeutic agent is an antimetabolite. In one aspect, the antimetabolite is selected from the group consisting of Aminopterin, Methotrexate, Pemetrexed, Raltitrexed, Cladribine, Clofarabine, Fludarabine, Mercaptopurine, Pentostatin, Thioguanine, Capecitabine, Cytarabine, Fluorouracil, Floxuridine, and Gemcitabine. In one particular aspect, the antimetabolite is capecitabine or gemcitabine. In another aspect, the antimetabolite is fluorouracil. In one aspect, the chemotherapeutic agent is an agent that affects microtubule formation. In one aspect, the agent that affects microtubule formation is selected from the group consisting of paclitaxel, docetaxel, vincristine, vinblastine, vindesine, vinorelbin, taxotere, etoposide, and teniposide. In another aspect, the chemotherapeutic agent is an alkylating agent such as cyclophosphamide. In one aspect, the chemotherapeutic agent is a cytotoxic antibiotic such as a topoisomerase II inhibitor. In one aspect, the topoisomerase II inhibitor is doxorubicin.

Bispecific Antibodies of the Invention

The invention provides novel bispecific antigen binding molecules comprising a new anti-FAP antibody (clone 212). The bispecific antigen binding molecules comprising this new anti-FAP antibody possess particularly advantageous properties such as producibility, stability, binding affinity, biological activity, targeting efficiency, reduced internalization, superior pharmacokinetic (PK) properties such as improved clearance, reduced toxicity, an extended dosage range that can be given to a patient and thereby a possibly enhanced efficacy. In addition, the bispecific antigen binding molecules have been prepared in advantageous formats depending on the OX40 antibody included.

Exemplary Bispecific Antigen Binding Molecules

In one aspect, the invention provides bispecific antigen binding molecules that are characterized by targeted agonistic binding to OX40. In particular, the bispecific antigen binding molecule is an OX40 agonist that is targeted against FAP. In another particular aspect, the bispecific antigen binding molecules of the invention comprise a Fc region composed of a first and a second subunit capable of stable association which comprises mutations that reduce effector function. The use of an Fc region comprising mutations that reduce or abolish effector function will prevent unspecific agonism by crosslinking via Fc receptors and will prevent ADCC of $OX40^+$ cells. The bispecific antigen binding molecules as described herein possess the advantage over conventional antibodies capable of specific binding to OX40 in that they selectively induce immune response at the target cells, which are typically close to the tumor, i.e. in the tumor stroma.

The bispecific antigen binding molecules are thus characterized by FAP-targeted agonistic binding to OX40. In the presence of FAP-expressing cells the bispecific antigen binding molecules are able to induce NFκB activation in human OX40 positive NFκB reporter cells.

In one aspect, the invention provides a bispecific antigen binding molecule, comprising
(a) at least two antigen binding domains capable of specific binding to OX40,
(b) an antigen binding domain capable of specific binding to Fibroblast Activation Protein (FAP) comprising a heavy chain variable region ($V_H$FAP) comprising
(i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8, and
(c) a Fc region composed of a first and a second subunit capable of stable association.

In one aspect, the antigen binding domain capable of specific binding to Fibroblast Activation Protein (FAP) comprises a heavy chain variable region ($V_H$FAP) comprising (i) CDR-H1 comprising the amino acid sequence of SEQ ID NO:3, (ii) CDR-H2 comprising the amino acid sequence selected from the group consisting of SEQ ID NO:4, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, (v) CDR-L2 comprising the amino acid sequence of SEQ ID NO:7, and (vi) CDR-L3 comprising the amino acid sequence of SEQ ID NO:8.

In one aspect, the Fc region comprises one or more amino acid substitution that reduces the binding affinity of the antibody to an Fc receptor and/or effector function.

In one further aspect, provided is a bispecific antigen binding molecule, wherein the antigen binding domain capable of specific binding to FAP comprises a heavy chain variable region ($V_H$FAP) comprising an amino acid sequence that is at least about 90% identical to the amino acid sequence of SEQ ID NO:9, and a light chain variable region ($V_L$FAP) comprising an amino acid sequence that is at least about 90% identical to the amino acid sequence of SEQ ID NO:10. In one aspect, the antigen binding domain capable of specific binding to FAP comprises a heavy chain variable region ($V_H$FAP) comprising the amino acid sequence of SEQ ID NO:9, and a light chain variable region ($V_L$FAP) comprising the amino acid sequence of SEQ ID NO:10.

In another aspect, the antigen binding domain capable of specific binding to FAP comprises a heavy chain variable region ($V_H$FAP) comprising an amino acid sequence selected from the group consisting of SEQ ID NO:15, SEQ ID NO:16, SEQ ID NO:17, SEQ ID NO:18. SEQ ID NO:19 and SEQ ID NO:20, and a light chain variable region ($V_L$FAP) comprising an amino acid sequence selected from the group consisting of SEQ ID NO:21, SEQ ID NO:22, SEQ ID NO:23, SEQ ID NO:24, SEQ ID NO:25 and SEQ ID NO:26. In one aspect, the antigen binding domain capable of specific binding to FAP comprises (a) a heavy chain variable region ($V_H$FAP) comprising the amino acid sequence of SEQ ID NO:15 and a light chain variable region ($V_L$FAP) comprising the amino acid sequence of SEQ ID NO:21, (b) a heavy chain variable region ($V_H$FAP) comprising the amino acid sequence of SEQ ID NO:16 and a light chain variable region ($V_L$FAP) comprising the amino acid sequence of SEQ ID NO:21, (c) a heavy chain variable region ($V_H$FAP) comprising the amino acid sequence of SEQ ID NO:16 and a light chain variable region ($V_L$FAP) comprising the amino acid sequence of SEQ ID NO:22, or (d) a heavy chain variable region ($V_H$FAP) comprising the amino acid sequence of SEQ ID NO:19 and a light chain variable region ($V_L$FAP) comprising the amino acid sequence of SEQ ID NO:25. Particularly, the antigen binding domain capable of specific binding to FAP comprises (a) a heavy chain variable region ($V_H$FAP) comprising the amino acid sequence of SEQ ID NO:15 and a light chain variable region ($V_L$FAP) comprising the amino acid sequence of SEQ ID NO:21.

In one aspect, the antigen binding domains capable of specific binding to OX40 bind to a polypeptide comprising, or consisting of, the amino acid sequence of SEQ ID NO:1.

In a further aspect, provided is a bispecific antigen binding molecule, wherein the antigen binding domain capable of specific binding to OX40 comprises
(a) a heavy chain variable region ($V_H$OX40) comprising (i) CDR-H1 comprising the amino acid sequence of SEQ ID NO:27, (ii) CDR-H2 comprising the amino acid sequence of SEQ ID NO:28, and (iii) CDR-H3 comprising the amino acid sequence of SEQ ID NO:29, and a light chain variable region ($V_L$OX40) comprising (iv) CDR-L1 comprising the amino acid sequence of SEQ ID NO:30, (v) CDR-L2 comprising the amino acid sequence of SEQ ID NO:31, and (vi) CDR-L3 comprising the amino acid sequence of SEQ ID NO:32, or
(b) a heavy chain variable region ($V_H$OX40) comprising (i) CDR-H1 comprising the amino acid sequence of SEQ ID NO:35, (ii) CDR-H2 comprising the amino acid sequence of SEQ ID NO:36, and (iii) CDR-H3 comprising the amino acid sequence of SEQ ID NO:37, and a light chain variable region ($V_L$OX40) comprising (iv) CDR-L1 comprising the amino acid sequence of SEQ ID NO:38, (v) CDR-L2 comprising the amino acid sequence of SEQ ID NO:39, and (vi) CDR-L3 comprising the amino acid sequence of SEQ ID NO:40, or
(c) a heavy chain variable region ($V_H$OX40) comprising (i) CDR-H1 comprising the amino acid sequence of SEQ ID NO:43, (ii) CDR-H2 comprising the amino acid sequence of SEQ ID NO:44, and (iii) CDR-H3 comprising the amino acid sequence of SEQ ID NO:45, and a light chain variable region (V$_L$OX40) comprising (iv) CDR-L1 comprising the amino acid sequence of SEQ ID NO:46, (v) CDR-L2 comprising the amino acid sequence of SEQ ID NO:47, and (vi) CDR-L3 comprising the amino acid sequence of SEQ ID NO:48, or (d) a heavy chain variable region (V$_H$OX40) comprising (i) CDR-H1 comprising the amino acid sequence of SEQ ID NO:51, (ii) CDR-H2 comprising the amino acid sequence of SEQ ID NO:52, and (iii) CDR-H3 comprising the amino acid sequence of SEQ ID NO:53, and a light chain variable region (V$_L$OX40) comprising (iv) CDR-L1 comprising the amino acid sequence of SEQ ID NO:54, (v) CDR-L2 comprising the amino acid sequence of SEQ ID NO:55, and (vi) CDR-L3 comprising the amino acid sequence of SEQ ID NO:56.

In one aspect, the antigen binding domains capable of specific binding to OX40 comprise a heavy chain variable region (V$_H$OX40) comprising (i) CDR-H1 comprising the amino acid sequence of SEQ ID NO:27, (ii) CDR-H2 comprising the amino acid sequence of SEQ ID NO:28, and (iii) CDR-H3 comprising the amino acid sequence of SEQ ID NO:29, and a light chain variable region (V$_L$OX40) comprising (iv) CDR-L1 comprising the amino acid sequence of SEQ ID NO:30, (v) CDR-L2 comprising the amino acid sequence of SEQ ID NO:31, and (vi) CDR-L3 comprising the amino acid sequence of SEQ ID NO:32. In a further aspect, the antigen binding domains capable of specific binding to OX40 comprise a heavy chain variable region (V$_H$OX40) comprising (i) CDR-H1 comprising the amino acid sequence of SEQ ID NO:35, (ii) CDR-H2 comprising the amino acid sequence of SEQ ID NO:36, and (iii) CDR-H3 comprising the amino acid sequence of SEQ ID NO:37, and a light chain variable region (V$_L$OX40) comprising (iv) CDR-L1 comprising the amino acid sequence of SEQ ID NO:38, (v) CDR-L2 comprising the amino acid sequence of SEQ ID NO:39, and (vi) CDR-L3 comprising the amino acid sequence of SEQ ID NO:40. In another aspect, the antigen binding domains capable of specific binding to OX40 comprise a heavy chain variable region (V$_H$OX40) comprising (i) CDR-H1 comprising the amino acid sequence of SEQ ID NO:43, (ii) CDR-H2 comprising the amino acid sequence of SEQ ID NO:44, and (iii) CDR-H3 comprising the amino acid sequence of SEQ ID NO:45, and a light chain variable region (V$_L$OX40) comprising (iv) CDR-L1 comprising the amino acid sequence of SEQ ID NO:46, (v) CDR-L2 comprising the amino acid sequence of SEQ ID NO:47, and (vi) CDR-L3 comprising the amino acid sequence of SEQ ID NO:48. In yet another aspect, the antigen binding domains capable of specific binding to OX40 comprise a heavy chain variable region (V$_H$OX40) comprising (i) CDR-H1 comprising the amino acid sequence of SEQ ID NO:51, (ii) CDR-H2 comprising the amino acid sequence of SEQ ID NO:52, and (iii) CDR-H3 comprising the amino acid sequence of SEQ ID NO:53, and a light chain variable region (V$_L$OX40) comprising (iv) CDR-L1 comprising the amino acid sequence of SEQ ID NO:54, (v) CDR-L2 comprising the amino acid sequence of SEQ ID NO:55, and (vi) CDR-L3 comprising the amino acid sequence of SEQ ID NO:56. In one particular aspect, the antigen binding domains capable of specific binding to OX40 comprise a heavy chain variable region (V$_H$OX40) comprising (i) CDR-H1 comprising the amino acid sequence of SEQ ID NO:35, (ii) CDR-H2 comprising the amino acid sequence of SEQ ID NO:36, and (iii) CDR-H3 comprising the amino acid sequence of SEQ ID NO:37, and a light chain variable region (V$_L$OX40) comprising (iv) CDR-L1 comprising the amino acid sequence of SEQ ID NO:38, (v) CDR-L2 comprising the amino acid sequence of SEQ ID NO:39, and (vi) CDR-L3 comprising the amino acid sequence of SEQ ID NO:40.

In one aspect, provided is a bispecific antigen binding molecule as defined herein before, wherein the antigen binding domains capable of specific binding to OX40 comprise (i) a heavy chain variable region (V$_H$OX40) comprising the amino acid sequence of SEQ ID NO:33 and a light chain variable region (V$_L$OX40) comprising the amino acid sequence of SEQ ID NO:34, or (ii) a heavy chain variable region (V$_H$OX40) comprising the amino acid sequence of SEQ ID NO:41 and a light chain variable region (V$_L$OX40) comprising the amino acid sequence of SEQ ID NO:42, or (iii) a heavy chain variable region (V$_H$OX40) comprising the amino acid sequence of SEQ ID NO:49 and a light chain variable region (V$_L$OX40) comprising the amino acid sequence of SEQ ID NO:50, or (iv) a heavy chain variable region (V$_H$OX40) comprising the amino acid sequence of SEQ ID NO:57 and a light chain variable region (V$_L$OX40) comprising the amino acid sequence of SEQ ID NO:58.

In one aspect, provided is a bispecific antigen binding molecule as defined herein before, wherein the antigen binding domain capable of specific binding to OX40 comprises a heavy chain variable region (V$_H$OX40) comprising the amino acid sequence of SEQ ID NO:33 and a light chain variable region (V$_L$OX40) comprising the amino acid sequence of SEQ ID NO:34. In another aspect, provided is a bispecific antigen binding molecule as defined herein before, wherein the antigen binding domain capable of specific binding to OX40 comprises a heavy chain variable region (V$_H$OX40) comprising the amino acid sequence of SEQ ID NO:41 and a light chain variable region (V$_L$OX40) comprising the amino acid sequence of SEQ ID NO:42. In a further aspect, provided is a bispecific antigen binding molecule as defined herein before, wherein the antigen binding domain capable of specific binding to OX40 comprises a heavy chain variable region (V$_H$OX40) comprising the amino acid sequence of SEQ ID NO:49 and a light chain variable region (V$_L$OX40) comprising the amino acid sequence of SEQ ID NO:50. In yet as further aspect, provided is a bispecific antigen binding molecule as defined herein before, wherein the antigen binding domain capable of specific binding to OX40 comprises a heavy chain variable region (V$_H$OX40) comprising the amino acid sequence of SEQ ID NO:57 and a light chain variable region (V$_L$OX40) comprising the amino acid sequence of SEQ ID NO:58. In one particular aspect, the antigen binding domains capable of specific binding to OX40 (each) comprise a heavy chain variable region (V$_H$OX40) comprising the amino acid sequence of SEQ ID NO:41 and a light chain variable region (V$_L$OX40) comprising the amino acid sequence of SEQ ID NO:42.

In another aspect, provided is a bispecific antigen binding molecule as defined herein before, the antigen binding domains capable of specific binding to OX40 comprise (i) a heavy chain variable region (V$_H$OX40) comprising the amino acid sequence of SEQ ID NO:59 and a light chain variable region (V$_L$OX40) comprising the amino acid sequence of SEQ ID NO:34, or (ii) a heavy chain variable region (V$_H$OX40) comprising the amino acid sequence of SEQ ID NO:60 and a light chain variable region (V$_L$OX40) comprising the amino acid sequence of SEQ ID NO:34, or (iii) a heavy chain variable region (V$_H$OX40) comprising the amino acid sequence of SEQ ID NO:61 and a light chain variable region (V$_L$OX40) comprising the amino acid sequence of SEQ ID NO:34.

In one aspect, provided is a bispecific antigen binding molecule as defined herein before, wherein the antigen binding domain capable of specific binding to OX40 comprises a heavy chain variable region (V$_H$OX40) comprising the amino acid sequence of SEQ ID NO:59 and a light chain variable region (V$_L$OX40) comprising the amino acid sequence of SEQ ID NO:34. In one aspect, the antigen binding domain capable of specific binding to OX40 comprises a heavy chain variable region (V$_H$OX40) comprising the amino acid sequence of SEQ ID NO:60 and a light chain variable region (V$_L$OX40) comprising the amino acid sequence of SEQ ID NO:34. In a further aspect, the antigen binding domain capable of specific binding to OX40 comprises a heavy chain variable region (V$_H$OX40) comprising the amino acid sequence of SEQ ID NO:61 and a light chain variable region (V$_L$OX40) comprising the amino acid sequence of SEQ ID NO:34. In one particular aspect, the antigen binding domains capable of specific binding to OX40 (each) comprise a heavy chain variable region (V$_H$OX40) comprising the amino acid sequence of SEQ ID NO:60 and a light chain variable region (V$_L$OX40) comprising the amino acid sequence of SEQ ID NO:34.

Bispecific Antigen Binding Molecules Binding to OX40 and FAP

In another aspect, provided is a bispecific antigen binding molecule, comprising
(a) at least two antigen binding domains capable of specific binding to OX40, comprising a heavy chain variable region (V$_H$OX40) comprising (i) CDR-H1 comprising the amino acid sequence of SEQ ID NO:27, (ii) CDR-H2 comprising the amino acid sequence of SEQ ID NO:28, and (iii) CDR-H3 comprising the amino acid sequence of SEQ ID NO:29, and a light chain variable region (V$_L$OX40) comprising (iv) CDR-L1 comprising the amino acid sequence of SEQ ID NO:30, (v) CDR-L2 comprising the amino acid sequence of SEQ ID NO:31, and (vi) CDR-L3 comprising the amino acid sequence of SEQ ID NO:32,
(b) an antigen binding domain capable of specific binding to Fibroblast Activation Protein (FAP) comprising a heavy chain variable region (V$_H$FAP) comprising
(i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region (V$_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8, and
(c) a Fc region composed of a first and a second subunit capable of stable association.

In a further aspect, provided is a bispecific antigen binding molecule, comprising
(a) at least two antigen binding domains capable of specific binding to OX40, comprising a heavy chain variable region (V$_H$OX40) comprising an amino acid sequence selected from the group consisting of SEQ ID NO:33, SEQ ID NO:59, SEQ ID NO:60 and SEQ ID NO:61, and a light chain variable region (V$_L$OX40) comprising the amino acid sequence selected from the group consisting of SEQ ID NO:34,
(b) at least one antigen binding domain capable of specific binding to FAP, comprising a heavy chain variable region (V$_H$FAP) comprising an amino acid sequence selected from the group consisting of SEQ ID NO:15, SEQ ID NO:16, SEQ ID NO:17, SEQ ID NO:18. SEQ ID NO:19 and SEQ ID NO:20, and a light chain variable region (V$_L$FAP) comprising an amino acid sequence selected from the group consisting of SEQ ID NO:21, SEQ ID NO:22, SEQ ID NO:23, SEQ ID NO:24, SEQ ID NO:25 and SEQ ID NO:26, and
(c) a Fc region composed of a first and a second subunit capable of stable association.

In a particular aspect, provided is a bispecific antigen binding molecule, comprising
(a) at least two antigen binding domains capable of specific binding to OX40, comprising a heavy chain variable region (V$_H$OX40) comprising an amino acid sequence selected from the group consisting of SEQ ID NO:59, SEQ ID NO:60 and SEQ ID NO:61, and a light chain variable region (V$_L$OX40) comprising the amino acid sequence selected from the group consisting of SEQ ID NO:34,
(b) at least one antigen binding domain capable of specific binding to FAP, comprising a heavy chain variable region (V$_H$FAP) comprising an amino acid sequence selected from the group consisting of SEQ ID NO:15, and a light chain variable region (V$_L$FAP) comprising an amino acid sequence selected from the group consisting of SEQ ID NO:21, and
(c) a Fc region composed of a first and a second subunit capable of stable association.

In another aspect, provided is a bispecific antigen binding molecule, comprising
(a) at least two antigen binding domains capable of specific binding to OX40, comprising a heavy chain variable region (V$_H$OX40) comprising (i) CDR-H1 comprising the amino acid sequence of SEQ ID NO:35, (ii) CDR-H2 comprising the amino acid sequence of SEQ ID NO:36, and (iii) CDR-H3 comprising the amino acid sequence of SEQ ID NO:37, and a light chain variable region (V$_L$OX40) comprising (iv) CDR-L1 comprising the amino acid sequence of SEQ ID NO:38, (v) CDR-L2 comprising the amino acid sequence of SEQ ID NO:39, and (vi) CDR-L3 comprising the amino acid sequence of SEQ ID NO:40,
(b) an antigen binding domain capable of specific binding to Fibroblast Activation Protein (FAP) comprising a heavy chain variable region (V$_H$FAP) comprising
(i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region (V$_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8, and
(c) a Fc region composed of a first and a second subunit capable of stable association.

In a further aspect, provided is a bispecific antigen binding molecule, comprising
(a) at least two antigen binding domains capable of specific binding to OX40, comprising a heavy chain variable region (V$_H$OX40) comprising an amino acid sequence selected from the group consisting of SEQ ID NO:41, and a light chain variable region (V$_L$OX40) comprising the amino acid sequence selected from the group consisting of SEQ ID NO:42, (b) at least one antigen binding domain capable of specific binding to FAP, comprising a heavy chain variable region (V$_H$FAP) comprising an amino acid sequence selected from the group consisting of SEQ ID NO:15, SEQ ID NO:16, SEQ ID NO:17, SEQ ID NO:18. SEQ ID NO:19 and SEQ ID NO:20, and a light chain variable region (V$_L$FAP) comprising an amino acid sequence selected from the group consisting of SEQ ID NO:21, SEQ ID NO:22, SEQ ID NO:23, SEQ ID NO:24, SEQ ID NO:25 and SEQ ID NO:26, and (c) a Fc region composed of a first and a second subunit capable of stable association.

In a particular aspect, provided is a bispecific antigen binding molecule, comprising (a) at least two antigen binding domains capable of specific binding to OX40, comprising a heavy chain variable region (V$_H$OX40) comprising an amino acid sequence selected from the group consisting of SEQ ID NO:41 and a light chain variable region (V$_L$OX40) comprising the amino acid sequence selected from the group consisting of SEQ ID NO:42, (b) at least one antigen binding domain capable of specific binding to FAP, comprising a heavy chain variable region (V$_H$FAP) comprising an amino acid sequence selected from the group consisting of SEQ ID NO:15, and a light chain variable region (V$_L$FAP) comprising an amino acid sequence selected from the group consisting of SEQ ID NO:21, and (c) a Fc region composed of a first and a second subunit capable of stable association.

In another aspect, provided is a bispecific antigen binding molecule, comprising
(a) at least two antigen binding domains capable of specific binding to OX40, comprising a heavy chain variable region (V$_H$OX40) comprising (i) CDR-H1 comprising the amino acid sequence of SEQ ID NO:43, (ii) CDR-H2 comprising the amino acid sequence of SEQ ID NO:44, and (iii) CDR-H3 comprising the amino acid sequence of SEQ ID NO:45, and a light chain variable region (V$_L$OX40) comprising (iv) CDR-L1 comprising the amino acid sequence of SEQ ID NO:46, (v) CDR-L2 comprising the amino acid sequence of SEQ ID NO:47, and (vi) CDR-L3 comprising the amino acid sequence of SEQ ID NO:48,
(b) an antigen binding domain capable of specific binding to Fibroblast Activation Protein (FAP) comprising a heavy chain variable region (V$_H$FAP) comprising
(i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region (V$_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8, and
(c) a Fc region composed of a first and a second subunit capable of stable association.

In a further aspect, provided is a bispecific antigen binding molecule, comprising (a) at least two antigen binding domains capable of specific binding to OX40, comprising a heavy chain variable region (V$_H$OX40) comprising an amino acid sequence selected from the group consisting of SEQ ID NO:49, and a light chain variable region (V$_L$OX40) comprising the amino acid sequence selected from the group consisting of SEQ ID NO:50, (b) at least one antigen binding domain capable of specific binding to FAP, comprising a heavy chain variable region (V$_H$FAP) comprising an amino acid sequence selected from the group consisting of SEQ ID NO:15, SEQ ID NO:16, SEQ ID NO:17, SEQ ID NO:18. SEQ ID NO:19 and SEQ ID NO:20, and a light chain variable region (V$_L$FAP) comprising an amino acid sequence selected from the group consisting of SEQ ID NO:21, SEQ ID NO:22, SEQ ID NO:23, SEQ ID NO:24, SEQ ID NO:25 and SEQ ID NO:26, and (c) a Fc region composed of a first and a second subunit capable of stable association.

In a particular aspect, provided is a bispecific antigen binding molecule, comprising (a) at least two antigen binding domains capable of specific binding to OX40, comprising a heavy chain variable region (V$_H$OX40) comprising an amino acid sequence selected from the group consisting of SEQ ID NO:49 and a light chain variable region (V$_L$OX40) comprising the amino acid sequence selected from the group consisting of SEQ ID NO:50, (b) at least one antigen binding domain capable of specific binding to FAP, comprising a heavy chain variable region (V$_H$FAP) comprising an amino acid sequence selected from the group consisting of SEQ ID NO:15, and a light chain variable region (V$_L$FAP) comprising an amino acid sequence selected from the group consisting of SEQ ID NO:21, and (c) a Fc region composed of a first and a second subunit capable of stable association.

In yet another aspect, provided is a bispecific antigen binding molecule, comprising
(a) at least two antigen binding domains capable of specific binding to OX40, comprising a heavy chain variable region (V$_H$OX40) comprising (i) CDR-H1 comprising the amino acid sequence of SEQ ID NO:51, (ii) CDR-H2 comprising the amino acid sequence of SEQ ID NO:52, and (iii) CDR-H3 comprising the amino acid sequence of SEQ ID NO:53, and a light chain variable region (V$_L$OX40) comprising (iv) CDR-L1 comprising the amino acid sequence of SEQ ID NO:54, (v) CDR-L2 comprising the amino acid sequence of SEQ ID NO:55, and (vi) CDR-L3 comprising the amino acid sequence of SEQ ID NO:56,
(b) an antigen binding domain capable of specific binding to Fibroblast Activation Protein (FAP) comprising a heavy chain variable region (V$_H$FAP) comprising
(i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region (V$_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8, and
(c) a Fc region composed of a first and a second subunit capable of stable association.

In a further aspect, provided is a bispecific antigen binding molecule, comprising
(a) at least two antigen binding domains capable of specific binding to OX40, comprising a heavy chain variable region (V$_H$OX40) comprising an amino acid sequence selected from the group consisting of SEQ ID NO:57, and a light chain variable region (V$_L$OX40) comprising the amino acid sequence selected from the group consisting of SEQ ID NO:58, (b) at least one antigen binding domain capable of specific binding to FAP, comprising a heavy chain variable region (V$_H$FAP) comprising an amino acid sequence selected from the group consisting of SEQ ID NO:15, SEQ ID NO:16, SEQ ID NO:17, SEQ ID NO:18. SEQ ID NO:19 and SEQ ID NO:20, and a light chain variable region (V$_L$FAP) comprising an amino acid sequence selected from the group consisting of SEQ ID NO:21, SEQ ID NO:22, SEQ ID NO:23, SEQ ID NO:24, SEQ ID NO:25 and SEQ ID NO:26, and (c) a Fc region composed of a first and a second subunit capable of stable association.

In a particular aspect, provided is a bispecific antigen binding molecule, comprising (a) at least two antigen binding domains capable of specific binding to OX40, comprising a heavy chain variable region (V$_H$OX40) comprising an amino acid sequence selected from the group consisting of SEQ ID NO:57 and a light chain variable region (V$_L$OX40) comprising the amino acid sequence selected from the group consisting of SEQ ID NO:58, (b) at least one antigen binding domain capable of specific binding to FAP, comprising a heavy chain variable region (V$_H$FAP) comprising an amino acid sequence selected from the group consisting of SEQ ID NO:15, and a light chain variable region (VLFAP) comprising an amino acid sequence selected from the group consisting of SEQ ID NO:21, and (c) a Fc region composed of a first and a second subunit capable of stable association.

Bispecific Antigen Binding Molecules Bivalent for Binding to OX40 and Monovalent for Binding to FAP (2+1 Format)

In another aspect, the invention provides a bispecific antigen binding molecule comprising
(a) two Fab fragments capable of specific binding to OX40,
(b) one cross-Fab fragment capable of specific binding to FAP comprising a heavy chain variable region (V$_H$FAP) comprising (i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region (VLFAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8, and
(c) a Fc domain composed of a first and a second subunit capable of stable association.

Thus, provided is a bispecific antigen binding molecule, wherein the bispecific antigen binding molecule binds bivalently to OX40 and monovalently to FAP.

In one aspect, provided is a bispecific antigen binding molecule, comprising
(a) two heavy chains, each heavy chain comprising a VH and CH1 domain of a Fab fragment capable of specific binding to OX40 and a Fc region subunit,
(b) two light chains, each light chain comprising a VL and CL domain of a Fab fragment capable of specific binding to OX40, and (c) a cross-fab fragment capable of specific binding to FAP comprising a VL-CH1 chain and a VH-CL chain, wherein the VH-CL chain is connected to the C-terminus of one of the two heavy chains of (a).

In one aspect, the VH-CL (VH-Ckappa) chain is connected to the C-terminus of the Fc knob heavy chain. In one aspect, the VH-Ckappa chain is connected to the C-terminus of an Fc knob heavy chain comprising the amino acid substitutions S354C and T366W (numbering according to Kabat EU index).

In another aspect, provided is a bispecific antigen binding molecule, comprising
(a) two heavy chains, each heavy chain comprising a VH and CH1 domain of a Fab fragment capable of specific binding to OX40 and a Fc region subunit,
(b) two light chains, each light chain comprising a VL and CL domain of a Fab fragment capable of specific binding to OX40, and
(c) a cross-fab fragment capable of specific binding to FAP comprising a VL-CH1 chain and a VH-CL chain, wherein the VL-CH1 chain is connected to the C-terminus of one of the two heavy chains of (a).

In one aspect, the VL-CH1 chain is connected to the C-terminus of the Fc knob heavy chain. In one aspect, the VL-CH1 chain is connected to the C-terminus of an Fc knob heavy chain comprising the amino acid substitutions S354C and T366W (numbering according to Kabat EU index).

In one aspect, the invention provides a bispecific antigen binding molecule comprising
(a) two light chains, each comprising an amino acid sequence that is at least about 90%, 95%, 96%, 97%, 98%, 99% or 100% identical to the sequence of SEQ ID NO:87, one light chain comprising an amino acid sequence that is at least about 90%, 95%, 96%, 97%, 98%, 99% or 100% identical to the sequence of SEQ ID NO:88, a first heavy chain comprising an amino acid sequence that is at least about 90%, 95%, 96%, 97%, 98%, 99% or 100% identical to the sequence of SEQ ID NO:91, and a second heavy chain comprising an amino acid sequence that is at least about 90%, 95%, 96%, 97%, 98%, 99% or 100% identical to the sequence of SEQ ID NO:90, or
(b) two light chains, each comprising an amino acid sequence that is at least about 90%, 95%, 96%, 97%, 98%, 99% or 100% identical to the sequence of SEQ ID NO:87, one light chain comprising an amino acid sequence that is at least about 90%, 95%, 96%, 97%, 98%, 99% or 100% identical to the sequence of SEQ ID NO:94, a first heavy chain comprising an amino acid sequence that is at least about 90%, 95%, 96%, 97%, 98%, 99% or 100% identical to the sequence of SEQ ID NO:91, and a second heavy chain comprising an amino acid sequence that is at least about 90%, 95%, 96%, 97%, 98%, 99% or 100% identical to the sequence of SEQ ID NO:90, or
(c) two light chains, each comprising an amino acid sequence that is at least about 90%, 95%, 96%, 97%, 98%, 99% or 100% identical to the sequence of SEQ ID NO:87, one light chain comprising an amino acid sequence that is at least about 90%, 95%, 96%, 97%, 98%, 99% or 100% identical to the sequence of SEQ ID NO:96, a first heavy chain comprising an amino acid sequence that is at least about 90%, 95%, 96%, 97%, 98%, 99% or 100% identical to the sequence of SEQ ID NO:91, and a second heavy chain an amino acid sequence that is at least about 90%, 95%, 96%, 97%, 98%, 99% or 100% identical to the sequence of SEQ ID NO:90. In one aspect, the invention provides a bispecific antigen binding molecule comprising (a) two light chains, each comprising the amino acid sequence of SEQ ID NO:87, one light chain comprising the amino acid sequence of SEQ ID NO:88, a first heavy chain comprising the amino acid sequence of SEQ ID NO:91, and a second heavy chain comprising the amino acid sequence of SEQ ID NO:90, or (b) two light chains, each comprising the amino acid sequence of SEQ ID NO:87, one light chain comprising the amino acid sequence of SEQ ID NO:94, a first heavy chain comprising the amino acid sequence of SEQ ID NO:91, and a second heavy chain comprising the amino acid sequence of SEQ ID NO:90, or (c) two light chains, each comprising the amino acid sequence of SEQ ID NO:87, one light chain comprising the amino acid sequence of SEQ ID NO:96, a first heavy chain comprising the amino acid sequence of SEQ ID NO:91, and a second heavy chain comprising the amino acid sequence of SEQ ID NO:90.

In another aspect, the invention provides a bispecific antigen binding molecule comprising
(a) two light chains, each comprising an amino acid sequence that is at least about 90%, 95%, 96%, 97%, 98%, 99% or 100% identical to the sequence of SEQ ID NO:93, one light chain comprising an amino acid sequence that is at least about 90%, 95%, 96%, 97%, 98%, 99% or 100% identical to the sequence of SEQ ID NO:88, a first heavy chain comprising an amino acid sequence that is at least about 90%, 95%, 96%, 97%, 98%, 99% or 100% identical to the sequence of SEQ ID NO:97, and a second heavy chain comprising an amino acid sequence that is at least about 90%, 95%, 96%, 97%, 98%, 99% or 100% identical to the sequence of SEQ ID NO:98, or
(b) two light chains, each comprising an amino acid sequence that is at least about 90%, 95%, 96%, 97%, 98%, 99% or 100% identical to the sequence of SEQ ID NO:93, one light chain comprising an amino acid sequence that is at least about 90%, 95%, 96%, 97%, 98%, 99% or 100% identical to the sequence of SEQ ID NO:94, a first heavy chain comprising an amino acid sequence that is at least about 90%, 95%, 96%, 97%, 98%, 99% or 100% identical to the sequence of SEQ ID NO:97, and a second heavy chain comprising an amino acid sequence that is at least about 90%, 95%, 96%, 97%, 98%, 99% or 100% identical to the sequence of SEQ ID NO:98, or
(c) two light chains, each comprising an amino acid sequence that is at least about 90%, 95%, 96%, 97%, 98%, 99% or 100% identical to the sequence of SEQ ID NO:93, one light chain comprising an amino acid sequence that is at least about 90%, 95%, 96%, 97%, 98%, 99% or 100% identical to the sequence of SEQ ID NO:96, a first heavy chain comprising an amino acid sequence that is at least about 90%, 95%, 96%, 97%, 98%, 99% or 100% identical to the sequence of SEQ ID NO:97, and a second heavy chain an amino acid sequence that is at least about 90%, 95%, 96%, 97%, 98%, 99% or 100% identical to the sequence of SEQ ID NO:98. In one aspect, the invention provides a bispecific antigen binding molecule comprising (a) two light chains, each comprising the amino acid sequence of SEQ ID NO:93, one light chain comprising the amino acid sequence of SEQ ID NO:88, a first heavy chain comprising the amino acid sequence of SEQ ID NO:97, and a second heavy chain comprising the amino acid sequence of SEQ ID NO:98, or (b) two light chains, each comprising the amino acid sequence of SEQ ID NO:93, one light chain comprising the amino acid sequence of SEQ ID NO:94, a first heavy chain comprising the amino acid sequence of SEQ ID NO:97, and a second heavy chain comprising the amino acid sequence of SEQ ID NO:98, or (c) two light chains, each comprising the amino acid sequence of SEQ ID NO:93, one light chain comprising the amino acid sequence of SEQ ID NO:96, a first heavy chain comprising the amino acid sequence of SEQ ID NO:97, and a second heavy chain comprising the amino acid sequence of SEQ ID NO:98.

In another aspect, the invention provides a bispecific antigen binding molecule comprising
(a) two light chains, each comprising an amino acid sequence that is at least about 90%, 95%, 96%, 97%, 98%, 99% or 100% identical to the sequence of SEQ ID NO:100, one light chain comprising an amino acid sequence that is at least about 90%, 95%, 96%, 97%, 98%, 99% or 100% identical to the sequence of SEQ ID NO:88, a first heavy chain comprising an amino acid sequence that is at least about 90%, 95%, 96%, 97%, 98%, 99% or 100% identical to the sequence of SEQ ID NO:99, and a second heavy chain comprising an amino acid sequence that is at least about 90%, 95%, 96%, 97%, 98%, 99% or 100% identical to the sequence of SEQ ID NO:102, or
(b) two light chains, each comprising an amino acid sequence that is at least about 90%, 95%, 96%, 97%, 98%, 99% or 100% identical to the sequence of SEQ ID NO:100, one light chain comprising an amino acid sequence that is at least about 90%, 95%, 96%, 97%, 98%, 99% or 100% identical to the sequence of SEQ ID NO:94, a first heavy chain comprising an amino acid sequence that is at least about 90%, 95%, 96%, 97%, 98%, 99% or 100% identical to the sequence of SEQ ID NO:99, and a second heavy chain comprising an amino acid sequence that is at least about 90%, 95%, 96%, 97%, 98%, 99% or 100% identical to the sequence of SEQ ID NO:102, or
(c) two light chains, each comprising an amino acid sequence that is at least about 90%, 95%, 96%, 97%, 98%, 99% or 100% identical to the sequence of SEQ ID NO:100, one light chain comprising an amino acid sequence that is at least about 90%, 95%, 96%, 97%, 98%, 99% or 100% identical to the sequence of SEQ ID NO:96, a first heavy chain comprising an amino acid sequence that is at least about 90%, 95%, 96%, 97%, 98%, 99% or 100% identical to the sequence of SEQ ID NO:99, and a second heavy chain an amino acid sequence that is at least about 90%, 95%, 96%, 97%, 98%, 99% or 100% identical to the sequence of SEQ ID NO:102. In one aspect, the invention provides a bispecific antigen binding molecule comprising (a) two light chains, each comprising the amino acid sequence of SEQ ID NO:100, one light chain comprising the amino acid sequence of SEQ ID NO:88, a first heavy chain comprising the amino acid sequence of SEQ ID NO:99, and a second heavy chain comprising the amino acid sequence of SEQ ID NO:102, or (b) two light chains, each comprising the amino acid sequence of SEQ ID NO:100, one light chain comprising the amino acid sequence of SEQ ID NO:94, a first heavy chain comprising the amino acid sequence of SEQ ID NO:99, and a second heavy chain comprising the amino acid sequence of SEQ ID NO:102, or (c) two light chains, each comprising the amino acid sequence of SEQ ID NO:100, one light chain comprising the amino acid sequence of SEQ ID NO:96, a first heavy chain comprising the amino acid sequence of SEQ ID NO:99, and a second heavy chain comprising the amino acid sequence of SEQ ID NO:102.

In another aspect, the invention provides a bispecific antigen binding molecule comprising
(a) two light chains, each comprising an amino acid sequence that is at least about 90%, 95%, 96%, 97%, 98%, 99% or 100% identical to the sequence of SEQ ID NO:104, one light chain comprising an amino acid sequence that is at least about 90%, 95%, 96%, 97%, 98%, 99% or 100% identical to the sequence of SEQ ID NO:88, a first heavy chain comprising an amino acid sequence that is at least about 90%, 95%, 96%, 97%, 98%, 99% or 100% identical to the sequence of SEQ ID NO:103, and a second heavy chain comprising an amino acid sequence that is at least about 90%, 95%, 96%, 97%, 98%, 99% or 100% identical to the sequence of SEQ ID NO:106, or (b) two light chains, each comprising an amino acid sequence that is at least about 90%, 95%, 96%, 97%, 98%, 99% or 100% identical to the sequence of SEQ ID NO:104, one light chain comprising an amino acid sequence that is at least about 90%, 95%, 96%, 97%, 98%, 99% or 100% identical to the sequence of SEQ ID NO:94, a first heavy chain comprising an amino acid sequence that is at least about 90%, 95%, 96%, 97%, 98%, 99% or 100% identical to the sequence of SEQ ID NO:103, and a second heavy chain comprising an amino acid sequence that is at least about 90%, 95%, 96%, 97%, 98%, 99% or 100% identical to the sequence of SEQ ID NO:106, or (c) two light chains, each comprising an amino acid sequence that is at least about 90%, 95%, 96%, 97%, 98%, 99% or 100% identical to the sequence of SEQ ID NO:104, one light chain comprising an amino acid sequence that is at least about 90%, 95%, 96%, 97%, 98%, 99% or 100% identical to the sequence of SEQ ID NO:96, a first heavy chain comprising an amino acid sequence that is at least about 90%, 95%, 96%, 97%, 98%, 99% or 100% identical to the sequence of SEQ ID NO:103, and a second heavy chain an amino acid sequence that is at least about 90%, 95%, 96%, 97%, 98%, 99% or 100% identical to the sequence of SEQ ID NO:106. In one aspect, the invention provides a bispecific antigen binding molecule comprising (a) two light chains, each comprising the amino acid sequence of SEQ ID NO:104, one light chain comprising the amino acid sequence of SEQ ID NO:88, a first heavy chain comprising the amino acid sequence of SEQ ID NO:103, and a second heavy chain comprising the amino acid sequence of SEQ ID NO:106, or (b) two light chains, each comprising the amino acid sequence of SEQ ID NO:104, one light chain comprising the amino acid sequence of SEQ ID NO:94, a first heavy chain comprising the amino acid sequence of SEQ ID NO:103, and a second heavy chain comprising the amino acid sequence of SEQ ID NO:106, or (c) two light chains, each comprising the amino acid sequence of SEQ ID NO:104, one light chain comprising the amino acid sequence of SEQ ID NO:96, a first heavy chain comprising the amino acid sequence of SEQ ID NO:103, and a second heavy chain comprising the amino acid sequence of SEQ ID NO:106.

Bispecific Antigen Binding Molecules Trivalent for Binding to OX40 and Monovalent for Binding to FAP (3+1 Format)

In another aspect, provided is a bispecific antigen binding molecule, wherein the bispecific antigen binding molecule comprises (aa) a first Fab fragment capable of specific binding to OX40, (ab) a second Fab fragment capable of specific binding to OX40, (ac) a third Fab fragment capable of specific binding to OX40, (b) a cross-Fab fragment capable of specific binding to FAP fused to the C-terminus of one of subunits of the Fc region, and (c) the Fc region composed of a first and a second subunit capable of stable association, wherein the second Fab fragment (ab) is fused at the C-terminus of the VH-CH1 chain to the N-terminus of the VH-CH1 chain of the first Fab fragment (aa), which is in turn fused at its C-terminus to the N-terminus of the first subunit, and the third Fab fragment (ac) is fused at the C-terminus of the Fab heavy chain to the N-terminus of the second subunit.

In one aspect, the bispecific antigen binding molecule consists of (aa) a first Fab fragment capable of specific binding to OX40, (ab) a second Fab fragment capable of specific binding to OX40, (ac) a third Fab fragment capable of specific binding to OX40, (b) a cross-Fab fragment capable of specific binding to FAP fused to the C-terminus of one of subunits of the Fc region, and (c) the Fc region composed of a first and a second subunit capable of stable association, wherein the second Fab fragment (ab) is fused at the C-terminus of the VH-CH1 chain to the N-terminus of the VH-CH1 chain of the first Fab fragment (aa), which is in turn fused at its C-terminus to the N-terminus of the first subunit, and the third Fab fragment (ac) is fused at the C-terminus of the Fab heavy chain to the N-terminus of the second subunit.

In another aspect, provided is a bispecific antigen binding molecule, comprising (a) a heavy chain comprising a VH-CH1 chain of a first Fab fragment capable of specific binding to OX40 fused at its N-terminus to the VH-CH1 chain of a second Fab fragment capable of specific binding to OX40, optionally via a peptide linker, and a Fc region subunit, (b) a heavy chain comprising a VH-CH1 domain of a Fab fragment capable of specific binding to OX40, a Fc region subunit, and a VH-CL chain of a Fab fragment capable of specific binding to FAP fused to the C-terminus of the Fc region subunit, optionally via a peptide linker, (c) three light chains, each light chain comprising a VL and CL domain of a Fab fragment capable of specific binding to OX40, and (d) a light chain comprising a VL and CH1 domain of a Fab fragment capable of specific binding to FAP.

In another aspect, provided is a bispecific antigen binding molecule, comprising (a) a heavy chain comprising a VH-CH1 chain of a first Fab fragment capable of specific binding to OX40 fused at its N-terminus to the VH-CH1 chain of a second Fab fragment capable of specific binding to OX40, optionally via a peptide linker, a Fc region subunit, and a VH-CL chain of a Fab fragment capable of specific binding to FAP fused to the C-terminus of the Fc region subunit, optionally via a peptide linker, (b) a heavy chain comprising a VH-CH1 domain of a Fab fragment capable of specific binding to OX40 and a Fc region subunit, (c) three light chains, each light chain comprising a VL and CL domain of a Fab fragment capable of specific binding to OX40, and (d) a light chain comprising a VL and CH1 domain of a Fab fragment capable of specific binding to FAP.

In another aspect, provided is a bispecific antigen binding molecule, comprising (a) a heavy chain comprising a VH-CH1 chain of a first Fab fragment capable of specific binding to OX40 fused at its N-terminus to the VH-CH1 chain of a second Fab fragment capable of specific binding to OX40, optionally via a peptide linker, and a Fc region subunit, (b) a heavy chain comprising a VH-CH1 domain of a Fab fragment capable of specific binding to OX40, a Fc region subunit, and a VL-CH1 chain of a Fab fragment capable of specific binding to FAP fused to the C-terminus of the Fc region subunit, optionally via a peptide linker, (c) three light chains, each light chain comprising a VL and CL domain of a Fab fragment capable of specific binding to OX40, and (d) a light chain comprising a VH and CL domain of a Fab fragment capable of specific binding to FAP.

In another aspect, provided is a bispecific antigen binding molecule, comprising (a) a heavy chain comprising a VH-CH1 chain of a first Fab fragment capable of specific binding to OX40 fused at its N-terminus to the VH-CH1 chain of a second Fab fragment capable of specific binding to OX40, optionally via a peptide linker, a Fc region subunit, and a VL-CH1 chain of a Fab fragment capable of specific binding to FAP fused to the C-terminus of the Fc region subunit, optionally via a peptide linker, (b) a heavy chain comprising a VH-CH1 domain of a Fab fragment capable of specific binding to OX40 and a Fc region subunit, (c) three light chains, each light chain comprising a VL and CL domain of a Fab fragment capable of specific binding to OX40, and (d) a light chain comprising a VH and CL domain of a Fab fragment capable of specific binding to FAP.

In one particular aspect, the peptide linker is selected from GGGGS (SEQ ID NO:67) GGGGSGGGGS (SEQ ID NO:68), SGGGGSGGGG (SEQ ID NO:69), GGGGSGGGGSGGGG (SEQ ID NO:70), GSPGSSSSGS (SEQ ID NO:71), (G4S)$_3$ (SEQ ID NO:72), (G4S)$_4$ (SEQ ID NO:73), GSGSGSGS (SEQ ID NO:74), GSGSGNGS (SEQ ID NO:75), GGSGSGSG (SEQ ID NO:76), GGSGSG (SEQ ID NO:77), GGSG (SEQ ID NO:78), GGSGNGSG (SEQ ID NO:79), GGNGSGSG (SEQ ID NO:80) and GGNGSG (SEQ ID NO:81). Peptide linkers of particular interest are (G4S) (SEQ ID NO:67), (G$_4$S)$_2$ or GGGGSGGGGS (SEQ ID NO:68), (G4S)$_3$ (SEQ ID NO:72) and (G4S)$_4$ (SEQ ID NO:73).

In one aspect, provided is a bispecific antigen binding molecule comprising
(a) a first heavy chain comprising an amino acid sequence that is at least about 90%, 95%, 96%, 97%, 98%, 99% or 100% identical to the sequence of SEQ ID NO:86, a second heavy chain comprising an amino acid sequence that is at least about 90%, 95%, 96%, 97%, 98%, 99% or 100% identical to the sequence of SEQ ID NO:90, three light chains each comprising an amino acid sequence that is at least about 90%, 95%, 96%, 97%, 98%, 99% or 100% identical to the sequence of SEQ ID NO:87 and a light chain comprising an amino acid sequence that is at least about 90%, 95%, 96%, 97%, 98%, 99% or 100% identical to the sequence of SEQ ID NO:88, or
(b) a first heavy chain comprising an amino acid sequence that is at least about 90%, 95%, 96%, 97%, 98%, 99% or 100% identical to the sequence of SEQ ID NO:86, a second heavy chain comprising an amino acid sequence that is at least about 90%, 95%, 96%, 97%, 98%, 99% or 100% identical to the sequence of SEQ ID NO:90, three light chains each comprising an amino acid sequence that is at least about 90%, 95%, 96%, 97%, 98%, 99% or 100% identical to the sequence of SEQ ID NO:87 and a light chain comprising an amino acid sequence that is at least about 90%, 95%, 96%, 97%, 98%, 99% or 100% identical to the sequence of SEQ ID NO:94, or
(c) a first heavy chain comprising an amino acid sequence that is at least about 90%, 95%, 96%, 97%, 98%, 99% or 100% identical to the sequence of SEQ ID NO:86, a second heavy chain comprising an amino acid sequence that is at least about 90%, 95%, 96%, 97%, 98%, 99% or 100% identical to the sequence of SEQ ID NO:90, three light chains each comprising an amino acid sequence that is at least about 90%, 95%, 96%, 97%, 98%, 99% or 100% identical to the sequence of SEQ ID NO:87 and a light chain comprising an amino acid sequence that is at least about 90%, 95%, 96%, 97%, 98%, 99% or 100% identical to the sequence of SEQ ID NO:96. In one aspect, provided is a bispecific antigen binding molecule comprising (a) a first heavy chain comprising the amino acid sequence of SEQ ID NO:86, a second heavy chain comprising the amino acid sequence of SEQ ID NO:90, three light chains each comprising the amino acid sequence of SEQ ID NO:87 and a light chain comprising the amino acid sequence of SEQ ID NO:88, or (b) a first heavy chain comprising the amino acid sequence of SEQ ID NO:86, a second heavy chain comprising the amino acid sequence of SEQ ID NO:90, three light chains each comprising the amino acid sequence of SEQ ID NO:87 and a light chain comprising the amino acid sequence of SEQ ID NO:94, or (c) a first heavy chain comprising the amino acid sequence of SEQ ID NO:86, a second heavy chain comprising the amino acid sequence of SEQ ID NO:90, three light chains each comprising the amino acid sequence of SEQ ID NO:87 and a light chain comprising the amino acid sequence of SEQ ID NO:96.

In one aspect, provided is a bispecific antigen binding molecule comprising
(a) a first heavy chain comprising an amino acid sequence that is at least about 90%, 95%, 96%, 97%, 98%, 99% or 100% identical to the sequence of SEQ ID NO:97, a second heavy chain comprising an amino acid sequence that is at least about 90%, 95%, 96%, 97%, 98%, 99% or 100% identical to the sequence of SEQ ID NO:95, three light chains each comprising an amino acid sequence that is at least about 90%, 95%, 96%, 97%, 98%, 99% or 100% identical to the sequence of SEQ ID NO:93 and a light chain comprising an amino acid sequence that is at least about 90%, 95%, 96%, 97%, 98%, 99% or 100% identical to the sequence of SEQ ID NO:88, or
(b) a first heavy chain comprising an amino acid sequence that is at least about 90%, 95%, 96%, 97%, 98%, 99% or 100% identical to the sequence of SEQ ID NO:97, a second heavy chain comprising an amino acid sequence that is at least about 90%, 95%, 96%, 97%, 98%, 99% or 100% identical to the sequence of SEQ ID NO:95, three light chains each comprising an amino acid sequence that is at least about 90%, 95%, 96%, 97%, 98%, 99% or 100% identical to the sequence of SEQ ID NO:93 and a light chain comprising an amino acid sequence that is at least about 90%, 95%, 96%, 97%, 98%, 99% or 100% identical to the sequence of SEQ ID NO:94, or
(c) a first heavy chain comprising an amino acid sequence that is at least about 90%, 95%, 96%, 97%, 98%, 99% or 100% identical to the sequence of SEQ ID NO:97, a second heavy chain comprising an amino acid sequence that is at least about 90%, 95%, 96%, 97%, 98%, 99% or 100% identical to the sequence of SEQ ID NO:95, three light chains each comprising an amino acid sequence that is at least about 90%, 95%, 96%, 97%, 98%, 99% or 100% identical to the sequence of SEQ ID NO:93 and a light chain comprising an amino acid sequence that is at least about 90%, 95%, 96%, 97%, 98%, 99% or 100% identical to the sequence of SEQ ID NO:96. In one aspect, provided is a bispecific antigen binding molecule comprising (a) a first heavy chain comprising the amino acid sequence of SEQ ID NO:97, a second heavy chain comprising the amino acid sequence of SEQ ID NO:95, three light chains each comprising the amino acid sequence of SEQ ID NO:93 and a light chain comprising the amino acid sequence of SEQ ID NO:88, or (b) a first heavy chain comprising the amino acid sequence of SEQ ID NO:97, a second heavy chain comprising the amino acid sequence of SEQ ID NO:95, three light chains each comprising the amino acid sequence of SEQ ID NO:93 and a light chain comprising the amino acid sequence of SEQ ID NO:94, or (c) a first heavy chain comprising the amino acid sequence of SEQ ID NO:97, a second heavy chain comprising the amino acid sequence of SEQ ID NO:95, three light chains each comprising the amino acid sequence of SEQ ID NO:93 and a light chain comprising the amino acid sequence of SEQ ID NO:96.

In another aspect, provided is a bispecific antigen binding molecule comprising
(a) a first heavy chain comprising an amino acid sequence that is at least about 90%, 95%, 96%, 97%, 98%, 99% or 100% identical to the sequence of SEQ ID NO:99, a second heavy chain comprising an amino acid sequence that is at least about 90%, 95%, 96%, 97%, 98%, 99% or 100% identical to the sequence of SEQ ID NO:101, three light chains each comprising an amino acid sequence that is at least about 90%, 95%, 96%, 97%, 98%, 99% or 100% identical to the sequence of SEQ ID NO:100 and a light chain comprising an amino acid sequence that is at least about 90%, 95%, 96%, 97%, 98%, 99% or 100% identical to the sequence of SEQ ID NO:88, or
(b) a first heavy chain comprising an amino acid sequence that is at least about 90%, 95%, 96%, 97%, 98%, 99% or 100% identical to the sequence of SEQ ID NO:99, a second heavy chain comprising an amino acid sequence that is at least about 90%, 95%, 96%, 97%, 98%, 99% or 100% identical to the sequence of SEQ ID NO:101, three light chains each comprising an amino acid sequence that is at least about 90%, 95%, 96%, 97%, 98%, 99% or 100% identical to the sequence of SEQ ID NO:100 and a light chain comprising an amino acid sequence that is at least about 90%, 95%, 96%, 97%, 98%, 99% or 100% identical to the sequence of SEQ ID NO:94, or
(c) a first heavy chain comprising an amino acid sequence that is at least about 90%, 95%, 96%, 97%, 98%, 99% or 100% identical to the sequence of SEQ ID NO:99, a second heavy chain comprising an amino acid sequence that is at least about 90%, 95%, 96%, 97%, 98%, 99% or 100% identical to the sequence of SEQ ID NO:101, three light chains each comprising an amino acid sequence that is at least about 90%, 95%, 96%, 97%, 98%, 99% or 100% identical to the sequence of SEQ ID NO:100 and a light chain comprising an amino acid sequence that is at least about 90%, 95%, 96%, 97%, 98%, 99% or 100% identical to the sequence of SEQ ID NO:96. In one aspect, provided is a bispecific antigen binding molecule comprising (a) a first heavy chain comprising the amino acid sequence of SEQ ID NO:99, a second heavy chain comprising the amino acid sequence of SEQ ID NO:101, three light chains each comprising the amino acid sequence of SEQ ID NO:100 and a light chain comprising the amino acid sequence of SEQ ID NO:88, or (b) a first heavy chain comprising the amino acid sequence of SEQ ID NO:99, a second heavy chain comprising the amino acid sequence of SEQ ID NO:101, three light chains each comprising the amino acid sequence of SEQ ID NO:100 and a light chain comprising the amino acid sequence of SEQ ID NO:94, or (c) a first heavy chain comprising the amino acid sequence of SEQ ID NO:99, a second heavy chain comprising the amino acid sequence of SEQ ID NO:101, three light chains each comprising the amino acid sequence of SEQ ID NO:100 and a light chain comprising the amino acid sequence of SEQ ID NO:96.

In another aspect, provided is a bispecific antigen binding molecule comprising
(a) a first heavy chain comprising an amino acid sequence that is at least about 90%, 95%, 96%, 97%, 98%, 99% or 100% identical to the sequence of SEQ ID NO:103, a second heavy chain comprising an amino acid sequence that is at least about 90%, 95%, 96%, 97%, 98%, 99% or 100% identical to the sequence of SEQ ID NO:105, three light chains each comprising an amino acid sequence that is at least about 90%, 95%, 96%, 97%, 98%, 99% or 100% identical to the sequence of SEQ ID NO:104 and a light chain comprising an amino acid sequence that is at least about 90%, 95%, 96%, 97%, 98%, 99% or 100% identical to the sequence of SEQ ID NO:88, or
(b) a first heavy chain comprising an amino acid sequence that is at least about 90%, 95%, 96%, 97%, 98%, 99% or 100% identical to the sequence of SEQ ID NO:103, a second heavy chain comprising an amino acid sequence that is at least about 90%, 95%, 96%, 97%, 98%, 99% or 100% identical to the sequence of SEQ ID NO:105, three light chains each comprising an amino acid sequence that is at least about 90%, 95%, 96%, 97%, 98%, 99% or 100% identical to the sequence of SEQ ID NO:104 and a light chain comprising an amino acid sequence that is at least about 90%, 95%, 96%, 97%, 98%, 99% or 100% identical to the sequence of SEQ ID NO:94, or
(c) a first heavy chain comprising an amino acid sequence that is at least about 90%, 95%, 96%, 97%, 98%, 99% or 100% identical to the sequence of SEQ ID NO:103, a second heavy chain comprising an amino acid sequence that is at least about 90%, 95%, 96%, 97%, 98%, 99% or 100% identical to the sequence of SEQ ID NO:105, three light chains each comprising an amino acid sequence that is at least about 90%, 95%, 96%, 97%, 98%, 99% or 100% identical to the sequence of SEQ ID NO:104 and a light chain comprising an amino acid sequence that is at least about 90%, 95%, 96%, 97%, 98%, 99% or 100% identical to the sequence of SEQ ID NO:96. In one aspect, provided is a bispecific antigen binding molecule comprising (a) a first heavy chain comprising the amino acid sequence of SEQ ID NO:103, a second heavy chain comprising the amino acid sequence of SEQ ID NO:105, three light chains each comprising the amino acid sequence of SEQ ID NO:104 and a light chain comprising the amino acid sequence of SEQ ID NO:88, or (b) a first heavy chain comprising the amino acid sequence of SEQ ID NO:103, a second heavy chain comprising the amino acid sequence of SEQ ID NO:105, three light chains each comprising the amino acid sequence of SEQ ID NO:104 and a light chain comprising the amino acid sequence of SEQ ID NO:94, or (c) a first heavy chain comprising the amino acid sequence of SEQ ID NO:103, a second heavy chain comprising the amino acid sequence of SEQ ID NO:105, three light chains each comprising the amino acid sequence of SEQ ID NO:104 and a light chain comprising the amino acid sequence of SEQ ID NO:96.

Bispecific Antigen Binding Molecules Tetravalent for Binding to OX40 and Monovalent for Binding to the Target Cell Antigen (4+1 Format)

In another aspect, the invention provides a bispecific antigen binding molecule comprising
(a) four antigen binding domains capable of specific binding to OX40,
(b) one antigen binding domain capable of specific binding to FAP comprising (i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8, and (c) a Fc domain composed of a first and a second subunit capable of stable association.

Thus, provided is a bispecific antigen binding molecule, wherein the bispecific antigen binding molecule binds tetravalently to OX40 and monovalently to FAP.

In one aspect, provided is a bispecific antigen binding molecule, wherein the four antigen binding domains capable of specific binding to OX40 are Fab fragments and each two thereof are fused to each other at the heavy chain, optionally via a peptide linker. In a particular aspect, the antigen binding molecule comprises two heavy chains comprising each a VHCH1-peptide linker-VHCH1 fragment. In a particular aspect, the peptide linker has the amino acid sequence of SEQ ID NO:68.

In one aspect, the bispecific antigen binding molecule consists of (aa) a first Fab fragment capable of specific binding to OX40, (ab) a second Fab fragment capable of specific binding to OX40, (ac) a third Fab fragment capable of specific binding to OX40, (ad) a fourth Fab fragment capable of specific binding to OX40, (b) a cross-Fab fragment capable of specific binding to FAP fused to the C-terminus of one of subunits of the Fc region, and (c) the Fc region composed of a first and a second subunit capable of stable association, wherein the second Fab fragment (ab) is fused at the C-terminus of the VH-CH1 chain to the N-terminus of the VH-CH1 chain of the first Fab fragment (aa), which is in turn fused at its C-terminus to the N-terminus of the first subunit, and the fourth Fab fragment (ad) is fused at the C-terminus of the VH-CH1 chain to the N-terminus of the VH-CH1 chain of the third Fab fragment (ac), which is in turn fused at its C-terminus to the N-terminus of the second subunit.

In one aspect, provided is antigen binding molecule consisting of (a) four light chains, each light chain comprising a VL and CL domain of a Fab fragment capable of specific binding to OX40, (b) two heavy chains, wherein each of the heavy chain comprises a VH-CH1 domain of a Fab fragment capable of specific binding to OX40 fused to the N-terminus of a VH-CH1 domain of a second Fab fragment capable of specific binding to OX40, and a Fc region subunit, and (c) a cross-fab fragment capable of specific binding to FAP, wherein the VH-CL domain is connected via a peptide linker to the C-terminus of one of the heavy chains.

In one aspect, provided is a bispecific antigen binding molecule comprising (a) four light chains, each comprising an amino acid sequence that is at least about 90%, 95%, 96%, 97%, 98%, 99% or 100% identical to the sequence of SEQ ID NO:87, one light chain comprising an amino acid sequence that is at least about 90%, 95%, 96%, 97%, 98%, 99% or 100% identical to the sequence of SEQ ID NO:88, a first heavy chain comprising an amino acid sequence that is at least about 90%, 95%, 96%, 97%, 98%, 99% or 100% identical to the sequence of SEQ ID NO:86, and a second heavy chain comprising an amino acid sequence that is at least about 90%, 95%, 96%, 97%, 98%, 99% or 100% identical to the sequence of SEQ ID NO:89, (b) four light chains, each comprising an amino acid sequence that is at least about 90%, 95%, 96%, 97%, 98%, 99% or 100% identical to the sequence of SEQ ID NO:87, one light chain comprising an amino acid sequence that is at least about 90%, 95%, 96%, 97%, 98%, 99% or 100% identical to the sequence of SEQ ID NO:94, a first heavy chain comprising an amino acid sequence that is at least about 90%, 95%, 96%, 97%, 98%, 99% or 100% identical to the sequence of SEQ ID NO:86, and a second heavy chain comprising an amino acid sequence that is at least about 90%, 95%, 96%, 97%, 98%, 99% or 100% identical to the sequence of SEQ ID NO:89, (c) four light chains, each comprising an amino acid sequence that is at least about 90%, 95%, 96%, 97%, 98%, 99% or 100% identical to the sequence of SEQ ID NO:87, one light chain comprising an amino acid sequence that is at least about 90%, 95%, 96%, 97%, 98%, 99% or 100% identical to the sequence of SEQ ID NO:96, a first heavy chain comprising an amino acid sequence that is at least about 90%, 95%, 96%, 97%, 98%, 99% or 100% identical to the sequence of SEQ ID NO:86, and a second heavy chain comprising an amino acid sequence that is at least about 90%, 95%, 96%, 97%, 98%, 99% or 100% identical to the sequence of SEQ ID NO:89. In one aspect, provided is a bispecific antigen binding molecule comprising (a) four light chains, each comprising the amino acid sequence of SEQ ID NO:87, one light chain comprising the amino acid sequence of SEQ ID NO:88, a first heavy chain comprising the amino acid sequence of SEQ ID NO:86, and a second heavy chain comprising the amino acid sequence of SEQ ID NO:89, (b) four light chains, each comprising the amino acid sequence of SEQ ID NO:87, one light chain comprising the amino acid sequence of SEQ ID NO:94, a first heavy chain comprising the amino acid sequence of SEQ ID NO:86, and a second heavy chain comprising the amino acid sequence of SEQ ID NO:89, or (c) four light chains, each comprising the amino acid sequence of SEQ ID NO:87, one light chain comprising the amino acid sequence of SEQ ID NO:96, a first heavy chain comprising the amino acid sequence of SEQ ID NO:86, and a second heavy chain comprising the amino acid sequence of SEQ ID NO:89.

In another aspect, provided is a bispecific antigen binding molecule comprising (a) four light chains, each comprising an amino acid sequence that is at least about 90%, 95%, 96%, 97%, 98%, 99% or 100% identical to the sequence of SEQ ID NO:93, one light chain comprising an amino acid sequence that is at least about 90%, 95%, 96%, 97%, 98%, 99% or 100% identical to the sequence of SEQ ID NO:88, a first heavy chain comprising an amino acid sequence that is at least about 90%, 95%, 96%, 97%, 98%, 99% or 100% identical to the sequence of SEQ ID NO:92, and a second heavy chain comprising an amino acid sequence that is at least about 90%, 95%, 96%, 97%, 98%, 99% or 100% identical to the sequence of SEQ ID NO:95, (b) four light chains, each comprising an amino acid sequence that is at least about 90%, 95%, 96%, 97%, 98%, 99% or 100% identical to the sequence of SEQ ID NO:93, one light chain comprising an amino acid sequence that is at least about 90%, 95%, 96%, 97%, 98%, 99% or 100% identical to the sequence of SEQ ID NO:94, a first heavy chain comprising an amino acid sequence that is at least about 90%, 95%, 96%, 97%, 98%, 99% or 100% identical to the sequence of SEQ ID NO:92, and a second heavy chain comprising an amino acid sequence that is at least about 90%, 95%, 96%, 97%, 98%, 99% or 100% identical to the sequence of SEQ ID NO:95, or
(c) four light chains, each comprising an amino acid sequence that is at least about 90%, 95%, 96%, 97%, 98%, 99% or 100% identical to the sequence of SEQ ID NO:93, one light chain comprising an amino acid sequence that is at least about 90%, 95%, 96%, 97%, 98%, 99% or 100% identical to the sequence of SEQ ID NO:96, a first heavy chain comprising an amino acid sequence that is at least about 90%, 95%, 96%, 97%, 98%, 99% or 100% identical to the sequence of SEQ ID NO:92, and a second heavy chain comprising an amino acid sequence that is at least about 90%, 95%, 96%, 97%, 98%, 99% or 100% identical to the sequence of SEQ ID NO:95. In one aspect, provided is a bispecific antigen binding molecule comprising (a) four light chains, each comprising the amino acid sequence of SEQ ID NO:93, one light chain comprising the amino acid sequence of SEQ ID NO:88, a first heavy chain comprising the amino acid sequence of SEQ ID NO:92, and a second heavy chain comprising the amino acid sequence of SEQ ID NO:95, (b) four light chains, each comprising the amino acid sequence of SEQ ID NO:93, one light chain comprising the amino acid sequence of SEQ ID NO:94, a first heavy chain comprising the amino acid sequence of SEQ ID NO:92, and a second heavy chain comprising the amino acid sequence of SEQ ID NO:95, or (c) four light chains, each comprising the amino acid sequence of SEQ ID NO:93, one light chain comprising the amino acid sequence of SEQ ID NO:96, a first heavy chain comprising the amino acid sequence of SEQ ID NO:92, and a second heavy chain comprising the amino acid sequence of SEQ ID NO:95.

In a further aspect, provided is a bispecific antigen binding molecule comprising
(a) four light chains, each comprising an amino acid sequence that is at least about 90%, 95%, 96%, 97%, 98%, 99% or 100% identical to the sequence of SEQ ID NO:87, one light chain comprising an amino acid sequence that is at least about 90%, 95%, 96%, 97%, 98%, 99% or 100% identical to the sequence of SEQ ID NO:88, a first heavy chain comprising an amino acid sequence that is at least about 90%, 95%, 96%, 97%, 98%, 99% or 100% identical to the sequence of SEQ ID NO:107, and a second heavy chain comprising an amino acid sequence that is at least about 90%, 95%, 96%, 97%, 98%, 99% or 100% identical to the sequence of SEQ ID NO:108,
(b) four light chains, each comprising an amino acid sequence that is at least about 90%, 95%, 96%, 97%, 98%, 99% or 100% identical to the sequence of SEQ ID NO:87, one light chain comprising an amino acid sequence that is at least about 90%, 95%, 96%, 97%, 98%, 99% or 100% identical to the sequence of SEQ ID NO:94, a first heavy chain comprising an amino acid sequence that is at least about 90%, 95%, 96%, 97%, 98%, 99% or 100% identical to the sequence of SEQ ID NO:107, and a second heavy chain comprising an amino acid sequence that is at least about 90%, 95%, 96%, 97%, 98%, 99% or 100% identical to the sequence of SEQ ID NO:108, or
(c) four light chains, each comprising an amino acid sequence that is at least about 90%, 95%, 96%, 97%, 98%, 99% or 100% identical to the sequence of SEQ ID NO:87, one light chain comprising an amino acid sequence that is at least about 90%, 95%, 96%, 97%, 98%, 99% or 100% identical to the sequence of SEQ ID NO:96, a first heavy chain comprising an amino acid sequence that is at least about 90%, 95%, 96%, 97%, 98%, 99% or 100% identical to the sequence of SEQ ID NO:107, and a second heavy chain comprising an amino acid sequence that is at least about 90%, 95%, 96%, 97%, 98%, 99% or 100% identical to the sequence of SEQ ID NO:108. In a further aspect, provided is a bispecific antigen binding molecule comprising (a) four light chains, each comprising the amino acid sequence of SEQ ID NO:87, one light chain comprising the amino acid sequence of SEQ ID NO:88, a first heavy chain comprising the amino acid sequence of SEQ ID NO:107, and a second heavy chain comprising the amino acid sequence of SEQ ID NO:108, or (b) four light chains, each comprising the amino acid sequence of SEQ ID NO:87, one light chain comprising the amino acid sequence of SEQ ID NO:94, a first heavy chain comprising the amino acid sequence of SEQ ID NO:107, and a second heavy chain comprising the amino acid sequence of SEQ ID NO:108, or (c) four light chains, each comprising the amino acid sequence of SEQ ID NO:87, one light chain comprising the amino acid sequence of SEQ ID NO:96, a first heavy chain comprising the amino acid sequence of SEQ ID NO:107, and a second heavy chain comprising the amino acid sequence of SEQ ID NO:108.

In a further aspect, provided is a bispecific antigen binding molecule comprising
(a) four light chains, each comprising an amino acid sequence that is at least about 90%, 95%, 96%, 97%, 98%, 99% or 100% identical to the sequence of SEQ ID NO:87, one light chain comprising an amino acid sequence that is at least about 90%, 95%, 96%, 97%, 98%, 99% or 100% identical to the sequence of SEQ ID NO:88, a first heavy chain comprising an amino acid sequence that is at least about 90%, 95%, 96%, 97%, 98%, 99% or 100% identical to the sequence of SEQ ID NO:109, and a second heavy chain comprising an amino acid sequence that is at least about 90%, 95%, 96%, 97%, 98%, 99% or 100% identical to the sequence of SEQ ID NO:110, or
(b) four light chains, each comprising an amino acid sequence that is at least about 90%, 95%, 96%, 97%, 98%, 99% or 100% identical to the sequence of SEQ ID NO:87, one light chain comprising an amino acid sequence that is at least about 90%, 95%, 96%, 97%, 98%, 99% or 100% identical to the sequence of SEQ ID NO:94, a first heavy chain comprising an amino acid sequence that is at least about 90%, 95%, 96%, 97%, 98%, 99% or 100% identical to the sequence of SEQ ID NO:109, and a second heavy chain comprising an amino acid sequence that is at least about 90%, 95%, 96%, 97%, 98%, 99% or 100% identical to the sequence of SEQ ID NO:110,
(c) four light chains, each comprising an amino acid sequence that is at least about 90%, 95%, 96%, 97%, 98%, 99% or 100% identical to the sequence of SEQ ID NO:87, one light chain comprising an amino acid sequence that is at least about 90%, 95%, 96%, 97%, 98%, 99% or 100% identical to the sequence of SEQ ID NO:96, a first heavy chain comprising an amino acid sequence that is at least about 90%, 95%, 96%, 97%, 98%, 99% or 100% identical to the sequence of SEQ ID NO:109, and a second heavy chain comprising an amino acid sequence that is at least about 90%, 95%, 96%, 97%, 98%, 99% or 100% identical to the sequence of SEQ ID NO:110. In one aspect, provided is a bispecific antigen binding molecule comprising (a) four light chains, each comprising the amino acid sequence of SEQ ID NO:87, one light chain comprising the amino acid sequence of SEQ ID NO:88, a first heavy chain comprising the amino acid sequence of SEQ ID NO:109, and a second heavy chain comprising the amino acid sequence of SEQ ID NO:110, or (b) four light chains, each comprising the amino acid sequence of SEQ ID NO:87, one light chain comprising the amino acid sequence of SEQ ID NO:94, a first heavy chain comprising the amino acid sequence of SEQ ID NO:109, and a second heavy chain comprising the amino acid sequence of SEQ ID NO:110, or (c) four light chains, each comprising the amino acid sequence of SEQ ID NO:87, one light chain comprising the amino acid sequence of SEQ ID NO:96, a first heavy chain comprising the amino acid sequence of SEQ ID NO:109, and a second heavy chain comprising the amino acid sequence of SEQ ID NO:110.

In a further aspect, provided is a bispecific antigen binding molecule comprising
(a) four light chains, each comprising an amino acid sequence that is at least about 90%, 95%, 96%, 97%, 98%, 99% or 100% identical to the sequence of SEQ ID NO:87, one light chain comprising an amino acid sequence that is at least about 90%, 95%, 96%, 97%, 98%, 99% or 100% identical to the sequence of SEQ ID NO:88, a first heavy chain comprising an amino acid sequence that is at least about 90%, 95%, 96%, 97%, 98%, 99% or 100% identical to the sequence of SEQ ID NO:111, and a second heavy chain comprising an amino acid sequence that is at least about 90%, 95%, 96%, 97%, 98%, 99% or 100% identical to the sequence of SEQ ID NO:112,
(b) four light chains, each comprising an amino acid sequence that is at least about 90%, 95%, 96%, 97%, 98%, 99% or 100% identical to the sequence of SEQ ID NO:87, one light chain comprising an amino acid sequence that is at least about 90%, 95%, 96%, 97%, 98%, 99% or 100% identical to the sequence of SEQ ID NO:94, a first heavy chain comprising an amino acid sequence that is at least about 90%, 95%, 96%, 97%, 98%, 99% or 100% identical to the sequence of SEQ ID NO:111, and a second heavy chain an amino acid sequence that is at least about 90%, 95%, 96%, 97%, 98%, 99% or 100% identical to the sequence of SEQ ID NO:112,
(c) four light chains, each comprising an amino acid sequence that is at least about 90%, 95%, 96%, 97%, 98%, 99% or 100% identical to the sequence of SEQ ID NO:87, one light chain comprising an amino acid sequence that is at least about 90%, 95%, 96%, 97%, 98%, 99% or 100% identical to the sequence of SEQ ID NO:96, a first heavy chain comprising an amino acid sequence that is at least about 90%, 95%, 96%, 97%, 98%, 99% or 100% identical to the sequence of SEQ ID NO:111, and a second heavy chain comprising an amino acid sequence that is at least about 90%, 95%, 96%, 97%, 98%, 99% or 100% identical to the sequence of SEQ ID NO:112. In a further aspect, provided is a bispecific antigen binding molecule comprising (a) four light chains, each comprising the amino acid sequence of SEQ ID NO:87, one light chain comprising the amino acid sequence of SEQ ID NO:88, a first heavy chain comprising the amino acid sequence of SEQ ID NO:111, and a second heavy chain comprising the amino acid sequence of SEQ ID NO:112, or (b) four light chains, each comprising the amino acid sequence of SEQ ID NO:87, one light chain comprising the amino acid sequence of SEQ ID NO:94, a first heavy chain comprising the amino acid sequence of SEQ ID NO:111, and a second heavy chain comprising the amino acid sequence of SEQ ID NO:112, or (c) four light chains, each comprising the amino acid sequence of SEQ ID NO:87, one light chain comprising the amino acid sequence of SEQ ID NO:96, a first heavy chain comprising the amino acid sequence of SEQ ID NO:111, and a second heavy chain comprising the amino acid sequence of SEQ ID NO:112.

Fc Domain Modifications Reducing Fc Receptor Binding and/or Effector Function

The bispecific antigen binding molecules of the invention further comprise a Fc domain composed of a first and a second subunit capable of stable association.

In certain aspects, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

The Fc domain confers favorable pharmacokinetic properties to the bispecific antibodies of the invention, including a long serum half-life which contributes to good accumulation in the target tissue and a favorable tissue-blood distribution ratio. At the same time it may, however, lead to undesirable targeting of the bispecific antibodies of the invention to cells expressing Fc receptors rather than to the preferred antigen-bearing cells. Accordingly, in particular embodiments the Fc domain of the bispecific antibodies of the invention exhibits reduced binding affinity to an Fc receptor and/or reduced effector function, as compared to a native IgG Fc domain, in particular an IgG1 Fc domain or an IgG4 Fc domain. More particularly, the Fc domain is an IgG1 Fc domain.

In one such aspect the Fc domain (or the bispecific antigen binding molecule comprising said Fc domain) exhibits less than 50%, preferably less than 20%, more preferably less than 10% and most preferably less than 5% of the binding affinity to an Fc receptor, as compared to a native IgG1 Fc domain (or the bispecific antigen binding molecule of the invention comprising a native IgG1 Fc domain), and/or less than 50%, preferably less than 20%, more preferably less than 10% and most preferably less than 5% of the effector function, as compared to a native IgG1 Fc domain (or the bispecific antigen binding molecule of the invention comprising a native IgG1 Fc domain). In one aspect, the Fc domain (or the bispecific antigen binding molecule of the invention comprising said Fc domain) does not substantially bind to an Fc receptor and/or induce effector function. In a particular aspect the Fc receptor is an Fcγ receptor. In one aspect, the Fc receptor is a human Fc receptor. In one aspect, the Fc receptor is an activating Fc receptor. In a specific aspect, the Fc receptor is an activating human Fcγ receptor, more specifically human FcγRIIIa, FcγRI or FcγRIIa, most specifically human FcγRIIIa. In one aspect, the Fc receptor is an inhibitory Fc receptor. In a specific aspect, the Fc receptor is an inhibitory human Fcγ receptor, more specifically human FcγRIIB. In one aspect the effector function is one or more of CDC, ADCC, ADCP, and cytokine secretion. In a particular aspect, the effector function is ADCC. In one aspect, the Fc domain domain exhibits substantially similar binding affinity to neonatal Fc receptor (FcRn), as compared to a native IgG1 Fc domain. Substantially similar binding to FcRn is achieved when the Fc domain (or the the bispecific antigen binding molecule of the invention comprising said Fc domain) exhibits greater than about 70%, particularly greater than about 80%, more particularly greater than about 90% of the binding affinity of a native IgG1 Fc domain (or the the bispecific antigen binding molecule of the invention comprising a native IgG1 Fc domain) to FcRn.

In a particular aspect, the Fc domain is engineered to have reduced binding affinity to an Fc receptor and/or reduced effector function, as compared to a non-engineered Fc domain. In a particular aspect, the Fc domain of the bispecific antigen binding molecule of the invention comprises one or more amino acid mutation that reduces the binding affinity of the Fc domain to an Fc receptor and/or effector function. Typically, the same one or more amino acid mutation is present in each of the two subunits of the Fc domain. In one aspect, the amino acid mutation reduces the binding affinity of the Fc domain to an Fc receptor. In another aspect, the amino acid mutation reduces the binding affinity of the Fc domain to an Fc receptor by at least 2-fold, at least 5-fold, or at least 10-fold. In one aspect, the bispecific antigen binding molecule of the invention comprising an engineered Fc domain exhibits less than 20%, particularly less than 10%, more particularly less than 5% of the binding affinity to an Fc receptor as compared to bispecific antibodies of the invention comprising a non-engineered Fc domain. In a particular aspect, the Fc receptor is an Fcγ receptor. In other aspects, the Fc receptor is a human Fc receptor. In one aspect, the Fc receptor is an inhibitory Fc receptor. In a specific aspect, the Fc receptor is an inhibitory human Fcγ receptor, more specifically human FcγRIIB. In some aspects the Fc receptor is an activating Fc receptor. In a specific aspect, the Fc receptor is an activating human Fcγ receptor, more specifically human FcγRIIIa, FcγRI or FcγRIIa, most specifically human FcγRIIIa. Preferably, binding to each of these receptors is reduced. In some aspects, binding affinity to a complement component, specifically binding affinity to C1q, is also reduced. In one aspect, binding affinity to neonatal Fc receptor (FcRn) is not reduced. Substantially similar binding to FcRn, i.e. preservation of the binding affinity of the Fc domain to said receptor, is achieved when the Fc domain (or the bispecific antigen binding molecule of the invention comprising said Fc domain) exhibits greater than about 70% of the binding affinity of a non-engineered form of the Fc domain (or the bispecific antigen binding molecule of the invention comprising said non-engineered form of the Fc domain) to FcRn. The Fc domain, or the the bispecific antigen binding molecule of the invention comprising said Fc domain, may exhibit greater than about 80% and even greater than about 90% of such affinity. In certain embodiments the Fc domain of the bispecific antigen binding molecule of the invention is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced dendritic cell maturation, or reduced T cell priming.

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581). Certain antibody variants with improved or diminished binding to FcRs are described. (e.g. U.S. Pat. No. 6,737,056; WO 2004/056312, and Shields, R. L. et al., J. Biol. Chem. 276 (2001) 6591-6604).

In one aspect, the Fc domain comprises an amino acid substitution at a position of E233, L234, L235, N297, P331 and P329. In some aspects, the Fc domain comprises the amino acid substitutions L234A and L235A ("LALA"). In one such embodiment, the Fc domain is an IgG1 Fc domain, particularly a human IgG1 Fc domain. In one aspect, the Fc domain comprises an amino acid substitution at position P329. In a more specific aspect, the amino acid substitution is P329A or P329G, particularly P329G. In one embodiment the Fc domain comprises an amino acid substitution at position P329 and a further amino acid substitution selected from the group consisting of E233P, L234A, L235A, L235E, N297A, N297D or P331S. In more particular embodiments the Fc domain comprises the amino acid mutations L234A, L235A and P329G ("P329G LALA"). The "P329G LALA" combination of amino acid substitutions almost completely abolishes Fcγ receptor binding of a human IgG1 Fc domain, as described in PCT Patent Application No. WO 2012/130831 A1. Said document also describes methods of preparing such mutant Fc domains and methods for determining its properties such as Fc receptor binding or effector functions. Such antibody is an IgG1 with mutations L234A and L235A or with mutations L234A, L235A and P329G (numbering according to EU index of Kabat et al, Kabat et al., Sequences of Proteins of Immunological Interest, 5th Ed. Public Health Service, National Institutes of Health, Bethesda, Md., 1991).

In one aspect, the Fc domain is an IgG4 Fc domain. In a more specific embodiment, the Fc domain is an IgG4 Fc domain comprising an amino acid substitution at position S228 (Kabat numbering), particularly the amino acid substitution S228P. In a more specific embodiment, the Fc domain is an IgG4 Fc domain comprising amino acid substitutions L235E and S228P and P329G. This amino acid substitution reduces in vivo Fab arm exchange of IgG4 antibodies (see Stubenrauch et al., Drug Metabolism and Disposition 38, 84-91 (2010)).

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan, A. R. and Winter, G., Nature 322 (1988) 738-740; U.S. Pat. Nos. 5,648,260; 5,624,821; and WO 94/29351 concerning other examples of Fc region variants.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. A suitable such binding assay is described herein. Alternatively, binding affinity of Fc domains or cell activating bispecific antigen binding molecules comprising an Fc domain for Fc receptors may be evaluated using cell lines known to express particular Fc receptors, such as human NK cells expressing FcγIIIa receptor. Effector function of an Fc domain, or bispecific antigen binding molecules of the invention comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in an animal model such as that disclosed in Clynes et al., Proc Natl Acad Sci USA 95, 652-656 (1998).

The following section describes preferred aspects of the bispecific antigen binding molecules of the invention comprising Fc domain modifications reducing Fc receptor binding and/or effector function. In one aspect, the invention relates to the bispecific antigen binding molecule (a) at least two antigen binding domains capable of specific binding to OX40, (b) an antigen binding domain capable of specific binding to FAP, and (c) a Fc domain composed of a first and a second subunit capable of stable association, wherein the Fc domain comprises one or more amino acid substitution that reduces the binding affinity of the antibody to an Fc receptor, in particular towards Fcγ receptor. In another aspect, the invention relates to the bispecific antigen binding molecule comprising (a) at least two antigen binding domain capable of specific binding to OX40, (b) an antigen binding domain capable of specific binding to FAP, and (c) a Fc domain composed of a first and a second subunit capable of stable association, wherein the Fc domain comprises one or more amino acid substitution that reduces effector function. In particular aspect, the Fc domain is of human IgG1 subclass with the amino acid mutations L234A, L235A and P329G (numbering according to Kabat EU index).

Fc Domain Modifications Promoting Heterodimerization

The bispecific antigen binding molecules of the invention comprise different antigen-binding sites, fused to one or the other of the two subunits of the Fc domain, thus the two subunits of the Fc domain may be comprised in two non-identical polypeptide chains. Recombinant co-expression of these polypeptides and subsequent dimerization leads to several possible combinations of the two polypeptides. To improve the yield and purity of the bispecific antigen binding molecules of the invention in recombinant production, it will thus be advantageous to introduce in the Fc domain of the bispecific antigen binding molecules of the invention a modification promoting the association of the desired polypeptides.

Accordingly, in particular aspects the invention relates to the bispecific antigen binding molecule comprising (a) at least two antigen binding domains capable of specific binding to OX40, (b) an antigen binding domain capable of specific binding to FAP, and (c) a Fc domain composed of a first and a second subunit capable of stable association, wherein the Fc domain comprises a modification promoting the association of the first and second subunit of the Fc domain. The site of most extensive protein-protein interaction between the two subunits of a human IgG Fc domain is in the CH3 domain of the Fc domain. Thus, in one aspect said modification is in the CH3 domain of the Fc domain.

In a specific aspect said modification is a so-called "knob-into-hole" modification, comprising a "knob" modification in one of the two subunits of the Fc domain and a "hole" modification in the other one of the two subunits of the Fc domain. Thus, the invention relates to the bispecific antigen binding molecule comprising (a) at least two antigen binding domains capable of specific binding to OX40, (b) an antigen binding domain capable of specific binding to FAP, and (c) a Fc domain composed of a first and a second subunit capable of stable association, wherein the first subunit of the Fc domain comprises knobs and the second subunit of the Fc domain comprises holes according to the knobs into holes method. In a particular aspect, the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in one aspect, in the CH3 domain of the first subunit of the Fc domain of the bispecific antigen binding molecules of the invention an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable. The protuberance and cavity can be made by altering the nucleic acid encoding the polypeptides, e.g. by site-specific mutagenesis, or by peptide synthesis. In a specific aspect, in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V). In one aspect, in the second subunit of the Fc domain additionally the threonine residue at position 366 is replaced with a serine residue (T366S) and the leucine residue at position 368 is replaced with an alanine residue (L368A).

In yet a further aspect, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C). Introduction of these two cysteine residues results in formation of a disulfide bridge between the two subunits of the Fc domain, further stabilizing the dimer (Carter (2001), J Immunol Methods 248, 7-15). In a particular aspect, the first subunit of the Fc domain comprises the amino acid substitutions S354C and T366W (EU numbering) and the second subunit of the Fc domain comprises the amino acid substitutions Y349C, T366S and Y407V (numbering according to Kabat EU index).

In an alternative aspect, a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable.

The C-terminus of the heavy chain of the bispecific antibody as reported herein can be a complete C-terminus ending with the amino acid residues PGK. The C-terminus of the heavy chain can be a shortened C-terminus in which one or two of the C terminal amino acid residues have been removed. In one preferred aspect, the C-terminus of the heavy chain is a shortened C-terminus ending PG. In one aspect of all aspects as reported herein, a bispecific antibody comprising a heavy chain including a C-terminal CH3 domain as specified herein, comprises the C-terminal glycine-lysine dipeptide (G446 and K447, numbering according to Kabat EU index).

In one aspect of all aspects as reported herein, a bispecific antibody comprising a heavy chain including a C-terminal CH3 domain, as specified herein, comprises a C-terminal glycine residue (G446, numbering according to Kabat EU index).

Modifications in the Fab Domains

In one aspect, the invention relates to a bispecific antigen binding molecule comprising (a) at least two Fab fragments capable of specific binding to OX40, (b) a Fab fragment capable of specific binding to FAP, and (c) a Fc domain composed of a first and a second subunit capable of stable association, wherein in one of the Fab fragments either the variable domains VH and VL or the constant domains CH1 and CL are exchanged. The bispecific antibodies are prepared according to the Crossmab technology.

Multispecific antibodies with a domain replacement/exchange in one binding arm (CrossMab VH-VL or CrossMab CH-CL) are described in detail in WO2009/080252 and Schaefer, W. et al, PNAS, 108 (2011) 11187-1191. They clearly reduce the byproducts caused by the mismatch of a light chain against a first antigen with the wrong heavy chain against the second antigen (compared to approaches without such domain exchange).

In one aspect, the invention relates to a bispecific antigen binding molecule comprising (a) at least two Fab fragments capable of specific binding to OX40, (b) a Fab fragment capable of specific binding to FAP, and (c) a Fc domain composed of a first and a second subunit capable of stable association, wherein in one of the Fab fragments the constant domains CL and CH1 are replaced by each other so that the CH1 domain is part of the light chain and the CL domain is part of the heavy chain. More particularly, in the second Fab fragment capable of specific binding to a target cell antigen the constant domains CL and CH1 are replaced by each other so that the CH1 domain is part of the light chain and the CL domain is part of the heavy chain.

In a particular aspect, the invention relates a bispecific antigen binding molecule comprising (a) at least two Fab fragments capable of specific binding to OX40, (b) a Fab fragment capable of specific binding to FAP, wherein in the Fab fragment capable of specific binding to FAP the constant domains CL and CH1 are replaced by each other so that the CH1 domain is part of the light chain and the CL (Ckappa) domain is part of the heavy chain.

Thus, in one aspect, the invention comprises a bispecific antigen binding molecule, comprising (a) two light chains and two heavy chains of an antibody comprising two Fab fragments capable of specific binding to OX40 and the Fc region, and (b) a crossFab fragment capable of specific binding to FAP fused to the C-terminus of one of subunits of the Fc region.

In another aspect, and to further improve correct pairing, the bispecific antigen binding molecule comprising (a) at least two Fab fragments capable of specific binding to OX40, (b) a crossFab fragment capable of specific binding to FAP, and (c) a Fc domain composed of a first and a second subunit capable of stable association, can contain different charged amino acid substitutions (so-called "charged residues"). These modifications are introduced in the crossed or non-crossed CH1 and CL domains. In a particular aspect, the invention relates to a bispecific antigen binding molecule, wherein in one of CL domains the amino acid at position 123 (EU numbering) has been replaced by arginine (R) and/or wherein the amino acid at position 124 (EU numbering) has been substituted by lysine (K) and wherein in one of the CH1 domains the amino acids at position 147 (EU numbering) and/or at position 213 (EU numbering) have been substituted by glutamic acid (E).

Exemplary Antibodies of the Invention

In one aspect, the invention provides new antibodies and antibody fragments that specifically bind to FAP. These antibodies bind to a different epitope than the known FAP antibodies 4B9 or 28H1 that make them especially suitable for the incorporation into bispecific antigen binding molecules that can be used in combination with other FAP-targeted molecules. The new antibodies are further characterized in that they are producable in high amounts and with high titers, that they show high thermal stability (as measured by the aggregation temperature $T_{agg}$), that they are supposed to possess excellent PK properties and that they bind with high affinity to human FAP as measured by Biacore assay.

In one aspect, provided is an antibody that specifically binds to FAP (clone 212), wherein said antibody comprises a heavy chain variable region ($V_H$FAP) comprising (i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8.

In one aspect, provided is a humanized antibody that specifically binds to FAP, wherein said antibody comprises a heavy chain variable region ($V_H$FAP) comprising (i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8.

In another aspect, provided is an antibody that competes for binding with an antibody that specifically binds to FAP, wherein said antibody comprises any of the heavy chain variable regions ($V_H$FAP) comprising an amino acid sequence selected from the group consisting of SEQ ID NO:15, SEQ ID NO:16, SEQ ID NO:17, SEQ ID NO:18. SEQ ID NO:19 and SEQ ID NO:20, and any of the light chain variable regions ($V_L$FAP) comprising an amino acid sequence selected from the group consisting of SEQ ID NO:21, SEQ ID NO:22, SEQ ID NO:23, SEQ ID NO:24, SEQ ID NO:25 and SEQ ID NO:26.

In one aspect, provided is an antibody that competes for binding with an antibody that specifically binds to FAP, wherein said antibody comprises a heavy chain variable region VH comprising an amino acid sequence of SEQ ID NO:15 and a light chain variable region VL comprising an amino acid sequence of SEQ ID NO:21.

In a further aspect, provided is an antibody that specifically binds to FAP, wherein said antibody comprises
(a) a heavy chain variable region ($V_H$FAP) comprising the amino acid sequence of SEQ ID NO:15 and a light chain variable region ($V_L$FAP) comprising the amino acid sequence of SEQ ID NO:21,
(b) a heavy chain variable region ($V_H$FAP) comprising the amino acid sequence of SEQ ID NO:16 and a light chain variable region ($V_L$FAP) comprising the amino acid sequence of SEQ ID NO:21,
(c) a heavy chain variable region ($V_H$FAP) comprising the amino acid sequence of SEQ ID NO:16 and a light chain variable region ($V_L$FAP) comprising the amino acid sequence of SEQ ID NO:22, or
(d) a heavy chain variable region ($V_H$FAP) comprising the amino acid sequence of SEQ ID NO:19 and a light chain variable region ($V_L$FAP) comprising the amino acid sequence of SEQ ID NO:25.

In a further aspect, provided is an antibody that specifically binds to FAP comprising a heavy chain variable region ($V_H$FAP) comprising the amino acid sequence of SEQ ID NO:15 and a light chain variable region ($V_L$FAP) comprising the amino acid sequence of SEQ ID NO:21.

In another aspect, the invention provides new antibodies and antibody fragments that specifically bind to OX40. These antibodies are variants of OX40 antibody 49B4 and have less positive charge patches compared to 49B4. These new antibodies are are supposed to possess improved PK properties compared to 49B4 and that they bind with high affinity to human OX40 as measured by Biacore assay.

Thus, provided is a humanized antibody that specifically binds to OX40, wherein said antibody comprises
(a) a heavy chain variable region ($V_H$OX40) comprising the amino acid sequence of SEQ ID NO:59 and a light chain variable region ($V_L$OX40) comprising the amino acid sequence of SEQ ID NO:34,
(b) a heavy chain variable region ($V_H$OX40) comprising the amino acid sequence of SEQ ID NO:60 and a light chain variable region ($V_L$OX40) comprising the amino acid sequence of SEQ ID NO:34,
(c) a heavy chain variable region ($V_H$OX40) comprising the amino acid sequence of SEQ ID NO:61 and a light chain variable region ($V_L$OX40) comprising the amino acid sequence of SEQ ID NO:34.

Polynucleotides

The invention further provides isolated nucleic acid encoding a bispecific antigen binding molecule as described herein or a fragment thereof or isolated nucleic acid encoding an antibody as described herein.

The isolated polynucleotides encoding bispecific antigen binding molecules of the invention may be expressed as a single polynucleotide that encodes the entire antigen binding molecule or as multiple (e.g., two or more) polynucleotides that are co-expressed. Polypeptides encoded by polynucleotides that are co-expressed may associate through, e.g., disulfide bonds or other means to form a functional antigen binding molecule. For example, the light chain portion of an immunoglobulin may be encoded by a separate polynucleotide from the heavy chain portion of the immunoglobulin. When co-expressed, the heavy chain polypeptides will associate with the light chain polypeptides to form the immunoglobulin.

In some aspects, the isolated polynucleotide encodes a polypeptide comprised in the bispecific molecule according to the invention as described herein.

In one aspect, the present invention is directed to an isolated polynucleotide encoding a bispecific antigen binding molecule, comprising (a) at least two antigen binding domains capable of specific binding to OX40, (b) an antigen binding domain capable of specific binding to a FAP comprising a heavy chain variable region ($V_H$FAP) comprising (i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8, and (c) a Fc domain composed of a first and a second subunit capable of stable association.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

Recombinant Methods

Bispecific antigen binding molecules of the invention may be obtained, for example, by recombinant production. For recombinant production one or more polynucleotide encoding the bispecific antigen binding molecule or polypeptide fragments thereof are provided. The one or more polynucleotide encoding the bispecific antigen binding molecule are isolated and inserted into one or more vectors for further cloning and/or expression in a host cell. Such polynucleotide may be readily isolated and sequenced using conventional procedures. In one aspect of the invention, a vector, preferably an expression vector, comprising one or more of the polynucleotides of the invention is provided. Methods which are well known to those skilled in the art can be used to construct expression vectors containing the coding sequence of the bispecific antigen binding molecule (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y. (1989). The expression vector can be part of a plasmid, virus, or may be a nucleic acid fragment. The expression vector includes an expression cassette into which the polynucleotide encoding the bispecific antigen binding molecule or polypeptide fragments thereof (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the bispecific antigen binding molecule of the invention or polypeptide fragments thereof, or variants or derivatives thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription.

Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit α-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the bispecific antigen binding molecule or polypeptide fragments thereof is desired, DNA encoding a signal sequence may be placed upstream of the nucleic acid encoding the bispecific antigen binding molecule of the invention or polypeptide fragments thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse (3-glucuronidase.

DNA encoding a short protein sequence that could be used to facilitate later purification (e.g. a histidine tag) or assist in labeling the fusion protein may be included within or at the ends of the polynucleotide encoding a bispecific antigen binding molecule of the invention or polypeptide fragments thereof.

In a further aspect of the invention, a host cell comprising one or more polynucleotides of the invention is provided. In certain aspects, a host cell comprising one or more vectors of the invention is provided. The polynucleotides and vectors may incorporate any of the features, singly or in combination, described herein in relation to polynucleotides and vectors, respectively. In one aspect, a host cell comprises (e.g. has been transformed or transfected with) a vector comprising a polynucleotide that encodes (part of) a bispecific antigen binding molecule of the invention of the invention. As used herein, the term "host cell" refers to any kind of cellular system which can be engineered to generate the fusion proteins of the invention or fragments thereof. Host cells suitable for replicating and for supporting expression of antigen binding molecules are well known in the art. Such cells may be transfected or transduced as appropriate with the particular expression vector and large quantities of vector containing cells can be grown for seeding large scale fermenters to obtain sufficient quantities of the antigen binding molecule for clinical applications. Suitable host cells include prokaryotic microorganisms, such as E. coli, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gemgross, Nat Biotech 22, 1409-1414 (2004), and Li et al., Nat Biotech 24, 210-215 (2006).

Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040,498, 6,420,548, 7,125,978, and 6,417,429 (describing PLANTIBODIES' technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr– CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell). Standard technologies are known in the art to express foreign genes in these systems. Cells expressing a polypeptide comprising either the heavy or the light chain of an immunoglobulin, may be engineered so as to also express the other of the immunoglobulin chains such that the expressed product is an immunoglobulin that has both a heavy and a light chain.

In one aspect, a method of producing a bispecific antigen binding molecule of the invention or polypeptide fragments thereof is provided, wherein the method comprises culturing a host cell comprising polynucleotides encoding the bispecific antigen binding molecule of the invention or polypeptide fragments thereof, as provided herein, under conditions suitable for expression of the bispecific antigen binding molecule of the invention or polypeptide fragments thereof, and recovering the bispecific antigen binding molecule of the invention or polypeptide fragments thereof from the host cell (or host cell culture medium).

Bispecific molecules of the invention prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the bispecific antigen binding molecule binds. For example, for affinity chromatography purification of fusion proteins of the invention, a matrix with protein A or protein G may be used. Sequential Protein A or G affinity chromatography and size exclusion chromatography can be used to isolate an antigen binding molecule essentially as described in the examples. The purity of the bispecific antigen binding molecule or fragments thereof can be determined by any of a variety of well-known analytical methods including gel electrophoresis, high pressure liquid chromatography, and the like. For example, the bispecific antigen binding molecules expressed as described in the Examples were shown to be intact and properly assembled as demonstrated by reducing and non-reducing SDS-PAGE.

Assays

The antigen binding molecules provided herein may be characterized for their binding properties and/or biological activity by various assays known in the art. In particular, they are characterized by the assays described in more detail in the examples.

1. Binding Assay

Binding of the bispecific antigen binding molecule provided herein to the corresponding target expressing cells may be evaluated for example by using a murine fibroblast cell line expressing human Fibroblast Activation Protein (FAP) and flow cytometry (FACS) analysis. Binding of the bispecific antigen binding molecules provided herein to OX40 may be determined by using activated human PBMCs as described in Example 3.1.

2. Activity Assays

Bispecific antigen binding molecules of the invention are tested for biological activity. Biological activity may include efficacy and specificity of the bispecific antigen binding molecules. Efficacy and specificity are demonstrated by assays showing agonistic signaling through the OX40 receptor upon binding of the target antigen. Furthermore, the stimulation of OX40 signaling is measures through induced NFκB activation in human OX40 positive NFκB reporter cells as described in Example 4.1.

Pharmaceutical Compositions, Formulations and Routes of Administration

In a further aspect, the invention provides pharmaceutical compositions comprising any of the bispecific antigen binding molecules provided herein, e.g., for use in any of the below therapeutic methods. In one aspect, a pharmaceutical composition comprises any of the bispecific antigen binding molecules provided herein and at least one pharmaceutically acceptable excipient. In another aspect, a pharmaceutical composition comprises any of the bispecific antigen binding molecules provided herein and at least one additional therapeutic agent, e.g., as described below.

Pharmaceutical compositions of the present invention comprise a therapeutically effective amount of one or more bispecific antigen binding molecules dissolved or dispersed in a pharmaceutically acceptable carrier. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one bispecific antigen binding molecule according to the invention and optionally an additional active ingredient will be known to those of skill in the art in light of the present disclosure, as exemplified by Remington's Pharmaceutical Sciences, 18th Ed. Mack Printing Company, 1990, incorporated herein by reference. In particular, the compositions are lyophilized formulations or aqueous solutions. As used herein, "pharmaceutically acceptable excipient" includes any and all solvents, buffers, dispersion media, coatings, surfactants, antioxidants, preservatives (e.g. antibacterial agents, antifungal agents), isotonic agents, salts, stabilizers and combinations thereof, as would be known to one of ordinary skill in the art.

Parenteral compositions include those designed for administration by injection, e.g. subcutaneous, intradermal, intra-lesional, intravenous, intra-arterial, intramuscular, intrathecal or intraperitoneal injection. For injection, the bispecific antigen binding molecules of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the bispecific antigen binding molecules may be in powder form for constitution with a suitable vehicle, e.g., sterile pyrogen-free water, before use. Sterile injectable solutions are prepared by incorporating the antigen binding molecules of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less than 0.5 ng/mg protein. Suitable pharmaceutically acceptable excipients include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

Exemplary pharmaceutically acceptable excipients herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

In addition to the compositions described previously, the antigen binding molecules may also be formulated as a depot preparation. Such long acting formulations may be administered by implantation (for example subcutaneously or intramuscularly) or by intramuscular injection.

Thus, for example, the fusion proteins may be formulated with suitable polymeric or hydrophobic materials (for example as emulsion in an acceptable oil) or ion exchange resins, or as sparingly soluble derivatives, for example, as a sparingly soluble salt.

Pharmaceutical compositions comprising the bispecific antigen binding molecules of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The bispecific antigen binding molecules may be formulated into a composition in a free acid or base, neutral or salt form. Pharmaceutically acceptable salts are salts that substantially retain the biological activity of the free acid or base. These include the acid addition salts, e.g. those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

The composition herein may also contain more than one active ingredients as necessary for the particular indication being treated, preferably those with complementary activities that do not adversely affect each other. Such active ingredients are suitably present in combination in amounts that are effective for the purpose intended.

The formulations to be used for in vivo administration are generally sterile. Sterility may be readily accomplished, e.g., by filtration through sterile filtration membranes.

Therapeutic Methods and Compositions

Any of the bispecific antigen binding molecules provided herein may be used in therapeutic methods. For use in therapeutic methods, bispecific antigen binding molecules of the invention can be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, bispecific antigen binding molecules of the invention for use as a medicament are provided.

In further aspects, bispecific antigen binding molecules of the invention for use (i) in inducing immune stimulation, (ii) in stimulating tumor-specific T cell response, (iii) in causing apoptosis of tumor cells, (iv) in the treatment of cancer, (v) in delaying progression of cancer, (vi) in prolonging the survival of a patient suffering from cancer, (vii) in the treatment of infections are provided. In a particular aspect, bispecific antigen binding molecules of the invention for use in treating a disease, in particular for use in the treatment of cancer, are provided.

In certain aspects, bispecific antigen binding molecules of the invention for use in a method of treatment are provided. In one aspect, the invention provides a bispecific antigen binding molecule as described herein for use in the treatment of a disease in an individual in need thereof. In certain aspects, the invention provides a bispecific antigen binding molecule for use in a method of treating an individual having a disease comprising administering to the individual a therapeutically effective amount of the bispecific antigen binding molecule. In certain aspects the disease to be treated is cancer. The subject, patient, or "individual" in need of treatment is typically a mammal, more specifically a human.

In one aspect, provided is a method for i) inducing immune stimulation, (ii) stimulating tumor-specific T cell response, (iii) causing apoptosis of tumor cells, (iv) treating of cancer, (v) delaying progression of cancer, (vi) prolonging the survival of a patient suffering from cancer, or (vii) treating of infections, wherein the method comprises administering a therapeutically effective amount of the bispecific antigen binding molecule of the invention to an individual in need thereof.

In a further aspect, the invention provides for the use of the bispecific antigen binding molecule of the invention in the manufacture or preparation of a medicament for the treatment of a disease in an individual in need thereof. In one aspect, the medicament is for use in a method of treating a disease comprising administering to an individual having the disease a therapeutically effective amount of the medicament. In certain aspects, the disease to be treated is a proliferative disorder, particularly cancer. Examples of cancers include, but are not limited to, bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other examples of cancer include carcinoma, lymphoma (e.g., Hodgkin's and non-Hodgkin's lymphoma), blastoma, sarcoma, and leukemia. Other cell proliferation disorders that can be treated using the bispecific antigen binding molecule or antibody of the invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of renal cell cancer, skin cancer, lung cancer, colorectal cancer, breast cancer, brain cancer, head and neck cancer. A skilled artisan readily recognizes that in many cases the the bispecific antigen binding molecule or antibody of the invention may not provide a cure but may provide a benefit. In some aspects, a physiological change having some benefit is also considered therapeutically beneficial. Thus, in some aspects, an amount of the bispecific antigen binding molecule or antibody of the invention that provides a physiological change is considered an "effective amount" or a "therapeutically effective amount".

For the prevention or treatment of disease, the appropriate dosage of a bispecific antigen binding molecule of the invention (when used alone or in combination with one or more other additional therapeutic agents) will depend on the type of disease to be treated, the route of administration, the body weight of the patient, the specific molecule, the severity and course of the disease, whether the bispecific antigen binding molecule of the invention is administered for preventive or therapeutic purposes, previous or concurrent therapeutic interventions, the patient's clinical history and response to the bispecific antigen binding molecule, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The bispecific antigen binding molecule of the invention is suitably administered to the patient at one time or over a series of treatments. Depending on the type and severity of the disease, about 1 μg/kg to 15 mg/kg (e.g. 0.1 mg/kg-10 mg/kg) of the bispecific antigen binding molecule can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the bispecific antigen binding molecule of the invention would be in the range from about 0.005 mg/kg to about 10 mg/kg. In other examples, a dose may also comprise from about 1 μg/kg body weight, about 5 μg/kg body weight, about 10 μg/kg body weight, about 50 μg/kg body weight, about 100 μg/kg body weight, about 200 μg/kg body weight, about 350 μg/kg body weight, about 500 μg/kg body weight, about 1 mg/kg body weight, about 5 mg/kg body weight, about 10 mg/kg body weight, about 50 mg/kg body weight, about 100 mg/kg body weight, about 200 mg/kg body weight, about 350 mg/kg body weight, about 500 mg/kg body weight, to about 1000 mg/kg body weight or more per administration, and any range derivable therein. In examples of a derivable range from the numbers listed herein, a range of about 0.1 mg/kg body weight to about 20 mg/kg body weight, about 5 μg/kg body weight to about 1 mg/kg body weight etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the fusion protein). In a particular aspect, the bispecific antigen binding molecule will be administered every three weeks. An initial higher loading dose, followed by one or more lower doses may be administered. However, other dosage regimens may be useful. The progress of this therapy is easily monitored by conventional techniques and assays.

The bispecific antigen binding molecule of the invention will generally be used in an amount effective to achieve the intended purpose. For use to treat or prevent a disease condition, the bispecific antigen binding molecule of the invention, or pharmaceutical compositions thereof, are administered or applied in a therapeutically effective amount. Determination of a therapeutically effective amount is well within the capabilities of those skilled in the art, especially in light of the detailed disclosure provided herein. For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the bispecific antigen binding molecule of the invention which are sufficient to maintain therapeutic effect. Usual patient dosages for administration by injection range from about 0.1 to 50 mg/kg/day, typically from about 0.1 to 1 mg/kg/day. Therapeutically effective plasma levels may be achieved by administering multiple doses each day. Levels in plasma may be measured, for example, by HPLC. In cases of local administration or selective uptake, the effective local concentration of the bispecific antigen binding molecule or antibody of the invention may not be related to plasma concentration. One skilled in the art will be able to optimize therapeutically effective local dosages without undue experimentation.

A therapeutically effective dose of the bispecific antigen binding molecule of the invention described herein will generally provide therapeutic benefit without causing substantial toxicity. Toxicity and therapeutic efficacy of a fusion protein can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Bispecific antigen binding molecules that exhibit large therapeutic indices are preferred. In one aspect, the bispecific antigen binding molecule or antibody of the invention exhibits a high therapeutic index. The data obtained from cell culture assays and animal studies can be used in formulating a range of dosages suitable for use in humans. The dosage lies preferably within a range of circulating concentrations that include the ED50 with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with fusion proteins of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The bispecific antigen binding molecule of the invention may be administered in combination with one or more other agents in therapy. For instance, the bispecific antigen binding molecule of the invention may be co-administered with at least one additional therapeutic agent. The term "therapeutic agent" encompasses any agent that can be administered for treating a symptom or disease in an individual in need of such treatment. Such additional therapeutic agent may comprise any active ingredients suitable for the particular indication being treated, preferably those with complementary activities that do not adversely affect each other. In certain aspects, an additional therapeutic agent is another anti-cancer agent, for example a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, or an antiangiogenic agent. In certain aspects, an additional therapeutic agent is an immunomodulatory agent, a cytostatic agent, an inhibitor of cell adhesion, a cytotoxic or cytostatic agent, an activator of cell apoptosis, or an agent that increases the sensitivity of cells to apoptotic inducers.

Thus, provided are bispecific antigen binding molecules of the invention or pharmaceutical compositions comprising them for use in the treatment of cancer, wherein the bispecific antigen binding molecule is administered in combination with a chemotherapeutic agent, radiation and/or other agents for use in cancer immunotherapy.

Such other agents are suitably present in combination in amounts that are effective for the purpose intended. The effective amount of such other agents depends on the amount of fusion protein used, the type of disorder or treatment, and other factors discussed above. The bispecific antigen binding molecule or antibody of the invention are generally used in the same dosages and with administration routes as described herein, or about from 1 to 99% of the dosages described herein, or in any dosage and by any route that is empirically/clinically determined to be appropriate. Other agents for use in cancer immunotherapy may also include vaccines, toll-like receptor (TLR) agents and oncolytic viruses.

Such combination therapies noted above encompass combined administration (where two or more therapeutic agents are included in the same or separate compositions), and separate administration, in which case, administration of the bispecific antigen binding molecule or antibody of the invention can occur prior to, simultaneously, and/or following, administration of the additional therapeutic agent and/or adjuvant.

In a further aspect, provided is the bispecific antigen binding molecule as described herein before for use in the treatment of cancer, wherein the bispecific antigen binding molecule is administered in combination with another immunomodulator.

The term "immunomodulator" refers to any substance including a monoclonal antibody that effects the immune system. The molecules of the inventions can be considered immunomodulators. Immunomodulators can be used as antineoplastic agents for the treatment of cancer. In one aspect, immunomodulators include, but are not limited to anti-CTLA4 antibodies (e.g. ipilimumab), anti-PD1 antibodies (e.g. nivolumab or pembrolizumab), PD-L1 antibodies (e.g. atezolizumab, avelumab or durvalumab), ICOS antibodies, 4-1BB antibodies and GITR antibodies. In a further aspect, provided is the bispecific antigen binding molecule as described herein before for use in the treatment of cancer, wherein the bispecific antigen binding molecule is administered in combination with an agent blocking PD-L1/PD-1 interaction. In one aspect, the agent blocking PD-L1/PD-1 interaction is an anti-PD-L1 antibody or an anti-PD1 antibody. More particularly, the agent blocking PD-L1/PD-1 interaction is an anti-PD-L1 antibody, in particular an anti-PD-L1 antibody selected from the group consisting of atezolizumab, durvalumab, pembrolizumab and nivolumab. In one specific aspect, the agent blocking PD-L1/PD-1 interaction is atezolizumab (MPDL3280A, RG7446). In another aspect, the agent blocking PD-L1/PD-1 interaction is an anti-PD-L1 antibody comprising a heavy chain variable domain VH(PDL-1) of SEQ ID NO:149 and a light chain variable domain VL(PDL-1) of SEQ ID NO:150. In another aspect, the agent blocking PD-L1/PD-1 interaction is an anti-PD-L1 antibody comprising a heavy chain variable domain VH(PDL-1) of SEQ ID NO:151 and a light chain variable domain VL(PDL-1) of SEQ ID NO:152. In another aspect, the agent blocking PD-L1/PD-1 interaction is an anti-PD1 antibody, in particular an anti-PD1 antibody selected from pembrolizumab or nivolumab. Such other agents are suitably present in combination in amounts that are effective for the purpose intended. The effective amount of such other agents depends on the amount of bispecific antigen binding molecule used, the type of disorder or treatment, and other factors discussed above. The bispecific antigen binding molecules as described herein before are generally used in the same dosages and with administration routes as described herein, or about from 1 to 99% of the dosages described herein, or in any dosage and by any route that is empirically/clinically determined to be appropriate.

In one aspect, provided is a bispecific agonistic OX40 antigen binding molecule or a pharmaceutical composition for use in the treatment of cancer, wherein the bispecific agonistic OX40 antigen binding molecule is for administration in combination with a T-cell activating anti-CD3 bispecific antibody. In one aspect, the T-cell activating anti-CD3 bispecific antibody specific for a tumor-associated antigen is an anti-CEA/anti-CD3 bispecific antibody.

In a particular aspect, the anti-CD3 bispecific antibody for use in the combination comprises a first antigen binding domain comprising a heavy chain variable region ($V_H$CD3) comprising CDR-H1 sequence of SEQ ID NO:117, CDR-H2 sequence of SEQ ID NO:118, and CDR-H3 sequence of SEQ ID NO:119; and/or a light chain variable region ($V_L$CD3) comprising CDR-L1 sequence of SEQ ID NO:120, CDR-L2 sequence of SEQ ID NO:121, and CDR-L3 sequence of SEQ ID NO:122. More particularly, the anti-CD3 bispecific comprises a first antigen binding domain comprising a heavy chain variable region (VHCD3) that is at least 90%, 95%, 96%, 97%, 98%, or 99% identical to the amino acid sequence of SEQ ID NO:123 and/or a light chain variable region ($V_L$CD3) that is at least 90%, 95%, 96%, 97%, 98%, or 99% identical to the amino acid sequence of SEQ ID NO:124. In a further aspect, the anti-CD3 bispecific antibody comprises a heavy chain variable region ($V_H$CD3) comprising the amino acid sequence of SEQ ID NO:123 and/or a light chain variable region ($V_L$CD3) comprising the amino acid sequence of SEQ ID NO:124.

In another aspect, the anti-CD3 bispecific antibody for use in the combination comprises a first antigen binding domain comprising a heavy chain variable region ($V_H$CD3) comprising CDR-H1 sequence of SEQ ID NO:125, CDR-H2 sequence of SEQ ID NO:126, and CDR-H3 sequence of SEQ ID NO:127; and/or a light chain variable region ($V_L$CD3) comprising CDR-L1 sequence of SEQ ID NO:128, CDR-L2 sequence of SEQ ID NO:129, and CDR-L3 sequence of SEQ ID NO:130. More particularly, the anti-CD3 bispecific comprises a first antigen binding domain comprising a heavy chain variable region ($V_H$CD3) that is at least 90%, 95%, 96%, 97%, 98%, or 99% identical to the amino acid sequence of SEQ ID NO:131 and/or a light chain variable region ($V_L$CD3) that is at least 90%, 95%, 96%, 97%, 98%, or 99% identical to the amino acid sequence of SEQ ID NO:132. In a further aspect, the anti-CD20/anti-CD3 bispecific antibody comprises a heavy chain variable region ($V_H$CD3) comprising the amino acid sequence of SEQ ID NO:131 and/or a light chain variable region (V$_L$CD3) comprising the amino acid sequence of SEQ ID NO:132.

In another aspect, the anti-CD3 bispecific antibody for use in the combination comprises a first antigen binding domain comprising a heavy chain variable region (V$_H$CD3) comprising CDR-H1 sequence of SEQ ID NO:133, CDR-H2 sequence of SEQ ID NO:134, and CDR-H3 sequence of SEQ ID NO:135; and/or a light chain variable region (V$_L$CD3) comprising CDR-L1 sequence of SEQ ID NO:136, CDR-L2 sequence of SEQ ID NO:137, and CDR-L3 sequence of SEQ ID NO:138. More particularly, the anti-CD3 bispecific comprises a first antigen binding domain comprising a heavy chain variable region (V$_H$CD3) that is at least 90%, 95%, 96%, 97%, 98%, or 99% identical to the amino acid sequence of SEQ ID NO:139 and/or a light chain variable region (V$_L$CD3) that is at least 90%, 95%, 96%, 97%, 98%, or 99% identical to the amino acid sequence of SEQ ID NO:140. In a further aspect, the anti-CD20/anti-CD3 bispecific antibody comprises a heavy chain variable region (V$_H$CD3) comprising the amino acid sequence of SEQ ID NO:139 and/or a light chain variable region (V$_L$CD3) comprising the amino acid sequence of SEQ ID NO:140.

In one particular aspect, the anti-CEA/anti-CD3 bispecific antibody comprises a polypeptide that is at least 95%, 96%, 97%, 98%, or 99% identical to the sequence of SEQ ID NO:141, a polypeptide that is at least 95%, 96%, 97%, 98%, or 99% identical to the sequence of SEQ ID NO:142, a polypeptide that is at least 95%, 96%, 97%, 98%, or 99% identical to the sequence of SEQ ID NO:143, and a polypeptide that is at least 95%, 96%, 97%, 98%, or 99% identical to the sequence of SEQ ID NO:144. In a further particular embodiment, the bispecific antibody comprises a polypeptide sequence of SEQ ID NO:141, a polypeptide sequence of SEQ ID NO:142, a polypeptide sequence of SEQ ID NO:143 and a polypeptide sequence of SEQ ID NO:144 (CEA TCB).

In another particular aspect, the anti-CEA/anti-CD3 bispecific antibody comprises a polypeptide that is at least 95%, 96%, 97%, 98%, or 99% identical to the sequence of SEQ ID NO:145, a polypeptide that is at least 95%, 96%, 97%, 98%, or 99% identical to the sequence of SEQ ID NO:146, a polypeptide that is at least 95%, 96%, 97%, 98%, or 99% identical to the sequence of SEQ ID NO:147, and a polypeptide that is at least 95%, 96%, 97%, 98%, or 99% identical to the sequence of SEQ ID NO:148. In a further particular embodiment, the bispecific antibody comprises a polypeptide sequence of SEQ ID NO:145, a polypeptide sequence of SEQ ID NO:146, a polypeptide sequence of SEQ ID NO:147 and a polypeptide sequence of SEQ ID NO:148 (CEACAM5 TCB).

Particular bispecific antibodies are further described in PCT publication no. WO 2014/131712 A1. In a further aspect, the anti-CEA/anti-CD3 bispecific antibody may also comprise a bispecific T cell engager (BiTEk). In a further aspect, the anti-CEA/anti-CD3 bispecific antibody is a bispecific antibody as described in WO 2007/071426 or WO 2014/131712.

Such combination therapies noted above encompass combined administration (where two or more therapeutic agents are included in the same or separate compositions), and separate administration, in which case, administration of the bispecific antigen binding molecule can occur prior to, simultaneously, and/or following, administration of the additional therapeutic agent and/or adjuvant.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper that is pierceable by a hypodermic injection needle). At least one active agent in the composition is a bispecific antigen binding molecule of the invention.

The label or package insert indicates that the composition is used for treating the condition of choice. Moreover, the article of manufacture may comprise (a) a first container with a composition contained therein, wherein the composition comprises a bispecific antigen binding molecule of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition.

Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

TABLE B (Sequences):

| SEQ ID NO: | Name | Sequence |
|---|---|---|
| 1 | hu OX40 | Uniprot No. P43489, aa 29-214 LH CVGDTYPSND RCCHECRPGNGMVSRCSRSQ NTVCRPCGPGFYNDVVSSKPCKPCTWCNLRSGSERKQLC TATQDTVCRCRAGTQPLDSYKPGVDCAPCPPGHFSPGDN QACKPWTNCTLAGKHTLQPASNSSDAICEDRDPPATQPQ ETQGPPARPITVQPTEAWPRTSQGPSTRPVEVPGGRAVA AILGLGLVLGLLGPLAILLALYLLRRDQRLPPDAHKPPG GGSFRTPIQEEQADAHSTLAKI |

TABLE B-continued (Sequences):

| SEQ ID NO: | Name | Sequence |
|---|---|---|
| 2 | hu FAP | UniProt no. Q12884, version 168<br>MKTWVKIVFGVATSAVLALLVMCIVLRPSRVHNSEENTM<br>RALTLKDILNGTFSYKTFFPNWISGQEYLHQSADNNIVL<br>YNIETGQSYTILSNRTMKSVNASNYGLSPDRQFVYLESD<br>YSKLWRYSYTATYYIYDLSNGEFVRGNELPRPIQYLCWS<br>PVGSKLAYVYQNNIYLKQRPGDPPFQITFNGRENKIFNG<br>IPDWVYEEEMLATKYALWWSPNGKFLAYAEFNDTDIPVI<br>AYSYYGDEQYPRTINIPYPKAGAKNPVVRIFIIDTTYPA<br>YVGPQEVPVPAMIASSDYYFSWLTWVTDERVCLQWLKRV<br>QNVSVLSICDFREDWQTWDCPKTQEHIEESRTGWAGGFF<br>VSTPVFSYDAISYYKIFSDKDGYKHIHYIKDTVENAIQI<br>TSGKWEAINIFRVTQDSLFYSSNEFEEYPGRRNIYRISI<br>GSYPPSKKCVTCHLRKERCQYYTASFSDYAKYYALVCYG<br>PGIPISTLHDGRTDQEIKILEENKELENALKNIQLPKEE<br>IKKLEVDEITLWYKMILPPQFDRSKKYPLLIQVYGGPCS<br>QSVRSVFAVNWISYLASKEGMVIALVDGRGTAFQGDKLL<br>YAVYRKLGVYEVEDQITAVRKFIEMGFIDEKRIAIWGWS<br>YGGYVSSLALASGTGLFKCGIAVAPVSSWEYYASVYTER<br>FMGLPTKDDNLEHYKNSTVMARAEYFRNVDYLLIHGTAD<br>DNVHFQNSAQIAKALVNAQVDFQAMWYSDQNHGLSGLST<br>NHLYTHMTHFLKQCFSLSD |
| 3 | FAP (212) CDR-H1 | DYNMD |
| 4 | FAP (212) CDR-H2 | DIYPNTGGTIYNQKFKG |
| 5 | FAP (212) CDR-H3 | FRGIHYAMDY |
| 6 | FAP (212) CDR-L1 | RASESVDNYGLSFIN |
| 7 | FAP (212) CDR-L2 | GTSNRGS |
| 8 | FAP (212) CDR-L3 | QQSNEVPYT |
| 9 | FAP (212) VH | EVLLQQSGPELVKPGASVKIACKASGYTLT<u>DYNMD</u>WVRQ<br>SHGKSLEWIG<u>DIYPNTGGTIYNQKFKG</u>KATLTIDKSSST<br>AYMDLRSLTSEDTAVYYCTR<u>FRGIHYAMDY</u>WGQGTSVTV<br>SS |
| 10 | FAP (212) VL | DIVLTQSPVSLAVSLGQRATISC<u>RASESVDNYGLSFIN</u>W<br>FQQKPGQPPKLLIY<u>GTSNRGS</u>GVPARFSGSGSGTDFSLN<br>IHPMEEDDTAMYFC<u>QQSNEVPYT</u>FGGGTNLEIK |
| 11 | FAP (VH1G3a) CDR-H2 | DIYPNTGGTIYAQKFQG |
| 12 | FAP (VH2G3a) CDR-H2 | DIYPNTGGTIYADSVKG |
| 13 | FAP (VL1G3a) CDR-L1 | RASESVDNYGLSFLA |
| 14 | FAP (VL2G3a) CDR-L1 | RASESIDNYGLSFLN |
| 15 | FAP (VH1G1a) | See Table 10 |
| 16 | FAP (VH1G2a) | See Table 10 |
| 17 | FAP (VH1G3a) | See Table 10 |
| 18 | FAP (VH2G1a) | See Table 10 |
| 19 | FAP (VH2G2a) | See Table 10 |
| 20 | FAP (VH2G3a) | See Table 10 |
| 21 | FAP (VL1G1a) | See Table 10 |
| 22 | FAP (VL1G2a) | See Table 10 |
| 23 | FAP (VL1G3a) | See Table 10 |
| 24 | FAP (VL2G1a) | See Table 10 |
| 25 | FAP (VL2G2a) | See Table 10 |
| 26 | FAP (VL2G3a) | See Table 10 |

TABLE B-continued (Sequences):

| SEQ ID NO: | Name | Sequence |
|---|---|---|
| 27 | OX40 (49B4) CDR-H1 | SYAIS |
| 28 | OX40 (49B4) CDR-H2 | GIIPIFGTANYAQKFQG |
| 29 | OX40 (49B4) CDR-H3 | EYYRGPYDY |
| 30 | OX40 (49B4) CDR-L1 | RASQSISSWLA |
| 31 | OX40 (49B4) CDR-L2 | DASSLES |
| 32 | OX40 (49B4) CDR-L3 | QQYSSQPYT |
| 33 | OX40 (49B4) VH | QVQLVQSGAEVKKPGSSVKVSCKASGGTFSSYAISWVRQ APGQGLEWMGGIIPIFGTANYAQKFQGRVTITADKSTST AYMELSSLRSEDTAVYYCAREYYRGPYDYWGQGTTVTVS S |
| 34 | OX40 (49B4) VL | DIQMTQSPSTLSASVGDRVTITCRASQSISSWLAWYQQK PGKAPKLLIYDASSLESGVPSRFSGSGSGTEFTLTISSL QPDDFATYYCQQYSSQPYTFGQGTKVEIK |
| 35 | OX40 (CLC563) CDR-H1 | SYAMS |
| 36 | OX40 (CLC563) CDR-H2 | AISGSGGSTYYADSVKG |
| 37 | OX40 (CLC563) CDR-H3 | DVGAFDY |
| 38 | OX40 (CLC563) CDR-L1 | RASQSVSSSYLA |
| 39 | OX40 (CLC563) CDR-L2 | GASSRAT |
| 40 | OX40 (CLC563) CDR-L3 | QQYGSSPLT |
| 41 | OX40 (CLC563) VH | EVQLLESGGGLVQPGGSLRLSCAASGFTFSSYAMSWVRQ APGKGLEWVSAISGSGGSTYYADSVKGRFTISRDNSKNT LYLQMNSLRAEDTAVYYCALDVGAFDYWGQGALVTVSS |
| 42 | OX40 (CLC563) VL | EIVLTQSPGTLSLSPGERATLSCRASQSVSSSYLAWYQQ KPGQAPRLLIYGASSRATGIPDRFSGSGSGTDFTLTISR LEPEDFAVYYCQQYGSSPLTFGQGTKVEIK |
| 43 | OX40 (MOXR0916) CDR-H1 | DSYMS |
| 44 | OX40 (MOXR0916) CDR-H2 | DMYPDNGDSSYNQKFRE |
| 45 | OX40 (MOXR0916) CDR-H3 | APRWYFSV |
| 46 | OX40 (MOXR0916) CDR-L1 | RASQDISNYLN |
| 47 | OX40 (MOXR0916) CDR-L2 | YTSRLRS |
| 48 | OX40 (MOXR0916) CDR-L3 | QQGHTLPPT |
| 49 | OX40 (MOXR0916) VH | EVQLVQSGAEVKKPGASVKVSCKASGYTFTDSYMSWVRQ APGQGLEWIGDMYPDNGDSSYNQKFRERVTITRDTSTST AYLELSSLRSEDTAVYYCVLAPRWYFSVWGQGTLVTVSS |
| 50 | OX40 (MOXR0916) VL | DIQMTQSPSSLSASVGDRVTITCRASQDISNYLNWYQQK PGKAPKLLIYYTSRLRSGVPSRFSGSGSGTDFTLTISSL QPEDFATYYCQQGHTLPPTFGQGTKVEIK |
| 51 | OX40 (8H9) CDR-H1 | SYAIS |
| 52 | OX40 (8H9) CDR-H2 | GIIPIFGTANYAQKFQG |
| 53 | OX40 (8H9) CDR-H3 | EYGWMDY |
| 54 | OX40 (8H9) CDR-L1 | RASQSISSWLA |

TABLE B-continued (Sequences):

| SEQ ID NO: | Name | Sequence |
|---|---|---|
| 55 | OX40 (8H9) CDR-L2 | DASSLES |
| 56 | OX40 (8H9) CDR-L3 | QQYLTYSRFT |
| 57 | OX40 (8H9) VH | QVQLVQSGAEVKKPGSSVKVSCKASGGTFSSYAISWVRQ APGQGLEWMGGIIPIFGTANYAQKFQGRVTITADKSTST AYMELSSLRSEDTAVYYCAREYGWMDYWGQGTTVTSS |
| 58 | OX40 (8H9) VL | DIQMTQSPSTLSASVGDRVTITCRASQSISSWLAWYQQK PGKAPKLLIYDASSLESGVPSRFSGSGSGTEFTLTISSL QPDDFATYYCQQYLTYSRFTFGQGTKVEIK |
| 59 | OX40 (49B4_K73E) VH | QVQLVQSGAEVKKPGSSVKVSCKASGGTFSSYAISWVRQ APGQGLEWMGGIIPIFGTANYAQKFQGRVTITADESTST AYMELSSLRSEDTAVYYCAREYYRGPYDYWGQGTTVTVS S |
| 60 | OX40 (49B4_K23T_K73E) VH | QVQLVQSGAEVKKPGSSVKVSCTASGGTFSSYAISWVRQ APGQGLEWMGGIIPIFGTANYAQKFQGRVTITADESTST AYMELSSLRSEDTAVYYCAREYYRGPYDYWGQGTTVTVS S |
| 61 | OX40 (49B4_K23E_K73E) VH | QVQLVQSGAEVKKPGSSVKVSCEASGGTFSSYAISWVRQ APGQGLEWMGGIIPIFGTANYAQKFQGRVTITADESTST AYMELSSLRSEDTAVYYCAREYYRGPYDYWGQGTTVTVS S |
| 62 | hu FAP ectodomain + poly-lys-tag + his$_6$-tag | RPSRVHNSEENTMRALTLKDILNGTFSYKTFFPNWISGQ EYLHQSADNNIVLYNIETGQSYTILSNRTMKSVNASNYG LSPDRQFVYLESDYSKLWRYSYTATYYIYDLSNGEFVRG NELPRPIQYLCWSPVGSKLAYVYQNNIYLKQRPGDPPFQ ITFNGRENKIFNGIPDWVYEEEMLATKYALWWSPNGKFL AYAEFNDTDIPVIAYSYYGDEQYPRTINIPYPKAGAKNP VVRIFIIDTTYPAYVGPQEVPVPAMIASSDYYFSWLTWV TDERVCLQWLKRVQNVSVLSICDFREDWQTWDCPKTQEH IEESRTGWAGGFFVSTPVFSYDAISYYKIFSDKDGYKHI HYIKDTVENAIQITSGKWEAINIFRVTQDSLFYSSNEFE EYPGRRNIYRISIGSYPPSKKCVTCHLRKERCQYYTASF SDYAKYYALVCYGPGIPISTLHDGRTDQEIKILEENKEL ENALKNIQLPKEEIKKLEVDEITLWYKMILPPQFDRSKK YPLLIQVYGGPCSQSVRSVFAVNWISYLASKEGMVIALV DGRGTAFQGDKLLYAVYRKLGVYEVEDQITAVRKFIEMG FIDEKRIAIWGWSYGGYVSSLALASGTGLFKCGIAVAPV SSWEYYASVYTERFMGLPTKDDNLEHYKNSTVMARAEYF RNVDYLLIHGTADDNVHFQNSAQIAKALVNAQVDFQAMW YSDQNHGLSGLSTNHLYTHMTHFLKQCFSLDGKKKKKK GHHHHHH |
| 63 | Murine FAP | UniProt no. P97321 |
| 64 | Murine FAP ectodomain + poly-lys-tag + his$_6$-tag | RPSRVYKPEGNTKRALTLKDILNGTFSYKTYFPNWISEQ EYLHQSEDDNIVFYNIETRESYIILSNSTMKSVNATDYG LSPDRQFVYLESDYSKLWRYSYTATYYIYDLQNGEFVRG YELPRPIQYLCWSPVGSKLAYVYQNNIYLKQRPGDPPFQ ITYTGRENRIFNGIPDWVYEEEMLATKYALWWSPDGKFL AYVEFNDSDIPIIAYSYYGDGQYPRTINIPYPKAGAKNP VVRVFIVDTTYPHHVGPMEVPVPEMIASSDYYFSWLTWV SSERVCLQWLKRVQNVSVLSICDFREDWHAWECPKNQEH VEESRTGWAGGFFVSTPAFSQDATSYYKIFSDKDGYKHI HYIKDTVENAIQITSGKWEAIYIFRVTQDSLFYSSNEFE GYPGRRNIYRISIGNSPPSKKCVTCHLRKERCQYYTASF SYKAKYYALVCYGPGLPISTLHDGRTDQEIQVLEENKEL ENSLRNIQLPKVEIKKLKDGGLTFWYKMILPPQFDRSKK YPLLIQVYGGPCSQSVKSVFAVNWITYLASKEGIVIALV DGRGTAFQGDKFLHAVYRKLGVYEVEDQLTAVRKFIEMG FIDEERIAIWGWSYGGYVSSLALASGTGLFKCGIAVAPV SSWEYYASIYSERFMGLPTKDDNLEHYKNSTVMARAEYF RNVDYLLIHGTADDNVHFQNSAQIAKALVNAQVDFQAMW YSDQNHGILSGRSQNHLYTHMTHFLKQCFSLDGKKKKK KGHHHHHH |

TABLE B-continued (Sequences):

| SEQ ID NO: | Name | Sequence |
|---|---|---|
| 65 | Cynomolgus FAP ectodomain + poly-lys-tag + his$_6$-tag | RPPRVHNSEENTMRALTLKDILNGTFSYKTFFPNWISGQ EYLHQSADNNIVLYNIETGQSYTILSNRTMKSVNASNYG LSPDRQFVYLESDYSKLWRYSYTATYYIYDLSNGEFVRG NELPRPIQYLCWSPVGSKLAYVYQNNIYLKQRPGDPPFQ ITFNGRENKIFNGIPDWVYEEEMLATKYALWWSPNGKFL AYAEFNDTDIPVIAYSYYGDEQYPRTINIPYPKAGAKNP FVRIFIIDTTYPAYVGPQEVPVPAMIASSDYYFSWLTWV TDERVCLQWLKRVQNVSVLSICDFREDWQTWDCPKTQEH IEESRTGWAGGFFVSTPVFSYDAISYYKIFSDKDGYKHI HYIKDTVENAIQITSGKWEAINIFRVTQDSLFYSSNEFE DYPGRRNIYRISIGSYPPSKKCVTCHLRKERCQYYTASF SDYAKYYALVCYGPGIPISTLHDGRTDQEIKILEENKEL ENALKNIQLPKEEIKKLEVDEITLWYKMILPPQFDRSKK YPLLIQVYGGPCSQSVRSVFAVNWISYLASKEGMVIALV DGRGTAFQGDKLLYAVYRKLGVYEVEDQITAVRKFIEMG FIDEKRIAIWGWSYGGYVSSLALASGTGLFKCGIAVAPV SSWEYYASVYTERFMGLPTKDDNLEHYKNSTVMARAEYF RNVDYLLIHGTADDNVHFQNSAQIAKALVNAQVDFQAMW YSDQNHGLSGLSTNHLYTHMTHFLKQCFSLSDGKKKKKK GHHHHHH |
| 66 | Murine OX40 | UniProt no. P47741, version 143 MYVWVQQPTALLLLALTLGVTARRLNCVKHTYPSGHKCC RECQPGHGMVSRCDHTRDTLCHPCETGFYNEAVNYDTCK QCTQCNHRSGSELKQNCTPTQDTVCRCRPGTQPRQDSGY KLGVDCVPCPPGHFSPGNNQACKPWTNCTLSGKQTRHPA SDSLDAVCEDRSLLATLLWETQRPTFRPTTVQSTTVWPR TSELPSPPTLVTPEGPAFAVLLGLGLGLLAPLTVLLALY LLRKAWRLPNTPKPCWGNSFRTPIQEEHTDAHFTLAKI |
| 67 | Peptide linker (G4S) | GGGGS |
| 68 | Peptide linker (G4S)$_2$ | GGGGSGGGGS |
| 69 | Peptide linker (SG4)$_2$ | SGGGGSGGGG |
| 70 | Peptide linker G4(SG4)$_2$ | GGGGSGGGGSGGGG |
| 71 | peptide linker | GSPGSSSSGS |
| 72 | (G4S)$_3$ peptide linker | GGGGSGGGGSGGGGS |
| 73 | (G4S)$_4$ peptide linker | GGGGSGGGGSGGGGSGGGGS |
| 74 | peptide linker | GSGSGSGS |
| 75 | peptide linker | GSGSGNGS |
| 76 | peptide linker | GGSGSGSG |
| 77 | peptide linker | GGSGSG |
| 78 | peptide linker | GGSG |
| 79 | peptide linker | GGSGNGSG |
| 80 | peptide linker | GGNGSGSG |
| 81 | peptide linker | GGNGSG |
| 82 | Fc knob chain | DKTHTCPPCPAPELLGGPSVFLFPPKPKDTLMISRTPEV TCVVVDVSHEDPEVKFNWYVDGVEVHNAKTKPREEQYNS TYRVVSVLTVLHQDWLNGKEYKCKVSNKALPAPIEKTIS KAKGQPREPQVYTLPPCRDELTKNQVSLWCLVKGFYPSD IAVEWESNGQPENNYKTTPPVLDSDGSFFLYSKLTVDKS RWQQGNVFSCSVMHEALHNHYTQKSLSLSPGK |
| 83 | Fc hole chain | DKTHTCPPCPAPELLGGPSVFLFPPKPKDTLMISRTPEV TCVVVDVSHEDPEVKFNWYVDGVEVHNAKTKPREEQYNS TYRVVSVLTVLHQDWLNGKEYKCKVSNKALPAPIEKTIS KAKGQPREPQVCTLPPSRDELTKNQVSLSCAVKGFYPSD IAVEWESNGQPENNYKTTPPVLDSDGSFFLVSKLTVDKS RWQQGNVFSCSVMHEALHNHYTQKSLSLSPGK |

TABLE B-continued (Sequences):

| SEQ ID NO: | Name | Sequence |
|---|---|---|
| 84 | Acceptor framework IGHJ6*01/02 | YYYYYGMDVWGQGTTVTVSS |
| 85 | Acceptor framework IGKJ4* 01/02 | LTFGGGTKVEIK |
| 86 | OX40(49B4) VHCH1-OX40(49B4) VHCH1- Fc knob_PGLALA-FAP (1G1a) VHCL | See Table 13 |
| 87 | OX40(49B4) light chain | See Table 13 |
| 88 | FAP (1G1a) VLCH1-light chain | See Table 13 |
| 89 | OX40(49B4) VHCH1-OX40(49B4) VHCH1-Fc hole_PGLALA | See Table 13 |
| 90 | OX40(49B4) VHCH1- Fc hole_PGLALA | see Table 13 |
| 91 | OX40(49B4) VHCH1- Fc knob_PGLALA-FAP (1G1a) VHCL | see Table 13 |
| 92 | 0X(40(CLC563) VHCH1-OX40(CLC563) VHCH1-Fc knob_PGLALA-FAP (1G1a) VHCL | See Table 13 |
| 93 | OX40(CLC563) light chain | see Table 13 |
| 94 | FAP (1G1a) VLCH1-light chain (EPKSCD) | See Table 13 |
| 95 | OX40(CLC563)-VHCH1-OX40(CLC563) VHCH1-Fc hole_PGLALA | See Table 13 |
| 96 | FAP (1G1a) VLCH1-light chain (EPKSCS) | See Table 13 |
| 97 | OX40(CLC563) VHCH1- Fc knob_PGLALA-FAP (1G1a) VHCL | See Table 13 |
| 98 | OX40(CLC563) VHCH1 Fc hole_PGLALA | See Table 13 |
| 99 | OX40(MOXR0916) VHCH1- Fc knob_PGLALA-FAP (1G1a) VHCL | See Table 13 |
| 100 | OX40(MOXR0916) light chain | see Table 13 |
| 101 | OX40(MOXR0916) VHCH1-OX40(MOXR0916) VHCH1- Fc hole_PGLALA- | See Table 13 |
| 102 | OX40(MOXR0916) VHCH1- Fc hole_PGLALA | See Table 13 |
| 103 | OX40(8H9) VHCH1- Fc knob_PGLALA-FAP (1G1a) VHCL | See Table 13 |
| 104 | OX40(8H9) light chain | See Table 13 |

TABLE B-continued (Sequences):

| SEQ ID NO: | Name | Sequence |
|---|---|---|
| 105 | OX40(8H9) VHCH1-<br>OX40(8H9) VHCH1- Fc<br>hole_PGLALA | See Table 13 |
| 106 | OX40(8H9) VHCH1- Fc<br>hole_PGLALA | See Table 13 |
| 107 | OX40(49B4_K73E)<br>VHCH1-<br>OX40(49B4_K73E)<br>VHCH1- Fc<br>knob_PGLALA-<br>FAP (1G1a) VHCL | See Table 15 |
| 108 | OX40(49B4_K73E)<br>VHCH1-<br>OX40(49B4_K73E)<br>VHCH1-Fc hole_PGLALA | See Table 15 |
| 109 | OX40(49B4_K23T_K73E)<br>VHCH1-<br>OX40(49B4_K23T_K73E)<br>VHCH1- Fc<br>knob_PGLALA-<br>FAP (1G1a) VHCL | See Table 15 |
| 110 | OX40(49B4_K23T_K73E)<br>VHCH1-<br>OX40(49B4_K23T_K73E)<br>VHCH1-Fc hole_PGLALA | See Table 15 |
| 111 | OX40(49B4_K23E_K73E)<br>VHCH1-<br>OX40(49B4_K23E_K73E)<br>VHCH1- Fc<br>knob_PGLALA-<br>FAP (1G1a) VHCL | See Table 15 |
| 112 | OX40(49B4_K23E_K73E)<br>VHCH1-<br>OX40(49B4_K23E_K73E)<br>VHCH1-Fc hole_PGLALA | See Table 15 |
| 113 | OX40(49B4) VHCH1-<br>OX40(49B4) VHCH1- Fc<br>hole_PGLALA - FAP (4B9)<br>VL | QVQLVQSGAEVKKPGSSVKVSCKASGGTFSSYAISWVRQ<br>APGQGLEWMGGIIPIFGTANYAQKFQGRVTITADKSTST<br>AYMELSSLRSEDTAVYYCAREYYRGPYDYWGQGTTVTVS<br>SASTKGPSVFPLAPSSKSTSGGTAALGCLVKDYFPEPVT<br>VSWNSGALTSGVHTFPAVLQSSGLYSLSSVVTVPSSSLG<br>TQTYICNVNHKPSNTKVDKKVEPKSCDGGGGSGGGGSQV<br>QLVQSGAEVKKPGSSVKVSCKASGGTFSSYAISWVRQAP<br>GQGLEWMGGIIPIFGTANYAQKFQGRVTITADKSTSTAY<br>MELSSLRSEDTAVYYCAREYYRGPYDYWGQGTTVTVSSA<br>STKGPSVFPLAPSSKSTSGGTAALGCLVKDYFPEPVTVS<br>WNSGALTSGVHTFPAVLQSSGLYSLSSVVTVPSSSLGTQ<br>TYICNVNHKPSNTKVDKKVEPKSCDKTHTCPPCPAPEAA<br>GGPSVFLFPPKPKDTLMISRTPEVTCVVVDVSHEDPEVK<br>FNWYVDGVEVHNAKTKPREEQYNSTYRVVSVLTVLHQDW<br>LNGKEYKCKVSNKALGAPIEKTISKAKGQPREPQVCTLP<br>PSRDELTKNQVSLSCAVKGFYPSDIAVEWESNGQPENNY<br>KTTPPVLDSDGSFFLVSKLTVDKSRWQQGNVFSCSVMHE<br>ALHNHYTQKSLSLSPGGGGSGGGGSGGGGSGGGGSEIV<br>LTQSPGTLSLSPGERATLSCRASQSVTSSYLAWYQQKPG<br>QAPRLLINVGSRRATGIPDRFSGSGSGTDFTLTISRLEP<br>EDFAVYYCQQGIMLPPTFGQGTKVEIK |

TABLE B-continued (Sequences):

| SEQ ID NO: | Name | Sequence |
|---|---|---|
| 114 | OX40(49B4) VHCH1-OX40(49B4) VHCH1- Fc knob_PGLALA - FAP (4B9) VH | QVQLVQSGAEVKKPGSSVKVSCKASGGTFSSYAISWVRQ APGQGLEWMGGIIPIFGTANYAQKFQGRVTITADKSTST AYMELSSLRSEDTAVYYCAREYYRGPYDYWGQGTTVTVS SASTKGPSVFPLAPSSKSTSGGTAALGCLVKDYFPEPVT VSWNSGALTSGVHTFPAVLQSSGLYSLSSVVTVPSSSLG TQTYICNVNHKPSNTKVDKKVEPKSCDGGGGSGGGGSQV QLVQSGAEVKKPGSSVKVSCKASGGTFSSYAISWVRQAP GQGLEWMGGIIPIFGTANYAQKFQGRVTITADKSTSTAY MELSSLRSEDTAVYYCAREYYRGPYDYWGQGTTVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKKVEPKSCDKTHTCPPCPAPEAA GGPSVFLEPPKPKDTLMISRTPEVTCVVVDVSHEDPEVK FNWYVDGVEVHNAKTKPREEQYNSTYRVVSVLTVLHQDW LNGKEYKCKVSNKALGAPIEKTISKAKGQPREPQVYTLP PCRDELTKNQVSLWCLVKGFYPSDIAVEWESNGQPENNY KTTPPVLDSDGSFELYSKLTVDKSRWQQGNVFSCSVMHE ALHNHYTQKSLSLSPGGGGGSGGGGSGGGGSGGGGSEVQ LLESGGGLVQPGGSLRLSCAASGFTESSYAMSWVRQAPG KGLEWVSAIIGSGASTYYADSVKGRFTISRDNSKNTLYL QMNSLRAEDTAVYYCAKGWFGGFNYWGQGTLVTVSS |
| 115 | OX40 (49B4) VLCkappa | DIQMTQSPSTLSASVGDRVTITCRASQSISSWLAWYQQK PGKAPKLLIYDASSLESGVPSRFSGSGSGTEFTLTISSL QPDDFATYYCQQYSSQPYTFGQGTKVEIKRTVAAPSVFI FPPSDEQLKSGTASVVCLLNNFYPREAKVQWKVDNALQS GNSQESVTEQDSKDSTYSLSSTLTLSKADYEKHKVYACE VTHQGLSSPVTKSFNRGEC |
| 116 | OX40(49B4) VHCH1-OX40(49B4) VHCH1- IgG1 Fc _PGLALA | QVQLVQSGAEVKKPGSSVKVSCKASGGTFSSYAISWVRQ APGQGLEWMGGIIPIFGTANYAQKFQGRVTITADKSTST AYMELSSLRSEDTAVYYCAREYYRGPYDYWGQGTTVTVS SASTKGPSVFPLAPSSKSTSGGTAALGCLVKDYFPEPVT VSWNSGALTSGVHTFPAVLQSSGLYSLSSVVTVPSSSLG TQTYICNVNHKPSNTKVDKKVEPKSCDGGGGSGGGGSQV QLVQSGAEVKKPGSSVKVSCKASGGTFSSYAISWVRQAP GQGLEWMGGIIPIFGTANYAQKFQGRVTITADKSTSTAY MELSSLRSEDTAVYYCAREYYRGPYDYWGQGTTVTVSSA STKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKKVEPKSCDKTHTCPPCPAPEAA GGPSVFLEPPKPKDTLMISRTPEVTCVVVDVSHEDPEVK FNWYVDGVEVHNAKTKPREEQYNSTYRVVSVLTVLHQDW LNGKEYKCKVSNKALGAPIEKTISKAKGQPREPQVYTLP PSRDELTKNQVSLTCLVKGFYPSDIAVEWESNGQPENNY KTTPPVLDSDGSFELYSKLTVDKSRWQQGNVFSCSVMHE ALHNHYTQKSLSLSP |
| 117 | CD3 CDR-H1 | TYAMN |
| 118 | CD3 CDR-H2 | RIRSKYNNYATYYADSVKG |
| 119 | CD3 CDR-H2 | HGNFGNSYVSWFAY |
| 120 | CD3 CDR-L1 | GSSTGAVTTSNYAN |
| 121 | CD3 CDR-L2 | GTNKRAP |
| 122 | CD3 CDR-L3 | ALWYSNLWV |
| 123 | CD3 VH | EVQLLESGGGLVQPGGSLRLSCAASGFTFSTYAMNWVRQ APGKGLEWVSRIRSKYNNYATYYADSVKGRFTISRDDSK NTLYLQMNSLRAEDTAVYYCVRHGNFGNSYVSWFAYWGQ GTLVTVSS |
| 124 | CD3 VL | QAVVTQEPSLTVSPGGTVTLTCGSSTGAVTTSNYANWVQ EKPGQAFRGLIGGTNKRAPGTPARFSGSLLGGKAALTLS GAQPEDEAEYYCALWYSNLWVFGGGTKLTVL |
| 125 | CD3 (Cl22) CDR-H1 | SYAMN |
| 126 | CD3 (Cl22) CDR-H2 | RIRSKYNNYATYYADSVKG |
| 127 | CD3 (Cl22) CDR-H3 | HTTFPSSYVSYYGY |

TABLE B-continued (Sequences):

| SEQ ID NO: | Name | Sequence |
|---|---|---|
| 128 | CD3 (C122) CDR-L1 | GSSTGAVTTSNYAN |
| 129 | CD3 (C122) CDR-L2 | GTNKRAP |
| 130 | CD3 (C122) CDR-L3 | ALWYSNLWV |
| 131 | CD3 (C122) VH | EVQLLESGGGLVQPGGSLRLSCAASGFQFSSYAMNWVRQ APGKGLEWVSRIRSKYNNYATYYADSVKGRFTISRDDSK NTLYLQMNSLRAEDTAVYYCVRHTTFPSSYVSYYGYWGQ GTLVTVSS |
| 132 | CD3 (C122) VL | QAVVTQEPSLTVSPGGTVTLTCGSSTGAVTTSNYANWVQ EKPGQAFRGLIGGTNKRAPGTPARFSGSLLGGKAALTLS GAQPEDEAEYYCALWYSNLWVFGGGTKLTVL |
| 133 | CD3 (V9) CDR-H1 | GYSFTGYTMN |
| 134 | CD3 (V9) CDR-H2 | LINPYKGVSTYNQKFKD |
| 135 | CD3 (V9) CDR-H3 | SGYYGDSDWYFDV |
| 136 | CD3 (V9) CDR-L1 | RASQDIRNYLN |
| 137 | CD3 (V9) CDR-L2 | YTSRLES |
| 138 | CD3 (V9) CDR-L3 | QQGNTLPWT |
| 139 | CD3 (V9) VH | EVQLVESGGGLVQPGGSLRLSCAASGYSFTGYTMNWVRQ APGKGLEWVALINPYKGVSTYNQKFKDRFTISVDKSKNT AYLQMNSLRAEDTAVYYCARSGYYGDSDWYFDVWGQGTL VTVSS |
| 140 | CD3 (V9) VL | DIQMTQSPSSLSASVGDRVTITCRASQDIRNYLNWYQQK PGKAPKLLIYYTSRLESGVPSRFSGSGSGTDYTLTISSL QPEDFATYYCQQGNTLPWTFGQGTKVEIK |
| 141 | Light chain "CEA$_{2F1}$" (CEA TCB) | DIQMTQSPSSLSASVGDRVTITC<u>KASAAVGTYVA</u>WYQQK PGKAPKLLIY<u>SASYRKR</u>GVPSRFSGSGSGTDFTLTISSL QPEDFATYYC<u>HQYYTYPLFT</u>FGQGTKLEIKRTVAAPSVF IFPPSDEQLKSGTASVVCLLNNFYPREAKVQWKVDNALQ SGNSQESVTEQDSKDSTYSLSSTLTLSKADYEKHKVYAC EVTHQGLSSPVTKSFNRGEC |
| 142 | Light Chain humanized CD3 $_{CH2527}$ (Crossfab, VL-CH1) (CEA TCB) | QAVVTQEPSLTVSPGGTVTLTC<u>GSSTGAVTTSNYAN</u>WVQ EKPGQAFRGLIG<u>GTNKRAP</u>GTPARFSGSLLGGKAALTLS GAQPEDEAEYYC<u>ALWYSNLWV</u>FGGGTKLTVLSSASTKGP SVFPLAPSSKSTSGGTAALGCLVKDYFPEPVTVSWNSGA LTSGVHTFPAVLQSSGLYSLSSVVTVPSSSLGTQTYICN VNHKPSNTKVDKKVEPKSC |
| 143 | CEA $_{CH1A1A\ 98/99}$ - humanized CD3 $_{CH2527}$ (Crossfab VH-Ck)-Fc(knob) P329GLALA (CEA TCB) | QVQLVQSGAEVKKPGASVKVSCKASGYTFT<u>EFGMN</u>WVRQ APGQGLEWMG<u>WINTKTGEATYVEEFKG</u>RVTFTTDTSTST AYMELRSLRSDDTAVYYCAR<u>WDFAYYVEAMDY</u>WGQGTTV TVSSASTKGPSVFPLAPSSKSTSGGTAALGCLVKDYFPE PVTVSWNSGALTSGVHTFPAVLQSSGLYSLSSVVTVPSS SLGTQTYICNVNHKPSNTKVDKKVEPKSCDGGGSGGGG SEVQLLESGGGLVQPGGSLRLSCAASGFTES<u>TYAMN</u>WVR QAPGKGLEWVS<u>RIRSKYNNYATYYADSVKG</u>RFTISRDDS KNTLYLQMNSLRAEDTAVYYCVR<u>HGNFGNSYVSWFAY</u>WG QGTLVTVSSASVAAPSVFIFPPSDEQLKSGTASVVCLLN NFYPREAKVQWKVDNALQSGNSQESVTEQDSKDSTYSLS STLTLSKADYEKHKVYACEVTHQGLSSPVTKSFNRGECD KTHTCPPCPAPEAAGGPSVFLEPPKPKDTLMISRTPEVT CVVVDVSHEDPEVKFNWYVDGVEVHNAKTKPREEQYNST YRVVSVLTVLHQDWLNGKEYKCKVSNKALGAPIEKTISK AKGQPREPQVYTLPPCRDELTKNQVSLWCLVKGFYPSDI AVEWESNGQPENNYKTTPPVLDSDGSFFLYSKLTVDKSR WQQGNVFSCSVMHEALHNHYTQKSLSLSP |

TABLE B-continued (Sequences):

| SEQ ID NO: | Name | Sequence |
|---|---|---|
| 144 | CEA $_{CH1A1A\ 98/99}$ (VH-CH1)-Fc(hole) P329GLALA (CEA TCB) | QVQLVQSGAEVKKPGASVKVSCKASGYTFTEFGMNWVRQ APGQGLEWMGWINTKTGEATYVEEFKGRVTFTTDTSTST AYMELRSLRSDDTAVYYCARWDFAYYVEAMDYWGQGTTV TVSSASTKGPSVFPLAPSSKSTSGGTAALGCLVKDYFPE PVTVSWNSGALTSGVHTFPAVLQSSGLYSLSSVVTVPSS SLGTQTYICNVNHKPSNTKVDKKVEPKSCDKTHTCPPCP APEAAGGPSVFLFPPKPKDTLMISRTPEVTCVVVDVSHE DPEVKFNWYVDGVEVHNAKTKPREEQYNSTYRVVSVLTV LHQDWLNGKEYKCKVSNKALGAPIEKTISKAKGQPREPQ VCTLPPSRDELTKNQVSLSCAVKGFYPSDIAVEWESNGQ PENNYKTTPPVLDSDGSFFLVSKLTVDKSRWQQGNVFSC SVMHEALHNHYTQKSLSLSP |
| 145 | CD3 VH-CL (CEACAM5 TCB) | EVQLLESGGGLVQPGGSLRLSCAASGFTFSTYAMNWVRQ APGKGLEWVSRIRSKYNNYATYYADSVKGRFTISRDDSK NTLYLQMNSLRAEDTAVYYCVRHGNFGNSYVSWFAYWGQ GTLVTVSSASVAAPSVFIFPPSDEQLKSGTASVVCLLNN FYPREAKVQWKVDNALQSGNSQESVTEQDSKDSTYSLSS TLTLSKADYEKHKVYACEVTHQGLSSPVTKSFNRGEC |
| 146 | humanized CEA VH-CH1(EE)-Fc (hole, P329G LALA) (CEACAM5 TCB) | QVQLVQSGAEVKKPGSSVKVSCKASGENIKDTYMHWVRQ APGQGLEWMGRIDPANGNSKYVPKFQGRVTITADTSTST AYMELSSLRSEDTAVYYCAPFGYYVSDYAMAYWGQGTLV TVSSASTKGPSVFPLAPSSKSTSGGTAALGCLVEDYFPE PVTVSWNSGALTSGVHTFPAVLQSSGLYSLSSVVTVPSS SLGTQTYICNVNHKPSNTKVDEKVEPKSCDKTHTCPPCP APEAAGGPSVFLFPPKPKDTLMISRTPEVTCVVVDVSHE DPEVKFNWYVDGVEVHNAKTKPREEQYNSTYRVVSVLTV LHQDWLNGKEYKCKVSNKALGAPIEKTISKAKGQPREPQ VCTLPPSRDELTKNQVSLSCAVKGFYPSDIAVEWESNGQ PENNYKTTPPVLDSDGSFFLVSKLTVDKSRWQQGNVFSC SVMHEALHNHYTQKSLSLSP |
| 147 | humanized CEA VH-CH1(EE)-CD3 VL-CH1-Fc (knob, P329G LALA) (CEACAM5 TCB) | QVQLVQSGAEVKKPGSSVKVSCKASGENIKDTYMHWVRQ APGQGLEWMGRIDPANGNSKYVPKFQGRVTITADTSTST AYMELSSLRSEDTAVYYCAPFGYYVSDYAMAYWGQGTLV TVSSASTKGPSVFPLAPSSKSTSGGTAALGCLVEDYFPE PVTVSWNSGALTSGVHTFPAVLQSSGLYSLSSVVTVPSS SLGTQTYICNVNHKPSNTKVDEKVEPKSCDGGGSGGGG SQAVVTQEPSLTVSPGGTVTLTCGSSTGAVTTSNYANWV QEKPGQAFRGLIGGTNKRAPGTPARFSGSLLGGKAALTL SGAQPEDEAEYYCALWYSNLWVFGGGTKLTVLSSASTKG PSVFPLAPSSKSTSGGTAALGCLVKDYFPEPVTVSWNSG ALTSGVHTFPAVLQSSGLYSLSSVVTVPSSSLGTQTYIC NVNHKPSNTKVDKKVEPKSCDKTHTCPPCPAPEAAGGPS VFLFPPKPKDTLMISRTPEVTCVVVDVSHEDPEVKFNWY VDGVEVHNAKTKPREEQYNSTYRVVSVLTVLHQDWLNGK EYKCKVSNKALGAPIEKTISKAKGQPREPQVYTLPPCRD ELTKNQVSLWCLVKGFYPSDIAVEWESNGQPENNYKTTP PVLDSDGSFELYSKLTVDKSRWQQGNVFSCSVMHEALHN HYTQKSLSLSP |
| 148 | humanized CEA VL-CL(RK) (CEACAM5 TCB) | EIVLTQSPATLSLSPGERATLSCRAGESVDIFGVGFLHW YQQKPGQAPRLLIYRASNRATGIPARESGSGSGTDFTLT ISSLEPEDFAVYYCQQTNEDPYTFGQGTKLEIKRTVAAP SVFIFPPSDRKLKSGTASVVCLLNNFYPREAKVQWKVDN ALQSGNSQESVTEQDSKDSTYSLSSTLTLSKADYEKHKV YACEVTHQGLSSPVTKSFNRGEC |
| 149 | VH (PD-L1) | EVQLVESGGGLVQPGGSLRLSCAASGFTFSDSWIHWVRQ APGKGLEWVAWISPYGGSTYYADSVKGRFTISADTSKNT AYLQMNSLRAEDTAVYYCARRHWPGGFDYWGQGTLVTVS S |
| 150 | VL (PD-L1) | DIQMTQSPSSLSASVGDRVTITCRASQDVSTAVAWYQQK PGKAPKLLIYSASFLYSGVPSRFSGSGSGTDFTLTISSL QPEDFATYYCQQYLYHPATFGQGTKVEIK |
| 151 | VH (PD-L1) | EVQLVESGGGLVQPGGSLRLSCAASGFTFSRYWMSWVRQ APGKGLEWVANIKQDGSEKYYVDSVKGRFTISRDNAKNS LYLQMNSLRAEDTAVYYCAREGGWFGELAFDYWGQGTLV TVSS |

TABLE B-continued (Sequences):

| SEQ ID NO: | Name | Sequence |
|---|---|---|
| 152 | VL (PD-L1) | EIVLTQSPGTLSLSPGERATLSCRASQRVSSSYLAWYQQ KPGQAPRLLIYDASSRATGIPDRFSGSGSGTDFTLTISR LEPEDFAVYYCQQYGSLPWTFGQGTKVEIK |
| 153 | CH2 domain | APELLGGPSVFLFPPKPKDTLMISRTPEVTCVWDVSHED PEVKFNWYVDGVEVHNAKTKPREEQESTYRWSVLTVLHQ DWLNGKEYKCKVSNKALPAPIEKTISKAK |
| 154 | CH3 domain | GQPREPQVYTLPPSRDELTKNQVSLTCLVKGFYPSDIAV EWESNGQPENNYKTTPPVLDSDGSFFLYSKLTVDKSRWQ QGNVFSCSVMHEALHNHYTQKSLSLSP |
| 155 | Fc IgG1, caucasian allotype | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSCDKTHTCPPCPAPEL LGGPSVFLFPPKPKDTLMISRTPEVTCVVVDVSHEDPEV KFNWYVDGVEVHNAKTKPREEQYNSTYRVVSVLTVLHQD WLNGKEYKCKVSNKALPAPIEKTISKAKGQPREPQVYTL PPSRDELTKNQVSLTCLVKGFYPSDIAVEWESNGQPENN YKTTPPVLDSDGSFFLYSKLTVDKSRWQQGNVFSCSVMH EALHNHYTQKSLSLSPGK |
| 156 | Fc IgG1, afroamerican allotype | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSCDKTHTCPPCPAPEL LGGPSVFLFPPKPKDTLMISRTPEVTCVVVDVSHEDPEV KFNWYVDGVEVHNAKTKPREEQYNSTYRVVSVLTVLHQD WLNGKEYKCKVSNKALPAPIEKTISKAKGQPREPQVYTL PPSREEMTKNQVSLTCLVKGFYPSDIAVEWESNGQPENN YKTTPPVLDSDGSFFLYSKLTVDKSRWQQGNVFSCSVMH EALHNHYTQKSLSLSPGK |
| 157 | Fc IgG2 | ASTKGPSVFPLAPCSRSTSESTAALGCLVKDYFPEPVTV SWNSGALTSGVHTFPAVLQSSGLYSLSSVVTVPSSNFGT QTYTCNVDHKPSNTKVDKTVERKCCVECPPCPAPPVAGP SVFLFPPKPKDTLMISRTPEVTCVVVDVSHEDPEVQFNW YVDGVEVHNAKTKPREEQFNSTFRVVSVLTVVHQDWLNG KEYKCKVSNKGLPAPIEKTISKTKGQPREPQVYTLPPSR EEMTKNQVSLTCLVKGFYPSDISVEWESNGQPENNYKTT PPMLDSDGSFFLYSKLTVDKSRWQQGNVFSCSVMHEALH NHYTQKSLSLSPGK |
| 158 | Fc IgG3 | ASTKGPSVFPLAPCSRSTSGGTAALGCLVKDYFPEPVTV SWNSGALTSGVHTFPAVLQSSGLYSLSSVVTVPSSSLGT QTYTCNVNHKPSNTKVDKRVELKTPLGDTTHTCPRCPEP KSCDTPPPCPRCPEPKSCDTPPPCPRCPEPKSCDTPPPC PRCPAPELLGGPSVFLFPPKPKDTLMISRTPEVTCVVVD VSHEDPEVQFKWYVDGVEVHNAKTKPREEQYNSTFRVVS VLTVLHQDWLNGKEYKCKVSNKALPAPIEKTISKTKGQP REPQVYTLPPSREEMTKNQVSLTCLVKGFYPSDIAVEWE SSGQPENNYNTTPPMLDSDGSFFLYSKLTVDKSRWQQGN IFSCSVMHEALHNRFTQKSLSLSPGK |
| 159 | Fc IgG4 | ASTKGPSVFPLAPCSRSTSESTAALGCLVKDYFPEPVTV SWNSGALTSGVHTFPAVLQSSGLYSLSSVVTVPSSSLGT KTYTCNVDHKPSNTKVDKRVESKYGPPCPSCPAPEFLGG PSVFLFPPKPKDTLMISRTPEVTCVVVDVSQEDPEVQFN WYVDGVEVHNAKTKPREEQFNSTYRVVSVLTVLHQDWLN GKEYKCKVSNKGLPSSIEKTISKAKGQPREPQVYTLPPS QEEMTKNQVSLTCLVKGFYPSDIAVEWESNGQPENNYKT TPPVLDSDGSFFLYSRLTVDKSRWQEGNVFSCSVMHEAL HNHYTQKSLSLSLGK |
| 160 | Hinge full | DKTHTCPXCP with X being S or P |
| 161 | Hinge middle | HTCPXCP with X being S or P |
| 162 | Hinge short | CPXCP with X being S or P |
| 163 | CH1 connector C-terminal end | EPKSC |
| 164 | CH1 connector C-terminal end D-variant | EPKSCD |

TABLE B-continued (Sequences):

| SEQ ID NO: | Name | Sequence |
|---|---|---|
| 165 | CH1 connector C-terminal end S-variant | EPKSCS |
| 166 | CH1 domain | ASTKGPSVFPLAPSSKSTSGGTAALGCLVKDYFPE PVTVSWNSGALTSGVHTFPAVLQSSGLYSLSSVVT VPSSSLGTQTYICNVNHKPSNTKVDKKV |

The following numbered paragraphs (paras) describe aspects of the present invention:

1. A bispecific antigen binding molecule, comprising (a) at least two antigen binding domains capable of specific binding to OX40, (b) an antigen binding domain capable of specific binding to Fibroblast Activation Protein (FAP) comprising a heavy chain variable region ($V_H$FAP) comprising (i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region (VLFAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8, and (c) a Fc region composed of a first and a second subunit capable of stable association.

2. The bispecific antigen binding molecule of para 1, wherein the Fc region comprises one or more amino acid substitution that reduces the binding affinity of the antibody to an Fc receptor and/or effector function.

3. The bispecific antigen binding molecule of paras 1 or 2, wherein the antigen binding domain capable of specific binding to FAP comprises a heavy chain variable region ($V_H$FAP) comprising an amino acid sequence that is at least about 90% identical to the amino acid sequence of SEQ ID NO:9, and a light chain variable region ($V_L$FAP) comprising an amino acid sequence that is at least about 90% identical to the amino acid sequence of SEQ ID NO:10.

4. The bispecific antigen binding molecule of any one of paras 1 to 3, wherein the antigen binding domain capable of specific binding to FAP comprises a heavy chain variable region ($V_H$FAP) comprising an amino acid sequence selected from the group consisting of SEQ ID NO:15, SEQ ID NO:16, SEQ ID NO:17, SEQ ID NO:18. SEQ ID NO:19 and SEQ ID NO:20, and a light chain variable region ($V_L$FAP) comprising an amino acid sequence selected from the group consisting of SEQ ID NO:21, SEQ ID NO:22, SEQ ID NO:23, SEQ ID NO:24, SEQ ID NO:25 and SEQ ID NO:26.

5. The bispecific antigen binding molecule of any one of paras 1 to 4, wherein the antigen binding domain capable of specific binding to FAP comprises (a) a heavy chain variable region ($V_H$FAP) comprising the amino acid sequence of SEQ ID NO:15 and a light chain variable region ($V_L$FAP) comprising the amino acid sequence of SEQ ID NO:21, or (b) a heavy chain variable region ($V_H$FAP) comprising the amino acid sequence of SEQ ID NO:16 and a light chain variable region ($V_L$FAP) comprising the amino acid sequence of SEQ ID NO:21, or (c) a heavy chain variable region ($V_H$FAP) comprising the amino acid sequence of SEQ ID NO:16 and a light chain variable region ($V_L$FAP) comprising the amino acid sequence of SEQ ID NO:22, or (d) a heavy chain variable region ($V_H$FAP) comprising the amino acid sequence of SEQ ID NO:19 and a light chain variable region ($V_L$FAP) comprising the amino acid sequence of SEQ ID NO:25.

6. The bispecific antigen binding molecule of any one of paras 1 to 4, wherein the antigen binding domain capable of specific binding to FAP comprises a heavy chain variable region ($V_H$FAP) comprising the amino acid sequence of SEQ ID NO:15 and a light chain variable region ($V_L$FAP) comprising the amino acid sequence of SEQ ID NO:21.

7. The bispecific antigen binding molecule of any one of paras 1 to 6, wherein the antigen binding domain capable of specific binding to OX40 comprises (i) a heavy chain variable region ($V_H$OX40) comprising (i) CDR-H1 comprising the amino acid sequence of SEQ ID NO:27, (ii) CDR-H2 comprising the amino acid sequence of SEQ ID NO:28, and (iii) CDR-H3 comprising the amino acid sequence of SEQ ID NO:29, and a light chain variable region ($V_L$OX40) comprising (iv) CDR-L1 comprising the amino acid sequence of SEQ ID NO:30, (v) CDR-L2 comprising the amino acid sequence of SEQ ID NO:31, and (vi) CDR-L3 comprising the amino acid sequence of SEQ ID NO:32, or (ii) a heavy chain variable region ($V_H$OX40) comprising (i) CDR-H1 comprising the amino acid sequence of SEQ ID NO:35, (ii) CDR-H2 comprising the amino acid sequence of SEQ ID NO:36, and (iii) CDR-H3 comprising the amino acid sequence of SEQ ID NO:37, and a light chain variable region ($V_L$OX40) comprising (iv) CDR-L1 comprising the amino acid sequence of SEQ ID NO:38, (v) CDR-L2 comprising the amino acid sequence of SEQ ID NO:39, and (vi) CDR-L3 comprising the amino acid sequence of SEQ ID NO:40, or (iii) a heavy chain variable region ($V_H$OX40) comprising (i) CDR-H1 comprising the amino acid sequence of SEQ ID NO:43, (ii) CDR-H2 comprising the amino acid sequence of SEQ ID NO:44, and (iii) CDR-H3 comprising the amino acid sequence of SEQ ID NO:45, and a light chain variable region ($V_L$OX40) comprising (iv) CDR-L1 comprising the amino acid sequence of SEQ ID NO:46, (v) CDR-L2 comprising the amino acid sequence of SEQ ID NO:47, and (vi) CDR-L3 comprising the amino acid sequence of SEQ ID NO:48, or (iv) a heavy chain variable region ($V_H$OX40) comprising (i) CDR-H1 comprising the amino acid sequence of SEQ ID NO:51, (ii) CDR-H2 comprising the amino acid sequence of SEQ ID NO:52, and (iii) CDR-H3 comprising the amino acid sequence of SEQ ID NO:53, and a light chain variable region (V$_L$OX40) comprising (iv) CDR-L1 comprising the amino acid sequence of SEQ ID NO:54, (v) CDR-L2 comprising the amino acid sequence of SEQ ID NO:55, and (vi) CDR-L3 comprising the amino acid sequence of SEQ ID NO:56.

8. The bispecific antigen binding molecule of any one of paras 1 to 7, wherein the antigen binding domain capable of specific binding to OX40 comprises
  (i) a heavy chain variable region (V$_H$OX40) comprising the amino acid sequence of SEQ ID NO:33 and a light chain variable region (V$_L$OX40) comprising the amino acid sequence of SEQ ID NO:34, or
  (ii) a heavy chain variable region (V$_H$OX40) comprising the amino acid sequence of SEQ ID NO:41 and a light chain variable region (V$_L$OX40) comprising the amino acid sequence of SEQ ID NO:42, or
  (iii) a heavy chain variable region (V$_H$OX40) comprising the amino acid sequence of SEQ ID NO:49 and a light chain variable region (V$_L$OX40) comprising the amino acid sequence of SEQ ID NO:50, or
  (iv) a heavy chain variable region (V$_H$OX40) comprising the amino acid sequence of SEQ ID NO:57 and a light chain variable region (V$_L$OX40) comprising the amino acid sequence of SEQ ID NO:58.

9. The bispecific antigen binding molecule of any one of paras 1 to 7, wherein the antigen binding domain capable of specific binding to OX40 comprises
  (i) a heavy chain variable region (V$_H$OX40) comprising the amino acid sequence of SEQ ID NO:59 and a light chain variable region (V$_L$OX40) comprising the amino acid sequence of SEQ ID NO:34, or
  (ii) a heavy chain variable region (V$_H$OX40) comprising the amino acid sequence of SEQ ID NO:60 and a light chain variable region (V$_L$OX40) comprising the amino acid sequence of SEQ ID NO:34, or
  (iii) a heavy chain variable region (V$_H$OX40) comprising the amino acid sequence of SEQ ID NO:61 and a light chain variable region (V$_L$OX40) comprising the amino acid sequence of SEQ ID NO:34.

10. The bispecific antigen binding molecule of any one of paras 1 to 9, wherein the Fc region is an IgG, particularly an IgG1 Fc region or an IgG4 Fc region.

11. The bispecific antigen binding molecule of any one of paras 1 to 10, wherein the Fc region is of human IgG1 subclass with the amino acid mutations L234A, L235A and P329G (numbering according to Kabat EU index).

12. The bispecific antigen binding molecule of any one of paras 1 to 15, wherein the bispecific antigen binding molecule comprises
  (a) at least two Fab fragments capable of specific binding to OX40 each connected to the N-terminus of one of subunits of the Fc region, and
  (b) one cross-Fab fragment capable of specific binding to FAP fused to the C-terminus of one of subunits of the Fc region, and
  (c) the Fc region composed of a first and a second subunit capable of stable association.

13. The bispecific antigen binding molecule of para 12, wherein the VH-Ckappa chain of the cross-fab fragment capable of specific binding to FAP is fused to the C-terminus of one of subunits of the Fc region.

14. The bispecific antigen binding molecule of any one of paras 1 to 13, consisting of
  (aa) a first Fab fragment capable of specific binding to OX40,
  (ab) a second Fab fragment capable of specific binding to OX40,
  (b) a cross-Fab fragment capable of specific binding to FAP fused to the C-terminus of one of subunits of the Fc region, and
  (c) the Fc region composed of a first and a second subunit capable of stable association, wherein the first Fab fragment (ai) is fused at the C-terminus of the VH-CH1 chain to the N-terminus of the first subunit and the second Fab fragment (aii) is fused at the C-terminus of the VH-CH1 chain to the N-terminus of the second subunit.

15. The bispecific antigen binding molecule of any one of paras 1 to 13, consisting of
  (aa) a first Fab fragment capable of specific binding to OX40,
  (ab) a second Fab fragment capable of specific binding to OX40,
  (ac) a third Fab fragment capable of specific binding to OX40,
  (b) a cross-Fab fragment capable of specific binding to FAP fused to the C-terminus of one of subunits of the Fc region, and
  (c) the Fc region composed of a first and a second subunit capable of stable association, wherein the second Fab fragment (ab) is fused at the C-terminus of the VH-CH1 chain to the N-terminus of the VH-CH1 chain of the first Fab fragment (aa), which is in turn fused at its C-terminus to the N-terminus of the first subunit, and the third Fab fragment (ac) is fused at the C-terminus of the Fab heavy chain to the N-terminus of the second subunit.

16. The bispecific antigen binding molecule of any one of paras 1 to 13, consisting of
  (aa) a first Fab fragment capable of specific binding to OX40,
  (ab) a second Fab fragment capable of specific binding to OX40,
  (ac) a third Fab fragment capable of specific binding to OX40,
  (ad) a fourth Fab fragment capable of specific binding to OX40,
  (b) a cross-Fab fragment capable of specific binding to FAP fused to the C-terminus of one of subunits of the Fc region, and
  (c) the Fc region composed of a first and a second subunit capable of stable association, wherein the second Fab fragment (ab) is fused at the C-terminus of the VH-CH1 chain to the N-terminus of the VH-CH1 chain of the first Fab fragment (aa), which is in turn fused at its C-terminus to the N-terminus of the first subunit, and the fourth Fab fragment (ad) is fused at the C-terminus of the VH-CH1 chain to the N-terminus of the VH-CH1 chain of the third Fab fragment (ac), which is in turn fused at its C-terminus to the N-terminus of the second subunit.

17. Isolated nucleic acid encoding the bispecific antigen binding molecule of any one of paras 1 to 16.

18. An expression vector comprising the isolated nucleic acid of para 17.

19. A host cell comprising isolated nucleic acid of para 17 or the expression vector of para 18.

20. A method of producing a bispecific antigen binding molecule, comprising culturing the host cell of para 19 under conditions suitable for the expression of the bispecific antigen binding molecule, and isolating the bispecific antigen binding molecule.

21. A pharmaceutical composition comprising the bispecific antigen binding molecule of any one of paras 1 to 16 and a pharmaceutically acceptable carrier.

22. The pharmaceutical composition of para 21, further comprising an additional therapeutic agent.

23. The bispecific antigen binding molecule of any one of paras 1 to 16, or the pharmaceutical composition of para 21, for use as a medicament.

24. The bispecific antigen binding molecule of any one of claims 1 to 16, or the pharmaceutical composition of para 21, for use
(i) in inducing immune stimulation,
(ii) in stimulating tumor-specific T cell response,
(iii) in causing apoptosis of tumor cells,
(iv) in the treatment of cancer,
(v) in delaying progression of cancer,
(vi) in prolonging the survival of a patient suffering from cancer,
(vii) in the treatment of infections.

25. The bispecific antigen binding molecule of any one of paras 1 to 16, or the pharmaceutical composition of para 21, for use in the treatment of cancer.

26. The bispecific antigen binding molecule according to any one of paras 1 to 16 or the pharmaceutical composition according to para 21 for use in the treatment of cancer, wherein the bispecific antigen binding molecule or pharmaceutical composition is for administration in combination with a chemotherapeutic agent, radiation and/or other agents for use in cancer immunotherapy.

27. Use of the bispecific antigen binding molecule of any one of paras 1 to 16, or the pharmaceutical composition of para 21, in the manufacture of a medicament for the treatment of cancer.

28. A method of treating an individual having cancer comprising administering to the individual an effective amount of the bispecific antigen binding molecule of any one of paras 1 to 16, or the pharmaceutical composition of para 21.

EXAMPLES

The following are examples of methods and compositions of the invention. It is understood that various other embodiments may be practiced, given the general description provided above.

Recombinant DNA Techniques

Standard methods were used to manipulate DNA as described in Sambrook et al., Molecular cloning: A laboratory manual; Cold Spring Harbor Laboratory Press, Cold Spring Harbor, N.Y., 1989. The molecular biological reagents were used according to the manufacturer's instructions. General information regarding the nucleotide sequences of human immunoglobulin light and heavy chains is given in: Kabat, E. A. et al., (1991) Sequences of Proteins of Immunological Interest, Fifth Ed., NIH Publication No 91-3242.

DNA Sequencing

DNA sequences were determined by double strand sequencing.

Gene Synthesis

Desired gene segments were either generated by PCR using appropriate templates or were synthesized by Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells.

Protein Purification

Proteins were purified from filtered cell culture supernatants referring to standard protocols. In brief, antibodies were applied to a Protein A Sepharose column (GE healthcare) and washed with PBS. Elution of antibodies was achieved at pH 3.0 followed by immediate neutralization of the sample. Aggregated protein was separated from monomeric antibodies by ion exchange chromatography (Poros XS) with equilibration buffer 20 mM His, pH 5.5, 1.47 mS/cm and elution buffer 20 mM His, 500 mM NaCl, pH 5.5, 49.1 mS/cm, (gradient: to 100% elution buffer in 60 CV). In some cases a size exclusion chromatography (Superdex 200, GE Healthcare) in PBS or in 20 mM Histidine, 140 mM NaCl pH 6.0 was subsequently performed. Monomeric antibody fractions were pooled, concentrated (if required) using e.g., a MILLIPORE Amicon Ultra (30 MWCO) centrifugal concentrator, frozen and stored at −20° C. or −80° C. Part of the samples were provided for subsequent protein analytics and analytical characterization e.g. by SDS-PAGE, size exclusion chromatography (SEC) or mass spectrometry.

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer was used.

CE-SDS

Purity, antibody integrity and molecular weight of bispecific and control antibodies were analyzed by CE-SDS using microfluidic Labchip technology (Caliper Life Science, USA). 5 μl of protein solution was prepared for CE-SDS analysis using the HT Protein Express Reagent Kit according manufacturer's instructions and analysed on LabChip GXII system using a HT Protein Express Chip. Data were analyzed using LabChip GX Software version 3.0.618.0.

Analytical Size Exclusion Chromatography

The aggregate content of the molecule was analyzed using a BioSuite 250 5 μm.7.8×300 analytical size-exclusion column (Tosoh) in 200 mM K-Phosophat 250 mM KCl pH 6.2 running buffer at 25° C.

Mass Spectrometry

This section describes the characterization of the multispecific antibodies with VH/VL or CH/CL exchange (CrossMabs) with emphasis on their correct assembly. The expected primary structures were analyzed by electrospray ionization mass spectrometry (ESI-MS) of the deglycosylated intact CrossMabs and deglycosylated/FabALACTICA or alternatively deglycosylated/GingisKHAN digested CrossMabs.

The CrossMabs were deglycosylated with N-Glycosidase F in a phosphate or Tris buffer at 37° C. for up to 17 h at a protein concentration of 1 mg/ml. The FabALACTICA or GingisKHAN (Genovis AB; Sweden) digestions were performed in the buffers supplied by the vendor with 100 μg deglycosylated CrossMabs. Prior to mass spectrometry the samples were desalted via HPLC on a Sephadex G25 column (GE Healthcare). The total mass was determined via ESI-MS on a maXis 4G UHR-QTOF MS system (Bruker Daltonik) equipped with a TriVersa NanoMate source (Advion).

Example 1

Generation of New Antibodies Against Fibroblast Activation Protein (FAP)

1.1 Immunization of Mice

Balb/c and NMRI mice were used for immunization. The animals were housed according to the Appendix A "Guidelines for accommodation and care of animals" in an AAALACi accredited animal facility. All animal immunization protocols and experiments were approved by the Government of Upper Bavaria (permit number 55.2-1-54-2531-19-10) and performed according to the German Animal Welfare Act and the Directive 2010/63 of the European Parliament and Council. Balb/c and NMRI mice (n=5), 6-8 week old, received four rounds of immunization with recombinant produced extracellular domain of human fibroblast activation protein alpha (amino acid 27-759; accession number NP_004451) covalently attached to a His tag (SEQ ID NO:62). Before each immunization, mice were anesthetized with a gas mixture of oxygen and isoflurane. For the first immunization, 30 µg protein dissolved in PBS, pH 7.4, were mixed with an equal volume of CFA (BD Difco, #263810) and administered intraperitoneal (i.p.) Another 10 µg of protein emulsified in Abisco adjuvant was administered subcutaneously (s.c.) at week 6. A third dose of 5 µg protein without adjuvant was administered i.p. at week 10. Finally, three days prior to the preparation of splenocytes for antibody development using hybridoma technology, the mice were subjected to intravenous (i.v.) booster immunizations with 50 µg of protein. Serum was tested for antigen-specific total IgG antibody production by ELISA. Three days after the final immunization, mice were euthanized and the spleen was isolated aseptically and prepared for hybridoma generation. The mouse lymphocytes were isolated and fused with a mouse myeloma cell line using PEG based standard protocols to generate hybridomas. The resulting hybridoma cells were plated at approximately $10^4$ in flat bottom 96 well micro titer plate, followed by about two weeks of incubation in selective medium and then screened for the production of antigen-specific antibodies. Once extensive hybridoma growth occurs, the antibody secreting hybridomas are replated. Hybridoma supernatants were screened for specific binding to recombinant human fibroblast activation protein alpha (huFAP) by ELISA, followed by evaluation of kinetic binding parameters to recombinant huFAP using Biacore measurement.

Culture of hybridomas: Generated muMAb hybridomas were cultured in RPMI 1640 (PAN—Catalogue No. (Cat. No.) P04-17500) supplemented with 2 mM L-glutamine (GIBCO—Cat. No. 35050-038), 1 mM Na-Pyruvat (GIBCO—Cat. No. 11360-039), 1×NEAA (GIBCO—Cat. No. 11140-035), 10% FCS (PAA—Cat. No. A15-649), 1× Pen Strep (Roche—Cat. No. 1074440), 1× Nutridoma CS (Roche—Cat. No. 1363743), 50 µM Mercaptoethanol (GIBCO—Cat. No. 31350-010) and 50 U/ml IL 6 mouse (Roche—Cat. No. 1 444 581) at 37° C. and 5% $CO_2$.

1.2 Format-Depending Binding of Anti-huFAP Clones

In order to determine if the binding properties of the anti-FAP clones are not lost when they are C-terminally fused to an Fc domain, constructs comprising a Fc knob chain and a Fc hole chain wherein the VH domain is fused to the C-terminus of the Fc knob chain and the VL domain is fused to the C-terminus of the Fc hole chain (C-terminal VH/VL fusion) and constructs comprising a Fc knob chain and a Fc hole chain wherein the whole Fab is fused with its VH domain to the C-terminus of the Fc knob chain (C-terminal Fab fusion) were prepared. The Fc knob chain has the amino acid sequence of SEQ ID NO:82 and the Fc hole chain has the amino acid sequences of SEQ ID NO:83.

The affinity of the constructs towards biotinylated recombinant human FAP and biotinylated recombinant cynomolgus FAP as compared to the antibodies is shown in Table 3 below.

TABLE 3

Affinity to human FAP and cynomolgus FAP as measured by Biacore

| | Affinity to human FAP KD [nM] | | | Affinity to cynomolgus FAP KD [nM] | | |
|---|---|---|---|---|---|---|
| clone | free Fab | C-terminal Fab fusion | C-terminal VH/VL fusion | IgG | C-terminal Fab fusion | C-terminal VH/VL fusion |
| 209 | 0.31 | 1.52 | 42.40 | 0.33 | 1.60 | 50.00 |
| 210 | 0.07 | 0.17 | 3.95 | 0.12 | 0.20 | 3.44 |
| 211 | 0.28 | 1.20 | 10.90 | 0.32 | 1.30 | 11.40 |
| 212 | 0.12 | 0.62 | 5.72 | 0.14 | 0.64 | 6.19 |
| 214 | 0.06 | 0.19 | 2.49 | 0.09 | 0.21 | 2.77 |

Cellular binding of the constructs to FAP-transfected HEK cells has also been determined as described herein before. The $EC_{50}$ values are shown in Table 4. The C-terminal fusion constructs of all anti-FAP antibodies were able to bind to human and cynomolgus FAP, however the constructs wherein the whole Fab is fused with its VH domain to the C-terminus of the Fc knob chain were superior to those wherein the VH domain is fused to the C-terminus of the Fc knob chain and the VL domain is fused to the C-terminus of the Fc hole chain.

TABLE 4

Cellular binding to huFAP expressing cells

| | Cellular binding to human FAP $EC_{50}$ [µg/ml] | | | Cellular binding to cynomolgus FAP $EC_{50}$ [µg/ml] | | |
|---|---|---|---|---|---|---|
| clone | IgG | C-terminal Fab fusion | C-terminal VH/VL fusion | IgG | C-terminal Fab fusion | C-terminal VH/VL fusion |
| 209 | 0.15 | 1.2 | 5.7 | 0.4 | 1.1 | 7.9 |
| 210 | 0.13 | 1.8 | 9.0 | 0.4 | 1.3 | 7.1 |
| 211 | 0.20 | 3.7 | 9.3 | 0.3 | 2.9 | 6.7 |
| 212 | 0.12 | 2.8 | 8.8 | 0.3 | 2.3 | 11.1 |
| 214 | 0.09 | 1.7 | 9.4 | 0.3 | 1.3 | 3.6 |

1.3 Competitive Cellular Binding of Anti-huFAP Antibodies to FAP Clone 4B9 and 28H1

The resulting clones were tested for their binding behavior in comparison to FAP clone 4B9. The generation and preparation of FAP clones 4B9 and 28H1 is described in WO 2012/020006 A2, which is incorporated herein by reference. To determine whether the murine FAP clones recognize different epitopes as clones 4B9 and 28H1 a competition binding to human FAP expressed on transfected HEK cells was performed.

Briefly, the target cells were harvested with Cell Dissociation buffer, washed with FACS Buffer (PBS+2% FCS+5 mM EDTA+0.25% sodium acide) and seeded into 96-U bottom plates (1×105 cells/well). Unlabeled primary anti-human FAP antibodies (mu IgG1) were added to the cells (final concentrations 60 µg/ml to 0.2 µg/ml; 1:3 dilutions) and incubated for 20 min at 4° C. before addition of AlexaFluor647-labeled anti FAP antibody 4B9 or 28H1 (end concentration 20 µg/ml). After 30 min incubation at 4° C., cells were washed, fixed and the fluorescent signal intensities of the AF647-labeled clones 4B9 and 28H1 were measured using a Miltenyi MACSQuant.

10 hybridoma-derived murine antibodies were identified (named clones 209, 210, 211, 212, 213, 214, 215, 216, 217 and 218) that did not compete for binding with anti FAP antibodies 4B9 or 28H1.

1.4 Target Binding Specificity of Anti-huFAP Murine Antibodies

Fibroblast activation protein (FAP, FAP-α, seprase) is a type II transmembrane serine protease, belonging to the prolyl oligopeptidase family. This family comprises serine proteases that cleave peptides preferentially after proline residues. Other important members of this family that are expressed in the human proteome are prolyl oligopeptidase (PREP) and the dipeptidyl peptidases (DPPs). DPP-IV is the closest homolog of FAP. In contrast to FAP, DPP-IV is ubiquitously expressed and plays a role in various biological processes such as T cell co-stimulation, chemokine biology, glucose metabolism, and tumorigenesis and therefore the desired anti-human FAP antibodies should not bind to human DPP-IV.

Binding to human FAP and human DPP-IV was determined by flow cytometry using human FAP or human DPPIV-transfected HEK cells. Briefly, the target cells were harvested with Cell Dissociation buffer, washed with FACS Buffer (PBS+2% FCS+5 mM EDTA+0.25% sodium acide) and seeded into 96-U bottom plates (1×$10^5$ cells/well). Unlabeled primary antibodies were added to the cells (final concentration 10 µg/ml) and incubated for 30 min at 4° C. After washing, cells were incubated with a goat anti-mouse IgG-PE F(ab')2 (Serotec) for 30 min at 4° C. in the dark. Afterwards, cells were washed, fixed and measured using a BD FACS Canto™ II. No unspecific binding to human DPP-IV was detected for any of the 10 hybridoma derived anti-human FAP antibodies.

1.5 Generation of Anti-huFAP Antibodies in huIgG1_LALA_PG Format

The DNA sequences of the new anti-huFAP antibodies were determined with standard sequencing methods. Based on the VH and VL domains new anti-FAP antibodies were expressed as huIgG1 antibodies with an effector silent Fc (P329G; L234, L235A) to abrogate binding to Fcγ receptors according to the method described in WO 2012/130831 A1. In detail, antibodies were expressed by transient transfection of HEK293-F cells grown in suspension with expression vectors encoding the different peptide chains. Transfection into HEK293-F cells (Invitrogen, USA) was performed according to the cell supplier's instructions using Maxiprep (Qiagen, Germany) preparations of the antibody vectors, F17 based medium (Invitrogen, USA), PEIpro (Polyscience Europe GmbH) and an initial cell density of 1-2 million viable cells/ml in serum free FreeStyle 293 expression medium (Invitrogen). Cell culture supernatants were harvested after 7 days of cultivation in shake flasks or stirred fermenters by centrifugation at 14000 g for 30 minutes and filtered through a 0.22 µm filter.

The antibodies were purified from cell culture supernatants by affinity chromatography using MabSelectSure-Sepharose™ (GE Healthcare, Sweden) chromatography. Briefly, sterile filtered cell culture supernatants were captured on a MabSelect SuRe resin equilibrated with PBS buffer (10 mM $Na_2HPO_4$, 1 mM $KH_2PO_4$, 137 mM NaCl and 2.7 mM KCl, pH 7.4), washed with equilibration buffer and eluted with 25 mM citrate, pH 3.0. After neutralization with 1 M Tris pH 9.0, aggregated protein was separated from monomeric antibody species by size exclusion chromatography (Superdex 200, GE Healthcare) in 20 mM histidine, 140 mM NaCl, pH 6.0. Monomeric protein fractions were pooled, concentrated if required using e.g. a MILLIPORE Amicon Ultra (30 KD MWCO) centrifugal concentrator and stored at −80° C. Sample aliquots were used for subsequent analytical characterization e.g. by CE-SDS, size exclusion chromatography, mass spectrometry and endotoxin determination.

1.6 Cellular Binding of Anti-huFAP Antibodies

The binding of anti-FAP antibodies with a human IgG1 P329G LALA Fc to human FAP was determined by flow cytometry using human FAP-transfected HEK cells. Briefly, the target cells were harvested with Cell Dissociation buffer, washed with FACS Buffer (PBS+2% FCS+5 mM EDTA+0.25% sodium acide) and seeded into 96-U bottom plates (1×105 cells/well). Unlabeled primary antibodies were added to the cells (final concentrations 10 µg/ml to 0.64 ng/ml; 1:5 dilutions) and incubated for 30 min at 4° C. After washing, cells were incubated with a PE-conjugated AffiPure F(ab)$_2$ Fragment Goat anti-human IgG, Fcγ specific (Jackson Immunoresearch) for 30 min at 4° C. in the dark. Afterwards, cells were washed, fixed and measured using a BD FACS LSR Fortessa™.

All anti-FAP antibodies showed similar binding to human FAP as seen before. The $EC_{50}$ values of selected binders are shown in Table 1 below.

TABLE 1

Cellular binding of anti-FAP antibodies to huFAP expressing cells

| Sample ID | clone | $EC_{50}$ [µg/ml] cellular binding to FAP-transfected HEK cells |
|---|---|---|
|  | 4B9 | 0.089 |
| P1AD9427 | 209 | 0.145 |
| P1AD9436 | 210 | 0.125 |
| P1AD9437 | 211 | 0.198 |
| P1AD9438 | 212 | 0.118 |
| P1AD9440 | 214 | 0.086 |

1.7 Cellular Internalization of Anti-huFAP Antibodies

Internalization of FAP binders was determined using human FAP-transfected HEK cells as targets. Briefly, the target cells were harvested with Cell Dissociation buffer, washed with cold FACS Buffer (PBS+2% FCS+5 mM EDTA+0.25% sodium acide) and resuspended at 1.5×$10^6$ cells/ml in cold FACS Buffer. Cells were distributed in 15 ml tubes (each tube containing 3×10⁶ cells in 2 ml). 2 ml of anti-human FAP antibody solutions were added to the cells (final concentration 20 µg/ml) and incubated for 45 min at 4° C. Afterwards, cells were washed, resuspended in cold FACS Buffer and cells for time point "0" were seeded immediately into 96-U bottom plates (1.5×10⁵ cells/well) and kept at 4° C. whereas all other cells were centrifuged, resuspended in warm RPMI1640 medium containing 10% FCS and 1% Glutamax (1.5×10⁶ cells/ml) and shifted to 37° C. in a humidified incubator (5% $CO_2$). After each indicated time point, 100 µl/tube of cell suspension was transferred to plates, immediately cooled down with cold FACS Buffer and stored in the fridge until all time points have been collected. After collection of all time points, cells were washed with cold FACS Buffer and incubated with PE-labeled secondary antibody for 30 min at 4° C. Afterwards, cells were washed, fixed and and measured using a BD FACS Canto™ II.

The signals caused by the labeled secondary antibody stayed nearly constant over time, which means that no loss of antibody was observed over time, none of the tested anti-hu FAP antibodies was internalized.

1.8 Binding Kinetics of Anti-huFAP Antibodies

To evaluate human FAP binding kinetics, biotinylated human FAP was immobilized on a Series S Biacore CAPture Chip (GE Healthcare 28-9202-34) according to the manufacturer's instructions, resulting in a surface density of approximately 20 resonance units (RU). As running and dilution buffer, HBS-P+ (10 mM HEPES, 150 mM NaCl pH 7.4, 0.05% Surfactant P20) was used. A dilution series of anti-huFAP Fabs (3.7-300 nM, 1:3 dilution) was successively injected for 120 s each, dissociation was monitored for 1800 s at a flow rate of 30 µl/min (single cycle kinetics). The surface was regenerated by injecting 6 M guanidine-HCl, 0.25 M NaOH for 120 s. Bulk refractive index differences were corrected by subtracting blank injections and by subtracting the response obtained from the control flow cell without captured human FAP. Curve fitting was performed using the 1:1 Langmuir binding model within the Biacore evaluation software. The affinity data are shown in Table 2 below.

TABLE 2

Affinity of anti-FAP Fabs to human FAP as measured by Biacore

| Sample ID | clone | ka (1/Ms) | kd (1/s) | KD |
|---|---|---|---|---|
|  | 4B9_Fab | 1.82E+06 | 7.80E-04 | 430 pM |
| P1AD9427_Fab | 209 | 3.50E+06 | 1.77E-03 | 510 pM |
| P1AD9436_Fab | 210 | 1.87E+06 | <E-06 | <10 pM |
| P1AD9437_Fab | 211 | 8.13E+05 | 4.61E-05 | 60 pM |
| P1AD9438_Fab | 212 | 1.06E+06 | <E-06 | <10 pM |
| P1AD9440_Fab | 214 | 1.99E+06 | <E-06 | <10 pM |

1.9 Competitive Binding of Anti-Human FAP Clones as Determined by Biacore

Figure 3A:
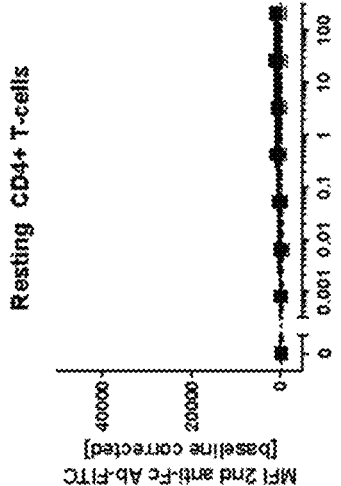
FIG. 3A to FIG. 3F show the cellular binding of bispecific antigen binding molecules comprising OX40 clone 8H9 in different formats and in comparison with a bispecific antigen binding molecule comprising OX40 clone 49B4 in 4+1 format (P1AE6838). Human FAP negative tumor cells (A549-NLR)(FIG. 3F), FAP positive fibroblasts (NIH/3T3-huFAP-clone 19) (FIG. 3E), OX40 positive activated PBMC (activated CD4 and CD8 T cells, FIG. 3A and FIG. 3C, respectively) as well as OX40 negative resting PBMC (resting CD4 and CD8 T cells, FIG. 3B and FIG. 3D, respectively) were incubated with indicated serial dilutions of test antibody detected then by fluorescently labeled 2nd antibody against human Fcγ. Living cells were gated and the mean fluorescence intensity of the secondary antibody, baseline corrected by the media-only sample, was plotted from duplicates. Error bars indicate the SEM. The clone 8H9 bound with subnanomolar affinity to OX40 positive cells and with comparable strength as tri- and bivalent antibody.
Figure 3B:
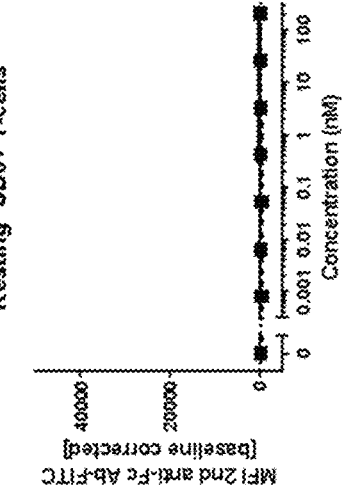
Figure 3C:
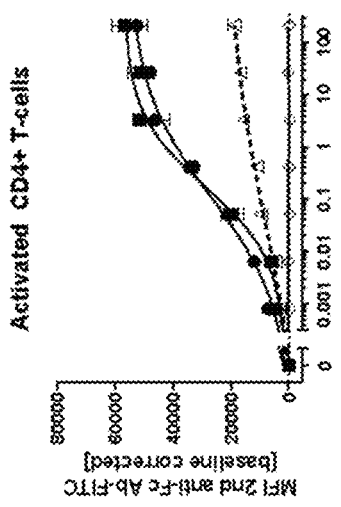

Epitope binning was performed using a surface plasmon resonance (SPR) based assay on a Biacore T200 instrument. FAP antigen was captured by an immobilized anti-His antibody. In a first step the FAP-binder was injected until saturation. A second FAP-binder was injected subsequently. The assay design is schematically shown in FIG. 3C. An increase in binding signal after addition of the second antibody indicates its binding to a different epitope from the first antibody. No additional binding indicated that the first and the second antibody recognize the same epitope region.

An anti-His antibody (GE Healthcare Kit 28-9950-56) with a concentration of 20 µg/ml was immobilized by amine coupling (GE Healthcare Kit BR-1000-50) to the surface of a CM5 sensor chip (GE Healthcare BR-1005-30). Injection time was 600 seconds at a flow rate of 10 µl/min to yield 12000 response units (RU) on two flow cells, one used as reference and one used as active flow cell. Running buffer was HBS-N (GE Healthcare BR-1006-70). For the measurement PBS-P+(GE Healthcare 28-9950-84) was used as running and dilution buffer. Flow cell temperature was set to 25° C., sample compartment to 12° C. The flow rate was set to 10 µl/min for the whole run.

His-tagged FAP antigen was captured with a concentration of 20 µg/ml for 180 seconds on the active flow cell. The first and second antibody (FAP-binder) were injected successively, each for 120 seconds at a concentration of 10 µg/ml over both flow cells. After each cycle the surface was regenerated with 10 mM glycine pH1.5 for 60 seconds (GE Healthcare BR-1003-54).

The results are shown in Table 5 below:

TABLE 5

Competitive Binding of anti-FAP antibodies to 4B9

|  | 4B9 | 209 | 210 | 211 | 212 | 214 |
|---|---|---|---|---|---|---|
| 4B9 | Competitive Binding | Simultaneous Binding | Simultaneous Binding | Simultaneous Binding | Simultaneous Binding | Simultaneous Binding |
| 209 | Simultaneous Binding | Competitive Binding | Simultaneous Binding | Simultaneous Binding | Simultaneous Binding | Simultaneous Binding |
| 210 | Simultaneous Binding | Simultaneous Binding | Competitive Binding | Competitive Binding | Competitive Binding | Competitive Binding |
| 211 | Simultaneous Binding | Simultaneous Binding | Competitive Binding | Competitive Binding | Competitive Binding | Competitive Binding |
| 212 | Simultaneous Binding | Simultaneous Binding | Competitive Binding | Competitive Binding | Competitive Binding | Competitive Binding |
| 214 | Simultaneous Binding | Simultaneous Binding | Competitive Binding | Competitive Binding | Competitive Binding | Competitive Binding |

Thus, three epitope bins were identified. None of the anti-FAP antibodies did compete for binding with antibody 4B9 (Epitope bin 1). Antibodies 210, 211, 212 and 214 competed with each other for binding and thus form one group (Epitope bin 3), whereas antibody 209 did not compete for binding with any other of the antibodies (Epitope bin 2).

1.9 Thermal Stability Evaluation of Anti-FAP Antibodies

Samples are prepared at a concentration of 1 mg/mL in 20 mM Histidine/Histidine chloride, 140 mM NaCl, pH 6.0, transferred into an optical 384-well plate by centrifugation through a 0.4 µm filter plate and covered with paraffine oil. The hydrodynamic radius is measured repeatedly by dynamic light scattering on a DynaPro Plate Reader (Wyatt) while the samples are heated with a rate of 0.05° C./min from 25° C. to 80° C. Alternatively, samples were transferred into a 10 µL micro-cuvette array and static light scattering data as well as fluorescence data upon excitation with a 266 nm laser were recorded with an Optim1000 instrument (Avacta Inc.), while they were heated at a rate of 0.1° C./min from 25° C. to 90° C. The aggregation onset temperature ($T_{agg}$) is defined as the temperature at which the hydrodynamic radius (DLS) or the scattered light intensity (Optim1000) starts to increase. The melting temperature is defined as the inflection point in a graph showing fluorescence intensity vs. wavelength. The aggregation onset temperatures of selected anti-FAP antibodies is shown in Table 6.

TABLE 6

Aggregation onset temperatures of anti-FAP antibodies

|  | 4B9 | 209 | 210 | 212 | 214 |
|---|---|---|---|---|---|
| $T_{agg}$ (° C.) | 60 | 66 | 61 | 67 | 61 |

The anti-FAP clone 212 was chosen for humanization as it binds with a comparable high affinity to human FAP as antibody 4B9 and showed favorable properties for the development. In silico analysis of its sequences indicated only one predicted degradation hotspot (Trp at position 401). The sequences of murine clone 212 are shown in Table 7.

1.10 Humanization of Anti-FAP Clone 212

1.10.1 Methodology

Suitable human acceptor frameworks were identified by querying a BLASTp database of human V- and J-region sequences for the murine input sequences (cropped to the variable part). Selective criteria for the choice of human acceptor framework were sequence homology, same or similar CDR lengths, and the estimated frequency of the human germline, but also the conservation of certain amino acids at the VH-VL domain interface. Following the germline identification step, the CDRs of the murine input sequences were grafted onto the human acceptor framework regions. Each amino acid difference between these initial CDR grafts and the parental antibodies was rated for possible impact on the structural integrity of the respective variable region, and "back mutations" towards the parental sequence were introduced whenever deemed appropriate. The structural assessment was based on Fv region homology models of both the parental antibody and the humanization variants, created with an in-house antibody structure homology modeling protocol implemented using the Biovia Discovery Studio Environment, version 17R2. In some humanization variants, "forward mutations" were included, i.e., amino acid exchanges that change the original amino acid occurring at a given CDR position of the parental binder to the amino acid found at the equivalent position of the human acceptor germline. The aim is to increase the overall human character of the humanization variants (beyond the framework regions) to further reduce the immunogenicity risk.

An in silico tool developed in-house was used to predict the VH-VL domain orientation of the paired VH and VL humanization variants (see WO 2016/062734). The results were compared to the predicted VH-VL domain orientation of the parental binders to select for framework combinations which are close in geometry to the original antibodies. The rationale is to detect possible amino acid exchanges in the VH-VL interface region that might lead to disruptive changes in the pairing of the two domains that in turn might have detrimental effects on the binding properties.

TABLE 7

Amino acid sequences of the variable domains of murine anti-FAP clone 212

| Description | Sequence | Seq ID No |
|---|---|---|
| FAP(212) VH | EVLLQQSGPELVKPGASVKIACKASGYTLT<u>DYNMD</u>WVRQS HGKSLEWIG<u>DIYPNTGGTIYNQKFKG</u>KATLTIDKSSSTAY MDLRSLTSEDTAVYYCTR<u>FRGIHYAMDY</u>WGQGTSVTSS | 9 |
| FAP(212) VL | DIVLTQSPVSLAVSLGQRATISC<u>RASESVDNYGLSFIN</u>WF QQKPGQPPKLLIY<u>GTSNRGS</u>GVPARFSGSGSGTDFSLNIH PMEEDDTAMYFC<u>QQSNEVPYT</u>FGGGTNLEIK | 10 |

1.10.2 Choice of Acceptor Framework and Adaptations Thereof

The following acceptor frameworks were chosen:

TABLE 8

Acceptor framework

| Murine V-region germline | Graft variant | Choice of human acceptor V-region germline | Identity to human V-region germline after grafting (BLASTp): |
|---|---|---|---|
| FAP (212) VH | VH1 | IGHV1-46*01 | 87.8% |
|  | VH2 | IGHV3-23*03 | 82.7% |
| FAP (212) VL | VL1 | IGKV3-11*01 | 85.1% |
|  | VL2 | IGKV1-39*01 | 82.8% |

Post-CDR3 framework regions were adapted from human IGHJ germline IGHJ6*01/02 (YYYYYGMDVWGQGTTVTVSS, SEQ ID NO:84) and human IGKJ germline IGKJ4*01/02 (LTFGGGTKVEIK, SEQ ID NO:85). The part relevant for the acceptor framework is indicated in bold script.

Based on structural considerations, back mutations from the human acceptor framework to the amino acid in the parental binder were introduced at positions H43 (Q>K), H44 (G>S), H48 (M>I), H71 (R>I), H73 (T>K), H93 (A>T) [VH1], H49 (S>G), H71 (R>I), H73 (N>K), H78 (L>A), H93 (A>T), H94 (K>R) [VH2], L36 (Y>F), L43 (A>P), L87 (Y>F) [VL1] and L36 (Y>F), L42 (K>Q), L43 (A>P), L85 (T>M), L87 (Y>F) [VL2].

Furthermore, the positions H60 (N>A), H64 (K>Q) [VH1], H60 (N>A), H61 (Q>D), H62 (K>S), H63 (F>V) [VH2], L33 (I>L), L34 (N>A) [VL1] and L27b (V>I), L33 (I>L) [VL2] were identified as promising candidates for forward mutations. All positions are given in the Kabat EU numbering scheme.

TABLE 9 list of variants

| Variant name | Back/forward mutations | Identity to human V-region germline (BLASTp) |
|---|---|---|
| VH1G1a | bM48I, bR71I, bA93T | 84.7% |
| VH1G2a | bQ43K, bG44S, bM48I, bR71I, bT73K, bA93T | 81.6% |
| VH1G3a | bM48I, fN60A, fK64Q, bR71I, bA93T | 86.7% |
| VH2G1a | bS49G, bA93T, bK94R | 79.6% |
| VH2G2a | bS49G, bR71I, bN73K, bL78A, bA93T, bK94R | 76.5% |
| VH2G3a | bS49G, fN60A, fQ61D, fK62S, fF63V, bA93T, bK94R | 83.7% |
| VL1G1a | bY36F, bY87F | 83% |
| VL1G2a | bY36F, bA43P, bY87F | 81.9% |
| VL1G3a | fI33L, fN34A, bY36F, bY87F | 85.1% |
| VL2G1a | bY36F, bY87F | 80.8% |
| VL2G2a | bY36F, bK42Q, bA43P, bT85M, bY87F | 77.8% |
| VL2G3a | fV27bI, fI33L, bY36F, bY87F | 82.8% |

Note: Back mutations are prefixed with b, forward mutations with f, e.g., bM48I refers to a back mutation (human germline amino acid to parental antibody amino acid) from methionine to isoleucine at position 48 (Kabat).

The resulting VH and VL domains of humanized FAP antibodies based on the acceptor framework can be found in Table 10 below.

TABLE 10

Amino acid sequences of the VH and VL domains of humanized FAP antibodies

| Description | Sequence | Seq ID No |
|---|---|---|
| VH1G1a | QVQLVQSGAEVKKPGASVKVSCKASGYTLT<u>DYNMD</u>WVRQ APGQGLEWIG<u>DIYPNTGGTIYNQKFKG</u>RVTMTIDTSTST VYMELSSLRSEDTAVYYCTR<u>FRGIHYAMDY</u>WGQGTTVTV SS | 15 |
| VH1G2a | QVQLVQSGAEVKKPGASVKVSCKASGYTLT<u>DYNMD</u>WVRQ APGKSLEWIG<u>DIYPNTGGTIYNQKFKG</u>RVTMTIDKSTST VYMELSSLRSEDTAVYYCTR<u>FRGIHYAMDY</u>WGQGTTVTV SS | 16 |
| VH1G3a | QVQLVQSGAEVKKPGASVKVSCKASGYTLT<u>DYNMD</u>WVRQ APGQGLEWIG<u>DIYPNTGGTIYAQKFQG</u>RVTMTIDTSTST VYMELSSLRSEDTAVYYCTR<u>FRGIHYAMDY</u>WGQGTTVTV SS | 17 |
| VH2G1a | EVQLLESGGGLVQPGGSLRLSCAASGYTLT<u>DYNMD</u>WVRQ APGKGLEWVG<u>DIYPNTGGTIYNQKFKG</u>RFTISRDNSKNT LYLQMNSLRAEDTAVYYCTR<u>FRGIHYAMDY</u>WGQGTTVTV SS | 18 |
| VH2G2a | EVQLLESGGGLVQPGGSLRLSCAASGYTLT<u>DYNMD</u>WVRQ APGKGLEWVG<u>DIYPNTGGTIYNQKFKG</u>RFTISIDKSKNT AYLQMNSLRAEDTAVYYCTR<u>FRGIHYAMDY</u>WGQGTTVTV SS | 19 |
| VH2G3a | EVQLLESGGGLVQPGGSLRLSCAASGYTLT<u>DYNMD</u>WVRQ APGKGLEWVG<u>DIYPNTGGTIYADSVKG</u>RFTISRDNSKNT LYLQMNSLRAEDTAVYYCTR<u>FRGIHYAMDY</u>WGQGTTVTV SS | 20 |

TABLE 10-continued

Amino acid sequences of the VH and VL domains of humanized FAP antibodies

| Description | Sequence | Seq ID No |
|---|---|---|
| VL1G1a | EIVLTQSPATLSLSPGERATLSCRASESVDNYGLSFINW FQQKPGQAPRLLIYGTSNRGSGIPARFSGSGSGTDFTLT ISSLEPEDFAVYFCQQSNEVPYTFGGGTKVEIK | 21 |
| VL1G2a | EIVLTQSPATLSLSPGERATLSCRASESVDNYGLSFINW FQQKPGQPPRLLIYGTSNRGSGIPARFSGSGSGTDFTLT ISSLEPEDFAVYFCQQSNEVPYTFGGGTKVEIK | 22 |
| VL1G3a | EIVLTQSPATLSLSPGERATLSCRASESVDNYGLSFLAW FQQKPGQAPRLLIYGTSNRGSGIPARFSGSGSGTDFTLT ISSLEPEDFAVYFCQQSNEVPYTFGGGTKVEIK | 23 |
| VL2G1a | DIQMTQSPSSLSASVGDRVTITCRASESVDNYGLSFINW FQQKPGKAPKLLIYGTSNRGSGVPSRFSGSGSGTDFTLT ISSLQPEDFATYFCQQSNEVPYTFGGGTKVEIK | 24 |
| VL2G2a | DIQMTQSPSSLSASVGDRVTITCRASESVDNYGLSFINW FQQKPGQPPKLLIYGTSNRGSGVPSRFSGSGSGTDFTLT ISSLQPEDFAMYFCQQSNEVPYTFGGGTKVEIK | 25 |
| VL2G3a | DIQMTQSPSSLSASVGDRVTITCRASESIDNYGLSFLNW FQQKPGKAPKLLIYGTSNRGSGVPSRFSGSGSGTDFTLT ISSLQPEDFATYFCQQSNEVPYTFGGGTKVEIK | 26 |

1.10.3 New Humanized Anti-FAP Fabs

Based on the new humanization variants of VH and VL new anti-FAP Fabs were expressed.

TABLE 11

Nomenclature for VH/VL combinations expressed as Fabs

| | VL1G1a | VL1G2a | VL1G3a | VL2G1a | VL2G2a | VL2G3a |
|---|---|---|---|---|---|---|
| VH1G1a | P1AE1689 | | | | | |
| VH1G2a | P1AE1690 | P1AE1693 | | | | |
| VH1G3a | | | | | | |
| VH2G1a | | | | | | |
| VH2G2a | | | | | | P1AE1702 |
| VH2G3a | | | | | | |

The affinity of the new humanized anti-FAP variants based on clone 212 was analyzed in comparison with anti-FAP antibody 4B9. Furthermore, the humanness of the humanized variants was calculated and its aggregation onset temperature was measured.

TABLE 12

Affinity of humanization variants of clone 212 as measured by Biacore

| Sample ID | ka (1/Ms) | kd (1/s) | KD (pM) | T ½ (min) | Identity to hu V germline | $T_{agg}$ [° C.] |
|---|---|---|---|---|---|---|
| P1AE1689_Fab | 4.43E+05 | 4.21E−05 | 95 | 274 | 83/84.7 | 72.7 |
| P1AE1690_Fab | 5.51E+05 | 6.30E−05 | 114 | 183 | 83/81.7 | 75.4 |
| P1AE1693_Fab | 5.30E+05 | 7.18E−05 | 135 | 161 | 81.9/81.7 | 75.4 |
| P1AE1702_Fab | 5.02E+05 | 1.07E−04 | 213 | 108 | 77.8/76.5 | 71.6 |
| 4B9_Fab | 7.47E+05 | 2.08E−04 | 279 | 55 | | 60 |

Antibody P1AE1689 is called FAP antibody 1G1a in the following.

1.11 FcRn/Heparin Binding and in Silico Charge Distribution

The charge distribution of antibodies 4B9 and 1G1a in PBS, pH 7.4, was calculated in an in-silico model. According to the model, 4B9 has a large positive patch which is sometimes correlated with increased heparin binding. 1G1a, on the other hand, shows a large negative charge patch which might be indicative for weak heparin interaction.

These predictions were confirmed by chromatography of both antibodies using a FcRn affinity column and pH gradient as well as a heparin affinity column and pH gradient. WO 2015/140126 discloses a method for the prediction of the in vivo half-life of an antibody based on the retention time determined on an FcRn affinity chromatography column, whereas heparin binding correlates with non-specific interactions with cell surface structures.

Example 2

Generation and Production of Bispecific Antigen Binding Molecules Targeting OX40 and Fibroblast Activation Protein (FAP)

2.1 Generation of Bispecific Antigen Binding Molecules Targeting OX40 and Fibroblast Activation Protein (FAP)

The cDNAs encoding variable heavy and light chain domains of anti OX40 antibodies (clones 49B4, 8H9 and CLC563 as described in WO 2017/055398 A2, or MOXR0916 as described in WO 2015/153513 A1) as well as anti-FAP antibody 1G1a were cloned in frame with the corresponding constant heavy or light chains of human IgG1 in suitable expression plasmids. Expression of heavy and light chain is driven by a chimeric MPSV promoter consisting of the MPSV core promoter and a CMV enhancer element. The expression cassette also contains a synthetic polyA signal at the 3' end of the cDNAs. In addition the plasmid vectors harbor an origin of replication (EBV OriP) for episomal maintenance of the plasmids.

Bispecific OX40-FAP antibodies were prepared in 2+1, 3+1 and 4+1 format consisting of two, three or four OX40 binding moieties combined with one FAP binding arm at the C-terminus of an Fc (FIG. 1A to FIG. 1C) The bispecific OX40-FAP antibodies included anti-FAP clone 212 (1G1a) as described in Example 1. To generate the 2+1, 3+1 and the 4+1 antigen binding molecules the knob-into-hole technology was used to achieve heterodimerization. The S354C/T366W mutations were introduced in the first heavy chain HC1 (Fc knob heavy chain) and the Y349C/T366S/L368A/Y407V mutations were introduced in the second heavy chain HC2 (Fc hole heavy chain). In the 2+1, 3+1 and 4+1 antigen binding molecules the CrossMab technology as described in WO 2010/145792 A1 ensured correct light chain pairing. Independent of the bispecific format, in all cases an effector silent Fc domain (P329G; L234A, L235A) was used to abrogate binding to Fcγ receptors according to the method described in WO 2012/130831 A1. Sequences of the bispecific molecules are shown in Table 13 below.

All genes were transiently expressed under control of a chimeric MPSV promoter consisting of the MPSV core promoter combined with the CMV promoter enhancer fragment. The expression vector also contained the oriP region for episomal replication in EBNA (Epstein Barr Virus Nuclear Antigen) containing host cells.

TABLE 13

| Amino acid sequences of the bispecific antigen binding molecules | | |
|---|---|---|
| Molecule | Sequence | Seq ID No |
| P1AE6838 OX40(49B4) x FAP (1G1a) (4 + 1) | | |
| OX40(49B4) VHCH1- OX40(49B4) VHCH1-Fc knob_PGLALA- FAP(1G1a) VHCL | QVQLVQSGAEVKKPGSSVKVSCKASGGTFSSYAISVR QAPGQGLEWMGGIIPIFGTANYAQKFQGRVTITADKST STAYMELSSLRSEDTAVYYCAREYYRGPYDYWGQGTTV TVSSASTKGPSVFPLAPSSKSTSGGTAALGCLVEDYFP EPVTVSWNSGALTSGVHTFPAVLQSSGLYSLSSVVTVP SSSLGTQTYICNVNHKPSNTKVDEKVEPKSCGGGGSGG SGGQVQLVQSGAEVKKPGSSVKVSCKASGGTFSSYAIS WVRQAPGQGLEWMGGIIPIFGTANYAQKFQGRVTITAD KSTSTAYMELSSLRSEDTAVYYCAREYYRGPYDYWGQG TTVTVSSASTKGPSVFPLAPSSKSTSGGTAALGCLVED YFPEPVTVSWNSGALTSGVHTFPAVLQSSGLYSLSSVV TVPSSSLGTQTYICNVNHKPSNTKVDEKVEPKSCDKTH TCPPCPAPEAAGGPSVFLFPPKPKDTLMISRTPEVTCV VVDVSHEDPEVKFNWYVDGVEVHNAKTKPREEQYNSTY RVVSVLTVLHQDWLNGKEYKCKVSNKALGAPIEKTISK AKGQPREPQVYTLPPCRDELTKNQVSLWCLVKGFYPSD IAVEWESNGQPENNYKTTPPVLDSDGSFFLYSKLTVDK SRWQQGNVFSCSVMHEALHNHYTQKSLSLSPGGGGGSG GGGSGGGGSGGSGGQVQLVQSGAEVKKPGASVKVSCKA SGYILTDYNMDWVRQAPGQGLEWIGDIYPNIGGTIYNQ KFKGRVTMTIDTSTSTVYMELSSLRSEDTAVYYCTRFR GIHYAMDYWGQGTTVTVSSASVAAPSVFIFPPSDEQLK SGTASVVCLLNNFYPREAKVQWKVDNALQSGNSQESVT EQDSKDSTYSLSSILTLSKADYEKHKVYACEVTHQGLS SPVTKSFNRGEC | 86 |
| OX40(49B4) light chain | DIQMTQSPSTLSASVGDRVTITCRASQSISSWLAWYQQ KPGKAPKLLIYDASSLESGVPSRFSGSGSGTEFTLTIS SLQPDDFATYYCQQYSSQPYTFGQGTKVEIKRTVAAPS VFIFPPSDRKLKSGTASVVCLLNNFYPREAKVQWKVDN ALQSGNSQESVTEQDSKDSTYSLSSTLTLSKADYEKHK VYACEVTHQGLSSPVTKSFNRGEC | 87 |

TABLE 13-continued

Amino acid sequences of the bispecific antigen binding molecules

| Molecule | Sequence | Seq ID No |
|---|---|---|
| FAP(1G1a) VLCH1-light chain | EIVLTQSPATLSLSPGERATLSCRASESVDNYGLSFIN WFQQKPGQAPRLLIYGTSNRGSGIPARFSGSGSGTDFT LIISSLEPEDFAVYFCQQSNEVPYTFGGGTKVEIKSSA STKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKKVEPKSC | 88 |
| OX40(49B4) VHCH1-OX40(49B4) VHCH1-Fc hole PGLALA | QVQLVQSGAEVKKPGSSVKVSCKASGGTFSSYAISVR QAPGQGLEWMGGIIPIFGTANYAQKFQGRVTITADKST STAYMELSSLRSEDTAVYYCAREYYRGPYDYWGQGTTV TVSSASTKGPSVFPLAPSSKSTSGGTAALGCLVEDYFP EPVTVSWNSGALTSGVHTFPAVLQSSGLYSLSSVVTVP SSSLGTQTYICNVNHKPSNTKVDEKVEPKSCGGGGSGG SGGGQVQLVQSGAEVKKPGSSVKVSCKASGGTFSSYAIS WVRQAPGQGLEWMGGIIPIFGTANYAQKFQGRVTITAD KSTSTAYMELSSLRSEDTAVYYCAREYYRGPYDYWGQG TTVTVSSASTKGPSVFPLAPSSKSTSGGTAALGCLVED YFPEPVTVSWNSGALTSGVHTFPAVLQSSGLYSLSSVV TVPSSSLGTQTYICNVNHKPSNTKVDEKVEPKSCDKTH TCPPCPAPEAAGGPSVFLFPPKPKDTLMISRTPEVTCV VVDVSHEDPEVKFNWYVDGVEVHNAKTKPREEQYNSTY RVVSVLTVLHQDWLNGKEYKCKVSNKALGAPIEKTISK AKGQPREPQVCTLPPSRDELIKNQVSLSCAVKGFYPSD IAVEWESNGQPENNYKTTPPVLDSDGSFFLVSKLTVDK SRWQQGNVFSCSVMHEALHNHYTQKSLSLSPG | 89 |

P1AE8786
OX40(49B4) x FAP (1G1 a) (3 + 1)

| OX40(49B4) VHCH1-OX40(49B4) VHCH1-Fc knob_PGLALA-FAP(1G1a) VHCL | QVQLVQSGAEVKKPGSSVKVSCKASGGTFSSYAISVR QAPGQGLEWMGGIIPIFGTANYAQKFQGRVTITADKST STAYMELSSLRSEDTAVYYCAREYYRGPYDYWGQGTTV TVSSASTKGPSVFPLAPSSKSTSGGTAALGCLVEDYFP EPVTVSWNSGALTSGVHTFPAVLQSSGLYSLSSVVTVP SSSLGTQTYICNVNHKPSNTKVDEKVEPKSCGGGGSGG SGGGQVQLVQSGAEVKKPGSSVKVSCKASGGTFSSYAIS WVRQAPGQGLEWMGGIIPIFGTANYAQKFQGRVTITAD KSTSTAYMELSSLRSEDTAVYYCAREYYRGPYDYWGQG TTVTVSSASTKGPSVFPLAPSSKSTSGGTAALGCLVED YFPEPVTVSWNSGALTSGVHTFPAVLQSSGLYSLSSVV TVPSSSLGTQTYICNVNHKPSNTKVDEKVEPKSCDKTH TCPPCPAPEAAGGPSVFLFPPKPKDTLMISRTPEVTCV VVDVSHEDPEVKFNWYVDGVEVHNAKTKPREEQYNSTY RVVSVLTVLHQDWLNGKEYKCKVSNKALGAPIEKTISK AKGQPREPQVYTLPPCRDELTKNQVSLWCLVKGFYPSD IAVEWESNGQPENNYKTTPPVLDSDGSFFLYSKLTVDK SRWQQGNVFSCSVMHEALHNHYTQKSLSLSPGGGGGSG GGGSGGGGSGGSGGQVQLVQSGAEVKKPGASVKVSCKA SGYILTDYNMDWVRQAPGQGLEWIGDIYPNIGGTIYNQ KFKGRVTMTIDTSTSTVYMELSSLRSEDTAVYYCTRFR GIHYAMDYWGQGTTVTVSSASVAAPSVFIFPPSDEQLK SGTASVVCLLNNFYPREAKVQWKVDNALQSGNSQESVT EQDSKDSTYSLSSILTLSKADYEKHKVYACEVTHQGLS SPVTKSFNRGEC | 86 |
| OX40(49B4) light chain | DIQMTQSPSTLSASVGDRVTITCRASQSISSWLAWYQQ KPGKAPKLLIYDASSLESGVPSRFSGSGSGTEFTLTIS SLQPDDFATYYCQQYSSQPYTFGQGTKVEIKRTVAAPS VFIFPPSDRKLKSGTASVVCLLNNFYPREAKVQWKVDN ALQSGNSQESVTEQDSKDSTYSLSSTLTLSKADYEKHK VYACEVTHQGLSSPVTKSFNRGEC | 87 |
| FAP(1G1a) VLCH1-light chain | EIVLTQSPATLSLSPGERATLSCRASESVDNYGLSFIN WFQQKPGQAPRLLIYGTSNRGSGIPARFSGSGSGTDFT LIISSLEPEDFAVYFCQQSNEVPYTFGGGTKVEIKSSA STKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKKVEPKSC | 88 |

TABLE 13-continued

Amino acid sequences of the bispecific antigen binding molecules

| Molecule | Sequence | Seq ID No |
|---|---|---|
| OX40(49B4) VHCH1-Fc hole_PGLALA | QVQLVQSGAEVKKPGSSVKVSCKASGGTFSSYAISVR QAPGQGLEWMGGIIPIFGTANYAQKFQGRVTITADKST STAYMELSSLRSEDTAVYYCAREYYRGPYDYWGQGTTV TVSSASTKGPSVFPLAPSSKSTSGGTAALGCLVEDYFP EPVTVSWNSGALTSGVHTFPAVLQSSGLYSLSSVVTVP SSSLGTQTYICNVNHKPSNTKVDEKVEPKSCDKTHTCP PCPAPEAAGGPSVFLFPPKPKDTLMISRTPEVTCVVVD VSHEDPEVKFNWYVDGVEVHNAKTKPREEQYNSTYRVV SVLTVLHQDWLNGKEYKCKVSNKALGAPIEKTISKAKG QPREPQVCTLPPSRDELTKNQVSLSCAVKGFYPSDIAV EWESNGQPENNYKTTPPVLDSDGSFFLVSKLTVDKSRW QQGNVFSCSVMHEALHNHYTQKSLSLSPG | 90 |

P1AE6840
OX40(49B4) x FAP (1G1a) (2 + 1)

| OX40(49B4) VHCH1-Fc knob_PGLALA-FAP(1G1a) VHCL | QVQLVQSGAEVKKPGSSVKVSCKASGGTFSSYAISVR QAPGQGLEWMGGIIPIFGTANYAQKFQGRVTITADKST STAYMELSSLRSEDTAVYYCAREYYRGPYDYWGQGTTV TVSSASTKGPSVFPLAPSSKSTSGGTAALGCLVEDYFP EPVTVSWNSGALTSGVHTFPAVLQSSGLYSLSSVVTVP SSSLGTQTYICNVNHKPSNTKVDEKVEPKSCDKTHTCP PCPAPEAAGGPSVFLFPPKPKDTLMISRTPEVTCVVVD VSHEDPEVKFNWYVDGVEVHNAKTKPREEQYNSTYRVV SVLTVLHQDWLNGKEYKCKVSNKALGAPIEKTISKAKG QPREPQVYTLPPCRDELTKNQVSLWCLVKGFYPSDIAV EWESNGQPENNYKTTPPVLDSDGSFFLYSKLTVDKSRW QQGNVFSCSVMHEALHNHYTQKSLSLSPGGGGGSGGGG SGGGGSGGSGGQVQLVQSGAEVKKPGASVKVSCKASGY TLTDYNMDWVRQAPGQGLEWIGDIYPNTGGTIYNQKFK GRVTMTIDTSTSTVYMELSSLRSEDTAVYYCTRFRGIH YAMDYWGQGTTVTVSSASVAAPSVFIFPPSDEQLKSGT ASVVCLLNNFYPREAKVQWKVDNALQSGNSQESVTEQD SKDSTYSLSSTLTLSKADYEKHKVYACEVTHQGLSSPV TKSFNRGEC | 91 |
| OX40(49B4) light chain | DIQMTQSPSTLSASVGDRVTITCRASQSISSWLAWYQQ KPGKAPKLLIYDASSLESGVPSRFSGSGSGTEFTLTIS SLQPDDFATYYCQQYSSQPYTFGQGTKVEIKRTVAAPS VFIFPPSDRKLKSGTASVVCLLNNFYPREAKVQWKVDN ALQSGNSQESVTEQDSKDSTYSLSSTLTLSKADYEKHK VYACEVTHQGLSSPVTKSFNRGEC | 87 |
| FAP(1G1a) VLCH1-light chain | EIVLTQSPATLSLSPGERATLSCRASESVDNYGLSFIN WFQQKPGQAPRLLIYGTSNRGSGIPARFSGSGSGTDFT LIISSLEPEDFAVYFCQQSNEVPYTFGGGTKVEIKSSA STKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKKVEPKSC | 88 |
| OX40(49B4) VHCH1-Fc hole_PGLALA | QVQLVQSGAEVKKPGSSVKVSCKASGGTFSSYAISVR QAPGQGLEWMGGIIPIFGTANYAQKFQGRVTITADKST STAYMELSSLRSEDTAVYYCAREYYRGPYDYWGQGTTV TVSSASTKGPSVFPLAPSSKSTSGGTAALGCLVEDYFP EPVTVSWNSGALTSGVHTFPAVLQSSGLYSLSSVVTVP SSSLGTQTYICNVNHKPSNTKVDEKVEPKSCDKTHTCP PCPAPEAAGGPSVFLFPPKPKDTLMISRTPEVTCVVVD VSHEDPEVKFNWYVDGVEVHNAKTKPREEQYNSTYRVV SVLTVLHQDWLNGKEYKCKVSNKALGAPIEKTISKAKG QPREPQVCTLPPSRDELTKNQVSLSCAVKGFYPSDIAV EWESNGQPENNYKTTPPVLDSDGSFFLVSKLTVDKSRW QQGNVFSCSVMHEALHNHYTQKSLSLSPG | 90 |

TABLE 13-continued

Amino acid sequences of the bispecific antigen binding molecules

| Molecule | Sequence | Seq ID No |
|---|---|---|
| P1AF7205 OX40(CLC563) x FAP (1G1a_EPKSCD) (4 + 1) C-terminal crossfab fusion ||| 
| OX40(CLC563) VHCH1-OX40(CLC563) VHCH1-Fc knob PGLALA-FAP(1G1a) VHCL | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCALDVGAFDYWGQGALVTVSSASTKGPSVFPLAPSSKSTSGGTAALGCLVEDYFPEPVTVSWNSGALTSGVHTFPAVLQSSGLYSLSSVVTVPSSSLGTQTYICNVNHKPSNTKVDEKVEPKSCGGGGSGGGSGEVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCALDVGAFDYWGQGALVTVSSASTKGPSVFPLAPSSKSTSGGTAALGCLVEDYFPEPVTVSWNSGALTSGVHTFPAVLQSSGLYSLSSVVTVPSSSLGTQTYICNVNHKPSNTKVDEKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGGGGGSGGGGSGGGGSGGSGGQVQLVQSGAEVKKPGASVKVSCKASGYTLTDYNMDWVRQAPGQGLEWIGDIYPNTGGTIYNQKFKGRVTMTIDTSTSTVYMELSSLRSEDTAVYYCTRFRGIHYAMDYWGQGTTVTVSSASVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 92 |
| OX40(CLC563) light chain | EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPLTFGQGTKVEIKRTVAAPSVFIFPPSDRKLKSGTASVVCLLNNFYPREAKVQWKVDNALQSGNSQESVTEQDSKDSTYSLSSTLTLSKADYEKHKVYACEVTHQGLSSPVTKSFNRGEC | 93 |
| FAP(1G1a) VLCH1-light chain (EPKSCD) | EIVLTQSPATLSLSPGERATLSCRASESVDNYGLSFINWFQQKPGQAPRLLIYGTSNRGSGIPARFSGSGSGTDFTLIISSLEPEDFAVYFCQQSNEVPYTFGGGTKVEIKSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCD | 94 |
| OX40(CLC563) VHCH1-OX40(CLC563) VHCH1-Fc hole_PGLALA | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCALDVGAFDYWGQGALVTVSSASTKGPSVFPLAPSSKSTSGGTAALGCLVEDYFPEPVTVSWNSGALTSGVHTFPAVLQSSGLYSLSSVVTVPSSSLGTQTYICNVNHKPSNTKVDEKVEPKSCGGGGSGGGSGEVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCALDVGAFDYWGQGALVTVSSASTKGPSVFPLAPSSKSTSGGTAALGCLVEDYFPEPVTVSWNSGALTSGVHTFPAVLQSSGLYSLSSVVTVPSSSLGTQTYICNVNHKPSNTKVDEKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPG | 95 |

TABLE 13-continued

Amino acid sequences of the bispecific antigen binding molecules

| Molecule | Sequence | Seq ID No |
|---|---|---|
| | P1AF7217 OX40(CLC563) x FAP (1G1a_EPKSCS) (4 + 1) C-terminal crossfab fusion | |
| OX40(CLC563) VHCH1-OX40(CLC563) VHCH1-Fc knob_PGLALA-FAP(1G1a) VHCL | EVQLLESGGGLVQPGGSLRLSCAASGFTFSSYAMSWVR QAPGKGLEWVSAISGSGGSTYYADSVKGRFTISRDNSK NTLYLQMNSLRAEDTAVYYCALDVGAFDYWGQGALVTV SSASTKGPSVFPLAPSSKSTSGGTAALGCLVEDYFPEP VTVSWNSGALTSGVHTFPAVLQSSGLYSLSSVVTVPSS SLGTQTYICNVNHKPSNTKVDEKVEPKSCGGGGSGGSG GEVQLLESGGGLVQPGGSLRLSCAASGFTFSSYAMSWV RQAPGKGLEWVSAISGSGGSTYYADSVKGRFTISRDNS KNTLYLQMNSLRAEDTAVYYCALDVGAFDYWGQGALVT VSSASTKGPSVFPLAPSSKSTSGGTAALGCLVEDYFPE PVTVSWNSGALTSGVHTFPAVLQSSGLYSLSSVVTVPS SSLGTQTYICNVNHKPSNTKVDEKVEPKSCDKTHTCPP CPAPEAAGGPSVFLFPPKPKDTLMISRTPEVTCVVVDV SHEDPEVKFNWYVDGVEVHNAKTKPREEQYNSTYRVVS VLTVLHQDWLNGKEYKCKVSNKALGAPIEKTISKAKGQ PREPQVYTLPPCRDELTKNQVSLWCLVKGFYPSDIAVE WESNGQPENNYKTTPPVLDSDGSFFLYSKLTVDKSRWQ QGNVFSCSVMHEALHNHYTQKSLSLSPGGGGGSGGGGS GGGGSGGSGGQVQLVQSGAEVKKPGASVKVSCKASGYT LTDYNMDWVRQAPGQGLEWIGDIYPNTGGTIYNQKFKG RVTMTIDTSTSTVYMELSSLRSEDTAVYYCTRFRGIHY AMDYWGQGTTVTVSSASVAAPSVFIFPPSDEQLKSGTA SVVCLLNNFYPREAKVQWKVDNALQSGNSQESVTEQDS KDSTYSLSSTLTLSKADYEKHKVYACEVTHQGLSSPVT KSFNRGEC | 92 |
| OX40(CLC563) light chain | EIVLTQSPGTLSLSPGERATLSCRASQSVSSSYLAWYQ QKPGQAPRLLIYGASSRATGIPDRFSGSGSGTDFTLTI SRLEPEDFAVYYCQQYGSSPLTFGQGTKVEIKRTVAAP SVFIFPPSDRKLKSGTASVVCLLNNFYPREAKVQWKVD NALQSGNSQESVTEQDSKDSTYSLSSTLTLSKADYEKH KVYACEVTHQGLSSPVTKSFNRGEC | 93 |
| FAP(1G1a) VLCH1-light chain (EPKSCS) | EIVLTQSPATLSLSPGERATLSCRASESVDNYGLSFIN WFQQKPGQAPRLLIYGTSNRGSGIPARFSGSGSGTDFT LTISSLEPEDFAVYFCQQSNEVPYTFGGGTKVEIKSSA STKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKKVEPKSCS | 96 |
| OX40(CLC563) VHCH1-OX40(CLC563) VHCH1-Fc hole_PGLALA | EVQLLESGGGLVQPGGSLRLSCAASGFTFSSYAMSWVR QAPGKGLEWVSAISGSGGSTYYADSVKGRFTISRDNSK NTLYLQMNSLRAEDTAVYYCALDVGAFDYWGQGALVTV SSASTKGPSVFPLAPSSKSTSGGTAALGCLVEDYFPEP VTVSWNSGALTSGVHTFPAVLQSSGLYSLSSVVTVPSS SLGTQTYICNVNHKPSNTKVDEKVEPKSCGGGGSGGSG GEVQLLESGGGLVQPGGSLRLSCAASGFTFSSYAMSWV RQAPGKGLEWVSAISGSGGSTYYADSVKGRFTISRDNS KNTLYLQMNSLRAEDTAVYYCALDVGAFDYWGQGALVT VSSASTKGPSVFPLAPSSKSTSGGTAALGCLVEDYFPE PVTVSWNSGALTSGVHTFPAVLQSSGLYSLSSVVTVPS SSLGTQTYICNVNHKPSNTKVDEKVEPKSCDKTHTCPP CPAPEAAGGPSVFLFPPKPKDTLMISRTPEVTCVVVDV SHEDPEVKFNWYVDGVEVHNAKTKPREEQYNSTYRVVS VLTVLHQDWLNGKEYKCKVSNKALGAPIEKTISKAKGQ PREPQVCTLPPSRDELTKNQVSLSCAVKGFYPSDIAVE WESNGQPENNYKTTPPVLDSDGSFFLVSKLTVDKSRWQ QGNVFSCSVMHEALHNHYTQKSLSLSPG | 95 |

TABLE 13-continued

Amino acid sequences of the bispecific antigen binding molecules

| Molecule | Sequence | Seq ID No |
|---|---|---|
| | P1AE8874 OX40(CLC563) x FAP (1G1a) (3 + 1) C-terminal crossfab fusion | |
| OX40(CLC563) VHCH1-Fc knob_PGLALA-FAP(1G1a) VHCL | EVQLLESGGGLVQPGGSLRLSCAASGFTFSSYAMSWVR QAPGKGLEWVSAISGSGGSTYYADSVKGRFTISRDNSK NTLYLQMNSLRAEDTAVYYCALDVGAFDYWGQGALVTV SSASTKGPSVFPLAPSSKSTSGGTAALGCLVEDYFPEP VTVSWNSGALTSGVHTFPAVLQSSGLYSLSSVVTVPSS SLGTQTYICNVNHKPSNTKVDEKVEPKSCDKTHTCPPC PAPEAAGGPSVFLFPPKPKDTLMISRTPEVTCVVVDVS HEDPEVKFNWYVDGVEVHNAKTKPREEQYNSTYRVVSV LTVLHQDWLNGKEYKCKVSNKALGAPIEKTISKAKGQP REPQVYTLPPCRDELTKNQVSLWCLVKGFYPSDIAVEW ESNGQPENNYKTTPPVLDSDGSFFLYSKLTVDKSRWQQ GNVFSCSVMHEALHNHYTQKSLSLSPGGGGGSGGGGSG GGGSGGSGGQVQLVQSGAEVKKPGASVKVSCKASGYTL IDYNMDWVRQAPGQGLEWIGDIYPNTGGTIYNQKFKGR VTMTIDTSTSTVYMELSSLRSEDTAVYYCTRFRGIHYA MDYWGQGTTVTVSSASVAAPSVFIFPPSDEQLKSGTAS VVCLLNNFYPREAKVQWKVDNALQSGNSQESVTEQDSK DSTYSLSSILTLSKADYEKHKVYACEVTHQGLSSPVTK SFNRGEC | 97 |
| OX40(CLC563) light chain | EIVLTQSPGTLSLSPGERATLSCRASQSVSSSYLAWYQ QKPGQAPRLLIYGASSRATGIPDRFSGSGSGTDFTLTI SRLEPEDFAVYYCQQYGSSPLTFGQGTKVEIKRTVAAP SVFIFPPSDRKLKSGTASVVCLLNNFYPREAKVQWKVD NALQSGNSQESVTEQDSKDSTYSLSSTLTLSKADYEKH KVYACEVTHQGLSSPVTKSFNRGEC | 93 |
| FAP(1G1a) VLCH1-light chain | EIVLTQSPATLSLSPGERATLSCRASESVDNYGLSFIN WFQQKPGQAPRLLIYGTSNRGSGIPARFSGSGSGTDFT LIISSLEPEDFAVYFCQQSNEVPYTFGGGTKVEIKSSA STKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKKVEPKSC | 88 |
| OX40(CLC563) VHCH1-OX40(CLC563) VHCH1-Fc hole_PGLALA | EVQLLESGGGLVQPGGSLRLSCAASGFTFSSYAMSWVR QAPGKGLEWVSAISGSGGSTYYADSVKGRFTISRDNSK NTLYLQMNSLRAEDTAVYYCALDVGAFDYWGQGALVTV SSASTKGPSVFPLAPSSKSTSGGTAALGCLVEDYFPEP VTVSWNSGALTSGVHTFPAVLQSSGLYSLSSVVTVPSS SLGTQTYICNVNHKPSNTKVDEKVEPKSCGGGGSGGGS GEVQLLESGGGLVQPGGSLRLSCAASGFTFSSYAMSWV RQAPGKGLEWVSAISGSGGSTYYADSVKGRFTISRDNS KNTLYLQMNSLRAEDTAVYYCALDVGAFDYWGQGALVT VSSASTKGPSVFPLAPSSKSTSGGTAALGCLVEDYFPE PVTVSWNSGALTSGVHTFPAVLQSSGLYSLSSVVTVPS SSLGTQTYICNVNHKPSNTKVDEKVEPKSCDKTHTCPP CPAPEAAGGPSVFLFPPKPKDTLMISRTPEVTCVVVDV SHEDPEVKFNWYVDGVEVHNAKTKPREEQYNSTYRVVS VLTVLHQDWLNGKEYKCKVSNKALGAPIEKTISKAKGQ PREPQVCTLPPSRDELTKNQVSLSCAVKGFYPSDIAVE WESNGQPENNYKTTPPVLDSDGSFFLVSKLTVDKSRWQ QGNVFSCSVMHEALHNHYTQKSLSLSPG | 95 |

TABLE 13-continued

Amino acid sequences of the bispecific antigen binding molecules

| Molecule | Sequence | Seq ID No |
|---|---|---|
| \multicolumn{3}{c}{P1AF6454} |
| \multicolumn{3}{c}{OX40(CLC563) x FAP (1G1a_EPKSCD) (3 + 1) C-terminal crossfab fusion} |
| OX40(CLC563) VHCH1-Fc knob_PGLALA-FAP(1G1a) VHCL | EVQLLESGGGLVQPGGSLRLSCAASGFTFSSYAMSWVR QAPGKGLEWVSAISGSGGSTYYADSVKGRFTISRDNSK NTLYLQMNSLRAEDTAVYYCALDVGAFDYWGQGALVTV SSASTKGPSVFPLAPSSKSTSGGTAALGCLVEDYFPEP VTVSWNSGALTSGVHTFPAVLQSSGLYSLSSVVTVPSS SLGTQTYICNVNHKPSNTKVDEKVEPKSCDKTHTCPPC PAPEAAGGPSVFLFPPKPKDTLMISRTPEVTCVVVDVS HEDPEVKFNWYVDGVEVHNAKTKPREEQYNSTYRVVSV LTVLHQDWLNGKEYKCKVSNKALGAPIEKTISKAKGQP REPQVYTLPPCRDELTKNQVSLWCLVKGFYPSDIAVEW ESNGQPENNYKTTPPVLDSDGSFFLYSKLTVDKSRWQQ GNVFSCSVMHEALHNHYTQKSLSLSPGGGGSGGGGSG GGGSGGSGGQVQLVQSGAEVKKPGASVKVSCKASGYTL IDYNMDWVRQAPGQGLEWIGDIYPNTGGTIYNQKFKGR VTMTIDTSTSTVYMELSSLRSEDTAVYYCTRFRGIHYA MDYWGQGTTVTVSSASVAAPSVFIFPPSDEQLKSGTAS VVCLLNNFYPREAKVQWKVDNALQSGNSQESVTEQDSK DSTYSLSSILTLSKADYEKHKVYACEVTHQGLSSPVTK SFNRGEC | 97 |
| OX40(CLC563) light chain | EIVLTQSPGTLSLSPGERATLSCRASQSVSSSYLAWYQ QKPGQAPRLLIYGASSRATGIPDRFSGSGSGTDFTLTI SRLEPEDFAVYYCQQYGSSPLTFGQGTKVEIKRTVAAP SVFIFPPSDRKLKSGTASVVCLLNNFYPREAKVQWKVD NALQSGNSQESVTEQDSKDSTYSLSSTLTLSKADYEKH KVYACEVTHQGLSSPVTKSFNRGEC | 93 |
| FAP(1G1a) VLCH1-light chain (EPKSCD) | EIVLTQSPATLSLSPGERATLSCRASESVDNYGLSFIN WFQQKPGQAPRLLIYGTSNRGSGIPARFSGSGSGTDFT LIISSLEPEDFAVYFCQQSNEVPYTFGGGTKVEIKSSA STKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKKVEPKSCD | 94 |
| OX40(CLC563) VHCH1-OX40(CLC563) VHCH1-Fc hole_PGLALA | EVQLLESGGGLVQPGGSLRLSCAASGFTFSSYAMSWVR QAPGKGLEWVSAISGSGGSTYYADSVKGRFTISRDNSK NTLYLQMNSLRAEDTAVYYCALDVGAFDYWGQGALVTV SSASTKGPSVFPLAPSSKSTSGGTAALGCLVEDYFPEP VTVSWNSGALTSGVHTFPAVLQSSGLYSLSSVVTVPSS SLGTQTYICNVNHKPSNTKVDEKVEPKSCGGGGSGGGS GEVQLLESGGGLVQPGGSLRLSCAASGFTFSSYAMSWV RQAPGKGLEWVSAISGSGGSTYYADSVKGRFTISRDNS KNTLYLQMNSLRAEDTAVYYCALDVGAFDYWGQGALVT VSSASTKGPSVFPLAPSSKSTSGGTAALGCLVEDYFPE PVTVSWNSGALTSGVHTFPAVLQSSGLYSLSSVVTVPS SSLGTQTYICNVNHKPSNTKVDEKVEPKSCDKTHTCPP CPAPEAAGGPSVFLFPPKPKDTLMISRTPEVTCVVVDV SHEDPEVKFNWYVDGVEVHNAKTKPREEQYNSTYRVVS VLTVLHQDWLNGKEYKCKVSNKALGAPIEKTISKAKGQ PREPQVCTLPPSRDELTKNQVSLSCAVKGFYPSDIAVE WESNGQPENNYKTTPPVLDSDGSFFLVSKLTVDKSRWQ QGNVFSCSVMHEALHNHYTQKSLSLSPG | 95 |

TABLE 13-continued

Amino acid sequences of the bispecific antigen binding molecules

| Molecule | Sequence | Seq ID No |
|---|---|---|
| P1AF6455 OX40(CLC563) x FAP (1G1a_EPKSCS) (3 + 1) C-terminal crossfab fusion ||| 
| OX40(CLC563) VHCH1-Fc knob_PGLALA-FAP(1G1a) VHCL | EVQLLESGGGLVQPGGSLRLSCAASGFTFSSYAMSWVR QAPGKGLEWVSAISGSGGSTYYADSVKGRFTISRDNSK NTLYLQMNSLRAEDTAVYYCALDVGAFDYWGQGALVTV SSASTKGPSVFPLAPSSKSTSGGTAALGCLVEDYFPEP VTVSWNSGALTSGVHTFPAVLQSSGLYSLSSVVTVPSS SLGTQTYICNVNHKPSNTKVDEKVEPKSCDKTHTCPPC PAPEAAGGPSVFLFPPKPKDTLMISRTPEVTCVVVDVS HEDPEVKFNWYVDGVEVHNAKTKPREEQYNSTYRVVSV LTVLHQDWLNGKEYKCKVSNKALGAPIEKTISKAKGQP REPQVYTLPPCRDELTKNQVSLWCLVKGFYPSDIAVEW ESNGQPENNYKTTPPVLDSDGSFFLYSKLTVDKSRWQQ GNVFSCSVMHEALHNHYTQKSLSLSPGGGGGSGGGGSG GGGSGGSGGQVQLVQSGAEVKKPGASVKVSCKASGYTL IDYNMDWVRQAPGQGLEWIGDIYPNTGGTIYNQKFKGR VTMTIDTSTSTVYMELSSLRSEDTAVYYCTRFRGIHYA MDYWGQGTTVTVSSASVAAPSVFIFPPSDEQLKSGTAS VVCLLNNFYPREAKVQWKVDNALQSGNSQESVTEQDSK DSTYSLSSILTLSKADYEKHKVYACEVTHQGLSSPVTK SFNRGEC | 97 |
| OX40(CLC563) light chain | EIVLTQSPGTLSLSPGERATLSCRASQSVSSSYLAWYQ QKPGQAPRLLIYGASSRATGIPDRFSGSGSGTDFTLTI SRLEPEDFAVYYCQQYGSSPLTFGQGTKVEIKRTVAAP SVFIFPPSDRKLKSGTASVVCLLNNFYPREAKVQWKVD NALQSGNSQESVTEQDSKDSTYSLSSTLTLSKADYEKH KVYACEVTHQGLSSPVTKSFNRGEC | 93 |
| FAP(1G1a) VLCH1-light chain (EPKSCS) | EIVLTQSPATLSLSPGERATLSCRASESVDNYGLSFIN WFQQKPGQAPRLLIYGTSNRGSGIPARFSGSGSGTDFT LTISSLEPEDFAVYFCQQSNEVPYTFGGGTKVEIKSSA STKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKKVEPKSCS | 96 |
| OX40(CLC563) VHCH1-OX40(CLC563) VHCH1-Fc hole_PGLALA | EVQLLESGGGLVQPGGSLRLSCAASGFTFSSYAMSWVR QAPGKGLEWVSAISGSGGSTYYADSVKGRFTISRDNSK NTLYLQMNSLRAEDTAVYYCALDVGAFDYWGQGALVTV SSASTKGPSVFPLAPSSKSTSGGTAALGCLVEDYFPEP VTVSWNSGALTSGVHTFPAVLQSSGLYSLSSVVTVPSS SLGTQTYICNVNHKPSNTKVDEKVEPKSCGGGGSGGGS GEVQLLESGGGLVQPGGSLRLSCAASGFTFSSYAMSWV RQAPGKGLEWVSAISGSGGSTYYADSVKGRFTISRDNS KNTLYLQMNSLRAEDTAVYYCALDVGAFDYWGQGALVT VSSASTKGPSVFPLAPSSKSTSGGTAALGCLVEDYFPE PVTVSWNSGALTSGVHTFPAVLQSSGLYSLSSVVTVPS SSLGTQTYICNVNHKPSNTKVDEKVEPKSCDKTHTCPP CPAPEAAGGPSVFLFPPKPKDTLMISRTPEVTCVVVDV SHEDPEVKFNWYVDGVEVHNAKTKPREEQYNSTYRVVS VLTVLHQDWLNGKEYKCKVSNKALGAPIEKTISKAKGQ PREPQVCTLPPSRDELTKNQVSLSCAVKGFYPSDIAVE WESNGQPENNYKTTPPVLDSDGSFFLVSKLTVDKSRWQ QGNVFSCSVMHEALHNHYTQKSLSLSPG | 95 |

TABLE 13-continued

Amino acid sequences of the bispecific antigen binding molecules

| Molecule | Sequence | Seq ID No |
|---|---|---|
| P1AE8871 OX40(CLC563) x FAP (1G1a) (2 + 1) C-terminal crossfab fusion | | |
| OX40(CLC563) VHCH1-Fc knob_PGLALA-FAP(1G1a) VHCL | EVQLLESGGGLVQPGGSLRLSCAASGFTFSSYAMSWVR QAPGKGLEWVSAISGSGGSTYYADSVKGRFTISRDNSK NTLYLQMNSLRAEDTAVYYCALDVGAFDYWGQGALVTV SSASTKGPSVFPLAPSSKSTSGGTAALGCLVEDYFPEP VTVSWNSGALTSGVHTFPAVLQSSGLYSLSSVVTVPSS SLGTQTYICNVNHKPSNTKVDEKVEPKSCDKTHTCPPC PAPEAAGGPSVFLFPPKPKDTLMISRTPEVTCVVVDVS HEDPEVKFNWYVDGVEVHNAKTKPREEQYNSTYRVVSV LTVLHQDWLNGKEYKCKVSNKALGAPIEKTISKAKGQP REPQVYTLPPCRDELTKNQVSLWCLVKGFYPSDIAVEW ESNGQPENNYKTTPPVLDSDGSFFLYSKLTVDKSRWQQ GNVFSCSVMHEALHNHYTQKSLSLSPGGGGGSGGGGSG GGGSGGSGGGQVQLVQSGAEVKKPGASVKVSCKASGYTL IDYNMDWVRQAPGQGLEWIGDIYPNTGGTIYNQKFKGR VTMTIDTSTSTVYMELSSLRSEDTAVYYCTRFRGIHYA MDYWGQGTTVTVSSASVAAPSVFIFPPSDEQLKSGTAS VVCLLNNFYPREAKVQWKVDNALQSGNSQESVTEQDSK DSTYSLSSILTLSKADYEKHKVYACEVTHQGLSSPVTK SFNRGEC | 97 |
| OX40(CLC563) light chain | EIVLTQSPGTLSLSPGERATLSCRASQSVSSSYLAWYQ QKPGQAPRLLIYGASSRATGIPDRFSGSGSGTDFTLTI SRLEPEDFAVYYCQQYGSSPLTFGQGTKVEIKRTVAAP SVFIFPPSDRKLKSGTASVVCLLNNFYPREAKVQWKVD NALQSGNSQESVTEQDSKDSTYSLSSTLTLSKADYEKH KVYACEVTHQGLSSPVTKSFNRGEC | 93 |
| FAP(1G1a) VLCH1-light chain) | EIVLTQSPATLSLSPGERATLSCRASESVDNYGLSFIN WFQQKPGQAPRLLIYGTSNRGSGIPARFSGSGSGTDFT LIISSLEPEDFAVYFCQQSNEVPYTFGGGTKVEIKSSA STKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKKVEPKSC | 88 |
| OX40(CLC563) VHCH1 Fc hole_PGLALA | EVQLLESGGGLVQPGGSLRLSCAASGFTFSSYAMSWVR QAPGKGLEWVSAISGSGGSTYYADSVKGRFTISRDNSK NTLYLQMNSLRAEDTAVYYCALDVGAFDYWGQGALVTV SSASTKGPSVFPLAPSSKSTSGGTAALGCLVEDYFPEP VTVSWNSGALTSGVHTFPAVLQSSGLYSLSSVVTVPSS SLGTQTYICNVNHKPSNTKVDEKVEPKSCDKTHTCPPC PAPEAAGGPSVFLFPPKPKDTLMISRTPEVTCVVVDVS HEDPEVKFNWYVDGVEVHNAKTKPREEQYNSTYRVVSV LTVLHQDWLNGKEYKCKVSNKALGAPIEKTISKAKGQP REPQVCTLPPSRDELTKNQVSLSCAVKGFYPSDIAVEW ESNGQPENNYKTTPPVLDSDGSFFLVSKLTVDKSRWQQ GNVFSCSVMHEALHNHYTQKSLSLSPG | 98 |
| P1AE8875 OX40(MOXR0916) x FAP (1G1a) (3 + 1) C-terminal crossfab fusion | | |
| OX40(MOXR0916) VHCH1-Fc knob_PGLALA-FAP(1G1a) VHCL | EVQLVQSGAEVKKPGASVKVSCKASGYTFTDSYMSWVR QAPGQGLEWIGDMYPDNGDSSYNQKFRERVTITRDTST STAYLELSSLRSEDTAVYYCVLAPRWYFSVWGQGTLVT VSSASTKGPSVFPLAPSSKSTSGGTAALGCLVEDYFPE PVTVSWNSGALTSGVHTFPAVLQSSGLYSLSSVVTVPS SSLGTQTYICNVNHKPSNTKVDEKVEPKSCDKTHTCPP CPAPEAAGGPSVFLFPPKPKDILMISRTPEVTCVVVDV SHEDPEVKFNWYVDGVEVHNAKTKPREEQYNSTYRVVS VLTVLHQDWLNGKEYKCKVSNKALGAPIEKTISKAKGQ PREPQVYTLPPCRDELTKNQVSLWCLVKGFYPSDIAVE WESNGQPENNYKTTPPVLDSDGSFFLYSKLTVDKSRWQ QGNVFSCSVMHEALHNHYTQKSLSLSPGGGGGSGGGGS GGGGSGGSGGGQVQLVQSGAEVKKPGASVKVSCKASGYT LTDYNMDWVRQAPGQGLEWIGDIYPNTGGTIYNQKFKG RVIMTIDTSTSTVYMELSSLRSEDTAVYYCTRFRGIHY AMDYWGQGTTVTVSSASVAAPSVFIFPPSDEQLKSGTA SVVCLLNNFYPREAKVQWKVDNALQSGNSQESVTEQDS KDSTYSLSSTLTLSKADYEKHKVYACEVTHQGLSSPVT KSFNRGEC | 99 |

TABLE 13-continued

Amino acid sequences of the bispecific antigen binding molecules

| Molecule | Sequence | Seq ID No |
|---|---|---|
| OX40(MOXR0916) light chain | DIQMTQSPSSLSASVGDRVTITCRASQDISNYLNWYQQ KPGKAPKLLIYYTSRLRSGVPSRFSGSGSGTDFTLTIS SLQPEDFATYYCQQGHTLPPTFGQGTKVEIKRTVAAPS VFIFPPSDRKLKSGTASVVCLLNNFYPREAKVQWKVDN ALQSGNSQESVTEQDSKDSTYSLSSTLTLSKADYEKHK VYACEVTHQGLSSPVTKSFNRGEC | 100 |
| FAP(1G1a) VLCH1-light chain | EIVLTQSPATLSLSPGERATLSCRASESVDNYGLSFIN WFQQKPGQAPRLLIYGTSNRGSGIPARFSGSGSGTDFT LLISSLEPEDFAVYFCQQSNEVPYTFGGGTKVEIKSSA STKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKKVEPKSC | 88 |
| OX40(MOXR0916) VHCH1-OX40(MOXR0916) VHCH1-Fc hole_PGLALA- | EVQLVQSGAEVKKPGASVKVSCKASGYTFTDSYMSWVR QAPGQGLEWIGDMYPDNGDSSYNQKFRERVTITRDTST STAYLELSSLRSEDTAVYYCVLAPRWYFSVWGQGTLVT VSSASTKGPSVFPLAPSSKSTSGGTAALGCLVEDYFPE PVTVSWNSGALTSGVHTFPAVLQSSGLYSLSSVVTVPS SSLGTQTYICNVNHKPSNTKVDKVEPKSCGGGGSGGS GGEVQLVQSGAEVKKPGASVKVSCKASGYTFTDSYMSW VRQAPGQGLEWIGDMYPDNGDSSYNQKFRERVTITRDT STSTAYLELSSLRSEDTAVYYCVLAPRWYFSVWGQGTL VTVSSASTKGPSVFPLAPSSKSTSGGTAALGCLVEDYF PEPVTVSWNSGALTSGVHTFPAVLQSSGLYSLSSVVTV PSSSLGTQTYICNVNHKPSNTKVDEKVEPKSCDKTHTC PPCPAPEAAGGPSVFLFPPKPKDILMISRTPEVTCVVV DVSHEDPEVKFNWYVDGVEVHNAKTKPREEQYNSTYRV VSVLTVLHQDWLNGKEYKCKVSNKALGAPIEKTISKAK GQPREPQVCTLPPSRDELTKNQVSLSCAVKGFYPSDIA VEWESNGQPENNYKTTPPVLDSDGSFFLVSKLTVDKSR WQQGNVFSCSVMHEALHNHYTQKSLSLSPG | 101 |

P1AF4845
OX40(MOXR0916) x FAP (1G1a_EPKSCD) (3 + 1) C-terminal crossfab fusion

| OX40(MOXR0916) VHCH1-Fc knob_PGLALA-FAP(1G1a) VHCL | EVQLVQSGAEVKKPGASVKVSCKASGYTFTDSYMSWVR QAPGQGLEWIGDMYPDNGDSSYNQKFRERVTITRDTST STAYLELSSLRSEDTAVYYCVLAPRWYFSVWGQGTLVT VSSASTKGPSVFPLAPSSKSTSGGTAALGCLVEDYFPE PVTVSWNSGALTSGVHTFPAVLQSSGLYSLSSVVTVPS SSLGTQTYICNVNHKPSNTKVDEKVEPKSCDKTHTCPP CPAPEAAGGPSVFLFPPKPKDILMISRTPEVTCVVVDV SHEDPEVKFNWYVDGVEVHNAKTKPREEQYNSTYRVVS VLTVLHQDWLNGKEYKCKVSNKALGAPIEKTISKAKGQ PREPQVYTLPPCRDELTKNQVSLWCLVKGFYPSDIAVE WESNGQPENNYKTTPPVLDSDGSFFLYSKLTVDKSRWQ QGNVFSCSVMHEALHNHYTQKSLSLSPGGGGGSGGGGS GGGGSGGSGGQVQLVQSGAEVKKPGASVKVSCKASGYT LTDYNMDWVRQAPGQGLEWIGDIYPNTGGTIYNQKFKG RVIMTIDTSTSTVYMELSSLRSEDTAVYYCTRFRGIHY AMDYWGQGTTVTVSSASVAAPSVFIFPPSDEQLKSGTA SVVCLLNNFYPREAKVQWKVDNALQSGNSQESVTEQDS KDSTYSLSSTLTLSKADYEKHKVYACEVTHQGLSSPVT KSFNRGEC | 99 |
| OX40(MOXR0916) light chain | DIQMTQSPSSLSASVGDRVTITCRASQDISNYLNWYQQ KPGKAPKLLIYYTSRLRSGVPSRFSGSGSGTDFTLTIS SLQPEDFATYYCQQGHTLPPTFGQGTKVEIKRTVAAPS VFIFPPSDRKLKSGTASVVCLLNNFYPREAKVQWKVDN ALQSGNSQESVTEQDSKDSTYSLSSTLTLSKADYEKHK VYACEVTHQGLSSPVTKSFNRGEC | 100 |
| FAP(1G1a) VLCH1-light chain (EPKSCD) | EIVLTQSPATLSLSPGERATLSCRASESVDNYGLSFIN WFQQKPGQAPRLLIYGTSNRGSGIPARFSGSGSGTDFT LLISSLEPEDFAVYFCQQSNEVPYTFGGGTKVEIKSSA STKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKKVEPKSCD | 94 |

TABLE 13-continued

Amino acid sequences of the bispecific antigen binding molecules

| Molecule | Sequence | Seq ID No |
|---|---|---|
| OX40(MOXR0916) VHCH1- OX40(MOXR0916) VHCH1-Fc hole_PGLALA- | EVQLVQSGAEVKKPGASVKVSCKASGYTFTDSYMSWVR QAPGQGLEWIGDMYPDNGDSSYNQKFRERVTITRDTST STAYLELSSLRSEDTAVYYCVLAPRWYFSVWGQGTLVT VSSASTKGPSVFPLAPSSKSTSGGTAALGCLVEDYFPE PVTVSWNSGALTSGVHTFPAVLQSSGLYSLSSVVTVPS SSLGTQTYICNVNHKPSNTKVDEKVEPKSCGGGGSGGG GGEVQLVQSGAEVKKPGASVKVSCKASGYTFTDSYMSW VRQAPGQGLEWIGDMYPDNGDSSYNQKFRERVTITRDT STSTAYLELSSLRSEDTAVYYCVLAPRWYFSVWGQGTL VTVSSASTKGPSVFPLAPSSKSTSGGTAALGCLVEDYF PEPVTVSWNSGALTSGVHTFPAVLQSSGLYSLSSVVTV PSSSLGTQTYICNVNHKPSNTKVDEKVEPKSCDKTHTC PPCPAPEAAGGPSVFLFPPKPKDILMISRTPEVTCVVV DVSHEDPEVKFNWYVDGVEVHNAKTKPREEQYNSTYRV VSVLTVLHQDWLNGKEYKCKVSNKALGAPIEKTISKAK GQPREPQVCTLPPSRDELTKNQVSLSCAVKGFYPSDIA VEWESNGQPENNYKTTPPVLDSDGSFFLVSKLTVDKSR WQQGNVFSCSVMHEALHNHYTQKSLSLSPG | 101 |

P1AF4851
OX40(MOXR0916) x FAP (1G1a_EPKSCS) (3 + 1) C-terminal crossfab fusion

| Molecule | Sequence | Seq ID No |
|---|---|---|
| OX40(MOXR0916) VHCH1-Fc knob_PGLALA- FAP(1G1a) VHCL | EVQLVQSGAEVKKPGASVKVSCKASGYTFTDSYMSWVR QAPGQGLEWIGDMYPDNGDSSYNQKFRERVTITRDTST STAYLELSSLRSEDTAVYYCVLAPRWYFSVWGQGTLVT VSSASTKGPSVFPLAPSSKSTSGGTAALGCLVEDYFPE PVTVSWNSGALTSGVHTFPAVLQSSGLYSLSSVVTVPS SSLGTQTYICNVNHKPSNTKVDEKVEPKSCDKTHTCPP CPAPEAAGGPSVFLFPPKPKDTLMISRTPEVTCVVVDV SHEDPEVKFNWYVDGVEVHNAKTKPREEQYNSTYRVVS VLTVLHQDWLNGKEYKCKVSNKALGAPIEKTISKAKGQ PREPQVYTLPPCRDELTKNQVSLWCLVKGFYPSDIAVE WESNGQPENNYKTTPPVLDSDGSFFLYSKLTVDKSRWQ QGNVFSCSVMHEALHNHYTQKSLSLSPGGGGGSGGGGS GGGGSGGSGGQVQLVQSGAEVKKPGASVKVSCKASGYT LTDYNMDWVRQAPGQGLEWIGDIYPNTGGTIYNQKFKG RVTMTIDTSTSTVYMELSSLRSEDTAVYYCTRFRGIHY AMDYWGQGTTVTVSSASVAAPSVFIFPPSDEQLKSGTA SVVCLLNNFYPREAKVQWKVDNALQSGNSQESVTEQDS KDSTYSLSSTLTLSKADYEKHKVYACEVTHQGLSSPVT KSFNRGEC | 99 |
| OX40(MOXR0916) light chain | DIQMTQSPSSLSASVGDRVTITCRASQDISNYLNWYQQ KPGKAPKLLIYYTSRLRSGVPSRFSGSGSGTDFTLTIS SLQPEDFATYYCQQGHTLPPTFGQGTKVEIKRTVAAPS VFIFPPSDRKLKSGTASVVCLLNNFYPREAKVQWKVDN ALQSGNSQESVTEQDSKDSTYSLSSTLTLSKADYEKHK VYACEVTHQGLSSPVTKSFNRGEC | 100 |
| FAP(1G1a) VLCH1-light chain (EPKSCS) | EIVLTQSPATLSLSPGERATLSCRASESVDNYGLSFIN WFQQKPGQAPRLLIYGTSNRGSGIPARFSGSGSGTDFT LTISSLEPEDFAVYFCQQSNEVPYTFGGGTKVEIKSSA STKGPSVFPLAPSSKSTSGGTAALGCLVEDYFPEPVTV SWNSGALTSGVHTFPAVLQSSGLYSLSSVVTVPSSSLG TQTYICNVNHKPSNTKVDKKVEPKSCS | 96 |
| OX40(MOXR0916) VHCH1- OX40(MOXR0916) VHCH1-Fc hole_PGLALA- | EVQLVQSGAEVKKPGASVKVSCKASGYTFTDSYMSWVR QAPGQGLEWIGDMYPDNGDSSYNQKFRERVTITRDTST STAYLELSSLRSEDTAVYYCVLAPRWYFSVWGQGTLVT VSSASTKGPSVFPLAPSSKSTSGGTAALGCLVEDYFPE PVTVSWNSGALTSGVHTFPAVLQSSGLYSLSSVVTVPS SSLGTQTYICNVNHKPSNTKVDEKVEPKSCGGGGSGGG GGEVQLVQSGAEVKKPGASVKVSCKASGYTFTDSYMSW VRQAPGQGLEWIGDMYPDNGDSSYNQKFRERVTITRDT STSTAYLELSSLRSEDTAVYYCVLAPRWYFSVWGQGTL VTVSSASTKGPSVFPLAPSSKSTSGGTAALGCLVEDYF PEPVTVSWNSGALTSGVHTFPAVLQSSGLYSLSSVVTV PSSSLGTQTYICNVNHKPSNTKVDEKVEPKSCDKTHTC PPCPAPEAAGGPSVFLFPPKPKDTLMISRTPEVTCVVV DVSHEDPEVKFNWYVDGVEVHNAKTKPREEQYNSTYRV VSVLTVLHQDWLNGKEYKCKVSNKALGAPIEKTISKAK GQPREPQVCTLPPSRDELTKNQVSLSCAVKGFYPSDIA VEWESNGQPENNYKTTPPVLDSDGSFFLVSKLTVDKSR WQQGNVFSCSVMHEALHNHYTQKSLSLSPG | 101 |

TABLE 13-continued

Amino acid sequences of the bispecific antigen binding molecules

| Molecule | Sequence | Seq ID No |
|---|---|---|
| | P1AE8872<br>OX40(MOXR0916) x FAP (1G1a) (2 + 1) C-terminal crossfab fusion | |
| OX40(MOXR0916)<br>VHCH1-Fc<br>knob_PGLALA-<br>FAP(1G1a)<br>VHCL | EVQLVQSGAEVKKPGASVKVSCKASGYTFTDSYMSWVR<br>QAPGQGLEWIGDMYPDNGDSSYNQKFRERVTITRDTST<br>STAYLELSSLRSEDTAVYYCVLAPRWYFSVWGQGTLVT<br>VSSASTKGPSVFPLAPSSKSTSGGTAALGCLVEDYFPE<br>PVTVSWNSGALTSGVHTFPAVLQSSGLYSLSSVVTVPS<br>SSLGTQTYICNVNHKPSNTKVDEKVEPKSCDKTHTCPP<br>CPAPEAAGGPSVFLFPPKPKDTLMISRTPEVTCVVVDV<br>SHEDPEVKFNWYVDGVEVHNAKTKPREEQYNSTYRVVS<br>VLTVLHQDWLNGKEYKCKVSNKALGAPIEKTISKAKGQ<br>PREPQVYTLPPCRDELTKNQVSLWCLVKGFYPSDIAVE<br>WESNGQPENNYKTTPPVLDSDGSFFLYSKLTVDKSRWQ<br>QGNVFSCSVMHEALHNHYTQKSLSLSPGGGGSGGGGS<br>GGGGSGGSGGQVQLVQSGAEVKKPGASVKVSCKASGYT<br>LTDYNMDWVRQAPGQGLEWIGDIYPNTGGTIYNQKFKG<br>RVTMTIDTSTSTVYMELSSLRSEDTAVYYCTRFRGIHY<br>AMDYWGQGTTVTVSSASVAAPSVFIFPPSDEQLKSGTA<br>SVVCLLNNFYPREAKVQWKVDNALQSGNSQESVTEQDS<br>KDSTYSLSSTLTLSKADYEKHKVYACEVTHQGLSSPVT<br>KSFNRGEC | 99 |
| OX40(MOXR0916)<br>light chain | DIQMTQSPSSLSASVGDRVTITCRASQDISNYLNWYQQ<br>KPGKAPKLLIYYTSRLRSGVPSRFSGSGSGTDFTLTIS<br>SLQPEDFATYYCQQGHTLPPTFGQGTKVEIKRTVAAPS<br>VFIFPPSDRKLKSGTASVVCLLNNFYPREAKVQWKVDN<br>ALQSGNSQESVTEQDSKDSTYSLSSTLTLSKADYEKHK<br>VYACEVTHQGLSSPVTKSFNRGEC | 100 |
| FAP(1G1a)<br>VLCH1-light<br>chain | EIVLTQSPATLSLSPGERATLSCRASESVDNYGLSFIN<br>WFQQKPGQAPRLLIYGTSNRGSGIPARFSGSGSGTDFT<br>LIISSLEPEDFAVYFCQQSNEVPYTFGGGTKVEIKSSA<br>STKGPSVFPLAPSSKSTSGGTAALGCLVKDYFPEPVTV<br>SWNSGALTSGVHTFPAVLQSSGLYSLSSVVTVPSSSLG<br>TQTYICNVNHKPSNTKVDKKVEPKSC | 88 |
| OX40(MOXR0916)<br>VHCH1-Fc<br>hole_PGLALA | EVQLVQSGAEVKKPGASVKVSCKASGYTFTDSYMSWVR<br>QAPGQGLEWIGDMYPDNGDSSYNQKFRERVTITRDTST<br>STAYLELSSLRSEDTAVYYCVLAPRWYFSVWGQGTLVT<br>VSSASTKGPSVFPLAPSSKSTSGGTAALGCLVEDYFPE<br>PVTVSWNSGALTSGVHTFPAVLQSSGLYSLSSVVTVPS<br>SSLGTQTYICNVNHKPSNTKVDEKVEPKSCDKTHTCPP<br>CPAPEAAGGPSVFLFPPKPKDTLMISRTPEVTCVVVDV<br>SHEDPEVKFNWYVDGVEVHNAKTKPREEQYNSTYRVVS<br>VLTVLHQDWLNGKEYKCKVSNKALGAPIEKTISKAKGQ<br>PREPQVCTLPPSRDELTKNQVSLSCAVKGFYPSDIAVE<br>WESNGQPENNYKTTPPVLDSDGSFFLVSKLTVDKSRWQ<br>QGNVFSCSVMHEALHNHYTQKSLSLSPG | 102 |
| | P1AF4852<br>OX40(MOXR0916) x FAP (1G1a_EPKSCD) (2 + 1) C-terminal crossfab fusion | |
| OX40(MOXR0916)<br>VHCH1-Fc<br>knob_PGLALA-<br>FAP(1G1a)<br>VHCL | EVQLVQSGAEVKKPGASVKVSCKASGYTFTDSYMSWVR<br>QAPGQGLEWIGDMYPDNGDSSYNQKFRERVTITRDTST<br>STAYLELSSLRSEDTAVYYCVLAPRWYFSVWGQGTLVT<br>VSSASTKGPSVFPLAPSSKSTSGGTAALGCLVEDYFPE<br>PVTVSWNSGALTSGVHTFPAVLQSSGLYSLSSVVTVPS<br>SSLGTQTYICNVNHKPSNTKVDEKVEPKSCDKTHTCPP<br>CPAPEAAGGPSVFLFPPKPKDILMISRTPEVTCVVVDV<br>SHEDPEVKFNWYVDGVEVHNAKTKPREEQYNSTYRVVS<br>VLTVLHQDWLNGKEYKCKVSNKALGAPIEKTISKAKGQ<br>PREPQVYTLPPCRDELTKNQVSLWCLVKGFYPSDIAVE<br>WESNGQPENNYKTTPPVLDSDGSFFLYSKLTVDKSRWQ<br>QGNVFSCSVMHEALHNHYTQKSLSLSPGGGGSGGGGS<br>GGGGSGGSGGQVQLVQSGAEVKKPGASVKVSCKASGYT<br>LTDYNMDWVRQAPGQGLEWIGDIYPNTGGTIYNQKFKG<br>RVIMTIDTSTSTVYMELSSLRSEDTAVYYCTRFRGIHY<br>AMDYWGQGTTVTVSSASVAAPSVFIFPPSDEQLKSGTA<br>SVVCLLNNFYPREAKVQWKVDNALQSGNSQESVTEQDS<br>KDSTYSLSSTLTLSKADYEKHKVYACEVTHQGLSSPVT<br>KSFNRGEC | 99 |

TABLE 13-continued

Amino acid sequences of the bispecific antigen binding molecules

| Molecule | Sequence | Seq ID No |
|---|---|---|
| OX40(MOXR0916) light chain | DIQMTQSPSSLSASVGDRVTITCRASQDISNYLNWYQQ KPGKAPKLLIYYTSRLRSGVPSRFSGSGSGTDFTLTIS SLQPEDFATYYCQQGHTLPPTFGQGTKVEIKRTVAAPS VFIFPPSDRKLKSGTASVVCLLNNFYPREAKVQWKVDN ALQSGNSQESVTEQDSKDSTYSLSSTLTLSKADYEKHK VYACEVTHQGLSSPVTKSFNRGEC | 100 |
| FAP(1G1a) VLCH1-light chain (EPKSCD) | EIVLTQSPATLSLSPGERATLSCRASESVDNYGLSFIN WFQQKPGQAPRLLIYGTSNRGSIPARFSGSGSGTDFT LIISSLEPEDFAVYFCQQSNEVPYTFGGGTKVEIKSSA STKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKKVEPKSCD | 94 |
| OX40(MOXR0916) VHCH1-Fc hole_PGLALA | EVQLVQSGAEVKKPGASVKVSCKASGYTFTDSYMSWVR QAPGQGLEWIGDMYPDNGDSSYNQKFRERVTITRDTST STAYLELSSLRSEDTAVYYCVLAPRWYFSVWGQGTLVT VSSASTKGPSVFPLAPSSKSTSGGTAALGCLVEDYFPE PVTVSWNSGALTSGVHTFPAVLQSSGLYSLSSVVTVPS SSLGTQTYICNVNHKPSNTKVDEKVEPKSCDKTHTCPP CPAPEAAGGPSVFLFPPKPKDILMISRTPEVTCVVVDV SHEDPEVKFNWYVDGVEVHNAKTKPREEQYNSTYRVVS VLTVLHQDWLNGKEYKCKVSNKALGAPIEKTISKAKGQ PREPQVCTLPPSRDELTKNQVSLSCAVKGFYPSDIAVE WESNGQPENNYKTTPPVLDSDGSFFLVSKLTVDKSRWQ QGNVFSCSVMHEALHNHYTQKSLSLSPG | 102 |

P1AF4858
OX40(MOXR0916) x FAP (1G1a_EPKSCS) (2 + 1) C-terminal crossfab fusion

| | | |
|---|---|---|
| OX40(MOXR0916) VHCH1-Fc knob_PGLALA-FAP(1G1a) VHCL | EVQLVQSGAEVKKPGASVKVSCKASGYTFTDSYMSWVR QAPGQGLEWIGDMYPDNGDSSYNQKFRERVTITRDTST STAYLELSSLRSEDTAVYYCVLAPRWYFSVWGQGTLVT VSSASTKGPSVFPLAPSSKSTSGGTAALGCLVEDYFPE PVTVSWNSGALTSGVHTFPAVLQSSGLYSLSSVVTVPS SSLGTQTYICNVNHKPSNTKVDEKVEPKSCDKTHTCPP CPAPEAAGGPSVFLFPPKPKDTLMISRTPEVTCVVVDV SHEDPEVKFNWYVDGVEVHNAKTKPREEQYNSTYRVVS VLTVLHQDWLNGKEYKCKVSNKALGAPIEKTISKAKGQ PREPQVYTLPPCRDELTKNQVSLWCLVKGFYPSDIAVE WESNGQPENNYKTTPPVLDSDGSFFLYSKLTVDKSRWQ QGNVFSCSVMHEALHNHYTQKSLSLSPGGGGGSGGGGS GGGGSGGSGGQVQLVQSGAEVKKPGASVKVSCKASGYT LTDYNMDWVRQAPGQGLEWIGDIYPNTGGTIYNQKFKG RVTMTIDTSTSTVYMELSSLRSEDTAVYYCTRFRGIHY AMDYWGQGTTVTVSSASVAAPSVFIFPPSDEQLKSGTA SVVCLLNNFYPREAKVQWKVDNALQSGNSQESVTEQDS KDSTYSLSSTLTLSKADYEKHKVYACEVTHQGLSSPVT KSFNRGEC | 99 |
| OX40(MOXR0916) light chain | DIQMTQSPSSLSASVGDRVTITCRASQDISNYLNWYQQ KPGKAPKLLIYYTSRLRSGVPSRFSGSGSGTDFTLTIS SLQPEDFATYYCQQGHTLPPTFGQGTKVEIKRTVAAPS VFIFPPSDRKLKSGTASVVCLLNNFYPREAKVQWKVDN ALQSGNSQESVTEQDSKDSTYSLSSTLTLSKADYEKHK VYACEVTHQGLSSPVTKSFNRGEC | 100 |
| FAP(1G1a) VLCH1-light chain (EPKSCS) | EIVLTQSPATLSLSPGERATLSCRASESVDNYGLSFIN WFQQKPGQAPRLLIYGTSNRGSIPARFSGSGSGTDFT LTISSLEPEDFAVYFCQQSNEVPYTFGGGTKVEIKSSA STKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKKVEPKSCS | 96 |

TABLE 13-continued

Amino acid sequences of the bispecific antigen binding molecules

| Molecule | Sequence | Seq ID No |
|---|---|---|
| OX40(MOXR0916) VHCH1-Fc hole_PGLALA | EVQLVQSGAEVKKPGASVKVSCKASGYTFTDSYMSWVR QAPGQGLEWIGDMYPDNGDSSYNQKFRERVTITRDTST STAYLELSSLRSEDTAVYYCVLAPRWYFSVWGQGTLVT VSSASTKGPSVFPLAPSSKSTSGGTAALGCLVEDYFPE PVTVSWNSGALTSGVHTFPAVLQSSGLYSLSSVVTVPS SSLGTQTYICNVNHKPSNTKVDEKVEPKSCDKTHTCPP CPAPEAAGGPSVFLFPPKPKDTLMISRTPEVTCVVVDV SHEDPEVKFNWYVDGVEVHNAKTKPREEQYNSTYRVVS VLTVLHQDWLNGKEYKCKVSNKALGAPIEKTISKAKGQ PREPQVCTLPPSRDELTKNQVSLSCAVKGFYPSDIAVE WESNGQPENNYKTTPPVLDSDGSFFLVSKLTVDKSRWQ QGNVFSCSVMHEALHNHYTQKSLSLSPG | 102 |

P1AE8873
OX40(8H9) x FAP (1G1a) (3 + 1) C-terminal crossfab fusion

| | | |
|---|---|---|
| OX40(8H9) VHCH1-Fc knob_PGLALA-FAP(1G1a) VHCL | QVQLVQSGAEVKKPGSSVKVSCKASGGTFSSYAISWVR QAPGQGLEWMGGIIPIFGTANYAQKFQGRVTITADKST STAYMELSSLRSEDTAVYYCAREYGWMDYWGQGTTVTV SSASTKGPSVFPLAPSSKSTSGGTAALGCLVEDYFPEP VTVSWNSGALTSGVHTFPAVLQSSGLYSLSSVVTVPSS SLGTQTYICNVNHKPSNTKVDEKVEPKSCDKTHTCPPC PAPEAAGGPSVFLFPPKPKDTLMISRTPEVTCVVVDVS HEDPEVKFNWYVDGVEVHNAKTKPREEQYNSTYRVVSV LTVLHQDWLNGKEYKCKVSNKALGAPIEKTISKAKGQP REPQVYTLPPCRDELTKNQVSLWCLVKGFYPSDIAVEW ESNGQPENNYKTTPPVLDSDGSFFLYSKLTVDKSRWQQ GNVFSCSVMHEALHNHYTQKSLSLSPGGGGGSGGGGSG GGGSGGGSGGQVQLVQSGAEVKKPGASVKVSCKASGYTL IDYNMDWVRQAPGQGLEWIGDIYPNTGGTIYNQKFKGR VTMTIDTSTSTVYMELSSLRSEDTAVYYCTRFRGIHYA MDYWGQGTTVTVSSASVAAPSVFIFPPSDEQLKSGTAS VVCLLNNFYPREAKVQWKVDNALQSGNSQESVTEQDSK DSTYSLSSILTLSKADYEKHKVYACEVTHQGLSSPVTK SFNRGEC | 103 |
| OX40(8H9) light chain | DIQMTQSPSTLSASVGDRVTITCRASQSISSWLAWYQQ KPGKAPKLLIYDASSLESGVPSRFSGSGSGTEFTLTIS SLQPDDFATYYCQQYLTYSRFTFGQGTKVEIKRTVAAP SVFIFPPSDRKLKSGTASVVCLLNNFYPREAKVQWKVD NALQSGNSQESVTEQDSKDSTYSLSSTLTLSKADYEKH KVYACEVTHQGLSSPVTKSFNRGEC | 104 |
| FAP(1G1a) VLCH1-light chain | EIVLTQSPATLSLSPGERATLSCRASESVDNYGLSFIN WFQQKPGQAPRLLIYGTSNRGSGIPARFSGSGSGTDFT LIISSLEPEDFAVYFCQQSNEVPYTFGGGTKVEIKSSA STKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKKVEPKSC | 88 |
| OX40(8H9) VHCH1-OX40(8H9) VHCH1-Fc hole_PGLALA | QVQLVQSGAEVKKPGSSVKVSCKASGGTFSSYAISWVR QAPGQGLEWMGGIIPIFGTANYAQKFQGRVTITADKST STAYMELSSLRSEDTAVYYCAREYGWMDYWGQGTTVTV SSASTKGPSVFPLAPSSKSTSGGTAALGCLVEDYFPEP VTVSWNSGALTSGVHTFPAVLQSSGLYSLSSVVTVPSS SLGTQTYICNVNHKPSNTKVDEKVEPKSCGGGGSGGGS GGQVQLVQSGAEVKKPGSSVKVSCKASGGTFSSYAISV RQAPGQGLEWMGGIIPIFGTANYAQKFQGRVTITADKS ISTAYMELSSLRSEDTAVYYCAREYGWMDYWGQGTTVT VSSASTKGPSVFPLAPSSKSTSGGTAALGCLVEDYFPE PVTVSWNSGALTSGVHTFPAVLQSSGLYSLSSVVTVPS SSLGTQTYICNVNHKPSNTKVDEKVEPKSCDKTHTCPP CPAPEAAGGPSVFLFPPKPKDTLMISRTPEVTCVVVDV SHEDPEVKFNWYVDGVEVHNAKTKPREEQYNSTYRVVS VLTVLHQDWLNGKEYKCKVSNKALGAPIEKTISKAKGQ PREPQVCTLPPSRDELTKNQVSLSCAVKGFYPSDIAVE WESNGQPENNYKTTPPVLDSDGSFFLVSKLTVDKSRWQ QGNVFSCSVMHEALHNHYTQKSLSLSPG | 105 |

TABLE 13-continued

Amino acid sequences of the bispecific antigen binding molecules

| Molecule | Sequence | Seq ID No |
|---|---|---|
| | P1AE8870 OX40(8H9) x FAP (1G1a) (2 + 1) C-terminal crossfab fusion | |
| OX40(8H9) VHCH1-Fc knob_PGLALA- FAP(1G1a) VHCL | QVQLVQSGAEVKKPGSSVKVSCKASGGTFSSYAISWVR QAPGQGLEWMGGIIPIFGTANYAQKFQGRVTITADKST STAYMELSSLRSEDTAVYYCAREYGWMDYWGQGTTVTV SSASTKGPSVFPLAPSSKSTSGGTAALGCLVEDYFPEP VTVSWNSGALTSGVHTFPAVLQSSGLYSLSSVVTVPSS SLGTQTYICNVNHKPSNTKVDEKVEPKSCDKTHTCPPC PAPEAAGGPSVFLFPPKPKDTLMISRTPEVTCVVVDVS HEDPEVKFNWYVDGVEVHNAKTKPREEQYNSTYRVVSV LTVLHQDWLNGKEYKCKVSNKALGAPIEKTISKAKGQP REPQVYTLPPCRDELTKNQVSLWCLVKGFYPSDIAVEW ESNGQPENNYKTTPPVLDSDGSFFLYSKLTVDKSRWQQ GNVFSCSVMHEALHNHYTQKSLSLSPGGGGGSGGGGSG GGGSGGSGGQVQLVQSGAEVKKPGASVKVSCKASGYTL IDYNMDWVRQAPGQGLEWIGDIYPNTGGTIYNQKFKGR VTMTIDTSTSTVYMELSSLRSEDTAVYYCTRFRGIHYA MDYWGQGTTVTVSSASVAAPSVFIFPPSDEQLKSGTAS VVCLLNNFYPREAKVQWKVDNALQSGNSQESVTEQDSK DSTYSLSSILTLSKADYEKHKVYACEVTHQGLSSPVTK SFNRGEC | 103 |
| OX40(8H9) light chain | DIQMTQSPSTLSASVGDRVTITCRASQSISSWLAWYQQ KPGKAPKLLIYDASSLESGVPSRFSGSGSGTEFTLTIS SLQPDDFATYYCQQYLTYSRFTFGQGTKVEIKRTVAAP SVFIFPPSDRKLKSGTASVVCLLNNFYPREAKVQWKVD NALQSGNSQESVTEQDSKDSTYSLSSTLTLSKADYEKH KVYACEVTHQGLSSPVTKSFNRGEC | 104 |
| FAP(1G1a) VLCH1-light chain | EIVLTQSPATLSLSPGERATLSCRASESVDNYGLSFIN WFQQKPGQAPRLLIYGTSNRGSGIPARFSGSGSGTDFT LIISSLEPEDFAVYFCQQSNEVPYTFGGGTKVEIKSSA STKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKKVEPKSC | 88 |
| OX40(8H9) VHCH1-Fc hole_PGLALA | QVQLVQSGAEVKKPGSSVKVSCKASGGTFSSYAISWVR QAPGQGLEWMGGIIPIFGTANYAQKFQGRVTITADKST STAYMELSSLRSEDTAVYYCAREYGWMDYWGQGTTVTV SSASTKGPSVFPLAPSSKSTSGGTAALGCLVEDYFPEP VTVSWNSGALTSGVHTFPAVLQSSGLYSLSSVVTVPSS SLGTQTYICNVNHKPSNTKVDEKVEPKSCDKTHTCPPC PAPEAAGGPSVFLFPPKPKDTLMISRTPEVTCVVVDVS HEDPEVKFNWYVDGVEVHNAKTKPREEQYNSTYRVVSV LTVLHQDWLNGKEYKCKVSNKALGAPIEKTISKAKGQP REPQVCTLPPSRDELTKNQVSLSCAVKGFYPSDIAVEW ESNGQPENNYKTTPPVLDSDGSFFLVSKLTVDKSRWQQ GNVFSCSVMHEALHNHYTQKSLSLSPG | 106 |

For comparison, the following molecules were prepared:

Molecule P1AD4525, or OX40 (49B4)×FAP (4B9) (4+1) bispecific molecule, comprises four OX40 (49B4) binding Fab fragments combined with one FAP (4B9) binding moiety as VH and VL domain, wherein the VH domain is fused at the C-terminus of the Fc knob chain and the VL domain is fused at the C-terminus of the Fc hole chain (tetravalent for OX40 and monovalent for FAP). The molecule comprises a heavy chain comprising the amino acid sequence of SEQ ID NO:113, a heavy chain comprising the amino acid sequence of SEQ ID NO:114 and four light chains each comprising the amino acid sequence of SEQ ID NO:115. The molecule P1AD3690 is an untargeted OX40 agonist comprising four OX40 (49B4) binding Fab fragments. This molecule comprises two heavy chains comprising the amino acid sequence of SEQ ID NO:116 and four light chains each comprising the amino acid sequence of SEQ ID NO:115. The generation and production of the molecules is described in WO 2017/060144 A1.

2.2 Production of Bispecific Antigen Binding Molecules Targeting FAP and OX40

The molecules were produced by co-transfecting either HEK293-EBNA cells growing in suspension with the mammalian expression vectors using polyethylenimine (PEI) or co-transfecting CHO K1 cells growing in suspension with the mammalian expression using eviFECT (Evitria AG, Switzerland). The cells were transfected with the corresponding expression vectors.

Antibody constructs were expressed by transient transfection of HEK cells grown in suspension with expression vectors encoding the 4 different peptide chains. Transfection of Expi293F™ cells (Gibco™) was performed according to the cell supplier's instructions using Maxiprep (Macherey-Nagel) preparations of the antibody vectors, Expi293F™ Expression Medium (Gibco™), ExpiFectamine™ 293 Reagent, (GibCO™) and an initial cell density of 2-3 million viable cells/ml in Opti-MEM® 1× Reduced Serum Medium (Gibco™). On the day after transfection (Day 1, 18-22 hours post-transfection), ExpiFectamine™ 293 Transfection Enhancer 1 and ExpiFectamine™ 293 Transfection Enhancer 2 was added to the transfected culture. Transfected cultures were incubated at 37° C. in a humidified atmosphere of 8% $CO_2$ with shaking. Cell culture supernatants were harvested after 7 days of cultivation in shake flasks or stirred fermenters by centrifugation at 3000-5000 g for 20-30 minutes and filtered through a 0.22 μm filter.

For production in CHO K1 cells, CHO K1 cells were grown in eviGrow medium (Evitria AG, Switzerland), a chemically defined, animal-component free, serum-free medium and transfected with eviFect (Evitria AG, Switzerland). After transfection the cells were kept in eviMake (Evitria AG, Switzerland), a chemically defined, animal-component free, serum-free medium, at 37° C. and 5% $CO_2$ for 7 days. After 7 days the cultivation supernatant was collected for purification by centrifugation for 45 min at maximum speed in a Rotanta 460 RC. The solution was sterile filtered (0.22 μm filter) and kept at 4° C. The concentration of the molecules in the culture medium was either determined by Protein A-HPLC or Protein A-Bio-Layer Interferometry (BLI).

Antibodies were purified from cell culture supernatants by affinity chromatography using MabSelectSure-Sepharose™ (GE Healthcare, Sweden) chromatography. Briefly, sterile filtered cell culture supernatants were captured on a MabSelect SuRe resin equilibrated with PBS buffer (10 mM $Na_2HPO_4$, 1 mM $KH_2PO_4$, 137 mM NaCl and 2.7 mM KCl, pH 7.4), washed with equilibration buffer and eluted with 100 mM sodium acetate, pH 3.0. After neutralization with 1 M Tris pH 9.0, aggregated protein was separated from monomeric antibody species by ion exchange Chromatography (Poros XS) with equilibration buffer 20 mM His, pH 5.5, 1.47 mS/cm and elution buffer 20 mM His, 500 mM NaCl, pH 5.5, 49.1 mS/cm, (gradient: to 100% elution buffer in 60 CV). In some cases a size exclusion chromatography (Superdex 200, GE Healthcare) in 20 mM histidine, 140 mM NaCl, pH 6.0, was subsequently performed. Monomeric protein fractions were pooled, and if required concentrated using e.g. a MILLIPORE Amicon Ultra (30 KD MWCO) centrifugal concentrator. Purified proteins were stored at −80° C. Protein quantification was performed using a Nanodrop spectrophotometer and analyzed by CE-SDS under denaturing and reducing conditions and analytical SEC. Sample aliquots were used for subsequent analytical characterization e.g. by CE-SDS, size exclusion chromatography, mass spectrometry and endotoxin determination.

Purity and molecular weight of the bispecific antigen binding molecule after the final purification step were analyzed by CE-SDS analyses in the presence and absence of a reducing agent. The Caliper LabChip GXII system (Caliper Lifescience) was used according to the manufacturer's instruction.

The aggregate content of the bispecific antigen binding molecule was analyzed using a TSKgel G3000 SW XL analytical size-exclusion column (Tosoh) in 25 mM potassium phosphate, 125 mM sodium chloride, 200 mM L-arginine monohydrocloride, 0.02% (w/v) $NaN_3$, pH 6.7 running buffer at 25° C.

TABLE 14

Production yield and Quality of bispecific OX40 antigen binding molecules

| Molecule | Monomer [%] | CE-SDS (non-reduced) [%] | Yield [mg/l] |
|---|---|---|---|
| P1AE6838 OX40(49B4) × FAP(1G1a) 4 + 1 | 99 | 94 | 44 |
| P1AE8786 OX40(49B4) × FAP(1G1a) 3 + 1 | 99 | 93 | 21 |
| P1AE6840 OX40(49B4) × FAP(1G1a) 2 + 1 | 98 | 98 | 3.7 |
| P1AF7205 OX40(CLC563) × FAP(1G1a_EPKSCD) 4 + 1 | 99 | 96 | 25 |
| P1AF7217 OX40(CLC563) × FAP(1G1a_EPKSCS) 4 + 1 | 99 | 98 | 32 |
| P1AE8874 OX40(CLC563) × FAP(1G1a) 3 + 1 | 99 | 100 | 35 |
| P1AF6454 OX40(CLC563) × FAP(1G1a_EPKSCD) 3 + 1 | 98 | 98 | 122 |
| P1AF6455 OX40(CLC563) × FAP(1G1a_EPKSCS) 3 + 1 | 100 | 100 | 19 |
| P1AE8871 OX40(CLC563) × FAP(1G1a) 2 + 1 | 96 | 98 | 90 |
| P1AE8875 OX40(MOXR0916) × FAP(1G1a) 3 + 1 | 98 | 97 | 9 |
| P1AF4845 OX40(MOXR0916) × FAP(1G1a_EPKSCD) 3 + 1 | 86 | 100 | 0.2 |
| P1AF4851 OX40(MOXR0916) × FAP(1G1a_EPKSCS) 3 + 1 | 99 | 100 | 0.5 |
| P1AE8872 OX40(MOXR0916) × FAP(1G1a) 2 + 1 | 95 | 98 | 2.4 |
| P1AF4852 OX40(MOXR0916) × FAP(1G1a_EPKSCD) 2 + 1 | 95 | 100 | 2.7 |
| P1AF4858 OX40(MOXR0916) × FAP(1G1a_EPKSCS) 2 + 1 | 98 | 99 | 4.6 |
| P1AE8873 OX40(8H9) × FAP(1G1a) 3 + 1 | 100 | 100 | 13 |
| P1AE8870 OX40(8H9) × FAP(1G1a) 2 + 1 | 98 | 98 | 13 |

2.3 Generation of Further Bispecific Antigen Binding Molecules Targeting OX40 and Fibroblast Activation Protein (FAP)—Charge Patch Variants In analogy to Example 2.1, different variants of a 4+1 bispecific format consisting of four OX40 binding moieties combined with one FAP binding crossfab at the C-terminus of the Fc domain have been prepared. In all these constructs, the variable heavy and light chain domains of the anti-OX40 antibody correspond to the OX40 clone 49B34 as described in WO 2017/055398 A2. The generation and preparation of the FAP antibody 1G1a is described in Example 1. To generate the 4+1 antigen binding molecules, the knob-into-hole technology was used to achieve heterodimerization. The S354C/T366W mutations were introduced in the first heavy chain HC1 (Fc knob heavy chain) and the Y349C/T366S/L368A/Y407V mutations were introduced in the second heavy chain HC2 (Fc hole heavy chain). Furthermore, the CrossMab technology as described in WO 2010/

145792 A1 ensures correct light chain pairing. Independent of the bispecific format, in all cases an effector silent Fc (P329G; L234A, L235A) has been used to abrogate binding to Fcγ receptors according to the method described in WO 2012/130831 A1. Amino acid sequences of the bispecific antigen binding molecules are shown in Table 15.

All genes are transiently expressed under control of a chimeric MPSV promoter consisting of the MPSV core promoter combined with the CMV promoter enhancer fragment. The expression vector also contains the oriP region for episomal replication in EBNA (Epstein Barr Virus Nuclear Antigen) containing host cells.

TABLE 15

Amino acid sequences of the bispecific antigen binding molecules

| Molecule | Sequence | Seq ID No |
|---|---|---|
| P1AE9167 OX40(49B4_K73E) x FAP (1G1a) (4 + 1) | | |
| OX40(49B4_K73E) VHCH1-OX40(49B4_K73E) VHCH1-Fc TVS knob_PGLALA-FAP(1G1a) VHCL | QVQLVQSGAEVKKPGSSVKVSCKASGGTFSSYAISWVR QAPGQGLEWMGGIIPIFGTANYAQKFQGRVTITADEST STAYMELSSLRSEDTAVYYCAREYYRGPYDYWGQGTTV SASTKGPSVFPLAPSSKSTSGGTAALGCLVEDYFP EPVTVSWNSGALTSGVHTFPAVLQSSGLYSLSSVVTVP SSSLGTQTYICNVNHKPSNTKVDEKVEPKSCGGGGSGG SGGQVQLVQSGAEVKKPGSSVKVSCKASGGTFSSYAIS WVRQAPGQGLEWMGGIIPIFGTANYAQKFQGRVTITAD ESTSTAYMELSSLRSEDTAVYYCAREYYRGPYDYWGQG TTVTVSSASTKGPSVFPLAPSSKSTSGGTAALGCLVED YFPEPVTVSWNSGALTSGVHTFPAVLQSSGLYSLSSVV TVPSSSLGTQTYICNVNHKPSNTKVDEKVEPKSCDKTH TCPPCPAPEAAGGPSVFLFPPKPKDILMISRTPEVTCV VVDVSHEDPEVKFNWYVDGVEVHNAKTKPREEQYNSTY RVVSVLTVLHQDWLNGKEYKCKVSNKALGAPIEKTISK AKGQPREPQVYTLPPCRDELTKNQVSLWCLVKGFYPSD IAVEWESNGQPENNYKTTPPVLDSDGSFFLYSKLTVDK SRWQQGNVFSCSVMHEALHNHYTQKSLSLSPGGGGGSG GGGSGGGGSGGSGGQVQLVQSGAEVKKPGASVKVSCKA SGYILTDYNMDWVRQAPGQGLEWIGDIYPNIGGTIYNQ KFKGRVTMTIDTSTSTVYMELSSLRSEDTAVYYCTRFR GIHYAMDYWGQGTTVTVSSASVAAPSVFIFPPSDEQLK SGTASVVCLLNNFYPREAKVQWKVDNALQSGNSQESVT EQDSKDSTYSLSSTLTLSKADYEKHKVYACEVTHQGLS SPVTKSFNRGEC | 107 |
| OX40(49B4_K73E) light chain | DIQMTQSPSTLSASVGDRVTITCRASQSISSWLAWYQQ KPGKAPKLLIYDASSLESGVPSRFSGSGSGTEFTLTIS SLQPDDFATYYCQQYSSQPYTFGQGTKVEIKRTVAAPS VFIFPPSDRKLKSGTASVVCLLNNFYPREAKVQWKVDN ALQSGNSQESVTEQDSKDSTYSLSSTLTLSKADYEKHK VYACEVTHQGLSSPVTKSFNRGEC | 87 |
| FAP(1G1a) VLCH1-light chain | EIVLTQSPATLSLSPGERATLSCRASESVDNYGLSFIN WFQQKPGQAPRLLIYGTSNRGSGIPARFSGSGSGTDFT LIISSLEPEDFAVYFCQQSNEVPYTFGGGTKVEIKSSA STKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKKVEPKSC | 88 |
| OX40(49B4_K73E) VHCH1-OX40(49B4_K73E) VHCH1-Fc hole_PGLALA | QVQLVQSGAEVKKPGSSVKVSCKASGGTFSSYAISWVR QAPGQGLEWMGGIIPIFGTANYAQKFQGRVTITADEST STAYMELSSLRSEDTAVYYCAREYYRGPYDYWGQGTTV TVSSASTKGPSVFPLAPSSKSTSGGTAALGCLVEDYFP EPVTVSWNSGALTSGVHTFPAVLQSSGLYSLSSVVTVP SSSLGTQTYICNVNHKPSNTKVDEKVEPKSCGGGGSGG SGGQVQLVQSGAEVKKPGSSVKVSCKASGGTFSSYAIS WVRQAPGQGLEWMGGIIPIFGTANYAQKFQGRVTITAD ESTSTAYMELSSLRSEDTAVYYCAREYYRGPYDYWGQG TTVTVSSASTKGPSVFPLAPSSKSTSGGTAALGCLVED YFPEPVTVSWNSGALTSGVHTFPAVLQSSGLYSLSSVV TVPSSSLGTQTYICNVNHKPSNTKVDEKVEPKSCDKTH TCPPCPAPEAAGGPSVFLFPPKPKDILMISRTPEVTCV VVDVSHEDPEVKFNWYVDGVEVHNAKTKPREEQYNSTY RVVSVLTVLHQDWLNGKEYKCKVSNKALGAPIEKTISK AKGQPREPQVCTLPPSRDELIKNQVSLSCAVKGFYPSD IAVEWESNGQPENNYKTTPPVLDSDGSFFLVSKLTVDK SRWQQGNVFSCSVMHEALHNHYTQKSLSLSPG | 108 |

TABLE 15-continued

Amino acid sequences of the bispecific antigen binding molecules

| Molecule | Sequence | Seq ID No |
|---|---|---|
| | P1AE9169 OX40(49B4_K23T_K73E) x FAP (1G1a) (4 + 1) | |
| OX40(49B4_K231_K73E) VHCH1-OX40(49B4_K231_K73E) VHCH1-Fc knob PGLALA-FAP(1G1a) VHCL | QVQLVQSGAEVKKPGSSVKVSCTASGGTFSSYAISWVR QAPGQGLEWMGGIIPIFGTANYAQKFQGRVTITADEST STAYMELSSLRSEDTAVYYCAREYYRGPYDYWGQGTTV TVSSASTKGPSVFPLAPSSKSTSGGTAALGCLVEDYFP EPVTVSWNSGALTSGVHTFPAVLQSSGLYSLSSVVTVP SSSLGTQTYICNVNHKPSNTKVDEKVEPKSCGGGGSGG SGGGQVQLVQSGAEVKKPGSSVKVSCTASGGTFSSYAIS WVRQAPGQGLEWMGGIIPIFGTANYAQKFQGRVTITAD ESTSTAYMELSSLRSEDTAVYYCAREYYRGPYDYWGQG TTVTVSSASTKGPSVFPLAPSSKSTSGGTAALGCLVED YFPEPVTVSWNSGALTSGVHTFPAVLQSSGLYSLSSVV TVPSSSLGTQTYICNVNHKPSNTKVDEKVEPKSCDKTH TCPPCPAPEAAGGPSVFLFPPKPKDILMISRTPEVTCV VVDVSHEDPEVKFNWYVDGVEVHNAKTKPREEQYNSTY RVVSVLTVLHQDWLNGKEYKCKVSNKALGAPIEKTISK AKGQPREPQVYTLPPCRDELTKNQVSLWCLVKGFYPSD IAVEWESNGQPENNYKTTPPVLDSDGSFFLYSKLTVDK SRWQQGNVFSCSVMHEALHNHYTQKSLSLSPGGGGGSG GGGSGGGGSGGSGGQVQLVQSGAEVKKPGASVKVSCKA SGYILTDYNMDWVRQAPGQGLEWIGDIYPNIGGTIYNQ KFKGRVIMTIDTSTSTVYMELSSLRSEDTAVYYCTRFR GIHYAMDYWGQGTTVTVSSASVAAPSVFIFPPSDEQLK SGTASVVCLLNNFYPREAKVQWKVDNALQSGNSQESVT EQDSKDSTYSLSSILTLSKADYEKHKVYACEVTHQGLS SPVTKSFNRGEC | 109 |
| OX40(49B4_K23_K73E) light chain | DIQMTQSPSTLSASVGDRVTITCRASQSISSWLAWYQQ KPGKAPKLLIYDASSLESGVPSRFSGSGSGTEFTLTIS SLQPDDFATYYCQQYSSQPYTFGQGTKVEIKRTVAAPS VFIFPPSDRKLKSGTASVVCLLNNFYPREAKVQWKVDN ALQSGNSQESVTEQDSKDSTYSLSSTLTLSKADYEKHK VYACEVTHQGLSSPVTKSFNRGEC | 87 |
| FAP(1G1a) VLCH1-light chain | EIVLTQSPATLSLSPGERATLSCRASESVDNYGLSFIN WFQQKPGQAPRLLIYGTSNRGSGIPARFSGSGSGTDFT LIISSLEPEDFAVYFCQQSNEVPYTFGGGTKVEIKSSA STKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKKVEPKSC | 88 |
| OX40(49B4_K231_K73E) VHCH1-OX40(49B4_K231_K73E) VHCH1-Fc hole_PGLALA | QVQLVQSGAEVKKPGSSVKVSCTASGGTFSSYAISWVR QAPGQGLEWMGGIIPIFGTANYAQKFQGRVTITADEST STAYMELSSLRSEDTAVYYCAREYYRGPYDYWGQGTTV TVSSASTKGPSVFPLAPSSKSTSGGTAALGCLVEDYFP EPVTVSWNSGALTSGVHTFPAVLQSSGLYSLSSVVTVP SSSLGTQTYICNVNHKPSNTKVDEKVEPKSCGGGGSGG SGGGQVQLVQSGAEVKKPGSSVKVSCTASGGTFSSYAIS WVRQAPGQGLEWMGGIIPIFGTANYAQKFQGRVTITAD ESTSTAYMELSSLRSEDTAVYYCAREYYRGPYDYWGQG TTVTVSSASTKGPSVFPLAPSSKSTSGGTAALGCLVED YFPEPVTVSWNSGALTSGVHTFPAVLQSSGLYSLSSVV TVPSSSLGTQTYICNVNHKPSNTKVDEKVEPKSCDKTH TCPPCPAPEAAGGPSVFLFPPKPKDTLMISRTPEVTCV VVDVSHEDPEVKFNWYVDGVEVHNAKTKPREEQYNSTY RVVSVLTVLHQDWLNGKEYKCKVSNKALGAPIEKTISK AKGQPREPQVCTLPPSRDELIKNQVSLSCAVKGFYPSD IAVEWESNGQPENNYKTTPPVLDSDGSFFLVSKLTVDK SRWQQGNVFSCSVMHEALHNHYTQKSLSLSPG | 110 |

TABLE 15-continued

Amino acid sequences of the bispecific antigen binding molecules

| Molecule | Sequence | Seq ID No |
|---|---|---|
| | P1AE9176 OX40(49B4_K23E_K73E) x FAP (1G1a) (4 + 1) | |
| OX40(49B4_K23E_K73E) VHCH1-OX40(49B4_K23E_K73E) VHCH1-Fc knob_PGLALA-FAP(1G1a) VHCL | QVQLVQSGAEVKKPGSSVKVSCEASGGTFSSYAISWVR QAPGQGLEWMGGIIPIFGTANYAQKFQGRVTITADEST STAYMELSSLRSEDTAVYYCAREYYRGPYDYWGQGTTV TVSSASTKGPSVFPLAPSSKSTSGGTAALGCLVEDYFP EPVTVSWNSGALTSGVHTFPAVLQSSGLYSLSSVVTVP SSSLGTQTYICNVNHKPSNTKVDEKVEPKSCGGGGSGG SGGGQVQLVQSGAEVKKPGSSVKVSCEASGGTFSSYAIS WVRQAPGQGLEWMGGIIPIFGTANYAQKFQGRVTITAD ESTSTAYMELSSLRSEDTAVYYCAREYYRGPYDYWGQG TTVTVSSASTKGPSVFPLAPSSKSTSGGTAALGCLVED YFPEPVTVSWNSGALTSGVHTFPAVLQSSGLYSLSSVV TVPSSSLGTQTYICNVNHKPSNTKVDEKVEPKSCDKTH TCPPCPAPEAAGGPSVFLFPPKPKDTLMISRTPEVTCV VVDVSHEDPEVKFNWYVDGVEVHNAKTKPREEQYNSTY RVVSVLTVLHQDWLNGKEYKCKVSNKALGAPIEKTISK AKGQPREPQVYTLPPCRDELTKNQVSLWCLVKGFYPSD IAVEWESNGQPENNYKTTPPVLDSDGSFFLYSKLTVDK SRWQQGNVFSCSVMHEALHNHYTQKSLSLSPGGGGGSG GGGSGGGGSGGSGGQVQLVQSGAEVKKPGASVKVSCKA SGYILTDYNMDWVRQAPGQGLEWIGDIYPNIGGTIYNQ KFKGRVTMTIDTSTSTVYMELSSLRSEDTAVYYCTRFR GIHYAMDYWGQGTTVTVSSASVAAPSVFIFPPSDEQLK SGTASVVCLLNNFYPREAKVQWKVDNALQSGNSQESVT EQDSKDSTYSLSSILTLSKADYEKHKVYACEVTHQGLS SPVTKSFNRGEC | 111 |
| OX40(49B4_K23E_K73E) light chain | DIQMTQSPSTLSASVGDRVTITCRASQSISSWLAWYQQ KPGKAPKLLIYDASSLESGVPSRFSGSGSGTEFTLTIS SLQPDDFATYYCQQYSSQPYTFGQGTKVEIKRTVAAPS VFIFPPSDRKLKSGTASVVCLLNNFYPREAKVQWKVDN ALQSGNSQESVTEQDSKDSTYSLSSTLTLSKADYEKHK VYACEVTHQGLSSPVTKSFNRGEC | 87 |
| FAP(1G1a) VLCH1-light chain | EIVLTQSPATLSLSPGERATLSCRASESVDNYGLSFIN WFQQKPGQAPRLLIYGTSNRGSGIPARFSGSGSGTDFT LIISSLEPEDFAVYFCQQSNEVPYTFGGGTKVEIKSSA STKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKKVEPKSC | 88 |
| OX40(49B4_K23E_K73E) VHCH1-OX40(49B4_K23E_K73E) VHCH1-Fc hole_PGLALA | QVQLVQSGAEVKKPGSSVKVSCEASGGTFSSYAISVR QAPGQGLEWMGGIIPIFGTANYAQKFQGRVTITADEST STAYMELSSLRSEDTAVYYCAREYYRGPYDYWGQGTTV TVSSASTKGPSVFPLAPSSKSTSGGTAALGCLVEDYFP EPVTVSWNSGALTSGVHTFPAVLQSSGLYSLSSVVTVP SSSLGTQTYICNVNHKPSNTKVDEKVEPKSCGGGGSGG SGGGQVQLVQSGAEVKKPGSSVKVSCEASGGTFSSYAIS WVRQAPGQGLEWMGGIIPIFGTANYAQKFQGRVTITAD ESTSTAYMELSSLRSEDTAVYYCAREYYRGPYDYWGQG TTVTVSSASTKGPSVFPLAPSSKSTSGGTAALGCLVED YFPEPVTVSWNSGALTSGVHTFPAVLQSSGLYSLSSVV TVPSSSLGTQTYICNVNHKPSNTKVDEKVEPKSCDKTH TCPPCPAPEAAGGPSVFLFPPKPKDILMISRTPEVTCV VVDVSHEDPEVKFNWYVDGVEVHNAKTKPREEQYNSTY RVVSVLTVLHQDWLNGKEYKCKVSNKALGAPIEKTISK AKGQPREPQVCTLPPSRDELIKNQVSLSCAVKGFYPSD IAVEWESNGQPENNYKTTPPVLDSDGSFFLVSKLTVDK SRWQQGNVFSCSVMHEALHNHYTQKSLSLSPG | 112 |

TABLE 15-continued

Amino acid sequences of the bispecific antigen binding molecules

| Molecule | Sequence | Seq ID No |
|---|---|---|
| P1AF6456 OX40(49B4_K23E_K73E) x FAP (1G1a_EPKSCD) (4 + 1) | | |
| OX40(49B4_K23E_K73E) VHCH1-OX40(49B4_K23E_K73E) VHCH1-Fc knob_PGLALA-FAP(1G1a) VHCL | QVQLVQSGAEVKKPGSSVKVSCEASGGTFSSYAISWVR QAPGQGLEWMGGIIPIFGTANYAQKFQGRVTITADEST STAYMELSSLRSEDTAVYYCAREYYRGPYDYWGQGTTV TVSSASTKGPSVFPLAPSSKSTSGGTAALGCLVEDYFP EPVTVSWNSGALTSGVHTFPAVLQSSGLYSLSSVVTVP SSSLGTQTYICNVNHKPSNTKVDEKVEPKSCGGGGSGG SGGGGQVQLVQSGAEVKKPGSSVKVSCEASGGTFSSYAIS WVRQAPGQGLEWMGGIIPIFGTANYAQKFQGRVTITAD ESTSTAYMELSSLRSEDTAVYYCAREYYRGPYDYWGQG TTVTVSSASTKGPSVFPLAPSSKSTSGGTAALGCLVED YFPEPVTVSWNSGALTSGVHTFPAVLQSSGLYSLSSVV TVPSSSLGTQTYICNVNHKPSNTKVDEKVEPKSCDKTH TCPPCPAPEAAGGPSVFLFPPKPKDILMISRTPEVTCV VVDVSHEDPEVKFNWYVDGVEVHNAKTKPREEQYNSTY RVVSVLTVLHQDWLNGKEYKCKVSNKALGAPIEKTISK AKGQPREPQVYTLPPCRDELTKNQVSLWCLVKGFYPSD IAVEWESNGQPENNYKTTPPVLDSDGSFFLYSKLTVDK SRWQQGNVFSCSVMHEALHNHYTQKSLSLSPGGGGGSG GGGSGGGGSGGSGGQVQLVQSGAEVKKPGASVKVSCKA SGYILTDYNMDWVRQAPGQGLEWIGDIYPNIGGTIYNQ KFKGRVIMTIDTSTSTVYMELSSLRSEDTAVYYCTRFR GIHYAMDYWGQGTTVTVSSASVAAPSVFIFPPSDEQLK SGTASVVCLLNNFYPREAKVQWKVDNALQSGNSQESVT EQDSKDSTYSLSSILTLSKADYEKHKVYACEVTHQGLS SPVTKSFNRGEC | 111 |
| OX40(49B4_K23E_K73E) light chain | DIQMTQSPSTLSASVGDRVTITCRASQSISSWLAWYQQ KPGKAPKLLIYDASSLESGVPSRFSGSGSGTEFTLTIS SLQPDDFATYYCQQYSSQPYTFGQGTKVEIKRTVAAPS VFIFPPSDRKLKSGTASVVCLLNNFYPREAKVQWKVDN ALQSGNSQESVTEQDSKDSTYSLSSTLTLSKADYEKHK VYACEVTHQGLSSPVTKSFNRGEC | 87 |
| FAP(1G1a) VLCH1-light chain (EPKSCD) | EIVLTQSPATLSLSPGERATLSCRASESVDNYGLSFIN WFQQKPGQAPRLLIYGTSNRGSGIPARFSGSGSGTDFT LIISSLEPEDFAVYFCQQSNEVPYTFGGGTKVEIKSSA STKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKKVEPKSCD | 94 |
| OX40(49B4_K23E_K73E) VHCH1-OX40(49B4_K23E_K73E) VHCH1-Fc hole_PGLALA | QVQLVQSGAEVKKPGSSVKVSCEASGGTFSSYAISVR QAPGQGLEWMGGIIPIFGTANYAQKFQGRVTITADEST STAYMELSSLRSEDTAVYYCAREYYRGPYDYWGQGTTV TVSSASTKGPSVFPLAPSSKSTSGGTAALGCLVEDYFP EPVTVSWNSGALTSGVHTFPAVLQSSGLYSLSSVVTVP SSSLGTQTYICNVNHKPSNTKVDEKVEPKSCGGGGSGG SGGGGQVQLVQSGAEVKKPGSSVKVSCEASGGTFSSYAIS WVRQAPGQGLEWMGGIIPIFGTANYAQKFQGRVTITAD ESTSTAYMELSSLRSEDTAVYYCAREYYRGPYDYWGQG TTVTVSSASTKGPSVFPLAPSSKSTSGGTAALGCLVED YFPEPVTVSWNSGALTSGVHTFPAVLQSSGLYSLSSVV TVPSSSLGTQTYICNVNHKPSNTKVDEKVEPKSCDKTH TCPPCPAPEAAGGPSVFLFPPKPKDILMISRTPEVTCV VVDVSHEDPEVKFNWYVDGVEVHNAKTKPREEQYNSTY RVVSVLTVLHQDWLNGKEYKCKVSNKALGAPIEKTISK AKGQPREPQVCTLPPSRDELTKNQVSLSCAVKGFYPSD IAVEWESNGQPENNYKTTPPVLDSDGSFFLVSKLTVDK SRWQQGNVFSCSVMHEALHNHYTQKSLSLSPG | 112 |

TABLE 15-continued

Amino acid sequences of the bispecific antigen binding molecules

| Molecule | Sequence | Seq ID No |
|---|---|---|
| P1AF6457 OX40(49B4_K23E_K73E) x FAP (1G1a_EPKSCS) (4 + 1) | | |
| OX40(49B4_K23E_K73E) VHCH1-OX40(49B4_K23E_K73E) VHCH1-Fc knob_PGLALA-FAP(1G1a) VHCL | QVQLVQSGAEVKKPGSSVKVSCEASGGTFSSYAISWVR QAPGQGLEWMGGIIPIFGTANYAQKFQGRVTITADEST STAYMELSSLRSEDTAVYYCAREYYRGPYDYWGQGTTV TVSSASTKGPSVFPLAPSSKSTSGGTAALGCLVEDYFP EPVTVSWNSGALTSGVHTFPAVLQSSGLYSLSSVVTVP SSSLGTQTYICNVNHKPSNTKVDEKVEPKSCGGGGSGG SGGGQVQLVQSGAEVKKPGSSVKVSCEASGGTFSSYAIS WVRQAPGQGLEWMGGIIPIFGTANYAQKFQGRVTITAD ESTSTAYMELSSLRSEDTAVYYCAREYYRGPYDYWGQG TTVTVSSASTKGPSVFPLAPSSKSTSGGTAALGCLVED YFPEPVTVSWNSGALTSGVHTFPAVLQSSGLYSLSSVV TVPSSSLGTQTYICNVNHKPSNTKVDEKVEPKSCDKTH TCPPCPAPEAAGGPSVFLFPPKPKDILMISRTPEVTCV VVDVSHEDPEVKFNWYVDGVEVHNAKTKPREEQYNSTY RVVSVLTVLHQDWLNGKEYKCKVSNKALGAPIEKTISK AKGQPREPQVYTLPPCRDELTKNQVSLWCLVKGFYPSD IAVEWESNGQPENNYKTTPPVLDSDGSFFLYSKLTVDK SRWQQGNVFSCSVMHEALHNHYTQKSLSLSPGGGGGSG GGGSGGGGSGGSGGQVQLVQSGAEVKKPGASVKVSCKA SGYILTDYNMDWVRQAPGQGLEWIGDIYPNIGGTIYNQ KFKGRVIMTIDTSTSTVYMELSSLRSEDTAVYYCTRFR GIHYAMDYWGQGTTVTVSSASVAAPSVFIFPPSDEQLK SGTASVVCLLNNFYPREAKVQWKVDNALQSGNSQESVT EQDSKDSTYSLSSILTLSKADYEKHKVYACEVTHQGLS SPVTKSFNRGEC | 111 |
| OX40(49B4_K23E_K73E) light chain | DIQMTQSPSTLSASVGDRVTITCRASQSISSWLAWYQQ KPGKAPKLLIYDASSLESGVPSRFSGSGSGTEFTLTIS SLQPDDFATYYCQQYSSQPYTFGQGTKVEIKRTVAAPS VFIFPPSDRKLKSGTASVVCLLNNFYPREAKVQWKVDN ALQSGNSQESVTEQDSKDSTYSLSSTLTLSKADYEKHK VYACEVTHQGLSSPVTKSFNRGEC | 87 |
| FAP(1G1a) VLCH1-light chain (EPKSCS) | EIVLTQSPATLSLSPGERATLSCRASESVDNYGLSFIN WFQQKPGQAPRLLIYGTSNRGSGIPARFSGSGSGTDFT LTISSLEPEDFAVYFCQQSNEVPYTFGGGTKVEIKSSA STKGPSVFPLAPSSKSTSGGTAALGCLVKDYFPEPVTV SWNSGALTSGVHTFPAVLQSSGLYSLSSVVTVPSSSLG TQTYICNVNHKPSNTKVDKKVEPKSCS | 96 |
| OX40(49B4_K23E_K73E) VHCH1-OX40(49B4_K23E_K73E) VHCH1-Fc hole_PGLALA | QVQLVQSGAEVKKPGSSVKVSCEASGGTFSSYAISVR QAPGQGLEWMGGIIPIFGTANYAQKFQGRVTITADEST STAYMELSSLRSEDTAVYYCAREYYRGPYDYWGQGTTV TVSSASTKGPSVFPLAPSSKSTSGGTAALGCLVEDYFP EPVTVSWNSGALTSGVHTFPAVLQSSGLYSLSSVVTVP SSSLGTQTYICNVNHKPSNTKVDEKVEPKSCGGGGSGG SGGGQVQLVQSGAEVKKPGSSVKVSCEASGGTFSSYAIS WVRQAPGQGLEWMGGIIPIFGTANYAQKFQGRVTITAD ESTSTAYMELSSLRSEDTAVYYCAREYYRGPYDYWGQG TTVTVSSASTKGPSVFPLAPSSKSTSGGTAALGCLVED YFPEPVTVSWNSGALTSGVHTFPAVLQSSGLYSLSSVV TVPSSSLGTQTYICNVNHKPSNTKVDEKVEPKSCDKTH TCPPCPAPEAAGGPSVFLFPPKPKDILMISRTPEVTCV VVDVSHEDPEVKFNWYVDGVEVHNAKTKPREEQYNSTY RVVSVLTVLHQDWLNGKEYKCKVSNKALGAPIEKTISK AKGQPREPQVCTLPPSRDELIKNQVSLSCAVKGFYPSD IAVEWESNGQPENNYKTTPPVLDSDGSFFLVSKLTVDK SRWQQGNVFSCSVMHEALHNHYTQKSLSLSPG | 112 |

2.4 Production of Bispecific Antigen Binding Molecules Targeting FAP and OX40 (Charge Patch Variants)

Antibodies were expressed by transient transfection of HEK cells grown in suspension with expression vectors encoding the 4 different peptide chains. Transfection into HEK293-F cells (Invitrogen) was performed according to the cell supplier's instructions using MaxiPREP (Qiagen) preparations of the antibody vectors, Freestyle™ F17 medium (Invitrogen, USA), PEIpro® transfection reagent (Polyscience Europe GmbH) and an initial cell density of 1-2 million viable cells/ml in serum free FreeStyle 293 expression medium (Invitrogen). Cell culture supernatants were harvested after 7 days of cultivation in shake flasks or stirred fermenters by centrifugation at 14000×g for 30 minutes and filtered through a 0.22 m filter.

Antibodies were purified from cell culture supernatants by affinity chromatography using MabSelectSure-Sepharose™ (GE Healthcare, Sweden) chromatography. Briefly, sterile filtered cell culture supernatants were captured on a Mab-SelectSure resin equilibrated with PBS buffer (10 mM Na$_2$HPO$_4$, 1 mM KH$_2$PO$_4$, 137 mM NaCl and 2.7 mM KCl, pH 7.4), washed with equilibration buffer and eluted with 25 mM citrate, pH 3.0. After neutralization with 1 M Tris buffer pH 9.0, aggregated protein was separated from monomeric antibody species by size exclusion chromatography (Superdex 200, GE Healthcare) in 20 mM histidine, 140 mM NaCl, pH 6.0. Monomeric protein fractions were pooled, concentrated if required using e.g. a MILLIPORE Amicon Ultra (30 KD MWCO) centrifugal concentrator and stored at −80° C. Sample aliquots were used for subsequent analytical characterization e.g. by CE-SDS, size exclusion chromatography, mass spectrometry and endotoxin determination.

TABLE 16

Production yield and Quality of bispecific OX40 antigen binding molecules

| Molecule | Monomer [%] | CE-SDS (non-reduced) [%] | Yield [mg/l] |
|---|---|---|---|
| P1AE9167 OX40(49B4_K73E) × FAP(1G1a) 4 + 1 | 99 | 92 | 2.7 |
| P1AE9169 OX40(49B4_K23T_K73E) × FAP(1G1a) 4 + 1 | 95 | 98 | 6.7 |
| P1AE9176 OX40(49B4_K23E_K73E) × FAP(1G1a) 4 + 1 | 99 | 99 | 32 |
| P1AF6456 OX40(49B4_K23E_K73E) × FAP(1G1a_EPKSCD) 4 + 1 | 93 | 94 | 2.6 |
| P1AF6457 OX40(49B4_K23E_K73E) × FAP(1G1a_EPKSCS) 4 + 1 | 98 | 96 | 0.9 |

Example 3

Characterization of Bispecific Antigen Binding Molecules Targeting OX40 and FAP 3.1 Binding to Naïve Versus Activated Human PBMCs of FAP-Targeted Anti-OX40 Bispecific Antigen Binding Molecules Human PBMCs were isolated by ficoll density gradient centrifugation. Buffy coats were obtained from the Zurich blood donation center. To isolate fresh peripheral blood mononuclear cells (PBMCs), the buffy coat was diluted with the same volume of DPBS (Gibco by Life Technologies, Cat. No. 14190 326). 50 mL polypropylene centrifuge tubes (TPP, Cat.-No. 91050) were supplied with 15 mL Histopaque 1077 (SIGMA Life Science, Cat.-No. 10771, polysucrose and sodium diatrizoate, adjusted to a density of 1.077 g/mL) and the buffy coat solution was layered above the Histopaque 1077. The tubes were centrifuged for 30 min at 400×g, room temperature and with low acceleration and no break. Afterwards the PBMCs were collected from the interface, washed three times with DPBS and frozen for later use. PBMC were thawed, washed and resuspended in AIM-V medium (ThermoFischer, Cat. No. 12055091). PBMCs were used unstimulated (binding on resting human PBMCs) or they were stimulated to receive a strong human Ox40 expression on the cell surface of T cells (binding on activated human PBMCs). Therefore thawed PBMCs were cultured for three days at 37° C./5% CO$_2$ in Aim-V media in 6-well tissue culture plate pre-coated for 2 hours with [2 µg/mL] anti-human CD3 (clone OKT3) and [2 µg/mL] anti-human CD28 (clone CD28.2).

For detection, OX40 naïve human PBMCs and activated human PBMCs were mixed. To enable distinction of naïve from activated human PBMCs, naïve cells were labeled prior to the binding assay using the eFluor670 cell proliferation dye (eBioscience, Cat.-No. 65-0840-85). A 1 to 1 mixture of 1×10$^5$ naïve, eFluor670 labeled human PBMC and unlabeled activated human PBMCs were then added to each well of a round-bottom 96-well plate (TPP, Cat. No. 92097) and the binding assay was performed.

Cells were first stained 10 min with Zombie Aqua Fixable viability dye (Biolegend, Cat. No. 423102) in DPBS, followed by a 90 minutes incubation at 4° C. in the dark in 50 µL/well FACS buffer containing titrated anti-OX40 bispecific antibody constructs. After three times washing with excess FACS buffer, cells were stained for 30 minutes at 4° C. in the dark in 25 µL/well FACS buffer containing a mixture of fluorescently labeled anti-human CD4 (clone OKT-4, mouse IgG2b, BioLegend, Cat.-No. 317434), anti-human CD8 (clone RPA-T8, mouse IgG1k, BioLegend, Cat.-No. 301042) and Fluorescein isothiocyanate (FITC)-conjugated AffiniPure anti-human IgG Fcγ-fragment-specific goat IgG F(ab')2 fragment (Jackson ImmunoResearch, Cat.-No. 109-096-098). Samples were finally resuspended in 20 µL/well FACS-buffer and acquired the same day using iQue Cell Screener and ForeCyt software (Sartorius).

Figure 3D:
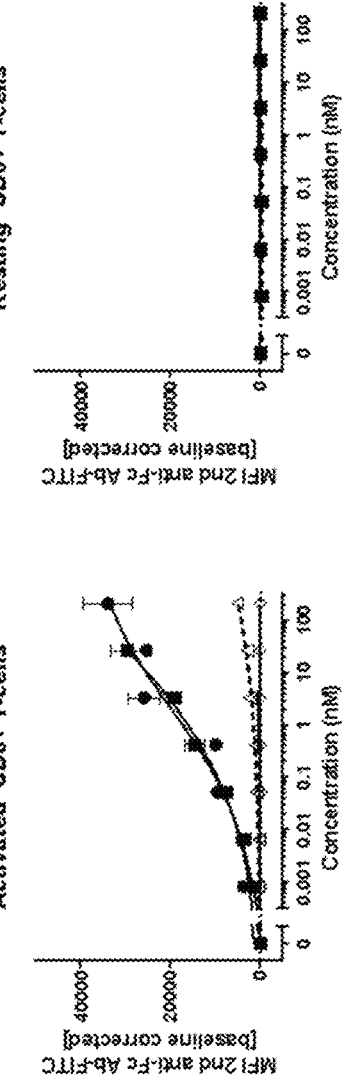
Figure 3F:
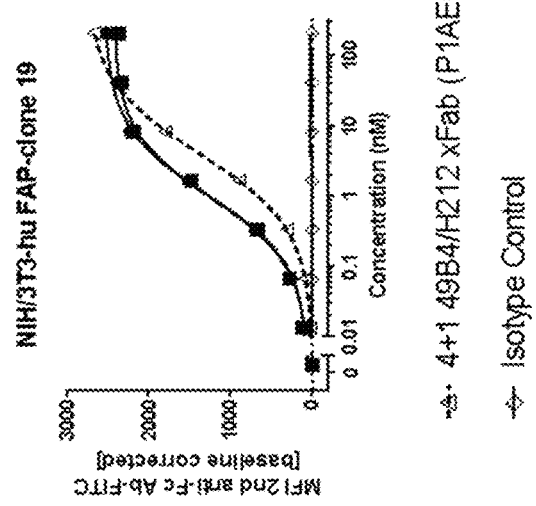
Figure 3E:
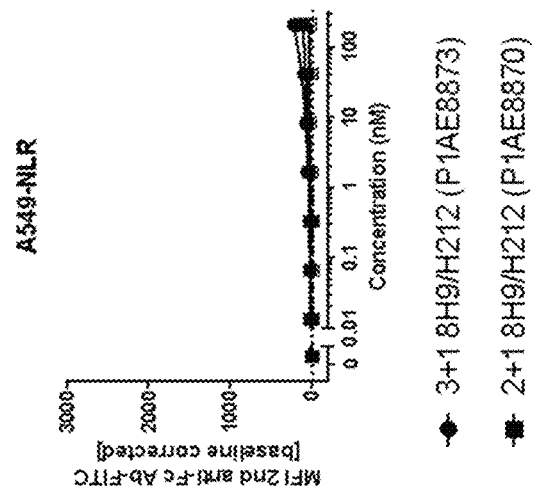
Figure 4A:
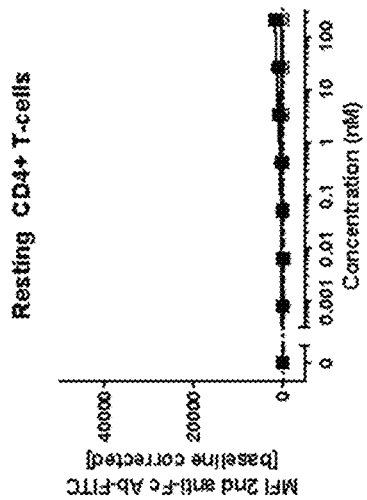
FIG. 4A to FIG. 4F show the cellular binding of bispecific antigen binding molecules comprising OX40 clone MOXR0916 in different formats and in comparison with a bispecific antigen binding molecule comprising OX40 clone 49B4 in 4+1 format (P1AE6838). Human FAP negative tumor cells (A549-NLR)(FIG. 4F), FAP positive fibroblasts (NIH/3T3-huFAP-clone 19) (FIG. 4E), OX40 positive activated PBMC (activated CD4 and CD8 T cells, FIG. 4A and FIG. 4C, respectively) as well as OX40 negative resting PBMC (resting CD4 and CD8 T cells, FIG. 4B and FIG. 4D, respectively) were incubated with indicated serial dilutions of test antibody detected then by fluorescently labeled 2nd antibody against human Fcγ. Living cells were gated and the mean fluorescence intensity of the secondary antibody, baseline corrected by the media-only sample, was plotted from duplicates. Error bars indicate the SEM. The clone MOXR0916 bound with nanomolar affinity to OX40 positive cells, with comparable strength as tri- and bivalent antibody.
Figure 4B:
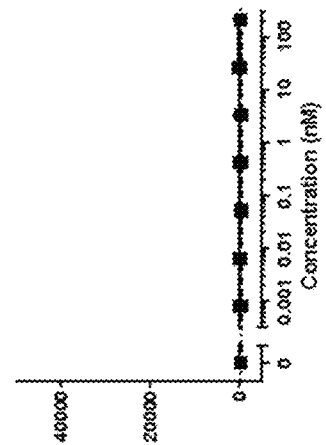
Figure 4C:
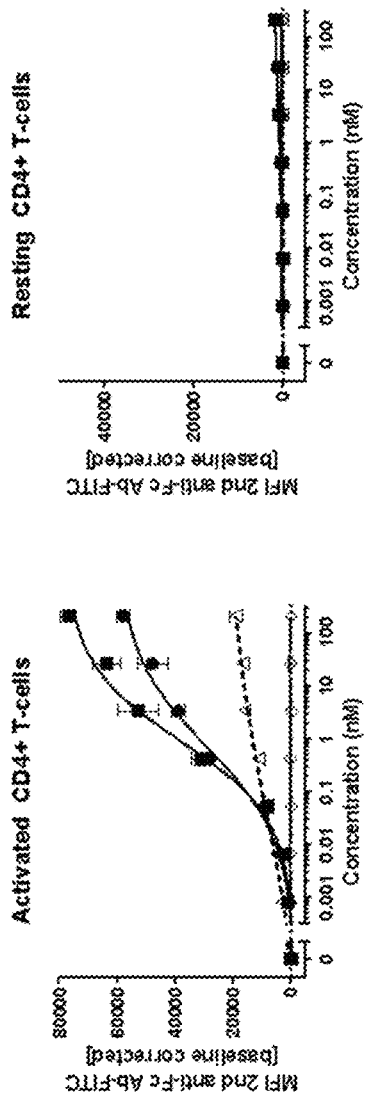
Figure 4D:
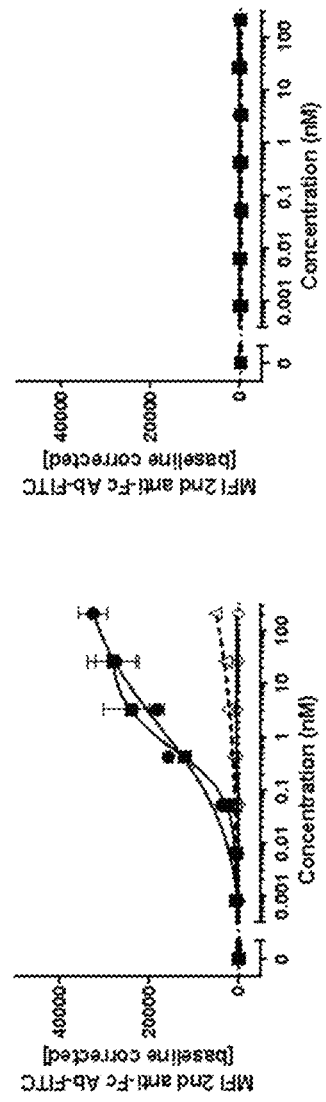
Figure 4E:
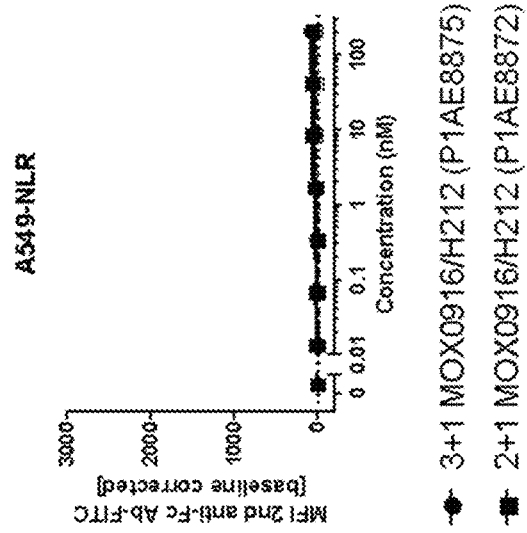
Figure 4F:
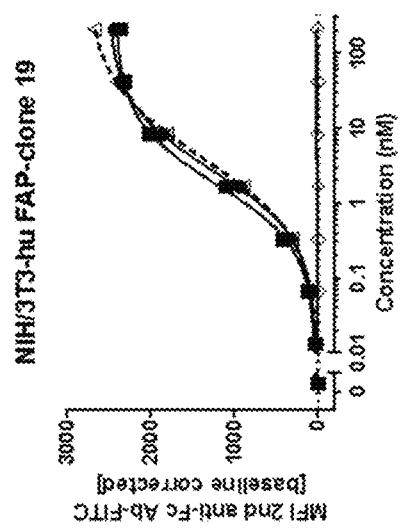
Figure 5F:
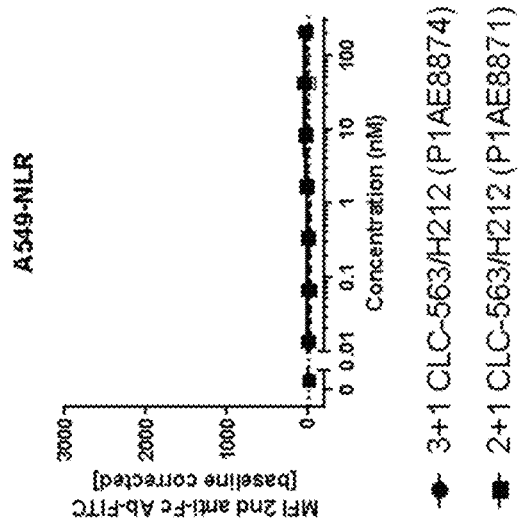
Figure 5E:
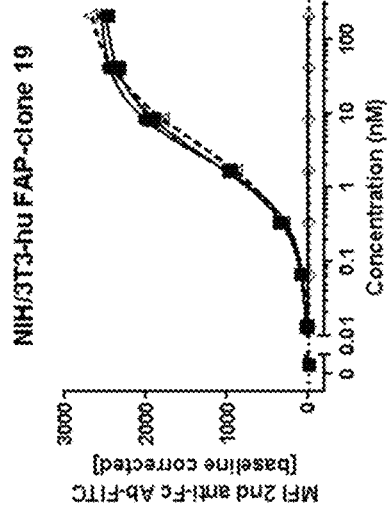

As can be seen in FIG. 2A and FIG. 2C, the bispecific OX40 (49B4)×FAP antigen binding molecule in tetravalent format (4+1) bound better to OX40 than as a trivalent (3+1) or bivalent (2+1) format (avidity of the 49B4 clone). Along the natural prevalence of OX40 on T cells, the bispecific formats bound stronger to activated CD4 than to CD8 T cells, and had no binding to target negative cells (resting CD4 and CD8 T cells, FIG. 2B and FIG. 2D). As shown in FIG. 3A and FIG. 3C, the bispecific antigen binding molecules comprising clone 8H9 bound with subnanomolar affinity to OX40 positive cells and with comparable strength as tri- and bivalent antibody. Along the natural prevalence of OX40 on T cells, the constructs bound stronger to activated CD4 than CD8 T cells, and had no binding to target negative cells (resting CD4 and CD8 T cells, FIG. 3B and FIG. 3D). In FIG. 4A and FIG. 4C it is shown that bispecific antibodies comprising clone MOX0916 bound with subnanomolar affinity to OX40 positive cells, with comparable strength as trivalent or bivalent antibody. Along the natural prevalence of OX40 on T cells, the constructs bound stronger to activated CD4 than to CD8 T cells, and had no binding to target negative cells (resting CD4 and CD8 T cells, see FIG. 4B and FIG. 4D). Bispecific antibodies comprising clone CLC-563 bound with nanomolar affinity to OX40 positive cells, with comparable strength as trivalent and bivalent antibody as is shown in FIG. 5A and FIG. 5C. Along the natural prevalence of OX40 on T cells, the constructs bound stronger to activated CD4 than to CD8 T cells, and had no binding to target negative cells (resting CD4 and CD8 T cells, see FIG. 5B and FIG. 5D).

Figure 6E:
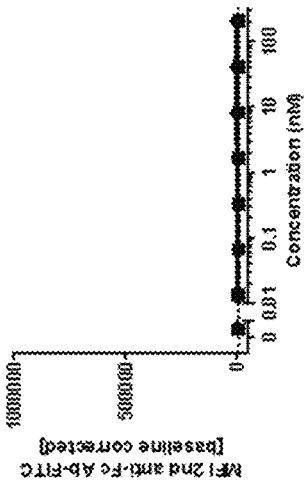
Figure 6F:
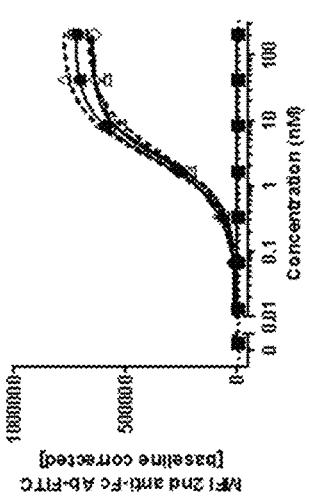

In FIG. 6A and FIG. 6C it is shown that all bispecific antigen binding molecules comprising 49B4 amino acid variant based clones showed slightly improved binding to OX40 positive cells compared to the parental antibody 49B4. Along the natural prevalence of OX40 on T cells, the constructs bound stronger to activated CD4 than CD8 T cells, and had no binding to target negative cells (resting CD4 and CD8 T cells, see FIG. 6B and FIG. 6D).

In another experiment, the binding of bispecific antigen binding molecules targeting OX40 and FAP with different C-terminal variants was tested. PBMC were used that were thawed, washed and resuspended in RPMI medium (Gibco, Cat. No. 72400-021) with (10% (v/v) Fetal calf serum (FCS, SIGMA, Cat.-No. F4135). PBMCs were stimulated to receive a strong human Ox40 expression on the cell surface of T cells (binding on activated human PBMCs). Therefore thawed PBMCs were cultured for three days at 37° C./5% $CO_2$ in in RPMI medium with 10% FCS in 6-well tissue culture plate pre-coated for 2 hours with [2 µg/mL] anti-human CD3 (clone OKT3) and [2 µg/mL] anti-human CD28 (clone CD28.2). For detection, $2\times10^5$ activated human PBMCs were added to each well of a round-bottom 96-well plate (TPP, Cat. No. 92097) and the binding assay was performed. Cells were first stained 20 min with LIVE/DEAD™ Fixable Aqua Dead Cell Stain (Molecular probes, Cat. No. L34957) in DPBS, followed after one washing step (200 µL 4° C. FACS buffer) by incubation of 90 minutes at 4° C. in the dark in 50 µL/well FACS buffer containing titrated anti-OX40 bispecific antigen binding molecules. After one washing with excess FACS buffer, cells were stained for 30 minutes at 4° C. in the dark in 50 µL/well FACS buffer containing a mixture of fluorescently labeled anti-human CD4 (clone A161A1, BioLegend, Cat.-No. 357406), anti-human CD8 (clone SKI, BioLegend, Cat.-No. 344742) and Phycoerythrin (PE)-conjugated AffiniPure anti-human IgG Fcγ-fragment-specific goat IgG F(ab')2 fragment (Jackson ImmunoResearch, Cat. No. 109-116-098). Samples were finally resuspended in 100 µL/well FACS-buffer and acquired the same day using with BD Fortessa running FACS Diva software.

As can be seen in FIG. 34A to FIG. 34F, all tested bispecific FAP-OX40 bispecific antibodies bound to activated CD4 T cells. Along the natural prevalence of OX40 on T cells, the bispecific formats bound stronger to activated CD4 than to CD8 T cells (FIG. 34A, FIG. 34C, FIG. 34E versus FIG. 34B, FIG. 34D, and FIG. 34F). For all tested compounds the D and the S variant showed comparable binding properties (compare for each plot open vs closed symbols).

3.2 Binding to Human FAP-Expressing Tumor Cells

The binding to cell surface FAP was tested using human fibroblast activating protein (huFAP) expressing NIH/3T3-huFAP clone 19 cells. This cell line was generated by the transfection of the mouse embryonic fibroblast NIH/3T3 cell line (ATCC CRL-1658) with the expression vector pETR4921 to express huFAP under 1.5 µg/mL Puromycin selection. The lack of binding to OX40 negative FAP negative tumor cells was tested using A549 NucLight™ Red Cells (Essen Bioscience, Cat. No. 4491) expressing the NucLight Red fluorescent protein restricted to the nucleus to allow separation from unlabeled human FAP positive NIH/3T3-huFAP clone 19 cells. Parental A549 (ATCC CCL-185) were transduced with the Essen CellPlayer NucLight Red Lentivirus (Essen Bioscience, Cat. No. 4476; EF1α, puromycin) at an MOI of 3 (TU/cell) in the presence of 8 µg/ml polybrene following the standard Essen protocol. This resulted in ≥70% transduction efficiency. Alternatively, the lack of binding to OX40 negative FAP negative tumor cells was tested using the HeLa cell line (ATCC, CCL2), a human cervix adenocarcinoma cell line. Enzyme free cell dissociation buffer was used for detachment to preserve trypsin sensitive surface proteins.

A mixture of $5\times10^4$ unlabeled NIH/3T3-huFAP clone 19 cells and A549 NucLight™ Red Cells in FACS buffer were added to each well of a round-bottom 96-well plates (TPP, Cat. No. 92097) and the binding assay was performed. Cells were first stained 10 min with Zombie Aqua Fixable viability dye (Biolegend, Cat. No. 423102) in DPBS, followed by a 75 minutes incubation at 4° C. in the dark in 50 µL/well FACS buffer containing titrated anti-OX40 bispecific antibody constructs. Afterwards the cells were washed three times with 200 µL 4° C. FACS buffer and resuspended by a short vortex. Cells were further stained with 25 µL/well of 4° C. cold secondary antibody solution containing Fluorescein isothiocyanate (FITC)-conjugated AffiniPure anti-human IgG Fcγ-fragment-specific goat IgG F(ab')2 fragment (Jackson ImmunoResearch, Cat. No. 109-096-098) and incubated for 30 minutes at 4° C. in the dark. Samples were finally resuspended in 20 µL/well FACS-buffer and acquired the same day using iQue Cell Screener and ForeCyt software (Sartorius).

As can be seen in FIG. 2E, FIG. 3E, FIG. 4E, FIG. 5E, and FIG. 6E, all bispecific antigen binding molecules, sharing the FAP (1G1a) antigen binding domain, had comparable binding to human FAP positive fibroblasts (NIH/3T3-huFAP-clone 19). Only in FIG. 3E it is shown, that there was a slightly enhanced binding to human FAP positive fibroblasts (NIH/3T3-huFAP-clone 19) when clone 8H9 was incorporated in the bispecific antigen binding molecules, despite of sharing the same FAP (1G1a) antigen binding domain. No binding was observed to target negative cells (A549-NLR cells, FIG. 2F, FIG. 3F, FIG. 4F, FIG. 5F, and FIG. 6F).

In another experiment, a mixture of $2\times10^5$ NIH/3T3-huFAP clone 19 cells and HeLa cells in FACS buffer were added to each well of a round-bottom 96-well plates (TPP, Cat. No. 92097) and the binding assay was performed. Cells were first stained 20 min with LIVE/DEAD™ Fixable Aqua Dead Cell Stain (Molecular probes, Cat. No. L34957) in DPBS, followed after one washing step with 200 µL 4° C. FACS buffer by a 75 minutes incubation at 4° C. in the dark in 50 µL/well FACS buffer containing titrated anti-OX40 bispecific antibody constructs. Afterwards the cells were washed once with 200 µL FACS buffer at 4° C. and resuspended by a short vortex. Cells were further stained with 50 µL/well of 4° C. cold secondary antibody solution containing Phycoerythrin (PE)-conjugated AffiniPure anti-human IgG Fcγ-fragment-specific goat IgG F(ab')2 fragment (Jackson ImmunoResearch, Cat. No. 109-116-098) and incubated for 30 minutes at 4° C. in the dark. Samples were finally resuspended in 100 µL/well FACS-buffer and acquired the same day using with BD Fortessa running FACS Diva software.

All bispecific antigen binding molecules sharing the FAP (1G1a) antigen binding domain, but comprising a C-terminal S or D variant, had comparable binding to human FAP positive fibroblasts (NIH/3T3-huFAP-clone 19), meaning that the variants had no impact on the binding to FAP (see data in Table 17 below). No binding was observed when targeting negative cells (HeLa cells).

3.3 Summary of Cellular Binding Properties of the Bispecific Antigen Binding Molecules For evaluation of the binding properties of the FAP-targeted OX40 antibodies human FAP negative tumor cells (A549-NLR or HeLa), FAP positive fibroblasts (NIH/3T3-huFAP-clone 19), OX40 positive activated PBMC (activated CD4 and CD8 T cells) as well as OX40 negative resting PBMC (resting CD4 and CD8 T cells) were incubated with indicated serial dilutions of test antibody detected then by fluorescently labeled 2nd antibody against human Fcγ.

All FAP-targeted OX40 antigen binding molecules bound efficiently to human FAP-expressing target cells and had no binding to target negative cells. This is expected to translate in patients to direct tumor-targeting and enrichment of the molecules. Along the natural prevalence of OX40 on T cells, all constructs bound stronger to activated CD4 than to CD8

T cells. The bispecific antigen binding molecules comprising clone 49B4 bound better to OX40 in a tetravalent format (4+1) than in a trivalent (3+1) or bivalent (2+1) format (avidity of the clone; see FIG. 2A and FIG. 2C). All 49B4 amino acid variant based bispecific antigen binding molecules showed slightly improved binding to OX40 positive cells compared to the parental antibody in a tetravalent format (see FIG. 6A and FIG. 6C). The clones 8H9 (FIG. 3A and FIG. 3C) and MOX0916 (FIG. 4A and FIG. 4C) bound with subnanomolar affinity, whereas clone CLC-563 (FIG. 5A and FIG. 5C) bound with nanomolar affinity to OX40 positive cells, with comparable strength as tri- and bivalent formats. For all tested C-terminal variants, the D and the S variant showed comparable binding properties. FAP binding was for all bispecific antigen binding molecules in a comparable nanomolar range.

$EC_{50}$ values of binding to activated human CD4 T cells and FAP positive tumor cells are summarized in Table 17.

TABLE 17

$EC_{50}$ values for binding of FAP-targeted OX40 antigen binding molecules to cell surface human FAP and human Ox40 (on CD4$^+$ T-cells)

| Molecule ID | anti-Ox40 clone | Format | Ox40 $EC_{50}$ [nM] | FAP $EC_{50}$ [nM] |
|---|---|---|---|---|
| P1AE6838 | 49B4 | 4 + 1 | 0.03 | 2.63 |
| P1AE9167 | 49B4 AA variant K73E | 4 + 1 | 0.11 | 2.51 |
| P1AE9169 | 49B4 AA variant K23T_K73E | 4 + 1 | 0.12 | 2.47 |
| P1AE9176 | 49B4 AA variant K23E_K73E | 4 + 1 | 0.20 | 2.97 |
| P1AE8786 | 49B4 | 3 + 1 | 17.08 | 2.91 |
| P1AE6840 | 49B4 | 2 + 1 | 73.57 | 2.26 |
| P1AE8873 | 8H9 | 3 + 1 | 0.11 | 1.01 |
| P1AE8870 | 8H9 | 2 + 1 | 0.17 | 0.95 |
| P1AE8875 | MOX0916 | 3 + 1 | 0.69 | 2.70 |
| P1AE8872 | MOX0916 | 2 + 1 | 0.90 | 1.78 |
| P1AE8874 | CLC-563 | 3 + 1 | 3.62 | 2.52 |
| P1AE8871 | CLC-563 | 2 + 1 | 3.19 | 2.51 |
| P1AF6455 | CLC-563, S-variant | 3 + 1 | 1.47 | 1.71 |
| P1AF6454 | CLC-563, D-variant | 3 + 1 | 1.64 | 1.22 |
| P1AF7217 | CLC-563, S-variant | 4 + 1 | 1.46 | 1.33 |
| P1AF7205 | CLC-563, D-variant | 4 + 1 | 2.11 | 1.04 |
| P1AF6457 | 49B4 AA variant K23E_K73E, S-variant | 4 + 1 | 0.05 | 0.69 |
| P1AF6456 | 49B4 AA variant K23E_K73E, D variant | 4 + 1 | 0.07 | 0.36 |

3.4 Biophysical and Biochemical Characterization of Bispecific Antigen Binding Molecules Targeting OX40 and FAP 3.4.1 Determination of Thermal Stability Thermal stability of the FAP-targeted OX40 antigen binding molecules prepared in Example 2 was monitored by Dynamic Light Scattering (DLS) and by monitoring of temperature dependent intrinsic protein fluorescence by applying a temperature ramp using an Optim 2 instrument (Avacta Analytical, UK). 10 μg of filtered protein sample with a protein concentration of 1 mg/ml was applied in duplicate to the Optim 2 instrument. The temperature was ramped from 25° C. to 85° C. at 0.1° C./min, with the ratio of fluorescence intensity at 350 nm/330 nm and scattering intensity at 266 nm being collected. The results are shown in Table 18. The aggregation temperature ($T_{agg}$) of all the tested FAP-Ox40 molecules produced in Example 2 is favorable than for the previously described OX40 (49B4)× FAP (4B9) (4+1) bispecific molecule (molecule P1AD4524) as described in WO 2017/060144 A1.

3.4.2 Hydrophobic Interaction Chromatography (HIC)

Apparent hydrophobicity was determined by injecting 20 μg of sample onto a HIC-Ether-5PW (Tosoh) column equilibrated with 25 mM Na-phosphate, 1.5 M ammonium sulfate, pH 7.0. Elution was performed with a linear gradient from 0 to 100% buffer B (25 mM Na-phosphate, pH 7.0) within 60 minutes. Retention times were compared to protein standards with known hydrophobicity. High HIC retention times were obtained for FAP×OX40 bispecific antigen binding molecules containing the clone 8H9 and charged patch variants of clone 49B4. Increased nonspecific interactions have been shown to correlate with high HIC retention time.

3.4.3 FcRn Affinity Chromatography

FcRn was expressed, purified and biotinylated as described (Schlothauer et al., MAbs 2013, 5(4), 576-86). For coupling, the prepared receptor was added to streptavidin-sepharose (GE Healthcare). The resulting FcRn-sepharose matrix was packed in a column housing. The column was equilibrated with 20 mM 2-(N-morpholine)-ethanesulfonic acid (MES) and 140 mM NaCl, pH 5.5 (eluent A) at a 0.5 ml/min flow rate. 30 μg of antibody samples were diluted at a volume ratio of 1:1 with eluent A and applied to the FcRn column. The column was washed with 5 column volumes of eluent A followed by elution with a linear gradient from 20 to 100% 20 mM Tris/HCl and 140 mM NaCl, pH 8.8 (eluent B) in 35 column volumes. The analysis was performed with a column oven at 25° C. The elution profile was monitored by continuous measurement of the absorbance at 280 nm. Retention times were compared to protein standards with known affinities.

3.4.4 Heparin Affinity Chromatography

Heparin affinity was determined by injecting 30-50 μg of sample onto a TSKgel Heparin-5PW (Tosoh) column equilibrated with 50 mM Tris, pH 7.4. Elution was performed with a linear gradient from 0 to 10000 buffer B (50 mM Tris, 1M NaCl, pH 7.4 mM) within 37 minutes. Retention times were compared to protein standards with known affinities.

TABLE 18

Biophysical and biochemical properties of tested FAP x OX40 bispecific antibodies

| Sample | | Thermal stability DLS $T_{agg}$ | Apparent hydro- phobicity | FcRn affinity | Heparin affinity |
|---|---|---|---|---|---|
| P1AE8870 | OX40 (8H9) × FAP (1G1a) 2 + 1 | 57.6 | 0.83 | 1.81 | 0.62 |

TABLE 18-continued

Biophysical and biochemical properties of tested FAP x OX40 bispecific antibodies

| Sample | | Thermal stability DLS $T_{agg}$ | Apparent hydrophobicity | FcRn affinity | Heparin affinity |
|---|---|---|---|---|---|
| P1AE8872 | OX40 (MOXR0916) × FAP (1G1a) 2 + 1 | 67.5 | 0.31 | 0.15 | 0.58 |
| P1AE8873 | OX40 (8H9) × FAP (1G1a) 3 + 1 | 56.9 | 0.89 | 2.02 | 0.65 |
| P1AE8874 | OX40 (CLC563) × FAP (1G1a) 3 + 1 | 66.2 | 0.15 | −0.14 | 0.51 |
| P1AE8875 | OX40 (MOXR0916) × FAP (1G1a) 3 + 1 | 67.4 | 0.32 | −0.22 | 0.6 |
| P1AE9176 | OX40 (49B4_K26E_K73E) × FAP (1G1a) 4 + 1 | 62 | 0.61 | −0.48 | 0.5 |
| P1AF7217 | OX40 (CLC563) × FAP (1G1a_EPKSCS) 4 + 1 | 66 | 0.14 | −0.3 | 0.5 |
| P1AF7205 | OX40 (CLC563) × FAP (1G1a_EPKSCD) 4 + 1 | 67 | 0.14 | −0.3 | 0.5 |
| P1AF6455 | OX40 (CLC563) × FAP (1G1a_EPKSCS) 3 + 1 | 67 | 0.14 | −0.1 | 0.5 |
| P1AF6454 | OX40 (CLC563) × FAP (1G1a_EPKSCD) 3 + 1 | 66 | 0.14 | −0.1 | 0.5 |
| P1AF6457 | OX40 (49B4_K23E_K73E) × FAP (1G1a_EPKSCS) 4 + 1 | 62 | 0.61 | −0.5 | 0.5 |
| P1AF6456 | OX40 (49B4_K23E_K73E) × FAP (1G1a_EPKSCD) 4 + 1 | 62 | 0.61 | −0.5 | 0.5 |
| P1AD4524 | OX40 (49B4) × FAP (4B9) (4 + 1) | 48 | 0.56 | 0 | 0.68 |

3.5 Characterization of Binding Potency by Surface Plasmon Resonance (SPR) after Stress The reduction in binding potency caused by incubation of the molecules for 14 days at 37° C., pH 7.4 and at 40° C., pH 6 was quantified by surface plasmon resonance using a Biacore T200 instrument (GE Healthcare). Samples stored at −80° C. and pH 6 were used as reference. The reference samples and the samples stressed at 40° C. were in 20 mM Histidine buffer, 140 mM NaCl, pH 6.0, and the samples stressed at 37° C. in PBS buffer, pH 7.4, all at a concentration of 1.0 mg/ml. After the stress period (14 days) samples in PBS buffer were dialyzed back to 20 mM Histidine buffer, 140 mM NaCl, pH 6.0 for further analysis.

All SPR experiments were performed at 25° C. with HBS-P+ buffer (10 mM HEPES, 150 mM NaCl, pH 7.4, 0.05% Surfactant P20) as running and dilution buffer. Biotinylated human OX40 and FAP, as well as biotinylated anti-hu IgG (Capture Select, Thermo Scientific, #7103262100) were immobilized on a Series S Sensor Chip SA (GE Healthcare, #29104992), resulting in surface densities of at least 1000 resonance units (RU). FAP-OX40 bispecific antibodies with a concentration of 2 μg/ml were injected for 30 s at a flow rate of 5 μl/min, and dissociation was monitored for 120 s. The surface was regenerated by injecting 10 mM glycine buffer, pH 1.5, for 60 s. Bulk refractive index differences were corrected by subtracting blank injections and by subtracting the response obtained from a blank control flow cell. For evaluation, the binding response 5 seconds after injection end was taken.

To normalize the binding signal, the OX40 and FAP binding was divided by the anti-hu IgG response (the signal (RU) obtained upon capture of the FAPxOX40 bispecific antibody on the immobilized anti-hu IgG antibody). The relative binding activity was calculated by referencing each temperature stressed sample to the corresponding, non-stressed sample. As shown in Table 19, all FAPxOX40 bispecific antibodies prepared in Example 2 show an improved binding upon stress to OX40 and FAP, as compared to a previously described FAP-OX40 bispecific antibody as described in WO 2017/060144 A1.

TABLE 19

Binding activity of FAP-OX40 bispecific antibodies to human to Ox40 and FAP after incubation at pH 6/40° C. or pH 7.4/37° C. for 2 weeks

| | | binding activity [%] | | | |
|---|---|---|---|---|---|
| | | 2 weeks at pH 6.0/40° C. | | 2 weeks at pH 7.4/37° C. | |
| | Sample | FAP | Ox40 | FAP | Ox40 |
| P1AE8870 | OX40 (8H9) × FAP (1G1a) 2 + 1 | >90 | >90 | >90 | >90 |
| P1AE8872 | OX40 (MOXR0916) × FAP (1G1a) 2 + 1 | >90 | >90 | >90 | >90 |
| P1AE8873 | OX40 (8H9) × FAP (1G1a) 3 + 1 | >90 | >90 | >90 | >90 |

TABLE 19-continued

Binding activity of FAP-OX40 bispecific antibodies to human to Ox40 and FAP after incubation at pH 6/40° C. or pH 7.4/37° C. for 2 weeks

| | | binding activity [%] | | | |
|---|---|---|---|---|---|
| | | 2 weeks at pH 6.0/40° C. | | 2 weeks at pH 7.4/37° C. | |
| | Sample | FAP | Ox40 | FAP | Ox40 |
| P1AE8874 | OX40 (CLC563) × FAP (1G1a) 3 + 1 | >90 | >90 | >90 | >90 |
| P1AE8875 | OX40 (MOXR0916) × FAP (1G1a) 3 + 1 | >90 | >90 | >90 | >90 |
| P1AE9176 | OX40 (49B4_K26E_K73E) × FAP (1G1a) 4 + 1 | >90 | >90 | >90 | >90 |
| P1AF7217 | OX40 (CLC563) × FAP (1G1a_EPKSCS) 4 + 1 | 98 | 100 | 94 | 100 |
| P1AF7205 | OX40 (CLC563) × FAP (1G1a_EPKSCD) 4 + 1 | 98 | 100 | 94 | 100 |
| P1AF6455 | OX40 (CLC563) × FAP (1G1a_EPKSCS) 3 + 1 | 98 | 100 | 96 | 100 |
| P1AF6454 | OX40 (CLC563) × FAP (1G1a_EPKSCD) 3 + 1 | 99 | 100 | 95 | 99 |
| P1AF6457 | OX40 (49B4_K23E_K73E) × FAP (1G1a_EPKSCS) 4 + 1 | 99 | 99 | 99 | 99 |
| P1AF6456 | OX40 (49B4_K23E_K73E) × FAP (1G1a_EPKSCD) 4 + 1 | 99 | 100 | 99 | 100 |
| P1AD4524 | OX40 (49B4) × FAP (4B9) (4 + 1) | ~90 | >90 | ~90 | >90 |

Example 4

Functional Properties of FAP-Targeted Anti-Human OX40 Antigen Binding Molecules 4.1 HeLa Cells Expressing Human OX40 and Reporter Gene NFκB-Luciferase Agonistic binding of OX40 to its ligand induces downstream signaling via activation of nuclear factor kappa B (NFκB) (A. D. Weinberg et al., J. Leukoc. Biol. 2004, 75(6), 962-972). The recombinant reporter cell line HeLa_hOx40_NFkB_Luc1 was generated to express human OX40 on its surface. Additionally, it harbors a reporter plasmid containing the luciferase gene under the control of an NFκB-sensitive enhancer segment. OX40 triggering induces dose-dependent activation of NFκB, which translocates to the nucleus, where it binds on the NFκB sensitive enhancer of the reporter plasmid to increase expression of the luciferase protein. Luciferase catalyzes luciferin-oxidation resulting in oxyluciferin which emits light. This can be quantified by a luminometer.

Thus, the capacity of the various FAP-targeted OX40 antigen binding molecules to induce NFκB activation in HeLa_hOx40_NFkB_Luc1 reporter cells was analyzed as a measure for bioactivity.

We tested the NFκB activating capacity of selected FAP-targeted OX40 antigen binding molecules in a bivalent, trivalent and tetravalent FAP-targeted cross-Fab format alone and with hyper-crosslinking of the constructs by either a secondary antibody or a FAP+ fibroblast cell line. The crosslinking of FAP-binding antibodies by cell surface FAP was tested using human fibroblast activating protein (huFAP) expressing NIH/3T3-huFAP clone 19. This cell line was generated by the transfection of the mouse embryonic fibroblast NIH/3T3 cell line (ATCC CRL-1658) with the expression vector pETR4921 to express huFAP under 1.5 μg/mL Puromycin selection.

Adherent HeLa_hOX40_NFkB_Luc1 cells were cultured over night at a cell density of $0.2 \times 10^5$ cells per well and were stimulated for 6 hours with assay medium containing titrated anti-OX40 antigen binding molecules. For testing the effect of hyper-crosslinking by secondary antibodies, 25 μL/well of medium containing secondary antibody anti-human IgG Fcγ-fragment-specific goat IgG F(ab')2 fragment (Jackson ImmunoResearch, 109-006-098) was added in a 1:2 ratio (primary to secondary antibodies). To test the effect of hyper-crosslinking by cell surface FAP binding, 25 μL/well of medium containing FAP+ tumor cells (NIH/3T3-huFAP clone 19) were co-cultured in a 3 to 1 ratio (three times more FAP+ tumor cells than reporter cells per well).

After incubation, assay supernatant was aspirated and plates washed two times with DPBS. Quantification of light emission was done using the luciferase 1000 assay system and the reporter lysis buffer (both Promega, Cat.-No. E4550 and Cat-No: E3971) according to manufacturer instructions. Briefly, cells were lysed for 30 minutes on dry ice by addition of 30 μL per well 1× lysis buffer. Cells were thawed for 20 minutes at 37° C. before 100 μL per well provided luciferase assay reagent was added. Light emission was quantified immediately with a Spark10M Tecan microplate reader using 500 ms integration time, without any filter to collect all wavelengths. Emitted relative light units (URL) were corrected by basal luminescence of HeLa_hOx40_NFkB_Luc1 cells and were plotted against the logarithmic primary antibody concentration using Prism7 (GraphPad Software, USA). Curves were fitted using the inbuilt sigmoidal dose response.

Figure 7B:
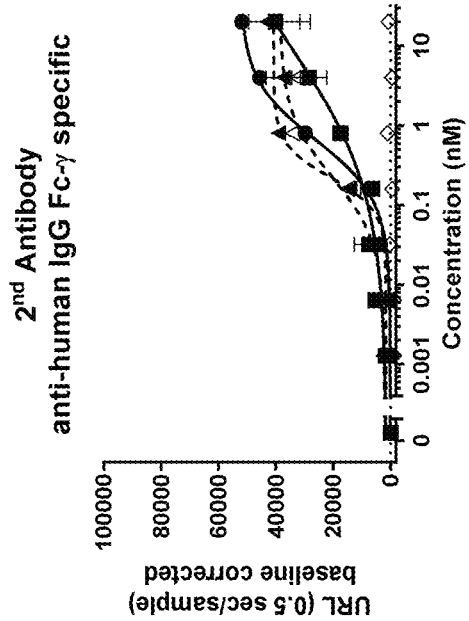
FIG. 7A to FIG. 7C show the NFκB-mediated luciferase expression activity in OX40 expressing reporter cell line HeLa_hOx40_NFκB_Luc1. The concentration of bispecific antigen binding molecules comprising OX40 clone 49B4 in different formats or its controls are blotted against the units of released light (URL) measured after incubation and addition of Luciferase detection solution. Shown is the NFκB induction of the 4+1, 3+1 or 2+1 formats, either crosslinked with human FAP expressing NIH/3T3 fibroblasts (FIG. 7A), a secondary antibody at a 2 to 1 ratio (FIG. 7B) or w/o further crosslinking (FIG. 7C). The isotype control antibody did not induce any NFκB activation. All OX40 containing constructs induced dose dependent NFκB activation. The tetravalent format comprising four OX40 Fab fragments induced a certain NFκB activation due to the assembly of the trimeric core OX40 receptor-signaling unit already in the absence of crosslinking. The same clone in a trivalent or bivalent format showed accordingly less bioactivity. The higher the valency of the OX40 antigen binding domains, the stronger was the extent of NFκB activation and the lower the required concentration. Shown is the mean of duplicates. Error bars represent the SEM.
Figure 7C:
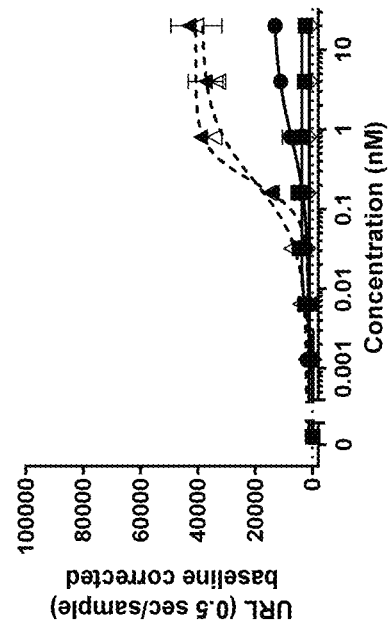
Figure 7A:
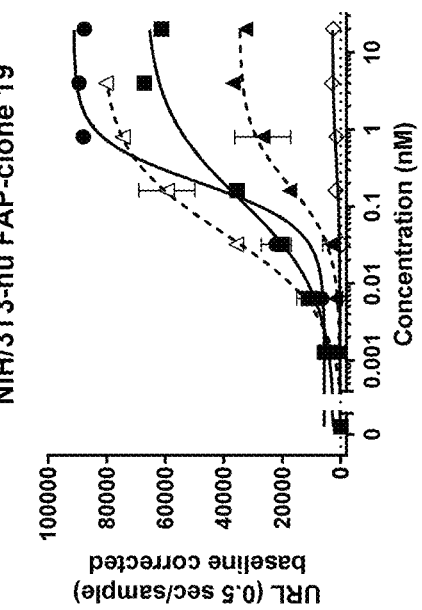
Figure 8B:
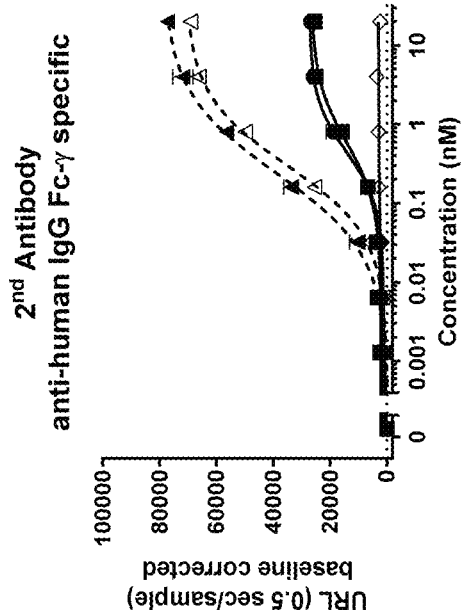
FIG. 8A to FIG. 8C show the NFκB-mediated luciferase expression activity in OX40 expressing reporter cell line HeLa_hOx40_NFκB_Luc1 of different bispecific antigen binding molecules comprising OX40 clone 8H9. The concentration of the bispecific antigen binding molecules in different formats or its controls are blotted against the units of released light (URL) measured after incubation and addition of Luciferase detection solution. Shown is the NFκB induction of the 3+1 or 2+1 formats, either crosslinked with human FAP expressing NIH/3T3 fibroblasts (FIG. 8A), a secondary antibody at a 2 to 1 ratio (FIG. 8B) or w/o further crosslinking (FIG. 8C). The isotype control antibody did not induce any NFκB activation. All OX40 containing constructs induced dose dependent NFκB activation. The tetravalent format comprising four OX40 Fab fragments induced a certain NFκB activation due to the assembly of the trimeric core OX40 receptor-signaling unit already in the absence of crosslinking and was most potent. The bispecific antigen binding molecules comprising OX40 clone 8H9 in a trivalent or bivalent format showed accordingly less bioactivity. Additional crosslinking by human FAP expressing fibroblasts via the FAP binding moiety, or by a secondary crosslinking antibody vie the Fc region of the OX40 antigen binding molecule further increased the NFκB activation. The clone OX40 (8H9) achieved the highest induction of NFκB activation already in the 2+1 format. Trivalency did not add further benefit. Shown is the mean of duplicates. Error bars represent the SEM.
Figure 8C:
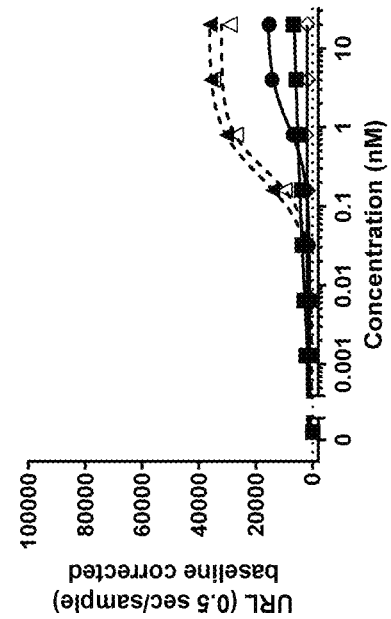
Figure 8A:
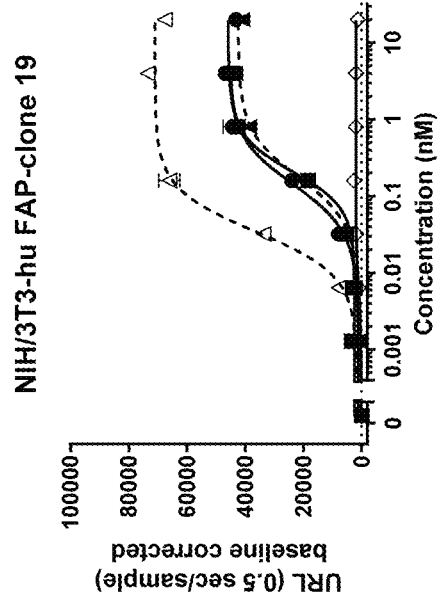

In FIG. 7A to FIG. 7C is shown the NFκB activation of bispecific antigen binding molecules comprising OX40 clone 49B4 in a 4+1, 3+1 and 2+1 format, either crosslinked with human FAP expressing NIH/3T3 fibroblasts, a secondary antibody at a 2 to 1 ratio or w/o further crosslinking. FIG. 8A to FIG. 8C show the NFκB activation of bispecific antigen binding molecules comprising OX40 clone 8H9 in a 3+1 and 2+1 format. FIG. 9A to FIG. 9C show the NFκB activation of bispecific antigen binding molecules comprising OX40 clone MOXR0916 in a 3+1 and 2+1 format and in FIG. 10A to FIG. 10C the NFκB activation of bispecific antigen binding molecules comprising OX40 clone CLC563 in a 3+1 and 2+1 format is shown. FIG. 11A to FIG. 11C demonstrate the NFκB activation of bispecific antigen binding molecules comprising amino acid variants of OX40 clone 49B4 in 4+1 format.

Thus, we tested the NFκB activating capacity of selected bispecific OX40 antigen binding molecules in a bivalent, trivalent and tetravalent FAP-targeted cross-Fab format alone and with hyper-crosslinking of the molecules by either a secondary antibody or a FAP⁺ fibroblast cell line. The crosslinking of FAP-binding antibodies by cell surface FAP was tested using human fibroblast activating protein (huFAP) expressing NIH/3T3-huFAP clone 19. All OX40 antigen binding molecules induced dose dependent NKκB activation. The tetravalent and trivalent use of OX40 antibodies induced a certain NFκB activation due to the assembly of the trimeric core OX40 receptor-signaling unit already in the absence of further external crosslinking of the constructs. OX40 antigen binding molecules with bivalent format (2+1) showed accordingly less bioactivity (49B4: FIG. 7; 8H9: FIG. 8, MOXR0916: FIG. 9; CLC-563: FIG. 10). Additional crosslinking by human FAP expressing fibroblasts via the FAP binding moiety, or by a secondary crosslinking antibody via the Fc region of the OX40 antigen binding molecule further increased the NFκB activation of all antigen binding molecules. For low-nanomolar bivalent OX40 antibodies (49B4, CLC-563), a higher valency of the OX40 resulted also with respect to bioactivity in an avidity gain (4+1>3+1>2+1), whereas no benefit of a 3+1 over 2+1 format was observed for sub-nanomolar bivalent OX40 binders (8H-9, MOXR0916). All amino acid variants of 49B4 in a 4+1 format induced dose dependent NKκB activation to a similar extent than the parental antibody in the 4+1 format (FIG. 11).

$EC_{50}$ values of NFκB induction dose response curves w/o further crosslinking and w/crosslinking by cell surface human FAP (NIH/3T3 huFAP clone 19) are summarized in Table 20.

In another experiment, adherent HeLa_hOX40_NFkB_Luc1 cells were cultured over night at a cell density of $0.3\times10^5$ cells per well and were stimulated for 6 hours with assay medium containing titrated anti-OX40 antigen binding molecules. To test the effect of hyper-crosslinking by cell surface FAP binding, 25 μL/well of medium containing FAP⁺ tumor cells (NIH/3T3-huFAP clone 19) were co-cultured in a 3 to 1 ratio (three times more FAP⁺ tumor cells than reporter cells per well).

After incubation, assay supernatant was aspirated and plates washed two times with DPBS. Quantification of light emission was done using the luciferase 1000 assay system and the reporter lysis buffer (both Promega, Cat.-No. E4550 and Cat-No: E3971) according to manufacturer instructions. Briefly, cells were lysed for 30 minutes on dry ice by addition of 30 μL per well 1× lysis buffer. Cells were thawed for 20 minutes at 37° C. before 100 μL per well provided luciferase assay reagent was added. Light emission was quantified immediately with a Spark10M Tecan microplate reader using 500 ms integration time, without any filter to collect all wavelengths. Emitted relative light units (URL) were corrected by basal luminescence of HeLa_hOx40_NFkB_Luc1 cells and were plotted against the logarithmic primary antibody concentration using Prism7 (GraphPad Software, USA). Curves were fitted using the inbuilt sigmoidal dose response.

Figure 35B:
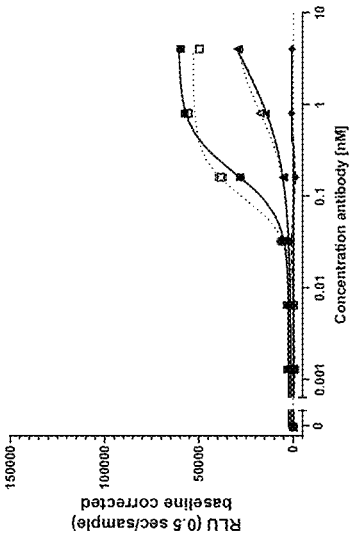
Figure 35D:
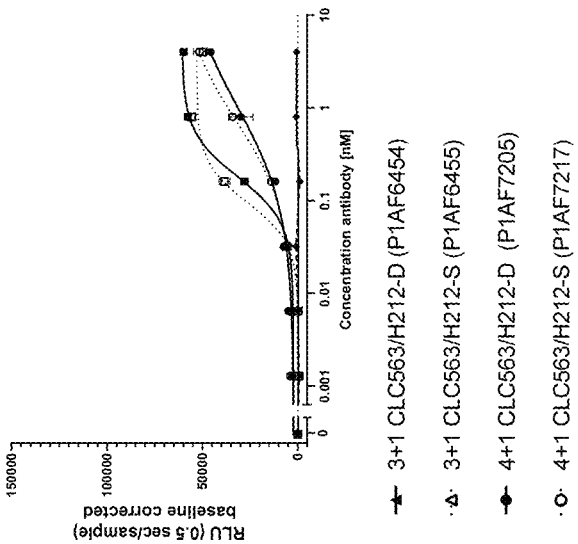

Thus, we tested the NFκB activating capacity of selected bispecific OX40 antigen binding molecules comprising clones OX40(49B4_K23E_K73E) or OX40(CLC563) in 3+1 and 4+1 formats as D and S variant alone and with hyper-crosslinking of the molecules by FAP fibroblast cell line. The results are shown in FIG. 35A to FIG. 35F. All OX40 antigen binding molecules induced dose dependent NKκB activation. The tetravalent and trivalent use of OX40 antibodies induced a certain NFκB activation due to the assembly of the trimeric core OX40 receptor-signaling unit already in the absence of further external crosslinking of the constructs (FIG. 35B, FIG. 35D, and FIG. 35F). Additional crosslinking by human FAP expressing fibroblasts via the

TABLE 20

$EC_{50}$ values for dose responses of NFκB activation by OX40 antigen binding molecules in a FAP targeted format in the presence or absence of cell surface human FAP⁺ fibroblasts

| Molecule ID | anti-Ox40 clone | Format | w/hu FAP EC50 [nM] | w/o | AUC compared to | w/hu FAP % of AUC | w/o |
|---|---|---|---|---|---|---|---|
| P1AD3690 | 49B4 | 4 + 0 | 0.18 | 0.23 | 49B4 | — | — |
| P1AE6838 | 49B4 | 4 + 1 | 0.04 | 0.38 | 4 + 0 | 225 | 89 |
| P1AE9167 | 49B4 AA variant K73E | 4 + 1 | 0.04 | 0.57 | | 214 | 75 |
| P1AE9169 | 49B4 AA variant K23T_K73E | 4 + 1 | 0.04 | 0.39 | | 221 | 84 |
| P1AE9176 | 49B4 AA variant K23E_K73E | 4 + 1 | 0.04 | 0.45 | | 206 | 78 |
| P1AE8786 | 49B4 | 3 + 1 | 0.20 | 0.83 | 49B4 | 100 | 29 |
| P1AE6840 | 49B4 | 2 + 1 | 0.12 | — | 4 + 1 | 77 | 17 |
| P1AE8873 | 8H9 | 3 + 1 | 0.14 | 0.44 | 8H9 | — | — |
| P1AE8870 | 8H9 | 2 + 1 | 0.21 | — | 3 + 1 | 75 | 76 |
| P1AE8875 | MOXR0916 | 3 + 1 | 0.31 | 3.94 | MOXR0916 | — | — |
| P1AE8872 | MOXR0916 | 2 + 1 | 0.19 | — | 3 + 1 | 73 | no curve |
| P1AE8874 | CLC563 | 3 + 1 | 0.24 | 0.79 | | — | — |
| P1AE8871 | CLC563 | 2 + 1 | 0.21 | — | CLC563 3 + 1 | 63 | 27 |

Figure 35A:
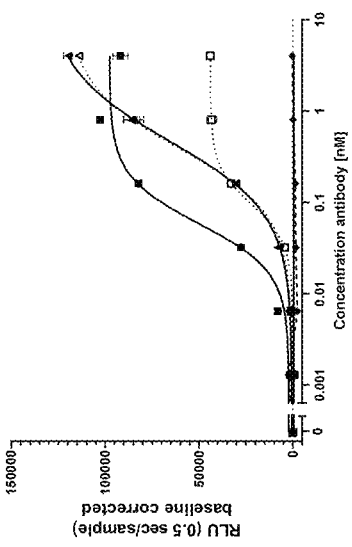
Figure 35C:
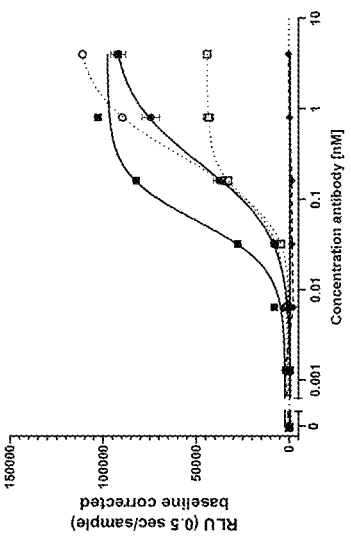
Figure 35E:
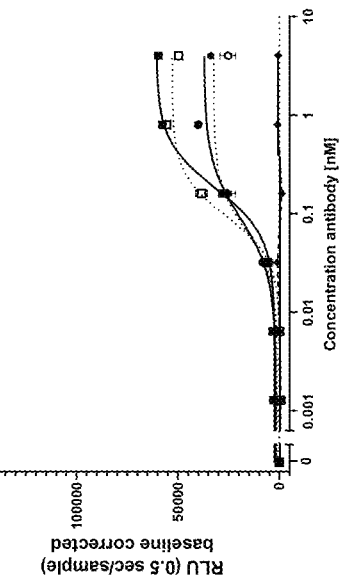
Figure 35F:
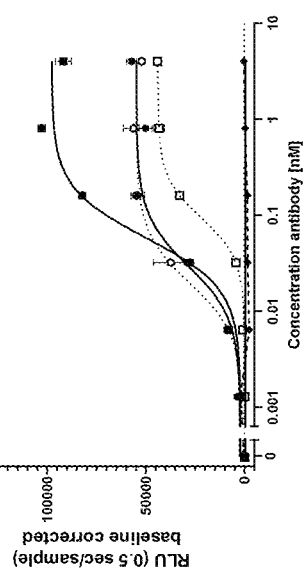

FAP binding moiety further increased the NFκB activation of all antigen binding molecules (FIG. 35A, FIG. 35C, and FIG. 35E). The bioactivity of the D and S variant was of comparable strength.

$EC_{50}$ values of NFκB induction dose response curves without further crosslinking and with crosslinking by cell surface human FAP (NIH/3T3 huFAP clone 19) are summarized in Table 21.

TABLE 21

$EC_{50}$ values for dose responses of NFκB activation by OX40 antigen binding molecules (D and S variants) in a FAP targeted format in the presence or absence of cell surface human FAP+ fibroblasts

| Molecule ID | anti-Ox40 clone | Variant | Format | w/hu FAP $EC_{50}$ [nM] | w/o $EC_{50}$ [nM] |
|---|---|---|---|---|---|
| P1AF6455 | CLC-563 | S | 3 + 1 | 0.2 | 0.8 |
| P1AF6454 | CLC-563 | D | 3 + 1 | 0.2 | 1.9 |
| P1AF7217 | CLC-563 | S | 4 + 1 | 0.18 | 0.7 |
| P1AF7205 | CLC-563 | D | 4 + 1 | 0.2 | 0.5 |
| P1AF6457 | 49B4 AA variant K23E_K73E | S | 4 + 1 | 0.02 | 0.06 |
| P1AF6456 | 49B4 AA variant K23E_K73E | D | 4 + 1 | 0.03 | 0.08 |

4.2 OX40 Mediated Co-Stimulation of Sub-Optimally TCR Triggered Resting Human PBMCs and Hyper-Crosslinking by Cell Surface FAP It was shown in Example 4.1 that addition of FAP+ tumor cells can strongly increase the NFκB activity induced by FAP targeted OX40 antigen binding molecules in human OX40 positive reporter cell lines by providing strong oligomerization of OX40 receptors. Likewise, we tested all constructs in a primary T cell assay for their ability to rescue suboptimal TCR stimulation of resting human PBMC cells in the presence of NIH/3T3-huFAP clone 19 cells.

Human PBMC preparations contain (1) resting OX40 negative CD4+ and CD8+ T cells and (2) antigen presenting cells with various Fc-γ receptor molecules on their cell surface e.g. B cells and monocytes. Anti-human CD3 antibody of human IgG1 isotype can bind with its Fc part to the present Fc-γ receptor molecules and mediate a prolonged TCR activation on resting OX40 negative CD4 and CD8 T cells. These cells then start to express OX40 within several hours. Functional agonistic compounds against OX40 can signal via the OX40 receptor present on activated CD8+ and CD4+ T cells and support TCR-mediated stimulation.

Resting human PBMC were stimulated for four days with a suboptimal concentration of anti-CD3 antibody in the presence of irradiated FAP+ NIH/3T3-huFAP clone 19 cells and titrated bispecific OX40 antigen binding molecules. Effects on T-cell survival and proliferation were analyzed through monitoring of total cell counts (CD4+ or CD8+ T cells) and co-staining with fluorescently-labeled antibodies against T-cell activation marker (CD25 expression on CD4+ T cells) by flow cytometry. Mouse embryonic fibroblast NIH/3T3-huFAP clone 19 cells were harvested using cell dissociation buffer (Invitrogen, Cat.-No. 13151-014) for 10 minutes at 37° C. Cells were washed once with DPBS. NIH/3T3-huFAP clone 19 cells were irradiated in an xRay irradiator using a dose of 4500 RAD to prevent later overgrowth of human PBMCs by the tumor cell line. Irradiated cells were cultured at a density of $0.2 \times 10^5$ cells per well in T cell media in a sterile 96-well round bottom adhesion tissue culture plate (TPP, Cat. No 92097) over night at 37° C./5% $CO_2$.

Human PBMCs were isolated from fresh blood by ficoll density centrifugation. Cells were added to each well at a density of $0.6 \times 10^5$ cells per well. Anti-human CD3 antibody (clone V9, human IgG1) at a final concentration of [10 nM] and FAP-targeted OX40 antigen binding molecules were added at the indicated concentrations. Cells were incubated for four days at 37° C./5% $CO_2$ prior to analysis.

Cells were first stained 10 min with Zombie Aqua Fixable viability dye (Biolegend, Cat. No. 423102) in DPBS, followed by surface staining with fluorescent dye-conjugated antibodies anti-human CD4 (clone RPA-T4, BioLegend, Cat.-No. 300532), CD8 (clone RPa-T8, BioLegend, Cat.-No. 3010441) and CD25 (clone M-A251, BioLegend, Cat.-No. 356112) for 20 min at 4° C. Cell pellets were washed twice with FACS buffer. Samples were finally resuspended in 20 μL/well FACS-buffer and acquired the same day using iQue Cell Screener and ForeCyt software (Sartorius). Table 22 summarizes the $EC_{50}$ values for dose responses of CD25 upregulation on CD4+ T cells of bispecific OX40 antigen binding molecules in a FAP targeted format following suboptimal TCR stimulation of primary human PBMCs.

TABLE 22

$EC_{50}$ values for dose responses of CD25 upregulation on CD4+ T cells following suboptimal TCR stimulation of primary human PBMCs

| MoleculeID | anti-Ox40 clone | Format | $EC_{50}$ [nM] | AUC compared to reference compound [%] | +/−SEM |
|---|---|---|---|---|---|
| P1AD3690 | 49B4 | 4 + 0 | no curve fit | 13 | 5 |
| P1AE6838 | 49B4 | 4 + 1 | 0.02/0.003 | 107 | 31 |
| P1AE9167 | 49B4 AA variant K73E | 4 + 1 | 0.001 | 137 | 9 |
| P1AE9169 | 49B4 AA variant K23T_K73E | 4 + 1 | 0.001 | 128 | 10 |
| P1AE9176 | 49B4 AA variant K23E_K73E | 4 + 1 | 0.001 | 128 | 10 |
| P1AE8786 | 49B4 | 3 + 1 | 0.04 | 97 | 16 |
| P1AE6840 | 49B4 | 2 + 1 | 0.09 | 59 | 22 |
| P1AE8873 | 8H9 | 3 + 1 | 0.01 | 134 | 31 |
| P1AE8870 | 8H9 | 2 + 1 | 0.01 | 113 | 32 |
| P1AE8875 | MOX0916 | 3 + 1 | 0.02 | 100 | 18 |
| P1AE8872 | MOX0916 | 2 + 1 | 0.01 | 106 | 22 |
| P1AE8874 | CLC-563 | 3 + 1 | 0.04 | 100 | 0 |
| P1AE8871 | CLC-563 | 2 + 1 | 0.06 | 99 | 15 |

Figure 12A:
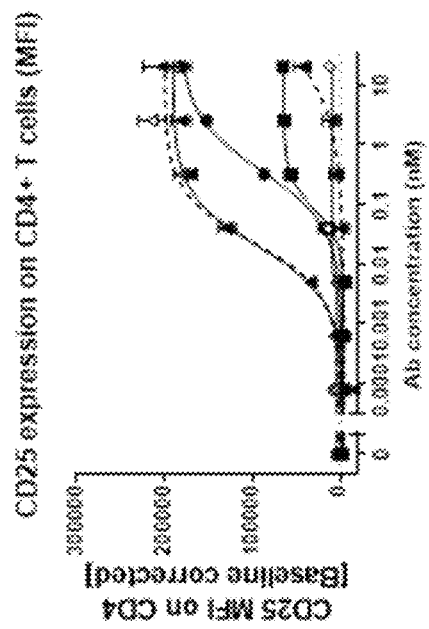
FIG. 12A and FIG. 12B show the primary T cell bioactivity of the bispecific antigen binding molecule P1AE6838 in comparison with different reference molecules (P1AD3690, an untargeted molecule comprising four OX40 (49B4) Fab fragments, P1AD4524, a molecule comprising four OX40 (49B4) Fab fragments and FAP antibody 4B9 as C-terminal VH/VL, P1AD4353, a molecule comprising two OX40 (49B4) Fab fragments and FAP antibody 4B9, and P1AD3691, a molecule comprising two OX40 (49B4) Fab fragments and two FAP (28H1) Fab fragments).
Figure 12B:
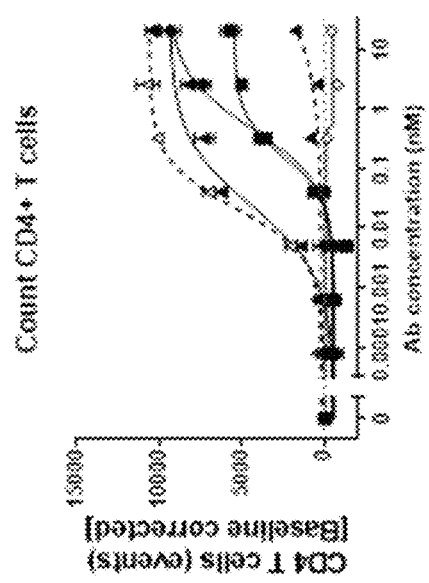
Figure 13B:
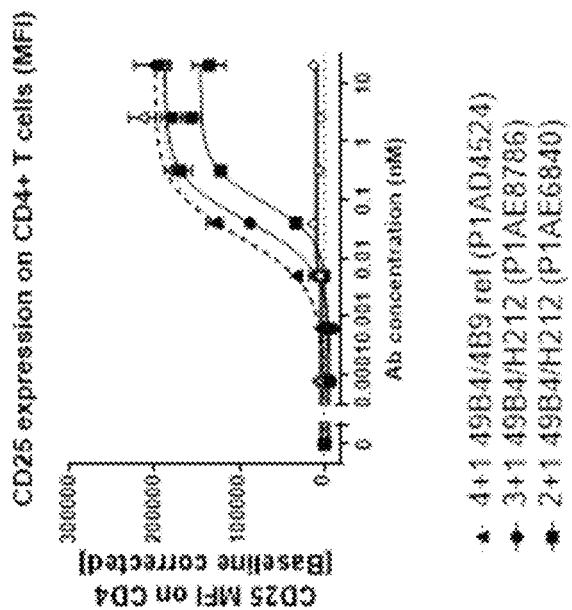
FIG. 13A and FIG. 13B show the primary T cell bioactivity of bispecific antigen binding molecules comprising OX40(49B4) and FAP (1G1a) in 4+1, 3+1 and 2+1 format in comparison to P1AD4524, a molecule comprising four OX40 (49B4) Fab fragments and FAP antibody 4B9 as C-terminal VH/VL.
Figure 13A:
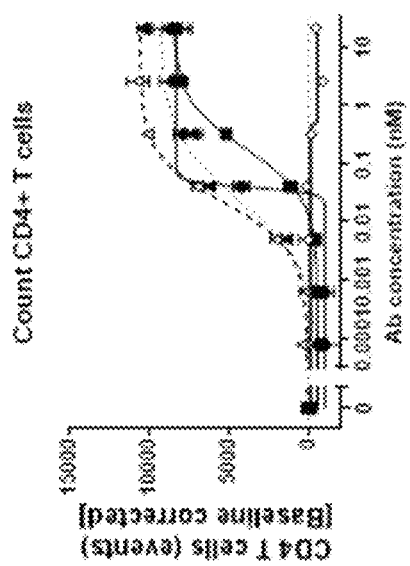
Figure 14B:
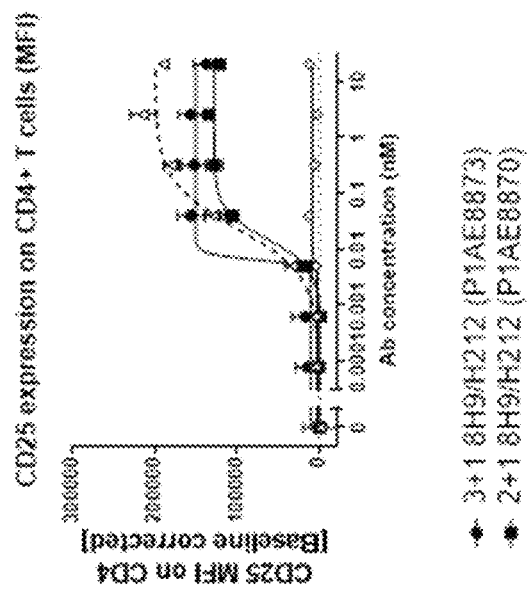
FIG. 14A and FIG. 14B show the primary T cell bioactivity of bispecific antigen binding molecules comprising clone OX40(8H9) in 3+1 and 2+1 format in comparison to P1AE6838, a molecule comprising four OX40 (49B4) Fab fragments.
Figure 14A:
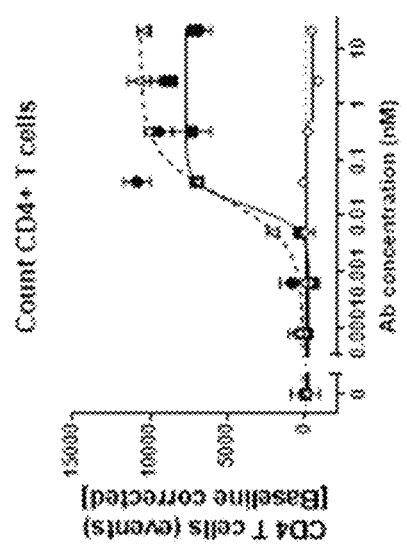
Figure 15B:
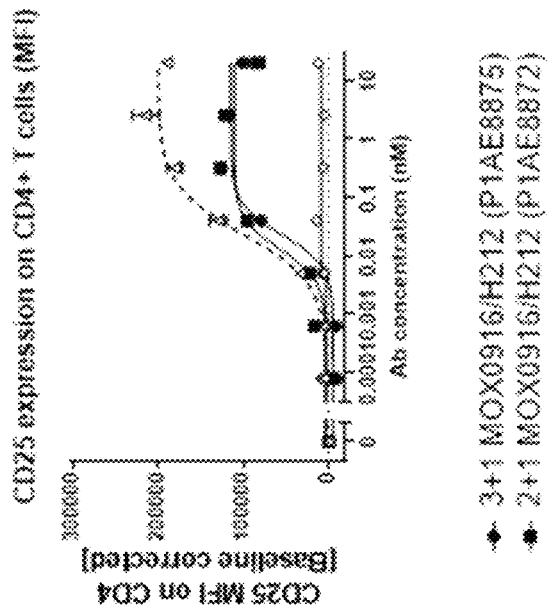
FIG. 15A and FIG. 15B show the primary T cell bioactivity of bispecific antigen binding molecules comprising clone OX40(MOXR0916) in 3+1 and 2+1 format in comparison to P1AE6838, a molecule comprising four OX40 (49B4) Fab fragments.
Figure 15A:
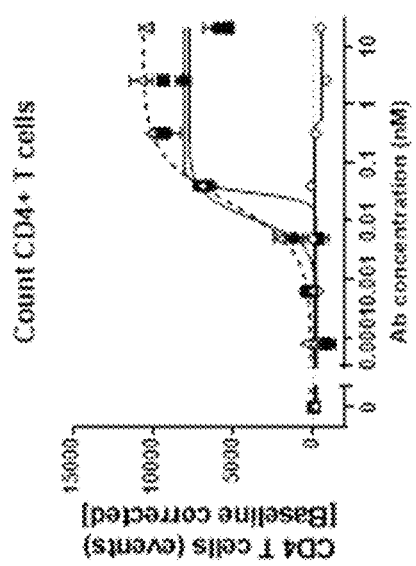
Figure 16B:
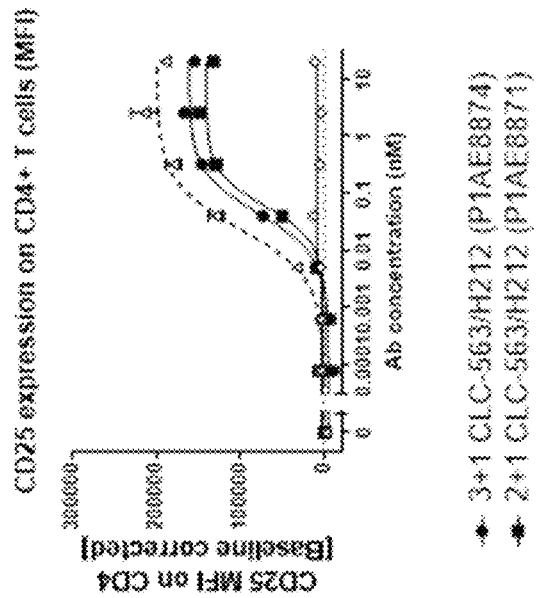
FIG. 16A and FIG. 16B show the primary T cell bioactivity of bispecific antigen binding molecules comprising clone OX40 (CLC563) in 3+1 and 2+1 format in comparison to P1AE6838, a molecule comprising four OX40 (49B4) Fab fragments.
Figure 16A:
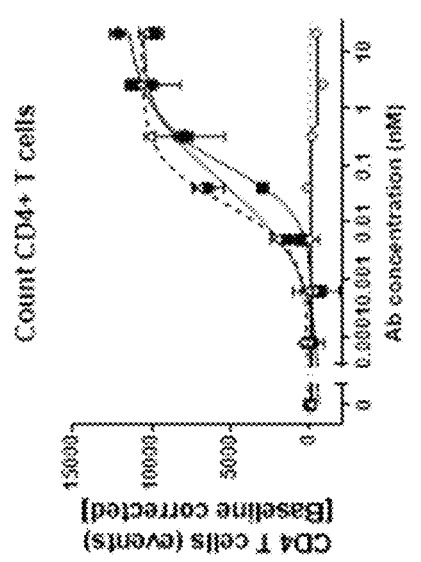
Figure 17B:
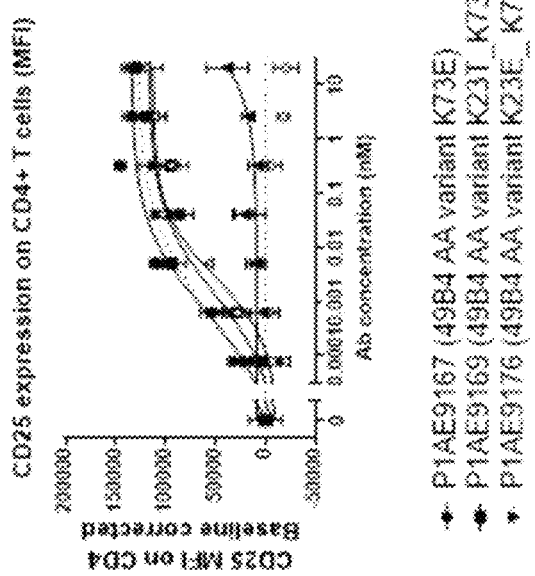
FIG. 17A and FIG. 17B show the primary T cell bioactivity of different variants of OX40 clone 49B4 with amino acid mutations in the VH domain in different formats and in comparison with a bispecific antigen binding molecule comprising OX40 clone 49B4 in 4+1 format (P1AE6838).
Figure 17A:
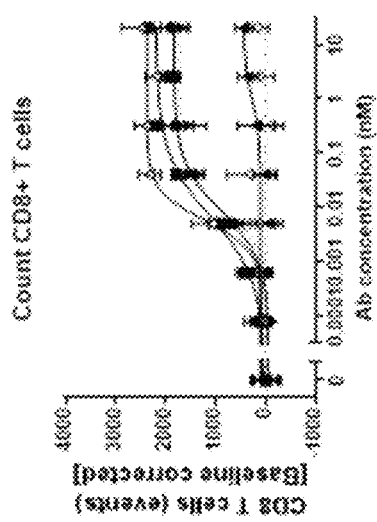

As shown in FIG. 12 to FIG. 17, co-stimulation with non-targeted anti-OX40 (49B4) 4+0 format barely rescued sub-optimally TCR stimulated CD4 and CD8 T cells. Hyper-crosslinking of the FAP targeted tetravalent, trivalent and bivalent OX40 antigen binding molecules in the presence of NIH/3T3-huFAP clone 19 cells strongly promoted survival and induced an enhanced activated phenotype in human CD4 T cells for all OX40 clones tested (49B4: FIG. 12 and FIG. 13; 8H9: FIG. 14, CLC563: FIG. 16, MOXR0916: FIG. 15). All amino acid variants of 49B4 in a 4+1 format supported T cell activation to an at least similar, if not even slightly improved extent than the parental antibody in the 4+1 format (FIG. 17).

The normalized areas under the curve for the bioactivity (as measured as CD25 upregulation on CD4+ T cells) of the various antigen binding molecules are shown in FIG. 18. The major enhancement of OX40 supported T cell activation was achieved by FAP mediated hyper-crosslinking and thus cell surface immobilization of the OX40 antigen binding molecules (compare normalized AUC of 49B4 4+0 vs 4+1 antigen binding molecules in FIG. 18 and Table 19). An increased valency for OX40 still added to the agonistic capacity of the targeted OX40 agonist antigen binding molecules, but to a lower extent than FAP crosslinking (compare normalized AUC of 4+1 vs 3+1 vs 2+1 formats in FIG. 18 and Table 19). The strongest increase of agonistic power of a higher valency was observed for the avidity clone 49B4, where the tetravalency doubled the normalized AUC over the one of the bivalent format. This indicates that when selecting a high affinity—and less avidity driven OX40 clone for targeted OX40 agonists, bivalent and trivalent molecules can maintain similar activity than tetravalent 49B4 in a primary T cell assay in vitro.

The molecule design requirement for optimal T cell costimulation seems to be slightly different to that of pure NFκB activation downstream of the OX40 receptor. The first requires strong surface immobilization of multiple OX40 agonistic antibodies, which cannot be compensated fully by antibody intrinsic valency of OX40 antibodies. The latter requires a high degree of OX40 receptor oligomerization by antibody intrinsic multivalent OX40 engagement, which cannot fully be compensated by surface immobilization of the agonists.

This might reflect the requirement for spatial restriction of response modulating phosphorylation and dephosphorylation events within primary T cells (termed T cell synapse) for optimal TCR engagement. A fully functional T cell synapse assembles the various signaling components (e.g. via lipid rafts) to achieve full functionality. The decreased lateral mobility of synapse component favors this, as might the cell surface immobilization of OX40 by FAP-targeted OX40 antigen binding molecules.

In a further experiment testing the C-terminal S and D variants, human PBMCs were labeled with the CFSE proliferation kit (Thermo Fisher, Cat-No. C34554) for 10 minutes at room temperature according to manufacturer's instruction at a final concentration of 0.2 [μM] CFSE. Cells were added to each well at a density of 0.6×105 cells per well in T cell media. Anti-human CD3 antibody (clone V9, human IgG1) at a final concentration of [10 nM] and the FAP-targeted OX40 antigen binding molecules, both prepared in T cell media, were added at the indicated concentrations. Cells were incubated for four days at 37° C./5% $CO_2$ prior to analysis.

Cells were first stained 20 min with LIVE/DEAD™ Fixable Aqua Dead Cell Stain (Molecular probes, Cat. No. L34957) in DPBS, followed by one washing step (200 μL 4° C. FACS buffer). Thereafter, surface staining with fluorescent dye-conjugated antibodies anti-human CD4 (clone OKT4, BioLegend, Cat.-No. 317440), CD8 (clone SK-1, BioLegend, Cat.-No. 344714) and CD25 (clone BC96, BioLegend, Cat.-No. 302626) for 30 min at 4° C. Cell pellets were washed twice with dPBS. Samples were finally resuspended in 100 μL/well FACS-buffer and acquired the same day using with BD Fortessa running FACS Diva software. Table 23 summarizes the $EC_{50}$ values for dose responses of CD25 upregulation on CD4+ T cells of bispecific OX40 antigen binding molecules in a FAP targeted format following suboptimal TCR stimulation of primary human PBMCs.

TABLE 23

$EC_{50}$ values for dose responses of CD25 upregulation on CD4+ T cells following suboptimal TCR stimulation of primary human PBMCs

| Molecule ID | anti-Ox40 clone | Variant | Format | $EC_{50}$ [nM] |
|---|---|---|---|---|
| P1AF6455 | CLC-563 | S | 3 + 1 | 0.003 |
| P1AF6454 | CLC-563 | D | 3 + 1 | 0.001 |
| P1AF7217 | CLC-563 | S | 4 + 1 | 0.002 |
| P1AF7205 | CLC-563 | D | 4 + 1 | 0.001 |
| P1AF6457 | 49B4 AA variant K23E_K73E | S | 4 + 1 | 0.001 |
| P1AF6456 | 49B4 AA variant K23E_K73E | D | 4 + 1 | 0.001 |

Figure 36A:
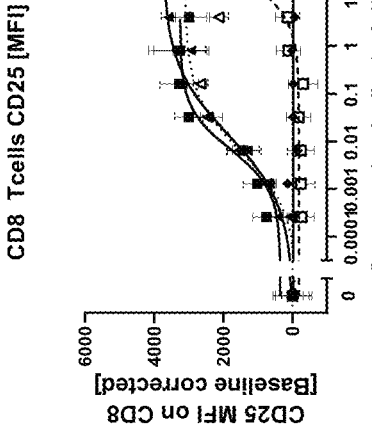
Figure 36C:
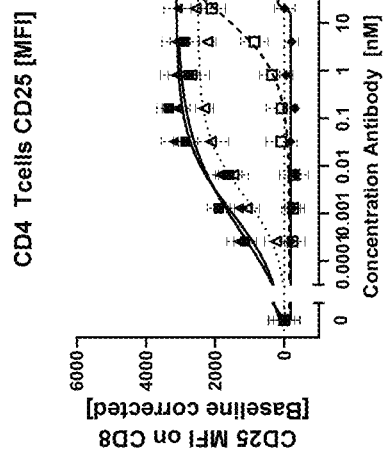
Figure 36B:
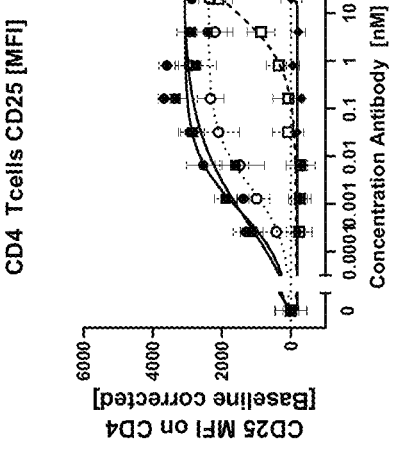
Figure 36D:
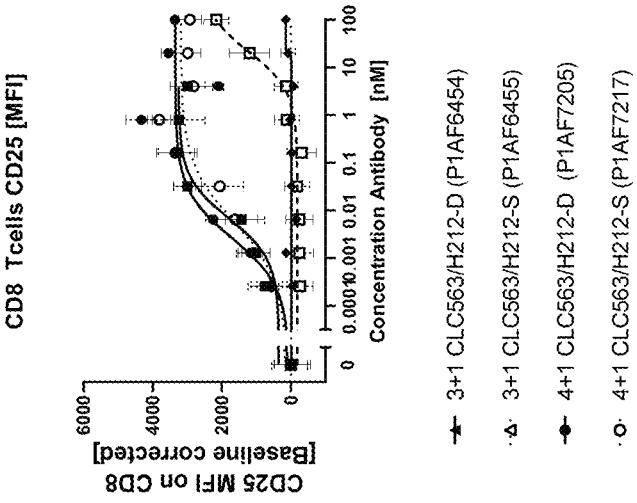
Figure 36E:
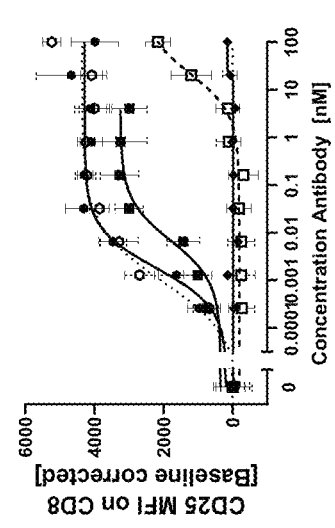
Figure 36F:
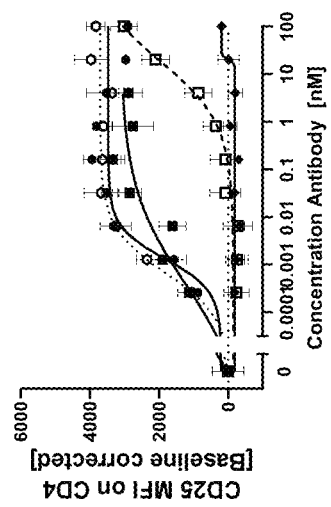
Figure 37E:
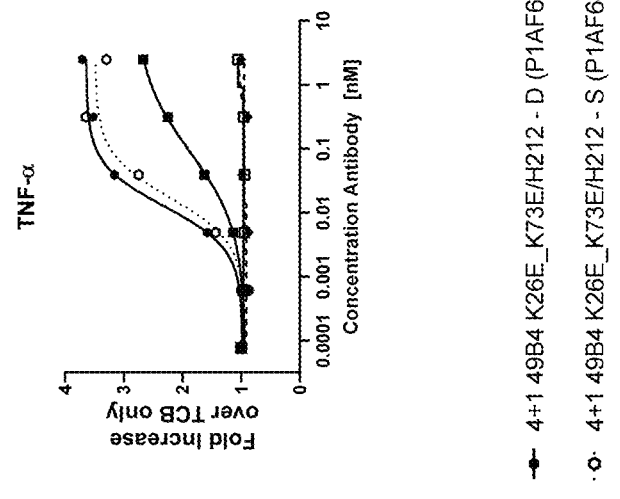
Figure 37F:
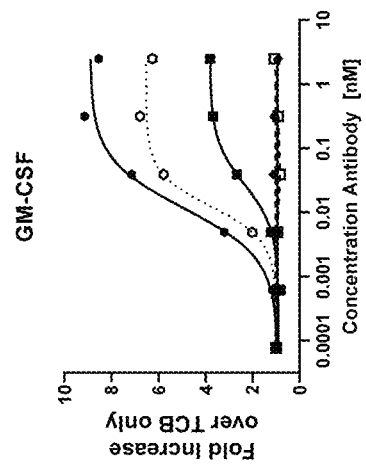

As shown in FIG. 36A to FIG. 36F, co-stimulation with a non-targeted tetravalent anti-OX40 (49B4) (4+0 format) rescued sub-optimally TCR stimulated CD4 and CD8 T cells only at concentrations higher than [1 nM]. Hyper-crosslinking of the FAP targeted tetravalent and trivalent OX40 antigen binding molecules in the presence of NIH/3T3-huFAP clone 19 cells strongly promoted proliferation and induced an enhanced activated phenotype in human CD4 (FIG. 36A, FIG. 36C, and FIG. 36E) and CD8 (FIG. 36B, FIG. 36D, and FIG. 36F). The S variant performed slightly, but not statistically significant, worse than the D variant for the CLC563 constructs (FIG. 36A to FIG. 36D). All amino acid variants of 49B4 in a 4+1 format supported T cell activation to an at least similar, if not even slightly improved extent than the parental antibody in the 4+1 format. Here, no difference was seen between the S and D variant (FIG. 36E and FIG. 36F).

4.3 OX40 Mediated Co-Stimulation Increases the Secretion of Cytokines of CECAM5 TCB Redirected PBMC that Lyse CEA+ Tumor Cells One clinically exploited way to recruit the patient's own immune system to fight cancer are T cell bispecific antibodies (TCB). These molecules are comprised of an agonistic anti-CD3 unit, specific for the T cell receptor (TCR) on T cells, and a targeting moiety specific for a unique cancer antigen. TCBs redirect polyclonal T cells to lyse cancer cells expressing the respective target antigen on their cell surface. No T cell activation occurs in the absence of such target antigen. The TCB used in this example is the CEACAM5 TCB targeting the carcinoembryonic antigen (CEA) and is described in detail in WO 2016/079076 A1. Triggering of the TCR increases, depending on the strength and duration of this primary stimulus, the expression of costimulatory molecules, e.g. OX40, a member of the Tumor necrosis factor receptor (TNFR) superfamily. Concomitant agonistic ligation of this receptor by its respective ligand promotes in turn hallmark T cell effector functions like proliferation, survival and secretion of certain proinflammatory cytokines (GM-CSF, IFN-γ, IL-2, TNF-α) (M. Croft et al., Immunol. Rev. 2009, 229(1), 173-191, I. Gramaglia et al., J. Immunol. 1998, 161(12), 6510-6517; S. M. Jensen et al., Seminars in Oncology 2010, 37(5), 524-532). This co-stimulation is needed to raise the full potential of T cells against tumor cells, especially in the context of weak tumor antigen priming, and to sustain the anti-tumor response beyond the first attack allowing for protective memory formation. In certain patients with a strong immune suppressed or exhausted phenotype, only the combination of polyclonal, yet tumor specific T cell recruitment (signal 1) and the restoration of tumor-restricted positive co-stimulation (signal 2) might facilitate sufficient anti-tumor efficacy and prolonged adaptive immune protection. This can persistently drive the tumor microenvironment towards a more immune activating and less immunosuppressive state. FAP-dependent costimulation of OX40 may also facilitate TCB mediated killing of tumor cells at lower intratumoral concentrations which would allow reduction of systemic exposure and correlated side effects. Additionally, the treatment intervals might be prolonged as lower TCB concentration could still be active.

MKN45 NucLight Red (NLR) cells, which naturally express the CEA antigen were used as target cells. MKN-45 (DSMZ; ACC409) were transduced with the Essen Cell-Player NucLight Red Lentivirus Reagent (Essenbioscience, Cat. No. 4476; EF1α, puromycin) at an MOI of 5 (TU/cell) in the presence of 8 µg/mL polybrene following the manufacturer's instructions to stable express a nuclear-restricted NucLight Red fluorescent protein. This enabled easy separation from non-fluorescent effector T cells or fibroblasts and monitoring of the tumor cell growth by high throughput life fluorescence microscopy.

The crosslinking of FAP-binding antibodies by cell surface FAP was provided by human fibroblast activating protein (huFAP) expressing NIH/3T3-huFAP clone 19 (see Example 3.2). Human PBMCs were isolated from fresh blood by ficoll density centrifugation (see Example 3.1).

MKN45 NucLight Red (NLR) cells were added in each well at a density of $0.1 \times 10^5$ cells per well in T cell media. NIH/3T3-huFAP clone 19 were pre-irradiated at 4600 RAD and were then added in each well at a density of $0.1 \times 10^5$ cells per well in T cell media. Human PBMC were added to each well at a density of $0.5 \times 10^5$ cells per well in T cell media. The CEACAM5 TCB at a final concentration of 2 nM and titrated dilutions of FAP-targeted OX40 antigen binding molecules, both prepared in T cell media, were added at the indicated concentrations. Cells were incubated for three days at 37° C./5% $CO_2$ prior to analysis. Samples were performed as triplicates.

After 72 hours, the supernatant was collected for subsequent analysis of selected cytokine using the Bio-Plex Pro Human Cytokine 8-Plex Assay Catalogue No. BIO-RAD M50000007A according to manufacturer's instructions. Triplicate samples were united to equal parts for each tested compound at the respective tested concentration and the mix was analyzed for the cytokine content. The fold increase of a respective cytokine (GM-CSF, IL-2, TNF-α, IFN-γ) compared to the concentration in the TCB-only control sample was calculated and plotted against the FAP-OX40 antibody concentration. Dose-response curves were calculated using GraphPAD Prism, AUC and the $EC_{50}$ values calculated and are reported in Table 24. Dose response curves for GM-CSF and TNF-α are depicted in FIG. 37A to FIG. 37F, and that for IFN-γ and IL-2 in FIG. 38A to FIG. 38F. The AUC was normalized for each cytokine to the AUC of the FAP-OX40 antigen binding molecule OX40(CLC563)×FAP (1G1a_EPKSCD) 3+1 (called 3+1 CLC563/H212-D in the Figure) and plotted for each compound as Box-Whisker plot in FIG. 39.

TABLE 24

$EC_{50}$ values for dose responses of increased TCB mediated cytokine secretion following FAP-OX40 costimulation of primary human PBMCs

| Molecule ID | anti-Ox40 clone | Variant | Format | $EC_{50}$ [nM] |
|---|---|---|---|---|
| P1AF6455 | CLC-563 | S | 3 + 1 | 0.058 |
| P1AF6454 | CLC-563 | D | 3 + 1 | 0.144 |
| P1AF7217 | CLC-563 | S | 4 + 1 | 0.058 |

TABLE 24-continued $EC_{50}$ values for dose responses of increased TCB mediated cytokine secretion following FAP-OX40 costimulation of primary human PBMCs

| Molecule ID | anti-Ox40 clone | Variant | Format | $EC_{50}$ [nM] |
|---|---|---|---|---|
| P1AF7205 | CLC-563 | D | 4 + 1 | 0.034 |
| P1AF6457 | 49B4 AA variant K23E__K73E | S | 4 + 1 | 0.022 |
| P1AF6456 | 49B4 AA variant K23E__K73E | D | 4 + 1 | 0.017 |

As shown in FIG. 37A to FIG. 37F and FIG. 38A to FIG. 38F, co-stimulation with non-targeted anti-OX40 (49B4) 4+0 format did not enhance the cytokine secretion of PBMC induced by CEACAM5 TCB mediated lysis of tumor cells. Hyper-crosslinking of the FAP targeted tetravalent and trivalent OX40 antigen binding molecules in the presence of NIH/3T3-huFAP clone 19 cells strongly promoted the secretion of GM-CSF (FIG. 37A, FIG. 37C, and FIG. 37E) and of TNF-α (FIG. 37B, FIG. 37D, and FIG. 37F), as well as that of IFN-γ (FIG. 38A, FIG. 38C, and FIG. 38E) and of IL-2 (FIG. 38B, FIG. 38D, and FIG. 38F). The S-variant performed slightly, but not statistically significant, worse than the D-variant for all tested constructs (FIG. 39). The amino acid variants of 49B4 in a 4+1 format supported T cell activation stronger than the parental clone in the 4+1 format. Here, the CLC563 showed stronger agonistic potential as tetra than as trivalent FAP targeted OX40 agonist (FIG. 39).

4.4 OX40 Mediated Co-Stimulation Reduces TGFβ Induced FoxP3 Expression

CD4+Foxp3+T regulatory cells (Tregs) play a critical role in immune homeostasis and peripheral tolerance (Sakaguchi S, Yamaguchi T, Nomura T, Ono M, Cell 2008, 133(5), 775-87). Their development, lineage stability, and suppressor functions are dependent on the expression of the transcription factor FoxP3, which is a "master" regulator of Treg identity (Hori S, Nomura T, Sakaguchi S, Science 2003, 299(5609), 1057-61). In addition to their thymic origin, CD4+FoxP3+ Treg cells can also be induced in the periphery from naive CD4+ T cells following activation, which are often called inducible Tregs (iTregs) or peripheral Tregs (pTregs) (Curotto de Lafaille M A, Lafaille J, Immunity 2009, 30(5), 626-35). The best characterized conditions for the induction of iTregs in vitro is the combination of transforming growth factor R (TGF-0) and CD28 costimulation. This cytokine potently induces de novo FoxP3 expression, which programs the conversion of activated conventional T cells to iTregs (Chen W, Jin W, Hardegen N, Lei K J, Li L, Marinos N, McGrady G, Wahl S M, J Exp. Med. 2003, 198(12), 1875-86). OX40 signaling has been described to inhibit FoxP3 expression and Treg induction (Zhang X, Xiao X, Lan P, et al., Cell Rep. 2018, 24(3), 607-618). It was shown in examples 4.1 to 4.3 that all FAP-OX40 bispecific antigen binding molecules were able to induce NFκB, and promote TCR stimulation resulting in enhanced activation phenotype and increased cytokine secretion. Likewise, we tested all constructs in a primary T cell assay for their ability to suppress TGF-β mediated FoxP3 induction.

Human PBMC preparations containing naive CD4 T cells were cultured in the presence of TGFβ during T cell activation with antibodies against CD28 and CD3. FoxP3 induction as well as OX40 expression occurs within several hours. Functional agonistic compounds against OX40, e.g. bispecific antigen binding molecules comprising OX40 clones OX40(49B4_K23E_K73E) or OX40(CLC563) n 3+1 and 4+1 formats as D- and S-variant, can signal via the OX40 receptor present on the activated CD4+ T cells, when crosslinking by FAP is provided (here FAP antigen coated to beads). This interferes with Treg induction visible by reduced FoxP3 expression.

Sterile 96-well round bottom adhesion tissue culture plates (TPP, Cat. No 92097) were pre-coated with anti-human CD3 antibodies (eBioscience, Cat. No. 16-0037-85) in dPBS at a concentration of 3 µg/mL for two hours 37° C./5% $CO_2$. Dynabeads® M-280 Streptavidin (ThermoFisher, Cat. No. 11205D) were coated with biotinylated human FAP antigen (Roche, P1AD8986; 0.01 µg protein for 1 µg beads) in dPBS for 30 minutes at room temperature according to manufacturer's instructions before storage at 4° C. for long-term in dPBS containing 0.1% (w/v) BSA. Human PBMCs were isolated from fresh blood by ficoll density centrifugation. Cells were labeled with the CFSE proliferation kit (Thermo Fisher, Cat-No. C34554) for 10 minutes at room temperature according to manufacturer's instruction at a final concentration of 0.4 µM CFSE. Cells were then added to each well of the pre-coated plates at a density of $1 \times 10^5$ cells per well in serum-free X-Vivo15 medium (Lonza, Cat. No. BE02-054Q). Recombinant human TGF-β (2 ng/mL, R&D Systems, Cat. No. 240-B-010), monoclonal anti-human CD28 (1 µg/mL, eBioscience, Cat. No. 16-0289-85) and FAP coated beads ($2 \times 10^5$ cells per well) were added. Titrated dilutions of FAP-targeted OX40 antigen binding molecules were added at the indicated concentrations. Cells were incubated for three days at 37° C./5% $CO_2$ prior to analysis.

Cells were first stained 10 min with LIVE/DEAD™ Fixable Aqua Dead Cell Stain (Molecular probes, Cat. No. L34957) in DPBS, followed by one washing step (200 µL 4° C. FACS buffer). Thereafter, surface staining with fluorescent dye-conjugated antibodies anti-human CD4 (clone RPA-T4, BioLegend, Cat.-No. 300532), CD8 (clone RPA-T8, BioLegend, Cat.-No. 301042) and CD25 (clone BC96, BioLegend, Cat.-No. 302610) for 30 min at 4° C. Cell pellets were washed twice with FACS buffer, before cells were fixed and permeabilized in FoxP3 Fixation/Permeabilization working solution (FoxP3 staining Kit, eBioscience, Cat. No. 00-5521) for 60 minutes at room temperature in the dark according to manufacturer's instructions. After washing twice with 1× Perm buffer solution (FoxP3 staining Kit, eBioscience, Cat. No. 00-5521), cells were stained with fluorescent dye-conjugated antibody against FoxP3 (clone 29D6, BioLegend, Cat.-No. 20108) in 1× Perm buffer for 40 minutes at room temperature in the dark. Cell pellets were washed twice with 1× Perm buffer and finally resuspended in 100 µL/well FACS-buffer and acquired the same day using with BD Fortessa running FACS Diva software. Alive CD4+CD25+Treg singlet cells were gated and the MFI of the cFoxP3 antibody reported. The FoxP3 MFI of each concentration was corrected by the MFI of the sample without OX40 bispecific antibody, thus only TGBβ, present.

FIG. 40A to FIG. 40C show that FAP-OX40 bispecific antigen bispecific antigen binding molecules suppressed FoxP3 induction on resting CD4 T cells activated in the presence of TGFβ in a dose dependent manner. The D- and S-variant of each FAP-OX40 bispecific antibody showed similar bioactivity properties. In Table 25 the $EC_{50}$ values were summarized for the FAP-OX40 agonists dose-responses of FoxP3 suppression (FoxP3 MFI) on CD4+ CD25+Treg cells.

TABLE 25

$EC_{50}$ values of FAP-OX40 suppressed FoxP3 induction on TGFβ-exposed resting CD4 T cells

| Molecule ID | anti-Ox40 clone | Variant | Format | $EC_{50}$ [nM] |
|---|---|---|---|---|
| P1AF6455 | CLC-563 | S | 3 + 1 | 0.25 |
| P1AF6454 | CLC-563 | D | 3 + 1 | 0.11 |
| P1AF7217 | CLC-563 | S | 4 + 1 | 0.01 |
| P1AF7205 | CLC-563 | D | 4 + 1 | 0.02 |
| P1AF6457 | 49B4 AA variant K23E__K73E | S | 4 + 1 | 0.01 |
| P1AF6456 | 49B4 AA variant K23E__K73E | D | 4 + 1 | 0.02 |

Summary of Results

For evaluation of the binding properties of targeted OX40 antigen binding molecules human FAP negative tumor cells (A549-NLR), FAP positive fibroblasts (NIH/3T3-huFAP-clone 19), OX40 positive activated PBMC (activated CD4 and CD8 T cells) as well as OX40 negative resting PBMC (resting CD4 and CD8 T cells) were incubated with indicated serial dilutions of test antibody detected then by fluorescently labeled 2nd antibody against human Fcγ. All FAP-targeted OX40 antigen binding molecules bound efficiently to human FAP-expressing target cells and had no binding to target negative cells. FAP binding was for all constructs in a comparable nanomolar range. This is expected to translate in patients to direct tumor targeting and enrichment of the molecules. Along the natural prevalence of OX40 on T cells, all FAP-targeted OX40 antigen binding molecules bound stronger to activated CD4 than CD8 T cells. Antigen binding molecules harboring the avidity binder OX40 (49B4) bound better to OX40 in a tetravalent format (4+1) than in a trivalent or bivalent format (>1000× shift in $EC_{50}$). The mutated amino acid variants of clone 49B4 showed a comparable behavior. All other evaluated OX40 clones did not show an avidity gain in a trivalent format (3+1) compared to a bivalent format (2+1). The clones 8H9 and MOXR0916 bound with subnanomolar affinity, whereas clone CLC-563 bound with nanomolar affinity to OX40 positive T cells.

The tetravalent and trivalent OX40 antigen binding molecules induced NFκB activation in human OX40 positive NFκB reporter cells (HeLa_hOx40_NFκB_Luc1 reporter cells). This is due to the assembly of the trimeric core OX40 receptor-signaling unit already in the absence of further external crosslinking of the constructs. Bivalent formats per se showed accordingly less bioactivity. Additional crosslinking of the bispecific OX40 agonists by human FAP expressing fibroblasts via the FAP binding moiety, or by a secondary crosslinking antibody via the Fc region of the OX40 antigen binding molecule further increased the NFκB activation of all antigen binding molecules. For low nanomolar bivalent OX40 clones (49B4, CLC-563), a higher valency of the OX40 resulted also with respect to bioactivity in an avidity gain (4+1>3+1>2+1), whereas no benefit of a 3+1 over 2+1 format was observed for sub-nanomolar bivalent OX40 clones (8H9, MOXR0916). All amino acid variants of 49B4 in a 4+1 format induced dose dependent NKκB activation to a similar extent than the parental antibody in the 4+1 format. The bi- and trivalent OX40 antigen binding molecules did not reach the NFκB activation level of the tetravalent 4+1 format even at plateau concentration and at optimal crosslinking conditions.

Other than in the NFκB reporter assay, co-stimulation with non-targeted anti-OX40 (49B4) 4+0 format barely rescued sub-optimally TCR stimulated CD4 and CD8 T cells. Hyper-crosslinking of the FAP-targeted tetravalent, trivalent and bivalent OX40 antigen binding molecules in the presence of NIH/3T3-huFAP clone 19 cells, however, strongly promoted survival and induced an enhanced activated phenotype in human CD4 T cells for all OX40 clones tested. All amino acid variants of 49B4 were equally bioactive than the parental antibody in the same format.

The major enhancement of OX40 supported T cell activation was achieved by FAP-mediated hypercrosslinking and thus cell surface immobilization of the OX40. An increased valency for OX40 still added to the agonistic capacity of the FAP-targeted OX40 agonists, but to a lower extent. Selection of a higher affinity, and less avidity driven OX40 clone for targeted OX40 agonists, allowed reaching similar bioactivity than the tetravalent OX40 agonist already with bi- and trivalent OX40 antigen binding molecules. This discrepancy in molecule design requirements to achieve optimal OX40 receptor stimulation compared to T cell activation might reflect the requirement for spatial restriction of response modulating phosphorylation and dephosphorylation events within primary T cells (termed T cell synapse) for optimal TCR engagement. A fully functional T cell synapse assembles the various signaling components (e.g. via lipid rafts) to achieve full functionality. The decreased lateral mobility of synapse component favors this, as might the cell surface immobilization of OX40 by FAP-targeted OX40 agonists.

Example 5

Engineering of PK Properties 5.1 Background and Properties of the Reference Compound The bispecific antigen binding molecule OX40 (49B4)×FAP (4B9) (4+1) (molecule P1AD4524) as described in WO 2017/060144 A1 was explored in single intravenous dose huFcRn and in single intravenous dose PK studies in the cynomolgus monkey and atypically high clearances (>10-12 mL/min/kg) were observed as shown in Table 26. The in vivo protocols and the bioanalytical assays are described in Example 6.

Hu FcRn mice carry the human FcRn instead of the mouse FcRn and are, therefore, considered more predictive for the clearance in human as in wild-type mice (C57/B16). Indeed, the clearance in wild-type mice (11.0 mL/day/kg) had been relevantly lower as for huFcRn mice (33.0 mL/day/kg), which was consistent with the usual assumption that clearance in cynomolgus monkeys may be more predictive for human as e.g. clearance in wild-type mice following allometric transformation. There were no signs indicative of target mediated disposition (TMDD) in the construct plasma concentration-time profiles (FIG. 19, very similar for monkey), as it is shown by similar clearances for increasing doses in the monkey (see Table 26).

TABLE 26

Single dose PK parameters of P1AD4524

| Dose [mg/kg] | Clearance [mL/day/kg] | | | |
|---|---|---|---|---|
| | Mouse C57/B16 | Hu FcRn | FcRn KO | Monkey Cynom. (M/F) |
| 5 | 11.9 | 33.0 | 190 | 30.7/25.7 |
| 25 | — | — | — | 29.5/19.7 |
| 100 | — | — | — | 34.3/31.1 |

Table 26 shows in addition the clearance in FcRn knockout mice, which is relevantly higher as expected for a usual human antibody (usually about 60-80 mL/day/kg are observed for a wild-type human antibody), although clearances in FcRn KO mice are always higher due to the lack of the FcRn rescue mechanism.

5.2 Surface Charge Patch Exploration

The pharmacokinetics of an IgG antibody is dependent on FcRn binding, however it has been found that also the variable domains of an antibody have an influence on the clearance of the antigen binding molecule. Thus, it has been found that an antibody with a lower isoelectric point (pI) has a longer half-life (Igawa et al., Protein Engineering, Design & Selection 2010. 23, 385-392). A method on how to reveal positive charge patches on antibodies has been described by Zhang et al, Anal. Chem. 2011, 83, 8501-8508. Unspecific clearance of antibody constructs is often associated with so-called charge patches, i.e. areas on the antibody construct surface, which show primarily a positive charge and bind then to the negatively charged glycocalix of the cell membranes, followed by internalisation and degradation without rescue via FcRn.

5.2.1 Surface Charge Patch Exploration of the FAP Clone

The observed in vivo results, especially the high clearance in the FcRn knockout (KO) mice point to a high unspecific clearance of molecule P1AD4524, an antigen binding molecule with a fourfold OX40 (49B4) Fab fragment and a single FAP (4B9) antigen binding domain in the format of single domains VH and VL that are each connected to a C-terminal end of the Fc region, respectively.

Therefore it was explored by an iso-potential surface simulation of the molecule P1AD4524, whether its surface would show such positive charge patches. In analogy to Example 1.11, the FAP(4B9) antigen binding domain shows such a positive charge patch of prominent size (FIG. 20), which could contribute to the unwanted high clearance of P1AD4524.

Furthermore, a similar VH/VL fragment as used in P1AD4524 was also included in a study with an unrelated molecule as published by Holland et al., J. Clin. Immunol. 2013, 33, 1192-1203. This VH/VL fragment was considered to be associated with immunological findings and potentially unspecific binding properties. Therefore, a replacement of the VH/VL fragment by a Fab fragment carrying the FAP binder was implemented for the antigen binding molecules of the present invention.

An antigen binding molecule P1AE6836 similar to P1AD4524, but without the FAP (4B9) antigen binding domain (a 4+0 molecule) was then tested in HuFcRn mice to check, whether the omission of the charge patch on the FAP (4B9) antigen binding domain and the VH/VL fragment would decrease the clearance relevantly.

The results are shown in FIG. 21 and Table 27. The omission of the positive charge patch of the FAP (4B9) antibody on the VH/VL fragment reduced clearance by about 7 mL/day/kg, but clearance was still at about 26 mL/day/kg and consequently above the desired range of not more than 10-12 mL/day/kg.

TABLE 27

Single dose PK parameters of P1AD4524

| | Clearance [mL/day/kg] | |
|---|---|---|
| Dose [mg/kg] | huFcRn mouse P1AD4524 | P1AE6836 |
| 5 | 33.0 | 25.7 |

Therefore, further changes in the antigen binding molecule are necessary to reduce the clearance of the molecule.

5.2.2 Surface Charge Patch Exploration of the OX40 (49B4) Clone

Since the elimination of the positive charge patch on the FAP (4B9) clone was not sufficient to reach a clearance at least below 12 mL/day/kg in HuFcRn mice, the OX40 (49B4) clone was also explored for potential charge patches and the simulated isopotential surface of its Fab region is shown in FIG. 22A-FIG. 22C. The positive charge patches on the OX40 (49B4) clone may be smaller as on the 4B9 FAP binder, but since they occur four times in the antigen binding molecule due to its 4+1 valency, they might nevertheless be relevant for the high clearance of P1AE4524.

Therefore, it was decided to explore also other OX40 antibodies and to try to reduce the positive charge patches in P1AE4524.

5.3 Change of OX40 Clones and Effects on In Vitro PK Parameters 5.3.1 Surface Charge Patch Exploration of Alternative FAP and OX40 Clones Three different alternative OX40 clones were available and tested apart from two sequence variants of the 49B4 binder to avoid such charge patches. The simulated isopotential surface area of the Fab regions are shown in FIG. 23A-FIG. 23C (clone 8H9), FIG. 24A-FIG. 24C (clone CLC563) and FIG. 25A-FIG. 25C (clone MOXR0916). The isopotential surface area of the Fab region for the alternative FAP clone 1G1a is shown in FIG. 26.

A very crude ranking in order of potentially increasing clearance due to existing charge patches was probably CLC563<8H9<MOXRO916, but this needed a test and confirmation by independent pharmacokinetic data, since the visual inspection of the isopotential surface is not quantitative. The three different binders were then explored by additional in vitro data and a selection needs to take also the bioactivity of the resulting construct into account to reach a balance between pharmacological bioactivity and clearance.

The FAP clone 4B9 on the VH/VL fragment was replaced by FAP clone 1G1a in a crossFab fragment connected to the C-terminal end of the antigen binding molecule. This FAP clone showed no prominent positive charge patch as shown in FIG. 20D to FIG. 20F.

5.3.2 ARC In Vitro Assay Results

It was not feasible to perform with each potential antigen binding molecule of the available clones a new huFcRn mouse PK study. Therefore a preselection was performed by an in vitro assay, which explores the differences in recovery from compounds loaded to epithelial cells at neutral pH (pH 7.4, low binding to FcRn) and at pH 6.0 when binding to FcRn is strong. The shift in recovery between the two pH values to a better rescue by FcRn should be high (wild-type antibody >10) and the value at pH 7.4 should be low (for a normal human wild-type antibody <0.10-0.20), otherwise there is unspecific binding with subsequent clearance expected. The assay is always controlled by a wild-type antibody and antibody not binding to FcRn, to have an internal control in each experiment.

The results of the in vitro ARC Assay are tabulated below in Table 28.

TABLE 28

Results of the ARC in vitro assay for various antigen binding molecules

| | | $1^{st}$ and $2^{nd}$ experiment | | | | $3^{rd}$ experiment | | | |
|---|---|---|---|---|---|---|---|---|---|
| Molecule ID | Valency | Shift | pH 6.0 | pH 7.4 | Recovery | Shift | pH 6.0 | pH 7.4 | Recovery |
| Wild-type | 2 + 0 | 10 | 1.17 | 0.12 | Not rep. | 29 | 1.77 | 0.06 | Not rep. |
| IgG | | >10 | 0.86 | <0.06 | Not rep. | | | | |
| Non-binder | 2 + 0 | 1.5 | 0.18 | 0.12 | Not rep. | 1.0 | 0.06 | 0.06 | Not rep. |
| | | 1.0 | 0.06 | 0.06 | Not rep. | | | | |
| P1AD4524 | 4 + 1 | 2.3 | 1.97 | 0.84 | Not rep. | 4.6 | 0.92 | 0.20 | 83% |
| | (VH/VL) | 1.4 | 0.74 | 0.54 | Not rep. | | | | |
| P1AE6838 | 4 + 1 | 2.0 | 0.40 | 0.20 | 83% | 2.7 | 0.64 | 0.24 | 100% |
| | (crossFab) | | | | | | | | |
| P1AE8786 | 3 + 1 | 3.0 | 0.36 | 0.12 | 75% | | | | |
| P1AE6840 | 2 + 1 | 11 | 0.67 | 0.06 | 60% | | | | |
| P1AE9167 | 4 + 1 | | | | | 3.3 | 0.40 | 0.12 | 100% |
| P1AE9176 | 4 + 1 | | | | | 2.9 | 0.40 | 0.14 | 78% |
| P1AE9169 | 4 + 1 | | | | | 2.3 | 0.40 | 0.20 | 100% |
| P1AE8873 | 3 + 1 | 5.2 | 2.31 | 0.44 | | | | | |
| P1AE8870 | 2 + 1 | 10 | 2.11 | 0.21 | 100% | 24 | 6.99 | 0.28 | 88% |
| P1AE8874 | 3 + 1 | 1.7 | 0.32 | 0.20 | 83% | 4.2 | 0.50 | 0.12 | 100% |
| P1AE8871 | 2 + 1 | 2.8 | 0.34 | 0.12 | 75% | | | | |
| P1AE8875 | 3 + 1 | 1.1 | 0.18 | 0.16 | 80% | | | | |
| P1AE8872 | 2 + 1 | 6.7 | 0.40 | 0.06 | 100% | 29 | 1.72 | 0.06 | 100% |

It is evident from Table 28 that the valency (how many OX40 binders are present in the antigen binding molecule) has a profound influence on the pH shift in the ARC assay. Higher valencies (4+1 vs 3+1 and 3+1 vs 2+1) lead to a lower shift and presumably a higher clearance in the same homologues series.

The highest pH shift values were obtained for the 2+1 8H9 construct, 4+1 compounds had always the lowest pH shift, suggesting lower FcRn rescue and higher clearances.

The value at pH7.4 is suggestive of a high unspecific binding and the original compound P1AD4524 showed indeed the highest values at pH 7.4. The result of the ARC assay is therefore consistent with the high clearance of P1AD4524 in FcRn KO mice and the observed charge patches. Similarly, also the 3+1 8H9 construct may have a high unspecific clearance according to these in vitro results.

Consistent with the at least partial removal of the charge patches in the 4+1 antigen binding molecules containing OX40 (49B4) amino acid variants, compounds P1AE9167, P1AE9176 and to a less degree P1AE9169 had lower values at pH 7.4 suggesting lower unspecific binding and added further evidence for the negative impact of positive charge patches on unspecific antibody clearance.

More generally, it can be concluded from the results of the ARC assay that the removal of charge patches may reduce unspecific clearance and that higher valency leads to a higher clearance, which may be in line with recent observations published by Pyzik et al, Front. Immunol. 2019, 10:1540, doi: 10.3389/fimmu.2019.01540.

5.3.3 Exploration of Selected Antigen Binding Molecules In Vivo in huFcRn

Three compounds were selected for an in vivo study in huFcRn mice based on the in vitro ARC assay and the bioactivity data: P1AE8870 (OX40 (8H9)×FAP (1G1a) 2+1), P1AE8873 (OX40 (8H9)×FAP (1G1a) 3+1) and P1AE9176 (OX40 (49B4_K23E_K73E)×FAP (1G1a) 4+1). The results are shown in Table 29. The results of the ARC assay were in good correlation to the in vivo results in huFcRn mice.

TABLE 29

Results of the HuFcRn mouse PK results in three selected antigen binding molecules vs. the original compound P1AD5424

| Molecule ID | hu FcRn mice CL [mL/day/kg] | hu FcRn KO mice CL [mL/day/kg] | ARC score | ARC ratio |
|---|---|---|---|---|
| P1AD4524 | 34 | 190 | 0.80 | 1.9 |
| P1AE9176 | 21 | 31 | 0.14 | 2.9 |
| P1AE8873 | 18 | 85 | 0.44 | 5.3 |
| P1AE8870 | 9.5 | 59 | 0.21 | 10 |
| Roughly usual for wild-type antibody | <5-10 | 60-80 | <0.1-0.2 | >10-15 |

Based on these in vitro and animal in vivo results it can be concluded that the removal of the charge patch on the FAP antibody reduced clearance in huFcRn mice by about 7 mL/day/kg and that a higher valency (e.g. 4+1 vs 2+1) of the OX40 antibodies is associated with higher clearance in huFcRn mice, which may be a good surrogate for human patients.

5.4 Comparison of the PK Properties of Selected Antigen Binding Molecules in 4+1 and 3+1 Format 5.4.1 Background and Properties of the Selected Antigen Binding Molecules The 4+1 variant of the OX40 (CLC563)×FAP (1G1a) bispecific antigen binding molecule (4×CLC563) tended to show improved activity properties in in-vitro assays in comparison to the respective 3+1 constructs (3×CLC563). Therefore, it was of interest to compare the pharmacokinetic (PK) properties of the two variants.

The bispecific antigen binding molecule OX40 (CLC563)×FAP (1G1a) 3+1 (molecule P1AF6454, S variant) was explored in single intravenous dose PK studies in human FcRn mice (Hu FcRn) and FcRn KO mice and relevantly improved lower clearances (target: <10-12 mL/day/kg for HuFcRn mice) were observed in comparison to the original 4+1 construct P1AD4524 as shown in Table 29. The in vitro and in vivo protocols as well as the bioanalytical assays are described in Example 6.5.

Hu FcRn mice carry the human FcRn instead of the mouse FcRn and are, therefore, considered more predictive for the clearance in humans as in wild-type mice (C57/B16). There were no signs indicative of target mediated disposition (TMDD) as e.g. a faster clearance below a certain concentration threshold in the construct plasma concentration-time profiles (FIG. 41).

Table 30 shows in addition the clearance in FcRn knock-out mice, which is relevantly higher as expected for a usual human antibody (usually about 60-80 mL/day/kg are observed for a wild-type human antibody), although clearances in FcRn KO mice are always higher due to the lack of the FcRn rescue mechanism.

TABLE 30

Single dose PK parameters of P1AF6455/P1AF6454 (3 + 1) vs P1AD4524 (4 + 1)

| Molecule ID | anti-Ox40 clone | huFcRn mice CL [ml/day/kg] | FcRnKO mice CL [ml/day/kg] |
|---|---|---|---|
| P1AD4524 | 4 + 1 49B4 | 34 | 190 |
| P1AF6455 | 3 + 1 CLC563 (S) | — | 28 |
| P1AF6454 | 3 + 1 CLC563 (D) | 6.1 | — |

5.4.2 Change of Valency from 3+1 to 4+1 and Effects on In Vitro PK Parameters

It was not feasible to perform with each potential antigen binding molecule of the available clones a new huFcRn mouse PK study. Therefore, a preselection was performed by two in vitro assays, the ARC assay and the LUCA assay. The ARC assay is already described in Example 5.3.2.

The LUCA assay makes use of a pH dependent difference in fluorescence intensity of a dye attached covalently to the antibody construct of interest during the in vitro procedure. The construct with the attached dye is then incubated with human primary liver endothelial cells which express human FcRn. The fluorescence in the endothelial cell remains low, if the labelled construct is well recycled by the FcRn in the endothelial cell, but increases, if the labelled construct is not well recycled and is processed in late endosomes and degraded in the lysosome, since the pH is decreasing in these late endosomes and the lysosome. The higher the LUCA value, the higher may be the in-vivo clearance.

The results of the in vitro ARC and LUCA Assay are tabulated below in Table 31.

TABLE 31

Results of the ARC and LUCA in vitro assays for various antigen binding molecules

| Molecule ID | Valency & anti-OX40 clone | pH 7.4 ARC score | ARC ratio | LUCA |
|---|---|---|---|---|
| P1AF6455 | 3 + 1 CLC563 (D) | 0.40 | 1.6 | 2.1 |
| P1AF6454 | 3 + 1 CLC563 (S) | 0.34 | 1.8 | — |

TABLE 31-continued

Results of the ARC and LUCA in vitro assays for various antigen binding molecules

| Molecule ID | Valency & anti-OX40 clone | pH 7.4 ARC score | ARC ratio | LUCA |
|---|---|---|---|---|
| P1AF7205 | 4 + 1 CLC563 (D) | 0.38 | 1.3 | 2.7 |
| P1AF7217 | 4 + 1 CLC563 (S) | 0.36 | 1.1 | 2.7 |

It is evident from Table 31 that the valency (how many OX40 binders are present in the antigen binding molecule) has a subtle influence on the results of the ARC assay, showing a higher ARC ratio for the 3+1 variants in comparison to the 4+1 construct, i.e. a lower in vivo clearance is theoretically expected for the 3+1 construct, if the unspecific uptake (pH7.4 ARC score is comparable), which was indeed the case here.

In contrast to the ARC assay results, the LUCA assay suggested minor advantages for the 4+1 construct, since here the LUCA value should be correlated to the fraction of construct handed over to the late endosome, indicating higher clearance for higher LUCA values.

Overall, the differences in the in vitro assays tended be rather subtle, therefore an in vivo study with the constructs was performed in hu FcRn and FcRn KO mice, since according to Pyzig et al., Front. Immunol. 2019, 10, 1540 (doi: 10.3389/fimmu.2019.01540) higher valency may be associated with higher clearance, as indicated by the—although moderate—difference in the ARC assay.

5.4.3 Exploration of Selected Antigen Binding Molecules In Vivo in Hu FcRn and FcRn KO Mice The following compounds were selected for an in vivo study in huFcRn mice based on the in vitro ARC assay and the bioactivity data: P1AE6455 (OX40(CLC563)×FAP (1G1a) 3+1 as C-terminal S variant,) P1AF7217 (OX40 (CLC563)×FAP(1G1a) 4+1 as C-terminal S-variant) and P1AF7205 (as the respective C-terminal D-variant of the 4+1 construct). The results are shown in Table 32. For the in vivo study in FcRn KO mice P1AE6455 was replaced by P1AE6454 (OX40(CLC563)×FAP(1G1a) 3+1 as C-terminal D-variant). The in vivo results in huFcRn mice were in good rank order correlation with the results of the ARC assay.

TABLE 32

Results of the HuFcRn mouse PK results for three selected antigen binding molecules vs. P1AD5424

| Molecule ID | hu FcRn mice CL [mL/day/kg] | hu FcRn KO mice CL [mL/day/kg] | pH 7.4 ARC score | ARC ratio pH 6/7.4 |
|---|---|---|---|---|
| P1AE6454 3 + 1 D-variant | — | 28 | 0.34 | 1.8 |
| P1AE6455 3 + 1 S-variant | 6.1 | — | 0.40 | 1.6 |
| P1AE7217 4 + 1 S-variant | 30 | 49 | 0.36 | 1.1 |
| P1AE7205 4 + 1 D-variant | 23 | 51 | 0.38 | 1.3 |
| Roughly usual for wild-type antibody | <5(−10) | 60-80 | <0.1-0.2 | >10-15 |

Based on these in vitro and animal in vivo results it can be concluded that the higher valency (4+1) lead to a higher clearance of the more bulky 4+1 construct vs the 3+1 construct in line with the higher values for the ARC ratio. The HuFcRn clearance values were relevantly higher as the target value of <10-12 mL/day/kg and therefore the 4+1 construct is less preferred than the 3+1 construct due to high clearance.

Example 6

Method Description of the PK In Vitro and In Vivo Assays 6.1 Approach to Detect Possible PK Liabilities of the OX40 (49B4) Clone and Antibody Engineering to Improve the Antibody Briefly, the isopotential surface area of the variable region of the OX40 binder was generated and assessed for large positively charged patches, which can be a cause of high unspecific clearance. One positively charged patch consisting of three positively charged amino acids were identified of which two were mutated to negatively charged amino acids. These amino acids are located in the framework and not in the CDRs and have therefore been predicted to preserve the ability of the antibody to bind to its target. Details to the approach can be found in patent application WO 2018/197533.

The amino acid sequence of the variable domain VH of the OX40 clone 49B4 was used to create a homology model using the MoFvAb software version 9 (MoFvAb is a Modeling tool for Antibody Fv regions, built internally by Roche). By using an in silico calculation method starting with the homology model, followed by pH-protonation of acidic and basic side-chains, we calculated the 3D charge distribution using the software CHARMM and Delphi as implemented in the software suite Discovery Studio (vendor: Dassault Systems). By visual inspection of the resulting three dimensional charge distribution, a positively charged patch was identified which can be a cause of high unspecific clearance. It is composed of three amino acids in the VH, of which two are in the framework and not in the CDRs. Choosing framework residues and avoiding CDRs increases the probability of preserving target-binding affinity. Subsequently, these two framework residues (K23 and K73) were chosen to be mutated to e.g. glutamic acid, carrying a negative charge, which should decrease unspecific clearance.

6.2 ARC Assay for the Determination of pH Dependent Uptake and Recovery In Vitro A cell-based FcRn transcytosis assay was established as screening assay and ranking tool that might help to predict the clearance of therapeutic antigen binding molecules (IgG molecule) and help in the selection of lead candidates.

Human FcRn-transfected Madin-Darby Canine Kidney (MDCK) cells were cultured as monolayers on Transwell® polycarbonate filters to assess IgG recycling and transcytosis at 37° C. either at pH 6.0 or pH 7.4. FIG. 26 shows a scheme illustrating the transwell system. The assay is conducted in a "Pulse-Chase" format. First, the cells are incubated with the IgG molecule at either pH 6.0 or pH 7.4 (Pulse). Both compartments are subsequently washed to remove non-loaded IgG molecule and then the buffer is replaced with pH 7.4 for the "Chase". The release of the IgG molecule from the cells is measured after 2 hours (Chase) and quantified by IgG ELISA where a mean amount in ng is calculated for each condition. Both the apical and basolateral compartment are sampled to represent recycling and transcytosis, respectively. At pH 7.4, IgG is uptaken only via fluid-phase pinocytosis. This investigation reveals the susceptibility of an IgG to undergo nonspecific uptake for example due to its physicochemical properties and subsequent interactions with the cellular surface.

A final ARC score is calculated at both pH values:

ARC Score pH 6.0=ng IgG recycled pH 6.0+ng IgG transcytosed pH 6.0

ARC Score pH 7.4=ng IgG recycled pH 7.4+ng IgG transcytosed pH 7.4

Equation 1 ARC score formula for both pH values.

6.3 Analysis of Serum Samples for Analyte Concentrations for the huFcRn Mouse Studies For the huFcRn and FcRn KO mouse studies, the concentration of analytes in mice serum was determined by an exploratory ELISA assay for mice serum which uses capture and detection reagents specific for a human antibody (Ckappa and CH1 region). Limit of quantification was 69 ng/mL. The assay was described for cynomolgus monkey serum by Stubenrauch et al., Journal of Pharmaceutical and Biomedical Analysis 2013, 72, 208-215, and adapted for mouse plasma.

6.4 Analysis of Serum for Anti-Drug Antibodies for the huFcRn Mouse Studies

For the huFcRn and FcRn KO mouse studies, the measurement of anti-drug antibodies directed against the drug in mouse serum was performed by an exploratory ELISA assay which uses an anti-human IgG Fab fragment (Ckappa and CH1 region) as capture and an anti-Mouse-IgG antibody as detection reagent in mouse serum. The assay was described for cynomolgus monkey serum by Stubenrauch et al., Journal of Pharmaceutical and Biomedical Analysis 52 (2010) 249-254, and adapted for mouse plasma.

6.5 In Vivo Studies: Hu FcRn Mouse and FcRn KO Mouse PK Studies

The test compounds were administered (5 mg/kg) intravenously to four male huFcRn Tg32+/+mice as a slow bolus and 20 microliter $K_3$EDTA blood was collected by microsampling at 0.0833, 7, 24, 48, 72, 168, 336, 408 and 504 h after the dose. Plasma was prepared by centrifugation and stored frozen until shipped on dry ice to be analyzed for human antibody concentrations and antidrug antibodies occurrence by generic assays described in section 6.3 and 6.4.

Furthermore, the test compounds were administered (5 mg/kg) intravenously to three male FcRn KO mice as a slow bolus and 20 microliter $K_3$EDTA blood was collected by microsampling at 0.167, 2, 7, 24, 30, 48, 72 and 96 hours after the dose. Plasma was prepared by centrifugation and stored frozen until shipped on dry ice to be analyzed for human antibody concentrations and antidrug antibodies occurrence by generic assays described in section 6.3 and 6.4. The pharmacokinetic evaluation was performed by established noncompartmetal procedures.

6.6 LUCA Assay for the Estimation of Unspecific Clearance of Antibodies

An in vitro assay was established for the prediction of unspecific clearance of therapeutic antigen binding molecules in primary human liver endothelial cells. Data is acquired by labeling the antigen binding molecules with a pH-sensitive dye exhibiting high fluorescence, when accumulating in the lysosome (acidic pH 5.5) and low fluorescence when remaining outside the cell (neutral pH 7.4). Human or animal endothelial cells are incubated with labeled antibodies for 2 and 4 hours and the fluorescent readout is recorded using a flow cytometer. The geo-mean intensities are used for linear regression analysis. The extracted slopes form, when normalized to standard antibodies, the so-called relative LUCA rate.

To test whether the clearance detected within the LUCA assay is only mediated by unspecific uptake mechanisms such as pinocytosis, the assay was modified to also test for potential target-mediated (or off-target mediated) drug disposition (TMDD). Therefore, cells were pre-incubated with the equivalent unlabeled antibody counterpart to saturate the clearance-contributing target. To monitor the effect, different concentrations of the unlabeled antibody are applied to the cells prior as well as together with the labeled antibody. If the molecule exhibits potential TMDD, the relative LUCA rate would decrease with increasing concentrations of unlabeled antibody.

Antibody Labeling: The Antibodies were labeled using the SiteClick™ Antibody Azido Modification Kit (Thermo Fisher Scientific) according to the manufactures instructions. Briefly, N-linked galactose residues of the Fc-region were removed by β-galactosidase and replaced by an azide-containing galactose (GalNaz) via β-1,4-galactosyltransferase (GalT). This azide modification enables a copper-free conjugation of sDIBO-modified dyes. The pH-sensitive amine-reactive dye (523 nm) was purchased from Promega and coupled to a sulfo DBCO PEG4 amine. Antibodies were labeled with a molar dye excess of 2. Excess dye was removed using the Amicon® Ultra-2 Centrifugal Filter with a MWCO of 50 kD (EMD Millipore, #UFC200324) and antibodies were re-buffered in 20 mM histidine buffer (pH 5.5). The concentration of the labeled antibodies [1] as well as the dye to antibody ratio (DAR) [2] was determined with a Nanodrop spectrometer at 280 nm and 532 nm.

$$CAB = [A280 \text{ nm} - [A280 \text{ nm} * CFDye]]/\varepsilon mAb \quad [1]$$

$$DAR = [A532 \text{ nm} * MWmAb]/[cmAb * \varepsilon Dye] \quad [2]$$

cDye=47225
CFDve=0.36

Cell Maintenance and Preparation: Cryopreserved human liver-derived endothelial Cells (HLEC-P2) were purchased from Lonza (Lonza, #HLECP2). Cell were maintained in EBM™-2 Endothelial Cell Growth Basal Medium-2 (Lonza, #CC-3156) supplemented with EGM™-2 MV Microvascular Endothelial Cell Growth Medium Single-Quots™ (Lonza, #CC-4176). Five days prior antibody treatment, cells were plated onto collagen I coated 100 mm culture dishes (Corning® BioCoat™, #354450) and two days prior treatment sub-cultured into collagen I coated 96-well plates (Corning® BioCoat™, #354407) at a cell density of $4 \times 10^4$ cells/well to allow adherence for 48 hours. Medium was changed after 24 hours and cells were kept at 37° C. and 5% $CO_2$.

On the day of the experiment, cells were washed twice with 200 μl pre-warmed medium and subsequently incubated with 400 nM labeled antibody or 20 mM histidine buffer (pH 5.5) as negative control in medium. If potential TMDD was tested, cells were pre-incubated with unlabeled counterparts (0, 0.2, 0.6, 1.2, 3, 6.2 μM) for 30 min at 37° C. before the labeled antibody was added. After 2 and 4 hours, the antibody solution was removed and cells were washed once with 200 μl ice-cold DPBS (without Mg and Ca) and detached by applying 100 μl Trypsin (with EDTA) for 2.5 minutes at 37° C. Trypsin was inactivated by the addition of 100 μl FACS Buffer (20% FCS, 1 mM EDTA in DPBS).

Quality control: Biophysical binding properties are key determinants affecting clearance mechanisms. Therefore, it was important to assess, whether the binding affinities of the antibodies changed during the labeling process. Heparin chromatography and neonatal Fc receptor binding has been previously shown to predict antibody clearance in vitro (Kraft et al, mAbs 2020). Herein, this method was used to account for potential aberrant binding properties introduced by the click label. To confirm the absence of unbound dye and to verify the concentration measured at the spectrometer, a size exclusion chromatography of the labeled antibodies was performed. Samples were separated using a BioSuite Diol (OH) column (Waters, 186002165) with a potassium dihydrogen phosphate buffer (pH 6.2) as the mobile phase at a flow rate of 0.5 ml/ml. Detectors at 280 inn and 532 nm were used to quantify and analyze the labeled antibodies. The area under the curve (AUCs) at 280 nm and 532 nm was extracted to calculate the concentration. The geo-mean of the AUCs from all antibodies was computed and the deviation from each antibody to this geo-mean was identified. For an antibody to be reliable within this assay, the difference from the geo-mean was expected to be below 15%.

Flow Cytometry and Pharmacokinetic Analysis: The mean fluorescent intensity (MFI, more specifically the geometric mean (geo-mean)) of the internalized antibodies was acquired using the MACSQuant® Analyzer 10 (Miltenyi Biotec) equipped with a laser to excite at 488 nm and a filter to collect emitted light at 585 nm/540 nm. The exact same conditions, gains and gates were used for both times points (2 hours and 4 hours). Data extraction was performed using the FloJo_V10 software. Values of the negative control was subtracted from all geo-mean values followed by normalization to the DAR. The normalized geo-mean values from each antibody were plotted as linear regression curve using GraphPad Prism to extract the slope (Geo Mean MFI/min for 120 and 240 min). Two standard antibodies were selected to normalize the slopes: Motavizumab-YTE (G. J. Robbie et al., Antimicrob. Agent Chemother. 2013, 57(12), 6147) was set to 0 and CD20-CD3 TCB (Hutchings et al., Blood 2019, 134, 2871) was set to 1. The final slopes were plotted against published in vivo human, cynomolgus and hFcRn Tg32+/+ mouse clearance values using the TIBCO Spotfire software.

In vivo Pharmacokinetic data: Human and cynomolgus clearance values were compiled from study reviews published by FDA, EMA and NCBI or personal communication with clinical pharmacologists. If several clearance values were available, dose linear clearance describing the unspecific clearance of molecules, was used. In case of linear pharmacokinetics parameter were determined by standard non-compartmental methods. Clearance was calculated according to following formula:

Clearance=Dose/Area under concentration–time curve

In cases of non-linear pharmacokinetics the linear fraction of the clearance was determined via following alternative methods: Either clearance values were estimated following IV administration at high dose levels, at which additional non-linear clearance pathways are virtually saturated. Alternatively, PK models comprising a linear and a non-linear, saturable clearance term were established. In these cases, the model-determined linear clearance fraction was used for correlations.

Murine clearance was obtained from internally performed studies as follows:

Mice: B6.Cg-Fcgrt tm1Dcr Tg(FCGRT)276Dcr mice deficient in mouse FcRn α-chain gene, but hemizygous transgenic for a human FcRn α-chain gene (muFcRn−/− huFcRn tg+/−, line 276) were used for the pharmacokinetic studies. Mouse husbandry was carried out under specific pathogen free conditions. Mice were obtained from the Jackson Laboratory (Bar Harbor, Me., USA) (female, age 4-10 weeks, weight 17-22 g at time of dosing). All animal experiments were approved by the Government of Upper Bavaria, Germany (permit number 55.2-1-54-2532.2-28-10) and performed in an AAALAC accredited animal facility according to the European Union Normative for Care and Use of Experimental Animals. The animals were housed in standard cages and had free access to food and water during the whole study period.

Pharmacokinetic study: A single dose of antibody was injected i.v. via the lateral tail vein at a dose level of 5 mg/kg. The mice were divided into 3 groups of 6 mice each to cover 9 serum collection time points in total (at 0.08, 2, 8, 24, 48, 168, 336, 504 and 672 hours post dose). Each mouse was subjected twice to retro-orbital bleeding, performed under light anesthesia with Isoflurane™ (CP-Pharma GmbH, Burgdorf, Germany): a third blood sample was collected at the time of euthanasia. Blood was collected into serum tubes (Microvette 500Z-Gel, Sarstedt, Nümbrecht, Germany). After 2 h of incubation, samples were centrifuged for 3 min at 9.300 g to obtain serum, After centrifugation, serum samples were stored frozen at −20° C. until analysis.

Determination of human antibody serum conditions: Concentrations of Ustekinumab, Briakinumab, mAb 8 and mAb 9 antibodies in murine serum were determined by specific enzyme-linked immunoassays. Biotinylated Interleukin 12 specific to the antibodies and digoxigenin-labeled anti-human-Fc mouse monoclonal antibody (Roche Diagnostics, Penzberg, Germany) were used for capturing and detection, respectively. Streptavidin-coated microtiter plates (Roche Diagnostics, Penzberg, Germany) were coated with biotinylated capture antibody diluted in assay buffer (Roche Diagnostics, Penzberg, Germany) for 1 h. After washing, serum samples were added at various dilutions followed by another incubation step for 1 h. After repeated washings, bound human antibodies were detected by subsequent incubation with detection antibody, followed by an anti-digoxigenin antibody conjugated to horseradish peroxidase (HRP; Roche Diagnostics, Penzberg, Germany). ABTS (2,2'Azino-di[3-ethylbenzthiazoline sulfonate]; Roche Diagnostics, Germany) was used as HRP substrate to form a colored reaction product. Absorbance of the resulting reaction product was read at 405 nm with a reference wavelength at 490 nm using a Tecan sunrise plate reader (Männedorf, Switzerland). All serum samples, positive and negative control samples were analyzed in duplicates and calibrated against reference standard.

PK analysis: The pharmacokinetic parameters were calculated by non-compartmental analysis using WinNonlin™ 1.1.1 (Pharsight, CA, USA). Briefly, area under the curve (AUC0-inf) values were calculated by logarithmic trapezoidal method due to non-linear decrease of the antibodies and extrapolated to infinity using the apparent terminal rate constant $\lambda z$, with extrapolation from the observed concentration at the last time point. Plasma clearance was calculated as Dose rate (D) divided by AUC0-inf. The apparent terminal half-life (T½) was derived from the equation T½ ln 2/$\lambda z$.

Example 7

Evaluation and Improvement of Preexisting Anti-Drug Antibody Reactivity 7.1 Evaluation of Preexisting Anti-Drug Antibody (ADA) Reactivity For the evaluation of the root cause of preexisting IgG interference, an exploratory ELISA in human individual plasma samples to detect anti-drug antibodies (ADA) was performed. It uses a biotinylated anti-PGLALA antibody against the amino acid mutations L234A, L235A and P329G ("PGLALA modification") in the Fc domain of the drug as a capture reagent and a digoxigenin labeled FcγReceptor I (CD64) as detection reagent, which binds to a human IgG with no PGLALA modification that is part of the ADA-drug complex. To compare preexisting IgG interference to different drug molecules, this assay was performed on the same panel of naïve human individual plasma samples.

2 μg/mL biotinylated anti-PGLALA antibody is coated to the streptavidin coated microtiterplate in the first step. In parallel, naïve human individual plasma samples (BioIVT) were pre-incubated with a buffer containing $6.7 \times 10^{-9}$ mol/L of the respective drug molecule for 30 minutes at room temperature to allow the formation of the Drug-anti-drug antibody complex. After incubation of the samples and a washing step, human IgG with no PGLALA modification that is part of the immune complexes and bound to the surface can be detected with 0.5 μg/mL digoxigenin labeled FcγReceptor I (CD64). After washing, a polyclonal anti-digoxigenin-horseradish peroxidase (HRP) conjugate (50 mU/mL) was added and incubated. After another washing step and the addition of the ABTS (2,2'-Azinobis [3-ethyl-benzothiazoline-6-sulfonic acid]-diammonium salt) substrate solution to the microtiterplate, the HRP of the antibody enzyme conjugate catalyzes the color reaction. An ELISA reader measures the absorption at 405 nm wavelength. [(Wessels et al, Bioanalysis 2017, 9(11), 849-859).

7.2 Improvement of Preexisting Anti-Drug Antibody (ADA) Reactivity

The bispecific antigen binding molecule OX40 (49B4)×FAP (4B9) (4+1) (molecule P1AA1119) as described in WO 2017/060144 A1 was explored in naive human plasma samples for preexisting IgG interference. High incidence with high signals was observed as shown in FIG. 27A. Holland et al., J. Clin. Immunol. 2013, 33, 1192-1203 published that a similar VH/VL fragment as included in P1AA1119 in another type of molecule has shown reactivity to human anti-VH autoantibodies. Therefore, it was questioned if a replacement of the VH/VL fragment by a Fab fragment carrying the FAP binder can lead to less ADA reactivity in the antigen binding molecules of the present invention.

An antigen binding molecule P1AE6836, similar to P1AA1119, but with a Fab fragment carrying the FAP binder, was produced and investigated for preexisting IgG reactivity in the same panel of naïve human plasma samples, as shown in FIG. 27A to FIG. 27C. P1AE6836 still showed preexisting IgG Interference, with reduced signals compared to P1AA1119, and in different individual human samples, indicating a different type of preexisting anti-drug antibodies against the Fab fragment carrying the FAP binder (FIG. 27B). A similar molecule, but comprising the humanized FAP clone 1G1a (P1AE6838, FIG. 27C), confirmed the results obtained with the molecule comprising the FAP 4B9 clone (P1AE6836), indicating that the FAP clone is not the root cause of the preexisting IgG reactivity.

As can be seen in FIG. 28, all bispecific antigen binding molecules, sharing the FAP (1G1a) antigen binding domain, but different anti-OX40 Clones (49B4, 8H9, MOX0916 and CLC-563) showed the same preexisting IgG interference, indicating that the OX40 Clone is not the root cause of preexisting IgG reactivity.

In FIG. 29A a subset of human individual plasma samples was tested with control molecules comprising the OX40 (49B4) clone (P1AD3690) (4+0), an untargeted molecule comprising four OX40(49B4) Fab fragments, a FAP(1G1a) molecule (P1AE1689) comprising the humanized FAP (1G1a) Fab fragment), and the Germline control antibody (P1AD5108, DP47). These molecules do not cause preexisting IgG reactivity and therefore show low background signals. FIG. 29B shows that all valences for OX40 (2+1, 3+1 and 4+1) result in preexisting IgG interference with a slight increasing trend of signal height 2+1>3+1>4+1, presumably due to sterical hindrance.

Literature (Kim et al, MABS 2016, 8, 1536-1547) suggests that several proteases associated with invasive diseases are able to cleave antibodies in the hinge-region, thus generating neoepitopes for anti-hinge antibodies. We thus produced molecules with different C-terminal amino acids in the CH1 domain of the Fab fragment that is fused to the C-terminus of the Fc domain and thus has a "free" hinge-like region. Whereas the original bispecific antibody has a C-terminal amino acid sequence of EPKSC (SEQ ID NO:163), variants with C-terminal amino acid sequences of EPKSCD (SEQ ID NO:164) and EPKSCS (SEQ ID NO:165) were produced.

To evaluate the C-terminal extension variants of antigen binding molecules OX40 (49B4)×FAP (1G1a) (3+1), the same panel of human individual serum samples was tested (FIG. 30A) and its individual background signal substracted (FIG. 30C). The individual background signal was measured by performing the assay without the drug molecule (FIG. 30B).

An extension of the C-terminus by naturally occurring aspartate at this position of the upper hinge region was generated in the molecule OX40 (MOXR0916)×FAP (1G1a) (3+1) (P1AF4845) (FIG. 31B). This modification resulted in a reduction of preexisting IgG reactivity compared to the molecule P1AE8786 with a free C-terminus (FIG. 31A). To eliminate the preexisting IgG reactivity completely, a variant with a C-terminal serine was generated. This serine is not naturally located at this position of the upper hinge region. The extension of the C-terminus by a serine of molecule P1AF4851 led to a complete elimination of the preexisting IgG reactivity, as shown in FIG. 31C.

FIG. 32A to FIG. 32C show a respective molecule set in 2+1 format, and confirm the previous results that a C-terminal extension of an aspartate (Molecule OX40 (MOXR0916)×FAP (1G1a) (2+1) with EPKSCD terminus, P1AF4852, FIG. 32B) reduces, while a C-terminal serine (molecule OX40 (MOXR0916)×FAP (1G1a) (2+1) with EPKSCS terminus, P1AF4858, FIG. 32C) eliminates the reactivity with preexisting antibodies in plasma compared to a molecule OX40 (49B4)×FAP (1G1a) (2+1) with a free C-terminus EPKSC (P1AE6840, FIG. 32A).

Figure 33C:
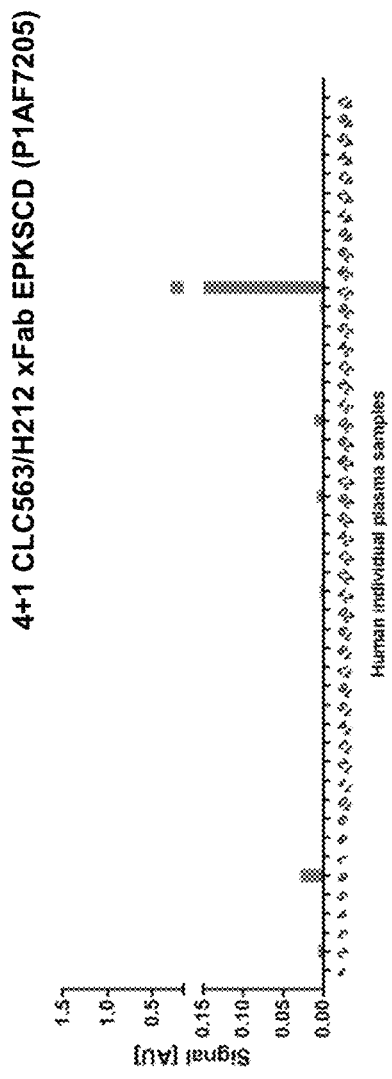
Figure 33D:
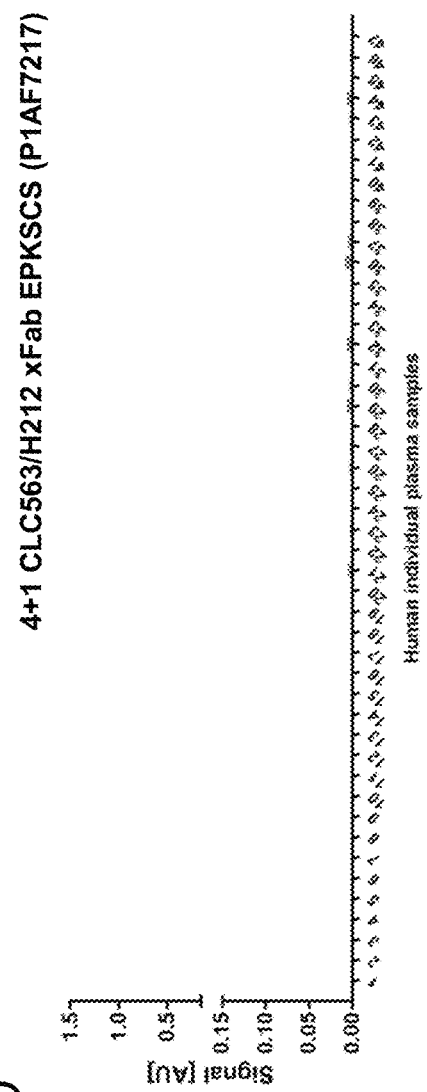
Figure 33E:
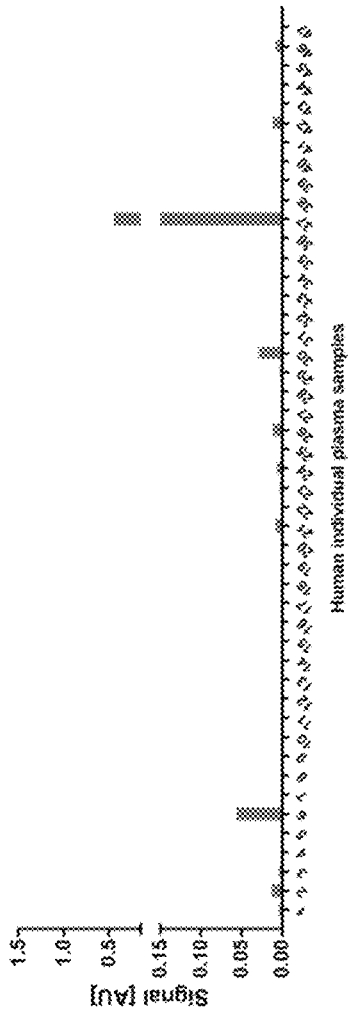
Figure 33F:
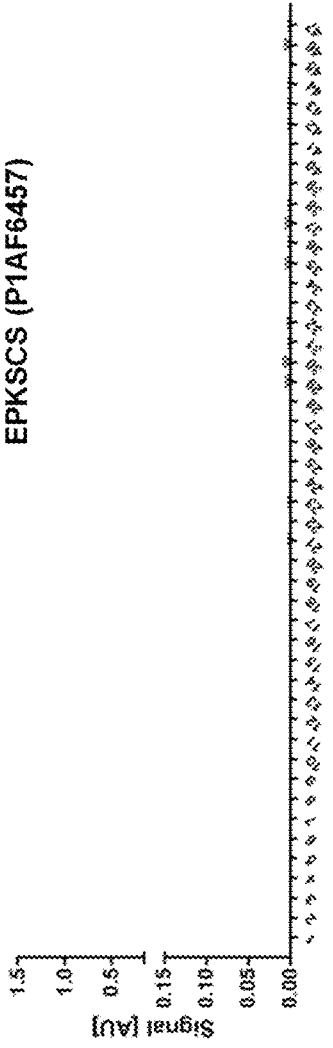

As can be seen in FIG. 33, three further molecule examples strengthen the finding that the additional C-terminal serine abolishes the preexisting ADA reactivity completely (FIG. 33B, FIG. 33D, and FIG. 33F), whereas the C-terminal aspartate reduces the unwanted interference (FIG. 33A, FIG. 33C, and FIG. 33E).

Example 8

Evaluation of FAP-Targeted Anti-OX40 Bispecific Antigen Binding Molecules for the Risk of Cytokine Release in an In Vitro 24-Hour Human Whole Blood Assay In order to evaluate potential safety risks relating to cytokine release upon first dosing in humans, in vitro non-GLP testing for FAP×OX40 bispecific-mediated cytokine secretion was conducted with fresh undiluted human whole blood samples from 10 healthy donors. The blood samples were incubated for 24 hours with concentrations of 0.1, 1, 10 and 50 µg/mL of FAP×OX40 bispecific molecules and subsequent release of cytokines in the plasma was measured. Erbitux®, an anti-EGFR IgG1 mAb, was used as a negative comparator and Lemtrada®, a humanized anti-CD52 IgG1, known to induce first infusion reactions (IRRs) in greater than 90% of recipients, was used as a positive comparator.

8.1 Material and Methods 8.1.1. Tested Molecules

The following FAP-targeted anti-OX40 bispecific antigen binding molecules were tested: C1: OX40(CLC563)×FAP (1G1a_EPKSCD) 3+1 (P1AF6454), concentration c=5.8 mg/ml, 20 mM His/HisCl, 140 mM NaCl, pH 6.0, received at −80° C. and after thawing stored at 4° C., C2: OX40 (CLC563)×FAP(1G1a_EPKSCS) 3+1 (P1AF6455), c=2.0 mg/ml, 20 mM His/HisCl, 140 mM NaCl, pH 6.0, received at −80° C. and after thawing stored at 4° C., C3: OX40 (49B4)×FAP (4B9) 4+1 (P1AD4524, R07194691), c=10.0 mg/ml, 20 mM His/HisCl, 140 mM NaCl, pH 6.0, received at −80° C. and after thawing stored at 4° C., C4: OX40 (CLC563)×FAP(1G1a_EPKSCS) 4+1 (P1AF7217), c=9.73 mg/ml, 20 mM His/HisCl, 140 mM NaCl, pH 6.0, received at −80° C. and after thawing stored at 4° C., C5: OX40 (CLC563)×FAP(1G1a_EPKSCD) 4+1 (P1AF7205), c=10.28 mg/ml, 20 mM His/HisCl, 140 mM NaCl, pH 6.0, received at −80° C. and after thawing stored at 4° C., C6: OX40(49B4_K23E_K73E)×FAP(1G1a_EPKSCS) 4+1 (P1AF6457), c=10.40 mg/ml, 20 mM His/HisCl, 140 mM NaCl, pH 6.0, received at −80° C. and after thawing stored at 4° C., and C7 OX40(49B4_K23E_K73E)×FAP (1G1a_EPKSCD) 4+1 (P1AF6456), c=10.17 mg/ml, 20 mM His/HisCl, 140 mM NaCl, pH 6.0, received at −80° C. and after thawing stored at 4° C.

TABLE 33

FAP-targeted anti-OX40 bispecific antigen binding molecules tested

| Molecule ID | anti-Ox40 clone | Variant | Format | Molecule name in FIGS. |
|---|---|---|---|---|
| P1AF6454 | CLC-563 | D | 3 + 1 | C1 |
| P1AF6455 | CLC-563 | S | 3 + 1 | C2 |
| P1AD4524 | 49B4 | — | 4 + 1 | C3 |
| P1AF7217 | CLC-563 | S | 4 + 1 | C4 |
| P1AF7205 | CLC-563 | D | 4 + 1 | C5 |
| P1AF6457 | 49B4 AA variant K23E_K73E | S | 4 + 1 | C6 |
| P1AF6456 | 49B4 AA variant K23E_K73E | D | 4 + 1 | C7 |

8.1.2. Control Substances

The following molecules were used as control:
Low Risk Comparator: Erbitux®, cetuximab, recombinant anti-EGFR, chimeric IgG1, Merck Serono, USA, stock 5 mg/mL, sterile liquid, stored at 4° C.
High Risk Comparator: Lemtrada®, alemtuzumab, recombinant anti-CD52, humanized IgG1, Genzyme, USA, stock 10 mg/mL, sterile liquid, stored at 4° C.
LPS: lipopolysaccharide derived from *Salmonella abortus*, Sigma, Product. No. L5886, stock conc: 1 mg/mL
PBS: Dulbecco's phosphate-buffered saline, Gibco No. 14190

8.1.3. Human Whole Blood Assay

Venous blood from healthy donors was collected in vacutainer tubes containing lithium heparin as anticoagulant (Roche Medical Center, Basel, Switzerland) and kept at room temperature until initiation of the assay (within 1-3 hours).

Pre-validation experiments revealed optimal performance conditions with blood processed within 3 hours, as otherwise lysis of erythrocytes occurred. Final test items concentrations ranged from 0.1 to 50 µg/ml of antigen binding molecule by adding 195 µl of blood in triplicates to U-bottom wells of 96-well plates containing 5 µl of the items to be tested (1:40). This concentration range was selected to cover the foreseen exposure following administration of P1AD4524 as known from earlier studies.

These conditions ensure optimal performance with respect to practicality and efficiency to gain at least 70 µl of plasma and sufficient cells to conduct multi-cytokine analysis and enumeration of cell subsets respectively. Endogenous activation of blood cells and responsiveness was assessed by including controls containing PBS or vehicle and LPS, respectively. After incubation for 24 hours at 37° C. with 5% $CO_2$, cells and plasma were separated by centrifugation at 1800 g for 5 min. Plasma samples were stored at −80° C. until analysis of cytokine content.

8.1.4. Multiplex Cytokine Assay

Determination of cytokine concentrations was performed on frozen plasma samples diluted 1:5. Pre-tests revealed that levels of cytokine did not differ between fresh and thawed samples. Analyte concentrations were determined by ELISA using the Human Cytokine chemiluminescent assay kit (Aushon Ciraplex, Cat. No 101-269-1-AB) with the SignaturePLUS™ imaging system and the Cirasoft analysis software. Results were expressed as pg/ml. Values above ULOQ concentration were assigned the concentration of the highest standard as follows: IFNγ, 500 pg/mL; IL-6, 2000 pg/mL; IL-8, 4000 pg/mL; TNFα, 1000 pg/ml. Sample values below LLOQ level were assigned LLOQ concentrations: IFNγ, 0.24 pg/mL; IL-6, 0.98 pg/mL; IL-8, 1.95 pg/mL; TNFα, 1.95 pg/ml.

8.2 Results and Conclusion

In this assay, the OX40(49B4)×FAP (4B9) 4+1 (P1AD4524, C3) led to the secretion of IL-6, IL-8 with maximum positive response of 33% and 33%, and maximum median cytokine upregulation of 1.0 fold (IL-6) and 2.73 fold (IL-8), respectively, relative to the negative comparator Erbitux®. The highest frequencies of responders and maximum median upregulation were observed at 10 µg/ml P1AD4525 for IL-6 and at 50 µg/ml P1AD4524 for IL-8.

Comparatively, less IL-6 and IL-8 release was observed for the panel of the bispecific FAP×OX40 antigen binding molecules as described herein (C1, C4, C5, C6 and C7), except for C2 which had even slightly elevated frequency of IL-8 responders (44%) at 50 µg/ml. C1 had the best cytokine profile (lowest IL-6 and IL-8 release) among all test molecules. C1 and C2 showed no IFNγ responders whereas C3 had 22% responders. TNF-α responses were low (0-11%) among all tested constructs.

FIG. 42A and FIG. 42B show the IL-6 secretion in every donor's blood sample after the addition of different concentrations of the tested molecules, the IL-8 secretion is shown in FIG. 43A and FIG. 43B.

Example 9

Immunogenicity Risk Evaluation

The sequence-related risk of immunogenicity was evaluated using an in vitro DC:$CD4^+$ T cells re-stimulation assay and the immunogenicity related to the mode of action was evaluated using transgenic mice that are tolerant to human IgG1 antibodies.

9.1 DC-T Cell Assay

The sequence-related immunogenicity of the FAPxOX40 bispecific antigen binding molecules was carried out using the DC:CD4+ T cells re-stimulation assay for the assessment of T cell activation with PBMCs from 30 healthy human donors. All proteins were tested in the same 30 healthy donors and the CD4+ T cell response induced by each condition was assessed by IFNγ FluoroSpot.

9.1.1. Materials

As controls, the Keyhole limpet haemocyanin (KLH) was reconstituted and stored at −80° C. in single use aliquots according to the manufacturer's recommendations under sterile conditions. Bevacizumab (Avastin®) and/or adalimumab (Humira®) was included as a benchmark protein. Avastin® was supplied by F. Hoffmann-La Roche AG and stored at +4° C. in single-use aliquots. Avastin® was used at a final concentration of 300 nM for both the DC stimulation stage and for the APC restimulation stage.

The tested FAPxOX40 bispecific antigen binding molecules were OX40(CLC563)xFAP(1G1a_EPKSCD) 3+1 (P1AF6454) and OX40(CLC563)xFAP(1G1a_EPKSCS) 3+1 (P1AF6455). In an earlier experiment, P1AD4524 was tested as well.

For the donor cells, all samples were collected under an ethical protocol approved by a local REC (research ethics committee) and written informed consent was obtained from each donor prior to sample donation. PBMC from healthy donors were prepared from whole blood within six hours of blood withdrawal. Cells were cryopreserved in vapour phase nitrogen until use in the assays. The quality and functionality of each PBMC preparation was analyzed by 7 day activation with positive controls such as KLH to assess naïve T cell responses. The MHC-Class II allotypes of the 30 healthy donors broadly cover for diversity and the HLA-DRB1 frequencies in the study match the world populations.

9.1.2. Methods 9.1.2.1 Epibase® DC:CD4+ T Cells Re-Stimulation Assay (According to Lonza Protocol)

Monocytes were isolated from frozen PBMC samples by magnetic bead selection (Miltenyi Biotec) and differentiated into immature DC (iDC) using GM-CSF and IL4. iDC were then harvested, washed and loaded with each individual test protein for 4 hours at 37° C. A DC maturation cocktail containing TNFα and IL-1B was then added for further 40-42 hours to activate/mature the DC (mDC). The expression of key DC surface markers (CD11c, CD14, CD40, CD80, CD83, CD86, CD209 and HLA-DR) at both the immature and mature stage were assessed by flow cytometry to ensure the DC were activated prior to T cell interaction. $1 \times 10^5$ mDC were then co-cultured with $1 \times 10^6$ autologous CD4+ T cells (isolated by negative magnetic selection for 6 days at 37° C., 5% $CO_2$ in a humidified atmosphere. On day 6, autologous monocytes were isolated from PBMC using negative magnetic bead selection and loaded with the selected protein/peptide that were initially used to load the DC. After incubation at 37° C., 5% $CO_2$ in a humidified atmosphere for 4 hours. $5 \times 10^4$ monocytes/well were added to anti-INFγ/anti-IL-5 pre-coated FluoroSpot plates (Mabtech) along with the corresponding DC:CD4 co-culture in quadruplicate ($2.5 \times 10^5$ CD4+ T cells/well). The FluoroSpot plates were incubated for 40-42 hours at 37° C., 5% $CO_2$ in a humidified atmosphere. After incubation the FluoroSpot plates were developed using an in-house procedure and the spot-forming cells (SFC) per well assessed for each cytokine in each test condition using an IRIS™ FluoroSpot Reader (Mabtech).

Surface marker QC checks were also performed on the monocyte derived DC at both the immature and mature stage to determine any possible influence of the test compound on the DC differentiation and allows for the assessment of the quality of the DCs before subsequent co-culture with CD4+ T cells. Surface markers are assessed by flow cytometry using fluorescently labelled antibodies and the Guava® easyCyte™ 8HT flow cytometer.

9.1.2.2 Data Management and QC

Documented QC and QA procedures were performed on all experimental data. Subsequent data analysis was carried out using Excel and the statistical program "R" with GraphPad Prism used for graphical representation of data.

9.1.2.3 Statistical Analysis

Response frequency: Data were analysed at donor level to determine if each individual test condition induces a significant T cell response in each donor. Spot forming units (SFU) per well (i.e. the number of cytokine-secreting cells per well) in response to each test condition were evaluated with the distribution free resampling (DFR) method (Moodie et al. 2010). The DFR method is a non-parametric statistical test that compares each test condition against the reference condition for each donor and indicates if the difference between test condition and the reference condition is statistically significant. The two described variations of this method are DFR(eq) and DFR(2x).

DFR(eq) utilizes permutation resampling and allows for a maximum false positive rating of 5% ($p \leq 0.05$) and a minimum of 1% ($p \leq 0.01$). DFR(2x) replaces permutation resampling with the Bootstrap test and controls false positive rating to <1% (p<0.01) through application of a stricter null hypothesis which incorporates a minimum response threshold in which the experimental results must be a minimum of 2-fold higher than the related negative controls in order to be judged statistically significant. These two DFR methods are coupled to Westfall-Young step down max T approach (onesided) to calculate p value and account for multiple comparisons. In this project, DFR(2x) was used to determine a statistically significant CD4+ t cell response.

Response Intensity: A stimulation index (SI) was calculated for each test condition in each donor by dividing the SFU/well in the test condition by the SFU/well in the blank (assay medium only) to highlight the magnitude of the T cell response in each donor. The Geometric mean along with the median and interquartile range over the 30 donor population was then calculated for each test condition.

9.1.2.4 Population Analysis of Immunogenicity

To assess the impact of each sample on the whole 30 donor population, the stimulation index (SI) was calculated for each test condition in each donor. The stimulation index was calculated by dividing the SFU/well in the test condition by the blank (assay medium only) to highlight the magnitude of the T cell response in each donor. The Geometric mean along with the median and interquartile range over the 30 donor population was then calculated for each test condition.

9.1.3. Results and Conclusion

KLH (positive control) was a potent stimulator of CD4+ T cells and induced high IFNγ (100%) and IL-5 (93.3%) responses in the majority of the donors, whereas the bevacizumab (Avastin, negative control) showed a low response based on IFNγ and IL-5 readouts. Both compounds, P1AF6454 and P1AF6455, induced a low donor T cell response frequency for IFNγ (P1AF6454: 6.6% and P1AF6455: 10%) (FIG. 44A and FIG. 44B) as well as for IL-5 (6.6% for both). Based on previous validation experiments the threshold for low responder frequencies has been set at higher than 10%; therefore both compounds tested are considered to be associated with a low risk of sequence-related immunogenicity.

Comparatively, P1AD4524 induced a higher donor T cell response frequency for INFγ (33%) and a higher INFγ stimulation (stimulation index of 2.5) (FIG. 45A and FIG. 45B) compared to the new FAP×OX40 antigen binding molecules P1AF6454 and P1AF6455.

9.2 a 4-Week Immunogenicity Study to Assess the Potential of FAP-Ox40 Candidates in Eliciting Antidrug Antibodies (ADA) in Transgenic Mice that are Immunologically Tolerant to Human IgG1 Antibodies The aim of the study is to investigate the immunogenic potential of the FAP-OX40 molecules by testing them in a C57BL/6-Tg (hIgG1,k,l) transgenic mouse model. In contrast to C57BL/6 wild type mice the C57BL/6-Tg (hIgG1,k,l) transgenic mice harbor transgenic non-rearranged human Ig-heavy and light chain gene loci. Upon B-cell differentiation these transgenic gene loci undergo functional Ig gene rearrangement with subsequent B-cell expression of soluble human IgG1. Therefore, the immune system of C57BL/6-Tg (hIgG1,k,l) transgenic mice is tolerant to a broad range of human IgG1 antibodies and can serve as an in vivo model to assess immunogenicity of IgG1 based drug compounds and potentially predict drug specific immunogenicity in humans. For each test item, 10 wild type mice and 10 transgenic mice were subcutaneously administered 10 μg per mouse per injection on days 1, 5, 8, 12, 15, 19, and 22. Blood samples were prepared for IgG measurements on days 1, 8, 15, 22 and 29 to monitor the progression of potential ADA responses. ELISA-based detection of mouse IgG antibodies specific to the compound injected was used as immunological read out.

9.2.1. Materials

The tested FAP×OX40 bispecific antigen binding molecules were OX40(CLC563)×FAP(1G1a_EPKSCD) 3+1 (P1AF6454), OX40(CLC563)×FAP(1G1a_EPKSCS) 3+1 (P1AF6455) and OX40(49B4)×FAP(4B9) 4+1 (P1AD4524).

The mouse strains used in the experiment were C57BL/6 wild type mice and –C57BL/6-Tg (hIgG1,k,l) transgenic mice.

9.2.2. Methods

ELISA testing: Nunc Maxisorp flat-bottom 96-well ELISA plates were coated with 100 μL per well test compound at 1p g/mL in NaHCO₃ 100 mM buffer overnight at +4° C. The next day the ELISA plates were washed three times with PBS+0.05% Tween. For blocking, 100 μL of PBS+2% BSA were added to each well and the ELISA plates were incubated two hours at room temperature. The sera were diluted 1 to 50 in PBS+1% FBS in the first row of round bottom dilution plate, following by a 1 to 3 serial dilution step, seven times in PBS+1% FBS. The ELISA plates were washed three times with PBS+0.05% Tween and 100 μL of the diluted sera were transferred from the dilution plate to the ELISA plate. After two hours of incubation at room temperature, the ELISA plates were washed three times with PBS+0.05% Tween. For detection of mouse anti-drug antibodies (ADA) in the blood serum of the immunized mice, 100 μL per well of goat anti-mouse IgG Alkaline Phosphatase conjugated (Jackson Cat no 115-055-071) diluted 1:2000 in PBS+1% FBS were added. After one hour of incubation at room temperature, the ELISA plates were washed three times with PBS+0.05% Tween. 100 μL of substrate P-nitrophenyl phosphate ready-touse (Life Technologies Cat no 002212) were added per well and after ten minutes of incubation at room temperature, the optical density (OD) at 405 nm was read as an endpoint measurement with a Versamax ELISA reader.

Statistical analysis: The principal readout of this assay is considered binary in nature (distinct immune response vs. no clear response) since OD changes from ELISA cannot be compared across different antibody detection assays and thus be easily translated into a universal quantitative measure. It was decided to focus on response frequencies in the two cohorts of ten mice per test item. For reproducible identification of an immune response, we defined a six-sigma criterion above baseline to call a positive response. Animals that reached an OD value 6 Standard Deviation (SD) above background in at least one-time point were counted as responders. For the determination of mean background level and background standard deviation, we pooled the transgenic and wild type group readouts at day 1 (before treatment, n=20), after verifying there is no evidence for a clear initial difference in baseline level or spread for the two genotypes (t- and F-test, respectively, p-values>0.05). Responders identified by this method correspond very well with those identified by human intuition from the graphical plots, as confirmed in a few sample data sets. 95% confidence intervals for response rates were calculated based on a binomial distribution model, taking the observed response numbers and group size (n=10) into account. ELISA OD values were taken at a dilution of 1:50, going for maximum signal after ensuring a clean baseline and no (matrix effects) from the performed dilution curves. OD values were imported directly from the plate reader format using a custom R script for processing, analyzing and visualizing the in vivo immunogenicity data.

9.2.3. Results and Conclusion

The ELISA results of the two individual mouse groups treated with P1AF6455 are shown in FIG. 46. These ELISA analyses revealed that 6/10 (60%) C57BL/6 wild type mice elicited an Ig-immune response, as measured by the presence of ADAs in immunized mouse sera against this compound. This prominent immune response was anticipated, given that P1AF6455 is a fully human IgG1 antibody and is therefore expected to be regarded as foreign by the murine immune system. In contrast, 0/10 (0%) C57BL/6-Tg (hIgG1,k,l) transgenic mice mounted an antibody response against P1AF6455.

The ELISA results of the two individual mouse groups treated with P1AF6454 are shown in FIG. 47. These ELISA analyses revealed that 0/10 (0%) C57BL/6 wild type mice elicited an Ig-immune response, as measured by the presence of ADAs in immunized mouse sera against this compound. Comparable to the situation in C57BL/6 wild type mice no ADA-responders (0/10 (0%)) against P1AF6454 were seen in C57BL/6-Tg (hIgG1,k,l) transgenic mice. This result indicates that P1AF6454 does not mounted an antibody response neither in C57BL/6 wild type mice nor in C57BL/6-Tg(hIgG1,k,l) transgenic mice.

The ELISA results of the two individual mouse groups treated with P1AD4524 are shown in FIG. 48. These ELISA analyses revealed that 5/8 (62.5%) C57BL/6 wild type mice elicited an Ig-immune response, as measured by the presence of ADAs in immunized mouse sera against this compound. This prominent immune response was anticipated, given that P1AD4524 is a fully human IgG1 antibody and is therefore expected to be regarded as foreign by the murine immune system. 6/9 (66.7%) C57BL/6-Tg(hIgG1,k,l) transgenic mice mounted an antibody response against R07194691, highlighting a high risk for immunogenicity in human.

The in vivo immunogenicity studies demonstrate a high risk of immunogenicity for the P1AD4524 and in contrast a low propensity for induction of humoral immune responses for the compounds P1AF6454 and P1AF6455. The difference seen may be attributed to altered sequence properties among the three tested compounds. These sequence alterations in P1AF6454 and P1AF6455 may either impact the MHC class II presentation of compound derived peptides or may lead to non-immunogenic peptide sequences which fail to induce immunogenic T-cell and B-cell responses.

Example 10

Efficacy Study with FAP×OX40 Bispecific Antigen Binding Molecules in Combination with CEACAM5 TCB in MKN45 Xenograft in Humanized Mice The efficacy study described herein was aimed to select the most potent FAP×OX40 bispecific antigen binding molecule in vivo in terms of tumor regression in fully humanized NSG mice.

Human MKN45 cells (human gastric carcinoma) were originally obtained from ATCC and after expansion deposited in the Glycart internal cell bank. Cells were cultured in DMEM containing 10% FCS at 37° C. in a water-saturated atmosphere at 5% $CO_2$. In vitro passage 7 was used for subcutaneous injection at a viability of 98%. Human fibroblasts NIH-3T3 were originally obtained from ATCC, engineered at Roche Nutley to express human FAP and cultured in DMEM containing 10% Calf serum, 1× Sodium Pyruvate and 1.5 µg/ml Puromycin. Clone 39 was used at an in vitro passage number 5 and at a viability of >95%.

50 microliters cell suspension ($1\times10^6$ MKN45 cells+1× $10^6$ 3T3-huFAP) mixed with 50 microliters Matrigel were injected subcutaneously in the flank of anaesthetized mice with a 22G to 30G needle.

Female NSG mice, age 4-5 weeks at start of the experiment (Jackson Laboratory) were maintained under specific-pathogen-free condition with daily cycles of 12 h light/12 h darkness according to committed guidelines (GV-Solas; Felasa; TierschG). The experimental study protocol was reviewed and approved by local government (P 2011/128). After arrival, animals were maintained for one week to get accustomed to the new environment and for observation. Continuous health monitoring was carried out on a regular basis.

Female NSG mice were injected i.p. with 15 mg/kg of Busulfan followed one day later by an i.v. injection of $1\times10^5$ human hematopoietic stem cells isolated from cord blood. At week 14-16 after stem cell injection mice were bled sublingual and blood was analyzed by flow cytometry for successful humanization. Efficiently engrafted mice were randomized according to their human T cell frequencies into the different treatment groups. At that time, mice were injected with the tumor/fibroblast cell mixture as described (FIG. 49) and treated once weekly with the compounds or Histidine buffer (Vehicle) when tumor size reached approximately 200 $mm^3$ (day29). All mice were injected i.v. with 200 µl of the appropriate solution. To obtain the proper amount of compounds per 200 µl, the stock solutions (Table 34) were diluted with Histidine buffer when necessary.

TABLE 34

Compositions used in the in vivo experiment

| Compound | Stock Solution concentration (mg/ml) | Formulation buffer |
|---|---|---|
| CEACAM5-TCB | 19.2 | 20 mM Histidine, 140 mM NaCl pH 6.0 |
| FAP × OX40 (49B CPV; 4 + 1) (P1AE6456) | 1.43 | 20 mM Histidine, 140 mM NaCl pH 6.0 |
| FAP-OX40 (CLC563; 3 + 1) (P1AF6454) | 4.4 | 20 mM Histidine, 140 mM NaCl pH 6.0 |
| FAP-OX40 (8H9; 2 + 1) (P1AE8870) | 3.99 | 20 mM Histidine, 140 mM NaCl pH 6.0 |
| FAP-OX40 (49B4, 4 + 1) (P1AD4524) | 24.32 | 20 mM Histidine, 140 mM NaCl pH 6.0 |

Tumor growth was measured twice weekly using a caliper and tumor volume was calculated as followed:

Tv: (W2/2)×L (W: Width, L: Length)

At day 50 the study was terminated.

FIG. 50A shows the tumor growth kinetics (Mean, +SEM) and FIG. 50B shows the percentage of change of tumor volume at study termination as compared to baseline (start of treatment) per individual mouse and group. As described here, the FAP×OX40 construct, containing the CLC563 clone in a 3+1 format, reveals best anti-tumor activity in combination with CEACAM5-TCB. In that treatment group, five out of 8 mice, showed tumor regression (Waterfall plot).

The invention claimed is:

1. A bispecific antigen binding molecule, comprising:
(a) at least two antigen binding domains capable of specific binding to OX40, wherein the antigen binding domain capable of specific binding to OX40 comprises
  (i) a heavy chain variable region ($V_H$OX40) comprising:
    (i) CDR-H1 comprising the amino acid sequence of SEQ ID NO:35,
    (ii) CDR-H2 comprising the amino acid sequence of SEQ ID NO:36, and
    (iii) CDR-H3 comprising the amino acid sequence of SEQ ID NO:37,
  and a light chain variable region ($V_L$OX40) comprising:
    (iv) CDR-L1 comprising the amino acid sequence of SEQ ID NO:38,
    (v) CDR-L2 comprising the amino acid sequence of SEQ ID NO:39, and
    (vi) CDR-L3 comprising the amino acid sequence of SEQ ID NO:40;
(b) an antigen binding domain capable of specific binding to Fibroblast Activation Protein (FAP) comprising a heavy chain variable region ($V_H$FAP) comprising (i) CDR-H1 comprising the amino acid sequence of SEQ ID NO:3, (ii) CDR-H2 comprising the amino acid sequence selected from the group consisting of SEQ ID NO:4, SEQ ID NO:11 and SEQ ID NO:12, and (iii) CDR-H3 comprising the amino acid sequence of SEQ ID NO:5, and a light chain variable region ($V_L$FAP) comprising (iv) CDR-L1 comprising the amino acid sequence selected from the group consisting of SEQ ID NO:6, SEQ ID NO:13 and SEQ ID NO:14, (v) CDR-L2 comprising the amino acid sequence of SEQ ID NO:7, and (vi) CDR-L3 comprising the amino acid sequence of SEQ ID NO:8, and
(c) a Fc region composed of a first and a second subunit capable of stable association.

2. The bispecific antigen binding molecule of claim 1, wherein the Fc region comprises one or more amino acid substitution that reduces the binding affinity of the antibody to an Fc receptor and/or effector function.

3. The bispecific antigen binding molecule of claim 1, wherein the antigen binding domain capable of specific binding to FAP comprises:
a heavy chain variable region ($V_H$FAP) comprising an amino acid sequence that is at least about 90% identical to the amino acid sequence of SEQ ID NO:9, and
a light chain variable region ($V_L$FAP) comprising an amino acid sequence that is at least about 90% identical to the amino acid sequence of SEQ ID NO:10.

4. The bispecific antigen binding molecule of claim 1, wherein the antigen binding domain capable of specific binding to FAP comprises:
a heavy chain variable region ($V_H$FAP) comprising an amino acid sequence selected from the group consisting of SEQ ID NO:15, SEQ ID NO:16, SEQ ID NO:17, SEQ ID NO:18, SEQ ID NO:19 and SEQ ID NO:20, and
a light chain variable region ($V_L$FAP) comprising an amino acid sequence selected from the group consisting of SEQ ID NO:21, SEQ ID NO:22, SEQ ID NO:23, SEQ ID NO:24, SEQ ID NO:25 and SEQ ID NO:26.

5. The bispecific antigen binding molecule of claim 1, wherein the antigen binding domain capable of specific binding to FAP comprises:
(a) a heavy chain variable region ($V_H$FAP) comprising the amino acid sequence of SEQ ID NO:15 and a light chain variable region ($V_L$FAP) comprising the amino acid sequence of SEQ ID NO:21, or
(b) a heavy chain variable region ($V_H$FAP) comprising the amino acid sequence of SEQ ID NO:16 and a light chain variable region ($V_L$FAP) comprising the amino acid sequence of SEQ ID NO:21, or
(c) a heavy chain variable region ($V_H$FAP) comprising the amino acid sequence of SEQ ID NO:16 and a light chain variable region ($V_L$FAP) comprising the amino acid sequence of SEQ ID NO:22, or
(d) a heavy chain variable region ($V_H$FAP) comprising the amino acid sequence of SEQ ID NO:19 and a light chain variable region ($V_L$FAP) comprising the amino acid sequence of SEQ ID NO:25.

6. The bispecific antigen binding molecule of claim 1, wherein the antigen binding domain capable of specific binding to FAP comprises:
a heavy chain variable region ($V_H$FAP) comprising the amino acid sequence of SEQ ID NO:15, and
a light chain variable region ($V_L$FAP) comprising the amino acid sequence of SEQ ID NO:21.

7. The bispecific antigen binding molecule of claim 1, wherein the antigen binding domain capable of specific binding to OX40 comprises a heavy chain variable region ($V_H$OX40) comprising the amino acid sequence of SEQ ID NO:41 and a light chain variable region ($V_L$OX40) comprising the amino acid sequence of SEQ ID NO:42.

8. The bispecific antigen binding molecule of claim 1, wherein the Fc region is an IgG Fc region.

9. The bispecific antigen binding molecule of claim 8, wherein the Fc region is of human IgG1 subclass with the amino acid mutations L234A, L235A and P329G, (as numbered according to the Kabat EU index.

10. The bispecific antigen binding molecule of claim 1, wherein the bispecific antigen binding molecule comprises:
(a) at least two Fab fragments capable of specific binding to OX40 each connected to the N-terminus of one of subunits of the Fc region, and
(b) one cross-Fab fragment capable of specific binding to FAP fused to the C-terminus of one of subunits of the Fc region, and (c) the Fc region composed of a first and a second subunit capable of stable association.

11. The bispecific antigen binding molecule of claim 10, wherein the VH-Ckappa chain of the cross-fab fragment capable of specific binding to FAP is fused to the C-terminus of one of subunits of the Fc region.

12. The bispecific antigen binding molecule of claim 1, consisting of:
   (aa) a first Fab fragment capable of specific binding to OX40,
   (ab) a second Fab fragment capable of specific binding to OX40,
   (b) a cross-Fab fragment capable of specific binding to FAP fused to the C-terminus of one of subunits of the Fc region, and
   (c) the Fc region composed of a first and a second subunit capable of stable association, wherein the first Fab fragment (aa) is fused at the C-terminus of the VH-CH1 chain to the N-terminus of the first subunit and the second Fab fragment (ab) is fused at the C-terminus of the VH-CH1 chain to the N-terminus of the second subunit.

13. The bispecific antigen binding molecule of claim 1, consisting of:
   (aa) a first Fab fragment capable of specific binding to OX40,
   (ab) a second Fab fragment capable of specific binding to OX40,
   (ac) a third Fab fragment capable of specific binding to OX40,
   (b) a cross-Fab fragment capable of specific binding to FAP fused to the C-terminus of one of subunits of the Fc region, and
   (c) the Fc region composed of a first and a second subunit capable of stable association, wherein the second Fab fragment (ab) is fused at the C-terminus of the VH-CH1 chain to the N-terminus of the VH-CH1 chain of the first Fab fragment (aa), which is in turn fused at its C-terminus to the N-terminus of the first subunit, and the third Fab fragment (ac) is fused at the C-terminus of the Fab heavy chain to the N-terminus of the second subunit.

14. The bispecific antigen binding molecule of claim 1, consisting of:
   (aa) a first Fab fragment capable of specific binding to OX40,
   (ab) a second Fab fragment capable of specific binding to OX40,
   (ac) a third Fab fragment capable of specific binding to OX40,
   (ad) a fourth Fab fragment capable of specific binding to OX40,
   (b) a cross-Fab fragment capable of specific binding to FAP fused to the C-terminus of one of subunits of the Fc region, and
   (c) the Fc region composed of a first and a second subunit capable of stable association, wherein the second Fab fragment (ab) is fused at the C-terminus of the VH-CH1 chain to the N-terminus of the VH-CH1 chain of the first Fab fragment (aa), which is in turn fused at its C-terminus to the N-terminus of the first subunit, and the fourth Fab fragment (ad) is fused at the C-terminus of the VH-CH1 chain to the N-terminus of the VH-CH1 chain of the third Fab fragment (ac), which is in turn fused at its C-terminus to the N-terminus of the second subunit.

15. An isolated nucleic acid encoding the bispecific antigen binding molecule of claim 1.

16. An expression vector comprising the isolated nucleic acid of claim 15.

17. A host cell comprising the expression vector of claim 16.

18. A method of producing a bispecific antigen binding molecule, comprising culturing the host cell of claim 17 under conditions suitable for the expression of the bispecific antigen binding molecule, and isolating the bispecific antigen binding molecule.

19. A pharmaceutical composition comprising the bispecific antigen binding molecule of claim 1 and a pharmaceutically acceptable carrier.

20. The pharmaceutical composition of claim 19, further comprising an additional therapeutic agent.

21. The pharmaceutical composition according to claim 20, wherein the additional therapeutic agent is a chemotherapeutic agent, radiation and/or other agent for use in cancer immunotherapy.

22. The pharmaceutical composition according to claim 20, wherein the additional therapeutic agent is a T-cell activating anti-CD3 bispecific antibody.

23. A method of treating an individual having cancer comprising administering to the individual an effective amount of the bispecific antigen binding molecule of claim 1.

24. The method of claim 8, wherein said IgG Fc region is an IgG1 Fc region or an IgG4 Fc region.

* * * * *